United States Patent
Jenkins et al.

(10) Patent No.: US 9,617,282 B2
(45) Date of Patent: Apr. 11, 2017

(54) MACROCYCLIC COMPOUNDS AS IRAK4 INHIBITORS FOR THE TREATMENT OF INFLAMMATORY DISEASES

(71) Applicant: BIOGEN MA INC., Cambridge, MA (US)

(72) Inventors: Tracy Jenkins, Cambridge, MA (US); Jeffery Vessels, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/770,030

(22) PCT Filed: Mar. 14, 2014

(86) PCT No.: PCT/US2014/027722
§ 371 (c)(1),
(2) Date: Aug. 24, 2015

(87) PCT Pub. No.: WO2014/143672
PCT Pub. Date: Sep. 18, 2014

(65) Prior Publication Data
US 2016/0002265 A1    Jan. 7, 2016

Related U.S. Application Data

(60) Provisional application No. 61/793,617, filed on Mar. 15, 2013.

(51) Int. Cl.
*C07D 498/18* (2006.01)
*C07D 498/22* (2006.01)
*C07D 513/18* (2006.01)
*C07D 513/22* (2006.01)
*C07D 471/22* (2006.01)

(52) U.S. Cl.
CPC ......... *C07D 513/22* (2013.01); *C07D 471/22* (2013.01); *C07D 498/18* (2013.01); *C07D 498/22* (2013.01); *C07D 513/18* (2013.01)

(58) Field of Classification Search
CPC .. C07D 498/18; C07D 498/22; C07D 513/18; C07D 513/22; C07D 471/22
See application file for complete search history.

(56) References Cited

FOREIGN PATENT DOCUMENTS

EP    2119718 A1    11/2009

OTHER PUBLICATIONS

Masson, Geraldine, et al., Intramolecular Staudinger Ligation towards Biaryl-Containing Lactams, Synlett, 6:865-868, 2006.
Wang, Zhulun, et al., IRAK-4 Inhibitors for Inflammation, Current Topics in Medicinal Chemistry, 9(8):724-737, 2009.
Buckley, George M., et al., IRAK-4 inhibitors, Part 1: A series of amides, Bioorganic & Medicinal Chemistry Letters, 18(11):3211-3214, 2008.
Souto, Jose A., et al., Synthesis and Biological Charactertization of the Histone Deacetylase Inhibitor Largazole and C7-Modified Analogues, Journal of Medicinal Chemistry, 53(12):4654-4667, 2010.

*Primary Examiner* — Bruck Kifle
(74) *Attorney, Agent, or Firm* — McCarter & English, LLP; Steven G. Davis; Xin Zhang

(57) ABSTRACT

Provided are compounds of Formula (I), or pharmaceutically acceptable salts thereof, wherein i.a. Ring A is phenylene or 5- to 6-membered heteroarylene; Ring B is phenylene, 5- to 6-membered heterocycloalkylene or 5- to 6-membered heteroarylen; $R^4$ is absent, heteroarylene, arylene, C1-3 alkylene, or $R^4$ and $R^3$ taken together with the nitrogen to which they are bound form a 3- to 7-membered heterocycloalkyl ring; $R^5$ is absent, C(O)NR$^{51}$, NR$^{52}$ or O; $R^6$ is C2-10 alkylene or alkenylene, wherein one or two of the carbon atoms in the alkylene chain is optionally replaced by an O, S, SO, SO$_2$ or NR$^{61}$, and wherein two of the carbon atoms in the alkylene chain are optionally connected by a two or three carbon atom alkylene chain to form a 5- to 7-membered ring; $R^7$ is absent, NR$^{71}$ or O. The compounds are IRAK4 inhibitors useful for the treatment of inflammatory diseases.

(I)

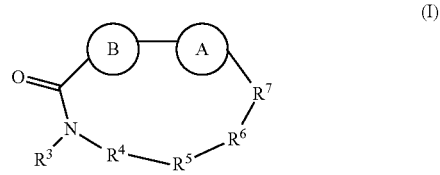

13 Claims, No Drawings

MACROCYCLIC COMPOUNDS AS IRAK4 INHIBITORS FOR THE TREATMENT OF INFLAMMATORY DISEASES

This application is a 35 U.S.C. §371 national stage filing of International Application No. PCT/US2014/027722, filed Mar. 14, 2014, which claims the benefit of U.S. Provisional Patent Application No. 61/793,617, filed Mar. 15, 2013. The entire contents of each of the foregoing applications are hereby incorporated by reference.

Provided are certain agents that inhibit IRAK4, and methods of making and using such agents.

Cellular immune responses depend on the ability of immune cells (e.g., macrophages, natural killer cells, T-cells) to detect and respond to cues in the extracellular environment by transmitting (transducing) signals across the cell membrane and into the intracellular (cytoplasmic) environment. Signals transmitted across the cell membrane may then effect a variety of "downstream" cytoplasmic and nuclear signal transduction pathways that subsequently produce a variety of immune cell responses (for example up- or down-regulation of gene transcription and translation or by releasing cytoplasmically stored components into the extracellular environment).

One cytoplasmic molecule responsible for the transmission of such downstream signals is known as "IRAK4". IRAK4 functions in cytoplasmic signal transduction pathways by interacting with components ("adaptor proteins") associated with the cytoplasmic portion of the Interleukin-1 receptor (IL-1R), Interleukin-18 receptor (IL-18R), and Toll-Like receptors (TLRs). These receptors (ILRs and the vertebrate TLRs) play important roles in innate immunity (i.e., general, non-specific immune system mechanisms of defense). In particular, TLRs play important roles in responding to microbial pathogens. TLRs are capable of eliciting a generalized immune response to pathogens via recognition of pathogen-associated molecular patterns (PAMPs). In response to such PAMPs, IL-1R/TLR signal transduction is initiated, across the cell membrane, by recruiting cytoplasmic adaptor proteins. Such adaptor proteins interact with homologous Toll/IL-1R (TIR) domains located in the cytoplasmic portion of IL-1R/TLR receptors.

The importance of adaptor proteins to immune system function is well established, as elimination of such adaptor proteins has been shown to induce significant disruptions of innate immune responses. Some examples of known IL-1R/TLR adaptor proteins are: MyD88; TIRAP/Mal; Trif/Ticam; and TRAM. MyD88, in particular, has a modular "death domain" (DD) that functions to recruit IRAK family proteins such as IRAK4. IRAK4 is thought to associate with MyD88 via IRAK4's own death domain. Moreover, loss of IRAK4/MyD88 association disrupts IL-1R/TLR signal transduction by preventing IRAK4 from phosphorylating (i.e., activating) IRAK1. Biologically, IRAK4 has been demonstrated to play a critical role in innate immunity.

SUMMARY

Provided is a compound of Formula I, or a pharmaceutically acceptable salt thereof,

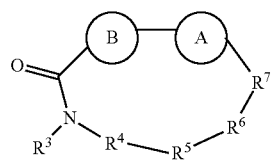

Formula I wherein
Ring A is phenylene or 5- to 6-membered heteroarylene containing 1-3 heteroatoms chosen from O, S, and N, wherein ring A is optionally substituted with lower alkyl that is further optionally substituted, Ring B is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl that is further optionally substituted, $R^3$ is chosen from hydrogen, lower alkyl optionally substituted with alkoxy, amino, N-(alkyl)amino, N,N-(dialkyl)amino, or phenyl, heterocycloalkyl, and heteroaryl, wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from $C(O)NR^{51}$, $NR^{52}$, and O or $R^5$ is absent, provided that if $R^4$ is absent, then $R^5$ is absent, $R^6$ is an alkylene or alkenylene chain having one or two double bonds,
wherein the alkylene or alkenylene chain has 2 to 10 carbon atoms,
wherein the alkylene or alkenylene chain is optionally substituted with one or two groups independently chosen from lower alkyl and cycloalkyl, each of which groups is optionally substituted with hydroxyl or alkoxy, and
further wherein one or two of the carbon atoms in the alkylene chain is optionally replaced by an O, S, SO, $SO_2$, or $NR^{61}$, and
wherein two of the carbon atoms in the alkylene chain, are optionally connected by a two or three carbon atom alkylene chain to form a 5- to 7-membered ring.

$R^7$ is chosen from $NR^{71}$ and O or $R^7$ is absent,
$R^{51}$ is chosen from hydrogen and lower alkyl,
$R^{52}$ is chosen from hydrogen, lower alkyl, and $-C(O)OR^{81}$,
$R^{61}$ is chosen from hydrogen, lower alkyl, and $-C(O)OR^{81}$,
$R^{71}$ is chosen from hydrogen, lower alkyl, and $-C(O)OR^{81}$, and
$R^{81}$ is lower alkyl.

Alternatively provided is a compound of Formula I*, or a pharmaceutically acceptable salt thereof,

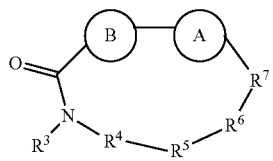

Formula I* wherein
Ring A is phenylene or 5- to 6-membered heteroarylene containing 1-3 heteroatoms chosen from O, S, and N, wherein ring A is optionally substituted with lower alkyl that is further optionally substituted, Ring B is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl or lower alkyloxyalkyl, either of which is is further optionally substituted, $R^3$ is chosen from hydrogen, lower alkyl optionally substituted with alkoxy, amino, N-(alkyl)amino, N,N-(dialkyl)amino, or phenyl, heterocycloalkyl, and heteroaryl,
wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from C(O)NR$^{51}$, NR$^{52}$, and O or $R^5$ is absent, provided that if $R^4$ is absent, then $R^5$ is absent, $R^6$ is an alkylene or alkenylene chain having one or two double bonds,
wherein the alkylene or alkenylene chain has 2 to 10 carbon atoms,
wherein the alkylene or alkenylene chain is optionally substituted with one or two groups independently chosen from lower alkyl, cycloalkyl and phenyl, each of which groups is optionally substituted with hydroxyl, alkoxy, —C(O)OR$^{85}$, C(O)NR$^{82}$R$^{83}$, benzoyl, and benzyl,
further wherein one or two of the carbon atoms in the alkylene or alkenylene chain is optionally replaced by an O, S, SO, SO$_2$, C(O)NR$^{51}$, or NR$^{61}$, and
wherein one of the carbon atoms in the alkylene or alkenylene chain, is optionally connected by the nitrogen atom of C(O)NR$^{51}$ or NR$^{61}$ to form a 5- to 7-membered ring, which may further be substituted with oxo,
wherein two of the carbon atoms in the alkylene or alkenylene chain, are optionally connected by a two or three carbon atom alkylene or alkenylene chain to form a 5- to 7-membered ring, $R^7$ is chosen from NR$^{71}$ and O or $R^7$ is absent, $R^{51}$ is chosen from hydrogen and lower alkyl, $R^{52}$ is chosen from hydrogen, lower alkyl, and —C(O)OR$^{81}$, $R^{61}$ is chosen from hydrogen, lower alkyl, —(CH$_2$)$_n$C(O)OR$^{81}$, —(CH$_2$)$_n$C(O)NR$^{82}$R$^{83}$, —C(O)R$^{84}$, —C(O)(CH$_2$)$_p$NR$^{82}$C(O)OR$^{81}$, —C(O)(CH$_2$)$_p$NR$^{82}$R$^{83}$, $R^{71}$ is chosen from hydrogen, lower alkyl, and —C(O)OR$^{81}$, $R^{81}$ is hydrogen or lower alkyl, $R^{82}$ is hydrogen or lower alkyl, $R^{83}$ is hydrogen or lower alkyl, $R^{84}$ is hydrogen, lower alkyl, C$_3$-C$_6$cycloalkyl or tetrahydropyran, wherein the lower alkyl is optionally substituted with hydroxy or —C(O)OR$^{81}$, $R^{85}$ is hydrogen, lower alkyl, or benzyl, n is 0, 1, 2, or 3 and p is 1 or 2.

Provided is a compound of Formula II, or a pharmaceutically acceptable salt thereof,

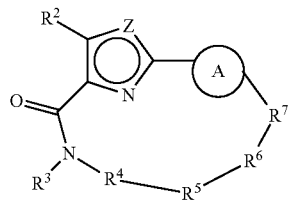

Formula II wherein

Ring A is phenylene or 5- to 6-membered heteroarylene containing 1-3 heteroatoms chosen from O, S, and N, wherein ring A is optionally substituted with lower alkyl that is further optionally substituted with hydroxyl, alkoxy, amino, N-(alkyl)amino, N,N-(dialkyl)amino, or halogen, Z is chosen from O, S, and NR$^{21}$, $R^2$ is chosen from hydrogen and lower alkyl, $R^3$ is chosen from hydrogen, lower alkyl optionally substituted with alkoxy, amino, N-(alkyl)amino, N,N-(dialkyl)amino, or phenyl, heterocycloalkyl, and heteroaryl,
wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from C(O)NR$^{51}$, NR$^{52}$, and O or $R^5$ is absent, provided that if $R^4$ is absent, then $R^5$ is absent, $R^6$ is an alkylene or alkenylene chain having one or two double bonds,
wherein the alkylene or alkenylene chain has 2 to 10 carbon atoms,
wherein the alkylene or alkenylene chain is optionally substituted with one or two groups independently chosen from lower alkyl and cycloalkyl, each of which groups is optionally substituted with hydroxyl or alkoxy, and
further wherein one or two of the carbon atoms in the alkylene chain is optionally replaced by an O, S, SO, SO$_2$, or NR$^{61}$, and
wherein two of the carbon atoms in the alkylene chain, are optionally connected by a two or three carbon atom alkylene chain to form a 5- to 7-membered ring.

$R^7$ is chosen from NR$^{71}$ and O or $R^7$ is absent, $R^{21}$ is chosen from hydrogen and lower alkyl optionally substituted with lower alkoxy, wherein lower alkoxy is optionally substituted with tri(alkyl)silyl, $R^{51}$ is chosen from hydrogen and lower alkyl, $R^{52}$ is chosen from hydrogen, lower alkyl, and —C(O)OR$^{81}$, $R^{61}$ is chosen from hydrogen, lower alkyl, and —C(O)OR$^{81}$, $R^{71}$ is chosen from hydrogen, lower alkyl, and —C(O)OR$^{81}$, and $R^{81}$ is lower alkyl.

Also provided is a pharmaceutical composition comprising at least one compound described herein, or a pharmaceutically acceptable salt thereof, and at least one pharmaceutically acceptable excipient.

Also provided is a method for treating an inflammatory disease in a patient, the method comprising administering to the patient a therapeutically effective amount of a compound described herein, or a pharmaceutically acceptable salt thereof.

Other features or advantages will be apparent from the following detailed description of several embodiments, and also from the appended claims.

DETAILED DESCRIPTION

As used in the present specification, the following words, phrases and symbols are generally intended to have the meanings as set forth below, except to the extent that the context in which they are used indicates otherwise.

As used herein, the term "alkyl" or "lower alkyl" refers to a fully saturated branched or unbranched hydrocarbon moiety. In some embodiments, the alkyl comprises 1 to 20 carbon atoms, such as 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

As used herein, the term "alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. In some embodiments, the haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Nonlimiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. In some embodiments, a haloalkyl group is trifluoromethyl or difluoromethyl.

As used herein, the term "halogen" or "halo" may be fluoro, chloro, bromo or iodo.

"Alkenyl" refers to an unsaturated hydrocarbon group which may be linear or branched and has at least one carbon-carbon double bond. Alkenyl groups with 2-8 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. In some embodiments, alkoxy groups have about 1-6 carbon atoms, such as about 1-4 carbon atoms.

As used herein, the term "carbocyclyl" refers to saturated or partially unsaturated (but not aromatic) monocyclic, bicyclic or tricyclic hydrocarbon groups of 3-14 carbon atoms, such as 3-9, for example, 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, such as 3-9, for example, 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. In some embodiments the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

As used herein, the term "aryl" refers to monocyclic, bicyclic or tricyclic aromatic hydrocarbon groups having from 6 to 14 carbon atoms in the ring portion. In some embodiments, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "arylene" refers to divalent monocyclic, bicyclic or tricyclic aromatic hydrocarbon groups having from 6 to 14 carbon atoms in the ring portion. In some embodiments, the term aryl refers to monocyclic and bicyclic aromatic hydrocarbon groups having from 6 to 10 carbon atoms. Representative examples of aryl groups include phenylene, naphthalenediyl.

The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, azepinyl, oxapinyl, oxazepinyl and diazepinyl.

The term "heterocycloalkylene" refers to a divalent, completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

"Heteroarylene" is a divalent 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. Some embodiments contain 5 to 6 ring atoms for example furandiyl, thiophenediyl, pyrrolediyl, imidazolediyl, oxazolediyl, thiazolediyl, isoxazolediyl, pyrazolediyl, isothiazolediyl, oxadiazolediyl, triazolediyl, thiadiazolediyl, pyridinediyl, pyrazinediyl, pyrimidinediyl, pyridazinediyl, triazinediyl, and the like. In addition, some embodiments include thienyldiyl. Some embodiments contain 8 to 14 ring atoms for example quinolizinediyl, quinolinediyl, isoquinolinediyl, cinnolinediyl, phthalazinediyl, quinazolinediyl, quinoxalinediyl, triazinediyl, indolediyl, isoindolediyl, indazolediyl, indolizinediyl, purinediyl, naphthyridinediyl, pteridinediyl, carbazolediyl, acridinediyl. phenazinediyl, phenothiazinediyl, phenoxazinediyl, benzoxazolediyl, benzothiazolediyl, 1H-benzimidazolediyl, imidazopyridinediyl, benzothienediyl, benzofurandiyl, isobenzofurandiyl, and the like.

As used herein, the term "amino" refers to a group having the formula $NH_2$. The term N-(alkyl)amino is an amino group in which one of the hydrogen atoms is replaced with an alkyl group. The term N,N-(dialkyl)amino is an amino group in which each hydrogen atoms is replaced with an alkyl group which may be the same or different.

As used herein, the term "bridged ring system," is a ring system that has a carbocyclyl or heterocyclyl ring wherein two non-adjacent atoms of the ring are connected (bridged) by one or more (such as from one to three) atoms. A bridged ring system can have more than one bridge within the ring system (e.g., adamantyl). A bridged ring system may have from 6-10 ring members, such as from 7-10 ring members. Examples of bridged ring systems include adamantly, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R,5S)-bicyclo[3.2.1]octanyl, 3-azabicyclo[3.3.1]nonanyl, and bicyclo[2.2.1]heptanyl. In some embodiments, the bridged ring system is selected from 9-azabicyclo[3.3.1]nonan-9-yl, 8-azabicyclo[3.2.1]octanyl, and bicyclo[2.2.2]octanyl.

The terms "optional" or "optionally" mean that the subsequently described event or circumstance may but need not occur, and that the description includes instances where the event or circumstance occurs and instances in which it does not. For example, "optionally substituted alkyl" means that the alkyl may be substituted as well as where the alkyl is not substituted.

"Optionally substituted" groups may be substituted or unsubstituted. Unless stated otherwise, optionally substituted alkyl, alkylene, alkenyl and alkynyl refer to alkyl, alkylene, alkenyl or alkynyl radicals, as defined herein, that may be optionally substituted by one or more substituents (e.g., by one to six substituents, such as one to four substituents, for example, one or two substituents, such as one substituent) independently selected from nitro, halo, azido, cyano, alicyclic, heteroaryl, heterocycloalkyl, —$OR_x$, —$N(R_y)(R_z)$, —$SR_x$, —$C(J)R_x$, —$C(J)OR_x$, —$C(J)N(R_y)(R_z)$, —$C(J)SR_x$, —$S(O)_tR_x$ (where t is 1 or 2), —$OC(J)R_x$, —$OC(J)OR_x$, —$OC(J)N(R_y)(R_z)$, —$OC(J)SR_x$, —$N(R_x)C(J)R_x$, —$N(R_x)C(J)OR_x$, —$N(R_x)C(J)N(R_y)(R_z)$, —$N(R_x)C(J)SR_x$, —$Si(R_w)_3$, —$N(R_x)S(O)_2R_w$, —$N(R_x)S(O)_2N(R_y)(R_z)$, —$S(O)_2N(R_y)(R_z)$, —$N(R_x)C(J)R_x$, —$P(O)(R_v)_2$, —$OP(O)(R_v)_2$, —$C(J)N(R_x)S(O)_2R_x$, —$C(J)N(R_x)N(R_x)S(O)_2R_x$, —$C(R_x)$=$N(OR_x)$, and —$C(R_x)$=$NN(R_y)(R_z)$, wherein each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; and each J is independently O, $NR_x$ or S.

In some embodiments, optionally substituted alkyl, alkylene, alkenyl and alkynyl refer to alkyl, alkylene, alkenyl or alkynyl radicals, as defined herein, that may be optionally substituted by one or more substituents (e.g., by one to six substituents, such as one to four substituents, for example, one or two substituents, such as one substituent) independently selected from halo, cyano, alicyclic, heteroaryl, heterocycloalkyl, —$OR_x$, —$N(R_y)(R_z)$, —$SR_x$, —$C(J)R_x$, —$C(J)OR_x$, —$C(J)N(R_y)(R_z)$, —$C(J)SR_x$, —$S(O)_tR_x$ (where t is 1 or 2), —$OC(J)R_x$, —$OC(J)OR_x$, —$OC(J)N(R_y)(R_z)$, —$OC(J)SR_x$, —$N(R_x)C(J)R_x$, —$N(R_x)C(J)OR_x$, —$N(R_x)C(J)N(R_y)(R_z)$, —$N(R_x)C(J)SR_x$, —$N(R_x)S(O)_2R_w$, —$N(R_x)S(O)_2N(R_y)(R_z)$, —$S(O)_2N(R_y)(R_z)$, —$N(R_x)C(J)R_x$, —$C(J)N(R_x)S(O)_2R_x$, and —$C(J)N(R_x)N(R_x)S(O)_2R_x$, wherein each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; and each J is independently O, $NR_x$ or S.

In some embodiments, optionally substituted alkyl, alkylene, alkenyl and alkynyl refer to alkyl, alkylene, alkenyl or alkynyl radicals, as defined herein, that may be optionally substituted by one or more substituents (e.g., by one to six substituents, such as one to four substituents, for example, one or two substituents, such as one substituent) independently selected from halo, cyano, alicyclic, heteroaryl, heterocycloalkyl, —$OR_x$, —$N(R_y)(R_z)$, —$C(J)R_x$, —$C(J)OR_x$, —$C(J)N(R_y)(R_z)$, —$OC(J)R_x$, —$OC(J)OR_x$, —$OC(J)N(R_y)(R_z)$, —$N(R_x)C(J)R_x$, —$N(R_x)C(J)OR_x$, —$N(R_x)C(J)N(R_y)(R_z)$, and —$N(R_x)C(J)R_x$, wherein each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; and each J is independently O, $NR_x$ or S.

In some embodiments, optionally substituted alkyl, alkylene, alkenyl and alkynyl refer to alkyl, alkylene, alkenyl or alkynyl radicals, as defined herein, that may be optionally substituted by one or more substituents (e.g., by one to six substituents, such as one to four substituents, for example, one or two substituents, such as one substituent) independently selected from halo, cyano, alicyclic, heteroaryl, heterocycloalkyl, —$OR_x$, —$N(R_y)(R_z)$, —$C(J)R_x$, —$C(J)OR_x$, —$C(J)N(R_y)(R_z)$, —$OC(J)R_x$, —$OC(J)OR_x$, —$OC(J)N(R_y)(R_z)$, —$N(R_x)C(J)R_x$, —$N(R_x)C(J)OR_x$, —$N(R_x)C(J)N(R_y)(R_z)$, and —$N(R_x)C(J)R_x$, wherein each $R_x$ is independently hydrogen, alkyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; each $R_w$ is independently alkyl, alicyclic, alicyclicalkyl, heterocycloalkyl, heterocycloalkyl-alkyl, aryl, arylalkyl, heteroaryl, or heteroarylalkyl; each $R_v$ is independently alkyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; and each J is independently O, $NR_x$ or S.

In some embodiments, optionally substituted alkyl, alkylene, alkenyl and alkynyl refer to alkyl, alkylene, alkenyl or alkynyl radicals, as defined herein, that may be optionally substituted by one or more substituents (e.g., by one to six substituents, such as one to four substituents, for example, one or two substituents, such as one substituent) independently selected from halo, cyano, alicyclic, heteroaryl, heterocycloalkyl, —$C(J)R_x$, —$C(J)OR_x$, and —$C(J)N(R_y)(R_z)$, wherein each $R_x$ is independently hydrogen, alkyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alicyclic, alicyclicalkyl, heterocycloalkyl, heterocycloalkyl alkyl, aryl, arylalkyl, heteroaryl, or heteroarylalkyl; or $R_y$ and $R_z$, together with the nitrogen atom to which they are attached, form a heterocycloalkyl or heteroaryl; each $R_w$ is independently alkyl, alicyclic, alicyclicalkyl, heterocycloalkyl, heterocycloalkyl-alkyl, aryl, arylalkyl, heteroaryl, or heteroarylalkyl; each $R_v$ is independently alkyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; and each J is independently O, $NR_x$ or S.

Unless stated otherwise, "optionally substituted aryl", including "optionally substituted phenyl", "optionally substituted heteroaryl", and "optionally substituted heterocycloalkyl" refer to aryl, including phenyl, heterocycloalkyl, and heteroaryl radicals, respectively, as defined herein, that are optionally substituted by one or more substituents (e.g., by one to six substituents, such as one to four substituents, for example, one or two substituents, such as one substituent) selected from nitro, halo, azido, cyano, alkyl, haloalkyl, alkenyl, alkynyl, alicyclic, alicyclicalkyl, heterocycloalkyl, heterocycloalkyl-alkyl, aryl, arylalkyl, heteroaryl, heteroarylalkyl, —$R_u$—$OR_x$, —$R_u$—$N(R_y)(R_z)$, —$R_u$—$SR_x$, —$R_u$—$C(J)R_x$, —$R_u$—$C(J)OR_x$, —$R_u$—$C(J)N(R_y)(R_z)$, —$R_u$—$C(J)SR_x$, —$R_u$—$S(O)_tR_x$ (where t is 1 or 2), —$R_u$—$OC(J)R_x$, —$R_u$—$OC(J)OR_x$, —$R_u$—$OC(J)N(R_y)(R_z)$, —$R_u$—$OC(J)SR_x$, —$R_u$—$N(R_x)C(J)R_x$, —$R_u$—$N(R_x)C(J)OR_x$, —$R_u$—$N(R_x)C(J)N(R_y)(R_z)$, —$R_u$—$N(R_x)C(J)SR_x$, —$R_u$—$Si(R_w)_3$, —$R_u$—$N(R_x)S(O)_2R_w$, —$R_u$—$N(R_x)S(O)_2N(R_y)(R_z)$, —$R_u$—$S(O)_2N(R_y)(R_z)$, —$R_u$—$N(R_x)C(J)R_x$, —$R_u$—$P(O)(R_v)_2$, —$R_u$—$OP(O)(R_v)_2$, —$R_u$—$C(J)N(R_x)S(O)_2R_x$, —$R_u$—$C(J)N(R_x)N(R_x)S(O)_2R_x$, —$R_u$—$C(R_x)$=$N(OR_x)$, and —$R_u$—$C(R_x)$=$NN(R_y)(R_z)$, wherein each $R_u$ is independently alkylene or a direct bond; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; and each J is O, $NR_x$ or S.

In some embodiments, "optionally substituted aryl", including "optionally substituted phenyl", "optionally substituted heteroaryl", and "optionally substituted heterocycloalkyl" refer to aryl, including phenyl, heterocycloalkyl, and heteroaryl radicals, respectively, as defined herein, that are optionally substituted by one or more substituents (e.g., by one to six substituents, such as one to four substituents, for example, one or two substituents, such as one substituent) selected from nitro, halo, cyano, alkyl, haloalkyl, alkenyl, alkynyl, alicyclic, alicyclicalkyl, heterocycloalkyl, heterocycloalkyl-alkyl, aryl, arylalkyl, heteroaryl, heteroarylalkyl, —$R_u$—$OR_x$, —$R_u$—$N(R_y)(R_z)$, —$R_u$—$SR_x$, —$R_u$—$C(J)R_x$, —$R_u$—$C(J)OR_x$, —$R_u$—$C(J)N(R_y)(R_z)$, —$R_u$—$C(J)SR_x$, —$R_u$—$S(O)_tR_x$ (where t is 1 or 2), —$R_u$—$OC(J)R_x$, —$R_u$—$OC(J)OR_x$, —$R_u$—$OC(J)N(R_y)(R_z)$, —$R_u$—$OC(J)SR_x$, —$R_u$—$N(R_x)C(J)R_x$, —$R_u$—$N(R_x)C(J)OR_x$, —$R_u$—$N(R_x)C(J)N(R_y)(R_z)$, —$R_u$—$N(R_x)C(J)SR_x$, —$R_u$—$N(R_x)S(O)_2R_w$, —$R_u$—$N(R_x)S(O)_2N(R_y)(R_z)$, —$R_u$—$S(O)_2N(R_y)(R_z)$, —$R_u$—$N(R_x)C(J)R_x$, —$R_u$—$C(J)N(R_x)S(O)_2R_x$, and —$R_u$—$C(J)N(R_x)N(R_x)S(O)_2R_x$, wherein each $R_u$ is independently alkylene or a direct bond; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, —$OR_x$ or —$N(R_y)(R_z)$; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; and each J is O, $NR_x$ or S.

In some embodiments, "optionally substituted aryl", including "optionally substituted phenyl", "optionally substituted heteroaryl", and "optionally substituted heterocycloalkyl" refer to aryl, including phenyl, heterocycloalkyl, and heteroaryl radicals, respectively, as defined herein, that are optionally substituted by one or more substituents (e.g., by one to six substituents, such as one to four substituents, for example, one or two substituents, such as one substituent) selected from the nitro, halo, cyano, alkyl, haloalkyl, alkenyl, alkynyl, alicyclic, alicyclicalkyl, heterocycloalkyl, heterocycloalkyl-alkyl, aryl, arylalkyl, heteroaryl, heteroarylalkyl, $-R_u-OR_x$, $-R_u-N(R_y)(R_z)$, $-R_u-C(J)R_x$, $-R_u-C(J)OR_x$, $-R_u-C(J)N(R_y)(R_z)$, $-R_u-OC(J)R_x$, $-R_u-OC(J)OR_x$, $-R_u-OC(J)N(R_y)(R_z)$, $-R_u-N(R_x)C(J)R_x$, $-R_u-N(R_x)C(J)OR_x$, $-R_u-N(R_x)C(J)N(R_y)(R_z)$, and $-R_u-N(R_x)C(J)R_x$, wherein each $R_u$ is independently alkylene or a direct bond; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, $-OR_x$ or $-N(R_y)(R_z)$; each $R_w$ is independently alkyl, alkenyl, alkynyl, alicyclic, alicyclicalkyl, heterocycloalkyl, heterocycloalkyl-alkyl, aryl, arylalkyl, heteroaryl, or heteroarylalkyl; each $R_x$ is independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alkenyl, alkynyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; and each J is O, $NR_x$ or S.

In some embodiments, "optionally substituted aryl", including "optionally substituted phenyl", "optionally substituted heteroaryl", and "optionally substituted heterocycloalkyl" refer to aryl, including phenyl, heterocycloalkyl, and heteroaryl radicals, respectively, as defined herein, that are optionally substituted by one or more substituents (e.g., by one to six substituents, such as one to four substituents, for example, one or two substituents, such as one substituent) selected from nitro, halo, cyano, alkyl, haloalkyl, alicyclic, alicyclicalkyl, heterocycloalkyl, heterocycloalkyl-alkyl, aryl, arylalkyl, heteroaryl, heteroarylalkyl, $-R_u-OR_x$, $-R_u-N(R_y)(R_z)$, $-R_u-C(J)R_x$, $-R_u-C(J)OR_x$, $-R_u-C(J)N(R_y)(R_z)$, $-R_u-OC(J)R_x$, $-R_u-OC(J)OR_x$, $-R_u-OC(J)N(R_y)(R_z)$, $-R_u-N(R_x)C(J)R_x$, $-R_u-N(R_x)C(J)OR_x$, $-R_u-N(R_x)C(J)N(R_y)(R_z)$, and $-R_u-N(R_x)C(J)R_x$, wherein each $R_u$ is independently alkylene or a direct bond; each $R_v$ is independently alkyl, alkenyl, alkynyl, alicyclic, alicyclicalkyl, heterocycloalkyl, heterocycloalkyl-alkyl, aryl, arylalkyl, heteroaryl, heteroarylalkyl, hydroxy, $-OR_x$ or $-N(R_y)(R_z)$; each $R_w$ is independently alkyl, alicyclic, alicyclicalkyl, heterocycloalkyl, heterocycloalkyl-alkyl, aryl, arylalkyl, heteroaryl, or heteroarylalkyl; each $R_x$ is independently hydrogen, alkyl, alicyclic, alicyclicalkyl, heterocycloalkyl, heterocycloalkyl-alkyl, aryl, arylalkyl, heteroaryl, or heteroarylalkyl; $R_y$ and $R_z$ are each independently hydrogen, alkyl, alicyclic, alicyclicalkyl, heterocycloalkyl, heterocycloalkyl-alkyl, aryl, arylalkyl, heteroaryl, or heteroarylalkyl; or $R_y$ and $R_z$, together with the nitrogen atom to which they are attached, form a heterocycloalkyl or heteroaryl; and each J is O, $NR_x$ or S.

Unless stated otherwise specifically in the specification, it is understood that the substitution can occur on any atom of the aryl, arylalkyl, heteroarylalkyl, heterocycloalkyl and heteroaryl groups. It will be understood by those skilled in the art, with respect to any group containing one or more substituents, that such groups are not intended to introduce any substitution or substitution patterns that are sterically impractical, synthetically non-feasible and/or inherently unstable.

Optionally substituted heterocycloalkyl may additionally be substituted with oxo, thiono, imino, oxime or hydrazone, on a saturated carbon of their respective ring system.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$aryl is an aryl group which has from 6 to 10 carbon atoms; $C_{1-4}$haloalkyl is a haloalkyl group which has from 1 to 4 carbon atoms; and N,N-di-$C_{1-6}$alkylamino is a N,N-dialkylamino group in which the nitrogen is substituted with two alkyl groups each of which is independently from 1 to 6 carbon atoms.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The disclosed compounds, or pharmaceutically acceptable salts thereof, can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The disclosed compounds may exist in tautomeric forms and mixtures and separate individual tautomers are contemplated. In addition, some compounds may exhibit polymorphism.

By way of clarity, compounds of the invention included all isotopes of the atoms present in formula (I) and any of the examples or embodiments disclosed herein. For example, H (or hydrogen) represents any isotopic form of hydrogen including $^{1}H$, $^{2}H$ (D), and $^{3}H$ (T); C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formula (I) comprises isotopes of the atoms therein in their naturally occurring abundance. However, in certain instances, it is desirable to enrich one or more atom in a particular isotope which would normally be present in less abundance. For example, $^{1}H$ would normally be present in greater than 99.98% abundance; however, a compound of the invention can be enriched in $^{2}H$ or $^{3}H$ at one or more positions where H is present. In particular embodiments of the compounds of formula (I), when, for example, hydrogen is enriched in the deuterium isotope, the symbol "D" may be used to represent the enrichment in deuterium. In one embodiment, when a compound of the invention is enriched in a radioactive isotope, for example $^{3}H$ and $^{14}C$, they may be useful in drug and/or substrate tissue distribution assays.

Provided is a compound of Formula I, or a pharmaceutically acceptable salt thereof,

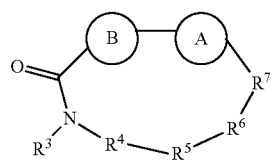

Formula I wherein
Ring A is phenylene or 5- to 6-membered heteroarylene containing 1-3 heteroatoms chosen from O, S, and N, wherein ring A is optionally substituted with lower alkyl that is further optionally substituted, Ring B is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl that is further optionally substituted, $R^3$ is chosen from hydrogen, lower alkyl optionally substituted with alkoxy, amino, N-(alkyl)amino, N,N-(dialkyl)amino, or phenyl, heterocycloalkyl, and heteroaryl,
  wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from $C(O)NR^{51}$, $NR^{52}$, and O or $R^5$ is absent, provided that if $R^4$ is absent, then $R^5$ is absent, $R^6$ is an alkylene or alkenylene chain having one or two double bonds,
  wherein the alkylene or alkenylene chain has 2 to 10 carbon atoms,
  wherein the alkylene or alkenylene chain is optionally substituted with one or two groups independently chosen from lower alkyl and cycloalkyl, each of which groups is optionally substituted with hydroxyl or alkoxy, and
  further wherein one or two of the carbon atoms in the alkylene chain is optionally replaced by an O, S, SO, $SO_2$, or $NR^{61}$, and
  wherein two of the carbon atoms in the alkylene chain, are optionally connected by a two or three carbon atom alkylene chain to form a 5- to 7-membered ring.

$R^7$ is chosen from $NR^{71}$ and O or $R^7$ is absent,
$R^{51}$ is chosen from hydrogen and lower alkyl,
$R^{52}$ is chosen from hydrogen, lower alkyl, and $—C(O)OR^{81}$,
$R^{61}$ is chosen from hydrogen, lower alkyl, and $—C(O)OR^{81}$,
$R^{71}$ is chosen from hydrogen, lower alkyl, and $—C(O)OR^{81}$, and
$R^{81}$ is lower alkyl.

Alternatively provided is a compound of Formula I*, or a pharmaceutically acceptable salt thereof,

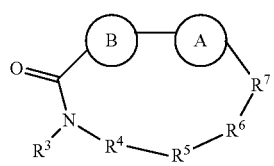

Formula I* wherein
Ring A is phenylene or 5- to 6-membered heteroarylene containing 1-3 heteroatoms chosen from O, S, and N, wherein ring A is optionally substituted with lower alkyl that is further optionally substituted,
Ring B is phenylene, 5- to 6-membered heterocycloalkylene containing 1-3 heteroatoms chosen from O, S, and N, or 5- to 6-membered heteroarylene containing 1-3 heteroatoms chosen from O, S, and N, wherein ring B is optionally substituted with lower alkyl or lower alkyloxy-alkyl, either of which is is further optionally substituted, $R^3$ is chosen from hydrogen, lower alkyl optionally substituted with alkoxy, amino, N-(alkyl)amino, N,N-(dialkyl)amino, or phenyl, heterocycloalkyl, and heteroaryl,
  wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from C(O)NR$^{51}$, NR$^{52}$, and O or $R^5$ is absent, provided that if $R^4$ is absent, then $R^5$ is absent, $R^6$ is an alkylene or alkenylene chain having one or two double bonds,
  wherein the alkylene or alkenylene chain has 2 to 10 carbon atoms,
  wherein the alkylene or alkenylene chain is optionally substituted with one or two groups independently chosen from lower alkyl, cycloalkyl and phenyl, each of which groups is optionally substituted with hydroxyl, alkoxy, —C(O)OR$^{85}$, C(O)NR$^{82}$R$^{83}$, benzoyl, and benzyl,
  further wherein one or two of the carbon atoms in the alkylene or alkenylene chain is optionally replaced by an O, S, SO, SO$_2$, C(O)NR$^{51}$, or NR$^{61}$, and
  wherein one of the carbon atoms in the alkylene or alkenylene chain, is optionally connected by the nitrogen atom of C(O)NR$^{51}$ or NR$^{61}$ to form a 5- to 7-membered ring, which may further be substituted with oxo,
  wherein two of the carbon atoms in the alkylene or alkenylene chain, are optionally connected by a two or three carbon atom alkylene or alkenylene chain to form a 5- to 7-membered ring, $R^7$ is chosen from NR$^{71}$ and O or $R^7$ is absent,
$R^{51}$ is chosen from hydrogen and lower alkyl,
$R^{52}$ is chosen from hydrogen and lower alkyl, and —C(O)OR$^{81}$,
$R^{61}$ is chosen from hydrogen, lower alkyl, —(CH$_2$)$_n$C(O)OR$^{81}$, —(CH$_2$)$_n$C(O)NR$^{82}$R$^{83}$, —C(O)R$^{84}$, —C(O)(CH$_2$)$_p$NR$^{82}$C(O)OR$^{81}$, —C(O)(CH$_2$)$_p$NR$^{82}$R$^{83}$,
$R^{71}$ is chosen from hydrogen, lower alkyl, and —C(O)OR$^{81}$,
$R^{81}$ is hydrogen or lower alkyl,
$R^{82}$ is hydrogen or lower alkyl,
$R^{83}$ is hydrogen or lower alkyl,
$R^{84}$ is hydrogen, lower alkyl, C$_3$-C$_6$cycloalkyl or tetrahydropyran, wherein the lower alkyl is optionally substituted with hydroxy or —C(O)OR$^{81}$,
$R^{85}$ is hydrogen, lower alkyl, or benzyl,
n is 0, 1, 2, or 3 and
p is 1 or 2.

In some embodiments, ring B is chosen from

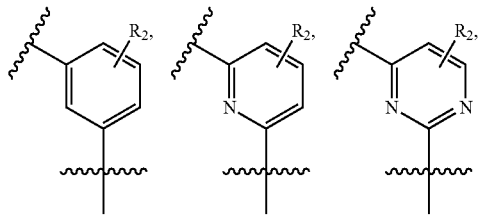

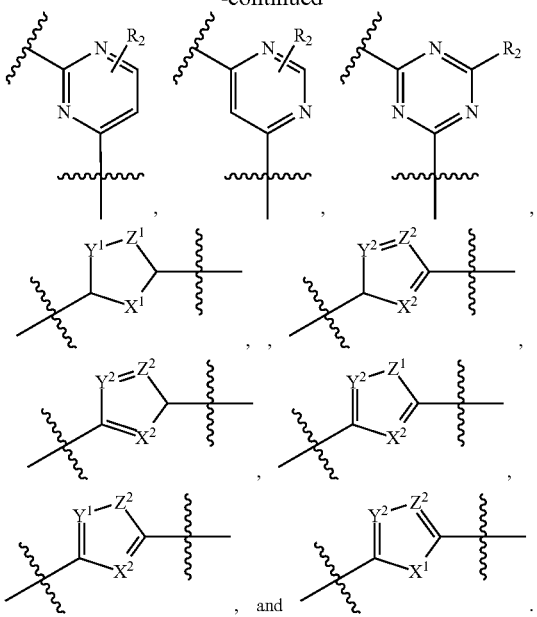

wherein
$X^1$, $Y^1$, and $Z^1$ are independently chosen from NR$^{21}$, O, C(R$^{21}$)$_2$, and S,
$X^2$, $Y^2$, and $Z^2$ are independently chosen from N and CR$^{21}$,
$R^2$ is chosen from hydrogen and lower alkyl, and
wherein for each occurrence, $R^{21}$ is independently chosen from hydrogen and lower alkyl optionally substituted with lower alkoxy, wherein lower alkoxy is optionally substituted with tri(alkyl)silyl.

In some embodiments, ring B is

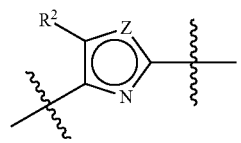

wherein
Z is chosen from O, S, and NR$^{21}$,
$R^2$ is chosen from hydrogen and lower alkyl, and
if present, $R^{21}$ is chosen from hydrogen and lower alkyl optionally substituted with lower alkoxy, wherein lower alkoxy is optionally substituted with tri(alkyl)silyl,
to thus provided, a compound of Formula II, or a pharmaceutically acceptable salt thereof,

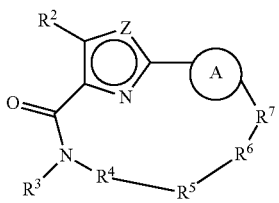

Formula II wherein
Ring A is phenylene or 5- to 6-membered heteroarylene containing 1-3 heteroatoms chosen from O, S, and N, wherein ring A is optionally substituted with lower alkyl that is further optionally substituted with hydroxyl, alkoxy, amino, N-(alkyl)amino, N,N-(dialkyl)amino, or halogen, Z is chosen from O, S, and $NR^{21}$, $R^2$ is chosen from hydrogen and lower alkyl, $R^3$ is chosen from hydrogen, lower alkyl optionally substituted with alkoxy, amino, N-(alkyl)amino, N,N-(dialkyl)amino, or phenyl, heterocycloalkyl, and heteroaryl,
wherein phenyl, heterocycloalkyl, and heteroaryl are optionally substituted with one or two groups independently chosen from lower alkyl and wherein alkoxy is optionally substituted with tri(alkyl)silyl, $R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, $R^5$ is chosen from $C(O)NR^{51}$, $NR^{52}$, and O or $R^5$ is absent, provided that if $R^4$ is absent, then $R^5$ is absent, $R^6$ is an alkylene or alkenylene chain having one or two double bonds,
wherein the alkylene or alkenylene chain has 2 to 10 carbon atoms,
wherein the alkylene or alkenylene chain is optionally substituted with one or two groups independently chosen from lower alkyl and cycloalkyl, each of which groups is optionally substituted with hydroxyl or alkoxy, and
further wherein one or two of the carbon atoms in the alkylene chain is optionally replaced by an O, S, SO, $SO_2$, or $NR^{61}$, and
wherein two of the carbon atoms in the alkylene chain, are optionally connected by a two or three carbon atom alkylene chain to form a 5- to 7-membered ring.

$R^7$ is chosen from $NR^{71}$ and O or $R^7$ is absent, if present, $R^{21}$ is chosen from hydrogen and lower alkyl optionally substituted with lower alkoxy, wherein lower alkoxy is optionally substituted with tri(alkyl)silyl, $R^{51}$ is chosen from hydrogen and lower alkyl, $R^{52}$ is chosen from hydrogen, lower alkyl, and —$C(O)OR^{81}$, $R^{61}$ is chosen from hydrogen, lower alkyl, and —$C(O)OR^{81}$, $R^{71}$ is chosen from hydrogen, lower alkyl, and —$C(O)OR^{81}$, and $R^{81}$ is lower alkyl.

In some embodiments, ring A is chosen from phenylene, pyridinediyl, pyridazinediyl, pyrimidinediyl, pyrazinediyl, triazinediyl, imidazolediyl, oxazolediyl, thiazolediyl, pyrazolediyl, isoxazolediyl, and isothiazolediyl, wherein ring A is optionally substituted with lower alkyl that is further optionally substituted with hydroxyl, alkoxy, amino, N-(alkyl)amino, N,N-(dialkyl)amino, or halogen.

In some embodiments, ring A is wherein $R^1$ is hydrogen or lower alkyl, X is O, S, or $NR^{11}$ wherein $R^{11}$ is hydrogen or lower alkyl, and Y is C, CH, or N.

In some embodiments, Z is O.

In some embodiments, Z is S.

In some embodiments, Z is $NR^{21}$. In some embodiments, $R^{21}$ is chosen from hydrogen and lower alkyl.

In some embodiments, $R^2$ is hydrogen.

In some embodiments, $R^3$ is chosen from hydrogen, lower alkyl optionally substituted with amino, N-(alkyl)amino) or N,N-(dialkyl)amino, benzyl, piperidin-1-yl, and 1H-pyrazol-4-yl, wherein each of benzyl, piperidin-1-yl, and 1H-pyrazol-4-yl is optionally substituted with one or two groups independently chosen from lower alkyl.

In some embodiments, $R^3$ is hydrogen.

In some embodiments, $R^4$ is heteroarylene optionally substituted with one or more $R^{41}$ wherein for each occurrence, $R^{41}$ is independently chosen from heterocycloalkyl, lower alkyl optionally substituted with —$C(O)OR^9$, amino, N-(alkyl)amino, N,N-(dialkyl)amino, cycloalkyl, or heterocycloalkyl,

—$C(O)OR^9$, hydroxyl, and

—$C(O)NR^{10}R^{11}$, wherein $R^9$ is chosen from hydrogen and lower alkyl, wherein $R^{10}$ and $R^{11}$ are independently hydrogen and lower alkyl, or $R^{10}$ and $R^{11}$, together with the nitrogen to which they are bound form a heterocycloalkyl, and wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In some embodiments, R$^4$ is heteroarylene optionally substituted with one or more R$^{41}$ wherein for each occurrence, R$^{41}$ is independently chosen from heterocycloalkyl, lower alkyl optionally substituted with —C(O)OR$^9$, —C(O)NR$^{10}$R$^{11}$, hydroxy, amino, N-(alkyl)amino, N,N-(dialkyl)amino, cycloalkyl, or heterocycloalkyl,

—C(O)OR$^9$, hydroxyl, and

—C(O)NR$^{10}$R$^{11}$, wherein R$^9$ is chosen from hydrogen and lower alkyl, wherein R$^{10}$ and R$^{11}$ are independently hydrogen and lower alkyl, or R$^{10}$ and R$^{11}$, together with the nitrogen to which they are bound form a heterocycloalkyl, and wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In some embodiments, R$^{41}$ is heterocycloalkyl chosen from tetrahydropyranyl, piperidinyl, hexahydropyrimidinyl, and morpholinyl, each of which is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In some embodiments, R$^4$ is

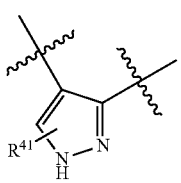

Formula V

In some embodiments, R$^{41}$ is attached at the nitrogen in the pyrazole ring.

Tautomers are possible when R$^{41}$ is not attached at the nitrogen. It is well understood and appreciated in the art that pyrazoles can exist in various tautomeric forms. Two possible tautomeric forms are illustrated below:

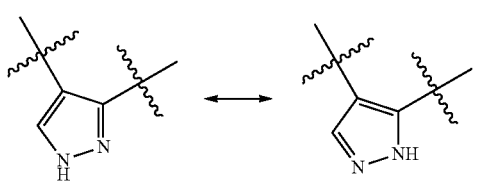 [SMILES: *c1c[nH]nc1* ; *c1cn[nH]c1*]

It is further understood that tautomeric forms can also have corresponding nomenclature for each represented tautomer. Therefore, the present invention includes all tautomers and the various nomenclature designations.

In some embodiments, R$^4$ is

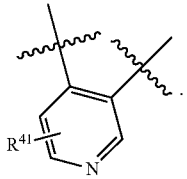

Formula VII

In some embodiments, R$^{41}$ is chosen from lower alkyl optionally substituted with heterocycloalkyl, amino, N-(alkyl)amino, N,N-(dialkyl)amino, hydroxyl, or —C(O)OH, tetrahydropyran-2-yl, and tetrahydropyran-4-yl.

In some embodiments, R$^4$ is arylene optionally substituted with one or more R$^{42}$ wherein for each occurrence, R$^{42}$ is independently chosen from heterocycloalkyl, lower alkyl optionally substituted with —C(O)OR$^9$, amino, N-(alkyl)amino, N,N-(dialkyl)amino, cycloalkyl, or heterocycloalkyl,

—C(O)OR$^9$, hydroxyl, and

—C(O)NR$^{10}$R$^{11}$, wherein R$^9$ is chosen from hydrogen and lower alkyl, wherein R$^{10}$ and R$^{11}$ are independently hydrogen and lower alkyl, or R$^9$ and R$^{10}$, together with the nitrogen to which they are bound form a heterocycloalkyl, and wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In certain embodiments, R$^{42}$ may further include halo.

In some embodiments, R$^4$ is

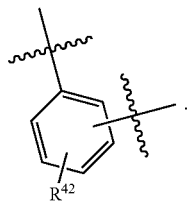

Formula IX

In some embodiments, R$^4$ is

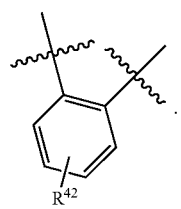

Formula X

In some embodiments, R$^4$ is

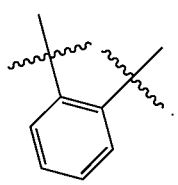

Formula XI

In some embodiments, R$^3$ and R$^4$ taken together with the nitrogen to which they are bound, form a 3- to 7-membered heterocycloalkyl ring optionally substituted with one or more $R^{44}$ wherein for each occurrence, $R^{44}$ is independently chosen from
heterocycloalkyl,
lower alkyl optionally substituted with —C(O)OR$^9$, amino, N-(alkyl)amino, N,N-(dialkyl)amino, cycloalkyl, or heterocycloalkyl,
—C(O)OR$^9$,
hydroxyl, and
—C(O)NR$^{10}$R$^{11}$,
wherein $R^9$ is chosen from hydrogen and lower alkyl,
wherein $R^{10}$ and $R^{11}$ are independently hydrogen and lower alkyl, or $R^9$ and $R^{10}$, together with the nitrogen to which they are bound form a heterocycloalkyl, and
wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

In some embodiments, $R^3$ and $R^4$ taken together with the nitrogen to which they are bound, form a 3- to 7-membered heterocycloalkyl ring of the formula

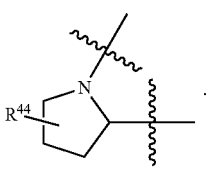

Formula XII

In some embodiments, $R^4$ is absent.
In some embodiments, $R^5$ is NR$^{52}$. In some embodiments, $R^{52}$ is hydrogen.
In some embodiments, $R^5$ is —C(O)NR$^{51}$—. In some embodiments, $R^{51}$ is hydrogen.
In some embodiments, $R^5$ is O.
In some embodiments, $R^5$ is absent.
In some embodiments, $R^5$ is C(O)NR$^{51}$.
In some embodiments, $R^6$ is an alkylene or alkenylene chain having one or two double bonds, wherein the alkylene or alkenylene chain has 4 to 8 carbon atoms and wherein the alkylene or alkenylene chain is optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, S, SO, SO$_2$, or NR$^{61}$, and further wherein two of the carbon atoms in the alkylene chain, are optionally connected by a two or three carbon atom alkylene chain to form a 5- to 7-membered ring.

In some embodiments, $R^6$ is an alkylene or alkenylene chain having one or two double bonds, wherein the alkylene or alkenylene chain has 4 to 8 carbon atoms and wherein the alkylene or alkenylene chain is optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, and further wherein two of the carbon atoms in the alkylene chain, are optionally connected by a two or three carbon atom alkylene chain to form a 5- to 7-membered ring.

In some embodiments, $R^6$ is an alkylene or alkenylene chain having one or two double bonds, wherein the alkylene or alkenylene chain has 4 to 8 carbon atoms and wherein the alkylene or alkenylene chain is optionally substituted with one or two groups independently chosen from from lower alkyl, cycloalkyl and phenyl, each of which groups is optionally substituted with hydroxyl, alkoxy, —C(O)OR$^{85}$, C(O)NR$^{82}$R$^{83}$, benzoyl, and benzyl, and further wherein one or two of the carbon atoms in the alkylene or alkenylene chain is optionally replaced by an O, C(O)NR$^{51}$, or NR$^{61}$, further wherein two of the carbon atoms in the alkylene chain or alkenylene chain, are optionally connected by a two or three carbon atom alkylene chain to form a 5- to 7-membered ring, and wherein one of the carbon atoms in the alkylene or alkenylene chain, is optionally connected by the nitrogen atom of C(O)NR$^{51}$ or NR$^{61}$ to form a 5- to 7-membered ring, which may further be substituted with oxo.

In some embodiments, $R^6$ is alkylene chain optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, S, SO, SO$_2$, or NR$^{61}$, and further wherein two of the carbon atoms in the alkylene chain, are optionally connected by a two or three carbon atom alkylene chain to form a 5- to 7-membered ring.

In some embodiments, $R^6$ is alkylene chain optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, and further wherein two of the carbon atoms in the alkylene chain, are optionally connected by a two or three carbon atom alkylene chain to form a 5- to 7-membered ring.

In some embodiments, is alkenylene chain having one or two double bonds optionally substituted with one or two groups independently chosen from lower alkyl optionally substituted with hydroxyl or alkoxy.

In some embodiments, is alkenylene chain having one or two double bonds optionally substituted with one or two groups independently chosen from lower alkyl or phenyl, each of which can be optionally substituted with hydroxyl or alkoxy.

In some embodiments, $R^7$ is NR$^{71}$. In some embodiments, $R^{71}$ is hydrogen.
In some embodiments, $R^7$ is O.
In some embodiments, $R^7$ is absent.

Also provided is a compound of Formula III, or a pharmaceutically acceptable salt thereof,

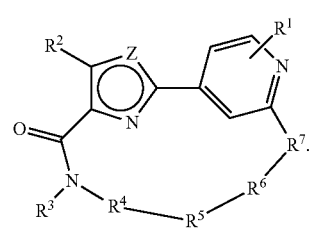

Formula III wherein Z, $R^2$, $R^3$, $R^4$, $R^5$, $R^6$, and $R^7$ are as described for compounds of Formula II and wherein $R^1$ is hydrogen or lower alkyl. In some embodiments, $R^1$ is hydrogen.

Also provided is a compound of Formula IV, or a pharmaceutically acceptable salt thereof, Formula IV

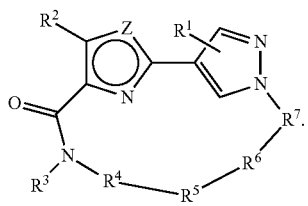

wherein Z, R², R³, R⁴, R⁵, R⁶, and R⁷ are as described for compounds of Formula II and wherein R¹ is hydrogen or lower alkyl. In some embodiments, R¹ is hydrogen.

Also provided is a compound of Formula VI, or a pharmaceutically acceptable salt thereof, Formula VI

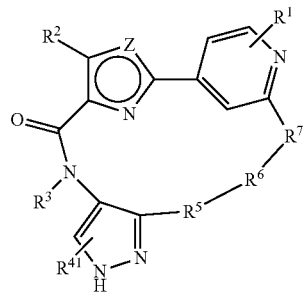

wherein
Z, R², R³, R⁵, R⁶, and R⁷ are as described for compounds of Formula II,
R¹ is hydrogen or lower alkyl, and
R⁴¹ is independently chosen from
heterocycloalkyl,
lower alkyl optionally substituted with —C(O)OR⁹, amino, N-(alkyl)amino, N,N-(dialkyl)amino, cycloalkyl, or heterocycloalkyl,
—C(O)OR⁹,
hydroxyl, and
—C(O)NR¹⁰R¹¹,
wherein R⁹ is chosen from hydrogen and lower alkyl,
wherein R¹⁰ and R¹¹ are independently hydrogen and lower alkyl, or R¹⁰ and R¹¹, together with the nitrogen to which they are bound form a heterocycloalkyl, and
wherein each lower alkyl, cycloalkyl and heterocycloalkyl is optionally substituted with one, two, or three groups independently chosen from —C(O)OR⁹, lower alkyl, lower alkoxy, hydroxyl, halogen, amino, N-(alkyl)amino, N,N-(dialkyl)amino, and heterocycloalkyl.

In some embodiments of compound of Formula VI, or a pharmaceutically acceptable salt thereof, R¹ is hydrogen.

In some embodiments of compound of Formula VI, or a pharmaceutically acceptable salt thereof, R⁴¹ is heterocycloalkyl chosen from tetrahydropyranyl, piperidinyl, hexahydropyrimidinyl, and morpholinyl, each of which is optionally substituted with one, two, or three groups independently chosen from —C(O)OR⁹, lower alkyl, lower alkoxy, hydroxyl, halogen, amino, N-(alkyl)amino, N,N-(dialkyl)amino, and heterocycloalkyl.

In some embodiments of compound of Formula VI, or a pharmaceutically acceptable salt thereof, R⁴¹ is chosen from
lower alkyl optionally substituted with heterocycloalkyl, amino, N-(alkyl)amino, N,N-(dialkyl)amino, hydroxyl, or —C(O)OH,
tetrahydropyran-2-yl, and
tetrahydropyran-4-yl.

Also provided is a compound of Formula VIII, or a pharmaceutically acceptable salt thereof, Formula VIII

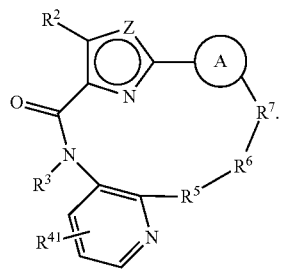

Z, R², R³, R⁵, R⁶, and R⁷ are as described for compounds of Formula II,
R¹ is hydrogen or lower alkyl, and
R⁴¹ is independently chosen from
heterocycloalkyl,
lower alkyl optionally substituted with —C(O)OR⁹, amino, N-(alkyl)amino, N,N-(dialkyl)amino, cycloalkyl, or heterocycloalkyl,
—C(O)OR⁹,
hydroxyl, and
—C(O)NR¹⁰R¹¹,
wherein R⁹ is chosen from hydrogen and lower alkyl,
wherein R¹⁰ and R¹¹ are independently hydrogen and lower alkyl, or R⁹ and R¹⁰, together with the nitrogen to which they are bound form a heterocycloalkyl, and
wherein each lower alkyl, cycloalkyl and heterocycloalkyl is optionally substituted with one, two, or three groups independently chosen from —C(O)OR⁹, lower alkyl, lower alkoxy, hydroxyl, halogen, amino, N-(alkyl)amino, N,N-(dialkyl)amino, and heterocycloalkyl.

In some embodiments of compound of Formula VIII, or a pharmaceutically acceptable salt thereof, R¹ is hydrogen.

In some embodiments of compound of Formula VIII, or a pharmaceutically acceptable salt thereof, R⁴¹ is heterocycloalkyl chosen from tetrahydropyranyl, piperidinyl, hexahydropyrimidinyl, and morpholinyl, each of which is optionally substituted with one, two, or three groups independently chosen from —C(O)OR⁹, lower alkyl, lower alkoxy, hydroxyl, halogen, amino, N-(alkyl)amino, N,N-(dialkyl)amino, and heterocycloalkyl.

In some embodiments of compound of Formula VIII, or a pharmaceutically acceptable salt thereof, R⁴¹ is chosen from
lower alkyl optionally substituted with heterocycloalkyl, amino, N-(alkyl)amino, N,N-(dialkyl)amino, hydroxyl, or —C(O)OH,
tetrahydropyran-2-yl, and
tetrahydropyran-4-yl.

Also provided is a compound or a pharmaceutically acceptable salt thereof, wherein the compound is chosen from compounds 1-161.

In another embodiment, the invention is any one the compounds disclosed in the Exemplification section as a neutral compound or a pharmaceutically acceptable salt thereof.

The compounds, or pharmaceutically acceptable salts thereof described herein may be used to decrease the expression or activity of IRAK-4, or to otherwise affect the properties and/or behavior of IRAK-4 polypeptides or polynucleotides, e.g., stability, phosphorylation, kinase activity, interactions with other proteins, etc.

The compounds, or pharmaceutically acceptable salts thereof described herein may be used to treat an inflammatory disease in a patient, including, but not limited to pulmonary diseases and diseases of the airway, transplant rejection, autoimmune diseases, cancer, cardiovascular diseases, diseases of the central nervous system, CD14 mediated sepsis, non-CD14 mediated sepsis, osteoarthritis, osteoporosis, psoriasis, diseases of the skin, inflammatory bowel disease, Behcet's syndrome, ankylosing spondylitis, sarcoidosis, gout, ophthalmic diseases and conditions, systemic sclerosis, and Sjogren's syndrome.

In some embodiments, the pulmonary disease and disease of the airway is selected from Adult Respiratory Disease Syndrome (ARDS), Chronic Obstructive Pulmonary Disease (OPD), pulmonary fibrosis, interstitial lung disease, asthma, chronic cough, and allergic rhinitis.

In some embodiments, the autoimmune disease is selected from rheumatoid arthritis, systemic lupus erythematosus, multiple sclerosis, and diabetes.

In some embodiments, the autoimmune disease is type 1 diabetes.

In some embodiments, cancer is selected from Waldenström's macroglobulinemia, solid tumors, skin cancer, and lymphoma.

In some embodiments, cardiovascular disease is selected from stroke and atherosclerosis.

In some embodiments, the disease of the central nervous system is a neurodegenerative disease.

In some embodiments, the disease of the skin is selected from rash, contact dermatitis, and atopic dermatitis.

In some embodiments, the inflammatory bowel disease is selected from Crohn's disease and ulcerative colitis.

The dose of a compound provided herein, or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering a compound described herein, or a pharmaceutically acceptable salt thereof, to a mammal comprises any delivery method whereby the a compound described herein, or a pharmaceutically acceptable salt thereof, comes in contact with any part of the mammal's body. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the compound, or a pharmaceutically acceptable salt thereof, can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering the compound, or a pharmaceutically acceptable salt thereof, to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound provided herein, or a pharmaceutically acceptable salt thereof. Monitoring a property can include monitoring the property after the sample or subject has been administered a compound, or a pharmaceutically acceptable salt thereof. Monitoring a property can include monitoring a property after the sample or subject has been administered a known concentration of a compound, or a pharmaceutically acceptable salt thereof.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

A compound of formula (I), or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes. Thus, compound provided herein, or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound, or a pharmaceutically acceptable salt thereof, may be combined with one or more excipients and used in the form of ingestible tablets, buccal tablets, troches, capsules, elixirs, suspensions, syrups, or wafers, and the like. Such compositions and preparations should contain at least about 0.1% of active compound, or a pharmaceutically acceptable salt thereof. The percentage of the compositions and preparations may, of course, be varied and may conveniently be between about 2 to about 60% of the weight of a given unit dosage form. The amount of active compound, or a pharmaceutically acceptable salt thereof, in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, or a pharmaceutically acceptable salt thereof, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound, or a pharmaceutically acceptable salt thereof, may be incorporated into sustained-release preparations and devices.

The active compound, or a pharmaceutically acceptable salt thereof, may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, isotonic agents, for example, sugars, buffers or sodium chloride, will be included. Prolonged absorption of the injectable compositions can be brought about by the use in the compositions of agents delaying absorption, for example, aluminum monostearate or gelatin.

Sterile injectable solutions can be prepared by incorporating the active compound, or a pharmaceutically acceptable salt thereof, in the required amount in the appropriate solvent with various of the other ingredients enumerated above, as required, followed by filter sterilization. In the case of sterile powders for the preparation of sterile injectable solutions, the methods of preparation can be vacuum drying and the freeze drying techniques, which can yield a powder of the active ingredient plus any additional desired ingredient present in the previously sterile-filtered solutions.

For topical administration, a compound provided herein, or a pharmaceutically acceptable salt thereof, may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds and salts can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds provided herein, or a pharmaceutically acceptable salt thereof, to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds provided herein, or a pharmaceutically acceptable salt thereof, can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) provided herein, or a pharmaceutically acceptable salt thereof, in a liquid composition, such as a lotion, can be from about 0.1 to about 25 weight percent, such as from about 0.5-10 weight percent. The concentration in a semi-solid or solid composition such as a gel or a powder can be about 0.1-5 wt-%, such as about 0.5-2.5 weight percent based on the total weight of the composition.

The amount of the compound, or a pharmaceutically acceptable salt thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound, or a pharmaceutically acceptable salt thereof, can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound, or a pharmaceutically acceptable salt thereof. The desired peak plasma concentration can be from about 0.5 μM to about 75 μM, such as, about 1 μM to 50 μM, or about 2 μM to about 30 μM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound provided herein, or a pharmaceutically acceptable salt thereof, and instructional material which can describe administering the compound, or a pharmaceutically acceptable salt thereof, or a composition comprising the compound, or a pharmaceutically acceptable salt thereof, to a cell or a subject. This should be construed to include other embodiments of kits that are known to those skilled in the art, such as a kit comprising a (such as sterile) solvent for dissolving or suspending the compound, or a pharmaceutically acceptable salt thereof, or composition prior to administering the compound or composition to a cell or a subject. In some embodiments, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

The compounds provided herein, or a pharmaceutically acceptable salt thereof, can be prepared from readily available starting materials using the following general methods and procedures. It will be appreciated that where typical or preferred process conditions (i.e., reaction temperatures, times, mol ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds provided herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Example 1

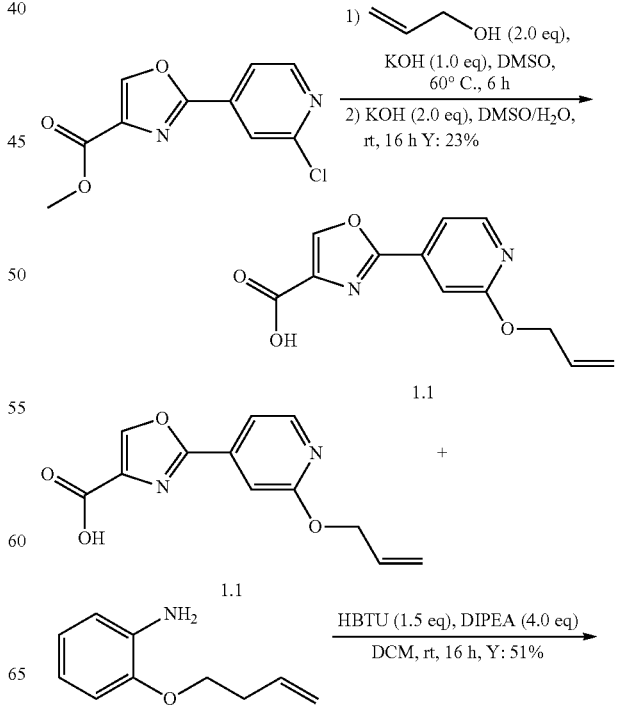

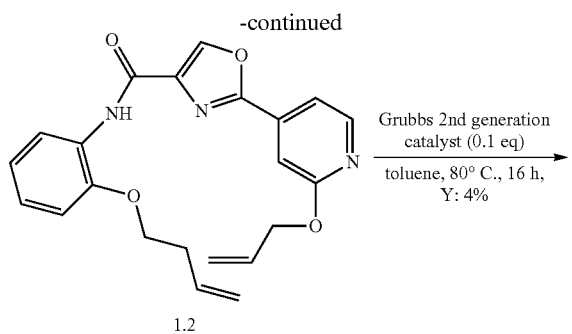

1.2

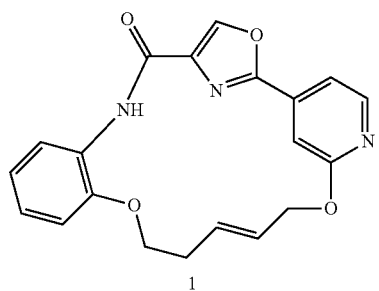

1

Synthesis of 1.1

To a solution of methyl 2-(2-chloropyridin-4-yl)oxazole-4-carboxylate (1.2 g, 5.0 mmol, 1.0 eq) in DMSO (5 mL), allyl alcohol (580 mg, 10.0 mmol, 2.0 eq) and KOH (280 mg, 5.0 mmol, 1.0 eq) were added. After stirring at 60° C. for 16 h, the mixture was allowed to cool to rt and then KOH (560 mg, 10.0 mmol, 2.0 eq) and $H_2O$ (3 mL) were added. After stirring at rt for another 16 h, the reaction mixture was adjusted pH=6 with $CH_3COOH$ (20% in water). The mixture was diluted with EtOAc (30 mL) and washed with water (10 mL×3). The organic layer was dried over anhydrous $Na_2SO_4$ and filtered. The filtrate was concentrated under reduced pressure to give the crude product, which was purified by pre-HPLC (MeOH/0.05% $NH_3 \cdot H_2O$ in $H_2O$=20%-95%) to furnish 1.1 (280 mg, yield: 23%) as a yellow oil. $^1$H NMR (400 MHz, $CDCl_3$) δ: 8.31 (s, 1H), 8.27 (d, J=5.2 Hz, 1H), 7.57 (d, J=4.8 Hz, 1H), 7.44 (s, 1H), 6.11-6.08 (m, 1H), 5.41 (d, J=17.2 Hz, 1H), 5.27 (d, J=10.4 Hz, 1H), 4.89 (d, J=4.4 Hz, 2H); ESI-MS (M+H)$^+$: 247.1.

Synthesis of 1.2

To a solution of 1.1 (240 mg, 1.0 mmol, 1.0 eq) in DCM (6 mL) was added 2-(but-3-en-1-yloxy)aniline (196 mg, 1.2 mmol, 1.2 eq), HBTU (568 mg, 1.5 mmol, 1.5 eq) and DIPEA (516 mg, 4.0 mmol, 4.0 eq). The mixture was stirred at room temperature for 16 h, diluted with DCM (20 mL), washed with water (5 mL×3) and brine (5 mL). The organic layer was dried over sodium sulfate and concentrated under reduced pressure. The residue was purified by pre-HPLC (MeOH/0.05% TFA in $H_2O$=20%-95%) to give 1.2 (194 mg, yield: 51%) as a yellow solid. $^1$H NMR (400 MHz, $CDCl_3$) δ: 9.54 (s, 1H), 8.52 (d, J=7.6 Hz, 1H), 8.37 (s, 1H), 8.30 (d, J=5.2 Hz, 1H), 7.51 (d, J=5.2 Hz, 1H), 7.42 (s, 1H), 7.09 (t, J=7.6 Hz, 1H), 7.02 (t, J=7.6 Hz, 1H), 6.94 (d, J=7.6 Hz, 1H), 6.15-6.05 (m, 2H), 5.43 (d, J=16.8 Hz, 1H), 5.34-5.28 (m, 2H), 5.19 (d, J=10.0 Hz, 1H), 4.91 (d, J=5.2 Hz, 2H), 4.18 (t, J=6.4 Hz, 2H), 2.71 (q, J=6.4 Hz, 2H); ESI-MS (M+H)$^+$: 392.1.

Synthesis of Compound 1

To a solution of 1.2 (330 mg, 0.84 mmol, 1.0 eq) in anhydrous toluene (160 mL) was added Grubbs 2nd Generation catalyst 246047-72-3 (73 mg, 0.08 mmol, 0.1 eq) under $N_2$ atmosphere. The mixture was stirred at 80° C. for 16 h. After cooling down, the mixture was concentrated via vacuum. The residue was purified with pre-HPLC (MeOH/0.05% TFA in $H_2O$=20%-95%) to afford 1 (11 mg, yield: 4%) as a yellow solid. $^1$H NMR (400 MHz, $CDCl_3$) δ: 10.27 (s, 1H), 8.50 (dd, J=1.6, 7.6 Hz, 1H), 8.43 (d, J=4.8 Hz, 1H), 8.31 (s, 1H), 8.02 (s, 1H), 7.38 (d, J=4.8 Hz, 1H), 7.10-7.02 (m, 2H), 6.92 (d, J=7.6 Hz, 1H), 6.42-6.38 (m, 1H), 5.92-5.88 (m, 1H), 4.90 (d, J=6.0 Hz, 2H), 4.20 (t, J=5.2 Hz, 2H), 2.84 (q, J=4.8 Hz, 2H); ESI-MS (M+H)$^+$: 364.0

Example 2

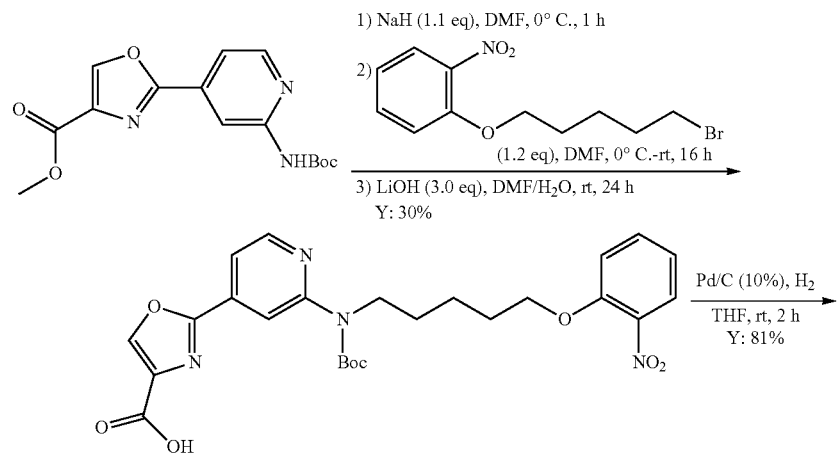

2.1

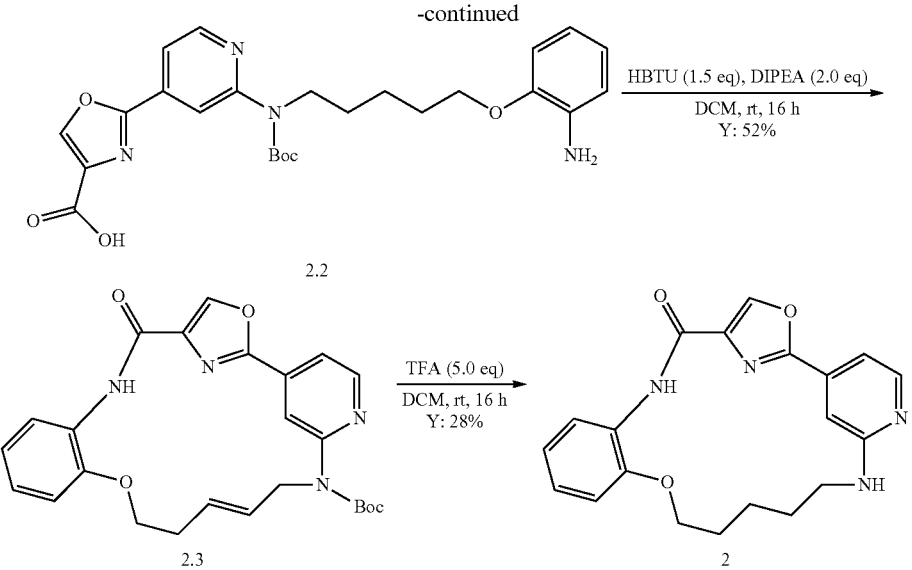

Synthesis of Compound 2.1

To a mixture of methyl 2-(2-((tert-butoxycarbonyl)amino)pyridin-4-yl)oxazole-4-carboxylate (500 mg, 1.57 mmol, 1.0 eq) in DMF (10 mL), NaH (42 mg, 1.73 mmol, 1.1 eq) was added at 0° C. After stirring at 0° C. for 1 h, 1-((5-bromopentyl)oxy)-2-nitrobenzene (540 mg, 1.88 mmol, 1.2 eq) was dropped into the reaction mixture. The mixture was allowed to warm to rt and stirred for 16 h. After that, LiOH H$_2$O (198 mg, 4.71 mmol, 3.0 eq) and H$_2$O (2 mL) were added. After stirring at rt for another 24 h, the reaction mixture was diluted with H$_2$O (20 mL), adjusted pH=6 with CH$_3$COOH (20% in water) and extracted with EtOAc (20 mL×3). The combined organic layers were washed with water (30 mL) and brine (30 mL), dried over anhydrous Na$_2$SO$_4$ and concentrated. The residue was purified by pre-HPLC (MeOH/0.05% TFA in H$_2$O=10%-95%) to furnish 2.1 (161 mg, yield: 20%) as a yellow solid. $^1$H NMR (400 MHz, CDCl$_3$) δ: 8.45 (d, J=5.2 Hz, 1H), 8.36 (s, 1H), 8.27 (s, 1H), 7.73 (dd, J=1.2, 8.0 Hz, 1H), 7.63 (dd, J=1.2, 7.2 Hz, 1H), 7.44-7.40 (m, 1H), 6.98-6.92 (m, 2H), 4.02 (t, J=6.4 Hz, 2H), 3.95 (t, J=7.2 Hz, 2H), 1.82-1.75 (m, 2H), 1.67-1.61 (m, 2H), 1.48-1.42 (m, 11H); ESI-MS (M+H)$^+$: 513.1.

Synthesis of Compound 2.2

A solution of 2.1 (161 mg, 0.31 mmol) in THF (25 mL) was flushed with N$_2$ for 3 times. Pd/C (16 mg, 10%) was added and the mixture was flushed with H$_2$ for 3 times. The resulting mixture was stirred at rt for 16 h under H$_2$ atmosphere. The mixture was filtered and the filtrate was concentrated in vacuo to afford 2.2 (127 mg, yield: 81%) as a brown oil; ESI-MS (M+H$^+$): 483.1.

Synthesis of Compound 2.3

To a solution of 2.2 (127 mg, 0.26 mmol, 1.0 eq) in DCM (52 mL) were added HBTU (148 mg, 0.39 mmol, 1.5 eq) and DIPEA (67 mg, 0.52 mmol, 2.0 eq). The mixture was stirred at room temperature for 16 h, diluted with DCM (100 mL), washed with water (50 mL) and brine (50 mL). The organic layer was dried over sodium sulfate and concentrated under reduced pressure. The residue was purified by pre-HPLC (MeOH/0.05% TFA in H$_2$O=10%~95%) to give 2.3 (54 mg, yield: 47%) as a yellow solid; ESI-MS (M+H)$^+$: 465.1.

Synthesis of Compound 2

To a solution of 2.3 (54 mg, 0.12 mmol, 1.0 eq) in DCM (5 mL) was added TFA (68 mg, 0.60 mmol, 5.0 eq). The mixture was stirred at room temperature for 16 h and concentrated under reduced pressure. The residue was purified by pre-HPLC (MeOH/0.05% TFA in H$_2$O=10%~95%) to afford 2 (12 mg, yield: 28%) as a yellow solid. $^1$H NMR (400 MHz, CD$_3$OD) δ: 10.15 (s, 1H), 8.59-8.58 (m, 1H), 8.44-8.42 (dd, J=1.2, 7.6 Hz, 1H), 8.08 (d, J=2.4, 6.4 Hz, 1H), 7.71 (s, 1H), 7.30 (br, 1H), 7.14 (t, J=8.0 Hz, 1H), 7.03 (t, J=8.0 Hz, 1H), 6.95 (d, J=8.0 Hz, 1H), 4.15 (br, 2H), 3.48 (t, J=6.8 Hz, 2H), 1.97 (br, 4H), 1.83 (br, 2H); ESI-MS (M+H)$^+$: 365.1

Example 3

Scheme 3

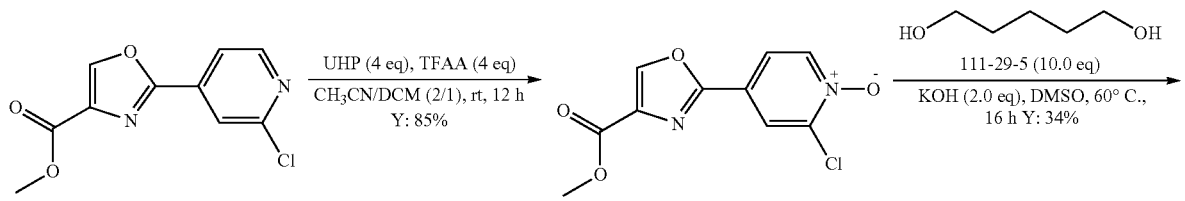

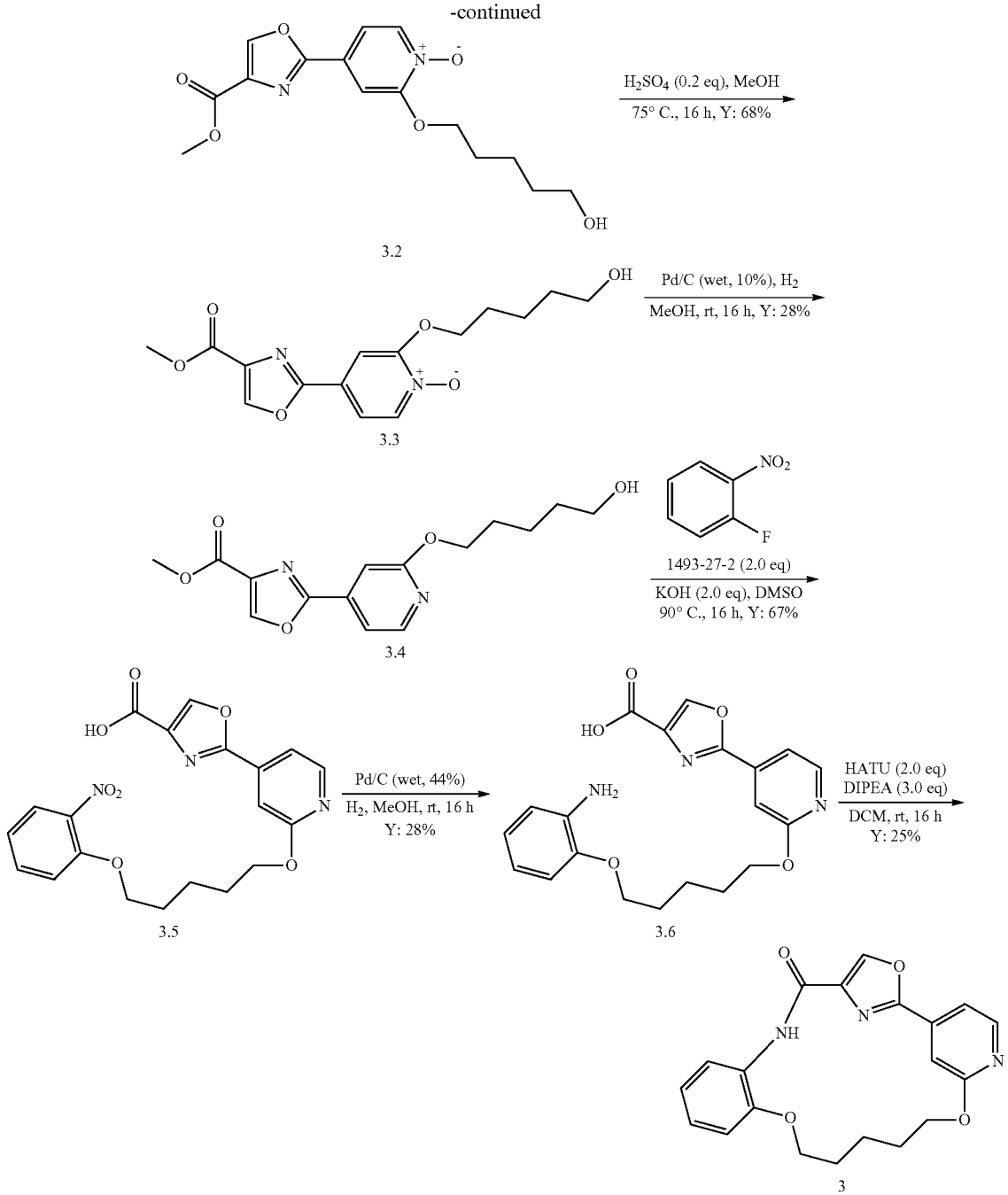

Synthesis of Compound 3.1

To a solution of methyl 2-(2-chloropyridin-4-yl)oxazole-4-carboxylate (2.4 g, 10 mmol) in CH$_3$CN/DCM (30 mL/15 mL), UHP (1.9 g, 20 mmol, 2.0 eq) was added. After cooled down to 0° C., the reaction mixture was slowly added TFAA (4.2 g, 20 mmol, 2.0 eq) and then stirred at room temperature for 12 h. The reaction was quenched with an aqueous solution of Na$_2$S$_2$O$_3$. The reaction solution was diluted with DCM (50 mL), washed with saturated NaHCO$_3$ aqueous solution. The organic layer was dried over anhydrous MgSO$_4$ and concentrated in vacuo. The residue was purified by silica-gel column (petroleum ether/ethyl acetate=1/2) to afford yellow solid 3.1 (1.7 g, yield: 66%). $^1$H NMR (400 MHz, CDCl$_3$) δ: 8.39 (d, J=6.4 Hz, 1H), 8.35 (s, 1H), 8.23 (s, 1H), 7.88 (d, J=7.2 Hz, 1H), 3.98 (s, 3H); ESI-MS (M+H$^+$): 255.1.

Synthesis of Compound 3.2

To a solution of 3.1 (150 mg, 0.59 mmol, 1.0 eq) in DMSO (2 mL) were added pentane-1,5-diol (614 mg, 5.91 mmol, 10.0 eq) and KOH (66 mg, 1.18 mmol, 2.0 eq). The mixture was stirred at 60° C. for 16 h. After cooled down to ambient temperature, the reaction solution was adjusted to pH=6 with acetic acid (20% in water) and concentrated under reduced pressure. The residue was purified by pre- HPLC (MeOH/H₂O with 0.05% TFA as mobile phase; from 0% to 95%) to furnish the target compound 3.2 (63 mg, Y: 34%) as a white solid; ESI-MS (M+H)⁺: 309.1.

Synthesis of Compound 3.3

To the solution of 3.2 (250 mg, 0.81 mmol, 1.0 eq) in MeOH (10 mL), conc. H₂SO₄ (16 mg, 0.16 mmol, 0.2 eq) was added at 0° C. The mixture was stirred at 75° C. for 16 h. After cooled down to ambient temperature, the reaction solution was adjusted to pH=7-8 with saturated NaHCO₃ aqueous solution and washed with the mixed solvent of DCM/MeOH (20/1, 50 mL). The organic layer was concentrated under reduced pressure to give 3.3 (180 mg, Y: 68%) as a yellow solid. ¹H NMR (400 MHz, CDCl₃) δ: 8.39 (s, 1H), 8.35 (d, J=6.4 Hz, 1H), 7.70 (s, 1H), 7.61 (d, J=6.4 Hz, 1H), 4.36 (t, J=6.0 Hz, 2H), 3.99 (s, 3H), 3.68-3.66 (t, J=6.0 Hz, 2H), 2.01 (m, 2H), 1.66 (m, 4H); ESI-MS (M+H)⁺: 323.0.

Synthesis of Compound 3.4

To a solution of 3.3 (200 mg, 0.62 mmol, 1.0 eq) in MeOH (10 mL), 10% Pd/C (20 mg, 10% wt) was added. The mixture was stirred at room temperature under H₂ atmosphere for 16 h. After filtered by celite, the filtrate was concentrated under reduced pressure. The residue was purified by column chromatography on silica gel (PE:EA=1:4) to give 3.4 (54 mg, Y: 28%) as a white solid. ¹H NMR (400 MHz, CDCl₃) δ δ: 8.34 (s, 1H), 8.28 (d, J=5.6 Hz, 1H), 7.54 (d, J=5.6 Hz, 1H), 7.40 (s, 1H), 4.35 (t, J=6.6 Hz, 2H), 3.97 (s, 3H), 3.69 (t, J=6.4 Hz, 2H), 1.86-1.81 (m, 2H), 1.68-1.63 (m, 2H), 1.59-1.53 (m, 2H); ESI-MS (M+H)⁺: 307.0.

Synthesis of Compound 3.5

To a solution of 3.4 (50 mg, 0.16 mmol, 1.0 eq) in DMSO (2 mL), 1-fluoro-2-nitrobenzene (46 mg, 0.32 mmol, 2.0 eq) and KOH (18 mg, 0.32 mmol, 2.0 eq) were added. The mixture was stirred at 90° C. for 16 h. After cooled down to ambient temperature, the reaction solution was adjusted to pH=6 with acetic acid (20% in water) and concentrated in vacuo. The residue was purified by prep-HPLC (MeOH/H₂O with 0.05% TFA as mobile phase; from 0% to 95%) to furnish the target compound 3.5 (45 mg, Y: 67%) as a white solid; ESI-MS (M+H⁺): 414.0.

Synthesis of Compound 3.6

To a solution of 3.5 (45 mg, 0.11 mmol, 1.0 eq) in MeOH (8 mL), 10% Pd/C (20 mg, 44% wt) was added. The mixture was stirred at room temperature under H₂ atmosphere for 16 h. After filtered by celite, the filtrate was concentrated under reduced pressure. The residue was purified by prep-HPLC (MeOH/H₂O with 0.05% TFA as mobile phase; from 0% to 95%) to give 3.6 (12 mg, Y: 28%) as a yellow solid; ESI-MS (M+H)⁺: 383.2.

Synthesis of Compound 3

To a solution of 3.6 (12 mg, 0.03 mmol, 1.0 eq) in DCM (6 mL), HATU (24 mg, 0.06 mmol, 2.0 eq) and DIPEA (12 mg, 0.09 mmol, 3.0 eq) were added. The mixture was stirred at room temperature for 16 h. The mixture was concentrated under reduced pressure. The residue was purified by prep-HPLC (MeOH/H₂O with 0.05% TFA as mobile phase; from 0% to 95%) to give 3 (2.9 mg, Y: 25%) as a yellow solid. ¹H NMR (400 MHz, CDCl₃) δ: 10.14 (s, 1H), 8.41-8.35 (m, 3H), 7.60 (s, 1H), 7.37-7.36 (m, 1H), 7.02-6.95 (m, 2H), 6.85-6.83 (m, 1H), 4.30 (br. s, 2H), 4.05 (br. s, 2H), 1.91-1.89 (m, 6H); ESI-MS (M+H)⁺: 366.2; HPLC: 214 nm: 100.00%, 254 nm: 100.00%.

Example 4

Scheme 4

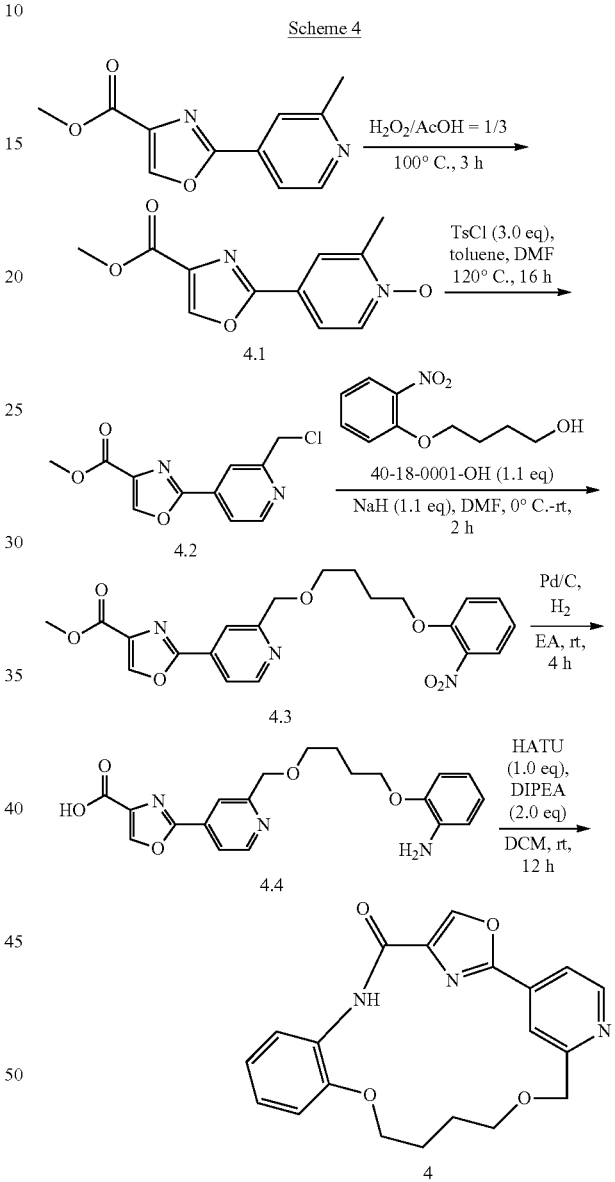

Synthesis of Compound 4.1

To the solution of methyl 2-(2-methylpyridin-4-yl)oxazole-4-carboxylate (3.8 g, 17.4 mmol, 1.0 eq) in AcOH (80 mL) was added H₂O₂ (30%, 23 mL). The reaction mixture was stirred at 100° C. for 3 h. The resulting mixture was concentrated under reduced pressure and recrystallized in MeOH (50 mL) to give 4.1 (2.7 g, yield: 66%) as a yellow solid. ¹H NMR (400 MHz, DMSO-d₆) δ: 9.05 (s, 1H), 8.37 (d, J=6.8 Hz, 1H), 8.11 (s, 1H), 7.81 (d, J=6.8 Hz, 1H), 3.85 (s, 3H), 2.43 (s, 3H); ESI-MS (M+H)⁺: 235.1.

Synthesis of Compound 4.2

To a mixture of 4.1 (1.0 g, 4.27 mmol, 1.0 eq) in anhydrous DMF (10 mL) and toluene (10 mL), TsCl (2.4 g, 12.6 mmol, 3.0 eq) was added. Then the mixture was stirred at 120° C. for 16 h, diluted with EA (200 mL). The organic layer was washed with water (100 mL×4), brine (100 mL), dried over sodium sulfate and concentrated under reduced pressure. The residue was purified by silica gel (PE/EA=2/1) to give 4.2 (570 mg, yield: 53%) as a yellow oil. $^1$H NMR (400 MHz, CDCl$_3$) δ: 8.73 (d, J=5.2 Hz, 1H), 8.38 (s, 1H), 8.17 (s, 1H), 7.90 (d, J=4.8 Hz, 1H), 4.74 (s, 2H), 3.98 (s, 3H); ESI-MS (M+1)$^+$: 252.9.

Synthesis of Compound 4.3

To a mixture of 4-(2-nitrophenoxyl)butan-1-ol (700 mg, 3 mmol, 1.1 eq) in anhydrous DMF (10 mL), NaH (132 mg, 3.3 mmol, 1.1 eq) was added at 0° C. The mixture was allowed to warm to room temperature and stirred for 20 min. Then 4.2 (760 mg, 3.0 mmol, 1.0 eq) was added at 0° C. The mixture was stirred at room temperature for 2 h. The reaction was quenched with H$_2$O (2 mL). The solution was acidified to pH=5 with HCl (1 N), diluted with ethyl acetate (100 mL) and washed with water (30 mL×3). The organic layer was dried over anhydrous sodium sulfate and concentrated under reduced pressure. The residue was purified by prep-HPLC (MeOH in water from 10% to 95%) to give 4.3 (150 mg, yield: 6%) as a yellow oil. $^1$H NMR (400 MHz, DMSO-d$_6$) δ: 8.97 (s, 1H), 8.72 (d, J=5.2 Hz, 1H), 7.95 (s, 1H), 7.85-7.83 (m, 2H), 7.64-7.59 (m, 1H), 7.40 (d, J=8.4 Hz, 1H), 7.08 (t, J=8.0 Hz, 1H), 4.66 (s, 2H), 4.21 (t, J=6.0 Hz, 2H), 3.64 (t, J=6.0 Hz, 2H), 1.86-1.74 (m, 4H); ESI-MS (M+H)$^+$: 413.9.

Synthesis of Compound 4.4

To a solution of 4.3 (150 mg, 0.12 mmol) in ethyl acetate (10 mL) was added Pd/C (30 mg, 20% wt). The mixture was stirred at room temperature for 4 h under H$_2$ atmosphere. The solution was filtered by Celite and the filtrate was concentrated under reduced pressure to give 4.4 (40 mg, yield: 29%) as a yellow oil; ESI-MS (M+H)$^+$: 384.0.

Synthesis of Compound 4

To a solution of 4.4 (40 mg, 0.1 mmol, 1.0 eq) in DCM (20 mL) were added HATU (38 mg, 0.1 mmol, 1.0 eq) and DIPEA (26 mg, 0.2 mmol, 2.0 eq). The mixture was stirred at room temperature for 12 h and washed with water (10 mL×4), brine (10 mL). The organic layer was dried over sodium sulfate and concentrated under reduced pressure. The residue was purified by pre-TLC (PE/EA=2/1) to give 4 (3 mg, yield: 8%) as a yellow solid. $^1$H NMR (400 MHz, CDCl$_3$) δ: 10.28 (s, 1H), 8.73 (d, J=5.2 Hz, 1H), 8.58 (s, 1H), 8.48 (d, J=8.0 Hz, 1H), 8.35 (s, 1H), 7.65 (d, J=4.0 Hz, 1H), 7.09-6.99 (m, 2H), 6.90 (d, J=7.6 Hz, 1H), 4.85 (s, 2H), 4.15 (t, J=5.6 Hz, 2H), 3.74 (t, J=7.2 Hz, 2H), 2.29-2.22 (m, 2H), 2.06-1.99 (m, 2H); ESI-MS (M+H)$^+$: 366.2

Example 5

Scheme 5

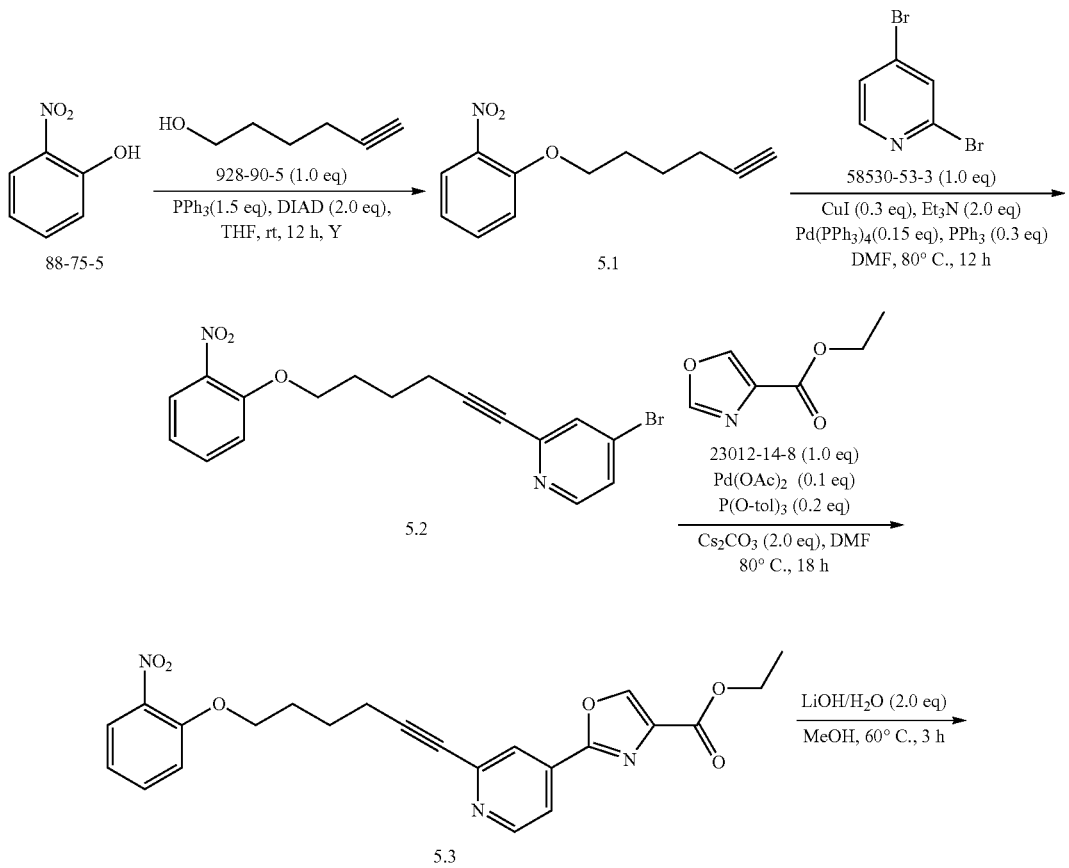

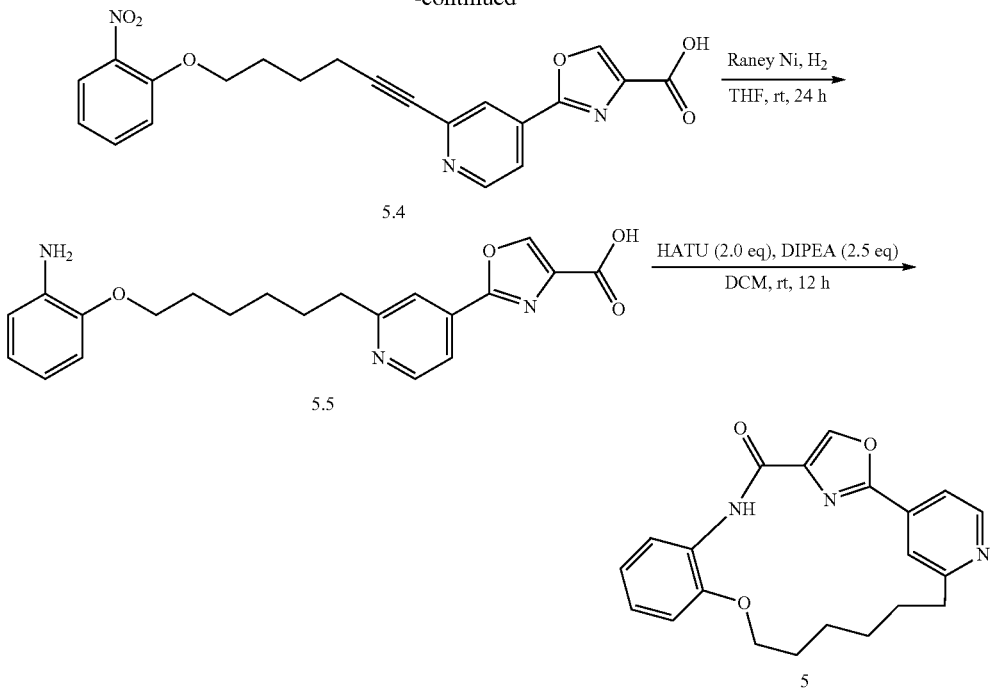

Synthesis of Compound 5.1

To a solution of 2-nitrophenol (4.5 g, 32 mmol, 1.0 eq), hex-5-yn-1-ol (3.2 g, 32 mmol, 1.0 eq) and $PPh_3$ (12.6 g, 48 mmol, 1.5 eq) in THF (100 ml), DIAD (12.9 g, 64 mmol, 2.0 eq) was added. The reaction mixture was stirred under nitrogen at room temperature for 12 h and then filtered. The filtrate was concentrated under reduced pressure. The residue was purified by silica gel column (PE/EA=50/1) to give 5.1 (4.3 g, yield: 58%) as a yellow oil. $^1$H NMR (400 MHz, $CDCl_3$) δ: 7.81 (m, 1H), 7.49-7.58 (m, 1H), 7.01-7.08 (m, 2H), 4.14 (m, 2H), 2.27-2.31 (m, 2H), 1.95-2.00 (m, 3H), 1.73-1.77 (m, 2H); ESI-MS $(M+Na)^+$: 242.1.

Synthesis of Compound 5.2

To a solution of 5.1 (3.3 g, 15 mmol, 1.0 eq) and 2,4-dibromopyridine (3.5 g, 15 mmol, 1.0 eq) in DMF (30 ml), CuI (855 mg, 4.5 mmol, 0.3 eq), $Pd(PPh_3)_4$ (952 mg, 2.3 mmol, 0.15 eq), $PPh_3$ (1.18 g, 4.5 mmol, 0.3 eq) and $Et_3N$ (3.0 g, 30 mmol, 2.0 eq) were added. The reaction mixture was stirred at 80° C. for 12 h. After cooling down to ambient temperature, the reaction solution was diluted with ethyl acetate (50 ml) and washed with brine (50 ml×2). The organic layer was dried over anhydrous sodium sulphate and concentrated under reduced pressure. The residue was purified by silica gel column (PE/EA=50/1) to give 5.2 (1.6 g, yield: 30%) as a colorless oil; ESI-MS $(M+H)^+$: 375.0.

Synthesis of Compound 5.3

To a mixture of 5.2 (600 mg, 1.6 mmol, 1.0 eq) and ethyl oxazole-4-carboxylate (230 mg, 1.6 mmol, 1.0 eq) in anhydrous DMF (10 ml), $Cs_2CO_3$ (1.05 g, 3.2 mmol, 2.0 eq), $Pd(OAc)_2$ (36 mg, 0.16 mmol, 0.1 eq) and P(O-tol)$_3$ (100 mg, 0.32 mmol, 0.2 eq) were added under $N_2$ atmosphere in a vial. The vial was sealed and heated at 80° C. for 18 h. After cooling down to ambient temperature, the precipitation was filtered off by Celite, the filtrate was diluted with water (20 ml) and extracted with ethyl acetate (50 ml×3). The combined organic layers were dried over anhydrous sodium sulfate and concentrated under reduced pressure. The residue was purified by silica gel column (PE/EA=5/1) to give 5.3 (120 mg, yield: 17%) as colorless oil; ESI-MS $(M+H)^+$: 436.1.

Synthesis of Compound 5.4

To a solution of 5.3 (120 mg, 0.23 mmol, 1.0 eq) in MeOH (10 ml) and $H_2O$ (2 ml), $LiOH.H_2O$ (19 mg, 0.46 mmol, 2.0 eq) was added. The reaction mixture was stirred at 60° C. for 3 h. Then the solution was adjusted pH=4 with hydrochloric acid (1 M) and extracted with ethyl acetate (20 ml×2). The combined organic layers were dried over anhydrous sodium sulfate and concentrated under reduced pressure to give 5.4 (117 mg, yield: 90%) as a white solid; ESI-MS $(M+H)^+$: 408.1.

Synthesis of Compound 5.5

To a solution of 5.4 (80 mg, 0.17 mmol, 1.0 eq) in THF (20 ml), catalytic amount Raney Ni was added. The reaction system was evacuated and recharged with hydrogen three times. Then the reaction mixture was stirred at room temperature for 16 h. The precipitation was filtered off by celite and the filtrate was concentrated under reduced pressure to give 5.5 (70 mg, yield: 90%) as white solid; ESI-MS $(M+H)^+$: 382.2.

Synthesis of Compound 5

To a solution of 5.5 (70 mg, 0.18 mmol, 1.0 eq) in $CH_2Cl_2$ (20 ml), DIPEA (60 mg, 0.45 mmol, 2.5 eq) and HATU (140 mg, 0.36 mmol, 2.0 eq) were added. The reaction mixture was stirred at room temperature for 12 h and then concentrated under reduced pressure. The residue was purified by pre-TLC (PE/EA=1/1) to give 5 (14 mg, yield: 20%) as yellow solid. $^1$H NMR (400 MHz, CDCl$_3$) δ: 10.13 (s, 1H), 8.72 (d, J=4.8 Hz, 1H), 8.34 (s, 1H), 8.13 (s, 1H), 7.58 (d, J=4.8 Hz, 1H), 7.26 (s, 1H), 6.98-7.09 (m, 2H), 6.89 (d, J=7.6 Hz, 1H), 4.10 (t, J=4.8 Hz, 2H), 3.03 (t, J=4.8 Hz, 2H), 1.92-1.98 (m, 6H), 1.48-1.71 (m, 2H); ESI-MS (M+H)$^+$: 364.2

Example 6 to room temperature, the reaction solution was diluted with ethyl acetate (200 mL). The precipitate was filtered off and the filtrate was concentrated under reduced pressure. The residue was purified by silica gel column (PE:EA=50:1) to give 45-3-0001 (7.8 g, yield: 78%) as a yellow oil. $^1$H NMR (400 MHz, CDCl$_3$) δ: 7.81 (d, J=8.0 Hz, 1H), 7.51 (t, J=8.4 Hz, 1H), 7.06 (d, J=8.0 Hz, 1H), 7.01 (t, J=8.4 Hz, 1H), 4.10 (t, J=6.4 Hz, 2H), 3.42 (t, J=6.8 Hz, 2H), 1.81-1.91 (m, 4H), 1.37-1.55 (m, 6H).

Scheme 6

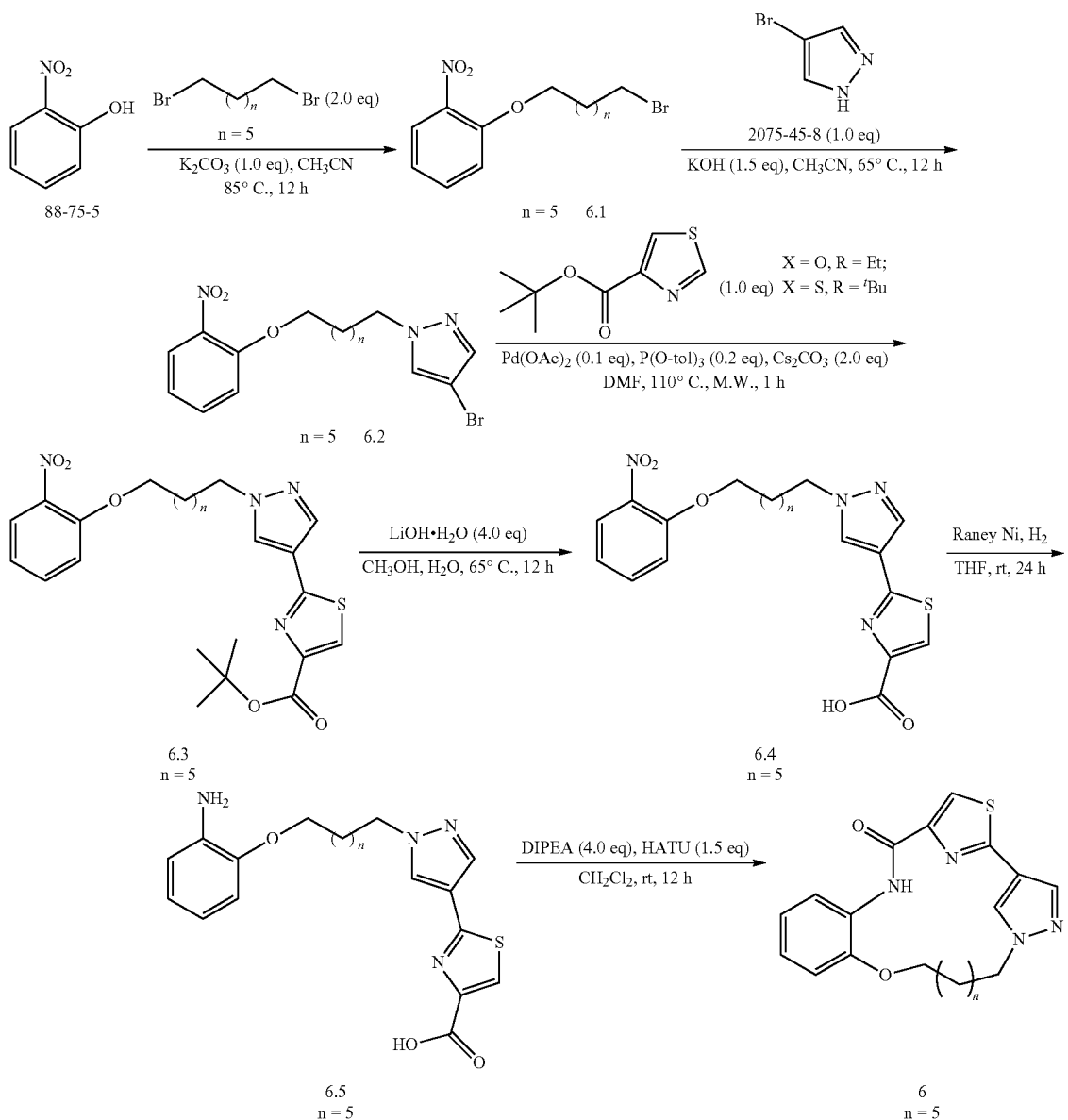

Synthesis of Compound 6.1

To a mixture of 2-nitrophenol (4.4 g, 32 mmol, 1.0 eq) and 1,7-dibromohepeane (16.2 g, 64 mmol, 2.0 eq) in CH$_3$CN (100 mL), K$_2$CO$_3$ (4.4 g, 32 mmol, 1.0 eq) was added. The reaction mixture was refluxed for 12 h. After cooling down Synthesis of Compound 6.2

To a mixture of 45-3-0002 (500 mg, 1.3 mmol, 1.0 eq) and 45-2-0201 (241 mg, 1.3 mmol, 1.0 eq) in anhydrous DMF (10 ml), Cs$_2$CO$_3$ (85 mg, 2.6 mmol, 2.0 eq), Pd(OAc)$_2$ (30 mg, 0.13 mmol, 0.1 eq) and P(o-tol)$_3$ (81 mg, 0.26 mmol, 0.2 eq) were added under N$_2$ atmosphere in a vial. The vial was sealed and heated at 110° C. for 1 h. After cooling down to room temperature, the precipitate was filtered off by Celite. The filtrate was diluted with water (200 ml) and extracted with ethyl acetate (50 ml×3). The combined organic layers were dried over anhydrous sodium sulfate and concentrated under reduced pressure. The residue was purified by silica gel column (PE:EA=5:1) to give 45-3-0003 (35 mg, yield: 7%) as a yellow oil. $^1$H NMR (400 MHz, CDCl$_3$) δ: 8.01 (s, 1H), 7.90 (s, 1H), 7.92 (s, 1H), 7.81 (d, J=8.0 Hz, 1H), 7.48-7.52 (m, 1H), 7.05 (d, J=8.0 Hz, 1H), 7.98-7.20 (m, 1H), 4.13-4.17 (m, 2H), 4.07-4.11 (m, 2H), 1.89-1.95 (m, 2H), 1.79-1.84 (m, 2H), 1.61 (s, 9H), 1.32-1.51 (m, 6H); ESI-MS (M+H)$^+$: 487.1.

Synthesis of Compound 6.3

To a solution of 45-3-0003 (127 mg, 0.26 mmol, 1.0 eq) in MeOH (9 ml) and H$_2$O (1 ml), LiOH.H$_2$O (44 mg, 1.0 mmol, 4.0 eq) was added. The reaction mixture was refluxed for 16 h. Then the solution was adjusted to pH=4 with hydrochloric acid (1 M) and extracted with ethyl acetate (50 ml×2). The combined organic layers were dried over anhydrous sodium sulfate and concentrated under reduced pressure to give 45-3-0004 (112 mg, yield: 99%) as a yellow oil; ESI-MS (M+H)$^+$: 431.1.

Synthesis of Compound 6.4

To a solution of 45-3-0004 (90 mg, 0.21 mmol, 1.0 eq) in THF (10 ml), raney Ni (18 mg, 20% wt) was added. The reaction system was evacuated and recharged with hydrogen three times. Then the reaction mixture was stirred at room temperature for 16 h. The solution was filtered by Celite and the filtrate was concentrated under reduced pressure to give 45-3-0005 (60 mg, yield: 71%) as a yellow oil; ESI-MS (M+H)$^+$: 401.1.

Synthesis of Compound 6

To a solution of 45-3-0005 (60 mg, 0.15 mmol, 1.0 eq) in CH$_2$Cl$_2$ (30 ml), DIPEA (77 mg, 0.60 mmol, 4.0 eq) and HATU (87 mg, 0.23 mmol, 1.5 eq) were added. The reaction mixture was stirred at room temperature for 16 h and then concentrated under reduced pressure. The residue was purified by pre-TLC (PE:EA=1:1) to give 45-3 (15 mg, yield: 26%) as a yellow solid. $^1$H NMR (400 MHz, CDCl$_3$) δ: 10.25 (s, 1H), 8.63 (d, J=8.0 Hz, 1H), 8.04 (s, 1H), 8.03 (s, 1H), 7.79 (s, 1H), 6.98-7.07 (m, 2H), 6.89 (d, J=8.0 Hz, 1H), 4.36 (t, J=6.0 Hz, 2H), 4.07 (t, J=5.6 Hz, 2H), 1.95-2.02 (m, 2H), 1.83-1.89 (m, 2H), 1.63-1.71 (m, 2H), 1.50-1.58 (m, 2H), 1.22-1.27 (m, 2H); ESI-MS (M+H)$^+$: 383.1; HPLC: 214 nm: 100.00%, 254 nm: 100.00%.

Examples 7 and 8

Scheme 7 and 8

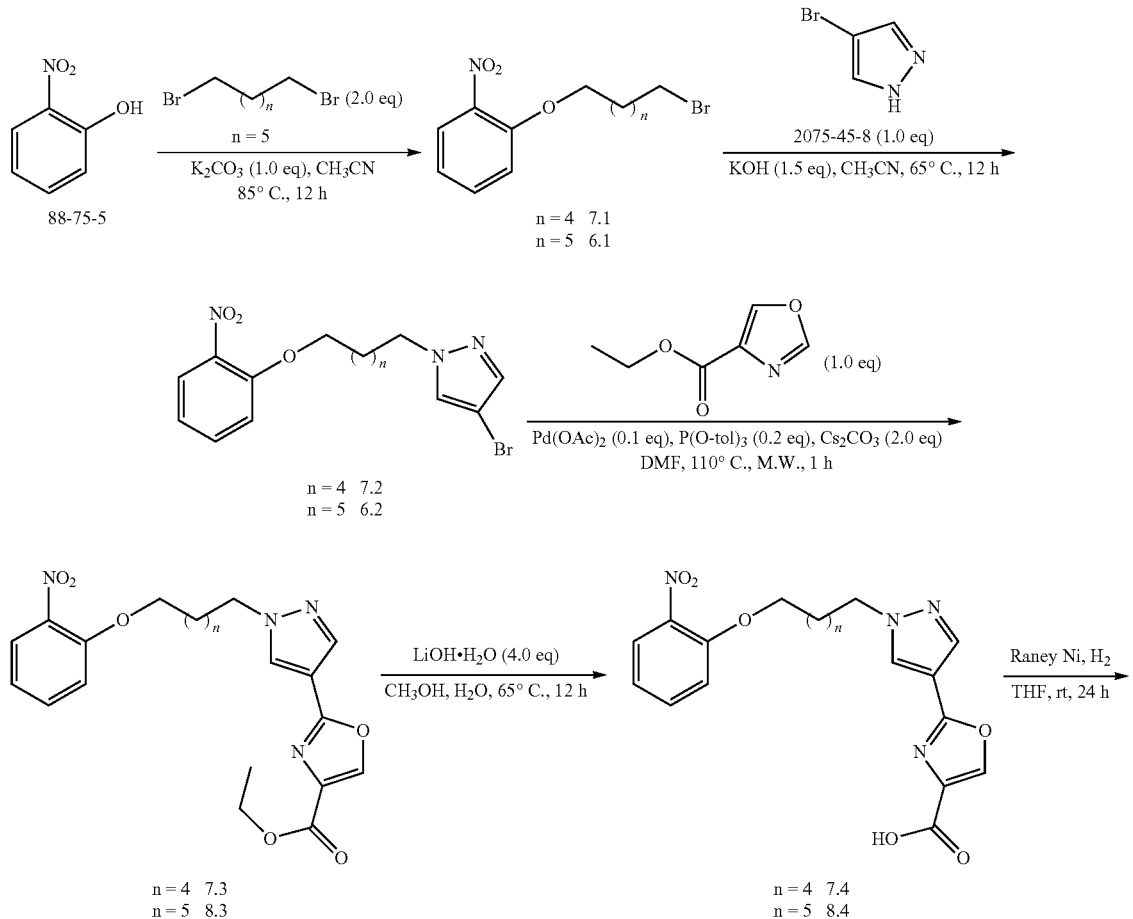

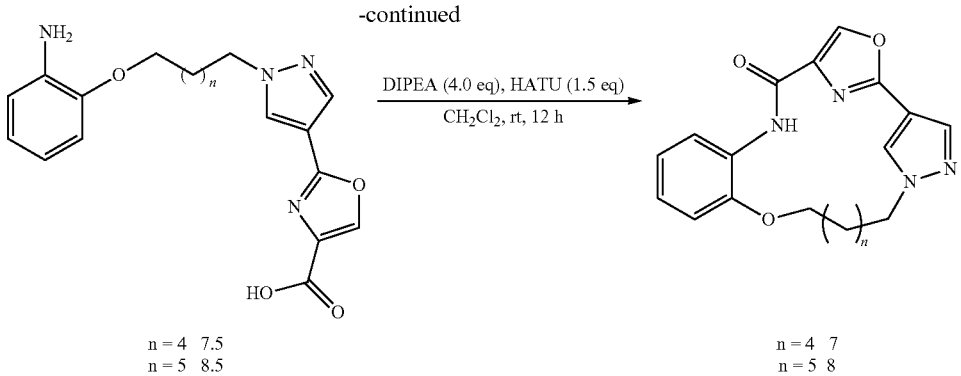

| n = 4 | 7.5 |
| n = 5 | 8.5 |

| n = 4 | 7 |
| n = 5 | 8 |

Synthesis of Compound 7.1

Compound 7.1 was prepared similar to compound 6.1. Purified by silica gel column (PE:EA=50:1). Weight: colorless oil 3.12 g, yield: 72%. $^1$H NMR (400 MHz, CD$_3$OD) δ: 7.83 (d, J=8.0 Hz, 1H), 7.53 (t, J=6.8 Hz, 1H), 7.07 (d, J=8.4 Hz, 1H), 7.03 (t, J=8.0 Hz, 1H), 4.12 (t, J=6.0 Hz, 2H), 3.45 (t, J=6.4 Hz, 2H), 1.93-1.82 (m, 4H), 1.57-1.48 (m, 4H).

Synthesis of Compound 7.2

Compound 7.2 was prepared similar to compound 6.2. Weight: light solid 122 mg, yield: 100%. $^1$H NMR (400 MHz, CDCl$_3$) δ: 7.83 (d, J=8.0 Hz, 1H), 7.52 (t, J=7.6 Hz, 1H), 7.43 (s, 1H), 7.41 (s, 1H), 7.05 (d, J=8.4 Hz, 1H), 7.03 (t, J=8.8 Hz, 1H), 4.12 (t, J=7.2 Hz, 2H), 4.09 (t, J=6.0 Hz, 2H), 1.91-1.79 (m, 4H), 1.57-1.50 (m, 2H), 1.39-1.31 (m, 2H); ESI-MS (M+H)$^+$: 370.0.

Synthesis of Compound 7.3

Compound 7.3 was prepared similar to compound 6.3. Purified by silica gel column (PE:EA=2:1). Weight: yellow solid 550 mg, yield: 55%. $^1$H NMR (400 MHz, DMSO-d$_6$) δ: 8.78 (s, 1H), 8.47 (s, 1H), 7.98 (s, 1H), 7.85 (d, J=8.0 Hz, 1H), 7.64 (t, J=8.4 Hz, 1H), 7.34 (d, J=8.4 Hz, 1H), 7.10 (t, J=7.6 Hz, 1H), 4.32 (q, J=6.8 Hz, 2H), 4.20 (t, J=6.8 Hz, 2H), 4.14 (t, J=6.4 Hz, 2H), 1.86-1.79 (m, 2H), 1.73-1.67 (m, 2H), 1.47-1.40 (m, 2H), 1.33-1.24 (m, 5H); ESI-MS (M+1)$^+$: 429.2.

Synthesis of Compound 7.4

Compound 7.4 was prepared similar to compound 6.4. Weight: yellow oil 200 mg, yield: 86%; ESI-MS (M+H)$^+$: 401.2.

Synthesis of Compound 7.5

Compound 7.5 was prepared similar to compound 6.5. Weight: yellow oil 113 mg, yield: 61%; ESI-MS (M+H)$^+$: 371.1.

Synthesis of Compound 7

Compound 7 was prepared similar to compound 6. Purified by prep-TLC (DCM:MeOH=20:1). Weight: yellow solid 37 mg, yield: 37%. $^1$H NMR (400 MHz, CDCl$_3$) δ: 10.44 (s, 1H), 8.44-8.41 (m, 2H), 8.11 (s, 1H), 7.82 (s, 1H), 7.05-6.97 (m, 2H), 6.87 (d, J=7.6 Hz, 1H), 4.24 (t, J=5.6 Hz, 2H), 4.08-4.04 (m, 2H), 2.15-2.09 (m, 2H), 1.90-1.86 (m, 4H), 1.55-1.49 (m, 2H); ESI-MS (M+H)$^+$: 353.2

Synthesis of Compound 8.3

Compound 8.3 was prepared similar to compound 6.3. Purified by silica gel column (PE:EA=5:1). Weight: yellow solid 432 mg, yield: 74%; ESI-MS (M+1)$^+$: 443.1.

Synthesis of Compound 7.4

Compound 7.4 was prepared similar to compound 6.4. Weight: yellow oil 370 mg, yield: 100%; ESI-MS (M+H)$^+$: 415.2.

Synthesis of Compound 7.5

Compound 7.5 was prepared similar to compound 6.5. Weight: yellow oil 340 mg, yield: 99%; $^1$H NMR (400 MHz, DMSO-d$_6$) δ: 8.35 (s, 1H), 8.02 (s, 1H), 7.91 (s, 1H), 6.74 (d, J=8.0 Hz, 1H), 6.66-6.60 (m, 2H), 6.49 (t, J=8.0 Hz, 1H), 4.62 (s, 2H), 4.18 (t, J=6.4 Hz, 2H), 3.90 (t, J=6.0 Hz, 2H), 1.84-1.77 (m, 2H), 1.72-1.65 (m, 2H), 1.44-1.30 (m, 4H), 1.27-1.20 (m, 2H); ESI-MS (M+H)$^+$: 385.2.

Synthesis of Compound 8

Compound 8 was prepared similar to compound 6 Purified by prep-TLC (PE:EA=1:1). Weight: white solid 150 mg, yield: 48%; $^1$H NMR (400 MHz, CDCl$_3$) δ: 10.14 (s, 1H), 8.51 (d, J=7.6 Hz, 1H), 8.16 (s, 1H), 8.11 (s, 1H), 7.84 (s, 1H), 7.06 (t, J=8.0 Hz, 1H), 7.01 (t, J=7.6 Hz, 1H), 6.89 (d, J=8.0 Hz, 1H), 4.37 (t, J=6.0 Hz, 2H), 4.09 (t, J=5.6 Hz, 2H), 2.04-1.95 (m, 2H), 1.86-1.80 (m, 2H), 1.74-1.63 (m, 2H), 1.56-1.48 (m, 2H), 1.18-1.11 (m, 2H); ESI-MS (M+H)$^+$: 367.2;

Example 9

Scheme 9

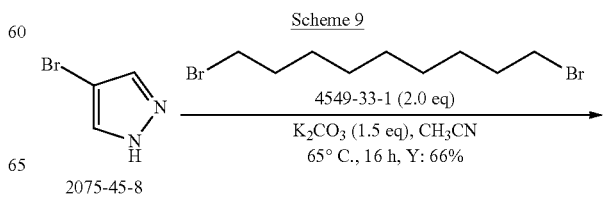

-continued

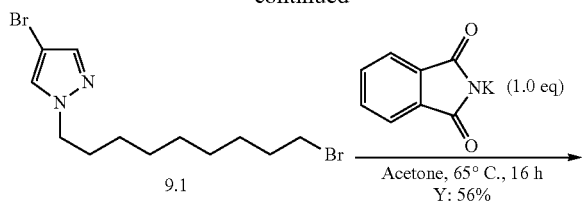

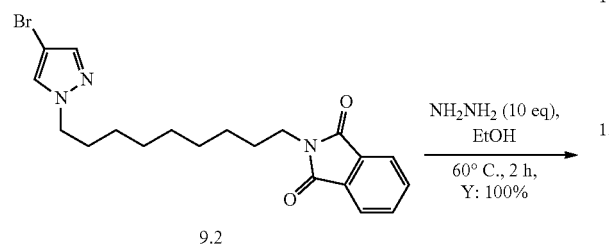

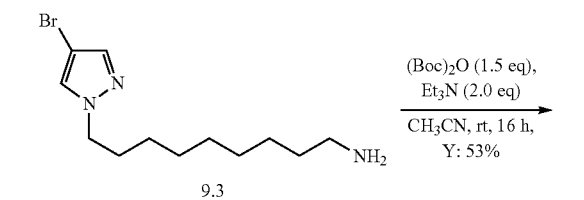

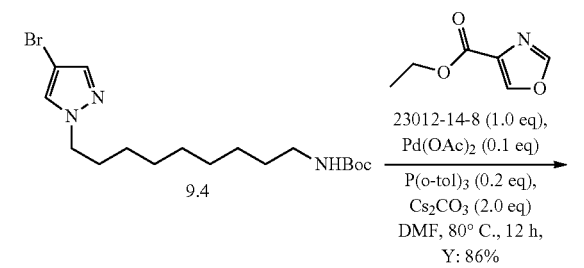

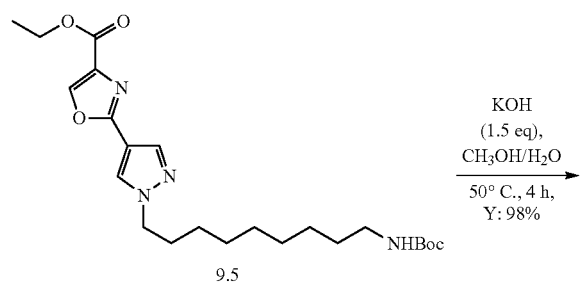

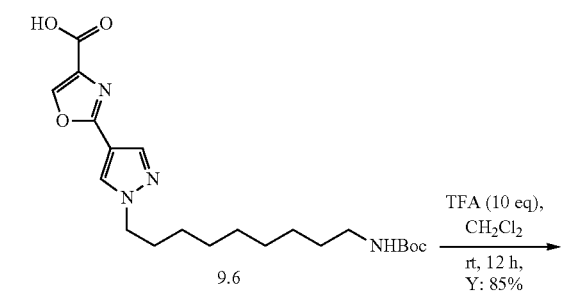

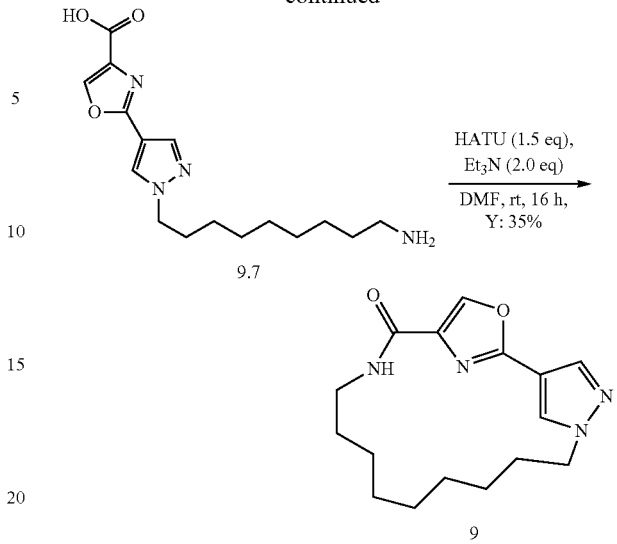

Synthesis of Compound 9.1

To a solution of 2075-45-8 (1.30 g, 8.84 mmol, 1.0 eq) in CH$_3$CN (20 ml) were added K$_2$CO$_3$ (1.41 g, 13.26 mmol, 1.5 eq) and 4549-33-1 (5.05 g, 7.68 mmol, 2.0 eq). The reaction mixture was stirred at 65° C. for 16 h. After cooling down to ambient temperature, the resulting solution was diluted with H$_2$O (100 mL), extracted with ethyl acetate (100 ml). The organic layer was dried over anhydrous sodium sulphate and concentrated in vacuo. The residue was purified by silica gel column (PE/EA=10/1) to give 9.1 (2.08 g, yield: 66%) as a white solid. $^1$H NMR (400 MHz, CDCl$_3$) δ: 7.44 (s, 1H), 7.38 (s, 1H), 4.09 (t, J=7.2 Hz, 2H), 3.41 (t, J=7.2 Hz, 2H), 1.87-1.80 (m, 4H), 1.42-1.37 (m, 2H), 1.29-1.24 (m, 8H); ESI-MS (M+H)$^+$: 351.0.

Synthesis of Compound 9.2

To a solution of 9.1 (1.09 g, 3.10 mmol, 1.0 eq) in acetone (20 ml) was added 1074-82-4 (576 mg, 3.10 mmol, 1.0 eq). The reaction mixture was stirred at 65° C. for 16 h. The resulting solution was concentrated in vacuo, diluted with H$_2$O (50 mL) and extracted with ethyl acetate (50 mL). The organic layer was dried over anhydrous sodium sulphate and concentrated under reduced pressure. The residue was purified by silica gel column (PE/EA=10/1) to give 9.2 (730 mg, yield: 56%) as a white solid. $^1$H NMR (400 MHz, CDCl$_3$) δ: 7.86-7.82 (m, 2H), 7.73-7.68 (m, 2H), 7.44 (s, 1H), 7.39 (s, 1H), 4.09 (t, J=7.2 Hz, 2H), 3.68 (t, J=7.2 Hz, 2H), 1.85-1.80 (m, 2H), 1.67-1.63 (m, 2H), 1.31-1.28 (m, 10H); ESI-MS (M+H)$^+$: 420.1.

Synthesis of Compound 9.3

To a solution of 9.2 (200 mg, 0.48 mmol, 1.0 eq) in EtOH (5 mL), NH$_2$NH$_2$H$_2$O (24 mg, 4.80 mmol, 10 eq) was added. The reaction mixture was stirred at 60° C. for 2 h. The resulting solution was filtered and the filtrate was concentrated in vacuo. The 9.3 residue (137 mg) was used directly in the next step without further purification; ESI-MS (M+H)$^+$: 290.0.

Synthesis of Compound 9.4

To a solution of 9.3 (2.2 g, 7.66 mmol, 1.0 eq) in $CH_3CN$ (30 mL), $Et_3N$ (1.55 g, 15.32 mmol, 2.0 eq) and $(Boc)_2O$ (2.62 g, 11.50 mmol, 1.5 eq) were added. The mixture was stirred at room temperature for 16 h. After concentrated in vacuo, the resulted mixture was diluted with EA (50 mL) and washed with $H_2O$ (50 mL×2). The organic layer was dried over anhydrous sodium sulfate and concentrated under reduced pressure. The residue was purified by silica gel column (PE/EA=10/1) to give 9.4 as a yellow oil (1.6 g, yield: 53%); ESI-MS $(M+H^+)$: 390.0.

Synthesis of Compound 9.5

To a solution of 9.2 (690 mg, 1.78 mmol, 1.0 eq) in DMF (15 mL), 23012-14-8 (251 mg, 1.78 mmol, 1.0 eq), $P(o-tol)_3$ (108 mg, 0.36 mmol, 0.2 eq), $Cs_2CO_3$ (1.16 g, 3.56 mmol, 2.0 eq) and $Pd(OAc)_2$ (40 mg, 0.18 mmol, 0.1 eq) were added. After stirred at 80° C. for 16 h, the resulting mixture was diluted with EA (100 mL) and filtered by celite. The filtrate was washed with water (100 mL×2), brine (100 mL), dried over sodium sulfate and concentrated under reduced pressure. The residue was purified by silica gel (PE/EA=2/1) to give 9.5 (800 mg, yield: 86%) as a yellow solid. $^1$H NMR (400 MHz, $CDCl_3$) □ δ: 8.17 (s, 1H), 8.02 (s, 1H), 8.01 (s, 1H), 4.44 (q, J=7.2 Hz, 2H), 4.17 (t, J=7.2 Hz, 2H), 3.11-3.06 (m, 2H), 1.91-1.86 (m, 2H), 1.67-1.66 (m, 1H), 1.43 (s, 9H), 1.41 (t, J=7.2 Hz, 3H), 1.28-1.24 (m, 11H); ESI-MS $(M+H^+)$: 449.2.

Synthesis of Compound 9.6

To a solution of 47-1-0203 (128 mg, 0.29 mmol, 1.0 eq) in MeOH (5 mL) was added KOH (24 mg, 0.43 mmol, 1.5 eq). The reaction mixture was stirred at 50° C. for 4 h. After cooled down to ambient temperature, the reaction solution was adjusted to pH=6 with HCl (1 N), diluted with water (40 mL) and extracted with EA (40 mL×3). The organic layers were dried over anhydrous sodium sulfate and concentrated under reduced pressure to give 9.6 as a yellow solid (100 mg, yield: 83%); ESI-MS $(M+H^+)$: 421.2. $^1$H NMR (400 MHz, DMSO-$d_6$) □ δ: 8.38 (s, 1H), 8.21 (s, 1H), 7.94 (s, 1H), 6.78 (t, J=4.2 Hz, 1H), 4.17 (t, J=6.8 Hz, 2H), 2.89 (q, J=6.8 Hz, 2H), 1.80-1.77 (m, 2H), 1.36 (s, 9H), 1.31-1.21 (m, 12H); ESI-MS $(M+H^+)$: 421.2.

Synthesis of Compound 9.7

To a solution of 9.6 (460 mg, 1.09 mmol, 1.0 eq) in DCM (10 mL) was added TFA (1.25 g, 10.90 mmol, 10.0 eq). The reaction mixture was stirred at room temperature for 12 h and then concentrated under reduced pressure. The residue was neutralized to pH=7 with saturated $NaHCO_3$ solution and then filtered. The precipitate was collected and washed with $H_2O$ (3 mL) and EA (3 mL) to give 9.7 (300 mg, yield: 85%) as a white solid; ESI-MS $(M+H^+)$: 321.2.

Synthesis of Compound 9

To a solution of 9.7 (150 mg, 0.468 mmol, 1.0 eq) in DMF (10 mL) were added HATU (267 mg, 0.702 mmol, 1.5 eq) and $Et_3N$ (94 mg, 0.936 mmol, 2.0 eq). After stirred at room temperature for 16 h, the resulting mixture was diluted with $H_2O$ (50 mL) and extracted with EA (50 mL×2). The combined organic layers were washed with brine (50 mL×2), dried over anhydrous sodium sulfate and concentrated under reduced pressure. The residue was purified by silica gel column (PE/EA=1/1) to give 9 (50 mg, yield: 35%) as a yellow solid. $^1$H NMR (400 MHz, DMSO-$d_6$) □ δ: 8.50 (s, 1H), 8.46 (s, 1H), 7.96 (s, 1H), 7.90 (t, J=6.8 Hz, 1H), 4.29 (t, J=6.0 Hz, 2H), 3.62 (m, 2H), 1.69-1.68 (m, 2H), 1.44-1.43 (m, 2H), 1.34-1.33 (m, 2H), 1.21-1.20 (m, 6H), 0.81-0.80 (m, 2H); ESI-MS $(M+H^+)$: 303.1; HPLC: 214 nm: 100.00%, 254 nm: 100.00%

Example 10

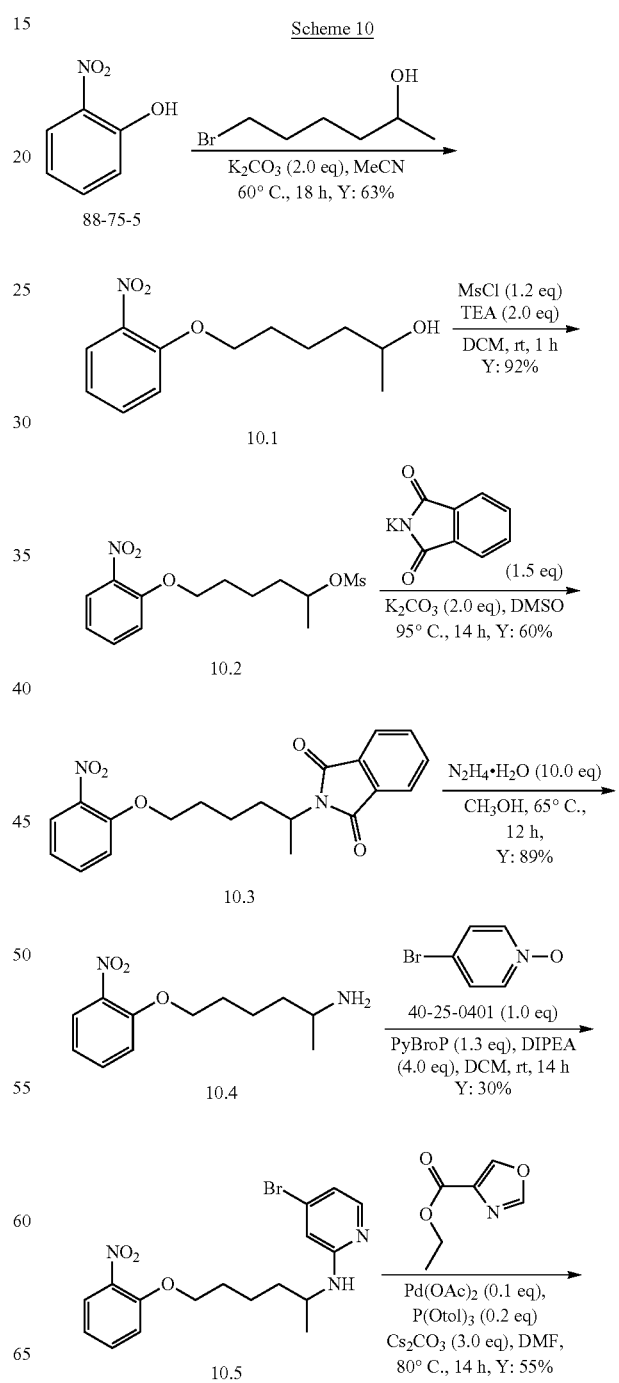

Scheme 10

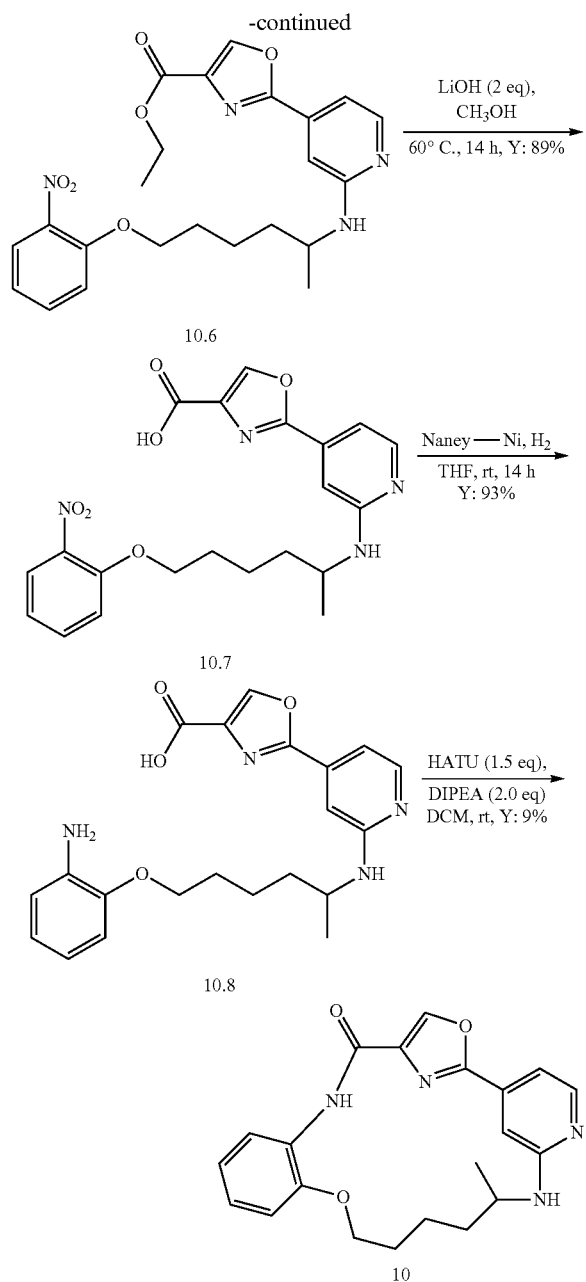

Synthesis of Compound 10.1

To a solution of 2-nitrophenol (2.6 g, 18.9 mmol, 1.0 eq) in CH₃CN (20 mL) were added 6-bromohexan-2-ol (3.4 g, 18.9 mmol, 1.0 eq) and K₂CO₃ (5.2 g, 37.8 mmol, 2.0 eq). The mixture was stirred at room temperature for 18 h. The solvent was removed in vacuo and the residue was diluted with water (80 mL), extracted with ethyl acetate (100 mL×3). The combined organic layers were washed with brine (80 mL×3), dried over Na₂SO₄ and concentrated under reduced pressure. The residue was purified by silica gel column (PE:EA=1:4) to give 10.1 (2.8 g, yield: 63%) as a yellow oil; ESI-MS (M+H)⁺: 240.1.

Synthesis of Compound 10.2

To a solution of 10.1 (2.8 g, 11.7 mmol, 1.0 eq) in DCM (20 mL) were added TEA (2.4 g, 23.4 mmol, 2.0 eq) and MsCl (1.6 g, 14.0 mmol, 1.2 eq) at 0° C. The mixture was stirred at room temperature for 1 h and washed with brine (20 mL×3). The organic layer was dried over Na₂SO₄ and concentrated under reduced pressure to give 10.2 (3.7 g, yield: 93%) as a yellow oil, which was used in the next step without further purification; ESI-MS (M+H)⁺: 318.1.

Synthesis of Compound 10.3

To a solution of 10.2 (3.7 g, 11.7 mmol, 1.0 eq) in DMSO (8 mL), K₂CO₃ (3.2 g, 23.4 mmol, 2.0 eq) and potassium 1,3-dioxoisoindolin-2-ide (3.2 g, 17.6 mmol, 1.5 eq) were added. The mixture was stirred at 95° C. for 14 h. The reaction solution was diluted with ethyl acetate (100 mL) and washed with brine (50 mL×3). The organic layer was dried over anhydrous Na₂SO₄, concentrated under reduced pressure. The residue was purified by silica gel column (PE:EA=1:3) to give 10.3 (2.6 g, yield: 60%) as a yellow solid; ESI-MS (M+H)⁺: 369.3.

Synthesis of Compound 10.4

To a solution of 10.3 (2.6 g, 7.07 mmol, 1.0 eq) in CH₃OH (20 mL), NH₂NH₂H₂O (3.5 g, 70.7 mmol, 10.0 eq) was added. The mixture was stirred at 65° C. for 12 h. The resulting mixture was filtered and the filtrate was evaporated in vacuo to afford 10.4 (1.5 g, yield: 89%) as a yellow oil; ESI-MS (M+H⁺): 239.1.

Synthesis of Compound 10.5

To a solution of 10.4 (1.6 g, 6.7 mmol, 1.0 eq) in DCM (20 mL) were added 4-bromopyridine 1-oxide (1.8 g, 10.0 mmol, 1.5 eq), PyBroP (4.1 g, 8.7 mmol, 1.3 eq) and DIPEA (3.5 g, 26.8 mmol, 4.0 eq). The mixture was stirred at room temperature for 14 h. The resulting mixture was washed with brine (20 mL×3). The organic layer was dried over sodium sulfate and concentrated under reduced pressure. The residue was purified by silica gel column (PE:EA=1:2) to give 10.5 (820 mg, yield: 30%) as a white solid; ESI-MS (M+H)⁺: 394.1.

Synthesis of Compound 10.6

To a solution of 10.5 (700 mg, 1.78 mmol, 1.0 eq) in DMF (10 mL) were added ethyl oxazole-4-carboxylate (251 mg, 1.78 mmol, 1.0 eq), Pd(OAc)₂ (40 mg, 0.18 mmol, 0.1 eq), P(Otol)₃ (108 mg, 0.36 mmol, 0.2 eq) and Cs₂CO₃ (1.74 g, 5.34 mmol, 3.0 eq). The mixture was stirred at 80° C. for 14 h, diluted with water (10 mL) and extracted with ethyl acetate (15 mL×3). The combined organic layers were washed with brine (10 mL×5), dried over anhydrous Na₂SO₄, concentrated under reduced pressure. The residue was purified by pre-TLC (PE:EA=2:1) to give 10.6 (437 mg, yield: 55%) as a white solid. ¹H NMR (400 MHz, DMSO-d₆) δ: 8.99 (s, 1H), 8.12 (d, J=5.2 Hz, 1H), 7.86-7.84 (m, 1H), 7.65-7.63 (m, 1H), 7.34 (d, J=8.0 Hz, 1H), 7.10 (d, J=8.0 Hz, 1H), 7.06 (s, 1H), 6.96-6.92 (m, 1H), 6.77 (d, J=8.0 Hz, 1H), 4.35 (q, J=7.2 Hz, 2H), 4.16 (t, J=6.4 Hz, 2H), 4.05-4.00 (m, 1H), 1.77-1.73 (m, 2H), 1.59-1.46 (m, 4H), 1.33 (t, J=7.2 Hz, 3H), 1.14 (d, J=6.4 Hz, 3H); ESI-MS (M+H)⁺: 455.3.

Synthesis of Compound 10.7

To a mixture of 10.6 (300 mg, 0.66 mmol, 1.0 eq) in CH₃OH (20 mL), a solution of LiOH (111 mg, 2.6 mmol, 4.0 eq) in water (5 mL) was added. The mixture was stirred at 60° C. for 14 h. The reaction mixture was adjusted to pH=5 with aqueous HCl solution (1N). The precipitate was collected by filtration and washed with MeOH (5 mL×3) to give 10.1 (250 mg, yield: 89%) as a yellow solid; ESI-MS (M+H)$^+$: 427.3.

Synthesis of Compound 10.8

To a solution of 10.7 (240 mg, 0.56 mmol) in THF (20 mL), Raney-Ni (48 mg, 20% wt) was added. The mixture was stirred under hydrogen atmosphere at room temperature for 14 h. The solution was filtered by Celite and the filtrate was concentrated in vacuo to afford 10.8 (207 mg, yield: 93%) as a yellow solid; ESI-MS (M+H)$^+$: 397.2.

Synthesis of Compound 10

To a solution of 10.8 (200 mg, 0.51 mmol, 1.0 eq) in DCM (50 mL) were added HATU (288 mg, 0.76 mmol, 1.5 eq) and DIPEA (145 mg, 1.12 mmol, 2.0 eq). The mixture was stirred at room temperature for 14 h and washed with water (40 mL×3), brine (40 mL×2). The organic layer was anhydrous Na$_2$SO$_4$ and concentrated under reduced pressure. The residue was purified by pre-TLC (PE:EA=3:1) to give 40-17 (17 mg, yield: 9%) as a white solid. $^1$H NMR (400 MHz, CDCl$_3$) δ: 10.18 (s, 1H), 8.55-8.51 (m, 1H), 8.32 (s, 1H), 8.25 (d, J=3.6 Hz, 1H), 7.10-7.00 (m, 3H), 6.91 (d, J=8.0 Hz, 1H), 5.16 (d, J=3.6 Hz, 1H), 4.19-4.16 (m, 1H), 4.07-4.02 (m, 1H), 3.32 (q, J=6.8 Hz, 1H), 2.33-2.23 (m, 1H), 2.10 (br. s, 1H), 1.97-1.87 (m, 3H), 1.64-1.45 (m, 2H), 1.43 (d, J=6.8 Hz, 3H); ESI-MS (M+H)$^+$: 379.2.

Example 11

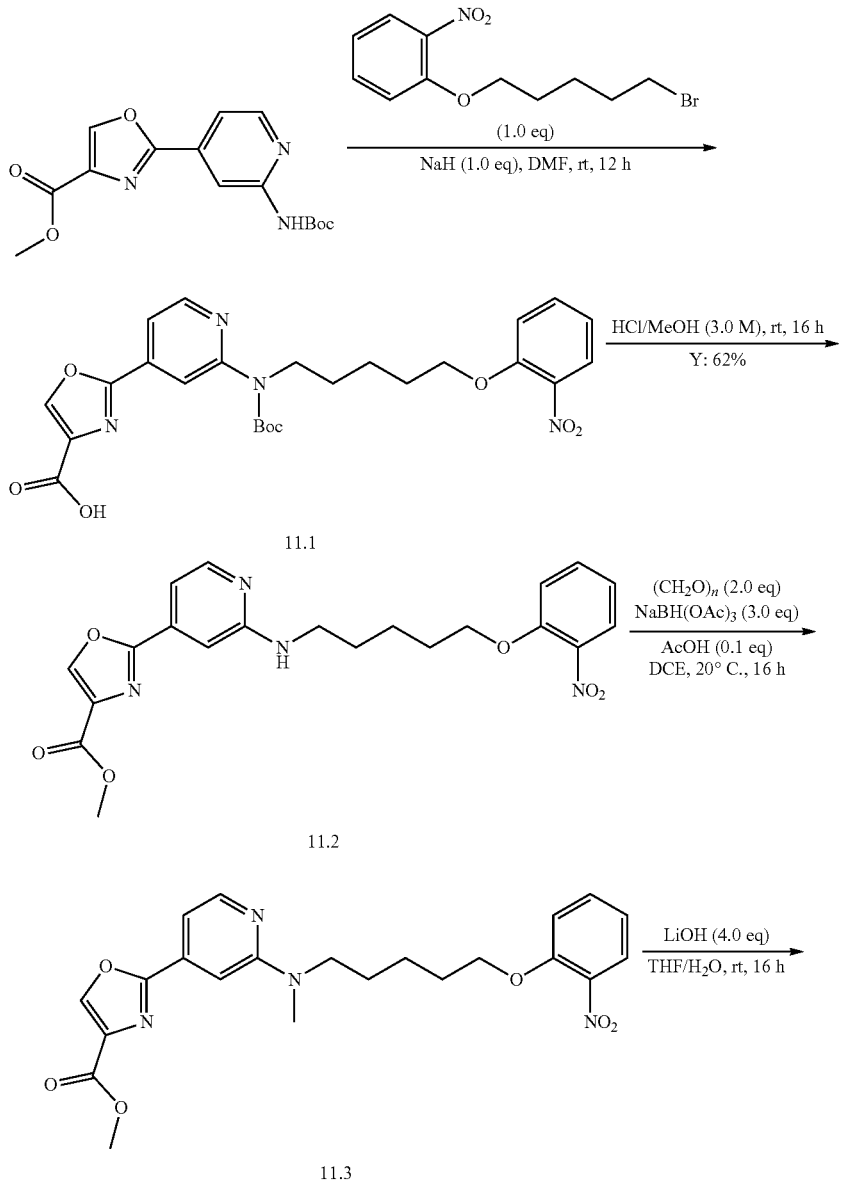

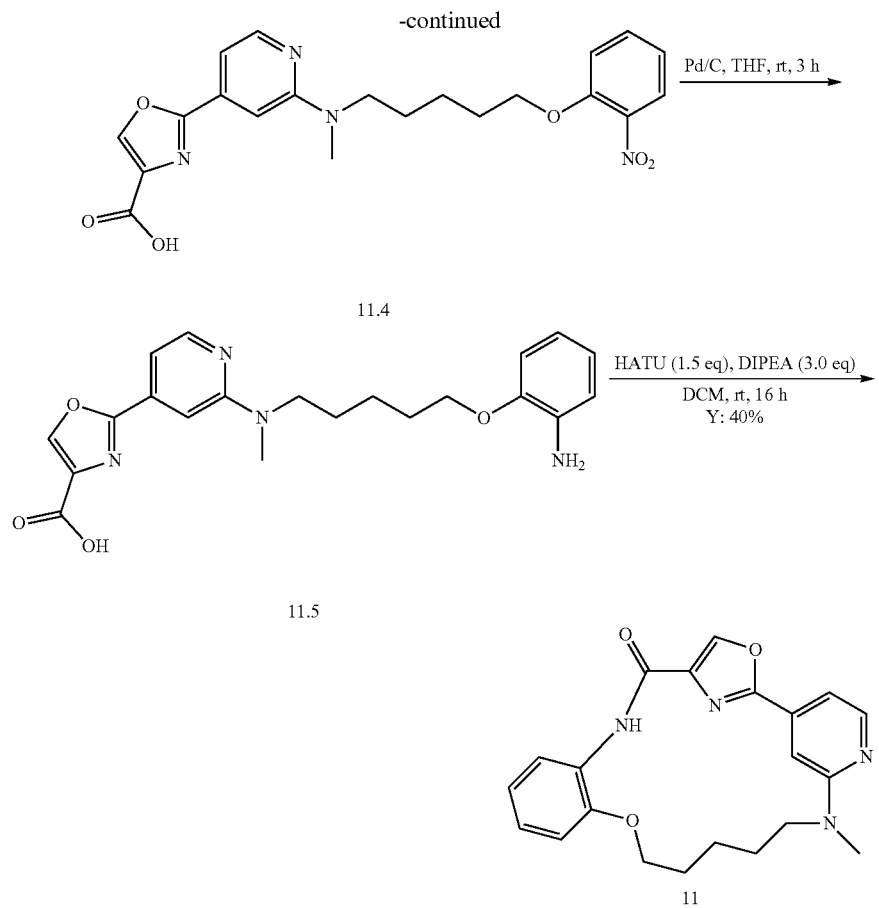

Synthesis of Compound 11.1

To a solution of methyl 2-(2-((tert-butoxycarbonyl)amino)pyridin-4-yl)oxazole-4-carboxylate (1.0 g, 3.13 mmol, 1.0 eq) in DMF (10 mL) was added NaH (138 mg, 3.44 mmol, 1.1 eq) at 0° C. The mixture was stirred at room temperature for 1 h. Then 1-((5-bromopentyl)oxy)-2-nitrobenzene (1.8 g, 6.26 mmol, 2.0 eq) was added at 0° C. The resulted mixture was stirred at room temperature for 16 h. The reaction solution was adjusted to pH=6 with acetic acid (20% in water), diluted with ethyl acetate (100 mL) and washed with water (50 mL×4), brine (50 mL). The organic layer was dried over anhydrous sodium sulfate and concentrated under reduced pressure. The residue was purified by prep-HPLC (MeOH/H$_2$O with 0.05% TFA as mobile phase; from 5% to 95%) to furnish the target compound 11.1 (500 mg, Y: 30%) as a white solid. $^1$H NMR (400 MHz, CDCl$_3$) δ: 8.45 (d, J=5.2 Hz, 1H), 8.36 (s, 1H), 8.27 (s, 1H), 7.73 (d, J=8.0 Hz, 1H), 7.63 (d, J=4.4 Hz, 1H), 7.44-7.40 (m, 1H), 6.98-6.92 (m, 2H), 4.02 (t, J=6.4 Hz, 2H), 3.95 (t, J=7.2 Hz, 2H), 3.87 (s, 3H), 1.81-1.77 (m, 3H), 1.66-1.61 (m, 3H), 1.46 (s, 9H); ESI-MS (M+H)$^+$: 513.1.

Synthesis of Compound 11.2

The solution of 11.1 (1.0 g, 1.9 mmol, 1.0 eq) in HCl/MeOH (3.0 M, 15 mL) was stirred at room temperature for 16 h, adjusted to pH=7 with saturated aqueous NaHCO$_3$ solution, concentrated under reduced pressure. The residue was dissolved in DCM (20 mL), filtered by Celite. The filtrate was concentrated under reduced pressure to give 11.2 (500 mg, Y: 62%) as a yellow oil. $^1$H NMR (400 MHz, CDCl$_3$) δ: 8.32 (s, 1H), 8.19 (d, J=5.6 Hz, 1H), 7.83-7.81 (m, 1H), 7.53-7.48 (m, 1H), 7.19 (d, J=5.2 Hz, 1H), 7.07-6.99 (m, 3H), 4.79-4.76 (m, 1H), 4.12 (t, J=6.2 Hz, 2H), 3.96 (s, 3H), 3.38 (q, J=6.4 Hz, 2H), 1.92-1.87 (m, 2H), 1.76-1.62 (m, 4H); ESI-MS (M+H)$^+$: 427.2.

Synthesis of Compound 11.3

To a solution of 11.2 (500 mg, 1.17 mmol, 1.0 eq) in DCE (5 mL), (CH$_2$O)$_n$(70 mg, 2.35 mmol, 1.1 eq), NaBH(OAc)$_3$ (744 mg, 3.51 mmol, 3.0 eq) and AcOH (7 mg, 0.12 mmol, 0.1 eq) were added. The mixture was stirred at room temperature for 16 h and diluted with DCM (20 mL). The solution was filtered by Celite, and the filtrate was concentrated under reduced pressure. The residue was purified by pre-TLC (PE:EA=1:1) to give 11.3 (90 mg, Y: 17%) as a white solid. $^1$H NMR (400 MHz, CDCl$_3$) δ: 8.32 (s, 1H), 8.25 (d, J=6.0 Hz, 1H), 7.82-7.80 (m, 1H), 7.52-7.47 (m, 1H), 7.15-7.14 (m, 2H), 7.06-6.98 (m, 2H), 4.11 (d, J=6.2 Hz, 2H), 3.97 (s, 3H), 3.63 (d, J=7.2 Hz, 2H), 3.11 (s, 3H), 1.92-1.88 (m, 2H), 1.72-1.68 (m, 2H), 1.59-1.56 (m, 2H); ESI-MS (M+H)$^+$: 441.2.

Synthesis of Compound 11.4

To a solution of 11.3 (200 mg, 0.45 mmol, 1.0 eq) in the mixed solvents of THF and H$_2$O (4/1, 2 mL), LiOH (44 mg, 1.82 mmol, 4.0 eq) was added. The reaction mixture was stirred at room temperature for 16 h, adjusted to pH=6 with acetic acid (20% in water) and concentrated under reduced pressure. The precipitate was collected by filtration to give 11.4 (150 mg, Y: 77%) as a yellow solid; ESI-MS (M+H)+: 427.2.

Synthesis of Compound 11.5

To a solution of 11.4 (150 mg, 0.35 mmol, 1.0 eq) in MeOH (4 mL) was added Pd/C (75 mg, 50% wt). The mixture was stirred at room temperature for 3 h under $H_2$ atmosphere. The solution was filtered by Celite and the filtrate was concentrated under reduced pressure to give 11.5 (100 mg, Y: 72%) as a yellow oil; ESI-MS (M+H)+: 397.2.

Synthesis of Compound 11

To a solution of 11.5 (130 mg, 0.33 mmol, 1.0 eq) in DCM (15 mL) were added HATU (188 mg, 0.50 mmol, 1.0 eq) and DIPEA (128 mg, 0.99 mmol, 3.0 eq). The mixture was stirred at room temperature for 16 h and concentrated under reduced pressure. The residue was purified by pre-TLC (PE:EA=1:2) to give 11 (50 mg, Y: 40%) as a yellow solid. $^1$H NMR (400 MHz, CDCl$_3$) □ δ: 10.13 (s, 1H), 8.54-8.51 (m, 1H), 8.35-8.31 (m, 2H), 7.35 (s, 1H), 7.07-6.98 (m, 3H), 6.89-6.87 (m, 1H), 4.09-4.08 (m, 2H), 3.41 (t, J=7.2 Hz, 2H), 3.27 (s, 3H), 1.92-1.78 (m, 6H); ESI-MS (M+H)+: 379.2

Example 12

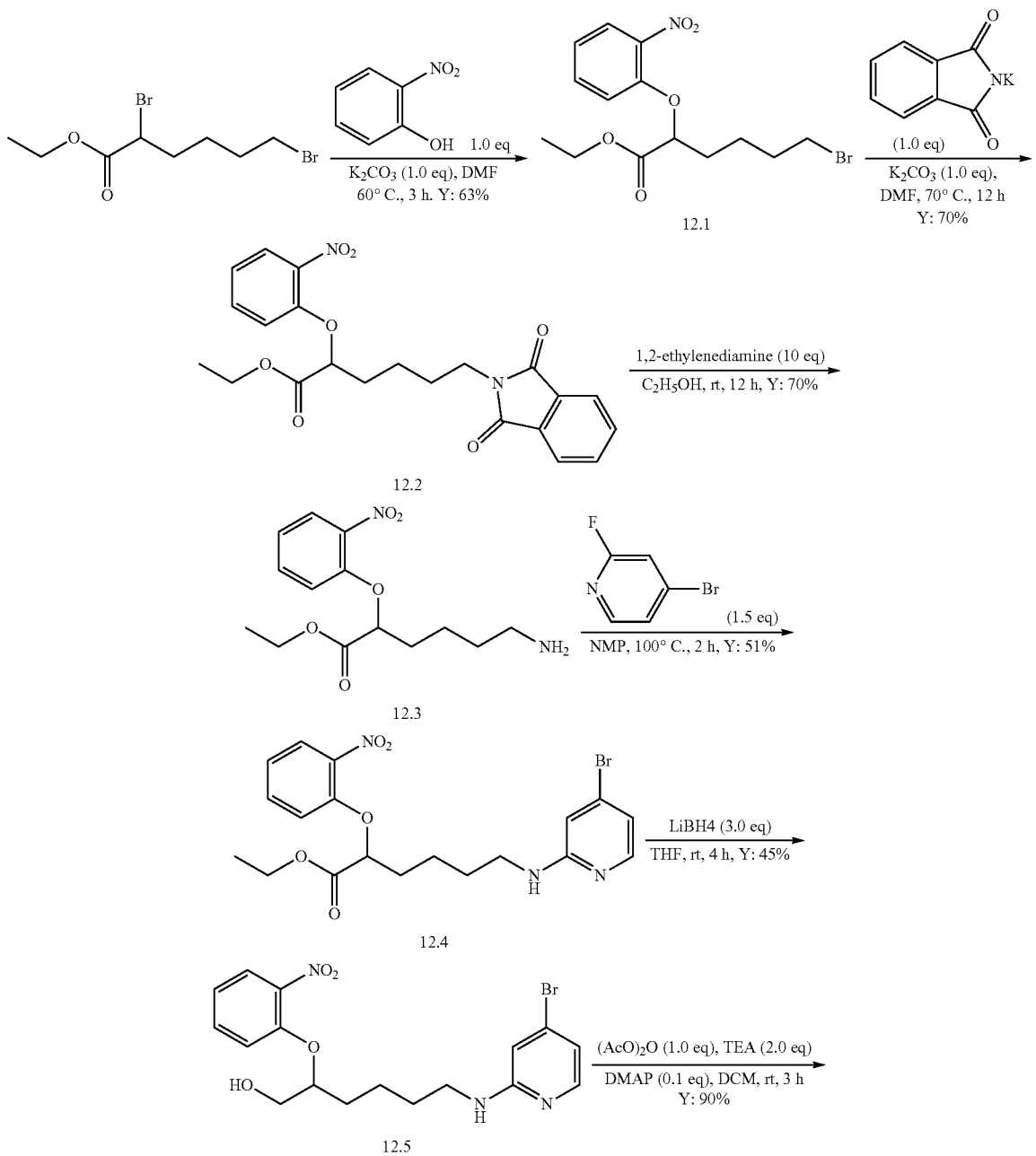

Scheme 12

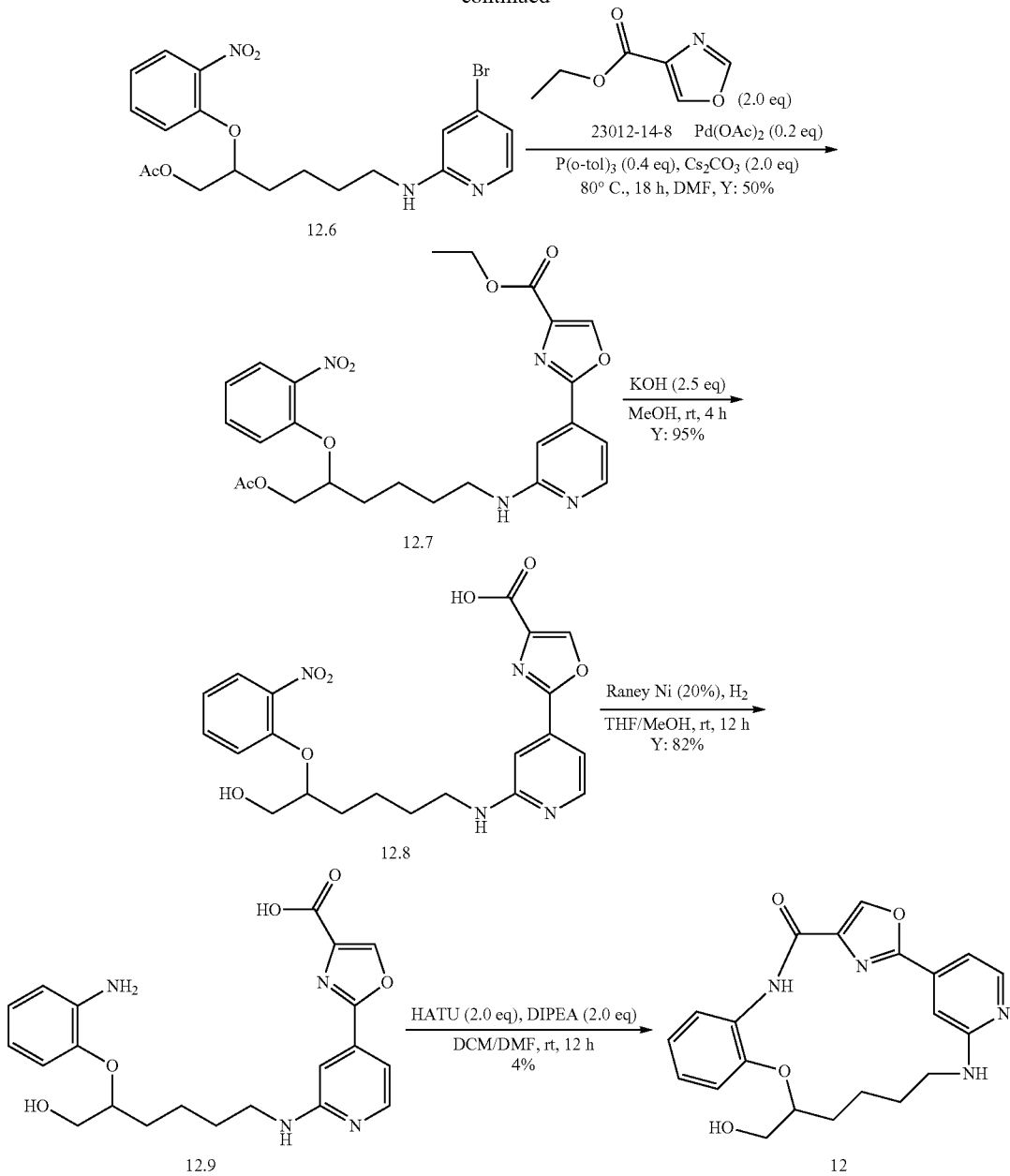

Synthesis of Compound 12.1

To a solution of ethyl 2,6-dibromohexanoate (3.0 g, 1.0 mmol) in DMF (10 mL) were added 2-nitrophenol (1.4 g, 1.0 mmol, 1.0 eq) and K$_2$CO$_3$ (1.4 g, 1.0 mmol, 1.0 eq). The reaction mixture was stirred at 60° C. for 3 h. The mixture was diluted with DCM (50 mL) and washed with water (50 mL), brine (50 mL×2). The organic layer was dried over anhydrous sodium sulfate and evaporated under vacuum. The residue was purified by silica gel column (PE/EA=5/1) to afford a yellow oil 12.1 (2.3 g, yield: 63%). $^1$H NMR (400 MHz, CDCl$_3$) δ: 7.84-7.81 (m, 1H), 7.49-7.45 (m, 1H), 7.08-7.06 (m, 1H), 7.00-6.88 (m, 1H), 4.73-4.71 (m, 1H), 4.24-4.18 (m, 2H), 3.43 (t, J=6.4 Hz, 2H), 2.06-2.02 (m, 2H), 1.95-1.90 (m, 2H), 1.75-1.69 (m, 2H), 1.23 (t, J=7.2 Hz, 3H); ESI-MS (M+Na)$^+$: 382.1.

Synthesis of Compound 12.2

To a solution of 12.1 (5.0 g, 13.9 mmol) in DMF (20 mL) were added potassium 1,3-dioxoisoindolin-2-ide (2.6 g, 13.9 mmol, 1.0 eq) and K$_2$CO$_3$ (2.0 g, 13.9 mmol, 1.0 eq). The reaction mixture was stirred at 70° C. for 12 h. The mixture was diluted with DCM (50 mL) and washed with water (50 mL), brine (50 mL×2). The organic layer was dried over anhydrous sodium sulfate and evaporated under vacuum. The residue was purified by silica gel column (PE/EA=3/1) to afford a yellow oil 12.2 (4.2 g, yield: 70%). $^1$H NMR (400 MHz, CDCl$_3$) δ: 7.86-7.81 (m, 3H), 7.75-7.70 (m, 2H), 7.49-7.44 (m, 1H), 7.07-7.03 (m, 1H), 6.88 (d, J=8.4 Hz, 1H), 4.72 (t, J=6.0 Hz, 1H), 4.20 (q, J=7.2 Hz, 2H), 3.72 (t, J=7.2 Hz, 2H), 2.09-2.04 (m, 2H), 1.79-1.73 (m, 2H), 1.65-1.59 (m, 2H), 1.22 (t, J=7.2 Hz, 3H); ESI-MS (M+H)$^+$: 427.1.

Synthesis of Compound 12.3

To a solution of 12.2 (1.0 g, 2.3 mmol) in ethanol (10 mL) was added 1,2-ethylenediamine (141 mg, 2.3 mmol, 2.0 eq). The mixture was stirred at room temperature for 12 h, and concentrated under reduced pressure. The residue was dissolved in DCM (20 mL) and washed with water (20 mL×2), brine (20 mL). The organic layer was dried over anhydrous sodium sulfate and evaporated under vacuum to afford a yellow oil 12.3 (500 mg, yield: 70%); ESI-MS (M+H)$^+$: 402.1.

Synthesis of Compound 12.4

To a solution of 12.3 (1.0 g, 3.4 mmol) in NMP (15 mL) was added 4-bromo-2-fluoropyridine (0.7 g, 4.1 mmol, 1.2 eq). The reaction mixture was stirred at 100° C. for 2 h. The mixture was diluted with DCM (15 mL), washed with water (15 mL×2) and brine (15 mL). The organic layer was dried over anhydrous sodium sulfate and evaporated under vacuum. The residue was purified by silica gel column (PE/EA=3/1) to afford a yellow solid 12.4 (780 mg, yield: 51%). $^1$H NMR (400 MHz, CDCl$_3$) □ δ: 7.85-7.80 (m, 2H), 7.49-7.45 (m, 1H), 7.08-7.04 (m, 1H), 6.87 (d, J=8.4 Hz, 1H), 6.68 (d, J=5.6 Hz, 1H), 6.55 (s, 1H), 4.74-4.71 (m, 1H), 4.20 (q, J=7.2 Hz, 2H), 3.29-3.27 (m, 2H), 2.09-2.02 (m, 2H), 1.68-1.64 (m, 4H), 1.23 (t, J=7.2 Hz, 3H); ESI-MS (M+H)$^+$: 452.1.

Synthesis of Compound 12.5

To a solution of 12.4 (1.5 g, 3.3 mmol) in THF (20 mL) was added LiBH$_4$ (200 mg, 10.0 mmol, 3.0 eq). The mixture was stirred at room temperature for 4 h. Then aqueous HCl (3 M, 5 mL) solution was added, and the resulted mixture was stirred 2 h at 70° C. The reaction solution was adjusted to pH=8 with saturated aqueous NaHCO$_3$ solution, diluted with DCM (40 mL), washed with water (30 mL×2) and brine (30 mL). The organic layer was dried over anhydrous sodium sulfate and evaporated under vacuum. The residue was purified by silica gel column (PE/EA=1/1) to afford a yellow solid 12.5 (610 mg, yield: 45%). $^1$H NMR (400 MHz, CDCl$_3$) □ δ: 7.86-7.82 (m, 1H), 7.80-7.77 (m, 1H), 7.53-7.49 (m, 1H), 7.14 (d, J=8.0 Hz, 1H), 7.09-7.05 (m, 1H), 6.71-6.68 (m, 1H), 6.53 (s, 1H), 4.65 (br. s, 1H), 4.53-4.50 (m, 1H), 3.83-3.75 (m, 2H), 3.28-3.24 (m, 2H), 1.85-1.83 (m, 2H), 1.82-1.79 (m, 2H), 1.61-1.56 (m, 2H); ESI-MS (M+H)$^+$: 410.1.

Synthesis of Compound 12.6

To a solution of 12.5 (500 mg, 1.2 mmol) in DCM (15 mL) were added (AcO)$_2$O (120 mg, 1.0 mmol, 1.2 eq), DMAP (14 mg, 0.12 mmol, 0.1 eq) and TEA (240 mg, 2.4 mmol, 2.0 eq). The mixture was stirred at room temperature for 3 h and washed with saturated aqueous NaHCO$_3$ solution (15 mL), water (15 mL×2), brine (15 mL). The organic layer was dried over anhydrous sodium sulfate and evaporated under vacuum. The residue was purified by pre-TLC (PE/EA=3/1) to afford a yellow solid 12.4 (500 mg, yield: 90%). $^1$H NMR (400 MHz, CDCl$_3$) □ δ: 7.87-7.81 (m, 2H), 7.62-7.61 (m, 1H), 7.44-7.36 (m, 1H), 7.13-7.11 (m, 1H), 6.78 (br. s, 1H), 6.65-6.61 (m, 2H), 4.82-4.76 (m, 1H), 4.24-4.13 (m, 2H), 3.20-3.17 (m, 2H), 1.92 (s, 3H), 1.71-1.67 (m, 2H), 1.54-1.50 (m, 2H), 1.35-1.33 (m, 2H); ESI-MS (M+H)$^+$: 452.1.

Synthesis of Compound 12.7

To a solution of 12.6 (550 mg, 8.6 mmol, 1.2 eq) in DMF (12 mL) were added 23012-14-8 (206 mg, 1.5 mmol, 1.2 eq), Pd(OAc)$_2$ (54 mg, 0.24 mmol, 0.2 eq), P(o-tol)$_3$ (146 mg, 0.48 mmol, 0.4 eq) and Cs$_2$CO$_3$ (780 mg, 2.4 mmol, 2.0 eq). After stirred at 80° C. for 18 h, the reaction mixture was diluted with water (10 mL) and extracted with ethyl acetate (20 mL×3). The combined organic layers were washed with brine (20 mL×5), dried over anhydrous Na$_2$SO$_4$ and concentrated under reduced pressure. The residue was purified by pre-TLC (PE/EA=3/1) to give 12.7 as yellow oil (300 mg, yield: 50%). $^1$H NMR (400 MHz, CDCl$_3$) □ δ: 8.90 (s, 1H), 8.11 (t, J=5.2 Hz, 1H), 7.86-7.79 (m, 1H), 7.63-7.58 (m, 1H), 7.44-7.35 (m, 1H), 7.11-7.07 (m, 1H), 7.04-7.02 (m, 1H), 6.96-6.92 (m, 2H), 4.80-4.78 (m, 1H), 4.30 (q, J=7.2 Hz, 2H), 4.27-4.11 (m, 2H), 3.28-3.25 (m, 2H), 1.91 (s, 3H), 1.71-1.69 (m, 2H), 1.57-1.53 (m, 2H), 1.47-1.44 (m, 2H), 1.30 (t, J=7.2 Hz, 3H); ESI-MS (M+H)$^+$: 512.1.

Synthesis of Compound 12.8

To a solution of 12.7 (350 mg, 0.7 mmol) in methanol (10 mL) was added KOH (95 mg, 1.7 mmol, 2.5 eq). The reaction mixture was stirred at room temperature for 4 h and then adjusted to pH=7 with HCl (3 M) at 0° C. The precipitate was collected by filtration to afford a white solid 12.8 (280 mg, yield: 95%). $^1$H NMR (400 MHz, CDCl$_3$) □ δ: 8.91 (s, 1H), 8.13-8.10 (m, 1H), 7.86-7.78 (m, 1H), 7.63-7.58 (m, 1H), 7.44-7.35 (m, 1H), 7.13-7.09 (m, 2H), 7.00-6.97 (m, 2H), 4.91 (br. s, 1H), 4.55-4.52 (m, 1H), 4.05-4.02 (m, 2H), 3.30-3.28 (m, 2H), 1.57-1.52 (m, 4H), 1.46-1.42 (m, 2H); ESI-MS (M+H)$^+$: 443.2.

Synthesis of Compound 12.9

To a solution of 12.8 (150 mg, 0.34 mmol) in THF/MeOH (60 mL/10 mL) was added raney Ni (30 mg, 20% wt). The reaction mixture was stirred for 12 h under H$_2$ atmosphere at room temperature. The solution was filtered by Celite and the filtrate was evaporated in vacuo to afford 12.9 as yellow oil (115 mg, yield: 82%); ESI-MS (M+H)$^+$: 413.2.

Synthesis of Compound 12

To a solution of 12.9 (150 mg, 0.36 mmol) in DCM/DMF (60 mL/10 mL) were added HATU (276 mg, 0.72 mmol, 2.0 eq) and DIPEA (185 mg, 1.4 mmol, 4.0 eq). The reaction mixture was stirred at room temperature for 12 h and washed with water (15 mL×3), brine (15 mL). The organic layer was dried over anhydrous sodium sulfate and concentrated under reduced pressure. The residue was purified by prep-HPLC (CH$_3$CN in H$_2$O—0.05% NH$_3$H$_2$O from 5%-90%) to afford a yellow solid 12 (7 mg, yield: 4%). $^1$H NMR (400 MHz, CDCl$_3$) □ δ: 8.55-8.53 (m, 1H), 8.34-8.32 (m, 1H), 8.23-8.19 (m, 1H), 7.36-7.31 (m, 1H), 7.09-7.01 (m, 4H), 5.30 (br. s, 1H), 4.27-4.25 (m, 1H), 4.12-4.09 (m, 2H), 3.41-3.36 (m, 2H), 1.98-1.97 (m, 2H), 1.83-1.80 (m, 4H); ESI-MS (M+H)$^+$: 395.1;

Example 13
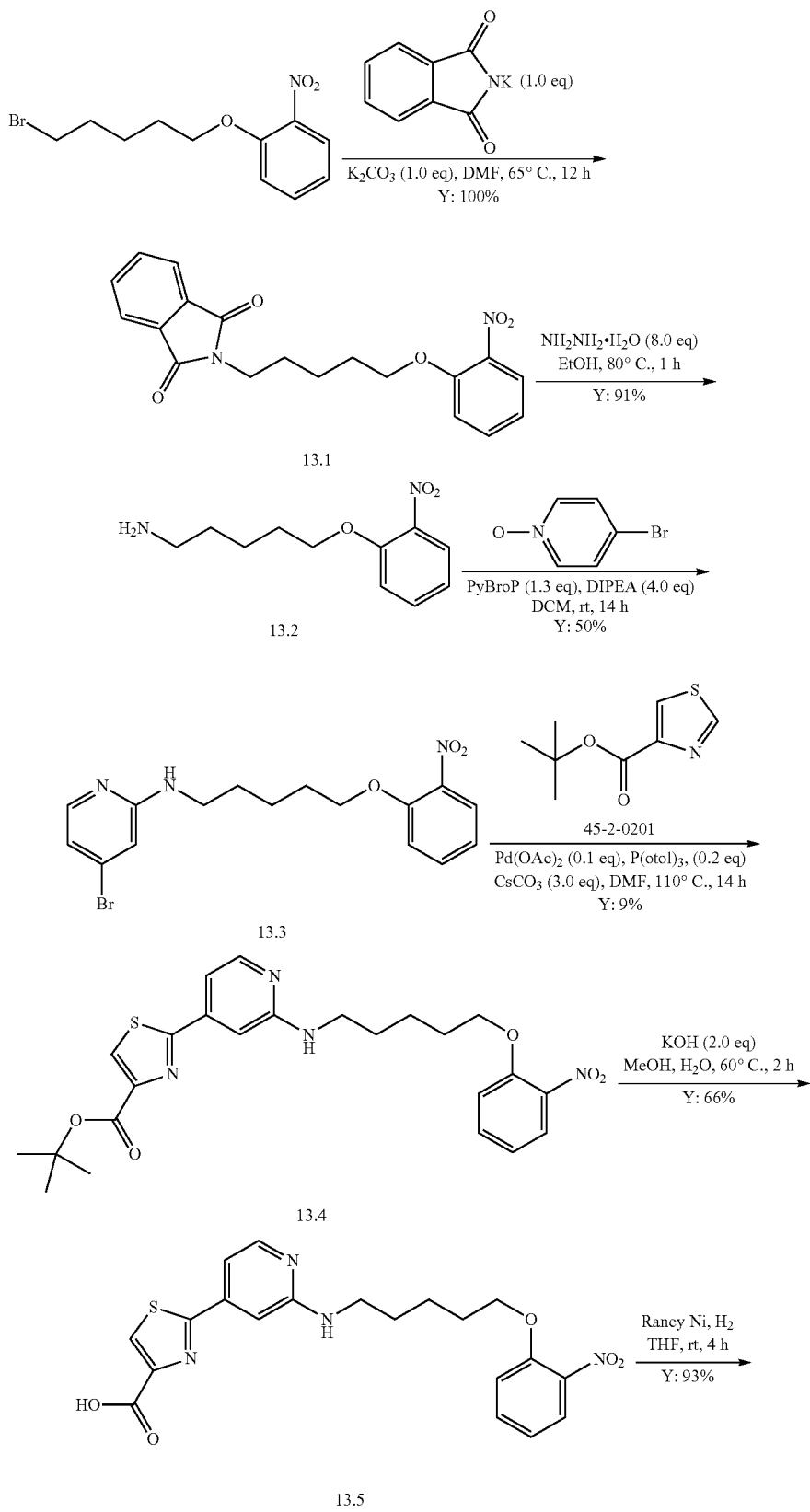

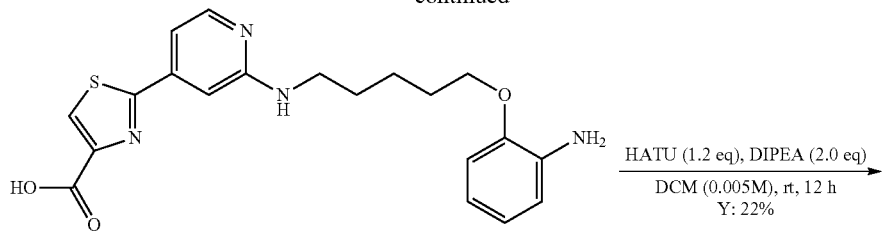

13.6

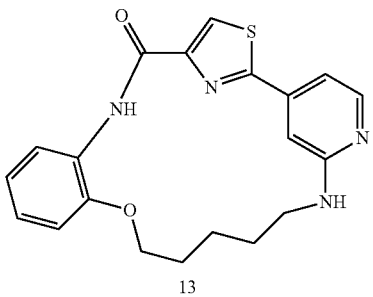

13

Synthesis of Compound 13.1

To a mixture of 1-((5-bromopentyl)oxy)-2-nitrobenzene (4.0 g, 14 mmol, 1.0 eq) and potassium phthalimide (2.8 g, 15 mmol, 1.1 eq) in DMF (40 mL) was added $K_2CO_3$ (1.9 g, 14 mmol, 1.0 eq). The mixture was stirred at 65° C. for 16 h. After cooling down, the mixture was diluted with EA (500 mL) and washed with water (200 mL×4), brine (200 mL). The organic layer was dried over sodium sulfate and concentrated under reduced pressure to give 13.1 (5.2 g, yield: 100%) as a yellow solid. $^1$H NMR (400 MHz, $CDCl_3$) □ δ: 7.85-7.79 (m, 3H), 7.72-7.70 (m, 2H), 7.52-7.47 (m, 1H), 7.05 (d, J=8.4 Hz, 1H), 6.99 (t, J=7.6 Hz, 1H), 4.09 (t, J=6.4 Hz, 2H), 3.72 (t, J=7.2 Hz, 2H), 1.93-1.86 (m, 2H), 1.82-1.73 (m, 2H), 1.59-1.52 (m, 2H); ESI-MS (M+23)$^+$: 355.2.

Synthesis of Compound 13.2

To the solution of 13.1 (5.2 g, 14.7 mmol, 1.0 eq) in EtOH (80 mL) was added $NH_2NH_2H_2O$ (5.9 g, 118 mmol, 8.0 eq). The reaction mixture was stirred at 80° C. for 1 h. After cooling down, the precipitate was filtered off and the filtrate was concentrated under reduced pressure to give 13.2 (3 g, yield: 91%) as a yellow oil. $^1$H NMR (400 MHz, $CDCl_3$) □δ: 7.81 (d, J=8.0 Hz, 1H), 7.53-7.49 (m, 1H), 7.06 (d, J=8.4 Hz, 1H), 7.00 (t, J=7.6 Hz, 1H), 4.12 (t, J=6.4 Hz, 2H), 2.72 (t, J=6.0 Hz, 2H), 1.87-1.82 (m, 2H), 1.54-1.51 (m, 4H), 1.35-1.28 (m, 2H); ESI-MS (M+H)$^+$: 225.1.

Synthesis of Compound 13.3

To a mixture of 4-bromopyridine 1-oxide (1.3 g, 5.8 mmol, 1.0 eq) in DCM (10 mL), DIPEA (3 g, 23.2 mmol, 4.0 eq), PyBrOP (3.5 g, 7.5 mmol, 1.3 eq) and 13.2 (1 g, 5.8 mmol, 1.0 eq) was added. The mixture was stirred at room temperature for 14 h, diluted with EA (200 mL) and washed with water (100 mL×4), brine (100 mL). The organic layer was dried over sodium sulfate and concentrated under reduced pressure. The residue was purified by silica gel (PE:EA=3:1) to give 13.3 (1.1 g, yield: 50%) as a yellow oil. $^1$H NMR (400 MHz, $CD_3OD$) □ δ: 7.78-7.75 (m, 2H), 7.58-7.54 (m, 1H), 7.23 (d, J=8.0 Hz, 1H), 7.05 (t, J=8.0 Hz, 1H), 6.69 (d, J=1.6 Hz, 1H), 6.64 (d, J=5.6 Hz, 1H), 4.15 (t, J=6.0 Hz, 2H), 3.28 (t, J=6.8 Hz, 2H), 1.89-1.82 (m, 2H), 1.70-1.57 (m, 4H); ESI-MS (M+1)$^+$: 380.0.

Synthesis of Compound 13.4

To a mixture of 13.3 (980 mg, 2.58 mmol, 1.0 eq), tert-butyl thiazole-4-carboxylate (478 mg, 2.58 mmol, 1.0 eq), $Cs_2CO_3$ (1.7 g, 5.2 mmol, 2.0 eq) in DMF (20 mL), $Pd(OAc)_2$ (58 mg, 0.26 mmol, 0.1 eq) and P(o-tol)$_3$ (156 mg, 0.52 mmol, 0.2 eq) were added under $N_2$ atmosphere. The mixture stirred at 110° C. for 14 h under $N_2$ atmosphere. After cooling down, the mixture was diluted with EA (200 mL) and washed with water (100 mL×4), brine (100 mL). The organic layer was dried over sodium sulfate and concentrated under reduced pressure. The residue was purified by silica gel column (PE:EA=3:1) to give 13.4 (110 mg, yield: 9%) as a yellow oil. $^1$H NMR (400 MHz, $CDCl_3$) □ δ: 8.15 (d, J=5.2 Hz, 1H), 8.09 (s, 1H), 7.81 (d, J=7.6 Hz, 1H), 7.52-7.48 (m, 1H), 7.07-6.98 (m, 4H), 4.77 (t, J=5.2 Hz, 1H), 4.12 (t, J=6.4 Hz, 2H), 3.95 (q, J=6.8 Hz, 2H), 1.94-1.87 (m, 2H), 1.75-1.70 (m, 2H), 1.67-1.65 (m, 2H), 1.63 (s, 9H); ESI-MS (M+H)$^+$: 485.2

Synthesis of Compound 13.5

To a solution of 13.4 (110 mg, 0.23 mmol, 1.0 eq) in MeOH (5 mL) and $H_2O$ (5 mL) was added KOH (25 mg, 0.46 mmol, 2.0 eq). The reaction mixture was stirred at 60° C. for 2 h. Then the reaction was cooled to 0° C., and adjusted to pH=6 with HCl (1 N). The precipitate was collected by filtration to give 13.5 as a yellow solid (65 mg, yield: 66%). $^1$H NMR (400 MHz, DMSO-$d_6$) □ δ: 8.53 (s, 1H), 8.08 (d, J=5.2 Hz, 1H), 7.84 (d, J=8.0 Hz, 1H), 7.65-7.61 (m, 1H), 7.35 (d, J=8.8 Hz, 1H), 7.09 (t, J=7.6 Hz, 1H), 7.04 (s, 1H), 6.93 (d, J=5.6 Hz, 1H), 6.88 (t, J=5.2 Hz, 1H), 4.18-4.15 (m, 2H), 3.32-3.28 (m, 2H), 1.78-1.73 (m, 2H), 1.62-1.46 (m, 4H); ESI-MS (M+H)$^+$: 429.2.

Synthesis of Compound 13.6

To a solution of 13.5 (130 mg, 0.3 mmol) in THF (10 mL) was added raney Ni (26 mg, 20% wt). The mixture was stirred at room temperature for 4 h under $H_2$ atmosphere. The catalyst was filtered off by Celite. The filtrate was concentrated under reduced pressure to give 13.6 (110 mg, yield: 93%); ESI-MS $(M+H)^+$: 399.0.

Synthesis of Compound 13

To a solution of 13.6 (130 mg, 0.33 mmol, 1.0 eq) in DCM (66 mL) were added HATU (150 mg, 0.39 mmol, 1.2 eq) and DIPEA (85 mg, 0.66 mmol, 2.0 eq). The mixture was stirred at room temperature for 12 h and washed with water (10 mL), brine (10 mL). The organic layer was dried over sodium sulfate and concentrated under reduced pressure. The residue was purified by pre-TLC (PE:EA=1:2) to give 13 (27 mg, yield: 22%) as a yellow solid. $^1$H NMR (400 MHz, CDCl$_3$) □ δ: 10.08 (s, 1H), 8.67 (d, J=7.6 Hz, 1H), 8.27 (s, 1H), 8.19 (d, J=5.2 Hz, 1H), 7.09-7.00 (m, 2H), 6.94-6.88 (m, 2H), 5.39 (t, J=6.0 Hz, 1H), 4.08 (t, J=4.4 Hz, 2H), 3.35 (q, J=6.8 Hz, 2H), 1.92-1.76 (m, 6H); ESI-MS $(M+H)^+$: 381.0; HPLC: 214 nm: 100.00%, 254 nm: 100.00%.

Examples 14 and 15

Scheme 14

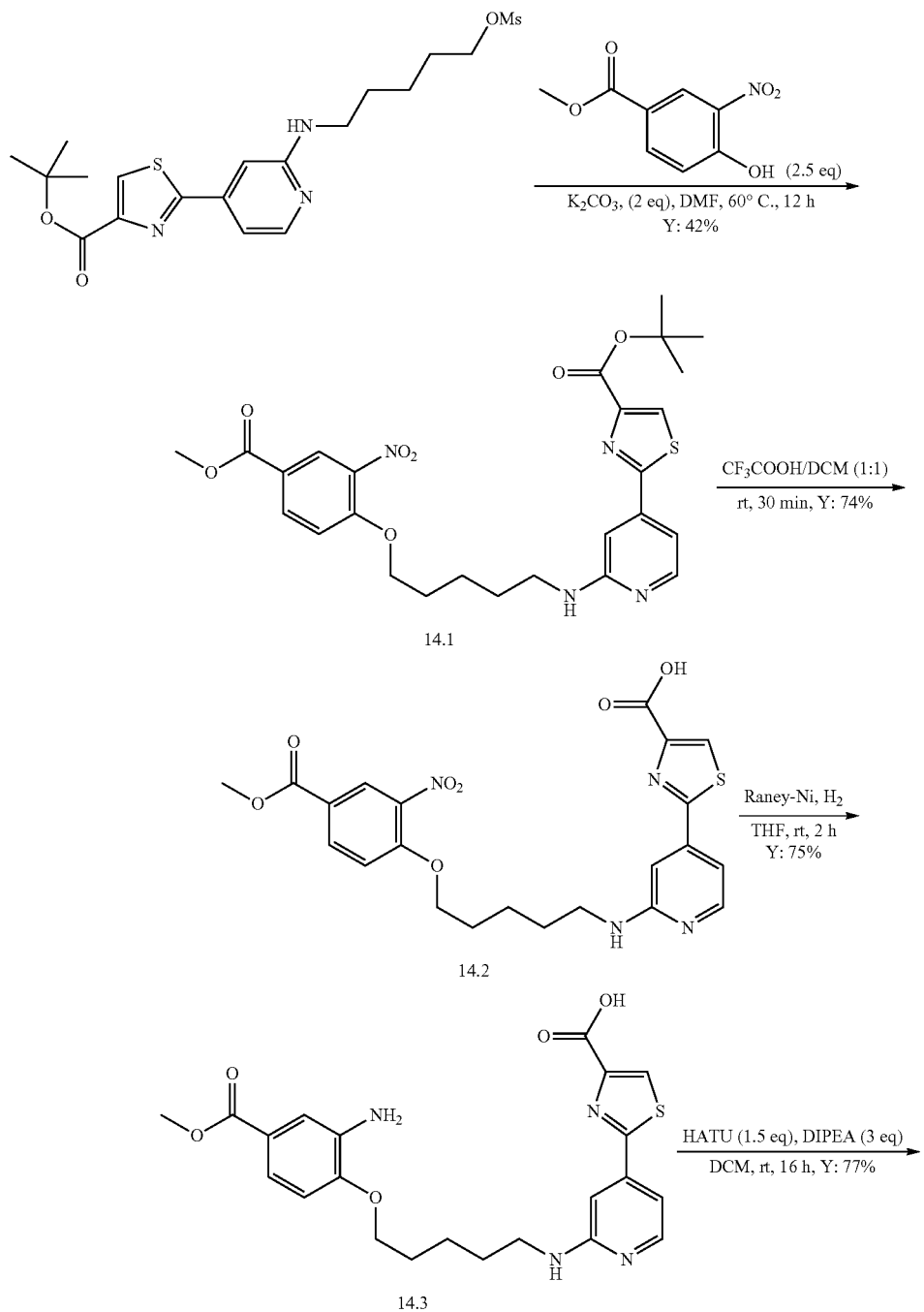

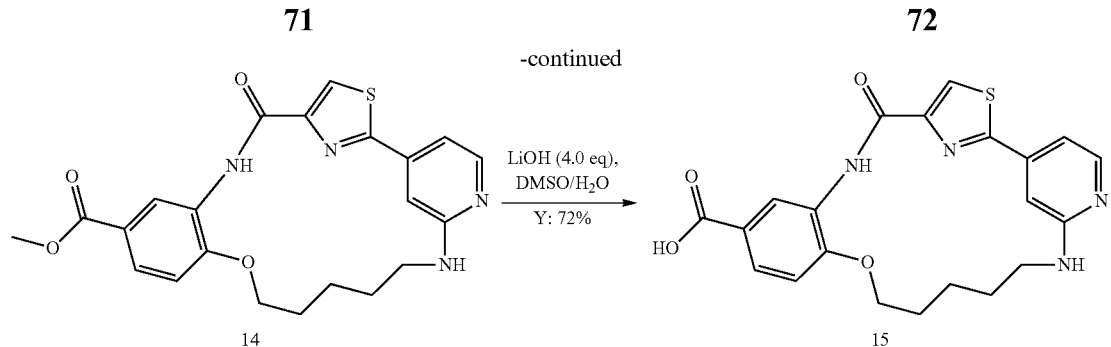

Synthesis of Compound 14.1

To a solution of 45-6-0301-Ms (2.10 g, 4.76 mmol, 1.0 eq) and methyl 4-hydroxy-3-nitrobenzoate (3.75 g, 19.04 mmol, 4.0 eq) in DMF (10 mL), $K_2CO_3$ (1.31 g, 9.52 mmol, 2.0 eq) was added. The reaction mixture was stirred at 60° C. for 12 h and then diluted with ethyl acetate (100 mL). The organic layer was washed with water (80 mL×4), brine (80 mL), dried over anhydrous sodium sulfate and concentrated under reduced pressure. The residue was purified by silica gel column (PE:EA=1:1) to give 14.1 (1.0 g, yield: 42%) as a yellow solid; ESI-MS (M+H)$^+$: 543.1.

Synthesis of Compound 14.2

To a solution of 14.1 (1.1 g, 2.03 mmol, 1.0 eq) in DCM (10 mL) was added TFA (10 mL). The reaction mixture was stirred at room temperature for 30 minutes and then concentrated under reduced pressure. The residue was neutralized with saturated anhydrous $NaHCO_3$ solution to pH=8, and then adjusted to pH=6 with HCl (1 N). The precipitate was collected by filtration to give 14.2 (770 mg, yield: 74%); ESI-MS (M+H)$^+$: 487.1.

Synthesis of Compound 14.3

To a solution of 14.2 (650 mg, 1.43 mmol, 1.0 eq) in THF/MeOH (1:1, 30 mL), raney Ni (250 mg) was added. The reaction mixture was stirred at room temperature for 3 h under $H_2$ atmosphere. The reaction solution was filtered by Celite. The filtrate was concentrated under reduced pressure to give 14.3 (450 mg, yield: 75%); ESI-MS (M+H)$^+$: 457.1.

Synthesis of Compound 14

To a solution of 14.3 (450 mg, 1.0 mmol, 1.0 eq) in DCM (250 mL) were added HATU (570 mg, 1.5 mmol, 1.5 eq) and DIPEA (387 mg, 3.0 mmol, 3.0 eq). The mixture was stirred at room temperature for 14 h. The precipitate was collected by filtration and washed with MeOH (10 mL) to give 14 (330 mg, yield: 76%) as a yellow solid. $^1$H NMR (400 MHz, CDCl$_3$) □ δ: 10.04 (s, 1H), 9.32 (s, 1H), 8.30 (s, 1H), 8.18 (d, J=4.0 Hz, 1H), 7.88-7.84 (m, 1H), 7.27 (d, J=5.6 Hz, 1H), 6.97-6.93 (m, 2H), 5.62 (br. s, 1H), 4.16 (t, J=3.6 Hz, 2H), 3.92 (s, 3H), 3.39 (t, J=5.2 Hz, 2H), 1.96-1.72 (m, 6H); ESI-MS (M+H)$^+$: 439.2

Synthesis of Compound 15

To a solution of 14 (300 mg, 0.71 mmol, 1.0 eq) in DMSO (20 mL) was added LiOH (68 mg, 2.84 mmol, 4.0 eq) in $H_2O$ (20 mL). The reaction mixture was stirred at 60° C. for 14 h, adjusted to pH=7 with HCl (1 N). The precipitate was collected by filtration and washed with MeOH (10 mL) to give 15 (210 mg, yield: 72%) as a yellow solid. $^1$H NMR (400 MHz, DMSO-d$_6$) □ δ: 9.91 (s, 1H), 9.00 (s, 1H), 8.61 (s, 1H), 8.16 (d, J=4.8 Hz, 1H), 7.66 (d, J=7.6 Hz, 1H), 7.09-7.07 (m, 2H), 7.02-6.98 (m, 1H), 4.11-4.07 (m, 2H), 3.20 (d, J=4.2 Hz, 2H), 1.83-1.79 (m, 4H), 1.64-1.57 (m, 2H); ESI-MS (M+H)$^+$: 425.0; HPLC: 214 nm: 95.53%, 254 nm: 100%.

Example 16

Synthesis of Compound 16

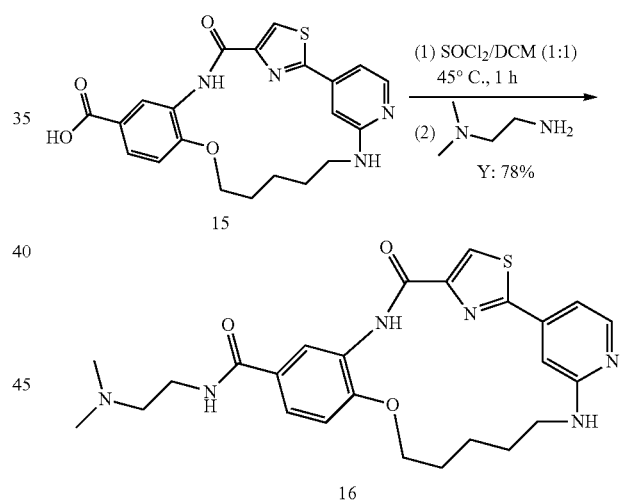

To a solution of 15 (20 mg, 0.05 mmol, 1.0 eq) in DCM (1.0 mL) was added SOCl$_2$ (1.0 mL). The reaction mixture was stirred at 45° C. for 1 h under N$_2$. The excess SOCl$_2$ was removed in vacuo. The residue was dissolved in DCM (2.0 mL) and N,N-dimethylethane-1,2-diamine (12 mg, 0.15 mmol, 3.0 eq) was added. The mixture was stirred at room temperature for 15 min, concentrated under reduced pressure. The residue was purified by prep-HPLC (MeOH/ 0.05% NH$_3$.H$_2$O in H$_2$O=10~95%) to give 16 (18 mg, yield: 78%) as a yellow solid. $^1$H NMR (400 MHz, CD$_3$OD) □ δ: 9.88 (s, 1H), 8.91 (s, 1H), 8.54 (s, 1H), 7.96 (d, J=6.4 Hz, 1H), 7.57-7.53 (m, 2H), 7.16 (d, J=6.0 Hz, 1H), 7.00-6.97 (m, 1H), 4.09-4.07 (m, 2H), 3.67-3.65 (m, 2H), 3.46-3.42 (m, 2H), 3.31-3.21 (m, 2H), 3.07 (s, 6H), 1.84-1.70 (m, 6H); ESI-MS (M+H)$^+$: 495.1; HPLC: 214 nm: 96.1%, 254 nm: 98.0%.

Example 17

Synthesis of Compound 17

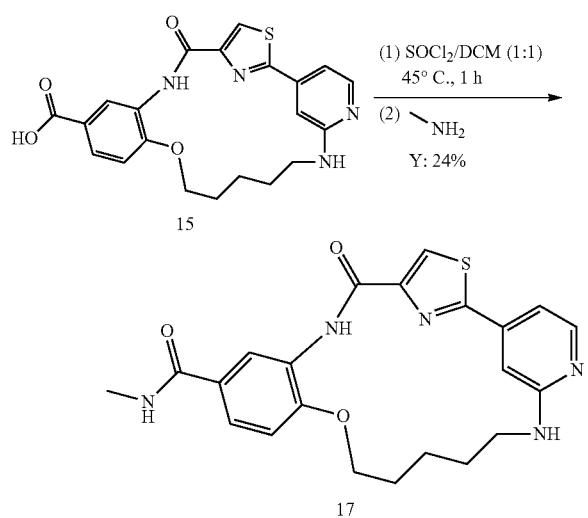

The experiment procedure was similar to compound 16. Purified by prep-HPLC (MeOH/0.05% NH$_3$H$_2$O in H$_2$O=10~95%). Weight: afforded 17 as yellow solid 15 mg, yield: 24%. $^1$H NMR (400 MHz, DMSO-d$_6$) □ δ: 9.97 (s, 1H), 8.99 (d, J=2.0 Hz, 1H), 8.65 (s, 1H), 8.35-8.33 (m, 1H), 8.19-8.15 (m, 1H), 7.60 (d, J=8.4 Hz, 1H), 7.15-7.10 (m, 2H), 7.08-7.05 (m, 1H), 7.01-7.00 (m, 1H), 4.17-4.13 (m, 2H), 3.20-3.16 (m, 2H), 2.78 (s, 3H), 1.82-1.62 (m, 6H); ESI-MS (M+H)$^+$: 356.2; HPLC: 214 nm: 100%, 254 nm: 93.3%.

Example 18

Synthesis of Compound 18

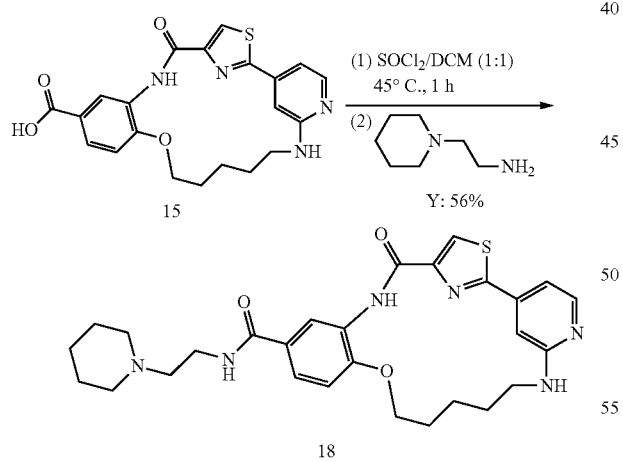

The experiment procedure was similar to compound 16 Purified by prep-HPLC (MeOH/0.05% NH$_3$H$_2$O in H$_2$O=10~95%). Afforded 18 yellow solid 15 mg, yield: 56%. $^1$H NMR (400 MHz, CD3OD) □ δ: 10.13 (s, 1H), 9.08 (d, J=2.4 Hz, 1H), 8.68 (s, 1H), 8.10 (d, J=6.4 Hz, 1H), 7.77-7.68 (m, 2H), 7.31 (d, J=6.4 Hz, 1H), 7.17 (d, J=8.4 Hz, 1H), 4.25-4.24 (m, 2H), 3.80-3.77 (m, 2H), 3.74-3.71 (m, 2H), 3.52-3.49 (m, 2H), 3.37-3.34 (m, 2H), 3.05-3.00 (m, 2H), 2.04-1.18 (m, 12H); ESI-MS (M+H)$^+$: 535.3; HPLC: 214 nm: 100%, 254 nm: 100%.

Example 19

Synthesis of Compound 19

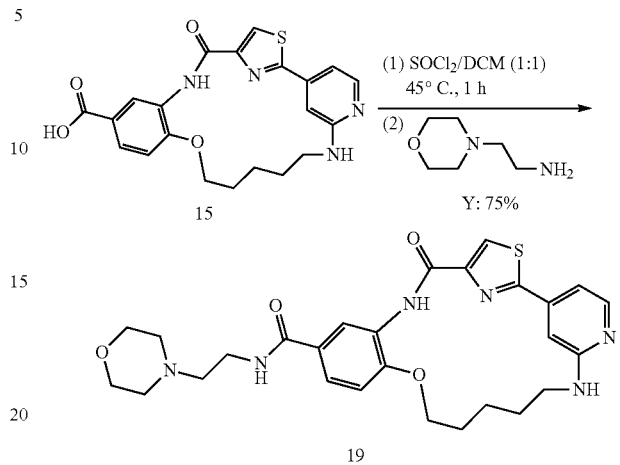

The experiment procedure was similar to compound 16 Purified by prep-HPLC (MeOH/0.05% NH$_3$H$_2$O in H$_2$O=10~95%). Weight: yellow solid 25 mg, yield: 75%. $^1$H NMR (400 MHz, CD$_3$OD) □ δ: 10.09 (s, 1H), 9.08 (d, J=2.0 Hz, 1H), 8.71 (s, 1H), 8.09 (d, J=6.8 Hz, 1H), 7.75 (s, 1H), 7.70 (d, J=8.4 Hz, 1H), 7.36-7.34 (m, 1H), 7.16 (d, J=8.4 Hz, 1H), 4.01-3.95 (m, 2H), 3.80-3.76 (m, 4H), 3.60-3.56 (m, 3H), 3.54-3.32 (m, 3H), 3.31-3.16 (m, 1H), 3.14-3.13 (m, 1H), 3.80-2.69 (m, 2H), 1.96-1.83 (m, 6H); ESI-MS (M+H)$^+$: 537.2; HPLC: 214 nm: 100%, 254 nm: 99.8%.

Example 20

Synthesis of Compound 20

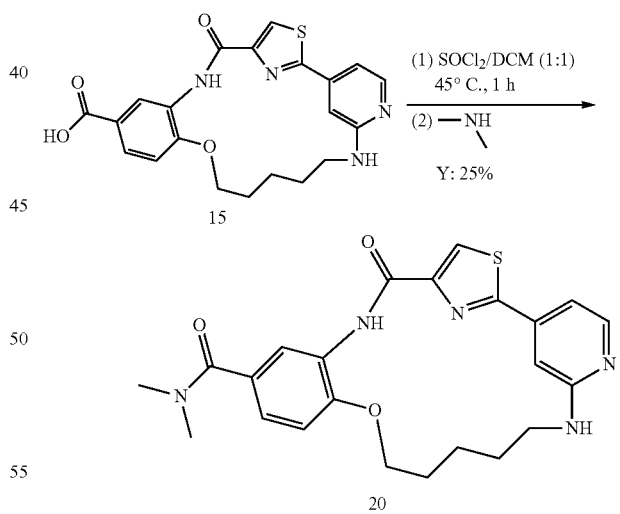

The experiment procedure was similar to compound 16 Purified by prep-HPLC (MeOH/0.05% NH$_3$H$_2$O in H$_2$O=10~95%). To afford 20 as a yellow solid 5.2 mg, yield: 25%. $^1$H NMR (400 MHz, CDCl$_3$) □ δ: 10.71-10.70 (m, 1H), 9.96 (s, 1H), 8.76 (d, J=2.4 Hz, 1H), 8.46 (s, 1H), 7.88 (d, J=6.4 Hz, 1H), 7.64 (s, 1H), 7.30-7.27 (m, 1H), 7.02-7.00 (m, 1H), 6.94 (d, J=8.4 Hz, 1H), 4.13-4.12 (m, 2H), 3.49-3.46 (m, 2H), 3.10 (s, 6H), 1.94-1.82 (m, 3H), 1.77-1.66 (m, 3H); ESI-MS (M+H)$^+$: 452.2; HPLC: 214 nm: 100%, 254 nm: 100%.

Example 21

Synthesis of Compound 21

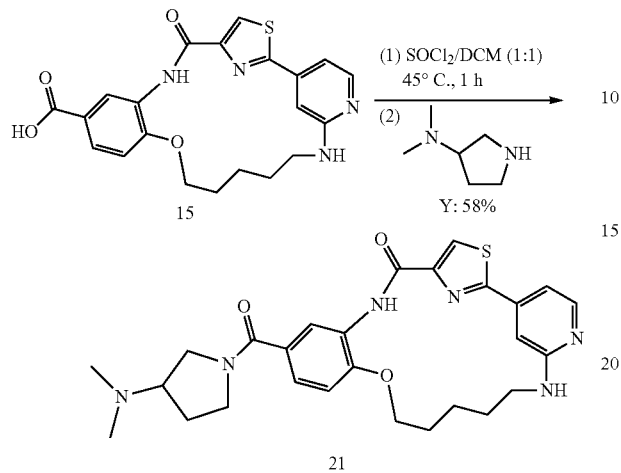

The experiment procedure was similar to compound 16 Purified by prep-HPLC (MeOH/0.05% NH$_3$H$_2$O in H$_2$O=10~95%). To afford 21 as a yellow solid 13 mg, yield: 58%. $^1$H NMR (400 MHz, CD$_3$OD) δ: 10.11 (s, 1H), 8.84 (s, 1H), 8.65 (s, 1H), 8.09 (d, J=6.8 Hz, 1H), 7.69 (s, 1H), 7.41 (d, J=8.4 Hz, 1H), 7.31 (d, J=6.4 Hz, 1H), 7.16 (d, J=8.4 Hz, 1H), 4.21-4.20 (m, 2H), 4.13-4.04 (m, 1H), 3.86-3.78 (m, 4H), 3.52-3.49 (m, 2H), 3.01 (s, 6H), 2.54-2.50 (m, 1H), 2.24-2.20 (m, 1H), 2.00-1.81 (m, 6H); ESI-MS (M+H)$^+$: 521.2; HPLC: 214 nm: 100%, 254 nm: 100%.

Example 22

Synthesis of Compound 22

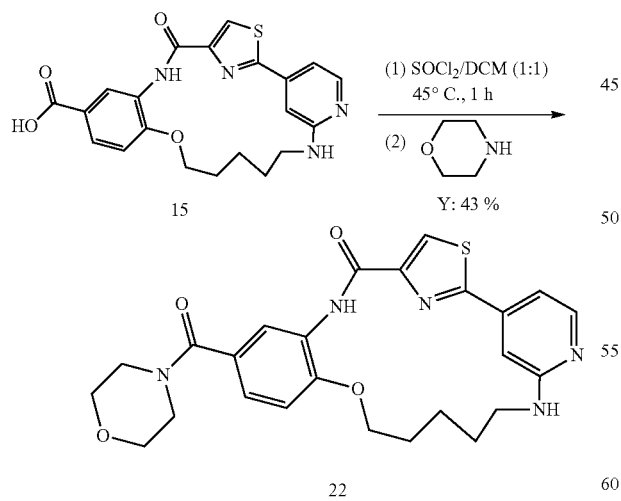

The experiment procedure was similar to compound 16 Purified by prep-HPLC (MeOH/0.05% NH3.H2O in H$_2$O=10~95%). To afford 22 as a yellow solid 10 mg, yield: 43%. 1H NMR (400 MHz, CDCl3) δ: 10.08 (s, 1H), 8.77-8.76 (m, 1H), 8.31 (s, 1H), 8.16 (d, J=5.6 Hz, 1H), 7.30-7.29 (m, 2H), 6.96-6.94 (m, 2H), 4.12-4.10 (m, 2H), 3.74-3.64 (m, 8H), 3.39-3.37 (m, 2H), 1.93-1.76 (m, 6H); ESI-MS (M+H)$^+$: 494.2; HPLC: 214 nm: 100%, 254 nm: 100%.

Example 23

Synthesis of Compound 23

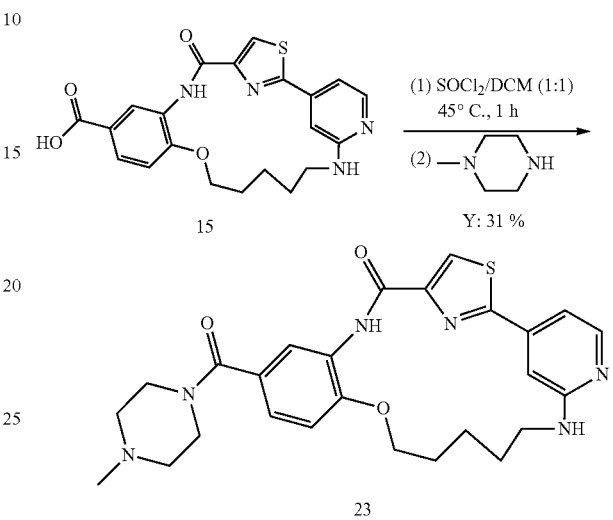

The experiment procedure was similar to compound 16 Purified by prep-HPLC (MeOH/0.05% NH$_3$H$_2$O in H$_2$O=10~95%). To afford 23 as a yellow solid 15 mg, yield: 31%. $^1$H NMR (400 MHz, CD$_3$OD) δ: 10.08 (s, 1H), 8.72 (d, J=2.0 Hz, 1H), 8.66 (s, 1H), 8.08 (d, J=6.4 Hz, 1H), 7.70 (s, 1H), 7.33-7.31 (m, 2H), 7.16 (d, J=8.4 Hz, 1H), 4.20-4.18 (m, 2H), 3.53-3.50 (m, 2H), 3.41-3.36 (m, 6H), 3.33-3.31 (m, 2H), 3.00 (s, 3H), 1.94-1.81 (m, 6H); ESI-MS (M+H)$^+$: 507.2; HPLC: 214 nm: 100%, 254 nm: 100%.

Example 24

Synthesis of Compound 24

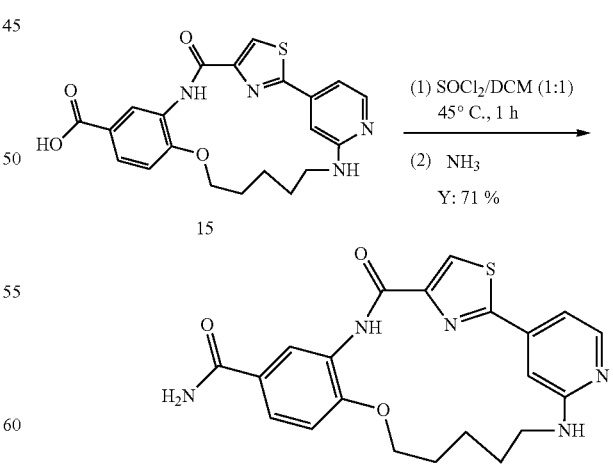

The experiment procedure was similar to compound 16 Purified by prep-HPLC (MeOH/0.05% NH$_3$H$_2$O in H$_2$O=10~95%). To afford 24 as a yellow solid 25 mg, yield:

71%. $^1$H NMR (400 MHz, DMSO-d$_6$) δ: 9.97 (s, 1H), 9.02 (d, J=2.0 Hz, 1H), 8.64 (s, 1H), 8.16 (d, J=5.2 Hz, 1H), 7.88 (s, 1H), 7.67-7.65 (m, 1H), 7.26-7.23 (m, 1H), 7.13-7.10 (m, 2H), 7.08-7.04 (m, 1H), 7.01-7.00 (m, 1H), 4.15-4.14 (m, 2H), 3.22-3.17 (m, 2H), 1.82-1.61 (m, 6H); ESI-MS (M+H)$^+$: 424.1; HPLC: 214 nm: 100%, 254 nm: 100%.
Example 25
Scheme 25
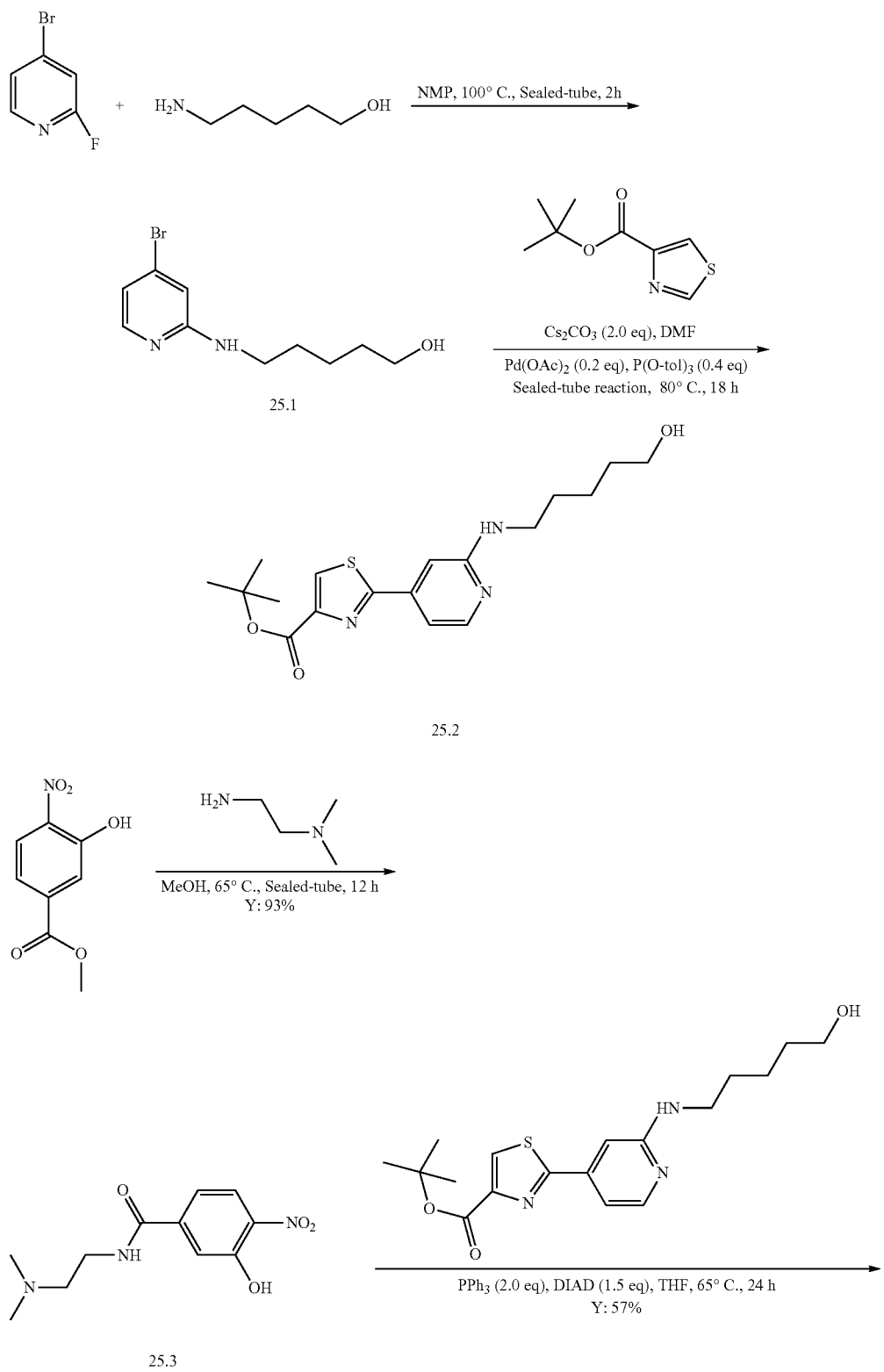

-continued

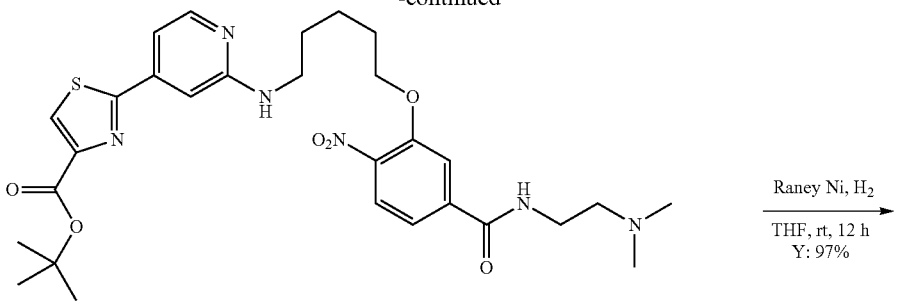

25.4

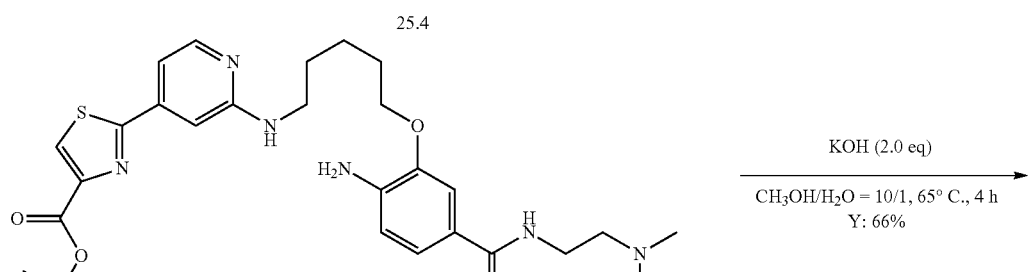

25.5

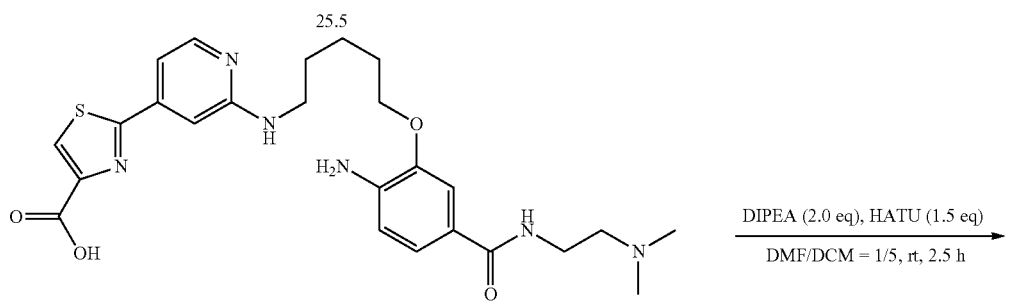

25.6

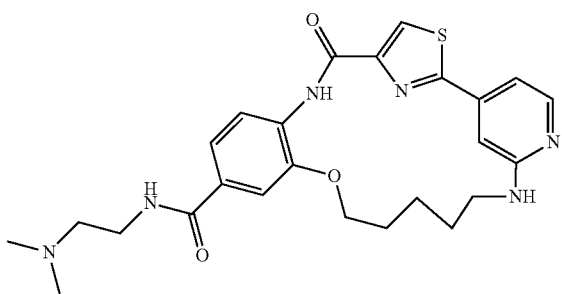

25

Synthesis of Compound 25.1

A mixture of 4-bromo-2-fluoropyridine (2.5 g, 14.2 mmol, 1.0 eq) and 5-aminopentan-1-ol (3.6 g, 28.4 mmol, 2.5 eq) in NMP (6 mL) was stirred at 100° C. in a sealed-tube for 2 h. After cooling down, EtOAc (200 mL) was added. The solution was washed by H$_2$O (50×mL). The organic layer was dried by Na$_2$SO$_4$ and concentrated under reduced pressure. The residue was purified by silica gel column (PE/EA=1/1) to give 25.1 (3.0 g, yield: 81%) as a white solid; ESI-MS (M+H)$^+$: 261.0.

Synthesis of Compound 25.2

To a mixture of 25.1 (800 mg, 3.1 mmol, 1.0 eq) and tert-butyl thiazole-4-carboxylate (571 mg, 3.1 mmol, 1.0 eq) in DMF (10 mL), Cs$_2$CO$_3$ (2.0 g, 6.2 mmol, 2.0 eq), Pd(OAc)$_2$ (70 mg, 0.31 mmol, 0.2 eq) and P(o-tol)$_3$ (188 mg, 0.62 mmol, 0.4 eq) were added under N$_2$ atmosphere. The mixture was stirred at 90° C. in a sealed-tube for 18 h under N$_2$ atmosphere. After cooling down, the solution was diluted EtOAc (200 mL) with and filtered by Celite. The filtrate was washed with water (100 mL×2), brine (100 mL×2). The organic layer was dried over sodium sulfate and concentrated under reduced pressure. The residue was purified by silica gel column (PE/EA=2/1) to give 25.2 (77 mg, yield: 7%) as a yellow oil. $^1$H NMR (400 MHz, CDCl$_3$) δ: 8.15 (d, J=5.2 Hz, 1H), 8.10 (s, 1H), 7.08 (s, 1H), 7.04 (d, J=5.2 Hz, 1H), 4.76 (t, J=5.6 Hz, 1H), 3.69 (t, J=6.4 Hz, 2H), 3.39-3.34 (m, 2H), 1.72-1.67 (m, 6H), 1.63 (s, 9H); ESI-MS (M+H)$^+$: 364.1.

Synthesis of Compound 25.3

A mixture of methyl 3-hydroxy-4-nitrobenzoate (500 mg, 2.5 mmol, 1.0 eq) and N1,N1-dimethylethane-1,2-diamine (223 mg, 25 mmol, 10.0 eq) in MeOH (5 mL) was stirred at 65° C. in sealed-tube for 12 h. After cooling down, EtOAc (50 mL) was added. The mixture was filtered, the filtrate was concentrated under reduced pressure to give 25.3 (595 mg, yield: 93%) as a yellow solid. $^1$H NMR (400 MHz, DMSO-d$_6$) δ: 8.58 (t, J=5.6 Hz, 1H), 7.88 (d, J=8.4 Hz, 1H), 7.43 (d, J=1.6 Hz, 1H), 7.15 (dd, J=1.6, 8.4 Hz, 1H), 3.40-3.75 (m, 2H), 2.52-2.50 (m, 2H), 2.28 (s, 6H).

Synthesis of Compound 25.4

To a mixture of 25.3 (240 mg, 0.95 mmol, 1.5 eq) and 25.2 (230 mg, 0.63 mmol, 1.0 eq) in THF (30 mL), PPh$_3$ (333 mg, 1.27 mmol, 2.0 eq) and DIAD (192 mg, 0.95 mmol, 1.5 eq) were added. The mixture was stirred at 65° C. for 12 h under N$_2$ atmosphere. After cooling down, EtOAc (50 mL) was added. The mixture was filtered and the filtrate was concentrated under reduced pressure. The residue was purified by silica gel column (PE/EA=5/1) to give 25.4 (217 mg, yield: 57%) as a yellow oil. $^1$H NMR (400 MHz, CDCl$_3$) δ: 8.14 (d, J=6.0 Hz, 1H), 8.10 (s, 1H), 7.82 (d, J=8.8 Hz, 1H), 7.69 (s, 1H), 7.38-7.36 (m, 1H), 7.06-7.03 (m, 2H), 4.23 (t, J=6.0 Hz, 2H), 3.64-3.60 (m, 2H), 3.42-3.37 (m, 2H), 2.76-2.68 (m, 2H), 2.42 (s, 6H), 1.79-1.68 (m, 6H), 1.63 (s, 9H); ESI-MS (M+H)$^+$: 599.3.

Synthesis of Compound 25.5

To a solution of 25.4 (190 mg, 0.32 mmol, 1.0 eq) in THF (15 mL), raney Ni (19 mg, 10% wt) was added. The mixture was stirred at room temperature for 12 h. The catalyst was filtered off by Celite and the filtrate was concentrated under reduced pressure to give 25.5 (175 mg, yield: 97%) as a yellow oil; ESI-MS (M+H)$^+$: 569.3.

Synthesis of Compound 25.6

To a solution of 25.5 (150 mg, 0.26 mmol, 1.0 eq) in MeOH (10 mL) and H$_2$O (1 mL), KOH (30 mg, 0.53 mmol, 2.0 eq) was added. The mixture was stirred at 65° C. for 4 h. After cooling down, the mixture was adjusted to pH=7 with HCl (1 M). The solvent was removed in vacuo and the residue was purified by pre-HPLC to give 25.6 (90 mg, yield: 66%) as a yellow oil; ESI-MS (M+H)$^+$: 513.2.

Synthesis of Compound 25

To a solution of 25.6 (90 mg, 0.18 mmol, 1.0 eq) in CH$_2$Cl$_2$ (35 mL) and DMF (10 mL), DIPEA (45 mg, 0.35 mmol, 2.0 eq) and HATU (100 mg, 0.26 mmol, 1.5 eq) were added. The mixture was stirred at room temperature for 2.5 h and concentrated under reduced pressure. The residue was purified by pre-HPLC to give 25 (40 mg, yield: 46%) as a yellow solid. $^1$H NMR (400 MHz, CDCl$_3$) δ: 10.05 (s, 1H), 9.49 (br. s, 1H), 8.79 (s, 1H), 8.75-8.74 (m, 1H), 8.58 (d, J=8.4 Hz, 1H), 8.21 (d, J=6.0 Hz, 1H), 7.59-7.57 (m, 2H), 7.35-7.33 (m, 1H), 7.25-7.24 (m, 1H), 4.18-4.15 (m, 2H), 3.64-3.60 (m, 2H), 3.34-3.28 (m, 4H), 2.87 (s, 6H), 1.86-1.84 (m, 4H), 1.68-1.63 (m, 2H); ESI-MS (M+H)$^+$: 495.2; HPLC: 214 nm: 100.00%, 254 nm: 100.00%.

Example 26

Scheme 26

-continued
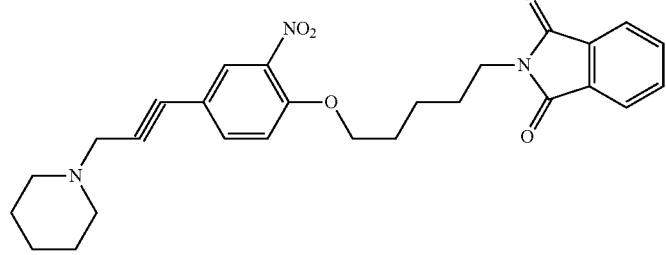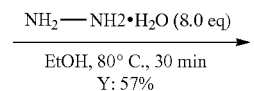
26.3
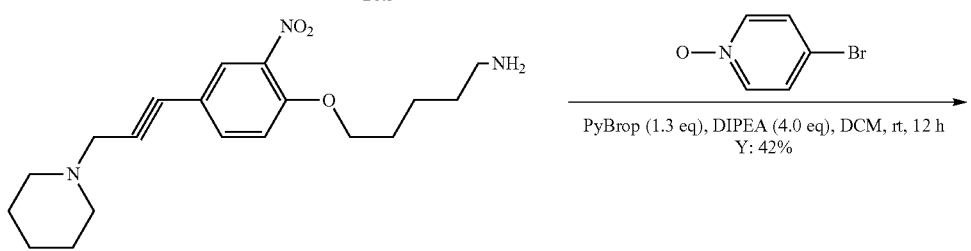
26.4
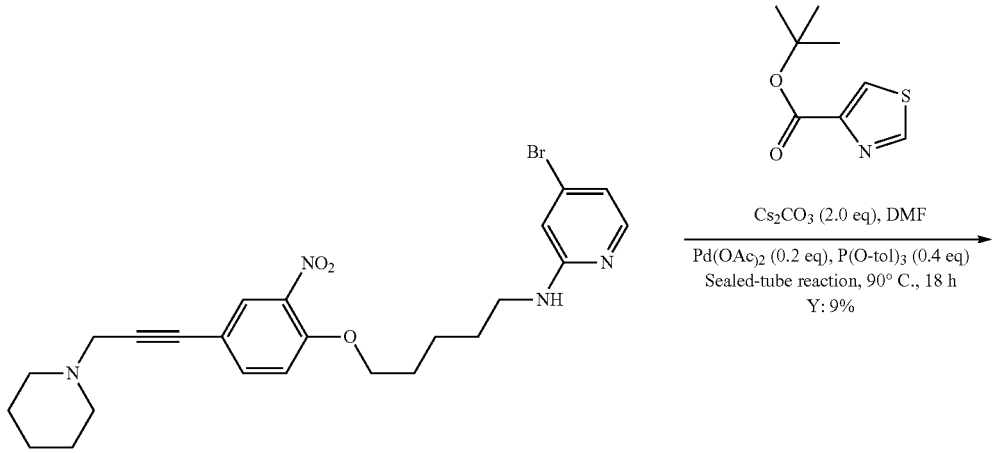
26.5
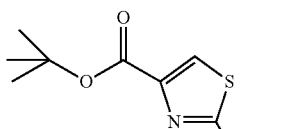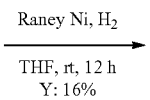
26.6

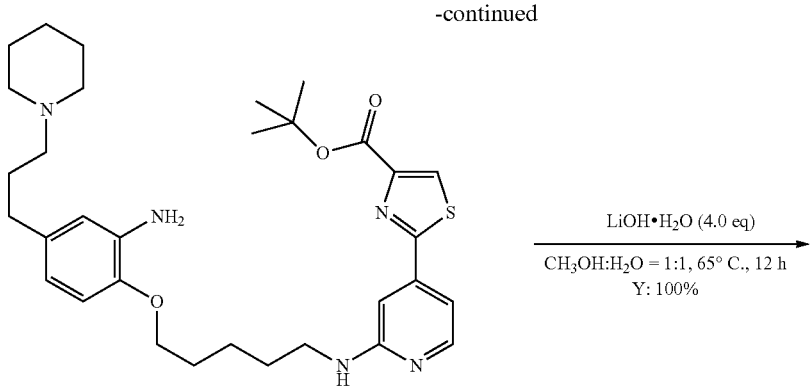

26.7

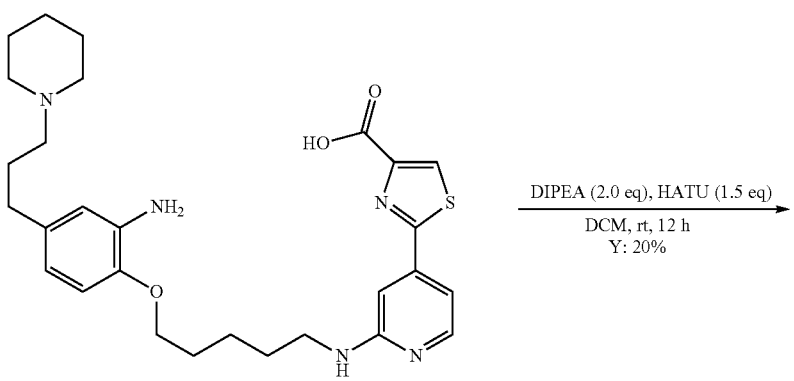

26.8

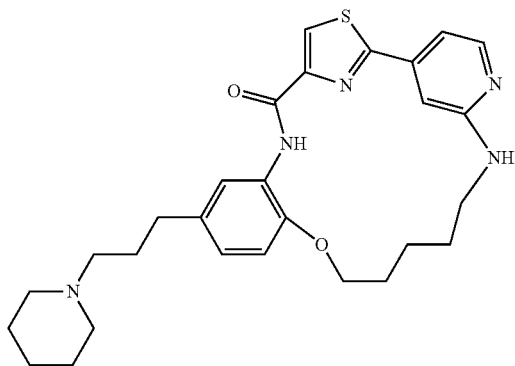

26

Synthesis of Compound 26.1

To a mixture of 4-bromo-2-nitrophenol (6.5 g, 30 mmol, 1.0 eq) and 1,5-dibromopentane (13.7 g, 60 mmol, 2.0 eq) in $CH_3CN$ (100 mL), $K_2CO_3$ (4.1 g, 30 mmol, 1.0 eq) was added. The mixture was stirred at 60° C. for 10 h. After cooling down, EtOAc (200 mL) was added. The mixture was filtered and the filtrate was concentrated under reduced pressure. The residue was purified by silica gel column (PE/EA=50/1) to give 26.1 (7.8 g, yield: 70%) as a yellow oil. $^1$H NMR (400 MHz, $CDCl_3$) δ: 7.96 (d, J=2.4 Hz, 1H), 7.61 (dd, J=2.4, 8.8 Hz, 1H), 6.96 (d, J=8.8 Hz, 1H), 4.10 (t, J=6.0 Hz, 2H), 3.44 (t, J=6.8 Hz, 2H), 1.97-1.84 (m, 4H), 1.69-1.62 (m, 2H).

Synthesis of Compound 26.2

To a mixture of 26.1 (10.1 g, 27.7 mmol, 1.0 eq) and potassium 1,3-dioxoisoindolin-2-ide (5.1 g, 27.7 mmol, 1.0 eq) in DMF (80 mL), $K_2CO_3$ (3.8 g, 27.7 mmol, 1.0 eq) was added. The mixture was stirred at 65° C. for 4.5 h. After cooling down, EtOAc (200 mL) was added. The mixture was washed with water (150 ml×3), brine (100 ml×2). The organic layer was dried over sodium sulfate and concentrated under reduced pressure to give 26.2 (11.8 g, yield: 99%) as a white solid. $^1$H NMR (400 MHz, DMSO-$d_6$) δ: 8.06 (s, 1H), 7.85-7.78 (m, 5H), 7.32 (d, J=9.2 Hz, 1H), 4.14 (t, J=6.4 Hz, 2H), 3.58 (t, J=6.8 Hz, 2H), 1.77-1.61 (m, 4H), 1.44-1.36 (m, 2H); ESI-MS (M+H)$^+$: 433.7.

Synthesis of Compound 26.3

To a mixture of 26.2 (8.0 g, 18.5 mmol, 1.0 eq) and 1-(prop-2-yn-1-yl)piperidine (6.8 g, 55.5 mmol, 3.0 eq) in anhydrous DMF (80 mL), $Et_3N$ (3.7 g, 37 mmol, 2.0 eq), $Pd(PPh_3)_4$ (30 mg, 8.3 mmol, 0.15 eq), $PPh_3$ (81 mg, 16.7 mmol, 0.3 eq) and CuI (81 mg, 16.7 mmol, 0.3 eq) were added under $N_2$ atmosphere. The mixture was stirred at 90° C. for 12 h under $N_2$ atmosphere. After cooling down, the solution was diluted with EtOAc (200 mL) and filtered by Celite. The filtrate was washed with water (150 mL×3), brine (100 mL×2). The organic layer was dried over sodium sulfate and concentrated under reduced pressure. The residue was purified by silica gel column (PE/EA=5/1) to give 26.3 (8.3 g, yield: 93%) as a yellow oil; ESI-MS $(M+H)^+$: 476.2.

Synthesis of Compound 26.4

To a mixture of 26.3 (6.22 g, 13.1 mmol, 1.0 eq) in EtOH (100 mL), $NH_2NH_2H_2O$ (5.24 g, 104.7 mmol, 8.0 eq) was added. The mixture was stirred at 80° C. for 30 min. The mixture was concentrated under reduced pressure. The residue was purified by silica gel column (EA) to give 26.4 (2.6 g, yield: 57%) as a yellow oil; ESI-MS (M+H)+: 346.3.

Synthesis of Compound 26.5

To a mixture of 26.4 (2.6 g, 7.5 mmol, 1.0 eq) and 4-bromopyridine 1-oxide (1.3 g, 7.5 mmol, 1.0 eq) in DCM (150 mL), PyBrop (4.6 g, 9.5 mmol, 1.3 eq) and DIPEA (3.9 g, 30.1 mmol, 4.0 eq) were added. The mixture was stirred at room temperature for 12 h. The mixture was washed with water (50 mL×2). The organic layer was dried over sodium sulfate and concentrated under reduced pressure. The residue was purified by silica gel column (PE/EA=2/1) to give 26.5 (1.6 g, yield: 42%) as a yellow oil. $^1H$ NMR (400 MHz, $CDCl_3$) δ: 7.89-7.86 (m, 2H), 7.56-7.54 (m, 1H), 6.98 (d, J=8.8 Hz, 1H), 6.69 (dd, J=1.6, 5.6 Hz, 1H), 6.56 (d, J=1.6 Hz, 1H), 4.75-4.72 (m, 1H), 4.11 (t, J=6.0 Hz, 2H), 3.46 (s, 2H), 3.30-3.25 (m, 2H), 2.60-2.53 (m, 4H), 1.19-1.84 (m, 2H), 1.70-1.60 (m, 8H), 1.51-1.41 (m, 2H); ESI-MS $(M+H)^+$: 503.1.

Synthesis of Compound 26.6

To a mixture of 26.5 (150 mg, 0.3 mmol, 1.0 eq) and tert-butyl thiazole-4-carboxylate (56 mg, 0.3 mmol, 1.0 eq) in anhydrous DMF (5 mL), $Cs_2CO_3$ (196 mg, 0.6 mmol, 2.0 eq), $Pd(OAc)_2$ (13 mg, 0.06 mmol, 0.2 eq) and $P(O-tol)_3$ (36 mg, 0.12 mmol, 0.4 eq) were added under $N_2$ atmosphere. The mixture was stirred in a sealed-tube at 90° C. for 18 h under $N_2$ atmosphere. After cooling down, the solution was diluted with EtOAc (200 mL) and filtered by Celite. The filtrate was washed with water (100 mL×3), brine (50 mL). The organic layer was dried over sodium sulfate and concentrated under reduced pressure. The residue was purified by pre-TLC (PE/EA=1/1) to give 26.6 (103 mg, yield: 9%) as a yellow oil. $^1H$ NMR (400 MHz, $CDCl_3$) δ: 8.15 (d, J=5.2 Hz, 1H), 8.10 (s, 1H), 7.89-7.87 (m, 1H), 7.55 (dd, J=2.0, 8.8 Hz, 1H), 7.07-7.04 (m, 1H), 7.00-6.97 (m, 1H), 4.77-4.74 (m, 1H), 4.14-4.10 (m, 2H), 3.47 (s, 2H), 3.42-3.35 (m, 2H), 2.62-2.51 (m, 4H), 1.99-1.94 (m, 2H), 1.90-1.81 (m, 10H), 1.63 (s, 9H); ESI-MS $(M/2+H)^+$: 303.7.

Synthesis of Compound 26.7

To a solution of 26.6 (70 mg, 0.12 mmol, 1.0 eq) in THF (2.5 mL), raney Ni (14 mg, 20% wt) was added. The mixture was stirred at room temperature for 4 h under $H_2$ atmosphere. The solution was filtered by Celite and the filtrate was concentrated under reduced pressure. The residue was purified by pre-TLC (DCM/MeOH=15/1) to give 26.7 (11 mg, yield: 16%) as a yellow oil; ESI-MS $(M+H)^+$: 580.3.

Synthesis of Compound 26.8

To a solution of 26.7 (11 mg, 0.019 mmol, 1.0 eq) in MeOH (0.5 mL) and $H_2O$ (0.5 mL), $LiOH.H_2O$ (3.2 mg, 0.076 mmol, 4.0 eq) was added. The mixture was stirred at 65° C. for 12 h. After cooling down, the mixture was adjusted to pH=4 with HCl (1 M). The mixture was extracted with EtOAc (100 mL). The organic layer was dried over sodium sulfate and concentrated under reduced pressure to give 26.8 (10 mg, yield: 100%) as a yellow oil; ESI-MS $(M+H)^+$: 524.2.

Synthesis of Compound 26

To a solution of 26.8 (10 mg, 0.019 mmol, 1.0 eq) in $CH_2Cl_2$ (5 mL), DIPEA (5 mg, 0.038 mmol, 2.0 eq) and HATU (11 mg, 0.028 mmol, 1.5 eq) were added. The mixture was stirred at room temperature for 12 h and concentrated under reduced pressure. The residue was purified prep-HPLC (MeOH in $H_2O$—0.05% TFA from 5% to 95%) to give 26 (2 mg, yield: 20%) as a yellow solid. $^1H$ NMR (400 MHz, $CDCl_3$) δ: 10.09 (s, 1H), 8.67 (s, 1H), 8.47 (s, 1H), 8.09 (d, J=6.4 Hz, 1H), 7.73 (s, 1H), 7.36-7.34 (m, 1H), 7.01 (s, 2H), 4.13-4.12 (m, 2H), 3.56-3.50 (m, 4H), 3.14-3.10 (m, 2H), 2.96-2.90 (m, 2H), 2.74-2.70 (m, 2H), 2.11-1.97 (m, 2H), 1.97-1.73 (m, 12H); ESI-MS $(M+H)^+$: 506.2.

Example 27

Scheme 27

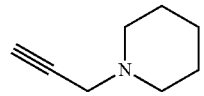

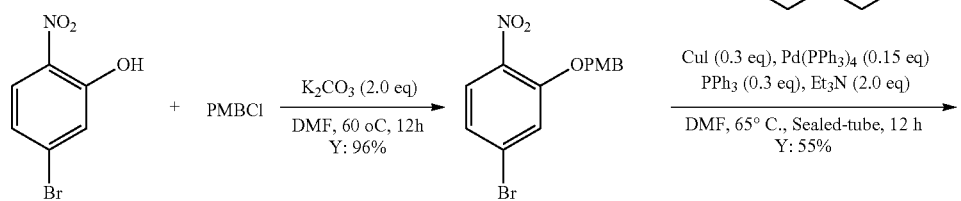

27.1

-continued
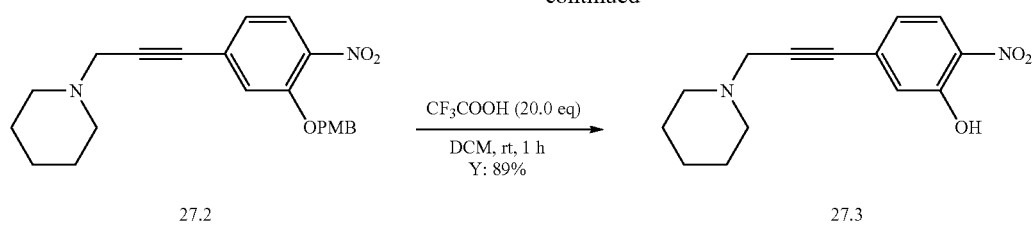
27.2 → 27.3
CF$_3$COOH (20.0 eq)
DCM, rt, 1 h
Y: 89%
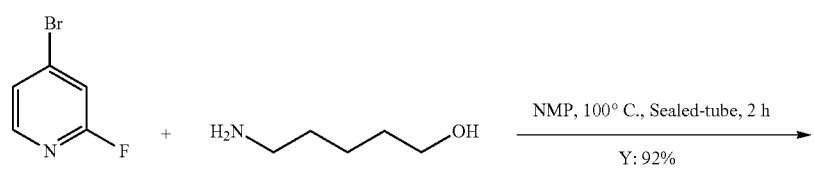
NMP, 100° C., Sealed-tube, 2 h
Y: 92%
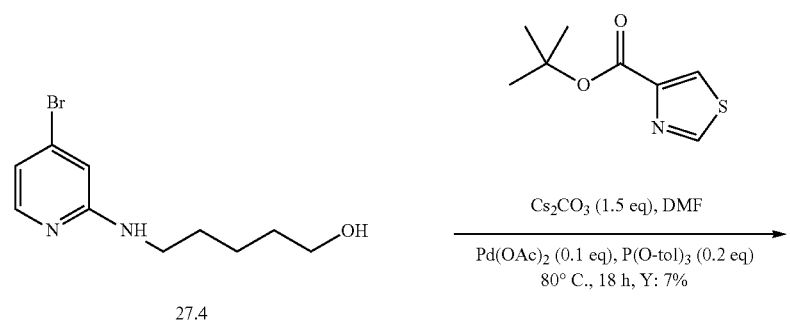
27.4
Cs$_2$CO$_3$ (1.5 eq), DMF
Pd(OAc)$_2$ (0.1 eq), P(O-tol)$_3$ (0.2 eq)
80° C., 18 h, Y: 7%
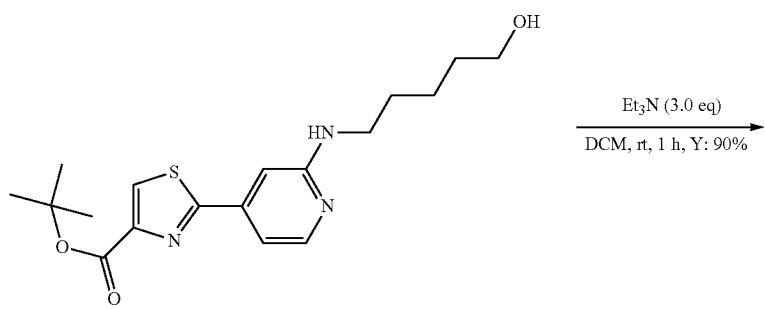
27.5
Et$_3$N (3.0 eq)
DCM, rt, 1 h, Y: 90%
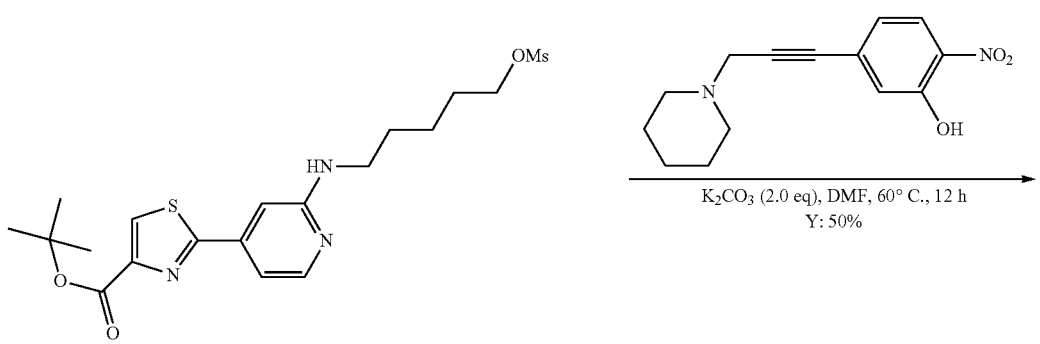
27.6
K$_2$CO$_3$ (2.0 eq), DMF, 60° C., 12 h
Y: 50%

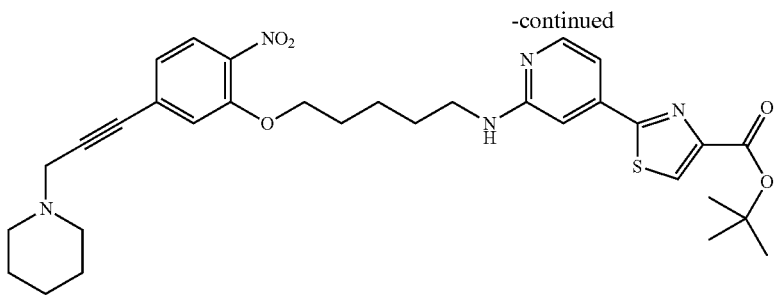
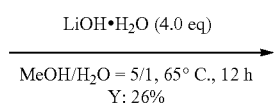

LiOH·H₂O (4.0 eq)

MeOH/H₂O = 5/1, 65° C., 12 h
Y: 26%

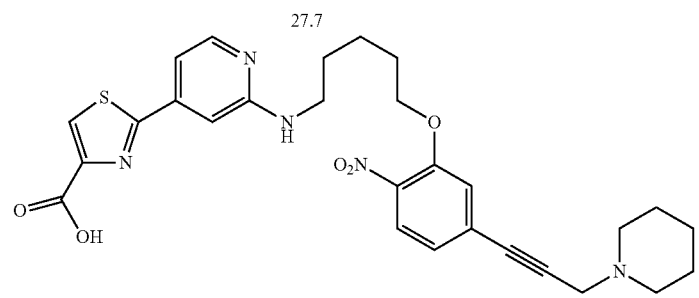
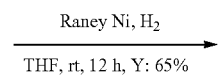

Raney Ni, H₂

THF, rt, 12 h, Y: 65%

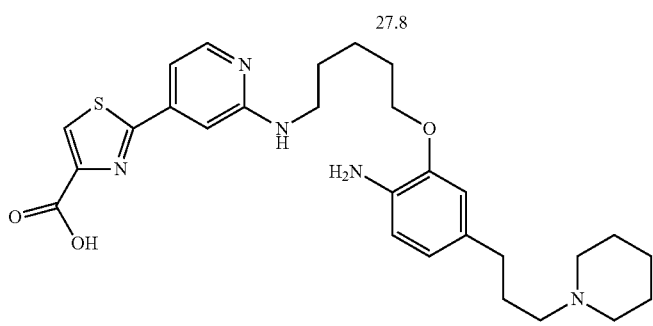
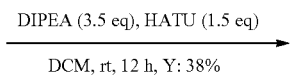

DIPEA (3.5 eq), HATU (1.5 eq)

DCM, rt, 12 h, Y: 38%

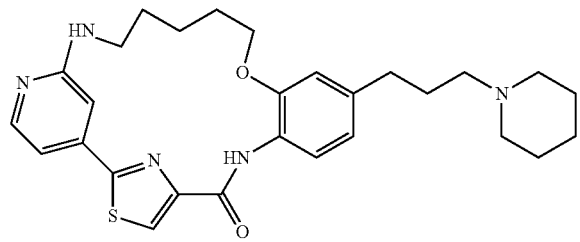

Synthesis of Compound 27.1

To a mixture of 5-bromo-2-nitrophenol (2.00 g, 9.2 mmol, 1.0 eq) and PMBCl (1.44 g, 9.2 mmol, 1.0 eq) in DMF (25 mL), K₂CO₃ (2.53 g, 18.3 mmol, 2.0 eq) was added. The mixture was stirred at 100° C. for 12 h. After cooling down, EtOAc (100 mL) was added. The solution was washed with water (75 mL×2), brine (75 mL×2). The organic layer was dried over sodium sulfate and concentrated to give 27.1 (3.0 g, yield: 96%) as a light yellow solid. $^1$H NMR (400 MHz, CDCl₃) δ: 7.75 (d, J=8.4 Hz, 1H), 7.39-7.37 (m, 2H), 7.30 (d, J=2.0 Hz, 1H), 7.18 (dd, J=8.8, 2.0 Hz, 1H), 6.94-6.92 (m, 2H), 5.16 (s, 2H), 3.83 (s, 3H).

Synthesis of Compound 27.2

To a mixture of 27.1 (1.0 g, 2.96 mmol, 1.0 eq) and 1-(prop-2-yn-1-yl)piperidine (1.1 g, 8.87 mmol, 3.0 eq) in anhydrous DMF (20 mL), Et₃N (598 mg, 5.92 mmol, 2.0 eq), Pd(PPh₃)₄ (508 mg, 0.44 mmol, 0.15 eq), PPh₃ (233 mg, 0.89 mmol, 0.3 eq) and CuI (169 mg, 0.89 mmol, 0.3 eq) were added under N₂ atmosphere. The mixture was stirred at 65° C. for 12 h under N₂ atmosphere. After cooling down, the solution was diluted with EA (80 mL) and filtered by Celite. The filtrate was washed with water (75 mL×3), brine (75 mL). The organic layer was dried over sodium sulfate and concentrated under reduced pressure. The residue was purified by silica gel column (PE/EA=5/1) to give 27.2 (620 mg, yield: 55%) as a yellow oil; ESI-MS (M+H)+: 381.1.

Synthesis of Compound 27.3

To a solution of 27.2 (620 mg, 1.63 mmol, 1.0 eq) in DCM (6 mL), CF$_3$COOH (3.72 g, 32.6 mmol, 20.0 eq) was added. The mixture was stirred at room temperature for 1 h. The solvent was removed under reduced pressure. The residue was purified by silica gel column (PE/EA=2/1) to give 27.3 (380 mg, yield: 89%) as a yellow oil. $^1$H NMR (400 MHz, CDCl$_3$) δ: 10.58 (s, 1H), 8.10 (d, J=8.8 Hz, 1H), 7.07-7.05 (m, 1H), 4.18 (s, 2H), 3.70-3.50 (m, 2H), 3.03-2.88 (m, 2H), 2.10-1.87 (m, 6H); ESI-MS (M+H)+: 261.1.

Synthesis of Compound 27.4

A mixture of 4-bromo-2-fluoropyridine (2.5 g, 14.2 mmol, 1.0 eq) and 5-aminopentan-1-ol (3.6 g, 28.4 mmol, 2.5 eq) in NMP (6 mL) was stirred at 100° C. in a sealed-tube for 2 h. After cooling down, EtOAc (200 mL) was added. The solution was washed by H$_2$O (50×mL). The organic layer was dried by Na$_2$SO$_4$ and concentrated under reduced pressure. The residue was purified by silica gel column (PE/EA=1/1) to give 27.4 (3.0 g, yield: 81%) as a white solid; ESI-MS (M+H)+: 261.0.

Synthesis of Compound 27.5

To a mixture of 27.4 (800 mg, 3.1 mmol, 1.0 eq) and tert-butyl thiazole-4-carboxylate (571 mg, 3.1 mmol, 1.0 eq) in DMF (10 mL), Cs$_2$CO$_3$ (2.0 g, 6.2 mmol, 2.0 eq), Pd(OAc)$_2$ (70 mg, 0.31 mmol, 0.2 eq) and P(o-tol)$_3$ (188 mg, 0.62 mmol, 0.4 eq) were added under N$_2$ atmosphere. The mixture was stirred at 90° C. in a sealed-tube for 18 h under N$_2$ atmosphere. After cooling down, the solution was diluted EtOAc (200 mL) with and filtered by Celite. The filtrate was washed with water (100 mL×2), brine (100 mL×2). The organic layer was dried over sodium sulfate and concentrated under reduced pressure. The residue was purified by silica gel column (PE/EA=2/1) to give 27.5 (77 mg, yield: 7%) as a yellow oil. $^1$H NMR (400 MHz, CDCl$_3$) δ: 8.15 (d, J=5.2 Hz, 1H), 8.10 (s, 1H), 7.08 (s, 1H), 7.04 (d, J=5.2 Hz, 1H), 4.76 (t, J=5.6 Hz, 1H), 3.69 (t, J=6.4 Hz, 2H), 3.39-3.34 (m, 2H), 1.72-1.67 (m, 6H), 1.63 (s, 9H); ESI-MS (M+H)+: 364.1.

Synthesis of Compound 27.6

To a solution of 27.5 (350 mg, 0.96 mmol, 1.0 eq) in DCM (15 mL), Et$_3$N (292 mg, 2.89 mmol, 3.0 eq) and MsCl (143 mg, 1.25 mmol, 1.3 eq) were added in ice base. The mixture was stirred at room temperature for 1 h and washed by water (30 mL×2). The organic layer was dried over sodium sulfate and concentrated under reduced pressure to give 27.6 (380 mg, yield: 90%) as a yellow solid; ESI-MS (M+H)+: 442.1.

Synthesis of Compound 27.7

To a mixture of 27.6 (380 mg, 0.86 mmol, 1.0 eq) and 27.3 (380 mg, 1.46 mmol, 1.7 eq) in DMF (8 mL), K$_2$CO$_3$ (237 mg, 1.72 mmol, 2.0 eq) was added. The mixture was stirred at 60° C. for 12 h. After cooling down, the solution was diluted with EtOAc (60 mL) and washed with water (50 mL×2), brine (25 mL). The organic layer was dried over sodium sulfate and concentrated under reduced pressure. The residue was purified by pre-TLC (PE/EA=3/1) to give 27.7 (260 mg, yield: 50%) as a yellow oil; ESI-MS (M/2+H)+: 303.7.

Synthesis of Compound 27.8

To a solution of 27.7 (210 mg, 0.35 mmol, 1.0 eq) in MeOH (20 mL) and H$_2$O (4 mL), LiOH.H$_2$O (58 mg, 1.39 mmol, 4.0 eq) was added. The mixture was stirred at 65° C. for 12 h. After cooling down, the mixture was adjusted to pH=4 with HCl (1 M). The solvent was removed under reduced pressure. The residue was purified by prep-HPLC to give 27.8 (51 mg, yield: 26%) as a light yellow solid; ESI-MS (M+H)+: 550.2.

Synthesis of Compound 27.9

To a solution of 27.8 (51 mg, 0.093 mmol, 1.0 eq) in THF (15 mL), raney Ni (20 mg, 40% wt) was added. The mixture was stirred at room temperature for 12 h under H$_2$ atmosphere. The solution was filtered by Celite and the filtrate was concentrated under reduced pressure to give 27.9 (32 mg, yield: 65%) as a light yellow solid; ESI-MS (M+H)+: 524.3.

Synthesis of Compound 27

To a solution of 27.9 (32 mg, 0.061 mmol, 1.0 eq) in CH$_2$Cl$_2$ (15 mL), DIPEA (28 mg, 0.214 mmol, 3.5 eq) and HATU (35 mg, 0.092 mmol, 1.5 eq) were added. The mixture was stirred at room temperature for 12 h. The mixture was concentrated under reduced pressure. The residue was purified by prep-HPLC to give 27 (12 mg, yield: 38%) as a light yellow solid. $^1$H NMR (400 MHz, CDCl$_3$) δ: 10.65-10.63 (m, 1H), 9.90 (s, 1H), 8.51 (d, J=9.0 Hz, 1H), 8.44 (s, 1H), 7.87 (d, J=6.4 Hz, 1H), 7.63 (s, 1H), 7.00 (d, J=6.4 Hz, 1H), 6.78-6.75 (m, 2H), 4.10-4.08 (m, 2H), 3.63-3.60 (m, 2H), 3.47-3.43 (m, 2H), 2.98-2.93 (m, 2H), 2.70-2.66 (m, 2H), 2.60-2.52 (m, 2H), 2.17-2.11 (m, 2H), 1.99-1.83 (m, 12H); ESI-MS (M+H)+: 506.3; HPLC: 214 nm: 100.00%, 254 nm: 100.00%.

Examples 28 and 29

Scheme 28

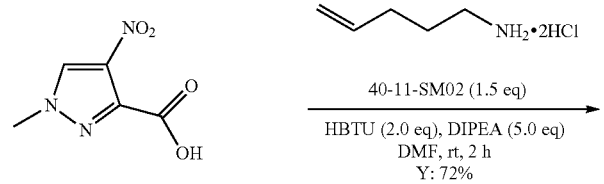

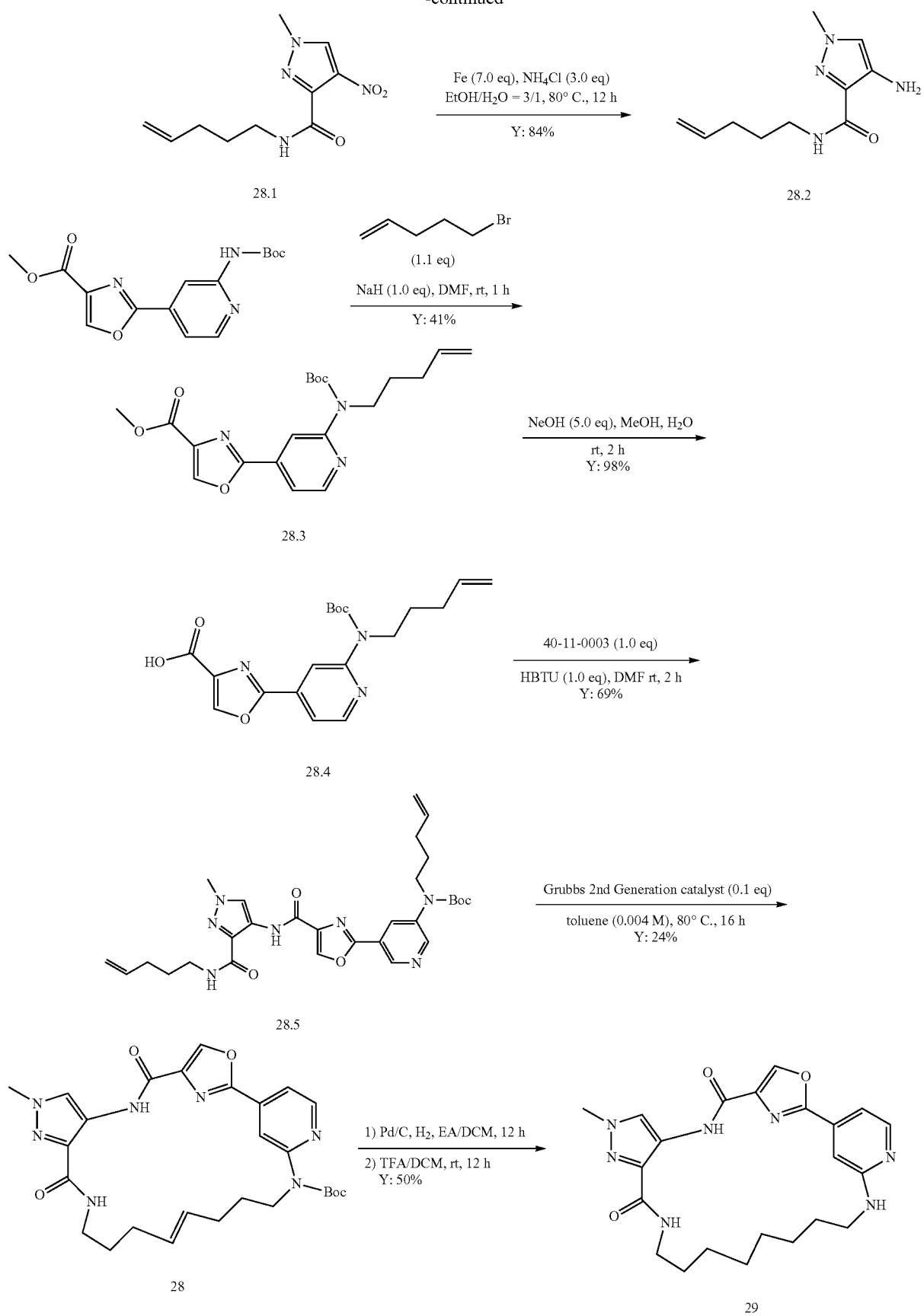
-continued

Synthesis of Compound 28.1

To a solution of 1-methyl-4-nitro-1H-pyrazole-3-carboxylic acid (1.63 g, 9.5 mmol, 1.0 eq) in DMF (10 mL) were added pent-4-en-1-amine (1.5 g, 14.3 mmol, 1.5 eq), HBTU (5.4 g, 14.3 mmol, 1.5 eq) and DIPEA (6.2 g, 48 mmol, 5.0 eq). The mixture was stirred at room temperature for 2 h, diluted with EA (100 mL). The mixture was washed with water (50 mL×4) and brine (50 mL), dried over sodium sulfate and concentrated under reduced pressure. The residue was purified by chromatography column (PE:EA=2:3) to give 28.1 (1.6 g, yield: 72%) as a yellow oil. $^1$H NMR (400 MHz, DMSO-$d_6$) □ δ: 8.84 (s, 1H), 8.61 (t, J=5.6 Hz, 1H), 5.88-5.78 (m, 1H), 5.07-4.96 (m, 2H), 3.90 (s, 3H), 3.22 (q, J=6.8 Hz, 2H), 2.07 (q, J=6.8 Hz, 2H), 1.61-1.54 (m, 2H); ESI-MS (M+H)$^+$: 239.1.

Synthesis of Compound 28.2

To the solution of 28.1 (900 mg, 3.8 mmol, 1.0 eq) in EtOH (30 mL) and H$_2$O (10 mL) were added Fe (1.5 g, 26.6 mmol, 7.0 eq) and NH$_4$Cl (604 mg, 11.4 mmol, 3.0 eq). The reaction mixture was stirred at 80° C. for 12 h. After cooling down, the mixture was filtered through a pad of celite. The filtrate was concentrated to give a yellow solid which was washed with EA (50 mL) and the organic layer was concentrated to give 28.2 as a yellow oil (660 mg, yield: 84%). $^1$H NMR (400 MHz, DMSO-$d_6$) □ δ: 7.82 (t, J=5.6 Hz, 1H), 7.11 (s, 1H), 5.87-5.77 (m, 1H), 5.05-4.94 (m, 4H), 3.74 (s, 3H), 3.17 (q, J=6.4 Hz, 2H), 2.01 (q, J=6.8 Hz, 2H), 1.58-1.51 (m, 2H); ESI-MS (M+H)$^+$: 209.2.

Synthesis of Compound 28.3

To a mixture of methyl 2-(2-((tert-butoxycarbonyl)amino)pyridin-4-yl)oxazole-4-carboxylate (1.0 eq) in anhydrous DMF (6 mL), NaH (1.1 eq) was added at 0° C. The mixture was allowed to warm to rt and stirred for 20 min. Then 5-bromopent-1-ene (1.1 eq) was dropped into the reaction mixture. The resulting mixture was stirred at rt for 1 h, quenched with H$_2$O carefully and diluted with ethylacetate. The mixture was washed with water, dried over sodium sulfate and concentrated under reduced pressure. The residue was purified by chromatography column (PE:EA=6:1) to give 28.3 as a white solid 200 mg, yield: 41%; $^1$H NMR (400 MHz, DMSO-$d_6$) □ δ: 9.10 (s, 1H), 8.57 (d, J=5.2 Hz, 1H), 8.29 (s, 1H), 7.65 (d, J=4.8 Hz, 1H), 5.86-5.76 (m, 1H), 5.03-4.94 (m, 2H), 3.93 (t, J=7.6 Hz, 2H), 3.87 (s, 3H), 2.05 (q, J=7.2 Hz, 2H), 1.73-1.65 (m, 2H), 1.49 (s, 9H); ESI-MS (M+H)$^+$: 388.2.

Synthesis of Compound 28.4

To a solution of 28.3 (1.0 eq) in MeOH (5 mL) and H$_2$O (5 mL) was added NaOH (4.0 eq). The reaction mixture was stirred at room temperature for 2 h. Then the reaction was cooled to 0° C. and adjusted pH=6 with CH$_3$COOH (20% in water). The mixture was extracted with EA. The combined organic layers were dried over sodium sulfate and concentrated under reduced pressure to give 28.4 as a white solid 168 mg, yield: 98%; $^1$H NMR (400 MHz, DMSO-$d_6$) □ δ: 8.53 (d, J=5.2 Hz, 1H), 8.36 (s, 1H), 8.18 (s, 1H), 7.78 (d, J=5.2 Hz, 1H), 5.86-5.76 (m, 1H), 5.03-4.94 (m, 2H), 3.90 (t, J=7.2 Hz, 2H), 2.04 (q, J=7.2 Hz, 2H), 1.72-1.65 (m, 2H), 1.49 (s, 9H); ESI-MS (M+H)$^+$: 374.2

Synthesis of Compound 28.5

To a solution of 28.4 (1.0 eq) in DMF (4 mL) were added 28.2 (1.0 eq), HBTU (1.0 eq) and DIPEA (2.0 eq). The mixture was stirred at room temperature for 2 h, diluted with EA, washed with water and brine. The organic layer was dried over sodium sulfate and concentrated under reduced pressure. The residue was purified by chromatography column (PE:EA=1:1) to give 28.5 as a white solid 200 mg, yield: 69%; $^1$H NMR (400 MHz, DMSO-$d_6$) □ δ: 10.97 (s, 1H), 9.04 (s, 1H), 8.61 (d, J=4.8 Hz, 1H), 8.45 (t, J=5.6 Hz, 1H), 8.38 (s, 1H), 8.26 (s, 1H), 7.66 (d, J=5.6 Hz, 1H), 5.89-5.76 (m, 2H), 5.08-4.94 (m, 4H), 3.95-3.92 (m, 5H), 3.27 (q, J=6.8 Hz, 2H), 2.08-2.03 (m, 4H), 1.73-1.58 (m, 4H), 1.53 (s, 9H); ESI-MS (M+H)$^+$: 564.3.

Synthesis of Compound 28

To a solution of 28.5 (170 mg, 0.30 mmol, 1.0 eq) in anhydrous toluene (100 mL) was added Grubbs 2nd Generation catalyst (26 mg, 0.03 mmol, 0.1 eq) under N$_2$ atmosphere. The mixture was stirred at 80° C. for 16 h. After cooling down, the mixture was concentrated via vacuum. The residue was purified by prep-TLC (PE:EA=1:1) to give 28 (39 mg, yield: 24%) as a white solid. $^1$H NMR (400 MHz, DMSO-$d_6$) □ δ: 11.53 (s, 1H), 8.68 (d, J=5.2 Hz, 1H), 8.35 (s, 1H), 8.19 (s, 1H), 8.09 (s, 1H), 7.69 (d, J=6.4 Hz, 1H), 6.81 (t, J=6.8 Hz, 1H), 5.79-5.63 (m, 2H), 3.93 (s, 3H), 3.67 (t, J=6.8 Hz, 2H), 3.52 (q, J=7.2 Hz, 2H), 2.20-2.14 (m, 2H), 2.06-2.02 (m, 2H), 1.96-1.88 (m, 2H), 1.70-1.64 (m, 2H), 1.43 (s, 9H); ESI-MS (M+H)$^+$: 536.3.

Synthesis of Compound 29

To a solution of 28 (24 mg, 0.045 mmol) in DCM (4 mL) and EA (4 mL) was added Pd/C (10%). The mixture was stirred at room temperature for 12 h under H$_2$ atmosphere. The catalyst was filtered out and TFA (2 mL) was added to the filtrate. The resulting mixture was stirred at room temperature for another 12 h. The mixture was diluted with EA (50 mL) and NaHCO$_3$ (sat., 20 mL). The organic layer was separated, dried over sodium sulfate and concentrated under reduced pressure. The residue was recrystallized from MeOH to give 29 (12 mg, yield: 50%). $^1$H NMR (400 MHz, DMSO-$d_6$) □ δ: 11.26 (s, 1H), 8.97 (s, 1H), 8.58 (t, J=5.6 Hz, 1H), 8.35 (s, 1H), 8.19 (d, J=5.6 Hz, 1H), 7.04-7.03 (m, 2H), 6.92 (t, J=2.4 Hz, 1H), 3.93 (s, 3H), 3.21-3.11 (m, 4H), 1.71-1.61 (m, 4H), 1.51-1.32 (m, 8H).

Examples 30 and 31

Scheme 30

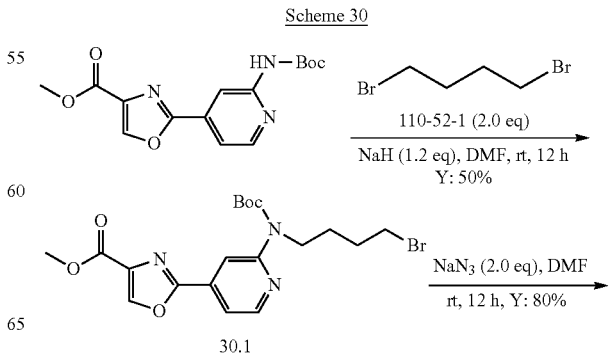

30.1

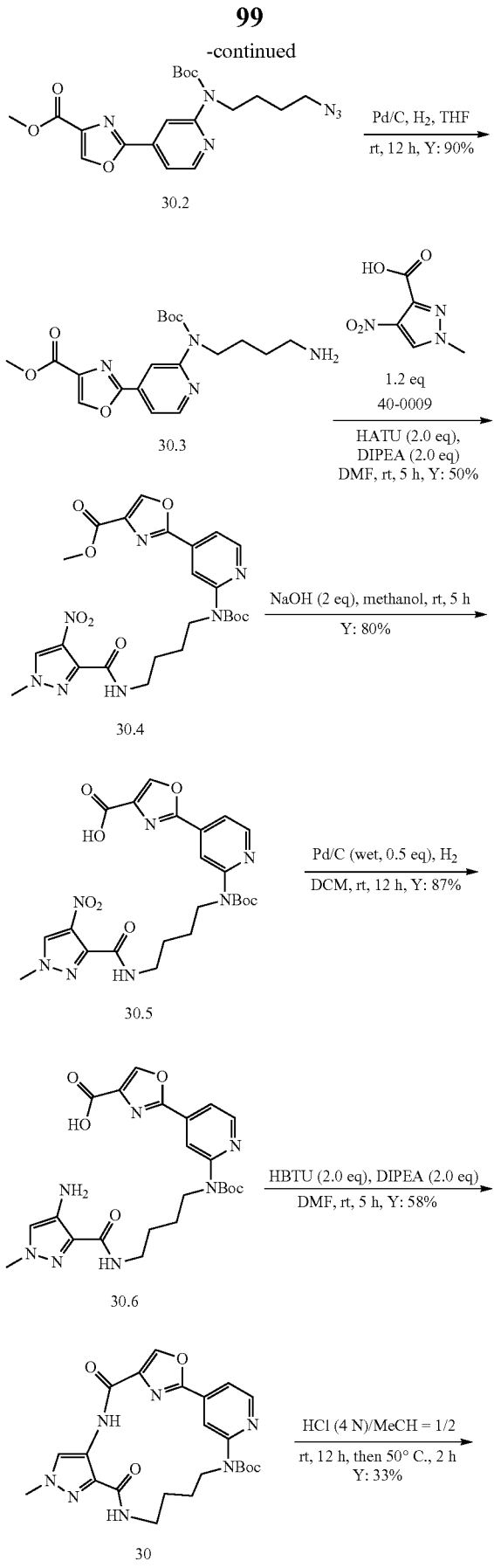

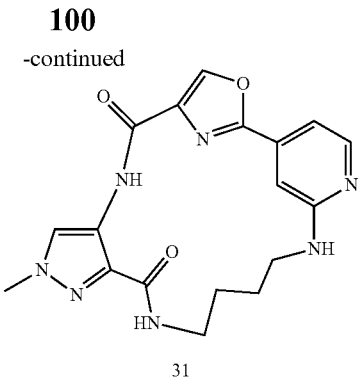

31

Synthesis of Compound 30.1

To a solution of methyl 2-(2-((tert-butoxycarbonyl)amino)pyridin-4-yl)oxazole-4-carboxylate (500 mg, 1.6 mmol) in DMF (10 mL) was added NaH (80 mg, 1.9 mmol, 1.2 eq) at 0° C. in several portions. The mixture was stirred at room temperature for 1 h. Then 1,4-dibromobutane (680 mg, 3.2 mmol, 2.0 eq) was added, and the mixture was stirred at room temperature for 12 h. The reaction mixture was diluted with DCM (20 mL) and washed with water (5 mL×3). The organic layer was dried over $Na_2SO_4$ and concentrated in vacuo. The residue was purified by silica gel column (petroleum ether/ethyl acetate=2/1) to afford 30.1 as yellow oil (350 mg, yield: 50%). $^1$H NMR (400 MHz, $CDCl_3$) □ δ: 8.50 (d, J=4.8 Hz, 1H), 8.37 (s, 1H), 8.35 (s, 1H), 7.70 (d, J=5.2 Hz, 1H), 4.04 (t, J=7.2 Hz, 2H), 3.97 (s, 3H), 3.43 (t, J=6.4 Hz, 2H), 1.92-1.86 (m, 2H), 1.82-1.78 (m, 2H), 1.56 (s, 9H); ESI-MS (M+H)$^+$: 454.1

Synthesis of Compound 30.2

To a solution of 30.1 (453 mg, 1.0 mmol) in DMF (8 mL) was added $NaN_3$ (70 mg, 1.1 mmol, 1.1 eq) at 0° C. The mixture was stirred at room temperature for 12 h. The solution was diluted with DCM (30 mL), washed with saturated sodium bicarbonate solution (10 mL) and brine (5 mL×5). The organic layer was dried over $Na_2SO_4$ and evaporated in vacuo to give 30.2. (360 mg, yield: 80%); ESI-MS (M+H)$^+$: 417.1.

Synthesis of Compound 30.3

A solution of 30.2 (400 mg, 1.0 mmol) in THF (25 mL) was flushed with $N_2$ for 3 times. 10% Pd/C (80 mg, 20% wt) was added and the mixture was flushed with $H_2$ for 3 times. The reaction mixture was stirred for 12 h under $H_2$ atmosphere at room temperature. After filtered through Celite, the filtrate was evaporated in vacuo to afford 30.3 as brown oil (300 mg, yield: 90%). $^1$H NMR (400 MHz, $CDCl_3$) □ δ: 8.40 (d, J=4.8 Hz, 1H), 8.35 (s, 1H), 8.34 (s, 1H), 7.55 (d, J=5.2 Hz, 1H), 3.98 (br, 2H), 3.96 (s, 3H), 2.93-2.91 (m, 2H), 1.74-1.64 (m, 4H), 1.56 (s, 9H); ESI-MS (M+H)$^+$: 391.1.

Synthesis of Compound 30.4

To a solution of 30.3 (350 mg, 0.9 mmol) in DMF (5 mL) were added 1-methyl-4-nitro-1H-pyrazole-3-carboxylic acid (190 mg, 1.1 mmol, 1.2 eq), HATU (513 mg, 1.4 mmol, 1.5 eq) and DIPEA (232 mg, 1.8 mmol, 2.0 eq). The mixture was stirred at room temperature for 5 h. The reaction mixture was diluted with DCM (20 mL) and washed with water (5 mL×3). The organic layer was dried over Na$_2$SO$_4$ and concentrated in vacuo. The residue was purified by silica gel column (petroleum ether/ethyl acetate=1/10) to afford 30.4 as a yellow solid (250 mg, yield: 50%). $^1$H NMR (400 MHz, DMSO-d$_6$) □ δ: 8.47 (d, J=4.8 Hz, 1H), 8.35 (s, 1H), 8.34 (s, 1H), 8.20 (s, 1H), 7.69 (d, J=4.8 Hz, 1H), 4.12 (t, J=6.8 Hz, 2H), 4.05 (s, 3H), 4.04 (s, 3H), 3.55-3.51 (m, 2H), 1.77-1.75 (m, 2H), 1.70-1.66 (m, 2H), 1.54 (s, 9H); ESI-MS (M+H)$^+$: 544.1.

Synthesis of Compound 30.5

To a solution of 30.4 (100 mg, 0.2 mmol) in methanol (5 mL) was added NaOH (1 M, 0.2 mL, 0.2 mmol, 1.2 eq). The reaction mixture was stirred at room temperature for 5 h. Then the reaction solution was cooled to 0° C., and adjusted pH=6 with HCl (3 M). The precipitate was collected by filtration as the desired product 30.5 (80 mg, yield: 80%); ESI-MS (M+H)$^+$: 530.1.

Synthesis of Compound 30.6

A solution of 30.5 in THF was flushed with N$_2$ for 3 times. 10% Pd/C (20% wt) was added and the mixture was flushed with H$_2$ for 3 times. The reaction mixture was stirred for 12 h under H$_2$ atmosphere at room temperature. After filtered through Celite, the filtrate was evaporated in vacuo to afford 30.6 as a yellow solid 80 mg, yield: 87%; ESI-MS (M+H)$^+$: 500.1.

Synthesis of Compound 30

To a solution of 30.6 (90 mg, 0.2 mmol) in DMF (3 mL) were added HBTU (115 mg, 0.3 mmol, 1.5 eq) and DIPEA (50 mg, 0.4 mmol, 2.0 eq). The mixture was stirred at room temperature for 5 h. The reaction mixture was diluted with DCM (20 mL) and washed with water (5 mL×3). The organic layer was dried over Na$_2$SO$_4$ and concentrated in vacuo. The residue was purified by silica gel column (DCM/MeOH=20/1) to afford pure 30 as a yellow solid (50 mg, yield: 58%). $^1$H NMR (400 MHz, CDCl$_3$) □ δ: 8.59 (d, J=4.8 Hz, 1H), 8.40 (s, 1H), 8.25 (s, 1H), 7.95 (s, 1H), 6.84 (br, 1H), 3.91 (s, 3H), 3.72-3.68 (m, 4H), 1.55-1.52 (m, 2H), 1.50 (s, 9H), 1.48-1.46 (m, 2H); ESI-MS (M+H)$^+$: 482.1.

Synthesis of Compound 31

To a solution of 30 (50 mg, 0.1 mmol) in methanol (5 mL) was added HCl (4 M, 2.5 mL). The reaction mixture was stirred at 50° C. for 2 h. Then the reaction solution was cooled to 0° C., and adjusted pH=7 with saturated sodium bicarbonate solution. The mixture was concentrated in vacuo, and the residue was purified by silica gel column (DCM/MeOH=10/1) to afford 31 as a yellow solid (13 mg, yield: 33%). $^1$H NMR (400 MHz, CDCl$_3$) □ δ: 8.22 (s, 1H), 8.10 (d, J=5.2 Hz, 1H), 7.91 (s, 1H), 7.81 (s, 1H), 6.97 (d, J=6.8 Hz, 1H), 3.90 (s, 3H), 3.41-3.37 (m, 4H), 2.13-2.09 (m, 2H), 1.72 (br, 2H); ESI-MS (M+H)$^+$: 382.1; HPLC: 214 nm: 100.00%, 254 nm: 98.43%

Example 32

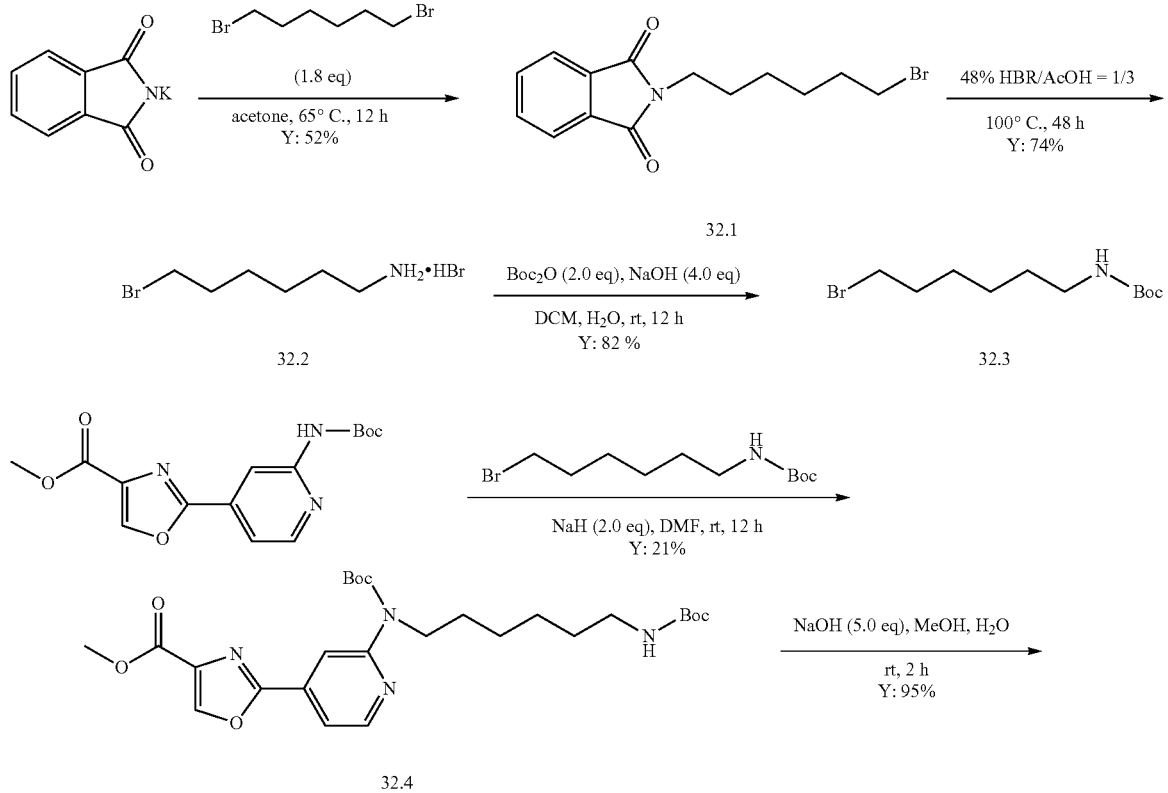

Scheme 32

-continued
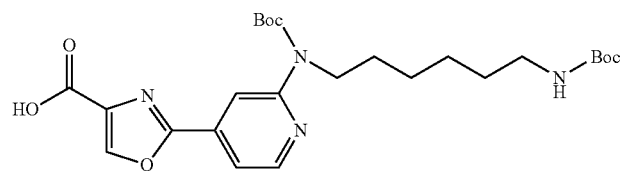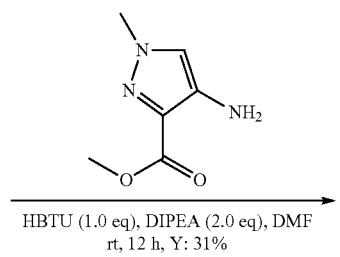
32.5
HBTU (1.0 eq), DIPEA (2.0 eq), DMF
rt, 12 h, Y: 31%
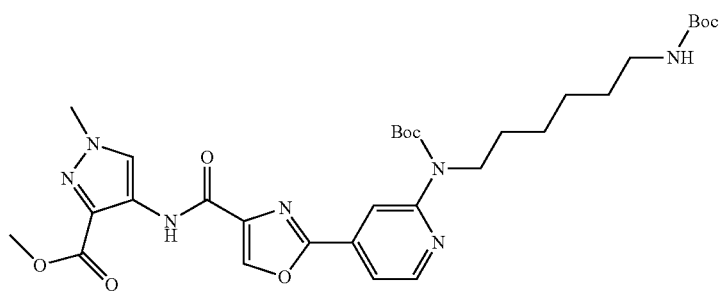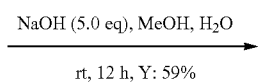
32.6
NaOH (5.0 eq), MeOH, H$_2$O
rt, 12 h, Y: 59%
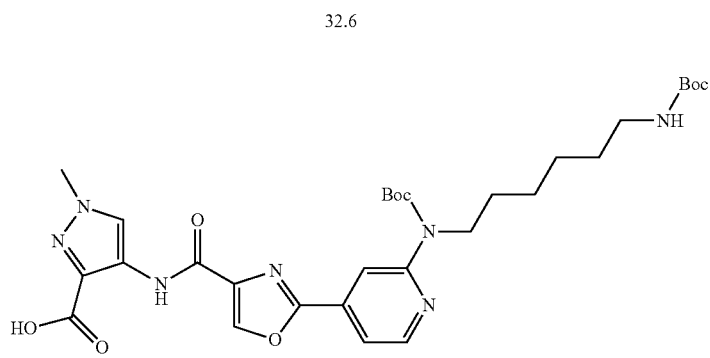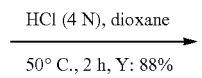
32.7
HCl (4 N), dioxane
50° C., 2 h, Y: 88%
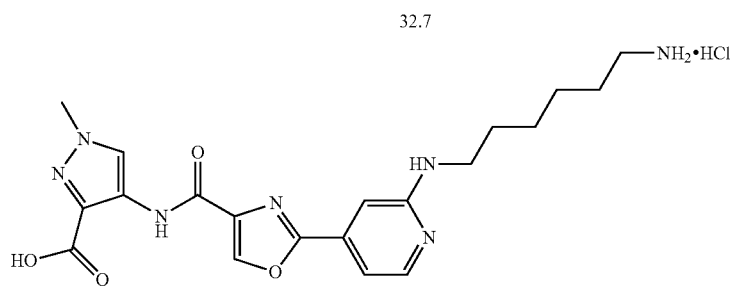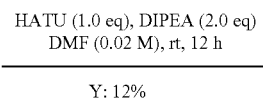
32.8
HATU (1.0 eq), DIPEA (2.0 eq)
DMF (0.02 M), rt, 12 h
Y: 12%
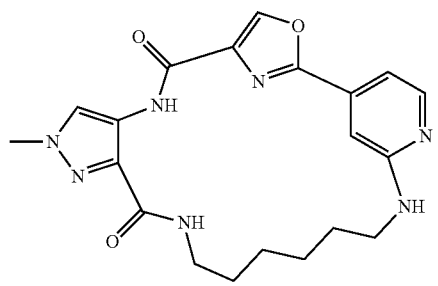
32

Synthesis of Compound 32.1

To a solution of potassium 1,3-dioxoisoindolin-2-ide (18.5 g, 0.1 mol, 1.0 eq) in acetone (200 mL) was added 1,6-dibromohexane (43.5 g, 0.18 mol, 1.8 eq). The mixture was stirred at 65° C. for 12 h. After cooling down, the mixture was filtered to remove the precipitated salt. The filtrate was concentrated and the residue purified by a short silica gel column (PE:EA=10:1) to remove the excess 1,6-dibromohexane. 16.1 g of 32.1 was obtained as a yellow oil (yield: 52%). $^1$H NMR (400 MHz, DMSO-d$_6$) □ δ: 7.88-7.82 (m, 4H), 3.58-3.49 (m, 4H), 1.81-1.74 (m, 2H), 1.63-1.55 (m, 2H), 1.44-1.27 (m, 4H); ESI-MS (M+H)$^+$: 312.1.

Synthesis of Compound 32.2

To the solution of 32.1 (4.8 g, 15.5 mmol, 1.0 eq) in AcOH (15 mL) was added HBr (48%, 5 mL). The reaction mixture was stirred at 100° C. for 48 h. After cooling down, the precipitated solid was filtered out. The filtrate was concentrated to give 32.2 (3.8 g, yield: 95%) as a colorless oil. ESI-MS (M+H)$^+$: 180.1.

Synthesis of Compound 32.3

To a mixture of 32.2 (3.8 g, 20 mmol, 1.0 eq) in DCM (20 mL) and H$_2$O (20 mL), NaOH (3.2 g, 80 mmol, 4.0 eq) was added. Then the mixture was stirred at rt for 12 h, diluted with DCM (100 mL). The organic layer was washed with water (50 mL), dried over sodium sulfate and concentrated under reduced pressure. The residue was purified by silica gel (PE: EA=10:1) to give 32.3 (3.8 g, yield: 82%) as a yellow oil. $^1$H NMR (400 MHz, DMSO-d$_6$) □ δ: 3.40 (t, J=6.8 Hz, 2H), 3.13 (br, 2H), 1.89-1.82 (m, 2H), 1.49-1.44 (m, 4H), 1.37 (s, 9H), 1.36-1.31 (m, 2H); ESI-MS (M−55)$^+$: 224.1.

Synthesis of Compound 32.4

To a mixture of 32.3 (800 mg, 2.5 mmol, 1.0 eq) in anhydrous DMF (10 mL), NaH (200 mg, 5.0 mmol, 2.0 eq) was added at 0° C. The mixture was allowed to warm to rt and stirred for 20 min. Then tert-butyl(6-bromohexyl)carbamate (1.4 g, 5.0 mmol, 2.0 eq) in anhydrous DMF (2 mL) was dropped into the reaction mixture. The mixture was stirred at rt for 1 h, quenched with H$_2$O (5 mL) carefully, and diluted with EA (100 mL). The organic layer was washed with water (30 mL×3), dried over sodium sulfate and concentrated under reduced pressure. The residue was purified by prep-HPLC (MeOH in water from 30% to 95%) to give 32.4 (270 mg, yield: 21%) as a white solid. $^1$H NMR (400 MHz, CDCl$_3$) □ δ: 8.49 (d, J=5.6 Hz, 1H), 8.35 (s, 1H), 8.33 (s, 1H), 6.89 (dd, J=1.2, 5.6 Hz, 1H), 4.51 (br, 1H), 3.98-3.95 (m, 5H), 3.10 (q, J=5.6 Hz, 2H), 1.69-1.64 (m, 4H), 1.59 (s, 9H), 1.43 (s, 9H), 1.32-1.28 (m, 4H); ESI-MS (M+H)$^+$: 519.3.

Synthesis of Compound 32.5

To a solution of 32.4 (250 mg, 0.48 mmol, 1.0 eq) in MeOH (5 mL) and H$_2$O (5 mL) was added NaOH (96 mg, 2.4 mmol, 5.0 eq). The reaction mixture was stirred at room temperature for 2 h. Then the reaction was cooled to 0° C., and adjusted pH=6 with CH$_3$COOH (20% in water). The mixture was extracted with EA (100 mL). The organic layer dried over sodium sulfate and concentrated under reduced pressure to give 32.5 as a white solid (230 mg, yield: 95%). $^1$H NMR (400 MHz, DMSO-d$_6$) □ δ: 8.54-8.53 (m, 2H), 8.21 (s, 1H), 7.68 (br, 1H), 6.77 (t, J=5.6 Hz, 1H), 3.89 (t, J=7.2 Hz, 2H), 2.87 (q, J=6.0 Hz, 2H), 1.58-1.55 (m, 2H), 1.49 (s, 9H), 1.35 (s, 9H), 1.29-1.19 (m, 6H); ESI-MS (M+H)$^+$: 505.0.

Synthesis of Compound 32.6

To a solution of 32.5 (250 mg, 0.5 mmol, 1.0 eq) in DMF (5 mL) were added methyl 4-amino-1-methyl-1H-pyrazole-3-carboxylate (155 mg, 1.0 mmol, 2.0 eq), HBTU (190 mg, 0.5 mmol, 1.0 eq) and DIPEA (130 mg, 1.1 mmol, 2.0 eq). The reaction was stirred at room temperature for 2 h, diluted with EA (100 mL). The mixture was washed with water (30 mL×3), brine (50 mL), dried over sodium sulfate and concentrated under reduced pressure. The residue was purified by prep-TLC (PE:EA=1:1) to give 32.6 (100 mg, yield: 31%) as a red oil. $^1$H NMR (400 MHz, DMSO-d$_6$) □ δ: 10.29 (s, 1H), 9.07 (s, 1H), 8.61 (d, J=5.2 Hz, 1H), 8.43 (s, 1H), 8.32 (s, 1H), 7.65 (d, J=4.8 Hz, 1H), 6.73 (t, J=5.6 Hz, 1H), 3.96 (s, 3H), 3.93-3.89 (m, 5H), 2.87 (q, J=6.4 Hz, 2H), 1.60-1.57 (m, 2H), 1.52 (s, 9H), 1.38 (s, 9H), 1.26-1.23 (m, 6H); ESI-MS (M+H)$^+$: 642.0.

Synthesis of Compound 32.7

To a solution of 32.6 (200 mg, 0.31 mmol, 1.0 eq) in MeOH (5 mL) and H$_2$O (5 mL) was added NaOH (62 mg, 1.55 mmol, 5.0 eq). The reaction mixture was stirred at room temperature for 2 h. Then the reaction was cooled to 0° C., and adjusted pH=6 with CH$_3$COOH (20% in water). The mixture was extracted with EA (100 mL). The organic layer was dried over sodium sulfate and concentrated under reduced pressure to give 32.7 as a white solid (115 mg, yield: 59%). $^1$H NMR (400 MHz, DMSO-d$_6$) □ δ: 11.64 (s, 1H), 8.96 (s, 1H), 8.60 (d, J=5.2 Hz, 1H), 8.23 (s, 1H), 8.20 (s, 1H), 7.67 (d, J=5.2 Hz, 1H), 6.73 (t, J=4.4 Hz, 1H), 3.92-3.88 (m, 5H), 2.87 (q, J=6.4 Hz, 2H), 1.64-1.52 (m, 2H), 1.51 (s, 9H), 1.35 (s, 9H), 1.22-1.17 (m, 6H); ESI-MS (M+H)$^+$: 628.3.

Synthesis of Compound 32.8

To a solution of 32.7 (100 mg, 0.16 mmol, 1.0 eq) in dioxane (4 mL) was added HCl (4N, 2 mL). The mixture was stirred at 50° C. for 2 h and concentrated under reduced pressure to give 40-11-0208 (65 mg, yield: 88%) as a yellow solid; ESI-MS (M+H)$^+$: 428.3.

Synthesis of Compound 32

To a solution of 32.8 (100 mg, 0.23 mmol, 1.0 eq) in DMF (10 mL) were added HATU (90 mg, 0.23 mmol, 1.0 eq) and DIPEA (89 mg, 0.69 mmol, 3.0 eq). The mixture was stirred at room temperature for 2 h, diluted with EA (100 mL) and washed with water (30 mL×3). The organic layer was dried over sodium sulfate and concentrated under reduced pressure. The residue was recrystallized from EA (2 mL) to give 32 (12 mg, yield: 12%) as a yellow solid. $^1$H NMR (400 MHz, CDCl$_3$) □ δ: 11.67 (s, 1H), 8.27 (s, 1H), 8.18 (d, J=4.8 Hz, 1H), 8.13 (s, 1H), 8.47 (s, 1H), 7.05 (d, J=5.2 Hz, 1H), 6.85 (t, J=6.4 Hz, 1H), 5.27 (t, J=6.4 Hz, 1H), 3.91 (s, 3H), 3.51 (q, J=6.8 Hz, 2H), 3.40 (q, J=6.4 Hz, 2H), 1.79-1.73 (m, 2H), 1.63-1.49 (m, 6H); ESI-MS (M+H)$^+$: 410.2; HPLC: 214 nm: 100.00%, 254 nm: 100.00%.

Example 33
Scheme 33
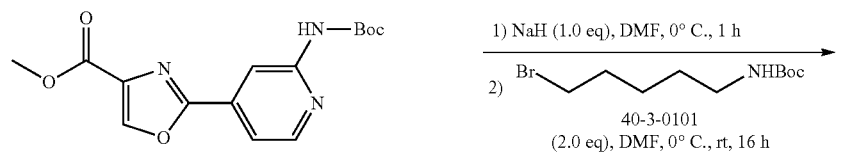
1) NaH (1.0 eq), DMF, 0° C., 1 h
2) Br~~~~~NHBoc
40-3-0101
(2.0 eq), DMF, 0° C., rt, 16 h
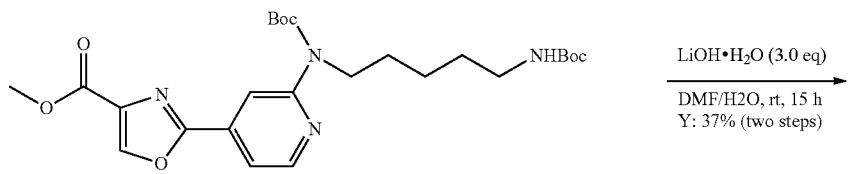
33.1
LiOH•H2O (3.0 eq)
DMF/H2O, rt, 15 h
Y: 37% (two steps)
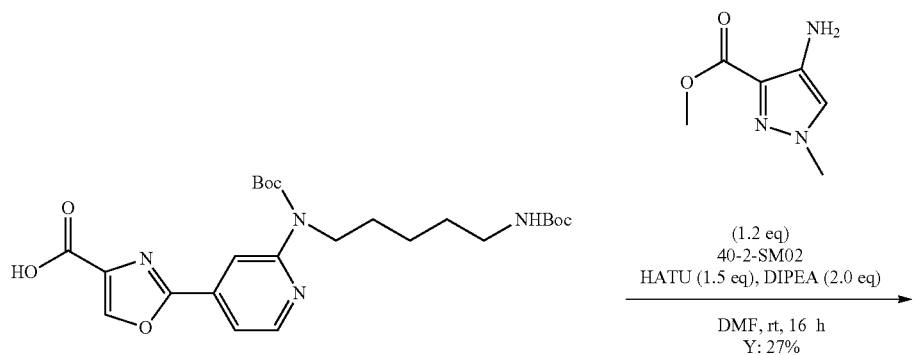
33.2
(1.2 eq)
40-2-SM02
HATU (1.5 eq), DIPEA (2.0 eq)
DMF, rt, 16 h
Y: 27%
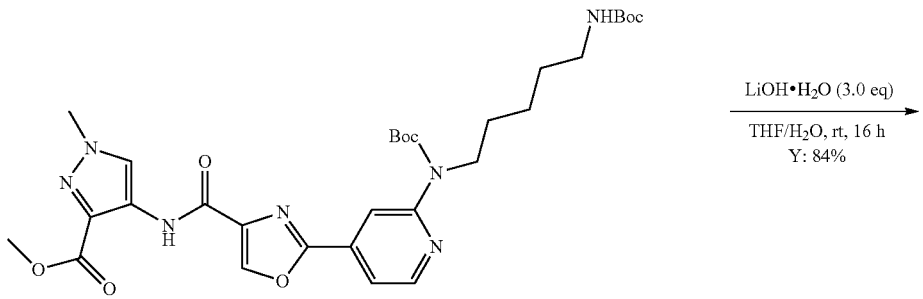
33.3
LiOH•H2O (3.0 eq)
THF/H2O, rt, 16 h
Y: 84%
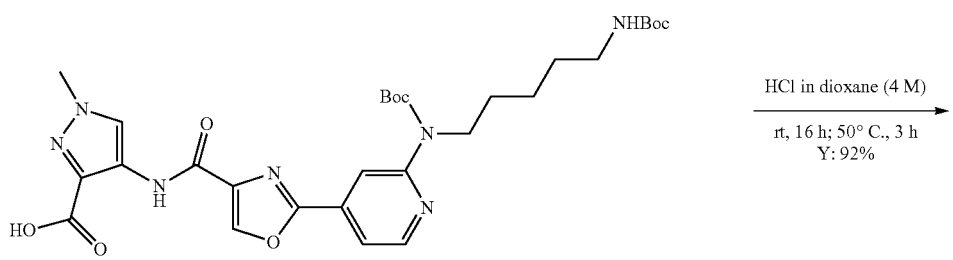
33.4
HCl in dioxane (4 M)
rt, 16 h; 50° C., 3 h
Y: 92%

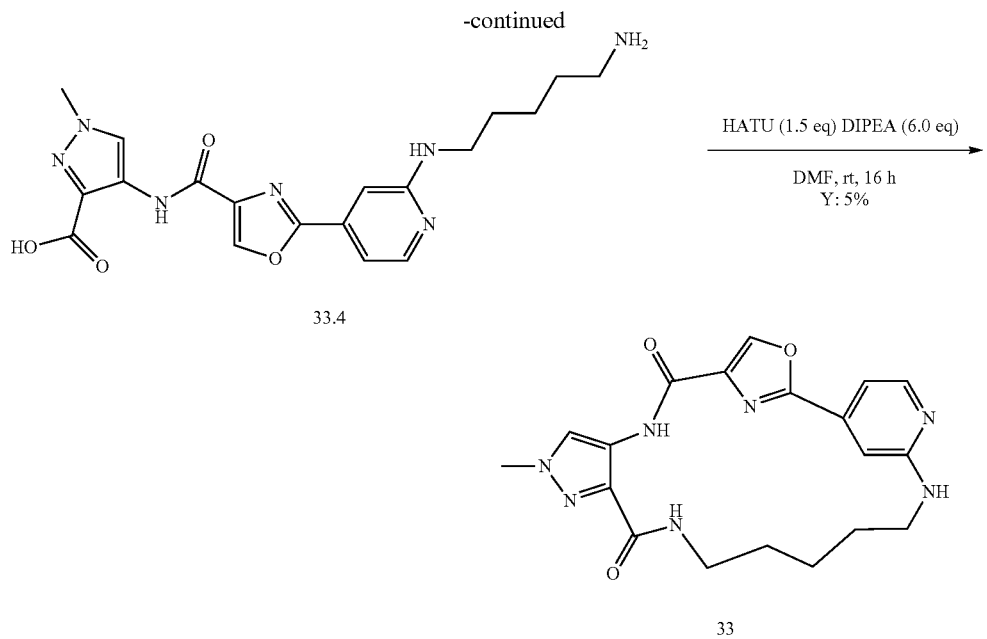

Synthesis of Compound 33.2

To a mixture of methyl 2-(2-((tert-butoxycarbonyl)amino)pyridin-4-yl)oxazole-4-carboxylate (1.0 g, 3.1 mmol, 1.0 eq) in DMF (10 mL), NaH (82 mg, 3.4 mmol, 1.1 eq) was added at 0° C. After stirring at 0° C. for 1 h, methyl 4-amino-1-methyl-1H-pyrazole-3-carboxylate (980 mg, 3.7 mmol, 1.2 eq) was dropped into the reaction mixture. The mixture was allowed to warm to rt and stirred for 16 h. After that, LiOH H$_2$O (391 mg, 9.3 mmol, 3.0 eq) and H$_2$O (3 mL) was added. After stirring at rt for 16 h, the reaction mixture was quenched with H$_2$O (5 mL) carefully and adjusted to pH=6 with CH$_3$COOH (20% in water). The mixture was diluted with EtOAc (100 mL), washed with water (30 mL*4). The organic layer was dried over anhydrous Na$_2$SO$_4$ and filtered. The filtrate was concentrated under reduced pressure to give the residue, which was purified with pre-HPLC (MeOH/H$_2$O with 0.05% TFA as mobile phase; from 20% to 95%) to furnish the compound 33.2, 700 mg (Y: 37%), as a yellow oil. $^1$H NMR (400 MHz, CDCl$_3$) δ: 8.50 (d, J=5.2 Hz, 1H), 8.38 (s, 1H), 8.31 (s, 1H), 7.65 (d, J=5.2 Hz, 1H), 3.41 (t, J=6.8 Hz, 2H), 3.13-3.11 (m, 2H), 1.88-1.86 (m, 2H), 1.54 (s, 9H), 1.51-1.46 (m, 4H), 1.45 (s, 9H). m/z 491.2 [M+H]$^+$

Synthesis of Compound 33.3

To a solution of 33.2 (1.6 g, 3.3 mmol, 1.0 eq) and methyl 4-amino-1-methyl-1H-pyrazole-3-carboxylate (620 mg, 4.0 mmol, 1.2 eq) in DMF (8 mL) was added HATU (1.9 g, 5.0 mmol, 1.5 eq) and DIPEA (851 mg, 6.6 mmol, 2.0 eq). The mixture was stirred at room temperature for 16 h, diluted with DCM (100 mL), washed with water (20 mL*3) and brine (20 mL). The organic layer was dried over sodium sulfate and concentrated under reduced pressure. The residue was purified with pre-HPLC (MeOH/H$_2$O with 0.05% TFA as mobile phase; from 20% to 95%) to furnish the compound 33.3, 542 mg (Y: 27%), as a yellow oil. $^1$H NMR (400 MHz, CDCl$_3$) δ: 10.43 (s, 1H), 8.53 (d, J=4.8 Hz, 1H), 8.38 (s, 2H), 8.33 (s, 1H), 7.69-7.67 (m, 1H), 4.58 (bs, 1H), 4.05 (s, 3H), 4.00 (s, 3H), 3.12-3.10 (m, 2H), 1.86-1.64 (m, 4H), 1.56 (s, 9H), 1.54-1.48 (m, 2H), 1.43 (s, 9H), 1.40-1.32 (m, 2H). LCMS m/z 628.3 [M+H]$^+$;

Synthesis of Compound 33.4

To a solution of 33.3 (500 mg, 0.81 mmol, 1.0 eq) in THF (10 mL) and H$_2$O (3. mL) was added LiOH H$_2$O (129 mg, 3.23 mmol, 3.0 eq). The reaction mixture was stirred at room temperature for 16 h. Then the reaction was adjusted pH=6 with CH$_3$COOH (20% in water). The mixture was extracted with EA (10 mL×4). The combined organic layers were dried over sodium sulfate and concentrated under reduced pressure to give 33.4 as a yellow oil (420 mg, yield: 84%). $^1$H NMR (400 MHz, DMSO-d$_6$) δ: 11.18 (bs, 1H), 9.01 (bs, 1H), 8.56 (d, J=4.8 Hz, 1H), 8.29 (s, 1H), 8.22 (s, 1H), 7.65 (d, J=4.8 Hz, 1H), 6.77 (t, J=5.2 Hz, 1H), 3.90 (s, 3H), 3.88-3.85 (m, 2H), 3.17 (s, 1H), 2.91-2.87 (m, 2H), 1.59-1.54 (m, 2H), 1.50 (s, 9H), 1.40-1.38 (m, 2H), 1.35 (s, 9H), 1.28-1.23 (m, 2H). LCMS m/z 614.3 [M+H]

Synthesis of Compound 33.5

To a solution of 33.4 (380 mg, 0.62 mmol, 1.0 eq) in dioxane (4 mL) was added HCl (4N, 2 mL). The mixture was stirred at 50° C. for 3 h and concentrated under reduced pressure to give 33.5 (235 mg, yield: 92%) as a yellow solid; $^1$H NMR (400 MHz, DMSO-d$_6$) 10.44 (s, 1H), 9.14 (s, 1H), 8.40 (s, 1H), 8.14 (bs, 2H), 8.09-8.08 (m, 1H), 7.69 (bs, 1H), 7.19 (d, J=6.4 Hz, 1H), 3.95 (s, 3H), 3.59-3.58 (m, 2H), 3.39 (s, 1H), 2.79-2.78 (m, 2H), 1.64-1.63 (m, 4H), 1.49-1.47 (m, 2H). m/z 414.2 [M+H]$^+$;

Synthesis of Compound 33

To a solution of 33.5 (290 mg, 0.71 mmol, 1.0 eq) in DMF (8 mL) were added HATU (418 mg, 1.1 mmol, 1.5 eq) and DIPEA (275 mg, 2.13 mmol, 3.0 eq). The mixture was stirred at room temperature for 16 h, diluted with EtOAc (100 mL) and washed with water (20 mL×3). The organic layer was dried over sodium sulfate and concentrated under reduced pressure. The residue was purified with pre-HPLC (MeOH/H$_2$O with 0.05% TFA as mobile phase; from 20% to 95%) to furnish the compound 33, 13 mg (Y: 5%), as a white solid. $^1$H NMR (400 MHz, CD$_3$OD) δ: 8.34 (s, 1H), 8.06 (d, J=5.2 Hz, 1H), 8.02 (s, 1H), 7.58 (s, 1H), 7.44 (s, 1H), 7.02 (d, J=4.8 Hz, 1H), 3.93 (s, 3H), 3.41 (t, J=6.4 Hz, 2H), 3.32-3.28 (m, 2H), 1.87-1.80 (m, 4H), 1.50-1.47 (m, 2H). m/z 396.1 [M+H]$^+$
Example 34
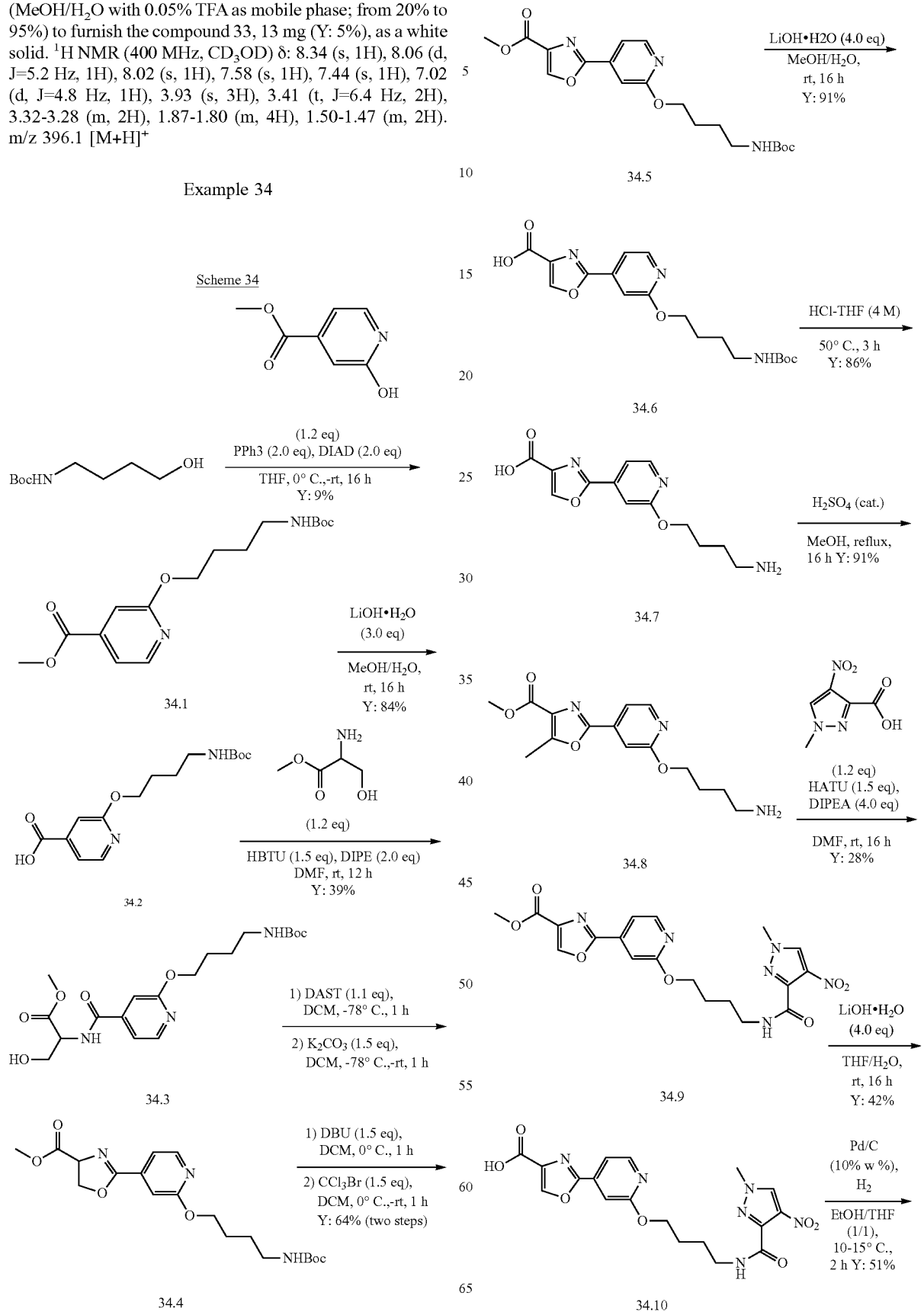

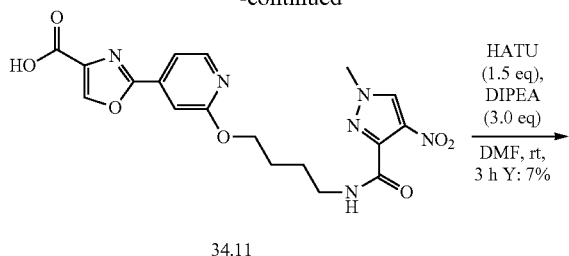

34.11

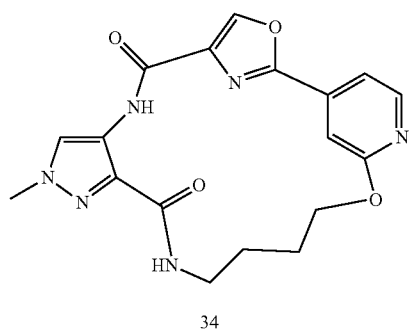

34

Synthesis of Compound 34.1

A mixture of tert-butyl(4-hydroxybutyl)carbamate (5.1 g, 27.0 mmol, 1.0 eq), methyl 2-hydroxyisonicotinate (5.0 g, 32.4 mmol, 1.2 eq), Et$_3$N (1.3 g, 13.1 mmol, 1.2 eq) and PPh$_3$ (14.1 g, 54.0 mmol, 2.0 eq) in THF (20 mL) was stirred at room temperature for 0.5 h. Then DIAD (10.9 g, 54.0 mmol, 2.0 eq) was added dropwise at 0° C. Then the reaction mixture was stirred at room temperature for additional 16 h. After removed the solvent under reduced pressure, the residue was purified by pre-HPLC (MeOH/H$_2$O with 0.05% TFA as mobile phase; from 20% to 95%) to give the compound 34.1 (960 mg, Y: 9%) as a pale yellow oil. $^1$H NMR (400 MHz, DMSO-d$_6$) δ: 8.25 (d, J=5.2 Hz, 1H), 7.38 (d, J=5.2 Hz, 1H), 7.29 (s, 1H), 4.65 (bs, 1H), 4.33 (t, J=6.8 Hz, 2H), 3.93 (s, 3H), 3.21-3.19 (m, 2H), 1.85-1.78 (m, 2H), 1.67-1.62 (m, 2H), 1.44 (s, 9H); ESI-MS (M+H)$^+$: 325.2.

Synthesis of Compound 34.2

To a solution of 34.1 (1.1 g, 3.4 mmol, 1.0 eq) in THF (10 mL) and H$_2$O (3 mL) was added LiOH H$_2$O (428 mg, 10.2 mmol, 3.0 eq). The reaction mixture was stirred at room temperature for 16 h. Then the solution was adjusted to pH=6 with acetic acid (20% in water) and extracted with EtOAc (10 mL×4). The combined organic layers were dried over anhydrous sodium sulfate and concentrated under reduced pressure to give 34.2 as a yellow solid (873 mg, Y: 84%); ESI-MS (M+H)$^+$: 311.1.

Synthesis of Compound 34.3

To a solution of 34.2 (1.5 g, 4.8 mmol, 1.0 eq) in DMF (10 mL) was added methyl 2-amino-3-hydroxypropanoate (690 mg, 5.8 mmol, 1.2 eq), HBTU (2.7 g, 7.2 mmol, 1.5 eq) and DIPEA (1.2 g, 9.6 mmol, 2.0 eq). After stirred at room temperature for 12 h, the reaction mixture was diluted with EtOAc (30 mL) and washed with water (5 mL×3). The organic layer was concentrated to give brown oil which was purified by pre-HPLC (MeOH/H$_2$O with 0.05% TFA as mobile phase; from 20% to 95%) to furnish the compound 34.3 (815 mg, Y: 39%) as a yellow oil. $^1$H NMR (400 MHz, DMSO-d$_6$) δ: 8.86 (d, J=7.2 Hz, 1H), 8.28 (d, J=5.2 Hz, 1H), 7.36 (d, J=1.2 Hz, J=5.2 Hz, 1H), 7.24 (s, 1H), 6.85 (t, J=5.6 Hz, 1H), 5.06 (t, J=5.6 Hz, 1H), 4.56-4.51 (m, 1H), 4.28 (t, J=1.2 Hz, 2H), 3.79 (t, J=5.6 Hz, 2H), 3.66 (s, 3H), 3.00-2.95 (m, 2H), 1.72-1.68 (m, 2H), 1.53-1.50 (m, 2H), 1.37 (s, 9H); ESI-MS (M+H)$^+$: 412.2.

Synthesis of Compound 34.4

To a solution of 34.3 (400 mg, 0.97 mmol, 1.0 eq) in DCM (20 mL) was added DAST (172 mL, 1.1 mmol, 1.1 eq) dropwise at −78° C. After stirred for 1 h at −78° C., the reaction mixture was added K$_2$CO$_3$ (201 mg, 1.5 mmol, 1.5 eq) and stirred at room temperature for additional 1 h. Then, the reaction solution was diluted with DCM (30 mL) and H$_2$O (8 mL). The organic layer was separated and concentrated to give the crude product which was used in next step without further purification; ESI-MS (M+H)$^+$: 394.2.

Synthesis of Compound 34.5

A solution of 34.4 from up step in DCM (20 mL) was added DBU (228 mg, 1.5 mmol, 1.5 eq) dropwise at 0° C. After stirred at 0° C. for 1 h, the reaction solution was added CCl$_3$Br (294 mg, 1.5 mmol, 1.5 eq) and stirred at room temperature for additional 1 h. Then the reaction was quenched with water (10 mL), diluted with DCM (30 mL), washed with saturated sodium bicarbonate solution (10 mL) and brine (10 mL). The organic layer was dried over anhydrous sodium sulphate and evaporated in vacuo. The residue was purified by pre-HPLC (MeOH/H$_2$O with 0.05% TFA as mobile phase; from 20% to 95%) to furnish the compound 34.5 (319 mg, Y: 64%) as a yellow oil. $^1$H NMR (400 MHz, CDCl$_3$) δ: 8.34 (s, 1H), 8.27 (d, J=5.2 Hz, 1H), 7.53 (d, J=1.2 Hz, J=5.2 Hz, 1H), 7.39 (s, 1H), 4.64 (bs, 1H), 4.35 (t, J=6.4 Hz, 2H), 3.97 (s, 3H), 3.23-3.18 (m, 2H), 1.86-1.79 (m, 2H), 1.70-1.60 (m, 2H), 1.45 (s, 9H); ESI-MS (M+H)$^+$: 392.2.

Synthesis of Compound 34.6

To a solution of 34.5 (600 mg, 1.5 mmol, 1.0 eq) in MeOH (10 mL) and H$_2$O (3 mL) was added LiOH H$_2$O (252 mg, 6.0 mmol, 4.0 eq). The reaction mixture was stirred at room temperature for 16 h. Then the reaction solution was adjusted pH=6 with acetic acid (20% in water) and extracted with EtOAc (10 mL×4). The combined organic layers were dried over anhydrous sodium sulfate and concentrated under reduced pressure to give 34.6 (520 mg, Y: 91%) as a yellow solid; ESI-MS (M+H)$^+$: 378.2.

Synthesis of Compound 34.7

A solution of 34.6 (500 mg, 1.3 mmol) in HCl-THF (10 mL, 4 N) was stirred at 50° C. for 3 h and concentrated under reduced pressure to give 34.7 (316 mg, Y: 86%) as a yellow solid; ESI-MS (M+H)⁺: 278.1.

Synthesis of Compound 34.8

To a solution of 34.7 (316 mg, 1.1 mmol, 1.0 eq) in MeOH (10 mL) was added H₂SO₄ (6 mg, 0.06 mmol, 0.05 eq). The mixture was refluxed for 16 h and concentrated under reduced pressure to give 34.8 (302 mg, Y: 91%) as a yellow solid; ESI-MS (M+H)⁺: 292.1.

Synthesis of Compound 34.9

To a solution of 34.8 (300 mg, 1.03 mmol, 1.0 eq) in DMF (8 mL) was added HATU (587 mg, 1.55 mmol, 1.5 eq) and DIPEA (398 mg, 3.09 mmol, 3.0 eq). The reaction mixture was stirred at room temperature for 16 h, diluted with EtOAc (50 mL) and washed with water (5 mL×3). The organic layer was dried over anhydrous sodium sulfate and concentrated under reduced pressure. The residue was purified by pre-HPLC (MeOH/H₂O with 0.05% TFA as mobile phase; from 20% to 95%) to furnish the compound 34.9 (128 mg, Y: 28%) as a yellow oil; ESI-MS (M+H)⁺: 445.1.

Synthesis of Compound 34.10

To a solution of 34.9 (415 mg, 0.93 mmol, 1.0 eq) in THF (10 mL) and H₂O (3 mL) was added LiOH H₂O (157 mg, 3.74 mmol, 4.0 eq). The reaction mixture was stirred at room temperature for 16 h. Then the reaction solution was adjusted pH=6 with acetic acid (20% in water) and extracted with EtOAc (5 mL×4). The combined organic layers were dried over anhydrous sodium sulfate and concentrated under reduced pressure to give 34.10 as a yellow oil (313 mg, Y: 42%); ESI-MS (M+H)⁺: 431.1.

Synthesis of Compound 34.11

A solution of 34.10 (279 mg, 0.65 mmol, 1.0 eq) in EtOH/THF (4 mL) was flushed with N₂ for 3 times. 10% Pd/C (28 mg, 10% wt) was added and the mixture was flushed with H₂ for 3 times. The resulting mixture was stirred at 10-15° C. for 2 h under H₂ atmosphere. After filtered through Celite, the filtrate was concentrated in vacuo to give the desired compound 34.11 (222 mg, Y: 51%), which was used in next step without further purification; ESI-MS (M+H)⁺: 401.1.

Synthesis of Compound 34

To a solution of 34.11 (200 mg, 0.50 mmol, 1.0 eq) in DMF (5 mL) and DCM (45 mL) was added HATU (285 mg, 0.75 mmol, 1.5 eq) and DIPEA (194 mg, 1.50 mmol, 3.0 eq). The mixture was stirred at room temperature for 16 h, diluted with EtOAc (20 mL) and washed with water (5 mL×3). The organic layer was dried over anhydrous sodium sulfate and concentrated under reduced pressure. The residue was purified by pre-HPLC (MeOH/H₂O with 0.05% TFA as mobile phase; from 20% to 95%) to furnish the compound 34 (28 mg, Y: 15%) as a white solid. ¹H NMR (400 MHz, CD₃OD) δ: 8.36 (s, 1H), 8.34 (d, J=5.2 Hz, 1H), 8.20 (s, 1H), 7.96 (s, 1H), 7.43 (s, 1H), 7.38 (d, J=4.4 Hz, 1H), 4.52-4.47 (m, 2H), 3.96 (s, 3H), 3.46-3.43 (m, 2H), 2.35-2.31 (m, 2H), 1.82-1.79 (m, 2H); ESI-MS (M+H)⁺: 383.0

Example 35

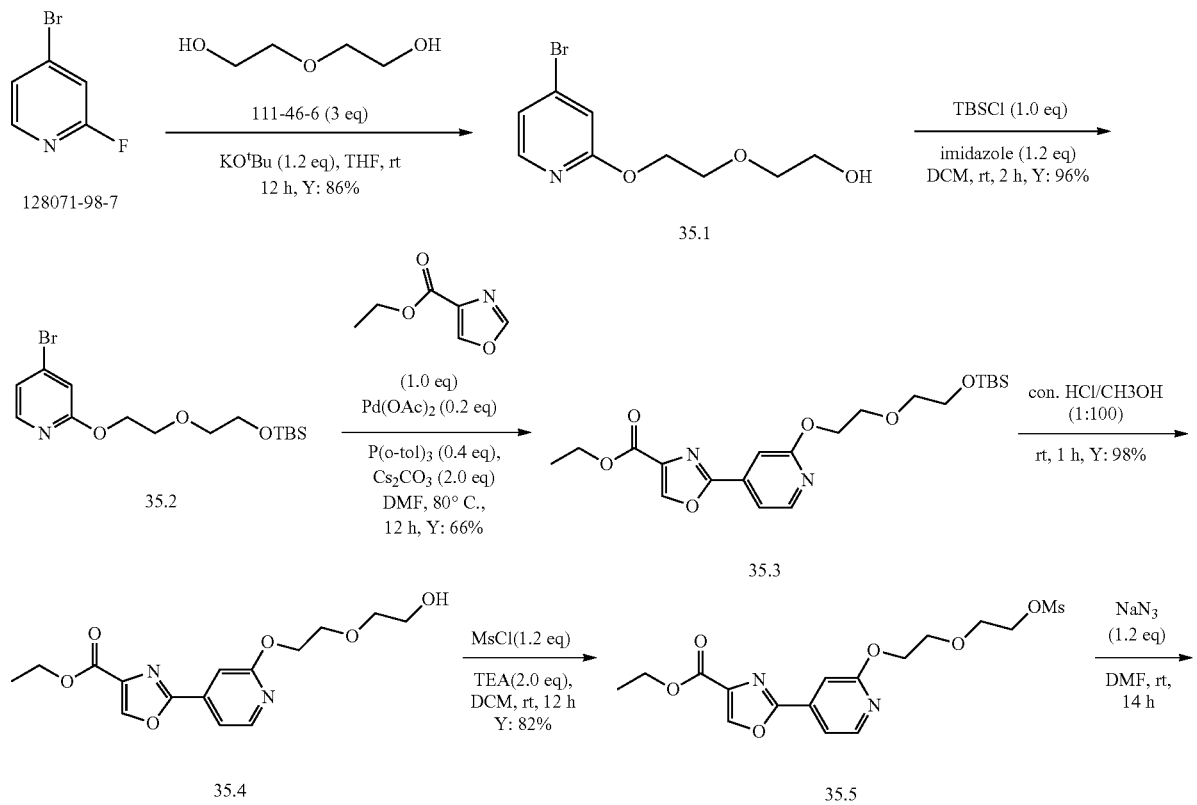

Scheme 35

-continued
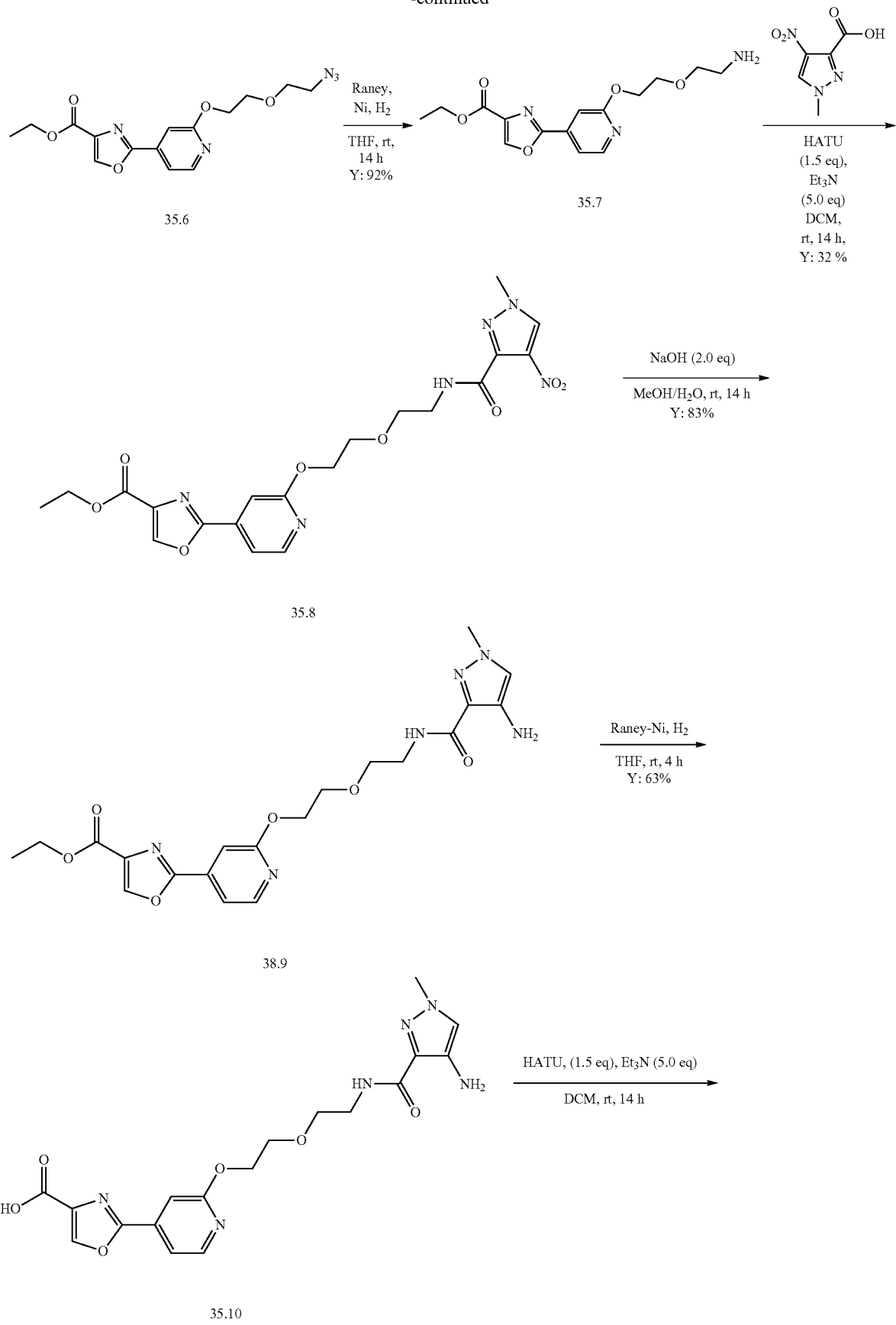

-continued

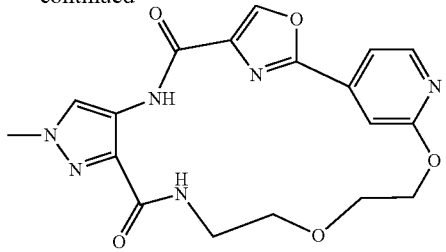

35

Synthesis of Compound 35.1

To a solution of 4-bromo-2-fluoropyridine (5.0 g, 28.6 mmol, 1.0 eq) in THF (50 mL) were added 2,2'-oxydiethanol (9.1 g, 85.8 mmol, 3.0 eq) and t-BuOK (3.8 g, 34.3 mmol, 1.2 eq). After stirred at room temperature for 12 h, the reaction mixture was diluted with water (20 mL) and extracted with EA (20 mL×3). The combined organic layers were washed with brine (20 mL×5), dried over anhydrous $Na_2SO_4$, and concentrated under reduced pressure. The residue was purified by chromatography column (PE:EA=3:1) to give 35.1 (6.4 g, yield: 86%) as a yellow oil; ESI-MS $(M+H)^+$: 262.1.

Synthesis of Compound 35.2

To a solution of 35.1 (2.5 g, 9.6 mmol, 1.0 eq) in DCM (40 mL) were added TBSCl (1.4 g, 9.6 mmol, 1.0 eq) and imidazole (783 mg, 11.5 mmol, 1.2 eq). After stirred at room temperature for 2 h, the reaction mixture was diluted with water (10 mL) and extracted with DCM (20 mL×3). The combined organic layers were washed with HCl (20 mL, 1 N) and brine (20 mL×5), dried over anhydrous $Na_2SO_4$, and concentrated under reduced pressure. The residue was purified by chromatography column (PE:EA=1:4) to give 35.2 (3.5 g, yield: 96%) as a yellow oil; ESI-MS $(M+H)^+$: 376.3.

Synthesis of Compound 35.3

To a solution of 35.2 (3.2 g, 8.6 mmol, 1.0 eq) in DMF (10 mL) were added ethyl oxazole-4-carboxylate (1.2 g, 8.6 mmol, 1.0 eq), $Pd(OAc)_2$ (385 mg, 1.72 mmol, 0.2 eq), $P(O\text{-tol})_3$ (1.05 mg, 3.44 mmol, 0.4 eq) and $Cs_2CO_3$ (5.6 g, 17.2 mmol, 2.0 eq). After stirred at 80° C. for 14 h, the reaction mixture was diluted with water (10 mL) and extracted with EA (20 mL×3). The combined organic layers were washed with brine (20 mL×5), dried over anhydrous $Na_2SO_4$ and concentrated under reduced pressure. The residue was purified by chromatography column (PE:EA=3:1) to give 35.3 (2.5 g, yield: 66%) as a white solid; ESI-MS $(M+H)^+$: 437.3.

Synthesis of Compound 35.4

To a solution of 35.3 (6.8 g, 15.6 mmol, 1.0 eq) in $CH_3OH$ (100 mL) was added conc. HCl (1.0 mL). After stirred at room temperature for 1 h, the solvents was removed under reduced pressure. The residue was diluted with water (10 mL) and extracted with EA (20 mL×5). The combined organic layers were washed with brine (20 mL×3), dried over anhydrous $Na_2SO_4$, and concentrated in vacuo to give 35.4 (4.8 g, yield: 98%) as a yellow oil. $^1$H NMR (400 MHz, DMSO-$d_6$) δ: 9.11 (s, 1H), 8.41 (dd, J=1.2 Hz, 1.2 Hz, 1H), 7.59 (dd, J=1.2 Hz, 1.2 Hz, 1H), 7.32 (s, 1H), 4.69 (t, J=6.0 Hz, 1H), 4.50 (t, J=4.8 Hz, 2H), 4.40 (q, J=7.2 Hz, 7.2 Hz, 2H), 3.82 (t, J=4.4 Hz, 2H), 3.57-3.52 (m, 4H), 1.38 (t, J=7.2 Hz, 3H); ESI-MS $(M+H)^+$: 322.9.

Synthesis of Compound 35.5

To a solution of 35.4 (5.0 g, 15.8 mmol, 1.0 eq) in DCM (30 mL) were added $Et_3N$ (3.2 g, 31.6 mmol, 2.0 eq) and MsCl (2.2 g, 19.0 mmol, 1.2 eq) at 0° C. After stirred at room temperature for 12 hours, the reaction mixture was washed with brine (20 mL×3), dried over anhydrous $Na_2SO_4$ and concentrated in vacuo to give 35.5 (5.1 g, yield: 82%) as a yellow oil. $^1$H NMR (400 MHz, DMSO-$d_6$) δ: 9.07 (s, 1H), 8.37 (d, J=5.2 Hz, 1H), 7.55 (dd, J=5.2 Hz, 5.6 Hz, 1H), 7.29 (s, 1H), 4.78 (t, J=4.4 Hz, 2H), 4.36-4.31 (m, 4H), 3.84 (t, J=4.8 Hz, 2H), 3.77 (t, J=4.8 Hz, 2H), 3.19 (s, 3H), 1.34 (t, J=7.2 Hz, 3H); ESI-MS $(M+H)^+$: 401.1.

Synthesis of Compound 35.6

To a solution of 35.5 (5.0 g, 12.5 mmol, 1.0 eq) in DMF (20 mL) was added $NaN_3$ (975 mg, 15 mmol, 1.2 eq). After stirred at room temperature for 14 h, the resulting mixture was adjusted to pH=9 with saturated $NaHCO_3$ and extracted with EA (20 mL×5). The combined organic layers were washed with brine (20 mL×3), dried over anhydrous $Na_2SO_4$ and concentrated in vacuo to give 35.6 (4.1 g, yield: 92%) as a yellow oil, which was used in the next step without further purification. $^1$H NMR (400 MHz, DMSO-$d_6$) δ: 9.06 (s, 1H), 8.37 (dd, J=4.2 Hz, 4.2 Hz, 1H), 7.54 (dd, J=4.2 Hz, 4.2 Hz, 1H), 7.28 (s, 1H), 4.78 (t, J=4.8 Hz, 2H), 4.36 (q, J=7.2 Hz, 7.2 Hz, 2H), 3.84 (t, J=4.8 Hz, 2H), 3.71 (t, J=4.8 Hz, 2H), 3.43 (t, J=5.2 Hz, 2H), 1.34 (t, J=7.6 Hz, 3H); ESI-MS $(M+H)^+$: 358.1.

Synthesis of Compound 35.7

To a solution of 35.6 (4.8 g, 13.4 mmol, 1.0 eq) in THF (50 mL), Catalytic Raney-Ni was added. The reaction mixture was stirred under $H_2$ atmosphere at room temperature for 14 h. After filtered by Celite, the filtrate was concentrated in vacuo to afford 35.7 (4.1 g, yield: 92%) as a yellow oil; ESI-MS $(M+H)^+$: 322.2.

Synthesis of Compound 35.8

To a solution of 35.7 (2.0 g, 6.3 mmol, 1.0 eq) in DCM (150 mL) were added 1-methyl-4-nitro-1H-pyrazole-3-carboxylic acid (1.1 g, 6.3 mmol, 1.0 eq), HATU (3.6 g, 9.5 mmol, 1.5 eq) and $Et_3N$ (3.2 g, 31.5 mmol, 5.0 eq). After stirred at room temperature for 14 h, the resulting mixture was washed with brine (30 mL×3), dried over anhydrous $Na_2SO_4$, concentrated under reduced pressure. The residue was purified by chromatography column (PE:EA=5:1) to give 35.8 (1.0 g, yield: 32%) as a white solid. $^1$H NMR (400 MHz, DMSO-$d_6$) δ: 9.07 (s, 1H), 8.84 (s, 1H), 8.68 (t, J=5.2 Hz, 1H), 8.36 (d, J=5.6 Hz, 1H), 7.54 (dd, J=5.2 Hz, 5.2 Hz, 1H), 7.28 (s, 1H), 4.47 (t, J=4.4 Hz, 2H), 4.36 (q, J=7.2 Hz, 2H), 3.90 (s, 3H), 3.81 (t, J=4.4 Hz, 2H), 3.61 (t, J=6.0 Hz, 2H), 3.43 (q, J=6.0 Hz, 5.6 Hz, 2H), 1.34 (t, J=7.2 Hz, 3H); ESI-MS (M+H)+: 475.1

Synthesis of Compound 35.9

To a solution of 35.8 (1.0 g, 2.1 mmol, 1.0 eq) in MeOH (20 mL) was added a solution of NaOH (168 mg, 4.2 mmol, 2.0 eq) in H$_2$O (4.0 mL). The mixture was stirred at room temperature for 14 h. After removed methanol under reduced pressure, the residue was acidified to Ph=6 with HCl (1 N) and then filtered. The white precipitate was collected as 35.9 (780 mg, yield: 83%). $^1$H NMR (400 MHz, DMSO-d$_6$) δ: 13.35 (s, 1H), 8.98 (s, 1H), 8.36 (s, 1H), 8.68 (t, J=5.2 Hz, 1H), 8.36 (dd, J=5.2 Hz, 5.2 Hz, 1H), 7.53 (dd, J=5.2 Hz, 5.2 Hz, 1H), 7.27 (s, 1H), 4.46 (t, J=4.4 Hz, 2H), 3.90 (s, 3H), 3.81 (t, J=4.8 Hz, 2H), 3.61 (t, J=6.0 Hz, 2H), 3.43 (q, J=6.0 Hz, 5.6 Hz, 2H); ESI-MS (M+H)+: 447.3

Synthesis of Compound 35.10

To the solution of 35.9 (850 mg, 1.9 mmol, 1.0 eq) in THF (30 mL), catalytic Raney-Ni was added. The resulting mixture was stirred under H$_2$ atmosphere at room temperature for 14 h. After filtered by Celite, the filtrate was concentrated in vacuo to afford 35.10 (450 mg, yield: 63%) as a colorless oil; ESI-MS (M+H+): 417.1.

Synthesis of Compound 35

To a solution of 35.10 (200 mg, 0.48 mmol, 1.0 eq) in DCM (20 mL) were added HATU (274 mg, 0.72 mmol, 1.5 eq) and Et$_3$N (97 mg, 0.96 mmol, 2.0 eq). After stirred at room temperature for 14 h, the resulting mixture was washed with brine (30 mL×3), dried over anhydrous Na$_2$SO$_4$ and concentrated under reduced pressure. The residue was purified by prep-HPLC (MeOH/H$_2$O with 0.05% NH$_3$H$_2$O as mobile phase; from 0% to 95%) to afford 35 (50 mg, yield: 26%) as a white solid. $^1$H NMR (400 MHz, CDCl$_3$) δ: 12.28 (s, 1H), 8.35 (d, J=4.8 Hz, 1.6 Hz, 1H), 8.20 (s, 1H), 8.04 (s, 1H), 7.92 (s, 1H), 7.33 (d, J=4.4 Hz, 1H), 6.76 (s, 1H), 4.48 (t, J=8.0 Hz, 2H), 4.06 (t, J=8.0 Hz, 2H), 3.86 (s, 3H), 3.80 (t, J=5.2 Hz, 2H), 3.56 (d, J=5.6 Hz, 2H); ESI-MS (M+H)+: 398.0; HPLC: 214 nm: 100%, 254 nm: 100%.

Example 36

Scheme 36

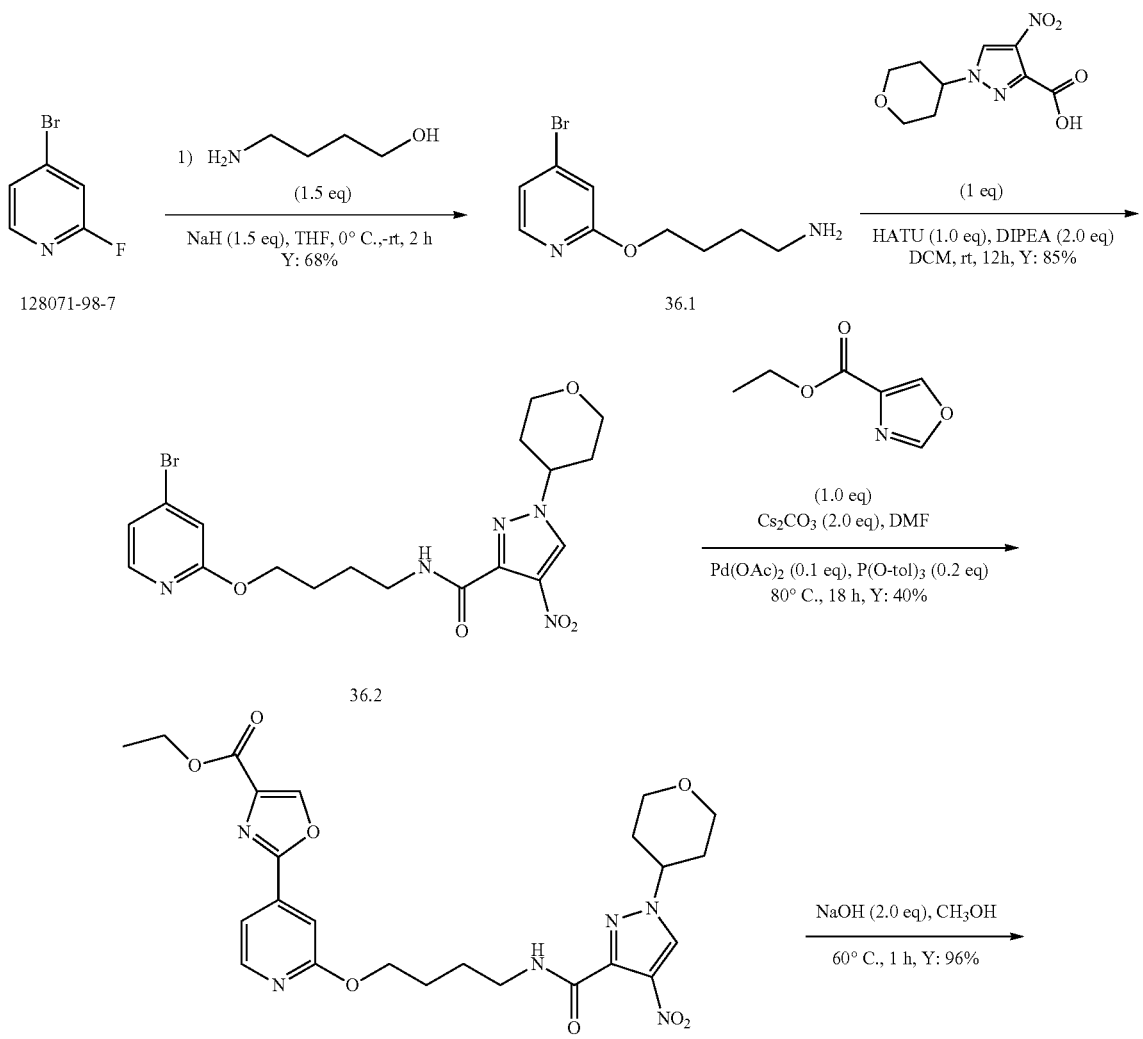

-continued

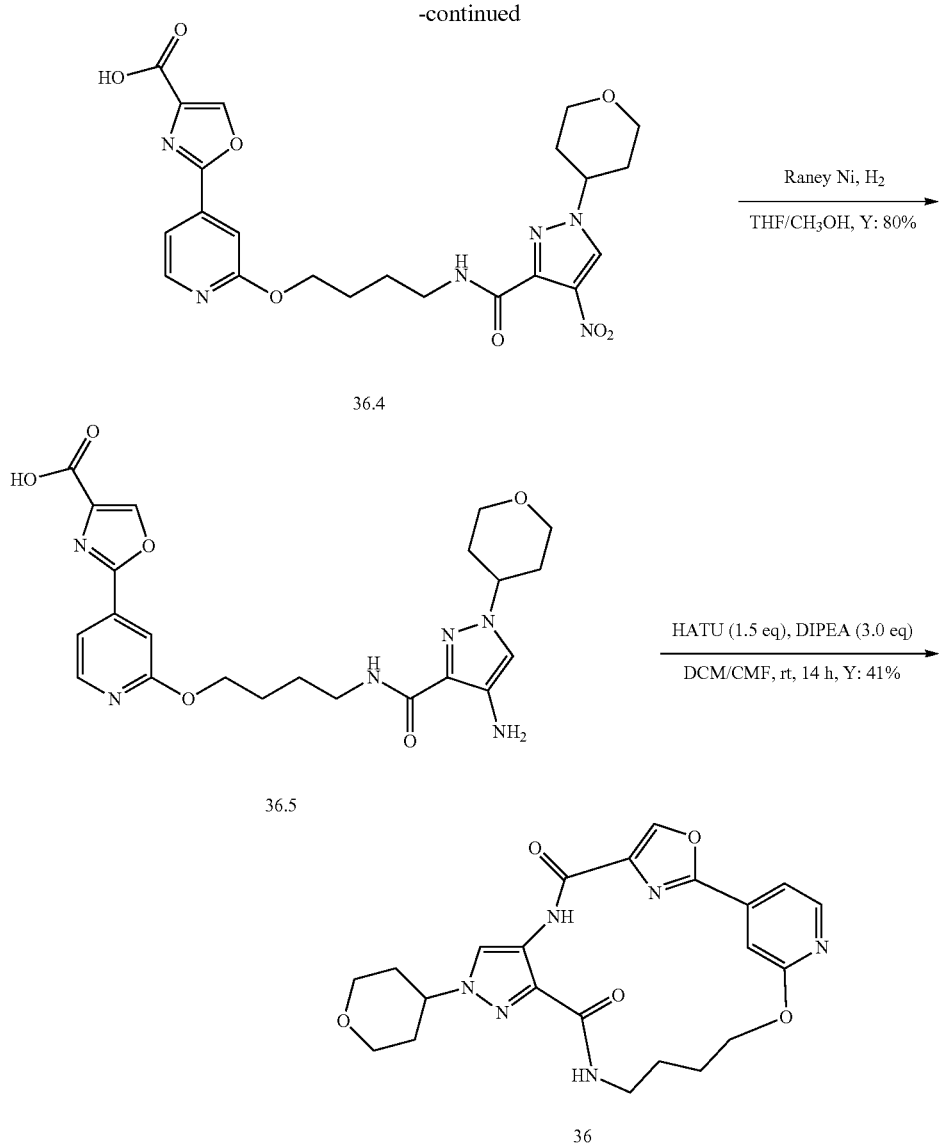

Synthesis of Compound 36.1

To a solution of 4-aminobutan-1-ol (1.3 g, 14.3 mmol, 1.0 eq) in THF (100 mL) were added NaH (343 mg, 14.3 mmol, 1.0 eq) and then 4-bromo-2-fluoropyridine (2.5 g, 14.3 mmol, 1.0 eq) at 0° C. The reaction mixture was stirred at room temperature for 2 h and then quenched with H$_2$O (10 mL). The resulting solution was concentrated under reduced pressure and extracted with DCM (20 mL×5). The combined organic layers were washed with brine (20 mL×3), dried over anhydrous sodium sulfate and evaporated in vacuo to give 36.1 (1.8 g, yield: 50%) as a yellow oil. $^1$H NMR (400 MHz, CD$_3$OD) δ: 7.99 (d, J=5.6 Hz, 1H), 7.12 (d, J=5.6 Hz, 1H), 7.01 (s, 1H), 4.32 (t, J=6.8 Hz, 2H), 2.73 (t, J=7.6 Hz, 2H), 1.84-1.77 (m, 2H), 1.67-1.59 (m, 2H); ESI-MS (M+H)$^+$: 245.3.

Synthesis of Compound 36.2

To a solution of 4-nitro-1-(tetrahydro-2H-pyran-4-yl)-1H-pyrazole-3-carboxylic acid (296 mg, 1.2 mmol, 1.0 eq) in DCM (20 mL) were added DIPEA (310 mg, 2.4 mmol, 2.0 eq), 36.1 (300 mg, 1.2 mmol, 1.0 eq) and HATU (684 mg, 1.8 mmol, 1.5 eq). After stirred at room temperature for 12 h, the resulting mixture was washed with brine (15 mL×3), dried over anhydrous sodium sulfate and concentrated under reduced pressure. The residue was purified by silica gel column (PE/EA=5/1) to give 36.2 (505 mg, yield: 85%) as a yellow oil; ESI-MS (M+H)$^+$: 468.1.

Synthesis of Compound 36.3

To the solution of 36.2 (500 mg, 1.07 mmol, 1.0 eq) in DMF (10 mL) were added ethyl oxazole-4-carboxylate (151 mg, 1.07 mmol, 1.0 eq), Pd(OAc)$_2$ (24 mg, 0.107 mmol, 0.1 eq), P(o-tol)$_3$ (65 mg, 0.214 mmol, 0.2 eq) and Cs$_2$CO$_3$ (1.05 g, 3.21 mmol, 3.0 eq) under nitrogen atmosphere. The reaction mixture was stirred at 80° C. for 18 h under nitrogen atmosphere. The resulting solution was diluted with water (40 mL), extracted with ethyl acetate (20 mL×3). The combined organic layers were washed with brine (40 mL×2), dried over anhydrous sodium sulfate, concentrated under reduced pressure. The residue was purified by silica gel column (PE/EA=2/1) to give 36.3 (220 mg, yield: 40%) as a white solid. $^1$H NMR (400 MHz, CD$_3$OD) δ: 8.69 (s, 2H), 8.30 (d, J=5.2 Hz, 1H), 7.57 (d, J=5.2 Hz, 1H), 7.41 (s, 1H), 4.53-4.46 (m, 1H), 4.44-4.39 (m, 4H), 4.12-4.05 (m, 2H), 3.59-3.53 (m, 2H), 3.51 (t, J=7.2 Hz, 2H), 2.13-2.07 (m, 4H), 1.96-1.91 (m, 2H), 1.87-1.81 (m, 2H), 1.42 (t, J=6.8 Hz, 3H); ESI-MS (M+H)$^+$: 529.3.

Synthesis of Compound 36.4

To a solution of 36.3 (220 mg, 0.42 mmol, 1.0 eq) in MeOH (40 mL) was added a solution of NaOH (33 mg, 0.84 mmol, 2.0 eq) in H$_2$O (10 mL). After stirred at 60° C. for 2 h, the reaction mixture was adjusted to pH=6 with HCl (1 N) and concentrated under reduced pressure. The precipitate was collected and washed with H$_2$O (5 mL) to give 36.4 (200 mg, yield: 96%) as a white solid. $^1$H NMR (400 MHz, CD$_3$OD) δ: 8.69 (s, 1H), 8.64 (s, 1H), 8.30 (d, J=5.2 Hz, 1H), 7.58 (d, J=5.2 Hz, 1H), 7.42 (s, 1H), 4.55-4.47 (m, 1H), 4.44 (t, J=6.0 Hz, 2H), 4.12-4.06 (m, 2H), 3.60-3.53 (m, 2H), 3.51 (t, J=6.8 Hz, 2H), 2.13-2.05 (m, 4H), 1.96-1.91 (m, 2H), 1.87-1.81 (m, 2H); ESI-MS (M+H)$^+$: 501.3.

Synthesis of Compound 36.5

To a solution of catalytic amount of Raney Ni (10% wt) in THF (20 mL) was added 36.4 (200 mg, 0.4 mmol). The reaction mixture was stirred at room temperature for 6 h under hydrogen atmosphere. After filtered by Celite, the filtrate was concentrated to give 36.5 (150 mg, yield: 80%) a colorless oil; ESI-MS (M+H)$^+$: 471.3.

Synthesis of Compound 36

To a solution of 36.5 (100 mg, 0.22 mmol, 1.0 eq) in DCM (40 mL) and DMF (4 mL) were added DIPEA (86 mg, 0.66 mmol, 3.0 eq) and HATU (122 mg, 0.32 mmol, 1.5 eq). The reaction mixture was stirred at room temperature for 14 h and then concentrated under reduced pressure. The residue was purified by prep-HPLC (CH$_3$CN/0.05% NH$_3$H$_2$O in H$_2$O=0~95%) to give 36 (39 mg, yield: 41%) as a white solid. $^1$H NMR (400 MHz, DMSO-d$_6$) δ: 12.77 (s, 1H), 8.40 (d, J=5.2 Hz, 1H), 8.24 (s, 1H), 8.20 (s, 1H), 7.99 (s, 1H), 7.33 (d, J=5.2 Hz, 1H), 6.95 (t, J=5.6 Hz, 1H), 4.52-4.48 (m, 2H), 4.34-4.29 (m, 1H), 4.18-4.13 (m, 2H), 3.58-3.49 (m, 2H), 3.47-3.45 (m, 2H), 2.38-2.30 (m, 2H), 2.15-2.09 (m, 4H), 1.81-1.78 (m, 2H); ESI-MS (M+H)$^+$: 453.1; HPLC: 214 nm: 99.55%, 254 nm: 100%.

Examples 37 and 38

Scheme 37

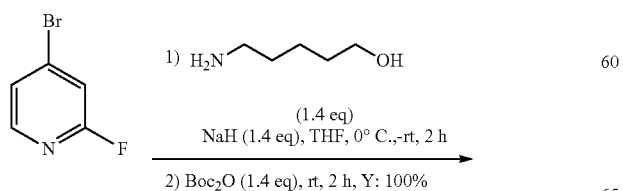

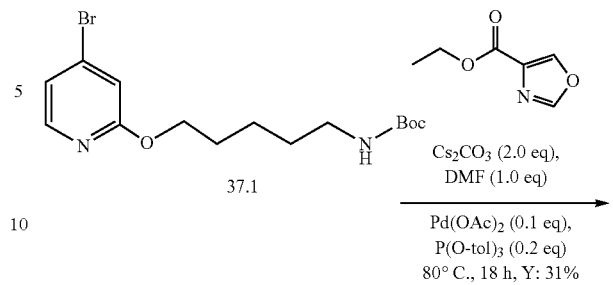

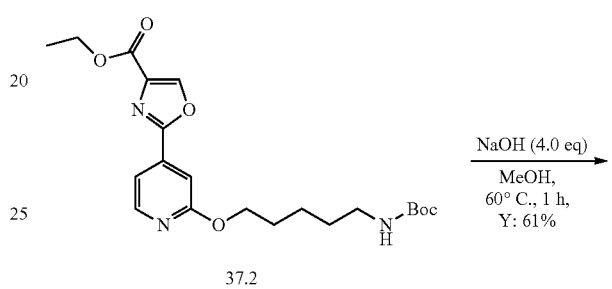

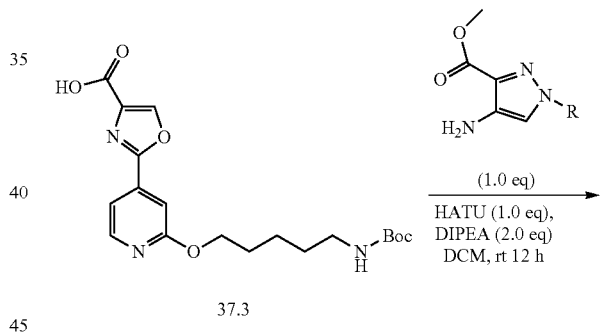

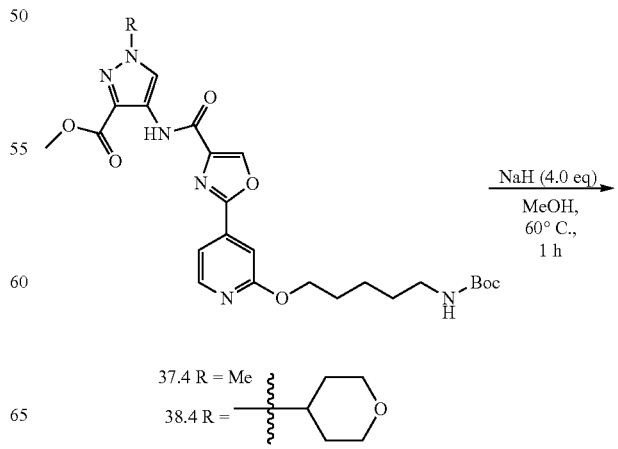

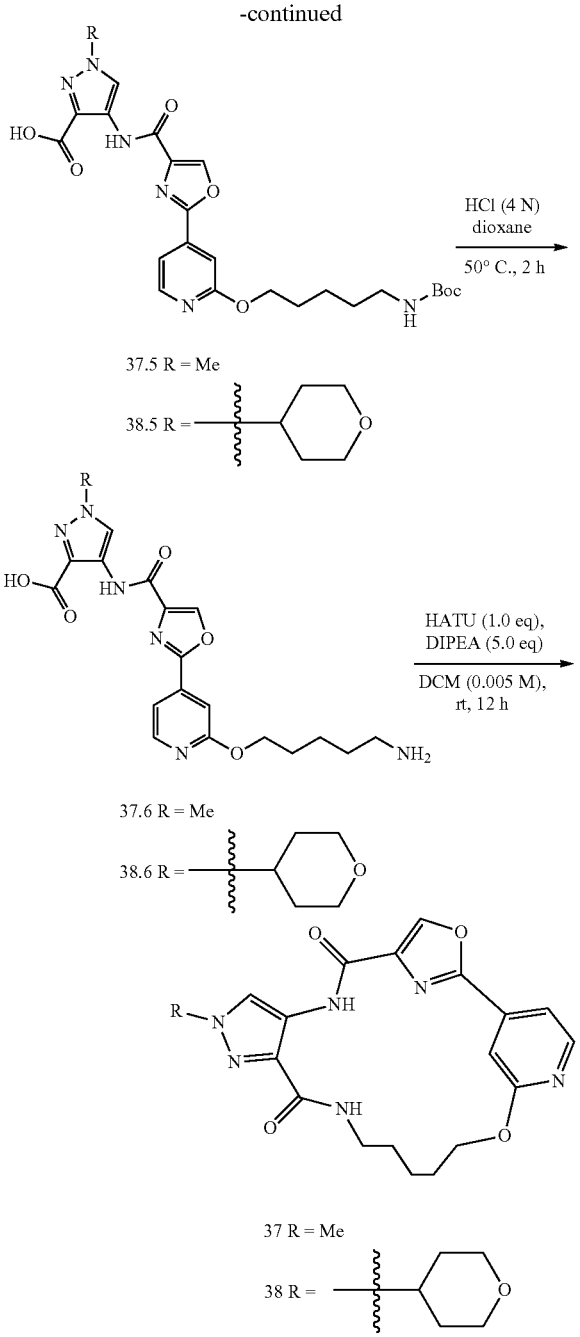

Synthesis of Compound 37.1

To a solution of 5-amino-1-pentanol (5 g, 48 mmol, 1.4 eq) in anhydrous THF (100 mL) was added NaH (2.8 g, 48 mmol, 1.4 eq) at 0° C. After stirred at room temperature for 30 min, 4-bromo-2-fluoropyridine (5 g, 34 mmol, 1.0 eq) was added at 0° C. After stirred at room temperature for 2 h, Boc₂O (10.5 g, 48 mmol, 1.4 eq) was added. After stirred at room temperature for another 2 h, the resulting solution was diluted with ethyl acetate (300 mL). The organic layer was washed with brine, dried over sodium sulfate and concentrated under reduced pressure. The residue was purified by silica gel column (PE/EA=8/1) to give 37.1 (13 g, yield: 100%) as a colorless oil. ¹H NMR (400 MHz, DMSO-d₆) □ δ: 8.06 (d, J=6.8 Hz, 1H), 7.21 (dd, J₁=1.2 Hz, J₂=6.8 Hz, 1H), 7.09 (d, J=1.2 Hz, 1H), 6.81 (t, J=5.6 Hz, 1H), 4.23 (t, J=6.4 Hz, 2H), 2.91 (q, J=6.0 Hz, 2H), 1.72-1.65 (m, 2H), 1.41-1.34 (m, 13H); ESI-MS (M+H)⁺: 359.1.

Synthesis of Compound 37.2

To a solution of 37.1 (2.5 g, 7 mmol, 1.0 eq) and ethyl oxazole-4-carboxylate (984 mg, 7 mmol, 1.0 eq), Cs₂CO₃ (4.5 g, 14 mmol, 2.0 eq) in DMF (30 ml) were added Pd(OAc)₂ (313 mg, 1.4 mmol, 0.2 eq) and P(o-tol)₃ (850 mg, 2.8 mmol, 0.4 eq). The reaction mixture was stirred at 80° C. for 18 h under nitrogen atmosphere. After cooling down to room temperature, the resulting solution was diluted with ethyl acetate (250 ml) and then filtered by Celite. The filtrate was washed with water (100 ml×2), brine (100 ml×2), dried over anhydrous sodium sulfate and concentrated under reduced pressure. The residue was purified by silica gel column (PE/EA=8/1) to give 37.2 (900 mg, yield: 31%) as a yellow oil; ESI-MS (M+H)⁺: 420.1.

Synthesis of Compound 37.3

To a solution of 37.2 (900 mg, 2.2 mmol, 1.0 eq) in MeOH (10 mL) and H₂O (10 mL) was added NaOH (343 mg, 8.8 mmol, 4.0 eq). After stirred at 60° C. for 1 h, the reaction solution was cooled down to room temperature, adjusted to pH=6 with HCl (1 N) and extracted with ethyl acetate (100 mL×3). The organic layers were dried over sodium sulfate and concentrated under reduced pressure to give 37.3 as a white solid. (524 mg, yield: 61%). ¹H NMR (400 MHz, DMSO-d₆) □ δ: 12.73 (s, 1H), 8.94 (s, 1H), 8.34 (d, J=5.2 Hz, 1H), 7.50 (d, J=5.2 Hz, 1H), 7.25 (s, 1H), 6.82 (t, J=5.2 Hz, 1H), 4.29 (t, J=6.8 Hz, 2H), 2.94-2.89 (m, 2H), 1.76-1.69 (m, 2H), 1.44-1.40 (m, 4H), 1.36 (s, 9H); ESI-MS (M+H)⁺: 392.2.

Synthesis of Compound 37.4

To a solution of 37.3 (200 mg, 0.51 mmol, 1.0 eq) in DCM (10 mL) were added methyl 4-amino-1-methyl-1H-pyrazole-3-carboxylate (80 mg, 0.51 mmol, 1.0 eq), HATU (194 mg, 0.51 mmol, 1.0 eq) and DIPEA (130 mg, 1.02 mmol, 2.0 eq). After stirred at room temperature for 12 h, the reaction mixture was washed with water (10 mL), brine (10 mL). The organic layer was dried over sodium sulfate and concentrated under reduced pressure. The residue was purified by prep-TLC (DCM/MeOH=30/1) to give 37.4 (320 mg, yield: 85%) as a white solid. ¹H NMR (400 MHz, DMSO-d₆) □ δ: 10.27 (s, 1H), 9.07 (s, 1H), 8.42 (s, 1H), 8.39 (d, J=5.6 Hz, 1H), 7.51 (d, J=5.6 Hz, 1H), 7.27 (s, 1H), 6.81 (t, J=5.6 Hz, 1H), 4.31 (t, J=6.4 Hz, 2H), 3.95 (s, 3H), 3.93 (s, 3H), 2.95-2.91 (m, 2H), 1.77-1.71 (m, 2H), 1.43-1.36 (m, 4H), 1.36 (s, 9H); ESI-MS (M+H)⁺: 529.2.

Synthesis of Compound 38.4

The synthesis of 38.4 is similar to the synthesis of compound 37.4 using methyl 4-amino-1-(tetrahydro-2H-pyran-4-yl)-1H-pyrazole-3-carboxylate. The residue was purified by prep-TLC (DCM/MeOH=20/1) to give 38.4 (205 mg, yield: 80%) as a white solid. ¹H NMR (400 MHz, DMSO-d₆) □ δ: 10.31 (s, 1H), 9.07 (s, 1H), 8.48 (s, 1H), 8.39 (d, J=5.2 Hz, 1H), 7.51 (d, J=5.2 Hz, 1H), 7.27 (s, 1H), 6.82 (t, J=5.2 Hz, 1H), 4.64-4.56 (m, 1H), 4.31 (t, J=6.4 Hz, 2H), 4.0-3.97 (m, 2H), 3.94 (s, 3H), 3.49-3.43 (m, 2H), 2.95-2.91 (m, 2H), 2.01-1.95 (m, 4H), 1.77-1.71 (m, 2H), 1.45-1.41 (m, 4H), 1.36 (s, 9H); ESI-MS (M+H)⁺: 599.2.

Synthesis of Compound 37.5

To a solution of 37.4 (320 mg, 0.6 mmol, 1.0 eq) in MeOH (5 mL) and H₂O (5 mL) was added NaOH (96 mg, 2.4 mmol, 4.0 eq). After stirred at 60° C. for 1 h, the reaction solution was cooled down to room temperature, adjusted pH=6 with HCl (1 N) and extracted with ethyl acetate (100 mL×3). The combined organic layers were dried over sodium sulfate and concentrated under reduced pressure to give 37.5 as a white solid (308 mg, yield: 100%). ¹H NMR (400 MHz, DMSO-d₆) □ δ: 13.47 (s, 1H), 10.57 (s, 1H), 9.06 (s, 1H), 8.39-8.38 (m, 2H), 7.49 (d, J=8.4 Hz, 1H), 7.27 (s, 1H), 6.82 (t, J=5.6 Hz, 1H), 4.31 (t, J=6.4 Hz, 2H), 3.94 (s, 3H), 2.95-2.90 (m, 2H), 1.77-1.70 (m, 2H), 1.45-1.41 (m, 4H), 1.36 (s, 9H); ESI-MS (M+H)⁺: 515.2.

Synthesis of Compound 38.5

The synthesis of 38.5 is similar to the synthesis of compound 37.5 to afford 38.5 as a white solid (271 mg, yield: 100%); ESI-MS (M+H)⁺: 585.3.

Synthesis of Compound 37.6

To a solution of 37.5 (308 mg, 0.6 mmol) in dioxane (10 mL) was added HCl (4 N, 10 mL). The reaction mixture was stirred at 50° C. for 2 h. The solvent was removed under reduced pressure. The residue was purified by prep-HPLC (CH₃CN in H₂O—0.05% NH₃H₂O from 5%-90%) to give 37.6 (197 mg, yield: 64%); ESI-MS (M+H)⁺: 415.1.

Synthesis of Compound 38.6

The synthesis of 38.6 is similar to the synthesis of compound 37.6 to to give 38.6 (110 mg, yield: 48%); ESI-MS (M+H)⁺: 485.2.

Synthesis of Compound 37

To a solution of 37.6 (180 mg, 0.43 mmol, 1.0 eq) in DCM (90 mL) were added HATU (250 mg, 0.65 mmol, 1.5 eq) and DIPEA (111 mg, 0.86 mmol, 2.0 eq). After stirred at room temperature for 12 h, the reaction mixture was washed with water (10 mL), brine (10 mL). The organic layer was dried over anhydrous sodium sulfate and concentrated under reduced pressure. The residue was purified by prep-HPLC (CH₃CN in H₂O—0.05% NH₃H₂O from 5%-90%) to give 37 (5 mg, yield: 3%) as a white solid. ¹H NMR (400 MHz, CDCl₃) □ δ: 12.56 (s, 1H), 8.40 (d, J=5.2 Hz, 1H), 8.25 (s, 1H), 8.02 (s, 1H), 7.98 (s, 1H), 7.36 (d, J=5.2 Hz, 1H), 6.82 (t, J=5.6 Hz, 1H), 4.36-4.32 (m, 2H), 3.93 (s, 3H), 3.49-3.45 (m, 2H), 2.26-2.18 (m, 2H), 1.83-1.76 (m, 2H), 1.57-1.52 (m, 2H); ESI-MS (M+H)⁺: 397.2; HPLC: 214 nm: 100.00%, 254 nm: 100.00%.

Synthesis of Compound 38

The synthesis of 38 is similar to the synthesis of compound 37 to give 38 (26 mg, yield: 28%) as a white solid. ¹H NMR (400 MHz, CDCl₃) □ δ: 12.61 (s, 0.5H), 10.85 (s, 0.5H), 8.41 (d, J=4.8 Hz, 0.5H), 8.35 (d, J=10.0 Hz, 1H), 8.27 (t, J=2.8 Hz, 1H), 8.05 (d, J=3.2 Hz, 1H), 7.63 (s, 0.5H), 7.39 (d, J=5.2 Hz, 1H), 6.85-6.78 (m, 1H), 4.39-4.28 (m, 3H), 4.15-4.12 (m, 2H), 3.58-3.46 (m, 4H), 2.28-2.09 (m, 4H), 1.89-1.51 (m, 6H); ESI-MS (M+H)⁺: 467.2; HPLC: 214 nm: 100.00%, 254 nm: 94.77%.

Examples 39 and 40

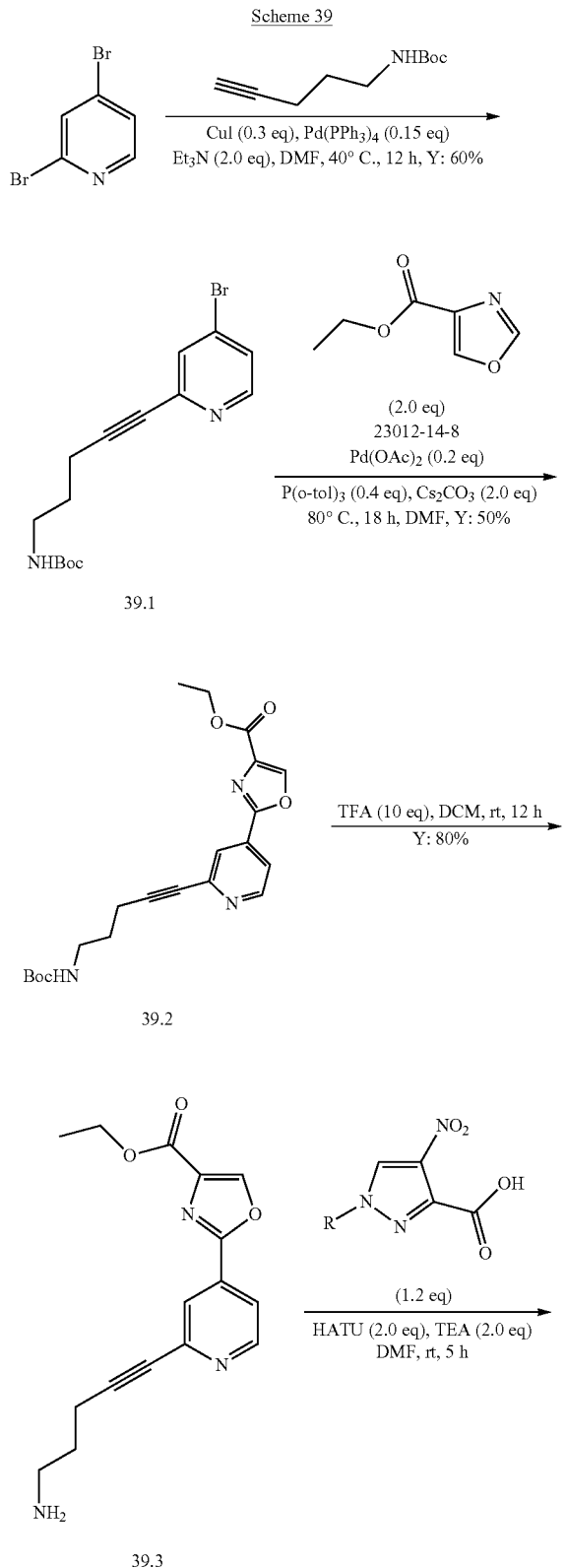

Scheme 39

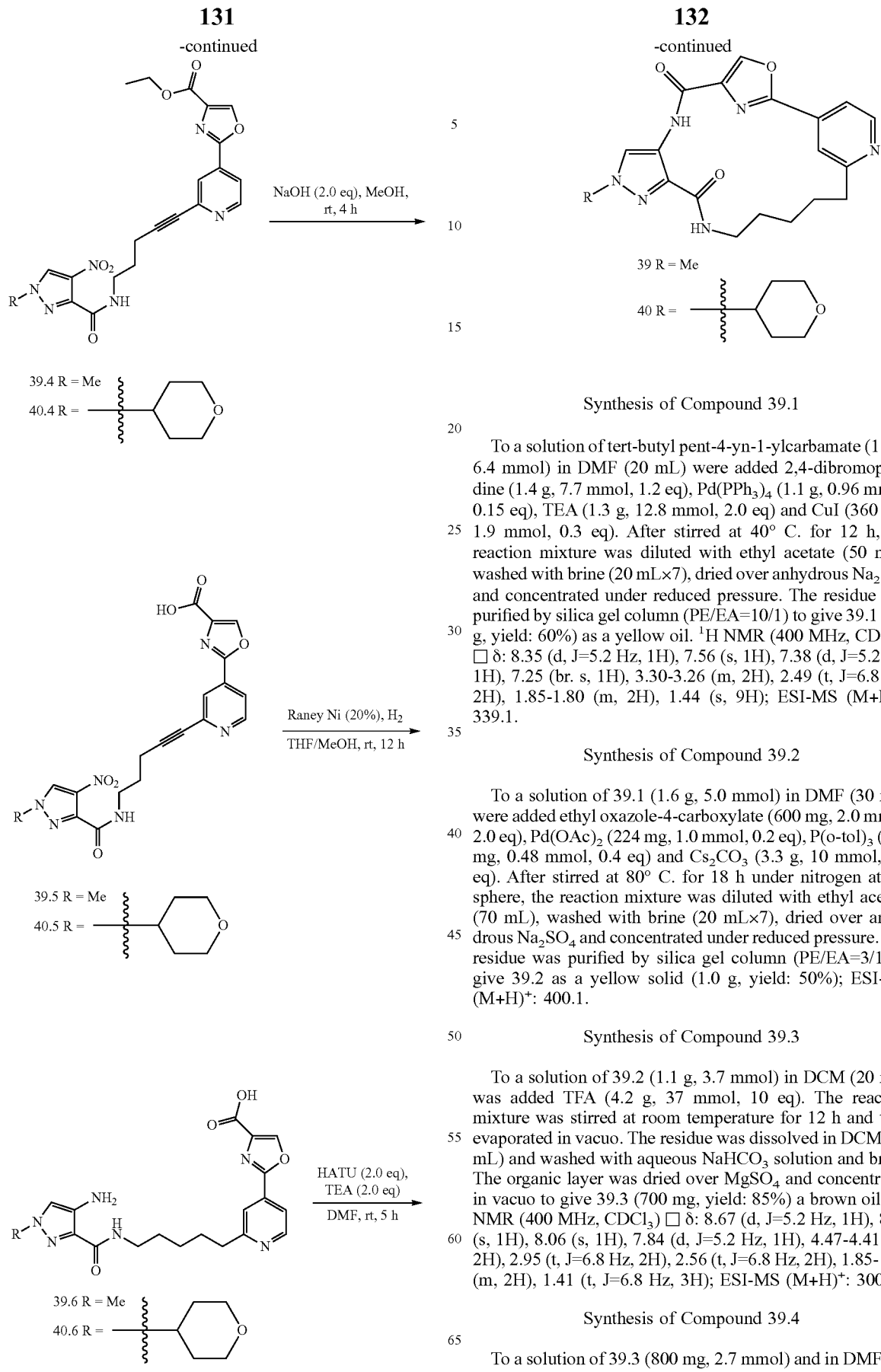

Synthesis of Compound 39.1

To a solution of tert-butyl pent-4-yn-1-ylcarbamate (1.5 g, 6.4 mmol) in DMF (20 mL) were added 2,4-dibromopyridine (1.4 g, 7.7 mmol, 1.2 eq), Pd(PPh$_3$)$_4$ (1.1 g, 0.96 mmol, 0.15 eq), TEA (1.3 g, 12.8 mmol, 2.0 eq) and CuI (360 mg, 1.9 mmol, 0.3 eq). After stirred at 40° C. for 12 h, the reaction mixture was diluted with ethyl acetate (50 mL), washed with brine (20 mL×7), dried over anhydrous Na$_2$SO$_4$ and concentrated under reduced pressure. The residue was purified by silica gel column (PE/EA=10/1) to give 39.1 (1.3 g, yield: 60%) as a yellow oil. $^1$H NMR (400 MHz, CDCl$_3$) δ: 8.35 (d, J=5.2 Hz, 1H), 7.56 (s, 1H), 7.38 (d, J=5.2 Hz, 1H), 7.25 (br. s, 1H), 3.30-3.26 (m, 2H), 2.49 (t, J=6.8 Hz, 2H), 1.85-1.80 (m, 2H), 1.44 (s, 9H); ESI-MS (M+H)$^+$: 339.1.

Synthesis of Compound 39.2

To a solution of 39.1 (1.6 g, 5.0 mmol) in DMF (30 mL) were added ethyl oxazole-4-carboxylate (600 mg, 2.0 mmol, 2.0 eq), Pd(OAc)$_2$ (224 mg, 1.0 mmol, 0.2 eq), P(o-tol)$_3$ (146 mg, 0.48 mmol, 0.4 eq) and Cs$_2$CO$_3$ (3.3 g, 10 mmol, 2.0 eq). After stirred at 80° C. for 18 h under nitrogen atmosphere, the reaction mixture was diluted with ethyl acetate (70 mL), washed with brine (20 mL×7), dried over anhydrous Na$_2$SO$_4$ and concentrated under reduced pressure. The residue was purified by silica gel column (PE/EA=3/1) to give 39.2 as a yellow solid (1.0 g, yield: 50%); ESI-MS (M+H)$^+$: 400.1.

Synthesis of Compound 39.3

To a solution of 39.2 (1.1 g, 3.7 mmol) in DCM (20 mL) was added TFA (4.2 g, 37 mmol, 10 eq). The reaction mixture was stirred at room temperature for 12 h and then evaporated in vacuo. The residue was dissolved in DCM (20 mL) and washed with aqueous NaHCO$_3$ solution and brine. The organic layer was dried over MgSO$_4$ and concentrated in vacuo to give 39.3 (700 mg, yield: 85%) a brown oil. $^1$H NMR (400 MHz, CDCl$_3$) δ: 8.67 (d, J=5.2 Hz, 1H), 8.34 (s, 1H), 8.06 (s, 1H), 7.84 (d, J=5.2 Hz, 1H), 4.47-4.41 (m, 2H), 2.95 (t, J=6.8 Hz, 2H), 2.56 (t, J=6.8 Hz, 2H), 1.85-1.81 (m, 2H), 1.41 (t, J=6.8 Hz, 3H); ESI-MS (M+H)$^+$: 300.1.

Synthesis of Compound 39.4

To a solution of 39.3 (800 mg, 2.7 mmol) and in DMF (10 mL) were added HATU (2.0 g, 5.4 mmol, 2.0 eq), 1-methyl- 4-nitro-1H-pyrazole-3-carboxylic acid (1.2 eq) and TEA (545 mg, 5.4 mmol, 2.0 eq). After stirred at room temperature for 5 h, the reaction mixture was diluted with ethyl acetate (30 mL) and washed with water (5 mL×6). The organic layer was dried over $Na_2SO_4$ and concentrated under reduced pressure. The residue was purified by prep-TLC (PE/EA=1/2) to afford 39.4 (500 mg, yield: 45%) as a yellow solid; ESI-MS $(M+H)^+$: 453.1.

Synthesis of Compound 40.4

The synthesis of 40.4 is similar to the synthesis of compound 39.4 using the appropriate acid to to afford 40.4 (120 mg, yield: 45%) as a yellow solid. $^1$H NMR (400 MHz, $CDCl_3$) □ δ: 8.68 (d, J=5.2 Hz, 1H), 8.35 (s, 1H), 8.27 (s, 1H), 8.05 (s, 1H), 7.89 (d, J=5.2 Hz, 1H), 7.80 (br. s, 1H), 4.44 (q, J=7.2 Hz, 2H), 4.43-4.41 (m, 1H), 4.15-4.11 (m, 2H), 3.72-3.67 (m, 2H), 3.56-3.50 (m, 2H), 2.62 (t, J=6.8 Hz, 2H), 2.18-2.17 (m, 2H), 2.09-1.99 (m, 4H), 1.42 (t, J=7.2 Hz, 3H); ESI-MS $(M+H)^+$: 523.1.

Synthesis of Compound 39.5

To a solution of 39.4 (350 mg, 0.8 mmol) in methanol (10 mL) was added NaOH (65 mg, 1.6 mmol, 2.0 eq). The reaction mixture was stirred at room temperature for 4 h and then adjusted to pH=7 with HCl (3 M). The precipitate was collected by filtration to afford 39.5 (300 mg, yield: 90%) as a white solid. $^1$H NMR (400 MHz, DMSO-$d_6$) □ δ: 8.86 (s, 1H), 8.75-8.73 (m, 1H), 8.68 (d, J=5.2 Hz, 1H), 8.46 (s, 1H), 8.02 (s, 1H), 7.89 (d, J=5.6 Hz, 1H), 3.91 (s, 3H), 3.41-3.37 (m, 2H), 2.58 (t, J=6.8 Hz, 2H), 1.85-1.82 (m, 2H); ESI-MS $(M+H)^+$: 425.2.

Synthesis of Compound 40.5

The synthesis of 40.5 is similar to the synthesis of compound 39.5 to afford 40.5 (110 mg, yield: 90%) as a white solid. $^1$HNMR (400 MHz, DMSO-$d_6$) □ δ: 8.99 (s, 1H), 8.77-8.74 (m, 1H), 8.68 (d, J=5.2 Hz, 1H), 8.31 (s, 1H), 8.08 (s, 1H), 7.90 (d, J=5.2 Hz, 1H), 4.54-4.51 (m, 1H), 3.98-3.95 (m, 2H), 3.48-3.40 (m, 4H), 2.58 (t, J=6.8 Hz, 2H), 2.01-1.94 (m, 4H), 1.85-1.82 (m, 2H); ESI-MS $(M+H)^+$: 495.1.

Synthesis of Compound 39.6

To a solution of 39.5 (300 mg, 0.70 mmol) in THF (60 mL) was added catalytic amount of Raney Ni. The reaction mixture was stirred for 12 h under $H_2$ atmosphere at room temperature. After filtered by Celite, the filtrate was evaporated in vacuo to afford 39.6 (250 mg, yield: 90%) as a yellow oil; ESI-MS $(M+H)^+$: 399.1.

Synthesis of Compound 40.6

The synthesis of 40.6 is similar to the synthesis of compound 39.6 to afford 49-4-0010B (100 mg, yield: 90%) as a yellow solid; ESI-MS $(M+H)^+$: 469.2.

Synthesis of Compound 39

To a solution of 39.6 (300 mg, 0.75 mmol) in DCM/DMF (140 mL/10 mL) were added HATU (570 mg, 1.5 mmol, 2.0 eq) and TEA (150 mg, 1.5 mmol, 2.0 eq). After stirred at room temperature for 5 h, the reaction mixture was washed with water (10 mL×6). The organic layer was dried over $Na_2SO_4$ and concentrated in vacuo. The residue was purified by prep-TLC (DCM/MeOH=10/1) to afford 39 (60 mg, yield: 20%) as a yellow solid. $^1$H NMR (400 MHz, DMSO-$d_6$) □ δ: 11.80 (s, 1H), 8.94 (s, 1H), 8.70 (br. s, 1H), 8.66 (d, J=5.2 Hz, 1H), 8.32 (s, 1H), 8.13 (s, 1H), 7.61 (d, J=6.8 Hz, 1H), 3.90 (s, 3H), 3.32 (m, 2H), 2.96 (m, 2H), 1.85 (m, 4H), 1.65 (m, 2H); ESI-MS $(M+H)^+$: 381.1.

Synthesis of Compound 40

The synthesis of 40 is similar to the synthesis of compound 39. The residue was purified by prep-TLC (DCM/MeOH=10/1) to afford 40 (20 mg, yield: 20%) as a yellow solid. $^1$HNMR (400 MHz, $CDCl_3$) □ δ: 12.40 (s, 1H), 8.65 (d, J=4.8 Hz, 1H), 8.65 (s, 1H), 8.53 (s, 1H), 8.01 (s, 1H), 7.50 (d, J=4.8 Hz, 1H), 6.85 (br. s, 1H), 4.34-4.29 (m, 1H), 4.14-4.11 (m, 2H), 3.58-3.47 (m, 4H), 3.11-3.08 (m, 2H), 2.15-1.99 (m, 8H), 1.78-1.74 (m, 2H); ESI-MS $(M+H)^+$: 451.2.

Examples 41 and 42

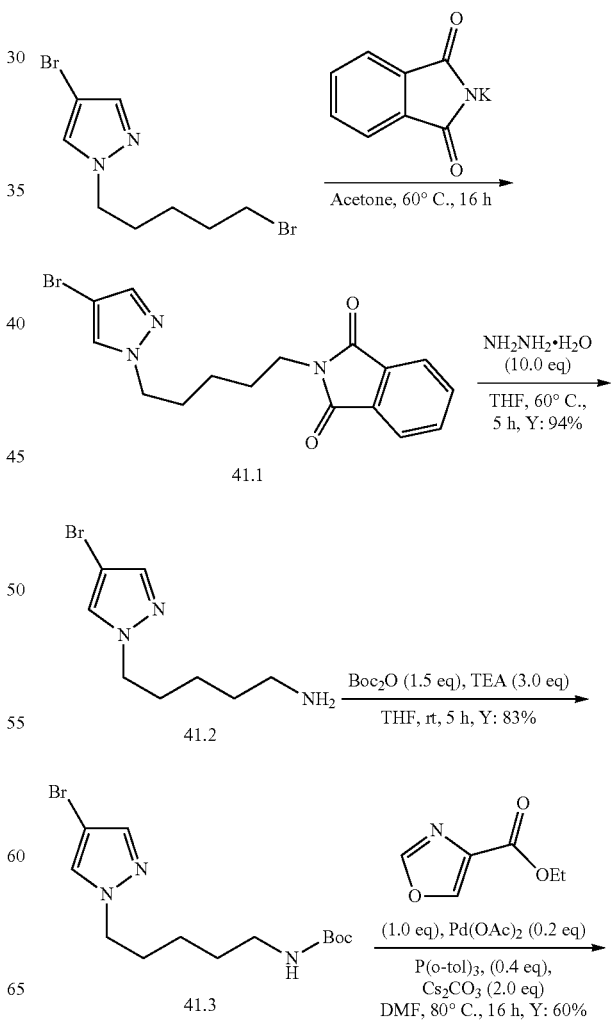

-continued

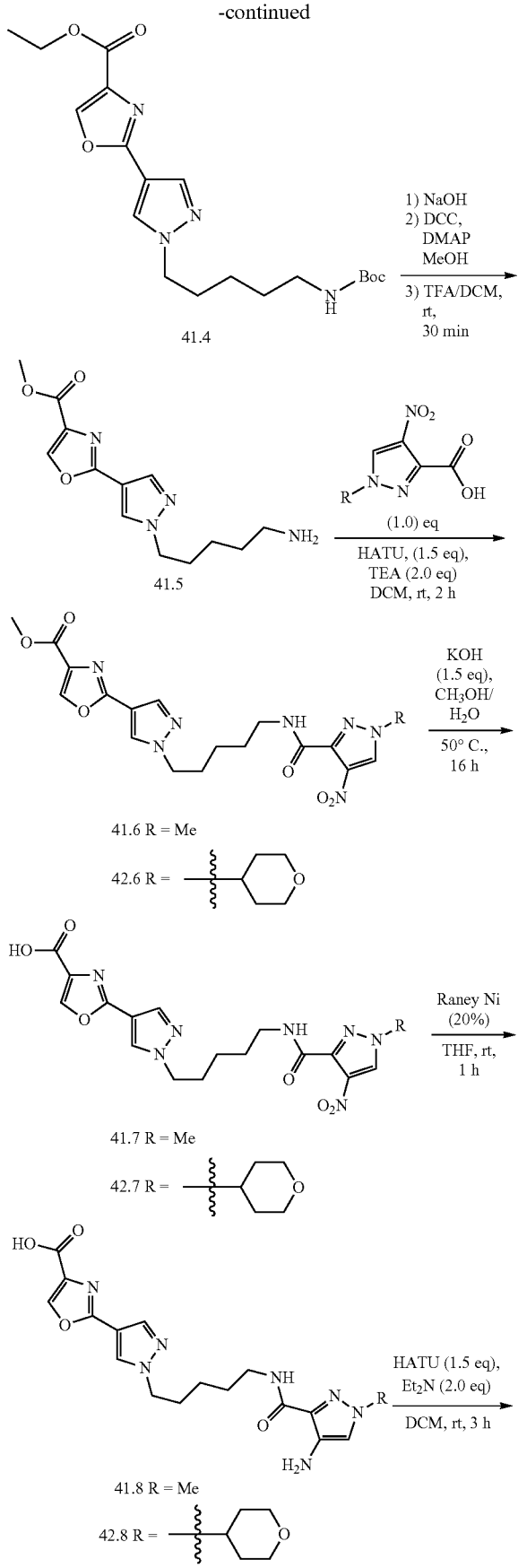

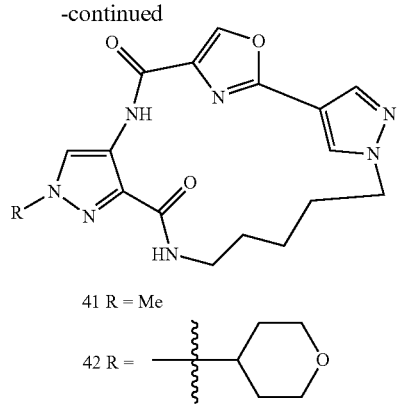

41 R = Me

42 R = <sub>tetrahydropyran-4-yl</sub>

Synthesis of Compound 41.1

To a solution of 4-bromo-1-(5-bromopentyl)-1H-pyrazole (4.5 g, 15.3 mmol, 1.0 eq) in acetone (100 mL) was added potassium 1,3-dioxoisoindolin-2-ide (2.9 g, 15.5 mmol, 1.0 eq). After stirred at 60° C. for 16 h, the reaction was concentrated under reduced pressure and diluted with $H_2O$ (100 mL). The resulting solution was extracted with ethyl acetate (100 mL×3). The combined organic layers were dried over anhydrous sodium sulfate and concentrated under reduced pressure. The residue was purified by silica gel column chromatography (PE/EA=1/1) to give 49-2-0002 (3.7 g, yield: 60%) as white solid; ESI-MS $(M+H)^+$: 284.2.

Synthesis of Compound 41.2

To a solution of 41.1 (3.5 g, 9.7 mmol, 1.0 eq) in THF (35 mL) was added $NH_2NH_2H_2O$ (4.8 g, 97 mmol, 10.0 eq). After stirred at 60° C. for 5 h, the reaction mixture was concentrated under reduced pressure and diluted with $H_2O$ (100 mL). The resulting solution was extracted with ethyl acetate (100 mL×3). The combined organic layers were washed with brine, dried over anhydrous sodium sulfate, concentrated in vacuo to give 41.2 (2.1 g, yield: 94%) as a yellow oil. $^1$H NMR (400 MHz, $CDCl_3$) δ: 7.45 (s, 1H), 7.40 (s, 1H), 4.10 (t, J=7.0 Hz, 2H), 2.69 (t, J=7.2 Hz, 2H), 1.88-1.82 (m, 2H), 1.49-1.43 (m, 2H), 1.36-1.30 (m, 2H); ESI-MS $(M+H)^+$: 232.1.

Synthesis of Compound 41.3

To a solution of 41.2 (2.1 g, 9.1 mmol, 1.0 eq) and TEA (2.7 g, 27.3 mmol, 3.0 eq) in THF (25 mL) was added $(Boc)_2O$ (3.1 g, 13.6 mmol, 1.5 eq). After stirred at room temperature for 5 h, the reaction mixture was diluted with $H_2O$ (50 mL) and extracted with ethyl acetate (30 mL×3). The combined organic layers were washed with brine, dried over anhydrous sodium sulfate and concentrated under reduced pressure. The residue was purified by silica gel column (PE/EA=3/1) to give 41.3 (2.5 g, yield: 83%) as a white solid. $^1$H NMR (400 MHz, $CDCl_3$) δ: 7.44 (s, 1H), 7.39 (s, 1H), 4.09 (t, J=7.2 Hz, 2H), 3.13-3.08 (m, 2H), 1.88-1.84 (m, 2H), 1.52-1.46 (m, 2H), 1.44 (s, 9H), 1.32-1.28 (m, 2H); ESI-MS $(M+H)^+$: 332.1.

Synthesis of Compound 41.4

To a solution of 41.3 (2.5 g, 7.55 mmol, 1.0 eq) in anhydrous DMF (20 mL) were added ethyl oxazole-4- carboxylate (1.1 g, 7.55 mmol, 1.0 eq), Pd(OAc)$_2$ (338 mg, 1.51 mmol, 0.2 eq), P(o-tol)3 (918 mg, 3.02 mmol, 0.4 eq) and Cs$_2$CO$_3$ (4.9 g, 15.1 mmol, 2.0 eq). The reaction mixture was stirred at 80° C. under nitrogen atmosphere for 16 h. After cooled down to room temperature, the resulting solution was filtered by Celite. The filtrate was diluted with H$_2$O (40 mL) and extracted with ethyl acetate (20 mL×3). The combined organic layers were washed with brine, dried over sodium sulfate and concentrated under reduced pressure. The residue was purified by silica gel column (PE/EA=3/1) to give 41.4 (1.8 g, yield: 60%) as a yellow oil. $^1$H NMR (400 MHz, CDCl$_3$) δ: 8.17 (s, 1H), 8.03-8.01 (m, 2H), 4.42 (q, J=7.2 Hz, 2H), 4.17 (t, J=7.2 Hz, 2H), 3.15-3.06 (m, 2H), 1.94-1.90 (m, 2H), 1.55-1.48 (m, 2H), 1.43 (s, 9H), 1.40 (t, J=7.2 Hz, 3H), 1.36-1.30 (m, 2H); ESI-MS (M+H)$^+$: 393.1.

Synthesis of Compound 41.5

To a solution of 41.4 (1.8 g, 4.59 mmol, 1.0 eq) in THF/H$_2$O (12 ml, 5/1) was added NaOH (367 mg, 9.18 mmol, 2.0 eq). After stirred at room temperature for 16 h, the resulted solution was adjusted to pH=6 with HCl (1 N) and extracted with ethyl acetate (10 ml×3). The combined organic layers were concentrated under reduced pressure to give the acid (1.6 g, yield: 95%) as a light yellow oil. $^1$H NMR (400 MHz, CDCl$_3$) δ: 8.24 (s, 1H), 8.05-8.03 (m, 2H), 4.19 (t, J=7.0 Hz, 2H), 3.11 (m, 2H), 1.96-1.89 (m, 2H), 1.54-1.49 (m, 2H), 1.43 (s, 9H), 1.37-1.29 (m, 2H); ESI-MS (M+H)$^+$: 365.2. The acid was then protected as the methyl ester. To a solution of the acid (1.0 g, 2.75 mmol, 1.0 eq) in THF (10 mL), MeOH (426 mg, 13.75 mmol, 5.0 eq) were added DMAP (68 mg, 0.55 mmol, 0.2 eq) and DCC (1.1 g, 5.5 mmol, 2.0 eq). After stirred at room temperature for 5 h, the reaction mixture was diluted with water (10 mL) and extracted with ethyl acetate (20 mL×2). The combined organic layers were dried over sodium sulfate and concentrated under reduced pressure. The residue was purified by silica gel column (PE/EA=2/1) to give the methyl ester (730 mg, yield: 70%) as a yellow solid. $^1$H NMR (400 MHz, CDCl$_3$) δ: 8.22 (s, 1H), 8.04-8.03 (m, 2H), 4.20 (t, J=7.0 Hz, 2H), 4.00 (s, 3H), 3.14-3.10 (m, 2H), 1.98-1.91 (m, 2H), 1.57-1.50 (m, 2H), 1.43 (s, 9H), 1.38-1.32 (m, 2H); ESI-MS (M+Na)$^+$: 401.1. The Boc was then removed. To a solution of the methyl ester (855 mg, 2.21 mmol, 1.0 eq) in DCM (10 mL) was added TFA (5.04 g, 44.2 mmol, 20.0 eq). After stirred at room temperature for 30 min, the resulted solution was concentrated under reduced pressure and adjusted to pH=7 with saturated aqueous NaHCO$_3$ solution. The residue was purified by prep-HPLC (MeOH in H$_2$O—0.05% NH$_3$H$_2$O from 5%-90%) to give 41.5 (630 mg, yield: 100%) as a white solid. H NMR (400 MHz, DMSO-d$_6$) □ δ: 8.83 (s, 1H), 8.49 (s, 1H), 8.01 (s, 1H), 4.20 (t, J=6.8 Hz, 2H), 3.82 (s, 3H), 2.78 (t, J=7.6 Hz, 2H), 1.86-1.79 (m, 2H), 1.58-1.50 (m, 2H), 1.29-1.22 (m, 2H); ESI-MS (M+H)$^+$: 279.1.

Synthesis of Compound 41.6

To a solution of 41.5 (330 mg, 1.15 mmol, 1.0 eq) in DCM (15 mL) were added 1-methyl-4-nitro-1H-pyrazole-3-carboxylic acid (197 mg, 1.15 mmol, 1.0 eq), HATU (655 mg, 1.72 mmol, 1.5 eq) and Et$_3$N (232 mg, 2.30 mmol, 2.0 eq). After stirred at room temperature for 2 h, the reaction mixture was diluted with DCM (50 mL), washed with water (50 mL×2). The organic layer was dried over anhydrous sodium sulfate and concentrated under reduced pressure. The residue was purified by silica gel column (PE/EA=1/2) to give 41.6 (140 mg, yield: 27%) as a white solid; ESI-MS (M+H)$^+$: 454.1.

Synthesis of Compound 42.6

The synthesis of 42.6 is similar to the synthesis of compound 41.6 except the using 4-nitro-1-(tetrahydro-2H-pyran-4-yl)-1H-pyrazole-3-carboxylic acid. The residue was purified by silica gel column (PE/EA=1/2) to give 42.6 (180 mg, yield: 33%) as a white solid; ESI-MS (M+H)$^+$: 502.1.

Synthesis of Compound 41.7

To a solution of 41.6 (140 mg, 0.325 mmol, 1.0 eq) in MeOH (5 mL) and H$_2$O (1 mL) was added KOH (29 mg, 0.525 mmol, 1.5 eq). After stirred at 50° C. for 2 h, the reaction solution was cooled down to room temperature, adjusted to pH=6 with aqueous HCl (1 N) and concentrated under reduced pressure. The residue was extracted with ethyl acetate (20 mL). After filtered by Celite, the filtrate was evaporated in vacuo to give 41.7 as a yellow solid (135 mg, yield: 100%); ESI-MS (M+H)$^+$: 418.2.

Synthesis of Compound 42.7

The synthesis of 42.7 is similar to the synthesis of compound 41.7 The filtrate was evaporated in vacuo to give 42.7 as a yellow solid (174 mg, yield: 100%); ESI-MS (M+H)$^+$: 488.2.

Synthesis of Compound 41.8

To a solution of 41.7 (135 mg, 0.32 mmol, 1.0 eq) in THF (20 mL) was added catalytic amount of Raney Ni. The reaction mixture was stirred at room temperature under hydrogen atmosphere for 1 h. After filtered by Celite, the filtrate was concentrated under reduced pressure to give 41.8 (125 mg, yield: 100%) as a yellow solid; ESI-MS (M+H)$^+$: 388.1.

Synthesis of Compound 42.8

The synthesis of 42.8 is similar to the synthesis of compound 41.8. The filtrate was concentrated under reduced pressure to give 42.8 (160 mg, yield: 98%) as a yellow solid; ESI-MS (M+H)$^+$: 458.1.

Synthesis of Compound 41

To a solution of 41.8 (125 mg, 0.32 mmol, 1.0 eq) in DCM (20 mL) were added HATU (182 mg, 0.48 mmol, 1.5 eq) and Et$_3$N (65 mg, 0.64 mmol, 2.0 eq). After stirred at room temperature for 3 h, the reaction mixture was diluted with H$_2$O (50 mL), extracted with DCM (30 mL×2). The combined organic layers was dried over anhydrous sodium sulfate and concentrated under reduced pressure. The residue was purified by prep-HPLC (CH$_3$CN in H$_2$O—0.05% NH$_3$H$_2$O from 5%-90%) to give 41 (28 mg, yield: 23%) as a white solid. $^1$H NMR (400 MHz, DMSO-d$_6$) □ δ: 8.28 (s, 1H), 8.46 (s, 1H), 8.14 (br. s, 1H), 7.92 (s, 1H), 7.86 (s, 1H), 4.26 (t, J=4.8 Hz, 2H), 3.85 (s, 3H), 3.16-3.15 (m, 2H), 1.75-1.74 (m, 2H), 1.58-1.57 (m, 2H), 1.22-1.21 (m, 2H); ESI-MS (M+H)$^+$: 370.1; HPLC: 214 nm: 98.28%, 254 nm: 97.36%.

Synthesis of Compound 42
The synthesis of 42 is similar to the synthesis of compound 41. The residue was purified by prep-HPLC (MeOH in H$_2$O—0.05% NH$_3$H$_2$O from 5%-90%) to give 49-5 (70 mg, yield: 46%) as a white solid. $^1$H NMR (400 MHz, DMSO-d$_6$) □ δ: 8.59 (s, 1H), 8.47 (s, 1H), 8.15 (br. s, 1H), 8.03 (s, 1H), 7.86 (s, 1H), 4.48-4.40 (m, 1H), 4.25 (t, J=4.8 Hz, 2H), 3.98-3.95 (m, 2H), 3.48-3.41 (m, 2H), 3.17 (m, 2H), 2.00-1.94 (m, 4H), 1.78 (m, 2H), 1.61-1.58 (m, 2H), 1.28 (m, 2H); ESI-MS (M+H)$^+$: 440.2; HPLC: 214 nm: 99.15%, 254 nm: 98.91%.
Examples 43 and 44
Scheme 43
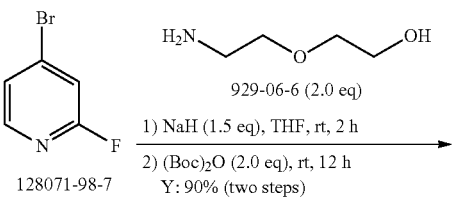
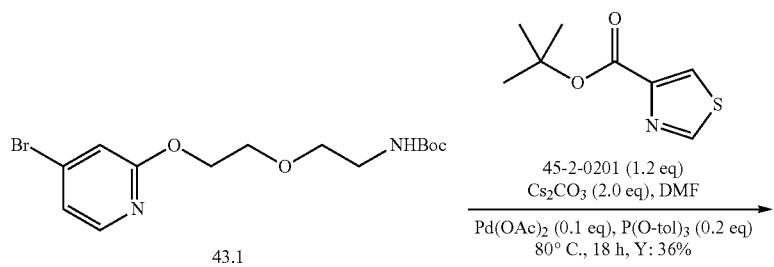
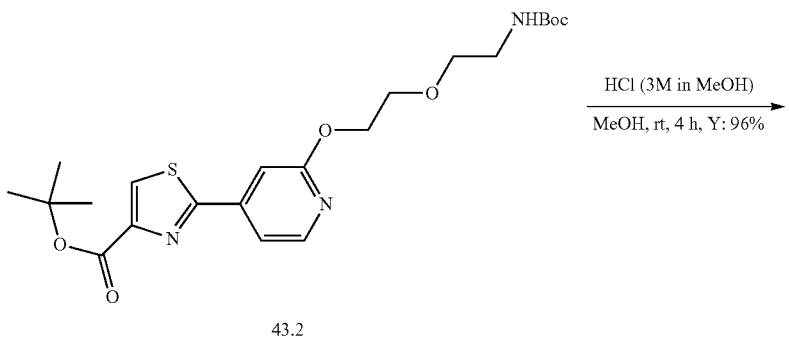
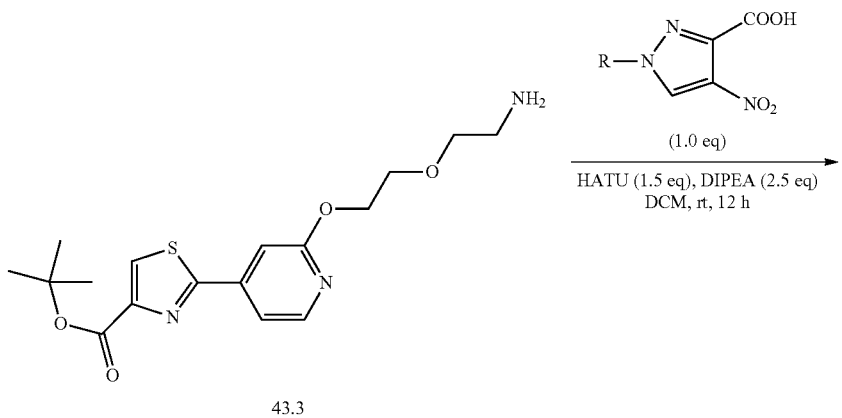

141

142

-continued

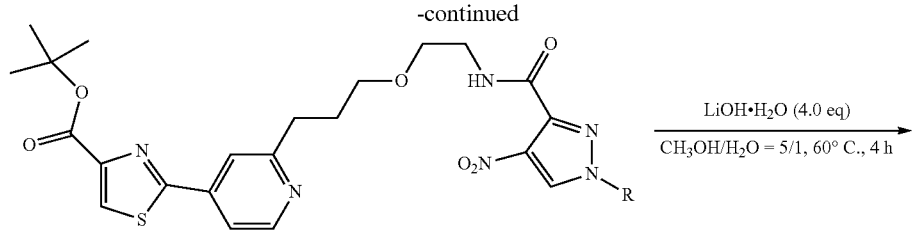

43.4 R = Me
44.4 R = tetrahydropyran-4-yl

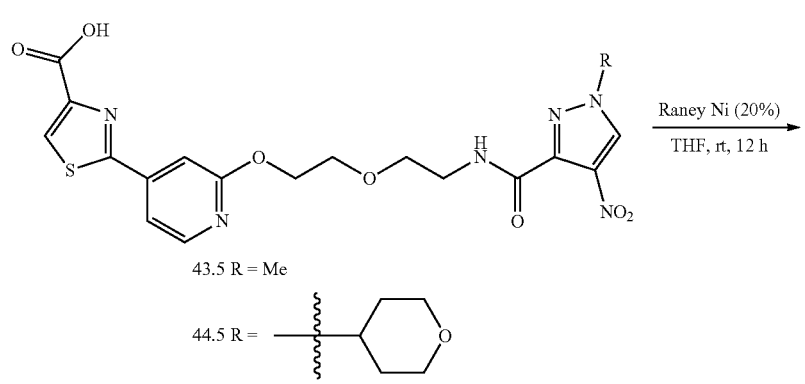

43.5 R = Me
44.5 R = tetrahydropyran-4-yl

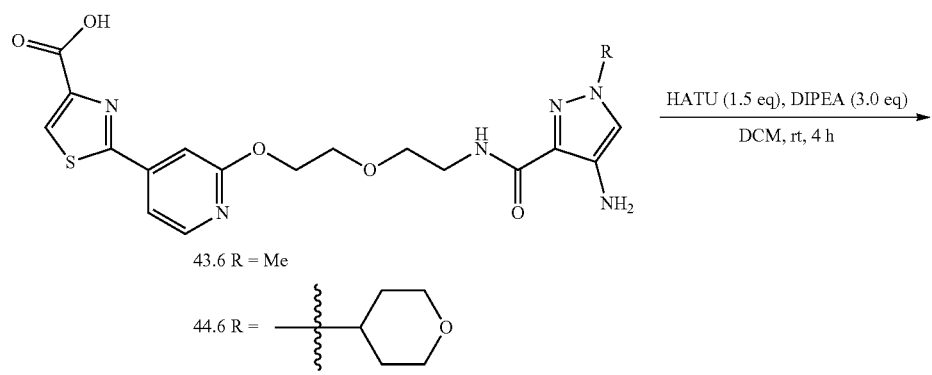

43.6 R = Me
44.6 R = tetrahydropyran-4-yl

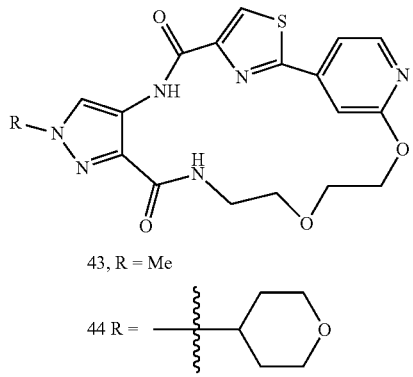

43, R = Me
44 R = tetrahydropyran-4-yl

Synthesis of Compound 43.1

To a solution of 2-(2-aminoethoxy)ethanol (12.0 g, 114.3 mmol, 2.0 eq) in dry THF (400 ml), NaH (3.43 g, 85.7 mmol, 1.5 eq) was added slowly at 0° C. After stirred at 0° C. for 10 min, the reaction solution was added 4-bromo-2-fluoropyridine (10.0 g, 57.1 mmol, 1.0 eq). After stirred at room temperature for 2 h, the reaction mixture was added (Boc)$_2$O (24.9 g, 114.2 mmol, 2.0 eq). After stirred at room temperature for 12 h, the reaction solution was evaporated in vacuo and the residue was diluted with ethyl acetate (600 ml). The solution was washed with water (300 ml×4), dried over anhydrous sodium sulfate and concentrated under reduced pressure to give 43.1 (18.5 g, yield: 90%) as a white solid; ESI-MS $(M+H)^+$: 363.0.

Synthesis of Compound 43.2

To a mixture of 43.1 (9.0 g, 25 mmol, 1.0 eq) and tert-butyl thiazole-4-carboxylate (5.6 g, 30 mmol, 1.2 eq) in anhydrous DMF (80 ml), $Cs_2CO_3$ (16.3 g, 50 mmol, 2.0 eq), $Pd(OAc)_2$ (565 mg, 2.5 mmol, 0.1 eq) and $P(o-tol)_3$ (1.52 g, 5.0 mmol, 0.2 eq) were added under $N_2$ atmosphere. The reaction mixture was stirred at 80° C. for 18 h under $N_2$ atmosphere. After cooling down to ambient temperature, the reaction mixture was diluted with ethyl acetate (400 ml). After filtered by Celite, the filtrate was washed with water (500 ml×4), dried over anhydrous sodium sulfate and concentrated under reduced pressure. The residue was purified by silica gel (PE/EA=8/1) to give 43.2 (4.2 g, yield: 36%) as a yellow oil. $^1$H NMR (400 MHz, $CDCl_3$) δ: 8.23 (d, J=5.2 Hz, 1H), 8.15 (s, 1H), 7.53 (d, J=5.2 Hz, 1H), 7.34 (s, 1H), 5.09 (s, 1H), 4.53-4.51 (m, 2H), 3.85-3.83 (m, 2H), 3.62 (t, J=4.8 Hz, 2H), 3.36-3.35 (m, 2H), 1.63 (s, 9H), 1.43 (s, 9H); ESI-MS $(M+H)^+$: 466.2.

Synthesis of Compound 43.3

To a solution of 43.2 (7.9 g, 17.0 mmol, 1.0 eq) in MeOH (60 ml), HCl in MeOH (17 ml, 3M, 51.0 mmol, 3.0 eq) was added. The reaction mixture was stirred at room temperature for 4 h. After evaporated under reduced pressure, the system was added DCM (200 ml), and then adjusted to pH=9 with DIPEA. The solid was filtered and the filtrate was concentrated under reduced pressure to give 43.3 (6.0 g, yield: 96%) as a yellow oil; ESI-MS $(M+H)^+$: 366.1.

Synthesis of Compound 43.4

To a mixture of 43.3 (1.0 g, 2.7 mmol, 1.0 eq) and 1-methyl-4-nitro-1H-pyrazole-3-carboxylic acid (460 mg, 2.7 mmol, 1.0 eq) in $CH_2Cl_2$ (50 ml), DIPEA (880 mg, 6.8 mmol, 2.5 eq) and HATU (1.56 g, 4.1 mmol, 1.5 eq) were added. The reaction mixture was stirred at room temperature for 12 h. After concentrated under reduced pressure, the residue was purified by pre-TLC (MeOH/DCM=1/100) to give 43.4 (800 mg, yield: 56%) as a yellow oil; ESI-MS $(M+H)^+$: 519.1

Synthesis of Compound 44.4

The synthesis of 44.4 is similar to the synthesis of compound 43.4 except using 4-nitro-1-(tetrahydro-2H-pyran-4-yl)-1H-pyrazole-3-carboxylic acid. The residue was purified by silica gel (MeOH/DCM=1/20) to give 44.4 (650 mg, yield: 54%) as a yellow oil; ESI-MS $(M+H)^+$: 589.2

Synthesis of Compound 43.5

To a solution of 43.4 (700 mg, 1.35 mmol, 1.0 eq) in MeOH (50 ml) and $H_2O$ (10 ml), $LiOH \cdot H_2O$ (216 mg, 5.4 mmol, 4.0 eq) was added. The reaction mixture was stirred at 60° C. for 4 h. After cooling down to ambient temperature, the reaction solution was adjusted to pH=4 with HCl (1 M) and then concentrated under reduced pressure. The residue was used directly in the next step without further purification; ESI-MS $(M+H)^+$: 463.1.

Synthesis of Compound 44.5

The synthesis of 44.5 is similar to the synthesis of compound 43.5. The residue was purified by pre-HPLC to give 56-2-0002 (450 mg, yield: 76%) as a white solid; ESI-MS $(M+H)^+$: 533.1.

Synthesis of Compound 43.6

To a solution of 43.5 (700 mg) in THF (100 ml), catalytic Raney Ni was added. The reaction mixture was stirred at room temperature for 12 h under $H_2$ atmosphere. After filtered by Celite, the filtrate was concentrated under reduced pressure. The residue was purified by pre-HPLC to give 43.6 (232 mg, yield: 34% (two steps)) as a light yellow solid; ESI-MS $(M+H)^+$: 433.1

Synthesis of Compound 44.6

To a solution of 44.5 (450 mg, 0.85 mmol, 1.0 eq) in THF (80 ml), catalytic Raney Ni was added. The mixture was stirred at room temperature for 12 h under $H_2$ atmosphere. After filtered by Celite, the filtrate was concentrated under reduced pressure to give 44.6 (300 mg, yield: 70%) as a light yellow oil; ESI-MS $(M+H)^+$: 503.1

Synthesis of Compound 43

To a solution of 43.5 (180 mg, 0.42 mmol, 1.0 eq) in $CH_2Cl_2$ (100 ml), DIPEA (161 mg, 1.25 mmol, 3.0 eq) and HATU (237 mg, 0.62 mmol, 1.5 eq) were added. The reaction mixture was stirred at room temperature for 4 h. After concentrated under reduced pressure, the residue was purified by pre-TLC (MeOH/DCM=1/20) to give 43 (89 mg, yield: 51%) as a white solid. $^1$H NMR (400 MHz, $CDCl_3$) δ: 12.65 (s, 1H), 8.36 (d, J=5.2 Hz, 1H), 8.19 (s, 1H), 8.14 (s, 1H), 8.06 (s, 1H), 7.25-7.24 (m, 1H), 6.90 (s, 1H), 4.60-4.55 (m, 2H), 4.19-4.15 (m, 2H), 3.94 (s, 3H), 3.84 (t, J=5.6 Hz, 2H), 3.64-3.60 (m, 2H); ESI-MS $(M+H)^+$: 415.1

Synthesis of Compound 44

The synthesis of 44 is similar to the synthesis of compound 43. The residue was purified by pre-TLC (MeOH/DCM=1/20) and followed recrystallization in methanol to give 44 (32 mg, yield: 13%) as a white solid. $^1$H NMR (400 MHz, $CDCl_3$) δ: 12.66 (s, 1H), 8.36 (d, J=4.8 Hz, 1H), 8.19 (s, 1H), 8.15-8.13 (m, 2H), 7.27 (s, 1H), 6.94 (s, 1H), 4.59-4.55 (m, 2H), 4.37-4.29 (m, 1H), 4.20-4.12 (m, 4H), 3.86-3.84 (m, 2H), 3.66-3.62 (m, 2H), 3.59-3.52 (m, 2H), 2.19-2.09 (m, 4H); ESI-MS $(M+H)^+$: 485.1;

Examples 45 and 46
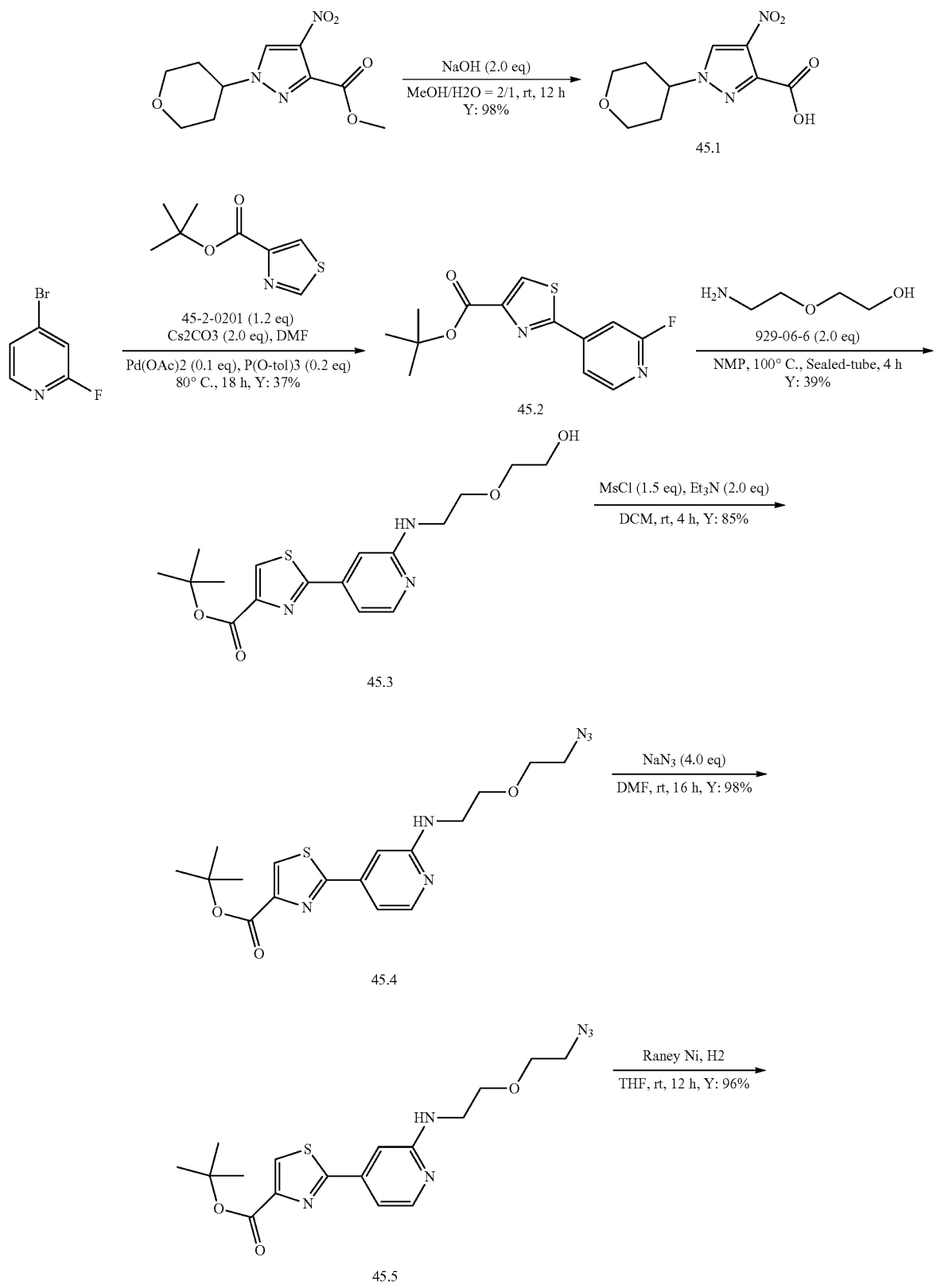

-continued
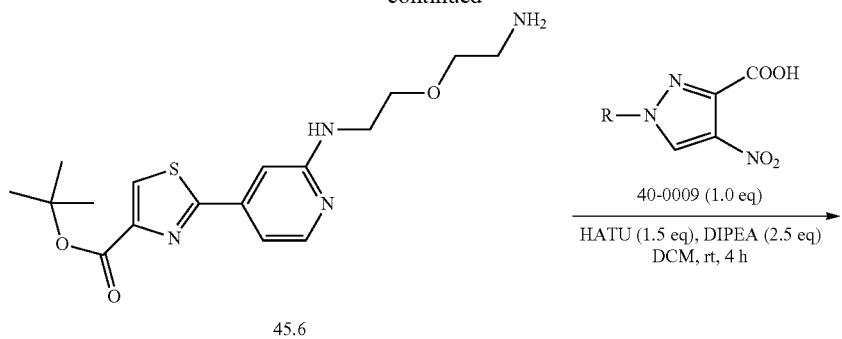
45.6
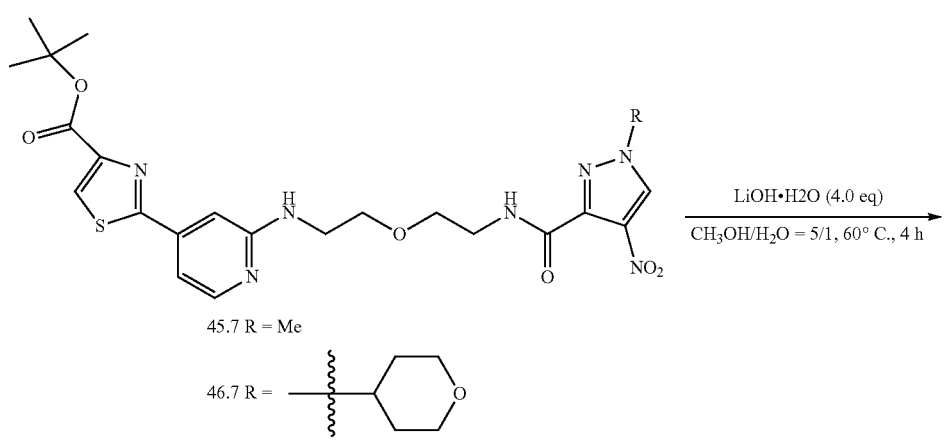
45.7 R = Me
46.7 R = tetrahydropyran-4-yl
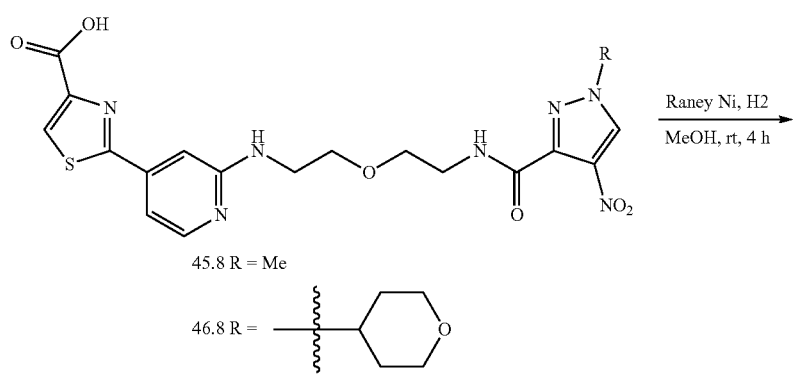
45.8 R = Me
46.8 R = tetrahydropyran-4-yl
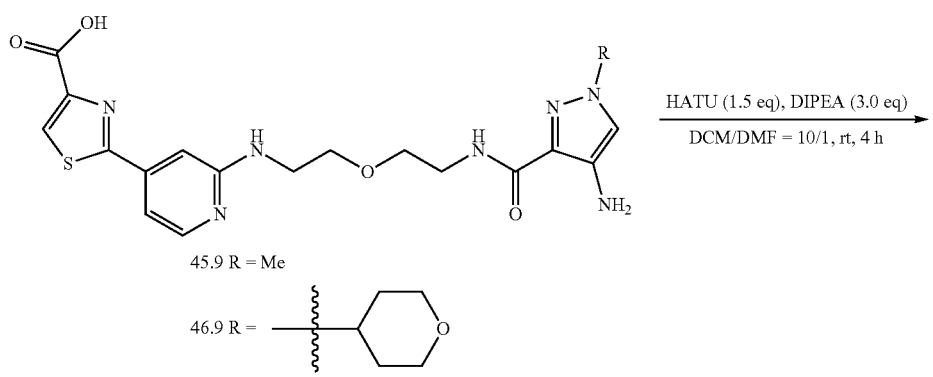
45.9 R = Me
46.9 R = tetrahydropyran-4-yl -continued

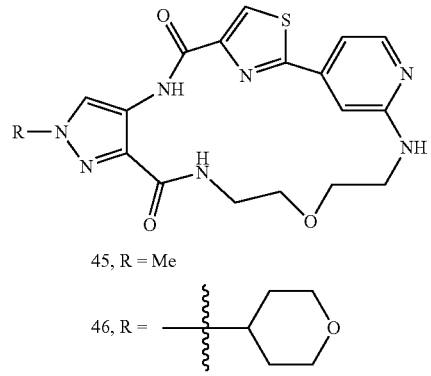

45, R = Me

46, R = ![tetrahydropyran]

Synthesis of Compound 45.1

To a solution of methyl 4-nitro-1-(tetrahydro-2H-pyran-4-yl)-1H-pyrazole-3-carboxylate (900 mg, 3.5 mmol, 1.0 eq) in MeOH (20 mL) and $H_2O$ (10 ml), NaOH (282 mg, 7.1 mmol, 2.0 eq) was added. After stirred at room temperature for 12 h, the reaction mixture was evaporated in vacuo, diluted with $H_2O$ (30 mL) and then adjusted to pH=4 with HCl (1 M). The precipitate was collected by filtration and washed with water (10 ml×3) to give 45.1 (840 mg, yield: 98%) as a white solid; ESI-MS $(M+H)^+$: 242.1.

Synthesis of Compound 45.2

To a mixture of 4-bromo-2-fluoropyridine (4.0 g, 22.9 mmol, 1.0 eq) and tert-butyl thiazole-4-carboxylate (5.07 g, 27.4 mmol, 1.2 eq) in DMF (150 ml), $Cs_2CO_3$ (14.9 g, 45.7 mmol, 2.0 eq), $Pd(OAc)_2$ (516 mg, 2.29 mmol, 0.1 eq) and $P(o-tol)_3$ (1.39 g, 4.57 mmol, 0.2 eq) were added under $N_2$ atmosphere. The reaction mixture was stirred at 80° C. for 18 h under $N_2$ atmosphere. After cooling down to ambient temperature, the reaction solution was diluted with ethyl acetate (400 ml). After filtered by Celite, the filtrate was washed with water (500 ml×4), dried over sodium sulfate and concentrated under reduced pressure. The residue was purified by silica gel column (PE/EA=10/1) to give 45.2 (2.5 g, yield: 37%) as a yellow oil; ESI-MS $(M+H)^+$: 281.0.

Synthesis of Compound 45.3

To a solution of 45.2 (2.5 g, 8.9 mmol, 1.0 eq) in NMP (18 ml), 2-(2-aminoethoxy)ethanol (1.87 g, 17.8 mmol, 2.0 eq) was added. The reaction mixture was stirred at 100° C. for 4 h in a sealed tube. After cooling down to ambient temperature, the reaction solution was diluted with ethyl acetate (200 ml), washed with water (100 ml×3). The organic layer was dried over sodium sulfate and concentrated under reduced pressure. The residue was purified by silica gel column (PE/EA=1/1) to give 45.3 (1.3 g, yield: 39%) as a yellow oil. $^1$H NMR (400 MHz, $CDCl_3$) δ: 8.15 (d, J=5.2 Hz, 1H), 8.10 (s, 1H), 7.13 (s, 1H), 7.05 (d, J=5.2 Hz, 1H), 5.35 (s, 1H), 3.79-3.77 (m, 2H), 3.74-3.72 (m, 2H), 3.64-3.57 (m, 4H), 1.63 (s, 9H); ESI-MS $(M+H)^+$: 366.1.

Synthesis of Compound 45.4

To a mixture of 45.3 (3.9 g, 10.7 mmol, 1.0 eq) and $Et_3N$ (2.16 g, 21.4 mmol, 2.0 eq) in DCM (100 ml), MsCl (1.83 g, 16.0 mmol, 1.5 eq) was added at 0° C. After stirred at room temperature for 4 h, the reaction mixture was washed with water (50 ml×2). The organic layer was dried over sodium sulfate and concentrated under reduced pressure to give 45.4 (4.0 g, yield: 85%) as a yellow solid. $^1$H NMR (400 MHz, $CDCl_3$) δ: 8.14 (s, 1H), 8.10 (d, J=5.6 Hz, 1H), 7.20 (s, 1H), 7.12-7.10 (m, 1H), 4.41-4.39 (m, 2H), 3.79-3.74 (m, 4H), 3.64-3.60 (m, 2H), 3.07 (s, 3H), 1.63 (s, 9H); ESI-MS $(M+H)^+$: 444.1.

Synthesis of Compound 45.5

To a solution of 45.4 (4.5 g, 10.1 mmol, 1.0 eq) in DMF (50 ml), $NaN_3$ (2.64 g, 40.6 mmol, 4.0 eq) was added. After stirred at room temperature for 48 h, the reaction mixture was diluted with water (200 ml) and extracted with ethyl acetate (150 ml×3). The combined organic layers were dried over sodium sulfate and concentrated under reduced pressure to give 45.5 (3.9 g, yield: 98%) as a yellow oil; ESI-MS $(M+H)^+$: 390.9.

Synthesis of Compound 45.6

To a solution of 45.5 (3.9 g, 10.0 mmol, 1.0 eq) in THF (100 ml), catalytic Raney Ni was added. The reaction mixture was stirred at room temperature for 12 h under $H_2$ atmosphere. After filtered by Celite, the filtrate was concentrated under reduced pressure to give 56-3-0004 (3.5 g, yield: 96%) as a yellow oil; ESI-MS $(M+H)^+$: 364.9.

Synthesis of Compound 45

To a mixture of 45.6 (500 mg, 1.4 mmol, 1.0 eq) and 1-methyl-4-nitro-1H-pyrazole-3-carboxylic acid (240 mg, 1.4 mmol, 1.0 eq) in $CH_2Cl_2$ (50 ml), DIPEA (440 mg, 3.4 mmol, 2.5 eq) and HATU (780 mg, 2.1 mmol, 1.5 eq) were added. After stirred at room temperature for 4 h, the reaction mixture was concentrated under reduced pressure. The residue was purified by pre-TLC (MeOH/DCM=1/100) to give 45.7 (500 mg, yield: 70%) as a yellow solid. $^1$H NMR (400 MHz, $CDCl_3$) δ: 8.23 (s, 1H), 8.15 (s, 1H), 8.11 (d, J=5.6 Hz, 1H), 7.24 (s, 1H), 7.17-7.15 (m, 1H), 3.97 (s, 3H), 3.78-3.76 (m, 2H), 3.73-3.72 (m, 4H), 3.66-3.65 (m, 2H), 1.63 (s, 9H); ESI-MS $(M+H)^+$: 517.8.

Synthesis of Compound 46.7

Synthesis similar to 45.7 except use 45.1 for acid. The residue was purified by pre-TLC (MeOH/DCM=1/100) to give 46.7 (680 mg, yield: 58%) as a yellow solid; ESI-MS $(M+H)^+$: 588.2.

Synthesis of Compound 45.8

To a solution of 45.7 (500 mg, 0.97 mmol, 1.0 eq) in MeOH (50 ml) and H$_2$O (10 ml), LiOH.H$_2$O (155 mg, 3.87 mmol, 4.0 eq) was added. The reaction mixture was stirred at 60° C. for 4 h. After concentrated under reduced pressure, the reaction solution was diluted with H$_2$O (30 ml). The resulted solution was adjusted to pH=4 with HCl (1 M). The precipitate was collected by filtration and washed with H$_2$O (5 ml×3) to give 45.8 (420 mg, yield: 94%) as a yellow solid; ESI-MS (M+H)$^+$: 462.0.

Synthesis of Compound 46.8

Prepared similar to 45.8 starting from 46.7. The precipitate was collected by filtration and washed with H$_2$O (5 ml×3) to give 46.8 (530 mg, yield: 97%) as a yellow solid; ESI-MS (M+H)$^+$: 532.1.

Synthesis of Compound 45.9

To a solution of 45.8 (420 mg, 0.91 mmol, 1.0 eq) in MeOH (100 ml), catalytic Raney Ni was added. The reaction mixture was stirred at room temperature for 4 h under H$_2$ atmosphere. After filtered by Celite, the filtrate was concentrated under reduced pressure to give 45.9 (380 mg, yield: 96%) as a light yellow oil; ESI-MS (M+H)$^+$: 432.1.

Synthesis of Compound 46.9

Prepared similar to 45.9 starting from 46.8. After filtered by Celite, the filtrate was concentrated under reduced pressure to give 46.9 (450 mg, yield: 90%) as a light yellow solid; ESI-MS (M+H)$^+$: 502.1.

Synthesis of Compound 45

To a solution of 45.9 (300 mg, 0.70 mmol, 1.0 eq) in CH$_2$Cl$_2$ (150 ml) and DMF (15 ml), DIPEA (271 mg, 2.1 mmol, 3.0 eq) and HATU (397 mg, 1.04 mmol, 1.5 eq) were added. After stirred at room temperature for 4 h, the reaction mixture was evaporated in vacuo. The residue was purified by pre-TLC (MeOH/DCM=1/20) to give 45 (72 mg, yield: 25%) as a light yellow solid. $^1$H NMR (400 MHz, CDCl$_3$) δ: 12.61 (s, 1H), 8.12-8.11 (m, 2H), 8.06 (s, 1H), 7.86 (s, 1H), 6.92-6.87 (m, 2H), 5.36 (s, 1H), 3.97-3.93 (m, 5H), 3.82-3.79 (m, 2H), 3.68-3.59 (m, 4H); ESI-MS (M+H)$^+$: 414.1; HPLC: 214 nm: 100.00%, 254 nm: 100.00%.

Synthesis of Compound 46

The synthesis of compound 46 was similar to the synthesis of compound 45. The residue was purified by pre-TLC (MeOH/DCM=1/20) to give 56-4 (87 mg, yield: 22%) as a yellow solid. $^1$H NMR (400 MHz, CDCl$_3$) δ: 12.62 (s, 1H), 8.15-8.11 (m, 3H), 7.80 (s, 1H), 6.94-6.90 (m, 2H), 5.10 (t, J=6.8 Hz, 1H), 4.36-4.28 (m, 1H), 4.15-4.12 (m, 2H), 3.98-3.93 (m, 2H), 3.83-3.80 (m, 2H), 3.66-3.60 (m, 4H), 3.58-3.52 (m, 2H), 2.09-2.20 (m, 4H); ESI-MS (M+H)$^+$: 484.2.

Examples 47 and 48

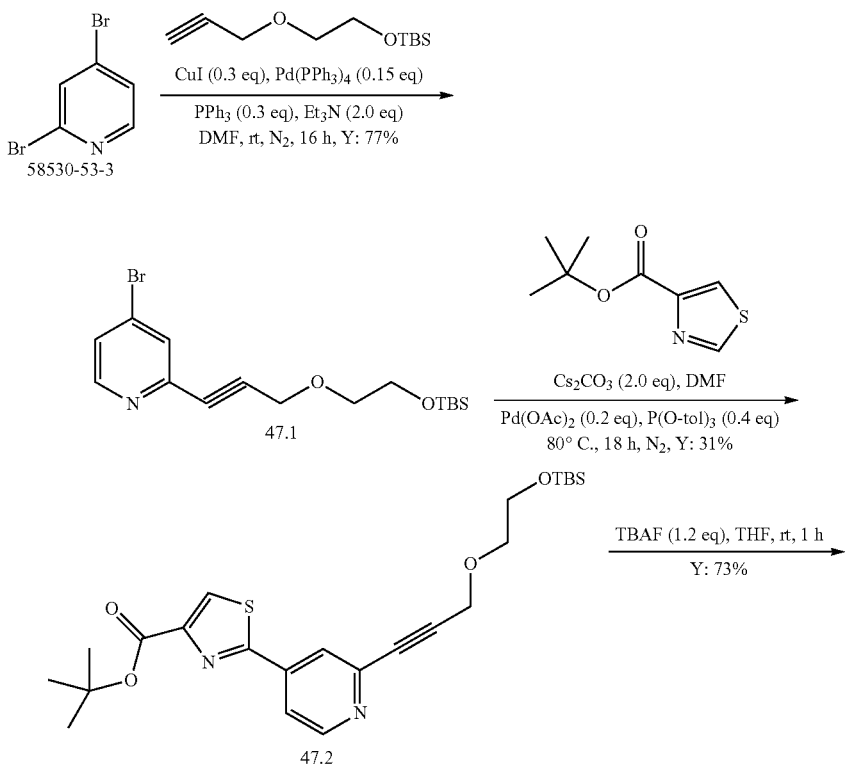

Scheme 47

-continued
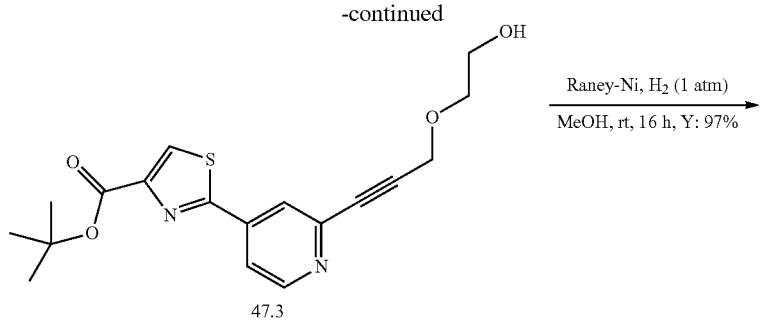
47.3
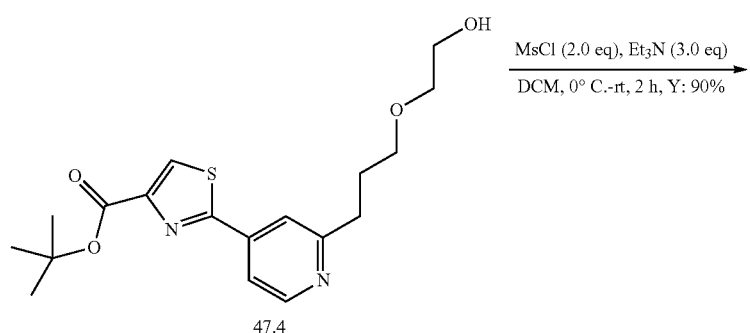
47.4
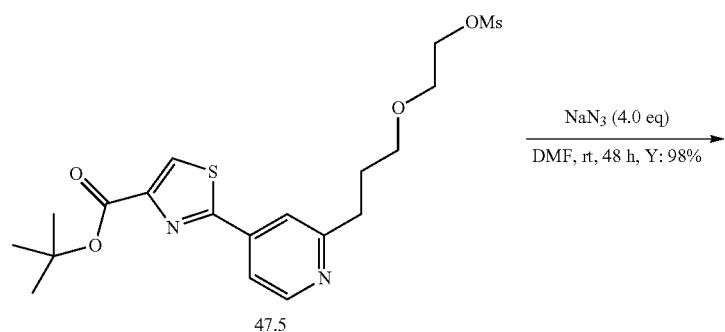
47.5
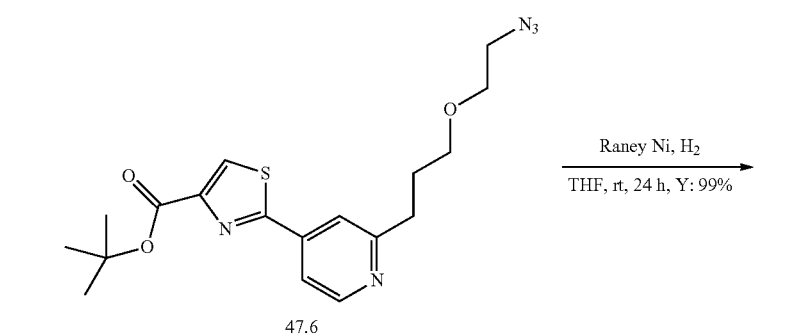
47.6
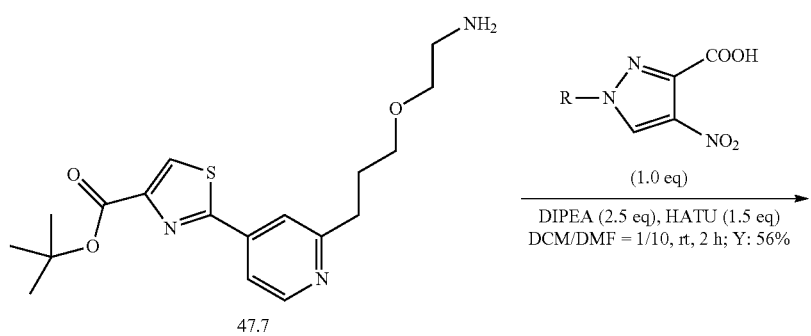
47.7

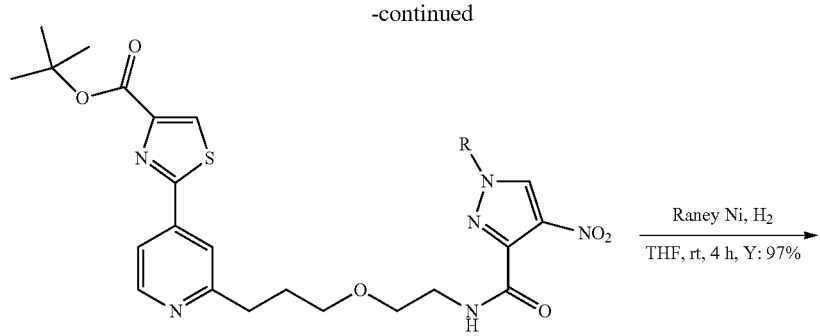
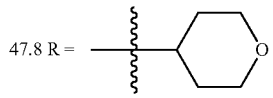
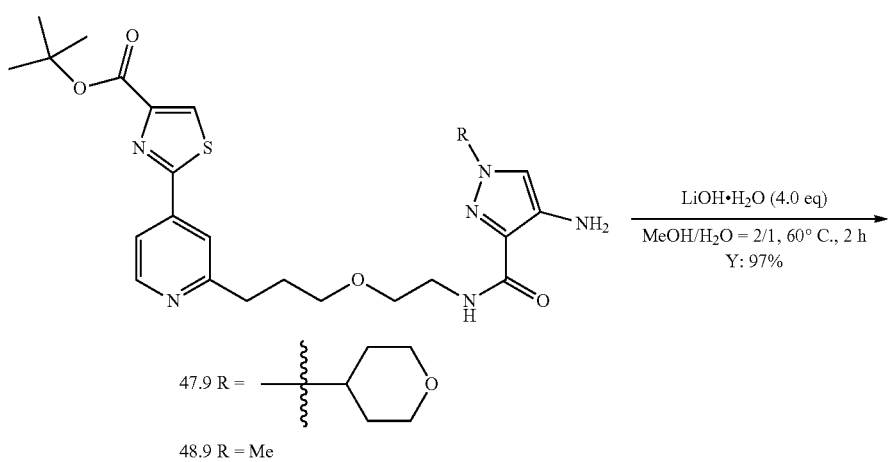
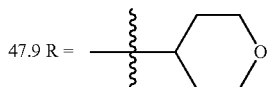
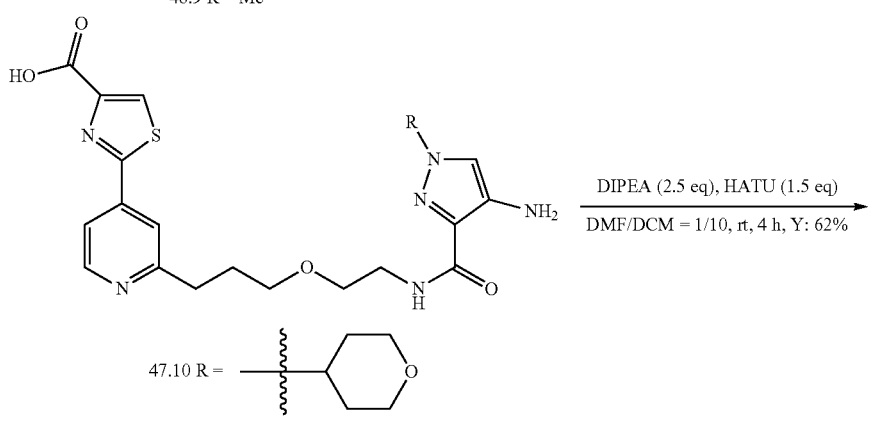
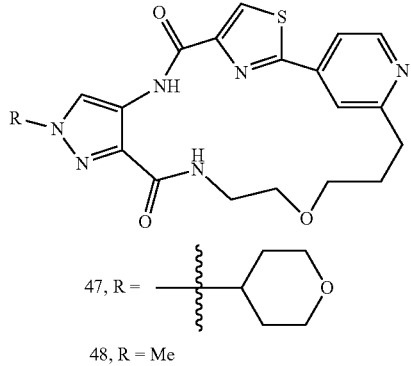

Synthesis of Compound 47.1

To a solution of 2,4-dibromopyridine (8 g, 33.9 mmol, 1.0 eq), tert-butyldimethyl(2-(prop-2-yn-1-yloxy)ethoxy)silane (7.25 g, 33.9 mmol, 1.0 eq) in DMF (150 mL), CuI (1.93 g, 10.17 mmol, 0.3 eq), Pd(PPh$_3$)$_4$ (5.88 g, 5.09 mmol, 0.15 eq), PPh$_3$ (2.7 g, 10.17 mmol, 0.3 eq) and Et$_3$N (9.39 mL, 67.8 mmol, 2.0 eq) were added under N$_2$ atmosphere. After stirred at 30° C. for 24 h under N$_2$ atmosphere, the reaction mixture was diluted with ethyl acetate (500 ml) and filtered by Celite. The filtrate was washed with H$_2$O (200 ml×3) and brine (200 ml×3). The organic layer was dried over anhydrous Na$_2$SO$_4$ and concentrated under reduced pressure. The residue was purified by silical gel column (PE/EA=10/1) to give 47.1 (9.65 g, yield: 77%) as a red oil. $^1$H NMR (400 MHz, CDCl$_3$) δ: 8.38 (d, J=5.2 Hz, 1H), 7.61 (d, J=2.0 Hz, 1H), 7.42 (dd, J=2.0, 5.2 Hz, 1H), 4.45 (s, 2H), 3.82 (t, J=5.6 Hz, 2H), 3.68 (t, J=5.6 Hz, 2H), 0.90 (s, 9H), 0.08 (s, 6H); ESI-MS (M+H)$^+$: 370.1.

Synthesis of Compound 47.2

To a solution of 47.1 (6.67 g, 18.02 mmol, 1.0 eq), tert-butyl thiazole-4-carboxylate (4.0 g, 21.62 mmol, 1.2 eq) in DMF (150 mL), Pd(OAc)$_2$ (0.81 g, 3.60 mmol, 0.2 eq), P(o-tol)$_3$ (2.19 g, 7.21 mmol, 0.4 eq) and Cs$_2$CO$_3$ (11.75 g, 36.04 mmol, 2.0 eq) were added under N$_2$ atmosphere. After stirred at 80° C. for 18 h under N$_2$ atmosphere, the reaction mixture was diluted with ethyl acetate (500 ml) and filtered by celite. The filtrate was washed with H$_2$O (200 ml×3) and brine (200 ml×3). The organic layer was dried over anhydrous Na$_2$SO$_4$ and concentrated under reduced pressure. The residue was purified by silical gel column (PE/EA=5/1) to give 47.2 (2.67 g, yield: 31%) as yellow oil; ESI-MS (M+H)$^+$: 475.2.

Synthesis of Compound 47.3

To a solution of 47.2 (2.67 g, 5.62 mmol, 1.0 eq) in THF (100 mL) was added TBAF (6.74 mL, 6.74 mmol, 1.2 eq, 1.0 M). The resulting mixture was stirred at room temperature for 1 h and then diluted with EtOAc (500 ml). The resulting solution was washed with H$_2$O (200 ml×3) and brine (200 ml×3), dried over anhydrous Na$_2$SO$_4$ and concentrated under reduced pressure. The residue was purified by silical gel column (PE/EA=3/1) to give 47.3 (1.48 g, yield: 73%) as yellow oil. $^1$H NMR (400 MHz, CDCl$_3$) δ: 8.68 (d, J=5.6 Hz, 1H), 8.16 (s, 1H), 8.04 (s, 1H), 7.83 (d, J=5.6 Hz, 1H), 4.49 (s, 2H), 3.83-3.81 (m, 2H), 3.77-3.75 (m, 2H), 1.63 (s, 9H); ESI-MS (M+H)$^+$: 361.1.

Synthesis of Compound 47.4

To a solution of 47.3 (1.48 g, 4.1 mmol, 1.0 eq) in THF (20 ml), catalytic Raney Ni was added. The resulted mixture was stirred at room temperature for 16 h under H$_2$ atmosphere. After filtered by Celite, the filtrate was concentrated under reduced pressure to give 47.4 (1.46 g, yield: 97%) as a yellow oil.
$^1$H NMR (400 MHz, CDCl$_3$) δ: 8.60 (d, J=5.2 Hz, 1H), 8.13 (s, 1H), 7.85 (s, 1H), 7.63 (d, J=5.2 Hz, 1H), 3.73 (t, J=4.8 Hz, 2H), 3.55 (t, J=4.8 Hz, 2H), 3.49 (t, J=6.4 Hz, 2H), 2.99 (t, J=7.2 Hz, 2H), 2.08-2.01 (m, 2H), 1.62 (s, 9H); ESI-MS (M+H)$^+$: 365.1.

Synthesis of Compound 47.5

To a mixture of 47.4 (1.44 g, 3.97 mmol, 1.0 eq) and Et$_3$N (1.66 mL, 11.91 mmol, 3.0 eq) in DCM (100 mL), MsCl (0.67 g, 7.94 mmol, 2.0 eq) was added at 0° C. After stirred at room temperature for 2 h, the reaction mixture was washed with saturated NaHCO$_3$ solution (50 ml×2) and brine (50 ml). The residue was purified by silical gel column (PE/EA=3/1) to give 47.5 (1.58 g, yield: 90%) as yellow oil. $^1$H NMR (400 MHz, CDCl$_3$) δ: 8.62 (d, J=5.2 Hz, 1H), 8.13 (s, 1H), 7.85 (s, 1H), 7.66 (d, J=5.2 Hz, 1H), 4.37-4.35 (m, 2H), 3.71-3.69 (m, 2H), 3.56 (t, J=6.4 Hz, 2H), 3.07 (s, 3H), 2.95 (t, J=7.6 Hz, 2H), 2.11-2.04 (m, 2H), 1.63 (s, 9H); ESI-MS (M+H)$^+$: 443.2

Synthesis of Compound 47.6

To a solution of 47.5 (1.5 g, 3.4 mmol, 1.0 eq) in DMF (25 ml), NaN$_3$ (882 mg, 13.6 mmol, 4.0 eq) was added. After stirred at room temperature for 48 h, the reaction mixture was diluted with H$_2$O (200 ml) and extracted with ethyl acetate (100 ml×2). The combined organic layers were washed with water (100 ml×2), dried over sodium sulfate and concentrated under reduced pressure to give 47.6 (1.3 g, yield: 98%) as a yellow oil; ESI-MS (M+H)$^+$: 390.1.

Synthesis of Compound 47.7

To a solution of 47.6 (1.3 g, 3.34 mmol, 1.0 eq) in THF (150 ml), catalytic Raney Ni was added. The reaction mixture was stirred at room temperature for 24 h under H$_2$ atmosphere. After filtered by Celite, the filtrate was concentrated under reduced pressure to give 47.7 (1.2 g, yield: 99%) as a yellow oil; ESI-MS (M+H)$^+$: 364.1.

Synthesis of Compound 47.8

To a solution of 47.7 (550 mg, 1.5 mmol, 1.0 eq) and 4-nitro-1-(tetrahydro-2H-pyran-4-yl)-1H-pyrazole-3-carboxylic acid (366 mg, 1.5 mmol, 1.0 eq) in CH$_2$Cl$_2$ (20 ml) and DMF (2 ml), DIPEA (490 mg, 3.8 mmol, 2.5 eq) and HATU (864 mg, 2.3 mmol, 1.5 eq) were added. After stirred at room temperature for 2 h, the reaction mixture was washed with water (20 ml×2), dried over sodium sulfate and concentrated under reduced pressure. The residue was purified by pre-TLC (MeOH/DCM=1/20) to give 47.8 (500 mg, yield: 56%) as a yellow oil; ESI-MS (M+H)$^+$: 587.3.

Synthesis of Compound 48.8

Compound 48.8 was prepared by similar procedure as described in the synthesis of Compound 47.8 using 47.7 and 1-methyl-4-nitro-1H-pyrazole-3-carboxylic acid. The residue was purified by purified by pre-TLC (MeOH/DCM=1/20) to give 48.8 (520 mg, yield: 66%) as a yellow oil; ESI-MS (M+H)$^+$: 517.2.

Synthesis of Compound 47.9

To a solution of 47.8 (500 mg, 0.85 mmol, 1.0 eq) in THF (150 ml), Catalytic Raney Ni was added. The reaction mixture was stirred at room temperature for 4 h under H$_2$ atmosphere. After filtered by Celite, the filtrate was concentrated under reduced pressure to give 47.9 (460 mg, yield: 97%) as a light yellow oil; ESI-MS (M+H)$^+$: 557.2.

Synthesis of Compound 48.9

Compound 48.9 was prepared by similar procedure as described in the synthesis of Compound 47.9 using 48.8. After filtered by Celite, the filtrate was concentrated under reduced pressure to give 48.9 (480 mg, yield: 98%) as a light yellow oil; ESI-MS (M+H)⁺: 487.2.

Synthesis of Compound 47.10

To a solution of 47.9 (400 mg, 0.72 mmol, 1.0 eq) in MeOH (20 ml) and H₂O (10 ml), LiOH.H₂O (121 mg, 2.88 mmol, 4.0 eq) was added. After stirred at 60° C. for 2 h, the reaction mixture was adjusted to pH=6 with HCl (1 M) and then evaporated in vacuo. The residue was purified by pre-HPLC to give 47.10 (350 mg, yield: 97%) as a yellow solid; ESI-MS (M+H)⁺: 501.1.

Synthesis of Compound 48.10

Compound 48 was prepared by similar procedure as described in the synthesis of Compound 47 using 48.10. The residue was purified by pre-HPLC to give 56-6-0003 (350 mg, yield: 92%) as a yellow oil; ESI-MS (M+H)⁺: 431.1.

Synthesis of Compound 47

To a solution of 47.10 (330 mg, 0.66 mmol, 1.0 eq) in CH₂Cl₂ (200 ml) and DMF (20 ml), DIPEA (213 mg, 1.65 mmol, 2.5 eq) and HATU (376 mg, 0.99 mmol, 1.5 eq) were added. The mixture was stirred at room temperature for 4 h and then washed with water (150 ml×3). The organic layer was dried over sodium sulfate and concentrated under reduced pressure. The residue was purified by pre-TLC (MeOH/DCM=1/20) and followed recrystallization in MeOH (2 ml) to give 47 (200 mg, yield: 62%) as a white solid. ¹H NMR (400 MHz, CDCl₃) δ: 12.67 (s, 1H), 8.72 (s, 1H), 8.61 (d, J=5.6 Hz, 1H), 8.15 (s, 1H), 8.13 (s, 1H), 7.44 (d, J=5.6 Hz, 1H), 6.92-6.89 (m, 1H), 4.36-4.29 (m, 1H), 4.15-4.12 (m, 2H), 3.82-3.78 (m, 4H), 3.70-3.65 (m, 2H), 3.59-3.52 (m, 2H), 3.09-3.05 (m, 2H), 2.30-2.17 (m, 2H), 2.15-2.10 (m, 4H); ESI-MS (M+H)⁺: 483.2; HPLC: 214 nm: 100.00%, 254 nm: 100.00%.

Synthesis of Compound 48

Compound 48 was prepared by similar procedure as described in the synthesis of Compound 47 using 48.10. The residue was purified by pre-TLC (MeOH/DCM=1/20) and followed recrystallization in MeOH (2 ml) to give 48 (37 mg, yield: 12%) as a light yellow solid. ¹H NMR (400 MHz, CDCl₃) δ: 12.67 (s, 1H), 8.78 (s, 1H), 8.62 (d, J=5.2 Hz, 1H), 8.17 (s, 1H), 8.06 (s, 1H), 7.48 (d, J=5.2 Hz, 1H), 6.88 (t, J=4.8 Hz, 1H), 3.94 (s, 3H), 3.81-3.77 (m, 4H), 3.68-3.64 (m, 2H), 3.13-3.09 (m, 2H), 2.31-2.24 (m, 2H); ESI-MS (M+H)⁺: 413.1

Examples 49-57

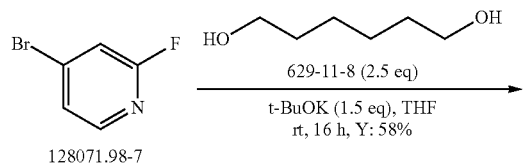

Scheme 49

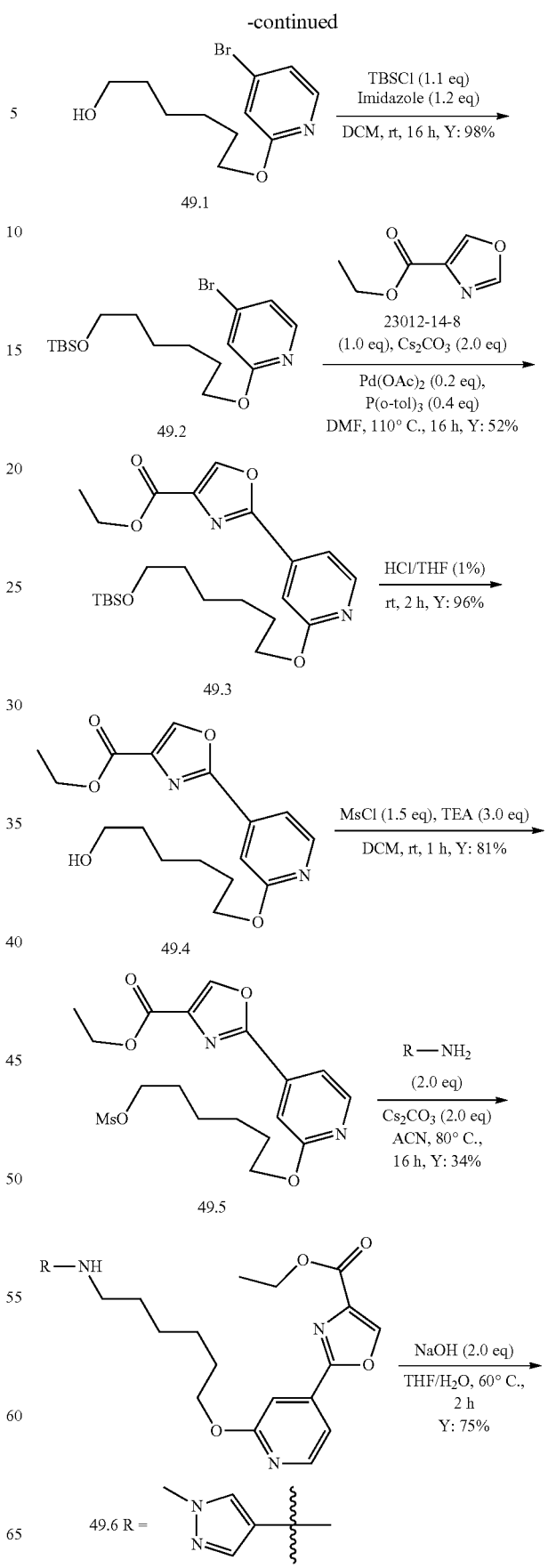

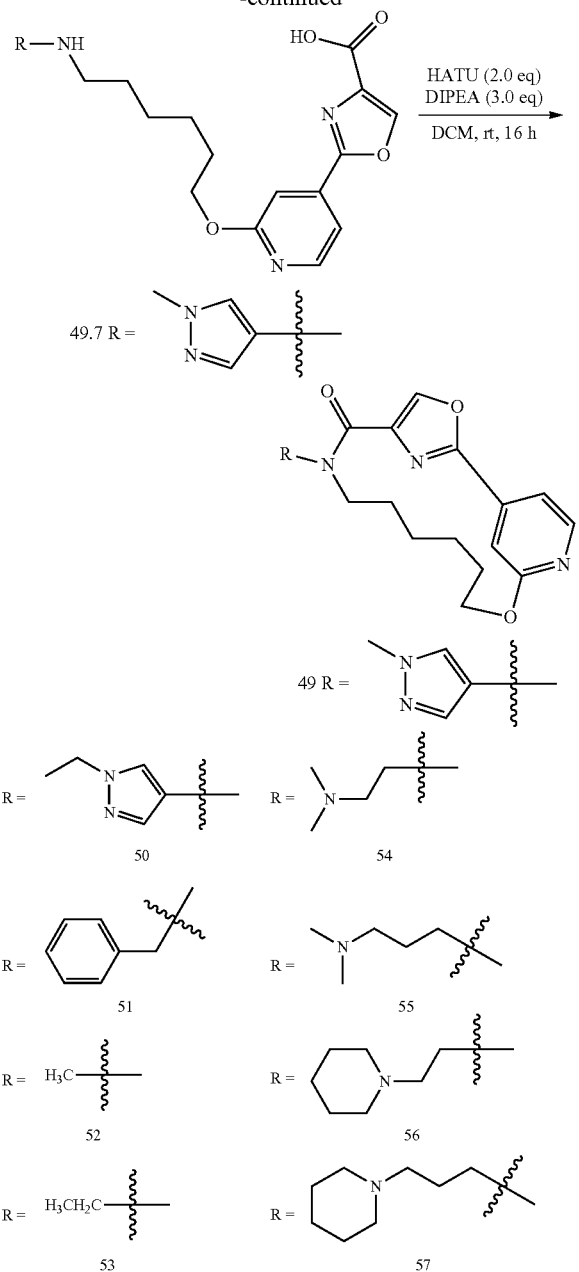

Synthesis of Compound 49.1

To a solution of 4-bromo-2-fluoropyridine (4.0 g, 22.7 mmol, 1.0 eq) in THF (100 mL), t-BuOK (3.8 g, 34.1 mmol, 1.5 eq) and hexane-1,6-diol (6.7 g, 56.8 mmol, 2.5 eq) was added. The mixture was stirred at room temperature for 16 h. The resulted solution was concentrated under reduced pressure, diluted with $H_2O$ (100 mL) and extracted with ethyl acetate (100 mL×3). The combined organic layers were dried over anhydrous sodium sulfate and concentrated under reduced pressure. The residue was purified by silica gel column (PE/EA=5/1) to give 49.1 (3.6 g, yield: 58%) as colorless oil. $^1$H NMR (400 MHz, $CDCl_3$) δ: 7.97 (d, J=5.6 Hz, 1H), 7.01 (d, J=5.6 Hz, 1H), 6.94 (s, 1H), 4.27 (t, J=6.6 Hz, 2H), 3.66 (t, J=6.6 Hz, 2H), 1.66-1.57 (m, 4H), 1.51-1.38 (m, 4H); ESI-MS (M+H)$^+$: 274.0.

Synthesis of Compound 49.2

To a solution of 49.1 (1.8 g, 6.6 mmol, 1.0 eq) in DCM (30 mL), TBSCl (1.1 g, 7.3 mmol, 1.1 eq) and imidazole (539 mg, 7.9 mmol, 1.2 eq) were added. The mixture was stirred at room temperature for 16 h and washed with water (30 mL×3). The organic layer was dried over anhydrous sodium sulfate and concentrated under reduced pressure. The residue was purified by silica gel column (PE/EA=50/1) to give 49.2 (2.5 g, yield: 98%) as colorless oil. $^1$H NMR (400 MHz, $CDCl_3$) δ: 7.92 (d, J=5.2 Hz, 1H), 6.95 (d, J=5.2 Hz, 1H), 6.88 (s, 1H), 4.22 (t, J=6.6 Hz, 2H), 3.56 (t, J=6.6 Hz, 2H), 1.75-1.68 (m, 2H), 1.53-1.46 (m, 2H), 1.42-1.30 (m, 4H), 0.85 (s, 9H), 0.00 (s, 6H); ESI-MS (M+H)$^+$: 388.1.

Synthesis of Compound 49.3

To a solution of 49.2 (2.3 g, 5.9 mmol, 1.0 eq) in DMF (25 mL), ethyl oxazole-4-carboxylate (838 mg, 5.9 mmol, 1.0 eq), $Pd(OAc)_2$ (264 mg, 1.2 mmol, 0.2 eq), $P(o-tol)_3$ (730 mg, 2.4 mmol, 0.4 eq) and $Cs_2CO_3$ (3.8 g, 11.8 mmol, 2.0 eq) were added. The mixture was stirred at 110° C. under $N_2$ atmosphere for 16 h. After cooled down to room temperature, the solution was diluted with ethyl acetate (100 mL) and filtered by Celite. The filtrate was washed with water (30 mL×3), brine (30 mL×2). The organic layer was dried over anhydrous sodium sulfate and concentrated under reduced pressure. The residue was purified by silica gel column (PE/EA=8/1) to give 49.3 (1.4 g, yield: 52%) as a yellow oil. $^1$H NMR (400 MHz, $CDCl_3$) δ: 8.27 (s, 1H), 8.22 (d, J=5.6 Hz, 1H), 7.49 (d, J=5.6 Hz, 1H), 7.34 (s, 1H), 4.28 (t, J=6.4 Hz, 2H), 4.01 (t, J=6.8 Hz, 2H), 3.56 (q, J=7.2 Hz, 2H), 1.79-1.72 (m, 2H), 1.52-1.40 (m, 6H), 1.37 (t, J=7.2 Hz, 3H), 0.84 (s, 9H), 0.00 (s, 6H); ESI-MS (M+H)$^+$: 449.2.

Synthesis of Compound 49.4

To a solution of 49.3 (1.4 g, 3.1 mmol, 1.0 eq) in EtOH (60 mL), conc. HCl (0.6 mL, 6.2 mmol, 2.0 eq) was added. The reaction mixture was stirred at room temperature for 16 h. The solution was adjusted to pH=7 with saturated $NaHCO_3$ solution, concentrated under reduced pressure, diluted with $H_2O$ (50 mL) and extracted with ethyl acetate (30 mL×3). The combined organic layers were dried over anhydrous sodium sulfate and concentrated under reduced pressure. The residue was purified by silica gel column (PE/EA=2/1) to give 49.4 (1.0 g, yield: 96%) as a white solid. $^1$H NMR (400 MHz, $CDCl_3$) δ: 8.32 (s, 1H), 8.27 (d, J=5.2 Hz, 1H), 7.54 (d, J=5.2 Hz, 1H), 7.39 (s, 1H), 4.45 (q, J=7.2 Hz, 2H), 4.33 (t, J=6.4 Hz, 2H), 3.67 (t, J=6.4 Hz, 2H), 1.85-1.78 (m, 2H), 1.65-1.45 (m, 6H), 1.41 (t, J=7.2 Hz, 3H); ESI-MS (M+H)$^+$: 335.1.

Synthesis of Compound 49.5

To a solution of 49.4 (530 mg, 1.6 mmol, 1.0 eq) in DCM (10 mL), MsCl (271 mg, 2.4 mmol, 1.5 eq) and TEA (485 mg, 4.8 mmol, 3.0 eq) were added. The mixture was stirred at room temperature for 1 h and then washed with water (10 mL×3). The organic layer was dried over anhydrous sodium sulfate and concentrated under reduced pressure. The residue was purified by silica gel column (PE/EA=3/1) to give 49.5 (530 mg, yield: 81%) as a white solid. $^1$H NMR (400 MHz, $CDCl_3$) δ: 8.32 (s, 1H), 8.27 (d, J=5.6 Hz, 1H), 7.54 (d, J=5.6 Hz, 1H), 7.40 (s, 1H), 4.44 (q, J=7.2 Hz, 2H), 4.34

(t, J=6.6 Hz, 2H), 4.25 (t, J=6.4 Hz, 2H), 1.83-1.78 (m, 4H), 1.58 (s, 3H), 1.52-1.50 (m, 4H), 1.41 (t, J=7.2 Hz, 3H); ESI-MS (M+H)$^+$: 413.1.

Synthesis of Compound 49.6

To a solution of 49.5 (330 mg, 0.8 mmol, 1.0 eq) in CH$_3$CN (6 mL), 1-methyl-1H-pyrazol-4-amine (155 mg, 1.6 mmol, 2.0 eq) and Cs$_2$CO$_3$ (527 mg, 1.6 mmol, 2.0 eq) were added. The mixture was stirred at 80° C. for 16 h. After cooled down to room temperature, the solution was filtered by Celite. The filtrate was concentrated under reduced pressure and the residue was purified by prep-HPLC (CH$_3$CN/H$_2$O with 0.05% TFA as mobile phase, from 5%-95%) to give 49.6 (115 mg, yield: 34%) as a yellow oil; ESI-MS (M+H)$^+$: 414.2.

Synthesis of Compound 49.7

To a solution of 49.6 (256 mg, 0.6 mmol, 1.0 eq) in the mixed solvents (THF/H$_2$O=5/1, 6 mL), NaOH (48 mg, 1.2 mmol, 2.0 eq) was added. The mixture was stirred at 60° C. for 2 h. After cooled down to room temperature, the solution was adjusted to pH=6 and concentrated under reduced pressure. The residue was purified by prep-HPLC (CH$_3$CN/H$_2$O with 0.05% TFA as mobile phase; from 5%-95%) to give 49.7 (178 mg, yield: 75%) as a yellow oil; ESI-MS (M+H)$^+$: 386.1.

Synthesis of Compound 49

To a solution of 49.7 (169 mg, 0.4 mmol, 1.0 eq) in DCM (45 mL) and DMF (3 mL) were added HATU (304 mg, 0.8 mmol, 2.0 eq) and DIPEA (155 mg, 1.2 mmol, 3.0 eq). The mixture was stirred at room temperature for 2 h. The solution was concentrated under reduced pressure and then MeOH (10 mL) was added. The precipitate was collected by filtration and washed with MeOH (5 mL), recrystallized in CHCl$_3$/MeOH (9/1) to give 49 (12 mg, yield: 10%) as a white solid. $^1$H NMR (400 MHz, CDCl$_3$) δ: 8.35 (s, 1H), 8.21 (d, J=5.2 Hz, 1H), 8.01 (s, 1H), 7.56 (d, J=5.2 Hz, 1H), 7.41 (s, 1H), 7.28 (s, 1H), 4.25 (m, 4H), 3.92 (s, 3H), 1.94-1.83 (m, 4H), 1.59-1.55 (m, 4H); ESI-MS (M+H)$^+$: 368.2.

Synthesis of Compound 50

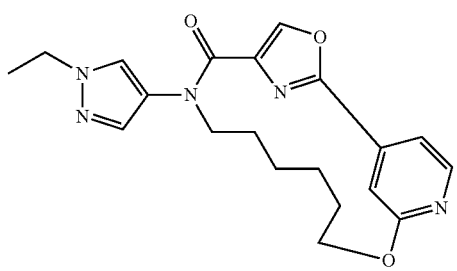

Compound 50 was prepared by similar procedure as described in the synthesis of Compound 49 using 1-ethyl-1H-pyrazol-4-amine. Purified by recrystallization in CHCl$_3$/MeOH (9/1). Afforded 50 white solid 20 mg, yield: 21%; $^1$HNMR (400 MHz, CDCl$_3$) δ 8.35 (s, 1H), 8.21 (d, J=5.2 Hz, 1H), 8.07 (s, 1H), 7.57 (s, 1H), 7.44-7.39 (m, 1H), 7.31-7.28 (m, 1H), 4.40-4.24 (m, 4H), 4.22-4.08 (m, 2H), 2.02-1.90 (m, 2H), 1.88-1.75 (m, 2H), 1.55-1.36 (m, 7H); ESI-MS (M+H)$^+$: 382.3; HPLC: 214 nm: 93%, 254 nm: 100%.

Synthesis of Compound 51

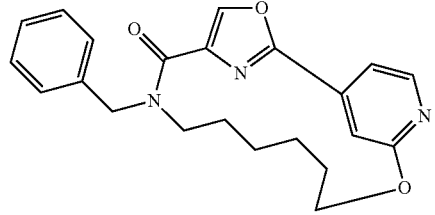

Compound 51 was prepared by similar procedure as described in the synthesis of Compound 49 using phenylmethanamine. Purified by pre-TLC (DCM/MeOH=20/1). Afforded 51 as a white solid 12 mg, yield: 52%; $^1$HNMR (400 MHz, CDCl$_3$) δ 8.29 (s, 1H), 8.11 (d, J=5.6 Hz, 1H), 7.31 (d, J=5.6 Hz, 1H), 7.29-7.26 (m, 3H), 7.23-7.17 (m, 3H), 4.69 (s, 2H), 4.15 (t, J=6.8 Hz, 2H), 3.75-3.71 (m, 2H), 1.79-1.65 (m, 4H), 1.48-1.36 (m, 4H); ESI-MS (M+H)$^+$: 378.3; HPLC: 214 nm: 68%, 254 nm: 97%.

Synthesis of Compound 52

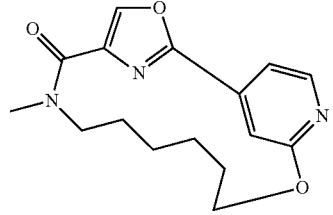

Compound 52 was prepared by similar procedure as described in the synthesis of Compound 49 using methanamine. Purified by prep-HPLC (CH$_3$CN/H$_2$O with 0.05% TFA as mobile phase; from 5%-95%). Afforded 52 as a pale yellow solid 6 mg, Y: 7%; $^1$H NMR (400 MHz, CDCl$_3$) δ: 8.29 (s, 1H), 8.17 (d, J=5.2 Hz, 1H), 7.39 (d, J=5.2 Hz, 1H), 7.22 (s, 1H), 3.86 (t, J=8.0 Hz, 2H), 3.41-3.36 (m, 2H), 3.10 (s, 3H), 1.83-1.78 (m, 4H), 1.54-1.44 (m, 4H). ESI-MS (M+H)$^+$: 302.1

Synthesis of Compound 53

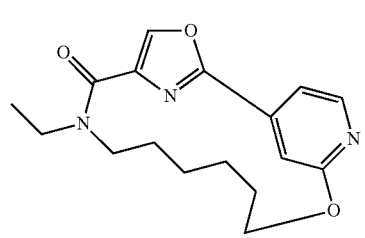

Compound 53 was prepared by similar procedure as described in the synthesis of Compound 49 using ethanamine. Purified by prep-HPLC (CH$_3$CN/H$_2$O with 0.05% TFA as mobile phase; from 5%-95%). Afforded 53 as a pale yellow solid 8 mg, Y: 5%; $^1$H NMR (400 MHz, CDCl$_3$) δ: 8.29 (s, 1H), 8.19 (d, J=5.2 Hz, 1H), 7.39 (d, J=5.2 Hz, 1H), 7.25 (s, 1H), 4.23 (t, J=6.8 Hz, 2H), 3.80 (t, J=8.0 Hz, 2H), 3.53 (q, J=7.6 Hz, 2H), 1.83-1.78 (m, 4H), 1.54-1.44 (m, 4H), 1.24 (t, J=7.6 Hz, 3H). ESI-MS (M+H)$^+$: 316.0

Synthesis of Compound 54

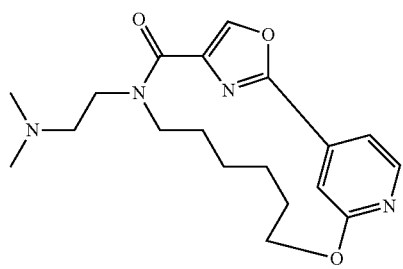

Compound 54 was prepared by similar procedure as described in the synthesis of Compound 49 using N1,N1-dimethylethane-1,2-diamine. Purified by prep-HPLC (CH$_3$CN/H$_2$O with 0.05% TFA as mobile phase; from 5%-95%). Afforded 54 as pale yellow solid 5.6 mg, Y: 11%; $^1$H NMR (400 MHz, CD$_3$OD) □ □: 8.37 (d, J=6.4 Hz, 1H), 8.30 (s, 1H), 7.50 (s, 1H), 7.40 (d, J=6.4 Hz, 1H), 4.42 (t, J=6.4, 2H), 3.92 (m, 2H), 3.11 (s, 3H), 2.91 (m, 2H), 2.51 (m, 2H), 2.31 (s, 3H), 1.80-1.73 (m, 2H), 1.62-1.51 (m, 4H), 1.49-1.41 (m, 2H); ESI-MS (M+H)$^+$: 359.2

Synthesis of Compound 55

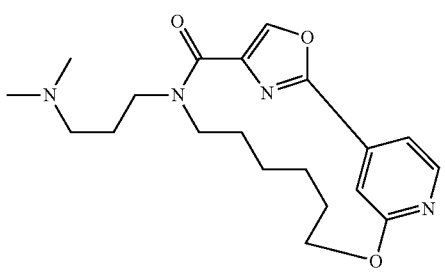

Compound 55 was prepared by similar procedure as described in the synthesis of Compound 49 using N1,N1-dimethylpropane-1,3-diamine. Purified by prep-HPLC (CH$_3$CN/H$_2$O with 0.05% TFA as mobile phase; from 5%-95%). Afforded 55 as a yellow solid 9 mg, yield: 2%; $^1$H NMR (400 MHz, DMSO-d$_6$) δ: 9.11 (s, 1H), 8.71-7.69 (m, 1H), 7.92-7.91 (m, 1H), 7.68 (s, 1H), 4.74-4.72 (m, 2H), 4.39-4.37 (m, 2H), 4.22-4.20 (m, 2H), 4.02-3.92 (m, 6H), 3.89-3.79 (m, 2H), 2.75-2.74 (m, 2H), 2.37-2.28 (m, 4H), 2.28-2.20 (m, 4H). ESI-MS (M+H)$^+$: 373.1.

Synthesis of Compound 56

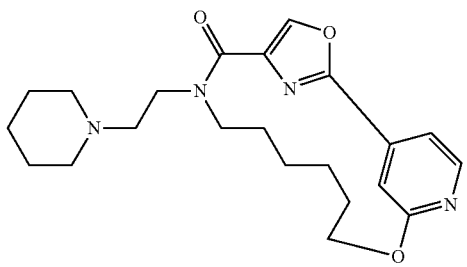

Compound 56 was prepared by similar procedure as described in the synthesis of Compound 49 using 2-(piperidin-1-yl)ethanamine. Purified by prep-HPLC (CH$_3$CN/H$_2$O with 0.05% TFA as mobile phase; from 5%-95%). Afforded 56 as a white solid 7.8 mg, Y: 9%; $^1$H NMR (400 MHz, CD$_3$OD) □ □: 8.29 (s, 1H), 8.19 (d, J=5.2 Hz, 1H), 7.37 (d, J=5.2 Hz, 1H), 7.22 (s, 1H), 4.13 (t, J=6.6 Hz, 2H), 3.85-3.76 (m, 4H), 3.62-3.55 (m, 2H), 3.34-3.20 (m, 2H), 2.96-2.77 (m, 2H), 1.84-1.42 (m, 14H); ESI-MS (M+H)$^+$: 399.2

Synthesis of Compound 57

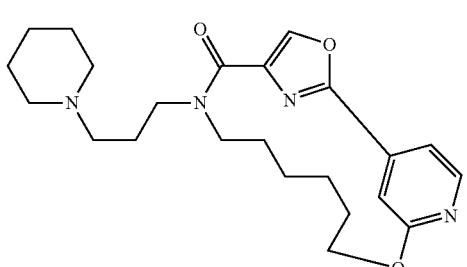

Compound 57 was prepared by similar procedure as described in the synthesis of Compound 49 using 3-(piperidin-1-yl)propan-1-amine. Purified by prep-HPLC (CH$_3$CN/H$_2$O with 0.05% TFA as mobile phase; from 5%-95%). To afford 57 as a pale yellow solid 18 mg, Y: 9%; $^1$H NMR (400 MHz, CD$_3$OD) δ: 8.61 (s, 1H), 8.19 (d, J=5.2 Hz, 1H), 7.45 (d, J=5.2 Hz, 1H), 7.11 (s, 1H), 4.17 (t, J=6.4 Hz, 2H), 3.86-3.82 (m, 2H), 3.60-3.49 (m, 4H), 3.11 (t, J=7.6 Hz, 2H), 2.96-2.85 (m, 2H), 2.10-2.07 (m, 2H), 1.84-1.74 (m, 8H), 1.49-1.38 (m, 6H). ESI-MS (M+H)$^+$: 412.2

Example 58

Scheme 58

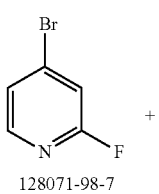

128071-98-7

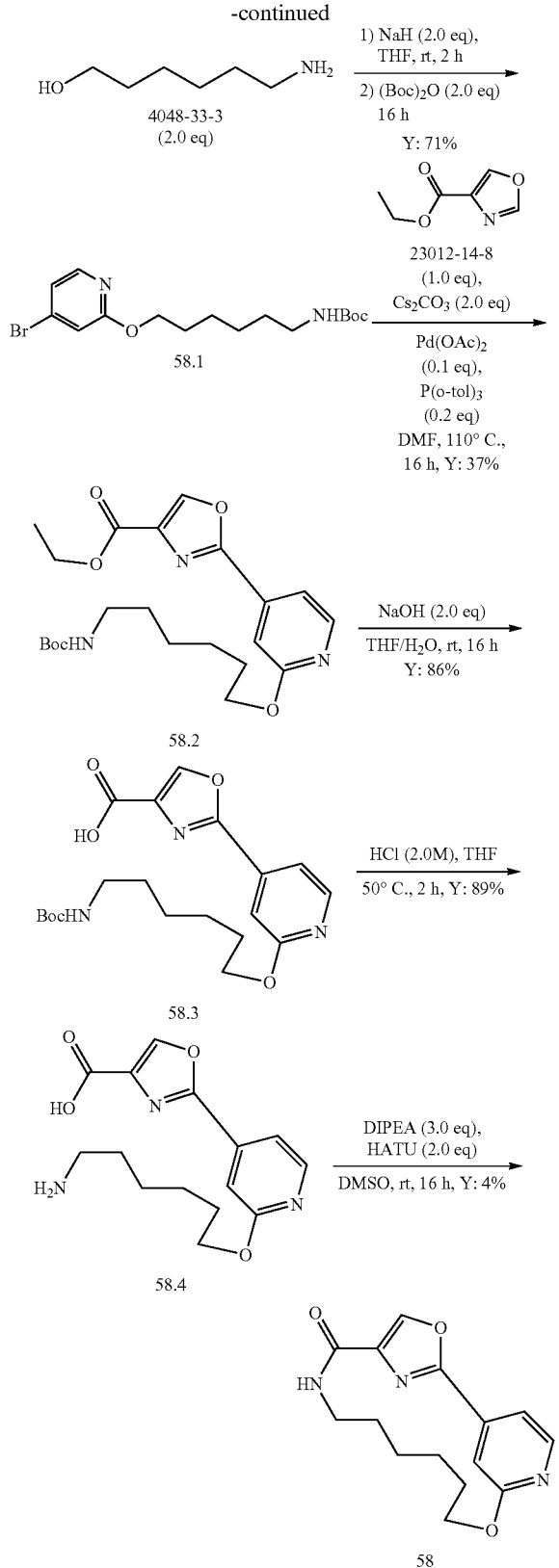

added at 0° C. The mixture was stirred at room temperature for 30 min and 4-bromo-2-fluoropyridine (2.0 g, 11 mmol) was added at 0° C. The resulted mixture was stirred at room temperature for 2 h and (Boc)₂O (5.2 g, 23 mmol) was added. The reaction mixture was stirred at room temperature for 1 h. The reaction was quenched with water (20 mL). The solvent was removed in vacuo and the mixture was extracted with ethyl acetate (20 mL×3). The combined organic layers were dried over anhydrous sodium sulfate and purified by silica gel column (PE/EA=3/1) to give a yellow solid 58.1 (3.0 g, yield: 71%). ¹H NMR (400 MHz, CDCl₃) □: 7.96 (d, J=5.2 Hz, 1H), 7.00 (d, J=5.6 Hz, 1H), 6.93 (s, 1H), 4.26 (t, J=6.6 Hz, 2H), 3.13-3.09 (m, 2H), 1.79-1.72 (m, 2H), 1.54-1.48 (m, 2H), 1.46-1.44 (m, 11H), 1.42-1.35 (m, 2H); ESI-MS (M+H)⁺: 373.1.

Synthesis of Compound 58.2

Compound 58.2 was prepared by similar procedure as described in the synthesis of Compound 49.3. Purified by silica gel column (PE/EA=3/1). To afford 58.2 as a yellow oil 1.3 g, yield: 37%; ESI-MS (M+H)⁺: 434.2.

Synthesis of Compound 58.3

Compound 58.3 was prepared by similar procedure as described in the synthesis of Compound 49.7. Purified by prep-HPLC (CH₃CN/H₂O with 0.05% TFA as mobile phase; from 5%-95%). To afford 58.3 as a yellow solid 800 mg, yield: 86%; ESI-MS (M+H)⁺: 406.2.

Synthesis of Compound 58.4

To the solution of 58.3 (300 mg, 0.74 mmol) in THF (3 mL), HCl (2.0 M, 1 mL, 2.0 mmol) was added. The mixture was stirred at 50° C. for 2 h and then concentrated under reduced pressure to give a yellow solid 58.4 (200 mg, yield: 89%). ¹H NMR (400 MHz, CDCl₃) □: 8.22 (s, 1H), 8.12 (d, J=6.0 Hz, 1H), 7.43-7.41 (m, 2H), 4.18 (t, J=7.6 Hz, 2H), 2.79 (t, J=8.0 Hz, 2H), 1.75-1.65 (m, 2H), 1.62-1.52 (m, 2H), 1.47-1.30 (m, 4H); ESI-MS (M+H)⁺: 306.1.

Synthesis of Compound 58

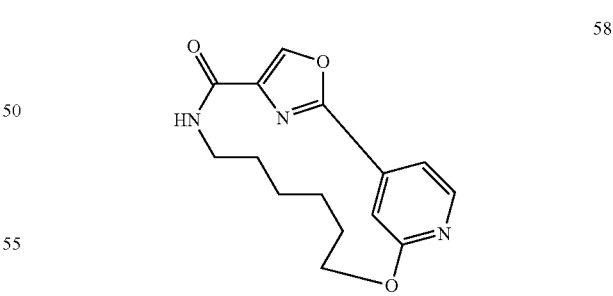

58

Compound 58 was prepared by similar procedure as described in the synthesis of Compound 49. Purified by prep-HPLC (CH₃CN/H₂O with 0.05% TFA as mobile phase; from 5%-95%). To afford 58 as a yellow solid 5.8 mg, yield: 4%; ¹HNMR (400 MHz, CDCl₃) □ □ □: 8.40 (d, J=5.2 Hz, 1H), 8.37 (s, 1H), 7.85 (s, 1H), 7.31 (d, J=5.2 Hz, 1H), 6.09 (s, 1H), 4.35 (t, J=7.2 Hz, 2H), 3.66-3.60 (m, 2H), 2.16-1.98 (m, 4H), 1.65-1.55 (m, 4H); ESI-MS (M+H)⁺: 288.1; HPLC: 214 nm: 100%, 254 nm: 100%.

Synthesis of Compound 58.1

To the solution of 6-aminohexan-1-ol (2.7 g, 23 mmol) in THF (50 mL), NaH (920 mg, 23 mmol, 60% in oil) was Example 59

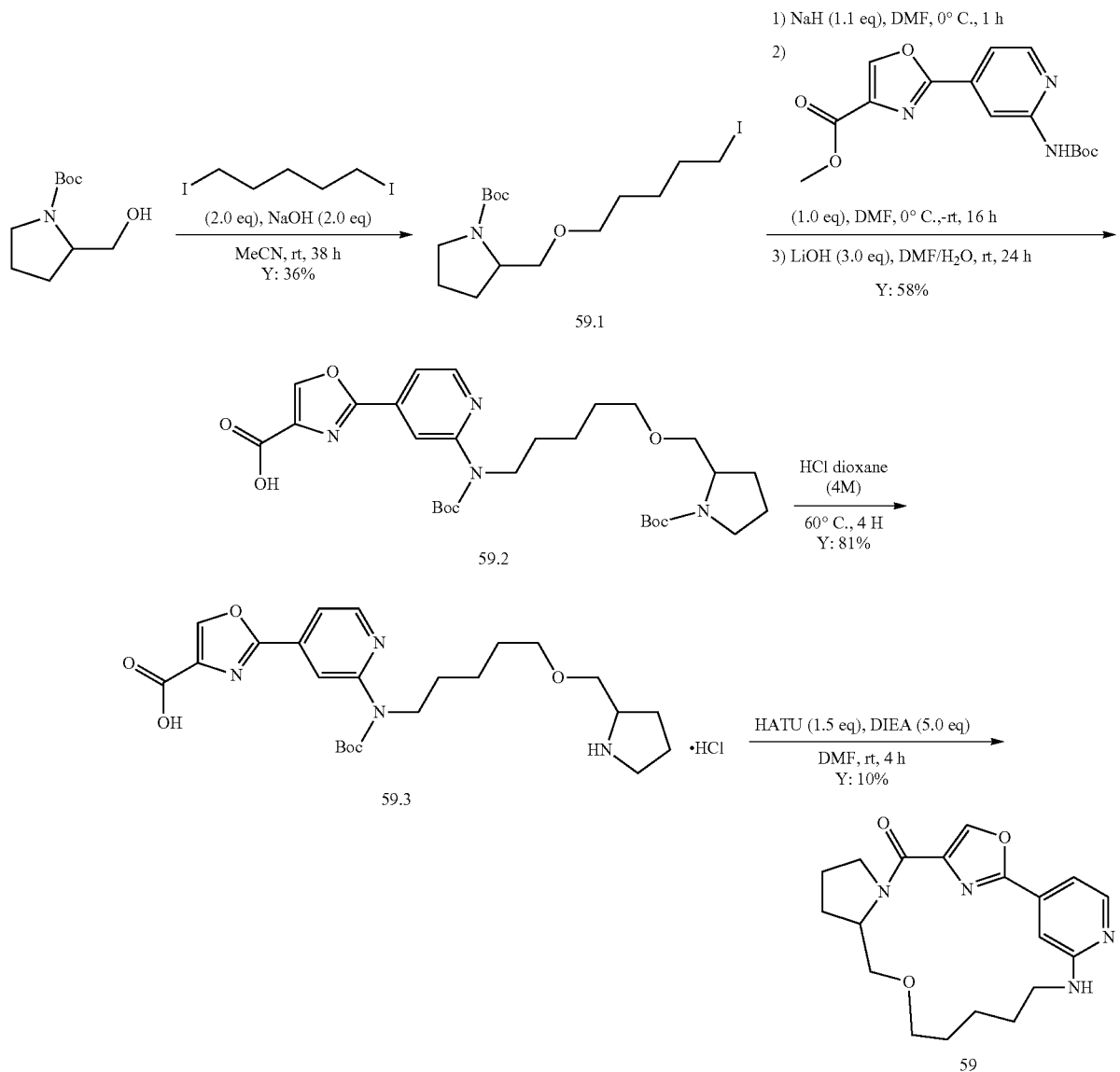

Scheme 59

Synthesis of Compound 59.1

To a solution of tert-butyl 2-(hydroxymethyl)pyrrolidine-1-carboxylate (1.0 g, 4.9 mmol, 1.0 eq) in MeCN (50 mL) were added NaOH (0.39 g, 9.8 mmol, 2.0 eq) and 1,5-diiodopentane (3.2 g, 9.9 mmol, 2.0 eq). The reaction mixture was stirred at room temperature for 48 h and concentrated under reduced pressure. The residue was diluted with ethyl acetate (100 mL), washed with H₂O (100 mL) and brine (50 mL). The organic layer was dried over anhydrous sodium sulfate and concentrated under reduced pressure. The residue was purified by silica gel column (PE:EA=5:1) to give 59.1 (0.7 g, Y: 36%) as a yellow oil. $^1$H NMR (400 MHz, CDCl₃) δ: 3.96-3.92 (m, 1H), 3.54-3.51 (m, 1H), 3.48-3.39 (m, 2H), 3.33-3.32 (m, 3H), 3.19 (t, J=6.8 Hz, 2H), 2.31-2.19 (m, 1H), 1.95-1.76 (m, 6H), 1.60-1.50 (m, 3H), 1.46 (s, 9H).

Synthesis of Compound 59.2

To a mixture of methyl 2-(2-((tert-butoxycarbonyl)amino)pyridin-4-yl)oxazole-4-carboxylate (467 mg, 1.46 mmol, 1.0 eq) in DMF (20 mL), NaH (64 mg, 1.60 mmol, 1.1 eq) was added at 0° C. After stirring at 0° C. for 1 h, 59.1 (700 mg, 1.76 mmol, 1.2 eq) was dropped into the reaction mixture. The mixture was allowed to warm to room temperature and stirred for 16 h. After that, LiOH H₂O (155 mg, 4.38 mmol, 3.0 eq) and H₂O (2 mL) were added. After stirring at room temperature for another 24 h, the reaction mixture was diluted with H₂O (40 mL), adjusted to pH=6 with acetic acid (20% in water) and extracted with ethyl acetate (30 mL×3). The combined organic layers were washed with water (30 mL) and brine (30 mL), dried over anhydrous sodium sulfate and concentrated under reduced pressure. The residue was purified by pre-HPLC (MeOH/ 0.05% TFA in H$_2$O=10%~95%) to furnish 59.2 (280 mg, Y: 58%) as a yellow solid; ESI-MS (M+H)$^+$: 575.2.

Synthesis of Compound 59.3

To a solution of 59.2 (280 mg, 0.48 mmol, 1.0 eq) was added 10 mL of HCl in dioxane (4 M). The mixture was stirred at room temperature for 16 h and concentrated under reduced pressure to give 59.3 (180 mg, Y: 81%) as yellow solid; ESI-MS (M+H)$^+$: 375.2.

Synthesis of Compound 59

To a solution of 59.3 (180 mg, 0.48 mmol, 1.0 eq) in DMF (30 mL) were added HATU (274 mg, 0.72 mmol, 1.5 eq) and DIPEA (123 mg, 0.96 mmol, 2.0 eq). The mixture was stirred at room temperature for 16 h, diluted with DCM (100 mL), washed with brine (20 mL×2). The organic layer was dried over anhydrous sodium sulfate and concentrated under reduced pressure. The residue was purified by silica gel column (PE: DCM=3:1) to give 59 (18 mg, Y: 10%) as a yellow solid. $^1$H NMR (400 MHz, CD$_3$OD) δ: 8.39 (s, 1H), 8.20-8.18 (m, 1H), 7.17 (s, 1H), 7.11 (d, J=4.4 Hz, 1H), 5.31 (br. s, 1H), 5.24-5.19 (m, 1H), 3.79 (dd, J$_1$=3.6 Hz, J$_2$=4.8 Hz, 1H), 3.68-3.64 (m, 2H), 3.55-3.50 (m, 2H), 3.38-3.22 (m, 3H), 2.29-2.26 (m, 1H), 1.99-1.87 (m, 5H), 1.65-1.60 (m, 1H), 1.55-1.37 (m, 3H); ESI-MS (M+H)$^+$: 357.1.

Examples 60 and 61

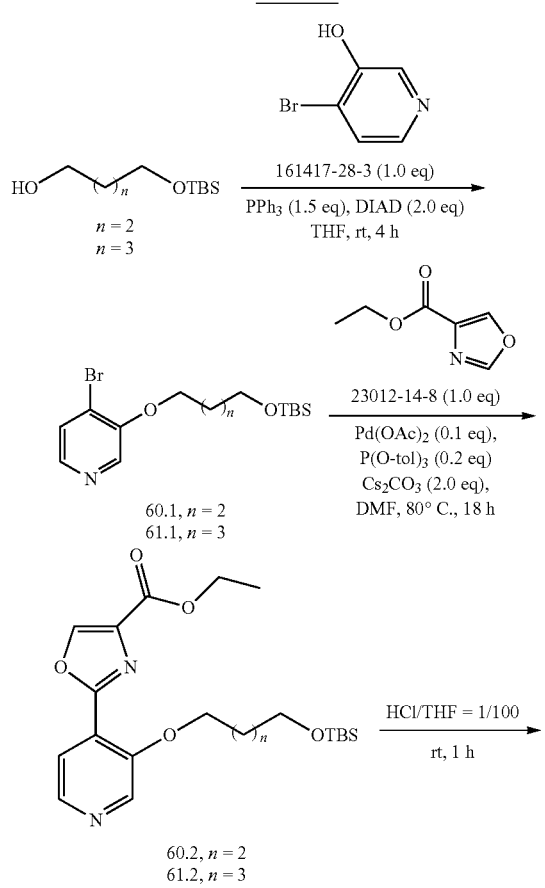

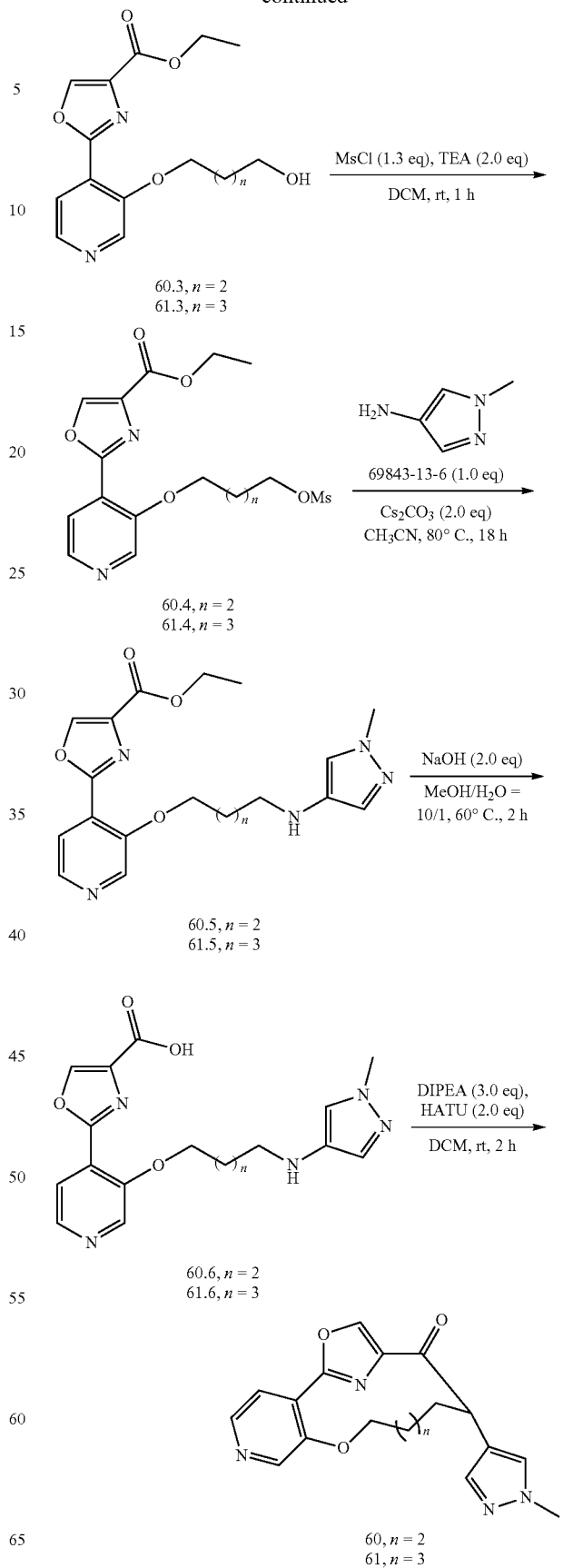

Synthesis of Compound 60.1

To a solution of 4-bromopyridin-3-ol (4.0 g, 23.0 mmol, 1.0 eq) and 4-((tert-butyldimethylsilyl)oxy)butan-1-ol (4.7 g, 23.0 mmol, 1.0 eq) in dry THF (60 mL), PPh₃ (9.0 g, 34.5 mmol, 1.5 eq) and DIAD (9.3 g, 46.0 mmol, 2.0 eq) were added under N₂ atmosphere. The resulting mixture was stirred at room temperature for 4 h and then the solvent was removed in vacuo. The residue was dissolved in ethyl acetate (200 mL) and then washed with water (100 mL×2). The organic layer was dried over anhydrous sodium sulfate and concentrated under reduced pressure. The residue was purified by silica gel (PE/EA=15/1) to give 60.1 (3.4 g, Y: 41%) as a colorless oil. $^1$H NMR (400 MHz, CDCl₃) δ: 8.16 (s, 1H), 7.98 (d, J=5.2 Hz, 1H), 7.42 (d, J=5.2 Hz, 1H), 4.11 (t, J=6.4 Hz, 2H), 3.65 (t, J=6.4 Hz, 2H), 1.91-1.84 (m, 2H), 1.72-1.65 (m, 2H), 0.84 (s, 9H), 0.00 (s, 6H); ESI-MS (M+H)⁺: 360.1.

Synthesis of Compound 60.2

To a solution of 60.1 (3.3 g, 9.20 mmol, 1.0 eq) and ethyl oxazole-4-carboxylate (1.3 g, 9.20 mmol, 1.0 eq) in anhydrous DMF (60 mL), Cs₂CO₃ (6.0 g, 18.4 mmol, 2.0 eq), Pd(OAc)₂ (207 mg, 0.92 mmol, 0.1 eq) and P(o-tol)₃ (559 mg, 1.84 mmol, 0.2 eq) were added under N₂ atmosphere. The mixture was stirred at 80° C. for 18 h under N₂ atmosphere. After cooled down to room temperature, the resulted solution was diluted with ethyl acetate (250 mL) and then filtered by Celite. The filtrate was washed with water (200 mL×3), brine (200 mL×2). The organic layer was dried over anhydrous sodium sulfate and concentrated under reduced pressure. The residue was purified by silica gel (PE/EA=10/1) to give 60.2 (3.3 g, Y: 85%) as a colorless oil. $^1$H NMR (400 MHz, CDCl₃) δ: 8.43 (s, 1H), 8.30-8.29 (m, 2H), 7.88 (d, J=4.8 Hz, 1H), 4.41-4.35 (m, 2H), 4.20 (t, J=6.4 Hz, 2H), 3.65 (t, J=6.0 Hz, 2H), 1.94-1.87 (m, 2H), 1.74-1.67 (m, 2H), 1.36 (t, J=6.8 Hz, 3H), 0.84 (s, 9H), 0.00 (s, 6H); ESI-MS (M+H)⁺: 421.2.

Synthesis of Compound 60.3

To a solution of 60.2 (3.2 g, 7.6 mmol, 1.0 eq) in THF (150 ml), conc. hydrochloric acid (1.3 mL, 15.2 mmol, 2.0 eq) was added. The mixture was stirred at room temperature for 1 h and concentrated under reduced pressure. The residue was diluted with water (100 mL) and then adjusted pH to 10 with saturated NaHCO₃ solution. The solution was extracted with DCM (50 mL×3). The combined organic layers were dried over anhydrous sodium sulfate and concentrated under reduced pressure. The residue was purified by silica gel (DCM/MeOH=30/1) to give 60.3 (2.2 g, Y: 95%) as a light yellow oil. $^1$H NMR (400 MHz, CDCl₃) δ: 8.50 (s, 1H), 8.36-8.34 (m, 2H), 7.88 (d, J=4.8 Hz, 1H), 4.53-4.40 (m, 2H), 4.30 (t, J=5.6 Hz, 2H), 3.79 (t, J=5.6 Hz, 2H), 2.08-2.01 (m, 2H), 1.91-1.84 (m, 2H), 1.40 (t, J=6.8 Hz, 3H); ESI-MS (M+H)⁺: 307.1.

Synthesis of Compound 60.4

To a solution of 60.3 (2.0 g, 6.53 mmol, 1.0 eq) and Et₃N (1.3 g, 13.10 mmol, 2.0 eq) in DCM (40 mL), MsCl (0.98 g, 8.50 mmol, 1.3 eq) was added at 0° C. The mixture was stirred at room temperature for 1 h and then the solvent was removed in vacuo. The residue was purified by silica gel (MeOH/DCM=1/50) to give 60.4 (2.1 g, Y: 84%) as a white solid. $^1$H NMR (400 MHz, CDCl₃) δ: 8.49 (s, 1H), 8.39-8.37 (m, 2H), 7.97 (d, J=5.2 Hz, 1H), 4.46-4.37 (m, 4H), 4.30-4.27 (m, 2H), 3.03 (s, 3H), 2.14-2.03 (m, 4H), 1.41 (t, J=6.8 Hz, 3H); ESI-MS (M+H)⁺: 385.1.

Synthesis of Compound 60.5

To a solution of 60.4 (450 mg, 1.17 mmol, 1.0 eq) and 1-methyl-1H-pyrazol-4-amine (125 mg, 1.29 mmol, 1.1 eq) in CH₃CN (20 mL), Cs₂CO₃ (764 mg, 2.34 mmol, 2.0 eq) was added. The mixture was stirred at 80° C. for 18 h. After cooled down to room temperature, the mixture was filtered by Celite and the filtrate was concentrated under reduced pressure. The residue was purified by pre-TLC (MeOH/DCM=1/20) to give 60.5 (120 mg, Y: 26%) as a yellow oil; ESI-MS (M+H)⁺: 386.2.

Synthesis of Compound 60.6

To a solution of 60.5 (200 mg, 0.52 mmol, 1.0 eq) in MeOH (20 mL) and H₂O (2 mL), NaOH (42 mg, 1.04 mmol, 2.0 eq) was added. The mixture was stirred at 60° C. for 2 h. After cooled down to room temperature, the solution was adjusted to pH=7 with HCl (1 N). The solvent was removed in vacuo and the residue was purified by prep-HPLC (CH₃CN in H₂O—0.05% NH₃H₂O from 5%-90%) to give 60.6 (180 mg, Y: 97%) as a yellow oil; ESI-MS (M+H)⁺: 357.7.

Synthesis of Compound 60

To a solution of 60.5 (130 mg, 0.36 mmol, 1.0 eq) in CH₂Cl₂ (300 mL) and DMF (3 ml), DIPEA (141 mg, 1.10 mmol, 3.0 eq) and HATU (277 mg, 0.73 mmol, 2.0 eq) were added. The mixture was stirred at room temperature for 2 h. The solvent was removed in vacuo and the MeOH (25 mL) was added. The precipitate was collected by filtration and washed with MeOH (10 mL×3) to give 60 (29 mg, Y: 23%) as a white solid. $^1$H NMR (400 MHz, CDCl₃) δ: 8.44 (s, 1H), 8.33-8.32 (m, 1H), 7.84-7.77 (m, 2H), 7.43 (s, 1H), 7.27 (s, 1H), 4.21 (m, 2H), 3.89-3.85 (m, 5H), 2.02-1.86 (m, 4H); ESI-MS (M+H)⁺: 340.2.

Synthesis of Compound 61

Compound 61 was prepared by similar procedure as described in the synthesis of Compound 60 using 5-((tert-butyldimethylsilyl)oxy)pentan-1-ol. Purified by pre-TLC (PE/EA=1/1). To afford 61 as a white solid 17 mg, Y: 18%; $^1$H NMR (400 MHz, CDCl₃) δ: 8.53 (s, 1H), 8.43 (d, J=5.2 Hz, 1H), 8.37 (s, 1H), 8.03 (s, 1H), 7.78 (d, J=5.2 Hz, 1H), 7.57 (s, 1H), 4.30 (t, J=5.6 Hz, 2H), 3.99-3.91 (m, 5H), 2.43-2.35 (m, 2H), 1.97-1.91 (m, 2H), 1.71-1.65 (m, 2H); ESI-MS (M+H)⁺: 354.1.

Examples 62 and 63

Scheme 62

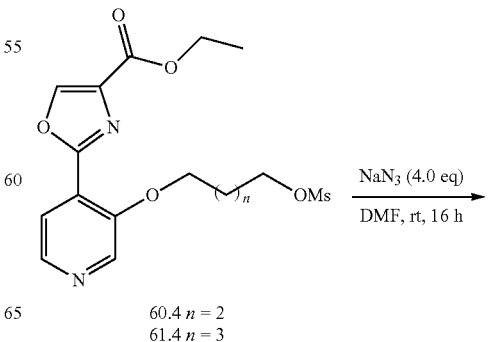

60.4 n = 2
61.4 n = 3

-continued

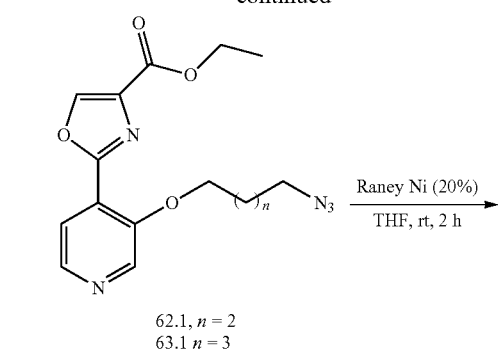

62.1, n = 2
63.1 n = 3

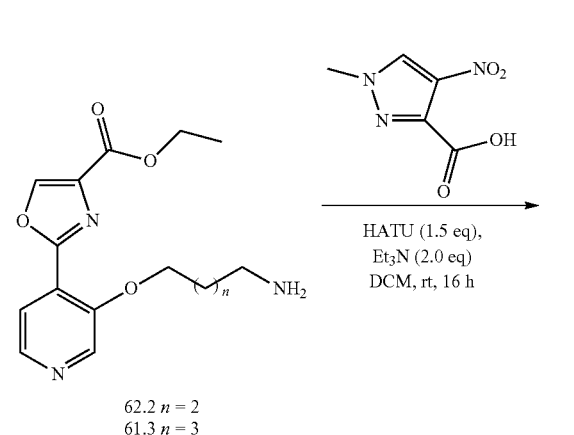

62.2 n = 2
61.3 n = 3

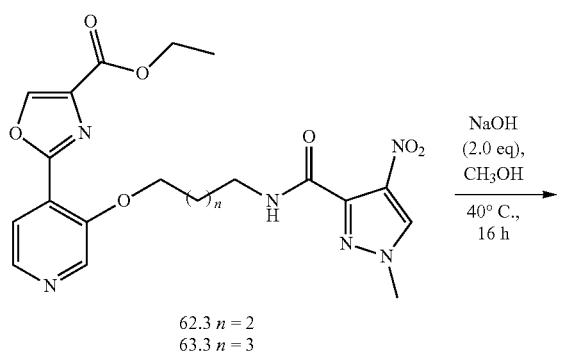

62.3 n = 2
63.3 n = 3

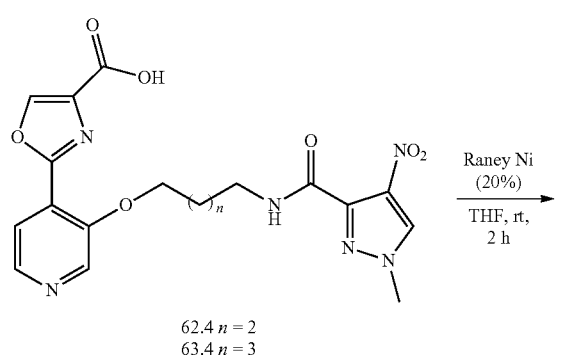

62.4 n = 2
63.4 n = 3

-continued

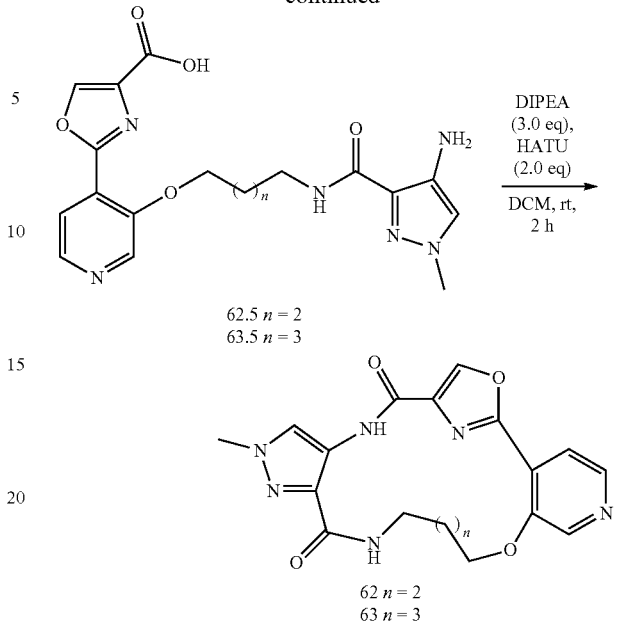

62.5 n = 2
63.5 n = 3

62 n = 2
63 n = 3

Synthesis of Compound 62.1

To a mixture of 60.4 (1.0 g, 2.6 mmol, 1.0 eq) in DMF (15 mL), NaN$_3$ (676 mg, 10.4 mmol, 4.0 eq) was added. The mixture was stirred at room temperature for 16 h and then diluted with water (100 mL). The solution was adjusted to pH=9 with saturated NaHCO$_3$ solution and extracted with ethyl acetate (100 mL). The organic layer was dried over sodium sulfate and concentrated under reduced pressure to give 62.1 (0.89 g, Y: 100%) as a colorless oil; ESI-MS (M+H)$^+$: 332.1.

Synthesis of Compound 62.2

To a solution of 62.1 (890 mg, 0.27 mmol, 1.0 eq) in THF (30 mL), Raney Ni (178 mg, 20% wt) was added. The mixture was stirred at room temperature under hydrogen for 2 h and then filtered by Celite. The filtrate was concentrated under reduced pressure to give 62.2 (850 mg, Y: 100%) as a light oil; ESI-MS (M+H)$^+$: 306.1.

Synthesis of Compound 62.3

To a solution of 1-methyl-4-nitro-1H-pyrazole-3-carboxylic acid (404 mg, 2.36 mmol, 1.2 eq) in DCM (100 mL), HATU (1.12 g, 2.96 mmol, 1.5 eq), Et$_3$N (388 mg, 3.94 mmol, 2.0 eq) and 62.2 (600 mg, 1.97 mmol, 1.0 eq) was added. The mixture was stirred at room temperature for 16 h. After concentrated under reduced pressure, the residue was purified by pre-TLC (EA) to give 62.3 (500 mg, Y: 55%) as a white solid. $^1$H NMR (400 MHz, DMSO-d$_6$) δ: 8.99 (s, 1H), 8.83 (s, 1H), 8.65 (s, 1H), 8.63 (t, J=5.6 Hz, 1H), 8.36 (d, J=4.8 Hz, 1H), 7.84 (d, J=4.8 Hz, 1H), 4.34-4.29 (m, 4H), 3.89 (s, 3H), 3.34 (t, J=5.2 Hz, 2H), 1.86-1.83 (m, 2H), 1.76-1.73 (m, 2H), 1.32 (t, J=7.2 Hz, 3H); ESI-MS (M+H)$^+$: 459.1.

Synthesis of Compound 62.4

To a solution of 62.3 (500 mg, 1.09 mmol, 1.0 eq) in MeOH (30 mL) was added NaOH (87 mg, 2.18 mmol, 2.0 eq). The reaction mixture was stirred at 40° C. for 16 h. After cooled down to room temperature, the solution was adjusted to pH=6 with HCl (1 N). After filtered by Celite, the filtrate was concentrated under reduced pressure to give 62.4 as a yellow solid (470 mg, Y: 100%); ESI-MS (M+H$^+$): 431.1.

Synthesis of Compound 62.5

To a mixture of 62.4 (470 mg, 1.09 mmol, 1.0 eq) in THF (30 mL), Raney Ni (94 mg, 20% wt) was added. The mixture was stirred at room temperature under hydrogen for 2 h. After filtered by Celite, the filtrate was concentrated under reduced pressure to give 62.5 (440 mg, Y: 100%) as a yellow solid; ESI-MS (M+H)$^+$: 401.1.

Synthesis of Compound 62

To a solution of 62.5 (440 mg, 1.10 mmol, 1.0 eq) in the mixed solvents (DCM/DMF=10/1, 100 mL) were added HATU (627 mg, 1.65 mmol, 1.5 eq) and Et$_3$N (222 mg, 2.20 mmol, 2.0 eq). The mixture was stirred at room temperature for 16 h and then diluted with water (100 mL). The precipitate was collected by filtration and recrystallation in methanol to give 62 (100 mg, Y: 23%) as a white solid. $^1$H NMR (400 MHz, DMSO-d$_6$) δ: 9.26 (s, 1H), 8.83 (s, 1H), 8.62 (s, 1H), 8.48 (t, J=5.6 Hz, 1H), 8.38 (d, J=4.8 Hz, 1H), 8.28 (s, 1H), 7.87 (d, J=4.8 Hz, 1H), 4.29 (t, J=4.4 Hz, 2H), 3.88 (s, 3H), 3.37-3.34 (m, 2H), 1.98-1.95 (m, 2H), 1.83-1.78 (m, 2H); ESI-MS (M+H)$^+$: 383.1.

Synthesis of Compound 63

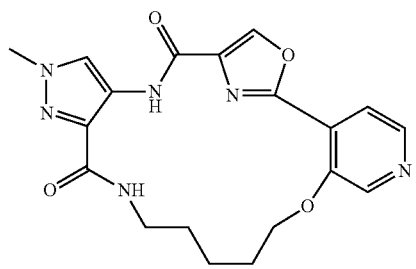

63

Compound 63 was prepared by similar procedure as described in the synthesis of Compound 62 using 5-((tert-butyldimethylsilyl)oxy)pentan-1-ol. Purified by recrystallization in MeOH. Afforded 63 as a solid 23 mg, Y: 13%; $^1$H NMR (400 MHz, CDCl$_3$) δ: 10.61 (s, 1H), 8.54 (s, 1H), 8.37 (d, J=5.2 Hz, 1H), 8.31 (s, 1H), 8.09 (s, 1H), 7.84 (d, J=4.8 Hz, 1H), 6.51 (t, J=6.0 Hz, 1H), 4.33 (t, J=5.2 Hz, 2H), 3.91 (s, 3H), 3.58-3.53 (m, 2H), 2.32-2.25 (m, 2H), 1.84-1.71 (m, 4H); ESI-MS (M+H)$^+$: 397.3.

Example 64

The compounds of the present invention provided in Table 1 were prepared by similar procedures as described above.

TABLE 1

| # | Structure |
|---|---|
| 64 | |
| 65 | |

TABLE 1-continued
| # | Stucture |
|---|---|
| 66 | 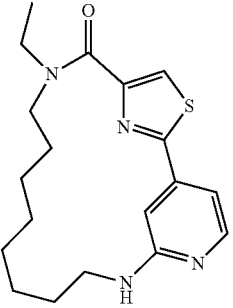 [SMILES: CCN1CCCCCCCCNc2cc(ccn2)-c2nc(cs2)C1=O] |
| 67 | 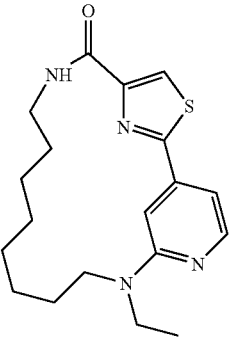 [SMILES: CCN1CCCCCCCCNC(=O)c2csc(n2)-c2ccnc1c2] |
| 68 | 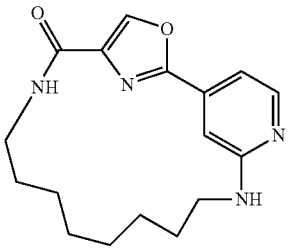 [SMILES: O=C1NCCCCCCCCNc2cc(ccn2)-c2nc1co2] |
| 69 | 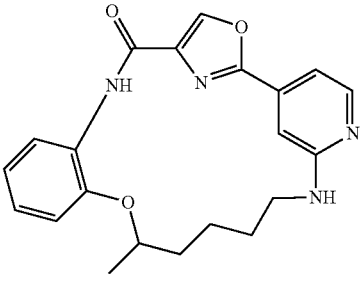 [SMILES: CC1CCCCNc2cc(ccn2)-c2nc(co2)C(=O)Nc2ccccc2O1] |
| 70 | 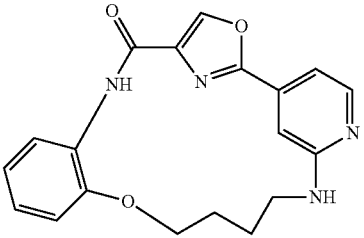 [SMILES: O=C1Nc2ccccc2OCCCCNc2cc(ccn2)-c2nc1co2] |

TABLE 1-continued
| # | Structure |
|---|---|
| 71 | 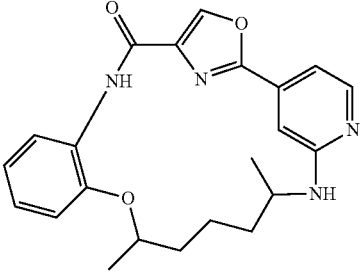 [SMILES: CC1CCCC(C)Oc2ccccc2NC(=O)c2coc(n2)-c2ccnc(c2)N1] |
| 72 | 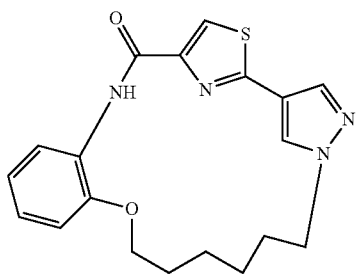 [SMILES: O=C1Nc2ccccc2OCCCCCCn2cc(cn2)-c2nc1cs2] |
| 73 | 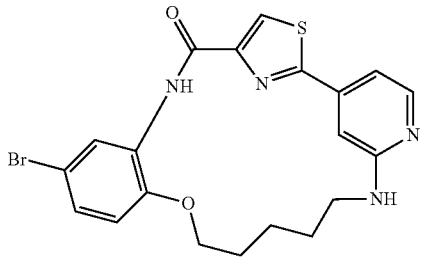 [SMILES: O=C1Nc2cc(Br)ccc2OCCCCCNc2cc(ccn2)-c2nc1cs2] |
| 74 | 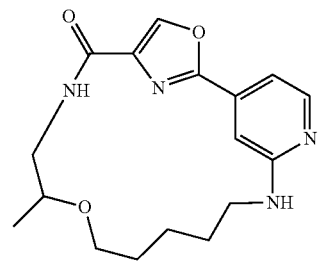 [SMILES: CC1CNC(=O)c2coc(n2)-c2ccnc(c2)NCCCCCO1] |
| 75 | 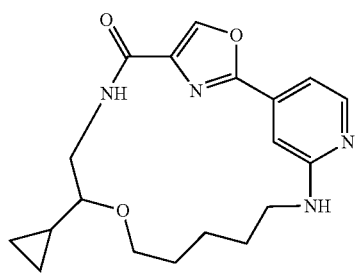 [SMILES: O=C1NCC(C2CC2)OCCCCCNc2cc(ccn2)-c2nc1co2] |

TABLE 1-continued

| # | Stucture |
|---|---|
| 76 | |
| 77 | |
| 78 | |
| 79 | |
| 80 | |
| 81 | |

TABLE 1-continued

| # | Structure |
|---|-----------|
| 82 | |
| 83 | |
| 84 | |
| 85 | |
| 86 | |
| 87 | |

TABLE 1-continued

| # | Stucture |
|---|---|
| 88 | |
| 89 | |
| 90 | |
| 91 | |
| 92 | |

TABLE 1-continued
| # | Stucture |
|---|---|
| 93 | 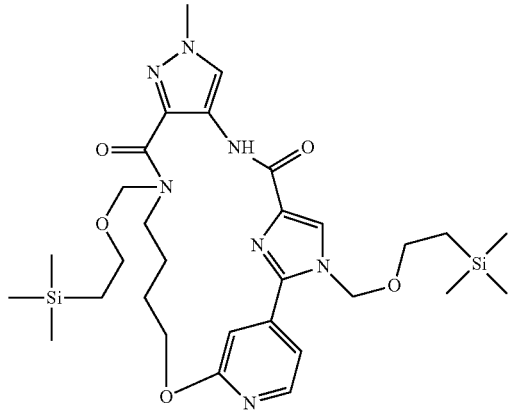 |
| 94 | 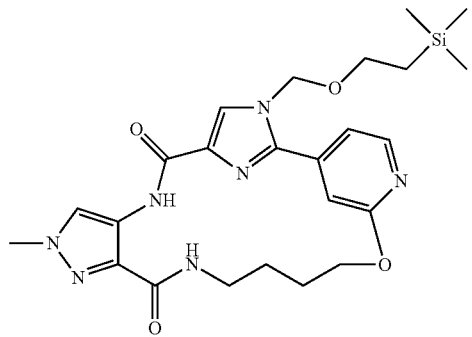 |
| 95 | 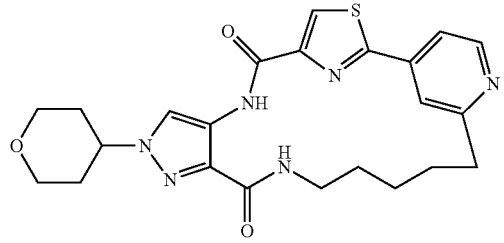 [SMILES: O=C1Nc2cn(C3CCOCC3)nc2C(=O)NCCCCCc2cc(ccn2)-c2nc1cs2] |
| 96 | 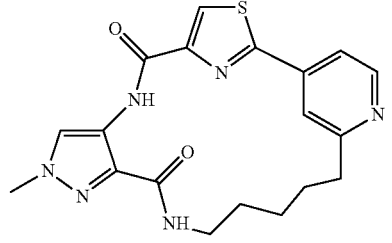 [SMILES: Cn1cc2c(n1)C(=O)NCCCCCc1cc(ccn1)-c1nc(cs1)C(=O)N2] |
| 97 | 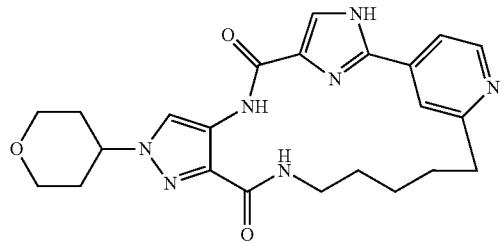 [SMILES: O=C1Nc2cn(C3CCOCC3)nc2C(=O)NCCCCCc2cc(ccn2)-c2nc1c[nH]2] |

TABLE 1-continued

| # | Stucture |
|---|---|
| 98 | |
| 99 | |
| 100 | |
| 101 | |
| 102 | |

TABLE 1-continued

| # | Structure |
|---|---|
| 103 | |
| 104 | |
| 105 | |
| 106 | |
| 107 | |

TABLE 1-continued
| # | Stucture |
|---|---|
| 108 | 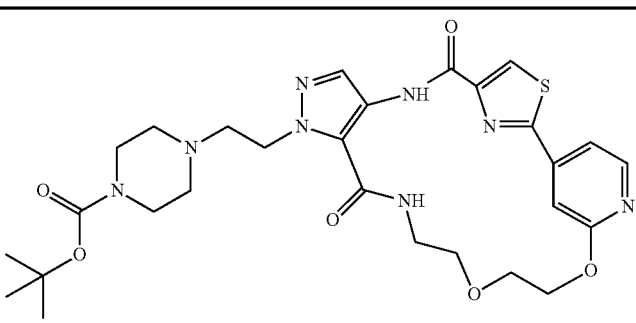 |
| 109 | 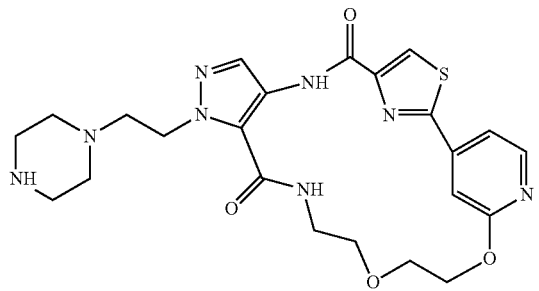 [SMILES: O=C1Nc2cnn(CCN3CCNCC3)c2C(=O)NCCOCCOc2cc(ccn2)-c2nc1cs2] |
| 110 | 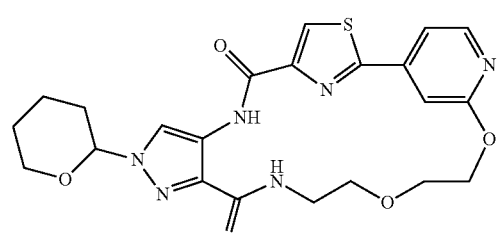 |
| 111 | 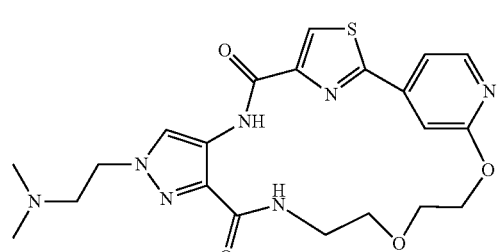 |
| 112 | 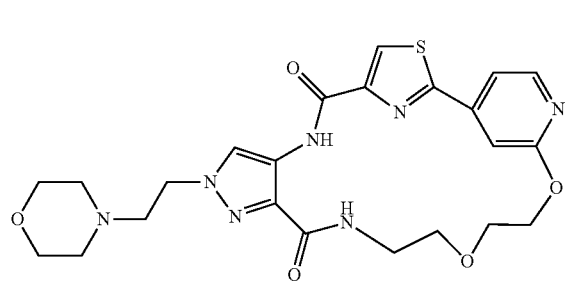 [SMILES: O=C1Nc2cn(CCN3CCOCC3)nc2C(=O)NCCOCCOc2cc(ccn2)-c2nc1cs2] |

TABLE 1-continued

| # | Structure |
|---|---|
| 113 | |
| 114 | |
| 115 | |
| 116 | |
| 117 | |
| 118 | |

US 9,617,282 B2
199                                                                                                          200
TABLE 1-continued
| # | Stucture |
|---|----------|
| 119 | 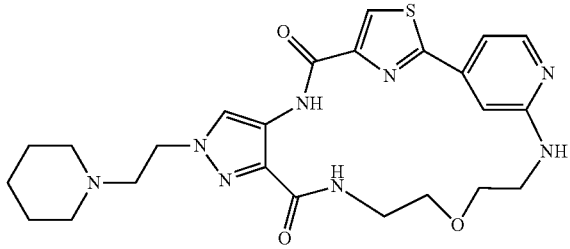 [SMILES: O=C1Nc2cn(CCN3CCCCC3)nc2C(=O)NCCOCCNc2cc(ccn2)-c2nc1cs2] |
| 120 | 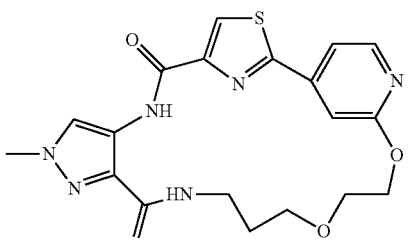 |
| 121 | 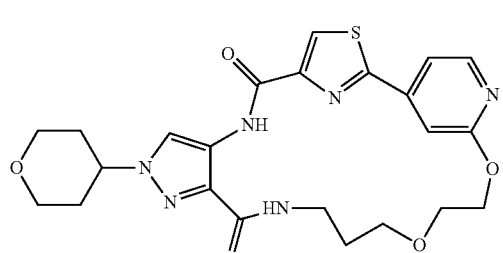 |
| 122 | 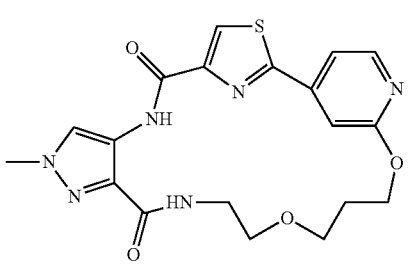 [SMILES: Cn1cc2c(n1)C(=O)NCCCOCCOc1cc(ccn1)-c1nc(cs1)C(=O)N2] |
| 123 | |
| 124 | 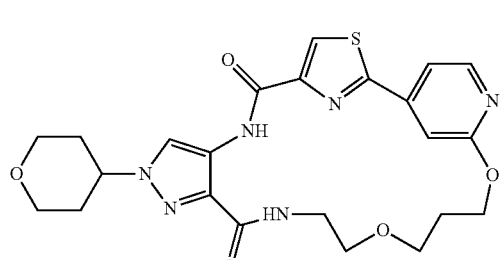 |

TABLE 1-continued
| # | Stucture |
|---|---|
| 125 | 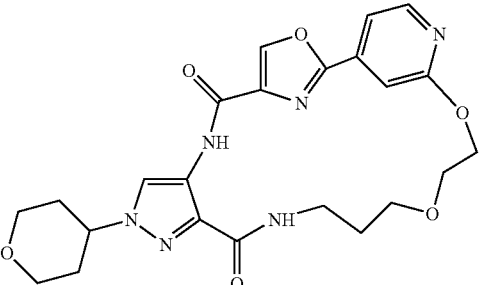 |
| 126 | 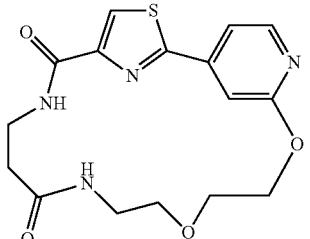 |
| 127 | 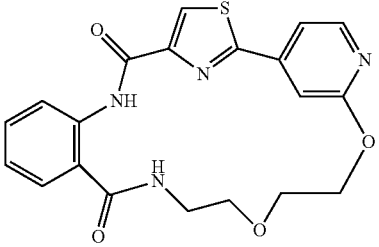 [SMILES: O=C1Nc2ccccc2C(=O)NCCOCCOc2cc(ccn2)-c2nc1cs2] |
| 128 | 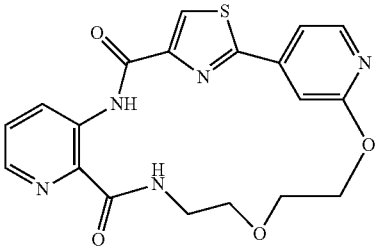 [SMILES: O=C1Nc2cccnc2C(=O)NCCOCCOc2cc(ccn2)-c2nc1cs2] |
| 129 | 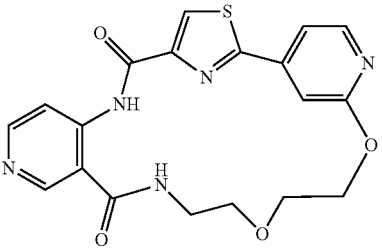 [SMILES: O=C1Nc2ccncc2C(=O)NCCOCCOc2cc(ccn2)-c2nc1cs2] |
| 130 | 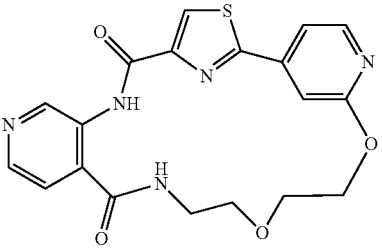 [SMILES: O=C1Nc2cnccc2C(=O)NCCOCCOc2cc(ccn2)-c2nc1cs2] |

TABLE 1-continued

| # | Structure |
|---|---|
| 131 | |
| 132 | |
| 133 | |
| 134 | |
| 135 | |
| 136 | |

TABLE 1-continued

| # | Stucture | |
|---|---|---|
| 137 | (structure) | |
| 138 | (structure) | |
| 139 | (structure) | |
| 140 | (structure) | |
| 141 | (structure) | $^1$H NMR (400 MHz, CDCl$_3$) δ: 11.09 (s, 1H), 9.12 (s, 1H), 8.36 (d, J = 4.8 Hz, 1H), 8.29 (s, 1H), 8.22 (s, 1H), 8.10 (s, 1H), 7.27-7.25 (m, 1H), 4.61 (t, J = 6.8 Hz, 2H), 4.49 (t, J = 5.6 Hz, 2H), 3.99 (t, J = 6.8 Hz, 2H), 3.89 (t, J = 6.0 Hz, 2H), 3.67-3.63 (m, 2H), 2.95 (t, J = 5.6 Hz, 2H), 2.53-2.42 (m, 8H), 2.29 (s, 3H); ESI-MS (M + H)$^+$: 527.3; HPLC: 214 nm: 100.00%, 254 nm: 100.00%. |

TABLE 1-continued

| # | Stucture | |
|---|---|---|
| 142 | | ¹H NMR (400 MHz, CDCl₃) δ: 8.31 (s, 1H), 8.19 (s, 1H), 8.15 (d, J = 5.2 Hz, 1H), 7.69 (s, 1H), 6.94-6.92 (m, 1H), 5.11-5.07 (m, 1H), 4.50-4.46 (m, 2H), 3.88-3.85 (m, 2H), 3.81-3.77 (m, 2H), 3.69-3.62 (m, 4H), 2.99 (t, J = 5.2 Hz, 2H), 2.56-2.35 (m, 11H); ESI-MS (M + H)⁺: 526.3; HPLC: 214 nm: 96.66%, 254 nm: 96.61%. |
| 143 | | ¹H NMR (400 MHz, CDCl₃) δ: 12.61 (s, 1H), 8.15-8.10 (m, 3H), 7.80 (s, 1H), 6.91-6.90 (m, 2H), 5.01-4.98 (m, 1H), 4.23 (t, J = 6.4 Hz, 2H), 3.98-3.93 (m, 2H), 3.83-3.79 (m, 2H), 3.66-3.60 (m, 4H), 2.86 (t, J = 6.4 Hz, 2H), 2.59-2.35 (m, 11H); ESI-MS (M + H)⁺: 526.1; HPLC: 214 nm: 93.08%, 254 nm: 97.56%. |
| 144 | | ¹H NMR (400 MHz, CDCl₃) δ: 12.60 (s, 1H), 8.14-8.10 (m, 3H), 7.87 (s, 1H), 6.93-6.88 (m, 2H), 5.55 (br. s, 1H), 4.24 (t, J = 6.4 Hz, 2H), 3.98-3.94 (m, 2H), 3.81 (t, J = 4.8 Hz, 2H), 3.68-3.60 (m, 4H), 3.43 (brs, 4H), 2.84 (t, J = 6.4 Hz, 2H), 2.45-2.41 (m, 4H), 1.45 (s, 9H); ESI-MS (M + H)⁺: 612.3; HPLC: 214 nm: 97.08%, 254 nm: 99.43% |
| 145 | | ¹H NMR (400 MHz, DMSO-d₆) δ: 12.54 (s, 1H), 9.41 (br. s, 1H), 8.83-8.80 (m, 1H), 8.72 (s, 1H), 8.39 (s, 1H), 8.22-8.20 (m, 1H), 7.90 (s, 1H), 7.36 (d, J = 6.0 Hz, 1H), 4.62-4.58 (m, 2H), 3.81-3.77 (m, 2H), 3.66-3.59 (m, 16H); ESI-MS (M + H)⁺: 512.3; HPLC: 214 nm: 98.83%, 254 nm: 99.47%. |
| 146 | | ¹H NMR (400 MHz, CD₃OD) δ: 8.27 (d, J = 5.6 Hz, 1H), 8.19 (s, 1H), 8.14 (s, 1H), 8.12 (s, 1H), 7.25 (d, J = 5.2 Hz, 1H), 4.88 (s, 2H), 4.53-4.49 (m, 2H), 4.13-4.09 (m, 2H), 3.80-3.77 (m, 2H), 3.57-3.54 (m, 2H); ESI-MS (M + H)⁺: 459.0; HPLC: 214 nm: 100.00%, 254 nm: 100.00%. |

TABLE 1-continued

| # | Structure | |
|---|---|---|
| 147 | | $^1$H NMR (400 MHz, DMSO-d$_6$) δ: 12.54 (s, 1H), 8.70 (t, J = 5.6 Hz, 1H), 8.60 (s, 1H), 8.37 (d, J = 5.2 Hz, 1H), 8.26 (s, 1H), 7.99 (s, 1H), 7.60 (s, 1H), 7.55-7.54 (m, 1H), 7.34 (s, 1H), 4.90 (s, 2H), 4.45-4.41 (m, 2H), 4.03-3.99 (m, 2H), 3.70-3.67 (m, 2H), 3.44-3.42 (m, 2H); ESI-MS (M + H)$^+$: 458.1; HPLC: 214 nm: 96.49%, 254 nm: 96.53%. |
| 148 | | $^1$H NMR (400 MHz, CDCl$_3$ + CD$_3$OD) δ: 8.31-8.30 (m, 2H), 8.21 (s, 1H), 8.14 (s, 1H), 7.39 (d, J = 6.4 Hz, 1H), 4.59-4.54 (m, 2H), 4.32 (t, J = 6.4 Hz, 2H), 4.19-4.15 (m, 2H), 3.85 (t, J = 5.6 Hz, 2H), 3.62-3.58 (m, 4H), 2.10 (t, J = 6.4 Hz, 2H); ESI-MS (M + H)$^+$: 458.8; HPLC: 214 nm: 97.26%, 254 nm: 99.19%. |
| 149 | | $^1$H NMR (400 MHz, CDCl$_3$ + CD$_3$OD) δ: 8.34 (d, J = 4.8 Hz, 1H), 8.29 (s, 1H), 8.26 (s, 1H), 8.15 (s, 1H), 7.41-7.39 (m, 1H), 4.62-4.58 (m, 2H), 4.47 (t, J = 6.8 Hz, 2H), 4.20-4.16 (m, 2H), 3.85 (t, J = 5.2 Hz, 2H), 3.61 (t, J = 5.2 Hz, 2H), 2.94 (t, J = 6.8 Hz, 2H); ESI-MS (M + H)$^+$: 473.0; HPLC: 214 nm: 98.42%, 254 nm: 98.60%. |
| 150 | | $^1$H NMR (400 MHz, CDCl$_3$) δ: 12.61 (s, 1H), 8.36 (d, J = 4.8 Hz, 1H), 8.19 (s, 1H), 8.14 (s, 1H), 8.12 (s, 1H), 7.25-7.24 (m, 1H), 6.92 (t, J = 5.6 Hz, 1H), 4.59-4.55 (m, 2H), 4.44 (t, J = 6.8 Hz, 2H), 4.20-4.14 (m, 4H), 3.84 (t, J = 5.6 Hz, 2H), 3.64-3.60 (m, 2H), 2.93 (t, J = 6.8 Hz, 2H), 1.26 (t, J = 6.8 Hz, 3H); ESI-MS (M + H)$^+$: 501.0; HPLC: 214 nm: 94.96%, 254 nm: 99.43%. |
| 151 | | $^1$H NMR (400 MHz, CDCl$_3$ + CD$_3$OD) δ: 8.32-8.28 (m, 2H), 8.21 (s, 1H), 8.14 (s, 1H), 7.38-7.37 (m, 1H), 4.65-4.61 (m, 2H), 4.51-4.47 (m, 2H), 4.19-4.15 (m, 2H), 3.86-3.84 (m, 2H), 3.62-3.60 (m, 2H), 2.84 (t, J = 6.4 Hz, 2H); ESI-MS (M + H)$^+$: 472.2; HPLC: 214 nm: 95.56%, 254 nm: 98.32%. |
| 152 | | $^1$H NMR (400 MHz, CDCl$_3$ + CD$_3$OD) δ: 8.31-8.30 (m, 2H), 8.21 (s, 1H), 8.14 (s, 1H), 7.39 (d, J = 6.4 Hz, 1H), 4.59-4.54 (m, 2H), 4.32 (t, J = 6.4 Hz, 2H), 4.19-4.15 (m, 2H), 3.85 (t, J = 5.6 Hz, 2H), 3.62-3.58 (m, 4H), 2.10 (t, J = 6.4 Hz, 2H); ESI-MS (M + H)$^+$: 458.8; HPLC: 214 nm: 97.26%, 254 nm: 99.19%. |

TABLE 1-continued

| # | Stucture | |
|---|---|---|
| 153 | | ¹H NMR (400 MHz, CDCl₃) δ: 12.57 (s, 1H), 8.28 (d, J = 5.2 Hz, 1H), 8.11 (s, 1H), 8.06 (s, 1H), 7.98 (s, 1H), 7.24-7.16 (m, 1H), 6.92-6.89 (m, 1H), 4.51-4.47 (m, 2H), 4.11-4.06 (m, 4H), 3.77 (t, J = 5.2 Hz, 2H), 3.57-3.53 (m, 2H), 2.83-2.80 (m, 2H), 2.22 (s, 3H), 1.90-1.85 (m, 2H), 1.80-1.75 (m, 2H), 1.66-1.63 (m, 2H), 1.35-1.18 (m, 3H); ESI-MS (M + H)⁺: 526.3; HPLC: 214 nm: 100.00%, 254 nm: 100.00%. |
| 154 | | ¹H NMR (400 MHz, CDCl₃) δ: 12.65 (s, 1H), 8.36 (d, J = 5.2 Hz, 1H), 8.20 (s, 1H), 8.14 (s, 1H), 8.07 (s, 1H), 7.27-7.25 (m, 1H), 6.90 (t, J = 6.0 Hz, 1H), 4.59-4.55 (m, 2H), 4.20-4.08 (m, 6H), 3.85 (t, J = 5.2 Hz, 2H), 3.65-3.61 (m, 2H), 2.69-2.64 (m, 2H), 1.88-1.83 (m, 2H), 1.70-1.67 (m, 2H), 1.46 (s, 9H), 1.43-1.35 (m, 1H), 1.20-1.14 (m, 2H); ESI-MS (M + H)⁺: 612.3; HPLC: 214 nm: 100.00%, 254 nm: 100.00%. |
| 155 | | ¹H NMR (400 MHz, CD₃OD) δ: 8.58 (s, 1H), 8.57 (s, 1H), 8.47 (d, J = 6.0 Hz, 1H), 8.20 (s, 1H), 7.87 (dd, J₁ = 6.0 Hz, J₂ = 1.2 Hz, 1H), 4.79 (t, J = 8.8 Hz, 2H), 4.31 (t, J = 6.8 Hz, 2H), 4.16 (t, J = 8.8 Hz, 2H), 3.81 (t, J = 5.6 Hz, 2H), 3.55 (t, J = 5.2 Hz, 2H), 3.40-3.36 (m, 2H), 2.96 (t, J = 6.8 Hz, 2H), 2.02-1.91 (m, 4H), 1.63-1.57 (m, 1H), 1.42-1.50 (m, 2H); ESI-MS (M + H)⁺: 512.3; HPLC: 214 nm: 100.00%, 254 nm: 100.00%. |
| 156 | | ¹H NMR (400 MHz, CDCl₃) δ: 9.43 (s, 1H), 8.28 (d, J = 4.4 Hz, 1H), 8.18 (s, 1H), 8.11 (s, 1H), 8.06 (s, 1H), 7.20-7.18 (m, 1H), 6.47 (br. s, 1H), 4.48-4.44 (m, 4H), 3.85-3.83 (m, 2H), 3.74-3.72 (m, 2H), 3.60-3.57 (m, 2H), 2.81-2.78 (m, 2H), 2.22 (s, 3H), 1.88-1.84 (m, 2H), 1.76-1.67 (m, 4H), 1.31-1.22 (m, 3H); ESI-MS (M + H)⁺: 526.3; HPLC: 214 nm: 100.00%, 254 nm: 100.00%. |
| 157 | | ¹H NMR (400 MHz, CDCl₃) δ: 9.48 (s, 1H), 8.35 (d, J = 5.6 Hz, 1H), 8.25 (s, 1H), 8.18 (s, 1H), 8.13 (s, 1H), 7.30-7.25 (m, 1H), 6.53 (t, J = 4.4 Hz, 1H), 4.55-4.51 (m, 4H), 4.09-4.07 (m, 2H), 3.91 (t, J = 4.4 Hz, 2H), 3.80 (t, J= 4.4 Hz, 2H), 3.67-3.64 (m, 2H), 2.67-2.64 (m, 2H), 1.84-1.79 (m, 2H), 1.73-1.70 (m, 2H), 1.48 (s, 9H), 1.29-1.18 (m, 1H), 1.17-1.11 (m, 2H); ESI-MS (M + H)⁺: 612.3; HPLC: 214 nm: 100.00%, 254 nm: 100.00%. |

| # | Structure | |
|---|---|---|
| 158 | | ¹H NMR (400 MHz, CD₃OD + CDCl₃) δ: 8.32 (br. s, 1H), 8.29 (s, 1H), 8.21 (s, 1H), 8.13 (s, 1H), 7.38-7.37 (m, 1H), 4.58-4.55 (m, 2H), 4.19-4.14 (m, 4H), 3.85 (t, J = 5.2 Hz, 2H), 3.62 (t, J = 5.2 Hz, 2H), 3.57-3.54 (m, 2H), 2.92-2.84 (m, 5H), 2.28-2.20 (m, 1H), 1.88-1.73 (m, 4H); ESI-MS (M + H)⁺: 512.3; HPLC: 214 nm: 100.00%, 254 nm: 100.00%. |
| 159 | | ¹H NMR (400 MHz, CDCl₃) δ: 12.64 (s, 1H), 8.36 (d, J = 5.2 Hz, 1H), 8.18 (s, 1H), 8.14 (s, 1H), 8.05 (s, 1H), 7.27-7.24 (m, 1H), 6.91 (t, J = 6.4 Hz, 1H), 4.58-4.54 (m, 2H), 4.20-3.99 (m, 6H), 3.86-3.83 (m, 2H), 3.65-3.61 (m, 2H), 2.71-2.64 (m, 2H), 2.10-2.02 (m, 1H), 1.61-1.56 (m, 2H), 1.45 (s, 9H), 1.25-1.19 (m, 2H); ESI-MS (M + H)⁺: 598.2; HPLC: 214 nm: 100.00%, 254 nm: 100.00%. |
| 160 | | ¹H NMR (400 MHz, CD₃OD) δ: 8.59 (s, 1H), 8.55 (s, 1H), 8.49-8.48 (m, 1H), 8.22 (s, 1H), 7.87 (d, J = 6.0 Hz, 1H), 4.78 (t, J = 8.0 Hz, 2H), 4.22-4.15 (m, 4H), 3.82 (t, J = 5.2 Hz, 2H), 3.57 (t, J = 5.2 Hz, 2H), 3.44-3.41 (m, 2H), 3.04-2.98 (m, 2H), 2.35-2.29 (m, 1H), 1.89-1.86 (m, 2H), 1.59-1.53 (m, 2H); ESI-MS (M + H)⁺: 498.1; HPLC: 214 nm: 100.00%, 254 nm: 100.00%. |
| 161 | | ¹H NMR (400 MHz, CDCl₃) δ: 12.63 (s, 1H), 8.37 (d, J = 5.2 Hz, 1H), 8.18-8.15 (m, 3H), 7.26-7.25 (m, 1H), 6.95 (t, J = 6.0 Hz, 1H), 5.54-5.53 (m, 1H), 4.84 (s, 2H), 4.57-4.53 (m, 2H), 4.20-4.16 (m, 2H), 3.86 (t, J = 5.2 Hz, 2H), 3.68-3.64 (m, 2H), 2.83-2.82 (m, 3H); ESI-MS (M + H)⁺: 472.2; HPLC: 214 nm: 100.00%, 254 nm: 100.00%. |
| 162 | | ¹H NMR (400 MHz, CDCl₃) δ: 12.66 (s, 1H), 8.36 (d, J = 4.4 Hz, 1H), 8.21 (s, 1H), 8.14 (s, 1H), 8.10 (s, 1H), 6.96-6.93 (m, 1H), 4.60-4.56 (m, 2H), 4.52-4.46 (m, 1H), 4.19-4.16 (m, 2H), 3.85 (t, J = 4.4 Hz, 2H), 3.65-3.61 (m, 2H), 1.54 (d, J = 5.6 Hz, 6H); ESI-MS (M + H)⁺: 442.9; HPLC: 214 nm: 96.85%, 254 nm: 96.11%. |

TABLE 1-continued

| # | Stucture | |
|---|---|---|
| 163 | | ¹H NMR (400 MHz, CD₃OD + CDCl₃) δ: 8.32 (br. s, 1H), 8.29 (s, 1H), 8.21 (s, 1H), 8.13 (s, 1H), 7.38-7.37 (m, 1H), 4.58-4.55 (m, 2H), 4.19-4.14 (m, 4H), 3.85 (t, J = 5.2 Hz, 2H), 3.62 (t, J = 5.2 Hz, 2H), 3.57-3.54 (m, 2H), 2.92-2.84 (m, 5H), 2.28-2.20 (m, 1H), 1.88-1.73 (m, 4H); ESI-MS (M + H)⁺: 512.3; HPLC: 214 nm: 100.00%, 254 nm: 100.00%. |
| 164 | | ¹H NMR (400 MHz, CD₃OD) δ: 8.30 (s, 1H), 8.25 (d, J = 5.6 Hz, 1H), 8.14-8.13 (m, 2H), 7.41 (d, J = 4.8 Hz, 1H), 4.51-4.49 (m, 2H), 4.44-4.40 (m, 1H), 4.23-4.20 (m, 2H), 4.09-4.05 (m, 2H), 3.77 (t, J = 5.2 Hz, 2H), 3.51 (t, J = 5.2 Hz, 2H), 2.99-2.95 (m, 2H), 2.13-2.10 (m, 2H), 2.03-1.97 (m, 2H), 1.49 (s, 9H); ESI-MS (M + H)⁺: 584.2; HPLC: 214 nm: 98.77%, 254 nm: 100.00%. |
| 165 | | ¹H NMR (400 MHz, DMSO-d₆) δ: 12.48 (s, 1H), 9.26-9.02 (m, 2H), 8.65-8.62 (m, 1H), 8.58 (s, 1H), 8.36 (d, J = 4.8 Hz, 1H), 8.23 (s, 1H), 7.98 (s, 1H), 7.55-7.54 (m, 1H), 4.66-4.60 (m, 1H), 4.43 (t, J = 8.0 Hz, 2H), 4.02-3.97 (m, 2H), 3.68-3.67 (m, 2H), 3.44-3.39 (m, 4H), 3.10-3.03 (m, 2H), 2.23-2.17 (m, 4H); ESI-MS (M + H)⁺: 484.2; HPLC: 214 nm: 100.00%, 254 nm: 100.00%. |
| 166 | | ¹H NMR (400 MHz, CDCl₃) δ: 12.63 (s, 1H), 8.35 (d, J = 5.2 Hz, 1H), 8.18-8.14 (m, 3H), 7.27-7.24 (m, 1H), 6.92 (t, J = 6.0 Hz, 1H), 4.99 (s, 2H), 4.58-4.54 (m, 2H), 4.18-4.14 (m, 2H), 3.83-3.80 (m, 2H), 3.62-3.58 (m, 2H), 3.08 (s, 3H), 3.02 (s, 3H); ESI-MS (M + H)⁺: 486.2; HPLC: 214 nm: 100.00%, 254 nm: 100.00%. |

Scheme 169

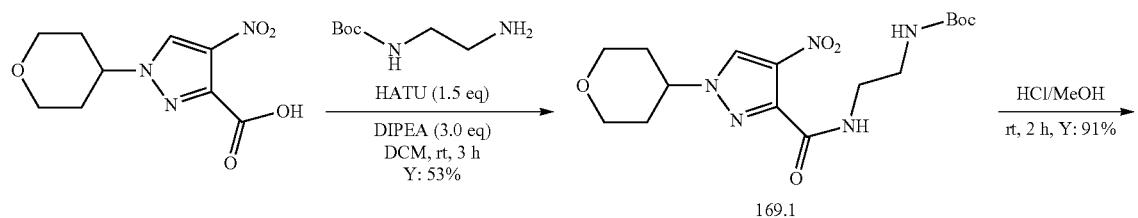

-continued
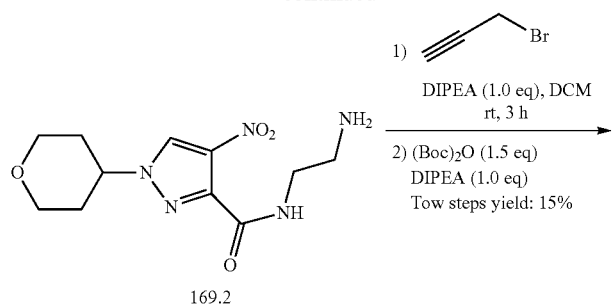
169.2
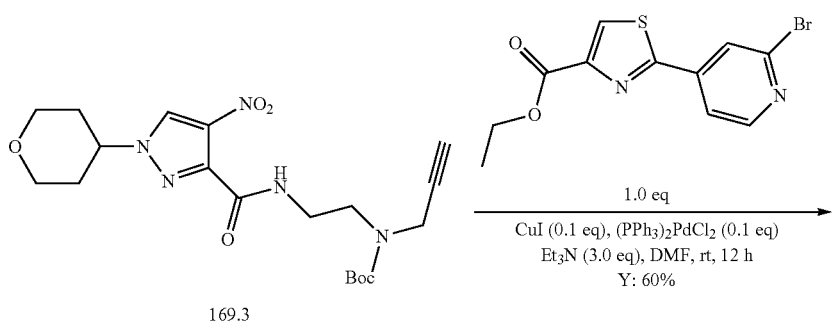
169.3
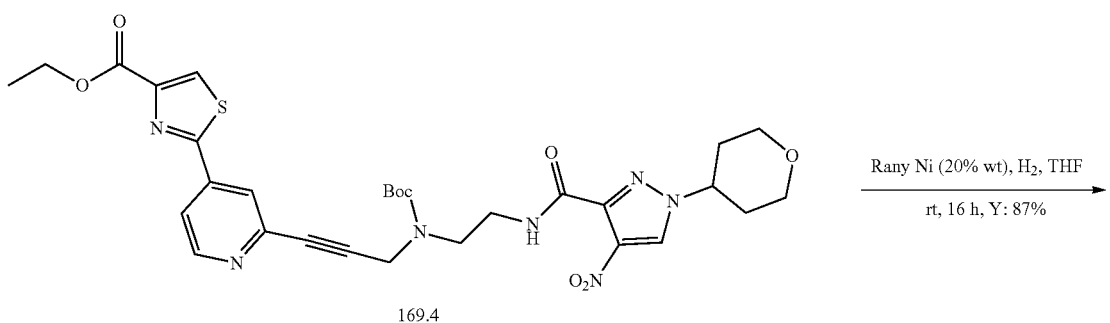
169.4
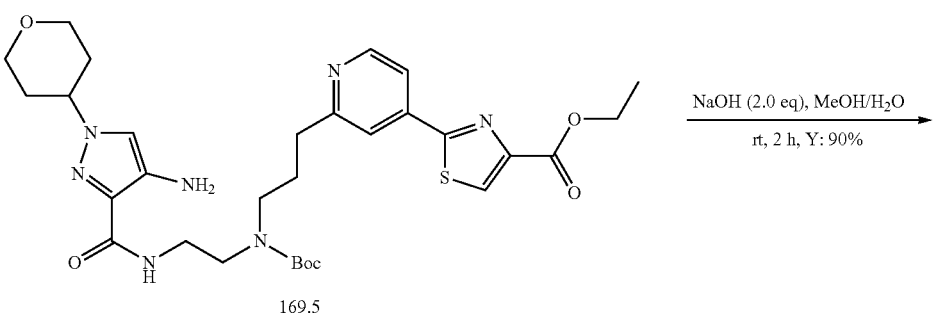
169.5
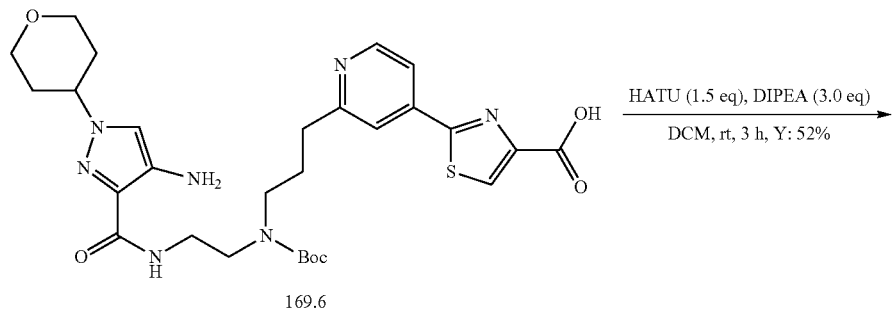
169.6

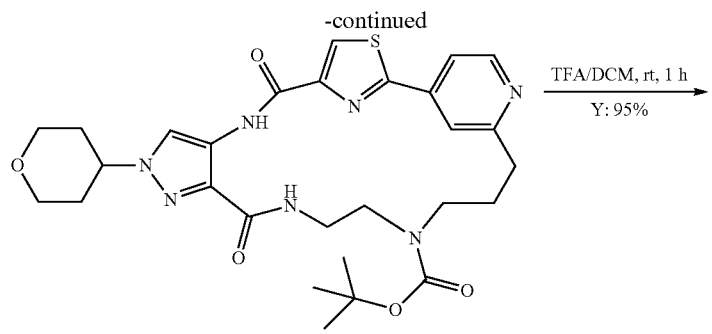

167

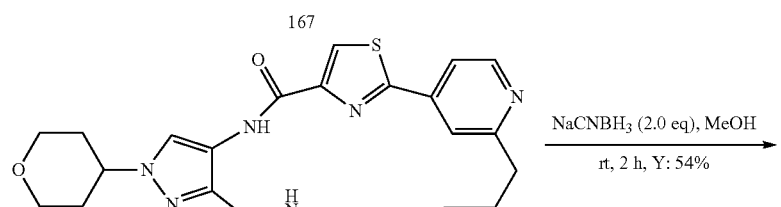

168

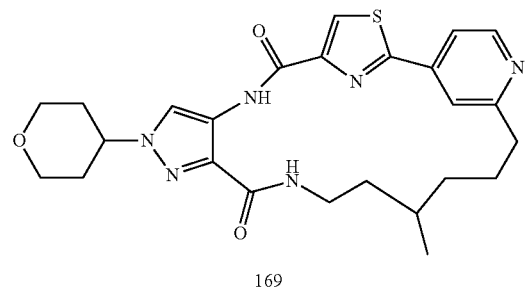

169

Synthesis Compound 169.1

To a solution of 4-nitro-1-(tetrahydro-2H-pyran-4-yl)-1H-pyrazole-3-carboxylic acid (5.0 g, 20.7 mmol, 1.0 eq) in $CH_2Cl_2$ (50 mL), DIPEA (8.0 g, 26.2 mmol, 3.0 eq), HATU (11.8 g, 31.1 mmol, 1.5 eq) and N-Boc-ethylenediamine (3.3 g, 20.7 mmol, 1.0 eq) were added. The mixture was stirred at room temperature for 2 h and then washed with $H_2O$ (50 mL×2). The organic layer was dried over anhydrous sodium sulfate and concentrated under reduced pressure. The residue was purified by silica gel column (MeOH/DCM=1/20) to give 169.1 (4.5 g, yield: 54%) as a yellow solid; ESI-MS $(M+H)^+$: 384.3.

Synthesis of 169.2

To a solution of 169.1 (4.5 g, 11.7 mmol, 1.0 eq) in MeOH (5 mL), HCl/MeOH (15 mL, 45.0 mmol, 3.8 eq, 3 M) was added. The mixture was stirred at room temperature for 1 h. The solvent was removed in vacuo. The residue was concentrated to give 169.2 (3.4 g, yield: 91%) as yellow oil; ESI-MS $(M+H)^+$: 284.1.

Synthesis of 169.3

To a solution of 169.2 (3.0 g, 11.2 mmol, 1.0 eq) and DIPEA (1.5 g, 11.2 mmol, 1.0 eq) in DCM (100 mL), 3-bromoprop-1-yne (1.3 g, 11.2 mmol, 1.0 eq) was added dropwise. The mixture was stirred at room temperature for 3 h, then DIPEA (2.9 g, 22.4 mmol, 2.0 eq) and $(Boc)_2O$ (3.7 g, 16.8 mmol, 1.5 eq) were added. The mixture was stirred at room temperature for 4 h and then washed with $H_2O$ (100 mL×3). The organic layer was dried over anhydrous sodium sulfate and concentrated under reduced pressure. The residue was purified by prep-HPLC ($CH_3CN$ in $H_2O$-0.05% $NH_4HCO_3$ from 5% to 95%) to give 169.3 (600 mg, yield: 15% (two steps)) as a yellow oil; ESI-MS $(M+H)^+$: 422.2.

Synthesis of 169.4

To a mixture of 169.3 (600 mg, 1.43 mmol, 1.0 eq) and ethyl 2-(2-bromopyridin-4-yl)thiazole-4-carboxylate (449 mg, 1.43 mmol, 1.0 eq) in $Et_3N$/DMF (1/1, 20 mL), CuI (27 mg, 0.14 mmol, 0.1 eq) and $Pd(PPh_3)_2Cl_2$ (100 mg, 0.14 mmol, 0.1 eq) were added. The mixture was stirred at room temperature for 12 h under $N_2$ atmosphere, concentrated under reduced pressure and diluted with ethyl acetate (200 mL). The precipitate was filtered off by Celite and the filtrate was washed with $H_2O$ (100 mL×2), brine (100 mL). The organic layer was dried over anhydrous $Na_2SO_4$ and concentrated under reduced pressure. The residue was purified by silica gel column (PE/EA=3/1) to give 169.4 (607 mg, yield: 65%) as a yellow oil; ESI-MS $(M+H)^+$: 654.2.

Synthesis of 169.5

To a solution of 169.4 (600 mg, 0.92 mmol, 1.0 eq) in THF (50 mL), raney Ni (60 mg, 10% wt) was added. The mixture was stirred at room temperature for 16 h under $H_2$ atmosphere. The catalyst was filtered off by Celite and the filtrate was concentrated under reduced pressure to give 169.5 (450 mg, yield: 86%) as a yellow oil; ESI-MS $(M+H)^+$: 628.1.

Synthesis of 169.6

To a solution of 196.5 (450 mg, 0.72 mmol, 1.0 eq) in MeOH (20 mL) and H₂O (10 mL), NaOH (58 mg, 1.44 mmol, 2.0 eq) was added. The mixture was stirred at 60° C. for 2 h. After cooling down, the mixture was adjusted to pH=4 with HCl (1 M) and concentrated under reduced pressure. The residue was purified by prep-HPLC (CH₃CN in H₂O—0.05% NH₄HCO₃ from 5% to 95%) to give 196.6 (380 mg, yield: 88%) as a yellow solid; ESI-MS (M+H)⁺: 600.3.

Synthesis of 167

To a solution of 169.6 (380 mg, 0.63 mmol, 1.0 eq) in CH₂Cl₂ (150 mL), DIPEA (164 mg, 1.27 mmol, 2.0 eq) and HATU (359 mg, 0.95 mmol, 1.5 eq) were added. The mixture was stirred at room temperature for 2 h and then washed with H₂O (100 mL×2). The organic layer was dried over anhydrous sodium sulfate and concentrated under reduced pressure. The residue was purified by prep-HPLC (CH₃CN in H₂O—0.05% NH₄HCO₃ from 5% to 95%) to give 167 (192 mg, yield: 52%) as a yellow solid. ¹HNMR (400 MHz, CDCl₃) δ: 12.71 (s, 1H), 8.73 (s, 1H), 8.62 (d, J=4.8 Hz, 1H), 8.15 (s, 1H), 8.14 (s, 1H), 7.42 (d, J=5.2 Hz, 1H), 6.96 (s, 1H), 4.35-4.30 (m, 1H), 4.16-4.12 (m, 2H), 3.59-3.52 (m, 8H), 3.01 (d, J=6.8 Hz, 2H), 2.54-2.48 (m, 2H), 2.17-2.11 (m, 4H), 1.49 (s, 9H); ESI-MS (M+H)⁺: 582.1.

Synthesis of 168

To a solution of 167 (190 mg, 0.33 mmol, 1.0 eq) in CH₂Cl₂ (5 mL), TFA (5 mL) were added. The mixture was stirred at room temperature for 3 h, concentrated under reduced pressure and diluted with MeOH (5 mL). The precipitate was collected by filtration and washed with MeOH (5 mL) to give 168 (151 mg, yield: 95%) as a white solid. ¹HNMR (400 MHz, CDCl₃) δ: 12.44 (s, 1H), 8.62 (d, J=4.2 Hz, 1H), 8.57 (s, 1H), 8.18 (s, 1H), 8.16 (s, 1H), 7.41 (d, J=4.2 Hz, 1H), 7.01 (s, 1H), 4.31-4.28 (m, 1H), 4.15-4.12 (m, 2H), 3.62-3.52 (m, 4H), 3.09-2.99 (m, 6H), 2.26 (t, J=7.6 Hz, 2H), 2.17-2.13 (m, 4H); ESI-MS (M+H)⁺: 482.1.

Synthesis of 169

To a solution of 168 (40 mg, 0.083 mmol, 1.0 eq) in MeOH (10 mL), (HCHO)ₙ (25 mg, 0.83 mmol, 10.0 eq) and NaBH₃CN (16 mg, 0.25 mmol, 1.5 eq) were added. The mixture was stirred at room temperature for 2 h and concentrated under reduced pressure. The residue was purified by prep-HPLC (CH₃CN in H₂O—0.05% NH₄HCO₃ from 5% to 95%) to give 169 (22 mg, yield: 54%) as a white solid. ¹HNMR (400 MHz, CDCl₃) δ: 12.80 (s, 1H), 8.83 (s, 1H), 8.60 (d, J=4.2 Hz, 1H), 8.14 (s, 1H), 8.12 (s, 1H), 7.40 (d, J=4.2 Hz, 1H), 6.92 (s, 1H), 4.33-4.28 (m, 1H), 4.15-4.11 (m, 2H), 3.62-3.52 (m, 4H), 3.01 (t, J=7.6 Hz, 2H), 2.92-2.88 (m, 2H), 2.79 (t, J=7.6 Hz, 2H), 2.46 (s, 3H), 2.37-2.32 (m, 2H), 2.16-2.09 (m, 4H); ESI-MS (M+H)⁺: 496.2.

Scheme 170

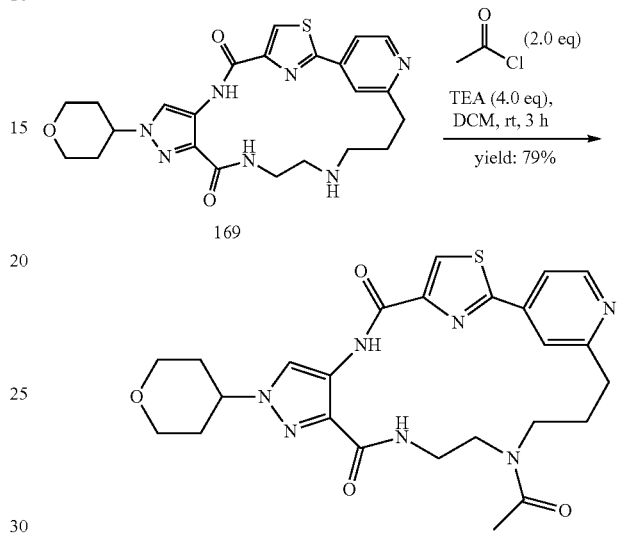

Synthesis of 170

To a solution of 169 (60 mg, 0.12 mmol, 1.0 eq) in CH₂Cl₂ (40 mL), TEA (48 mg, 0.48 mmol, 2.0 eq) and acetyl chloride (19 mg, 0.24 mmol, 2.0 eq) were added. The reaction mixture was stirred at room temperature for 3 h and quenched with MeOH (5 mL). The precipitate was collected by filtration and washed with MeOH (5 mL) to give 170 (60 mg, yield: 79%) as a yellow solid. ¹HNMR (400 MHz, CDCl₃) δ: 12.70 (s, 1H), 8.74 (s, 1H), 8.62 (d, J=5.6 Hz, 1H), 8.16 (s, 1H), 8.15 (s, 1H), 7.43 (d, J=5.2 Hz, 1H), 7.01 (s, 1H), 4.36-4.26 (m, 1H), 4.16-4.12 (m, 2H), 3.70-3.58 (m, 4H), 3.56-3.51 (m, 4H), 3.04-2.99 (m, 2H), 2.63-2.59 (m, 2H), 2.17 (s, 3H), 2.15-2.10 (m, 4H); ESI-MS (M+H)⁺: 524.1.

The following table of compounds was synthesized similar to Scheme 170 using an appropriate electrophile.

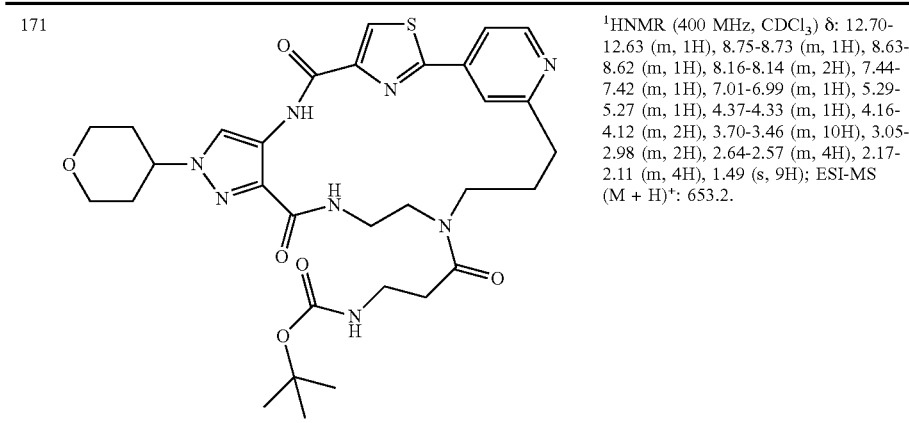

171

¹HNMR (400 MHz, CDCl₃) δ: 12.70-12.63 (m, 1H), 8.75-8.73 (m, 1H), 8.63-8.62 (m, 1H), 8.16-8.14 (m, 2H), 7.44-7.42 (m, 1H), 7.01-6.99 (m, 1H), 5.29-5.27 (m, 1H), 4.37-4.33 (m, 1H), 4.16-4.12 (m, 2H), 3.70-3.46 (m, 10H), 3.05-2.98 (m, 2H), 2.64-2.57 (m, 4H), 2.17-2.11 (m, 4H), 1.49 (s, 9H); ESI-MS (M + H)⁺: 653.2.

| | | |
|---|---|---|
| 172 | 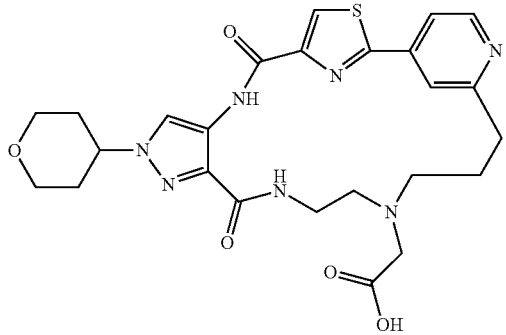 [SMILES: O=C(O)CN1CCCc2cc(ccn2)-c2nc(cs2)C(=O)Nc2cn(C3CCOCC3)nc2C(=O)NCC1] | ¹H NMR (400 MHz, CD₃OD) δ: 9.20 (s, 1H), 8.79 (d, J = 8.4 Hz, 1H), 8.57 (s, 1H), 8.28 (d, J = 8.4 Hz, 1H), 8.13 (s, 1H), 4.49-4.40 (m, 1H), 4.26 (s, 2H), 4.00-3.98 (m, 2H), 3.77-3.63 (m, 4H), 3.55-3.45 (m, 4H), 3.27-3.24 (m, 2H), 2.84-2.66 (m, 2H), 2.11-2.01 (m, 4H); ESI-MS (M + H)⁺: 540.1; HPLC: 214 nm: 99.21%, 254 nm: 99.22% |
| 173 | 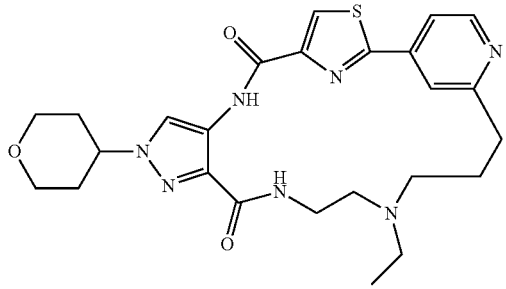 [SMILES: CCN1CCCc2cc(ccn2)-c2nc(cs2)C(=O)Nc2cn(C3CCOCC3)nc2C(=O)NCC1] | ¹HNMR (400 MHz, CDCl₃) δ: 12.78 (s, 1H), 8.84 (s, 1H), 8.60 (d, J = 4.8 Hz, 1H), 8.14-8.12 (m, 2H), 7.41 (d, J = 5.2 Hz, 1H), 7.11-7.07 (m, 1H), 4.33-4.28 (m, 1H), 4.15-4.11 (m, 2H), 3.69-3.52 (m, 4H), 3.11-2.95 (m, 4H), 2.84-2.78 (m, 2H), 2.51-2.48 (m, 2H), 2.15-2.02 (m, 6H), 1.21 (t, J = 7.2 Hz, 3H); ESI-MS (M + H)⁺: 510.1; HPLC: 214 nm: 100.00%, 254 nm: 100.00%. |
| 174 | 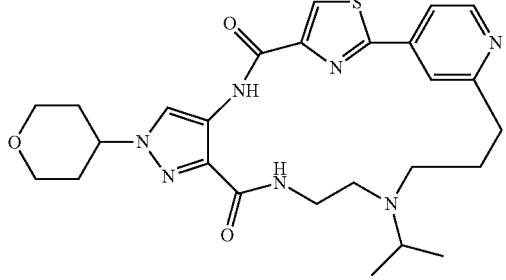 | ¹HNMR (400 MHz, CDCl₃) δ: 12.90 (s, 1H), 8.82 (s, 1H), 8.59 (d, J = 4.8 Hz, 1H), 8.12 (s, 1H), 8.11 (s, 1H), 7.40-7.38 (m, 1H), 6.94-6.90 (m, 1H), 4.35-4.27 (m, 1H), 4.15-4.11 (m, 2H), 3.58-3.45 (m, 4H), 2.98-2.90 (m, 3H), 2.88-2.83 (m, 2H), 2.74-2.70 (m, 2H), 2.47-2.39 (m, 2H), 2.19-2.10 (m, 4H), 1.06 (d, J = 6.4 Hz, 6H); ESI-MS (M + H)⁺: 524.2; HPLC: 214 nm: 96.08%, 254 nm: 98.87%. |
| 175 | 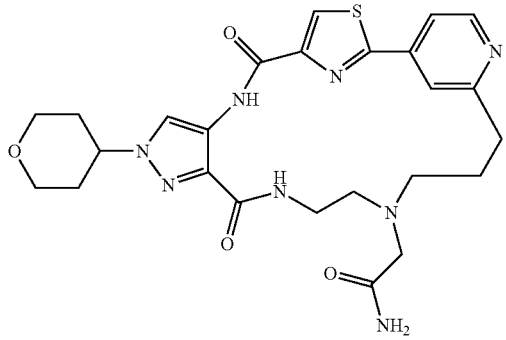 | ¹HNMR (400 MHz, CD₃OD) δ: 9.27 (s, 1H), 8.80 (d, J = 8.4 Hz, 1H), 8.58 (s, 1H), 8.31 (d, J = 7.2 Hz, 1H), 8.18 (s, 1H), 4.48-4.41 (m, 1H), 4.11 (s, 2H), 4.01-3.97 (m, 2H), 3.81-3.38 (m, 10H), 2.84-2.64 (m, 2H), 2.09-1.96 (m, 4H); ESI-MS (M + H)⁺: 539.1; HPLC: 214 nm: 100.00%, 254 nm: 98.29%. |
| 176 | 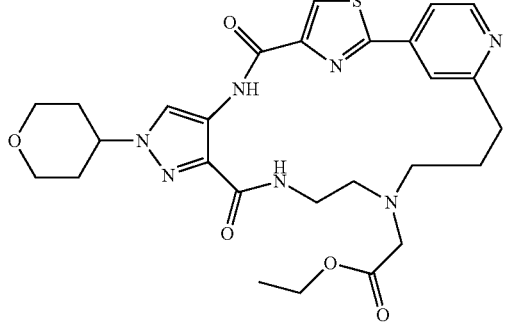 | ¹HNMR (400 MHz, CDCl₃) δ: 12.83 (s, 1H), 8.84 (s, 1H), 8.61 (d, J = 5.2 Hz, 1H), 8.14-8.13 (m, 2H), 7.42 (d, J = 4.8 Hz, 1H), 6.93-6.90 (m, 1H), 4.35-4.12 (m, 5H), 3.62-3.55 (m, 4H), 3.47 (s, 2H), 3.05-2.98 (m, 2H), 2.96-2.92 (m, 4H), 2.47-2.38 (m, 2H), 2.16-2.10 (m, 4H), 1.29 (t, J = 7.2 Hz, 3H); ESI-MS (M + H)⁺: 568.2; HPLC: 214 nm: 95.62%, 254 nm: 97.09%. |

| 177 | 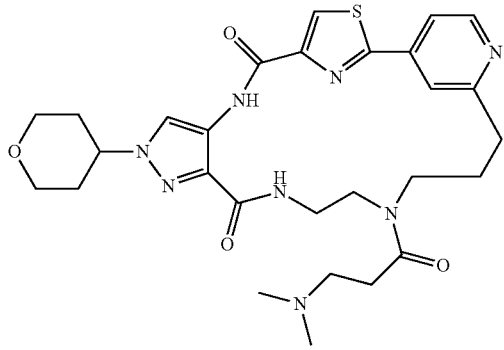 [SMILES: CN(C)CCC(=O)N1CCCc2cc(ccn2)-c2nc(cs2)C(=O)Nc2cn(C3CCOCC3)nc2C(=O)NCC1] | ¹HNMR (400 MHz, CDCl₃) δ: 12.70-12.63 (m, 1H), 8.75-8.73 (m, 1H), 8.62 (d, J = 5.2 Hz, 1H), 8.15-8.14 (m, 2H), 7.44 (d, J = 6.4 Hz, 1H), 7.00-6.97 (m, 1H), 4.39-4.30 (m, 1H), 4.16-4.12 (m, 2H), 3.75-3.52 (m, 8H), 3.02 (t, J = 8.0 Hz, 2H), 2.69-2.55 (m, 6H), 2.28 (s, 6H), 2.18-2.11 (m, 4H); ESI-MS (M + H)⁺: 581.2; HPLC: 214 nm: 100.00%, 254 nm: 100.00%. |
|---|---|---|
| 178 | 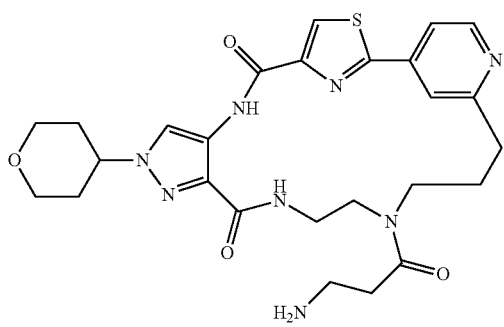 [SMILES: NCCC(=O)N1CCCc2cc(ccn2)-c2nc(cs2)C(=O)Nc2cn(C3CCOCC3)nc2C(=O)NCC1] | ¹HNMR (400 MHz, CD₃OD) δ: 9.09 (s, 1H), 8.76-8.73 (m, 1H), 8.52 (s, 1H), 8.23-8.21 (m, 1H), 8.10-8.07 (m, 1H), 4.45-4.41 (m, 1H), 4.01-3.98 (m, 2H), 3.68-3.44 (m, 8H), 3.21-3.11 (m, 4H), 2.88-2.83 (m, 2H), 2.60-2.45 (m, 2H), 2.08-2.02 (m, 4H); ESI-MS (M + H)⁺: 553.1; HPLC: 214 nm: 100.00%, 254 nm: 100.00%. |
| 179 | 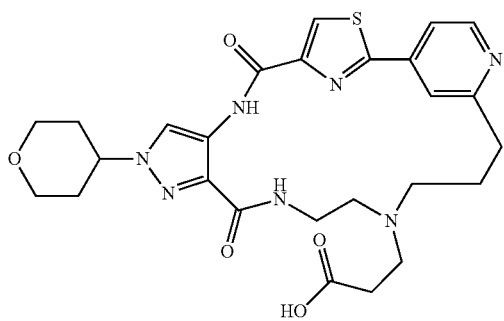 | ¹HNMR (400 MHz, CDCl₃) δ: 9.24 (s, 1H), 8.81 (d, J = 4.4 Hz, 1H), 8.61 (s, 1H), 8.28 (s, 1H), 8.21 (br.s, 1H), 4.56-4.51 (m, 1H), 4.12-4.08 (m, 2H), 3.85-3.81 (m, 2H), 3.67-3.52 (m, 8H), 3.27-3.19 (m, 2H), 2.98-2.94 (m, 2H), 2.86-2.76 (m, 2H), 2.20-2.10 (m, 4H); ESI-MS (M + H)⁺: 554.2; HPLC: 214 nm: 99.57%, 254 nm: 99.58%. |
| 180 | 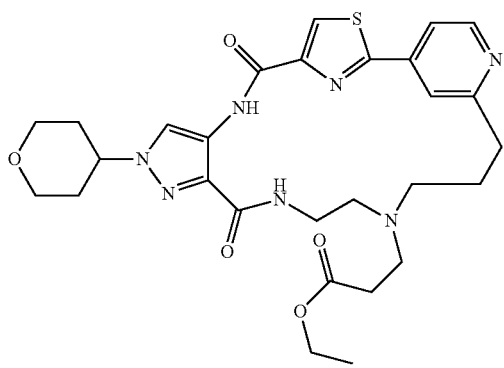 [SMILES: CCOC(=O)CCN1CCCc2cc(ccn2)-c2nc(cs2)C(=O)Nc2cn(C3CCOCC3)nc2C(=O)NCC1] | ¹HNMR (400 MHz, CDCl₃) δ: 12.66 (s, 1H), 8.74 (s, 1H), 8.62 (d, J = 5.2 Hz, 1H), 8.15 (s, 1H), 8.14 (s, 1H), 7.54-7.41 (m, 1H), 7.00-6.96 (m, 1H), 4.73-4.69 (m, 1H), 4.38-4.30 (m, 1H), 4.34-4.12 (m, 4H), 3.60-3.49 (m, 6H), 3.45-3.39 (m, 2H), 3.02-2.98 (t, J = 8.0 Hz, 2H), 2.65-2.56 (m, 2H), 2.20-2.11 (m, 4H), 1.33-1.21 (m, 5H); ESI-MS (M + H)⁺: 582.2; HPLC: 214 nm: 94.47%, 254 nm: 94.03%. |

| | | |
|---|---|---|
| 181 | 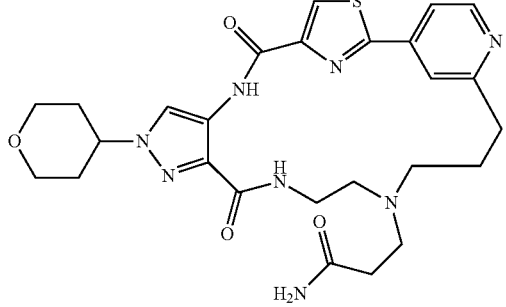 | ¹HNMR (400 MHz, CDCl₃ + CD₃OD) δ: 12.69 (s, 1H), 8.83 (s, 1H), 8.61 (d, J = 5.2 Hz, 1H), 8.15 (s, 1H), 8.14 (s, 1H), 7.43-7.41 (d, J = 5.2 Hz, 1H), 7.00-6.97 (m, 1H), 4.38-4.30 (m, 1H), 4.15-4.12 (m, 2H), 3.75-3.73 (m, 2H), 3.56-3.55 (m, 2H), 3.20-2.97 (m, 8H), 2.56-2.55 (m, 4H), 2.16-2.10 (m, 4H); ESI-MS (M + H)⁺: 553.2; HPLC: 214 nm: 96.23%, 254 nm: 97.89%. |
| 182 | 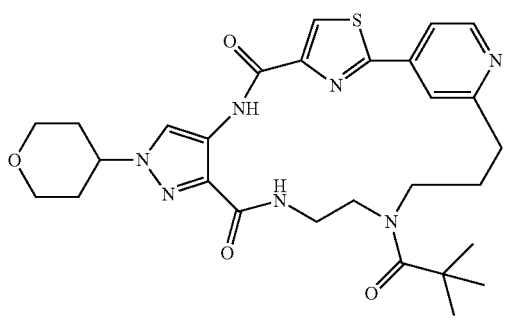 [SMILES: CC(C)(C)C(=O)N1CCCc2cc(ccn2)-c2nc(cs2)C(=O)Nc2cn(C3CCOCC3)nc2C(=O)NCC1] | ¹HNMR (400 MHz, CDCl₃) δ: 12.74 (s, 1H), 8.79 (s, 1H), 8.61 (d, J = 5.2 Hz, 1H), 8.15 (s, 1H), 8.14 (s, 1H), 7.42 (d, J = 5.6 Hz, 1H), 6.98 (br.s, 1H), 4.39-4.30 (m, 1H), 4.17-4.12 (m, 2H), 3.69-3.59 (m, 6H), 3.58-3.52 (m, 2H), 3.01-2.96 (m, 2H), 2.67-2.64 (m, 2H), 2.17-2.11 (m, 4H), 1.32 (s, 9H); ESI-MS (M + H)⁺: 566.2; HPLC: 214 nm: 98.16%, 254 nm: 98.59%. |
| 183 | 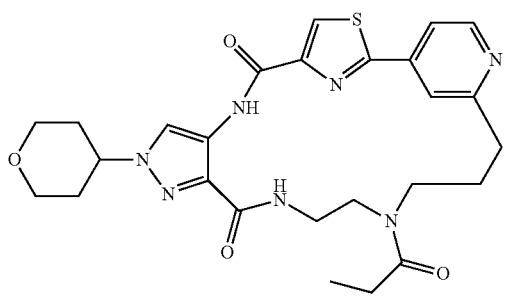 [SMILES: CCC(=O)N1CCCc2cc(ccn2)-c2nc(cs2)C(=O)Nc2cn(C3CCOCC3)nc2C(=O)NCC1] | ¹HNMR (400 MHz, CDCl₃) δ: 12.71 (s, 1H), 8.74-8.59 (m, 2H), 8.17-8.12 (m, 2H), 7.44-7.41 (m, 1H), 7.18-7.11 (m, 1H), 4.37-4.29 (m, 1H), 4.15-4.11 (m, 2H), 3.79-3.50 (m, 8H), 3.05-2.98 (m, 2H), 2.45-2.39 (m, 4H), 2.18-2.11 (m, 4H), 1.20-1.15 (m, 3H); ESI-MS (M + H)⁺: 538.3; HPLC: 214 nm: 100.00%, 254 nm: 100.00%. |
| 184 | 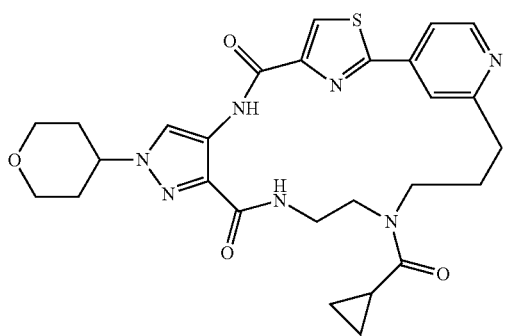 [SMILES: O=C1Nc2cn(C3CCOCC3)nc2C(=O)NCCN(C(=O)C2CC2)CCCc2cc(ccn2)-c2nc1cs2] | ¹HNMR (400 MHz, CDCl₃) δ: 12.68 (s, 1H), 8.73 (s, 1H), 8.61 (d, J = 5.2 Hz, 1H), 8.16-8.14 (m, 2H), 7.43-7.39 (m, 1H), 7.14-7.07 (m, 1H), 4.38-4.30 (m, 1H), 4.15-4.11 (m, 2H), 3.90-3.49 (m, 8H), 3.06-3.02 (m, 2H), 2.68-2.45 (m, 2H), 2.19-2.10 (m, 4H), 1.81-1.72 (m, 1H), 1.03-0.99 (m, 2H), 0.90-0.81 (m, 2H); ESI-MS (M + H)⁺: 550.2; HPLC: 214 nm: 97.28%, 254 nm: 96.95%. |
| 185 | 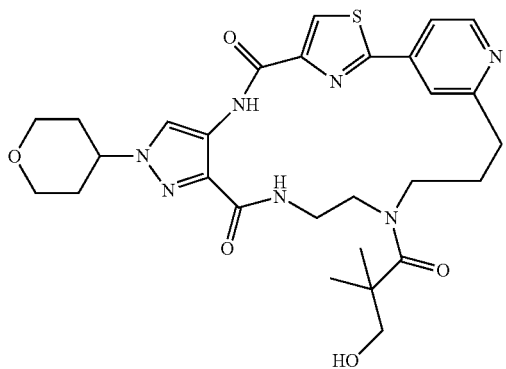 [SMILES: CC(C)(CO)C(=O)N1CCCc2cc(ccn2)-c2nc(cs2)C(=O)Nc2cn(C3CCOCC3)nc2C(=O)NCC1] | ¹HNMR (400 MHz, CDCl₃) δ: 12.71 (s, 1H), 8.78 (s, 1H), 8.61 (d, J = 5.2 Hz, 1H), 8.15 (s, 1H), 8.14 (s, 1H), 7.43 (d, J = 5.2 Hz, 1H), 7.09 (br.s, 1H), 4.38-4.32 (m, 1H), 4.15-4.12 (m, 2H), 3.77-3.50 (m, 10H), 3.02-2.97 (m, 2H), 2.67-2.54 (m, 2H), 2.19-2.10 (m, 4H), 1.33 (s, 6H); ESI-MS (M + H)⁺: 582.2; HPLC: 214 nm: 100.00%, 254 nm: 100.00%. |

| 186 | 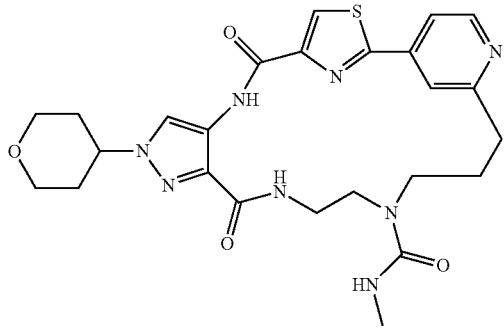 [SMILES: CNC(=O)N1CCCc2cc(ccn2)-c2nc(cs2)C(=O)Nc2cn(C3CCOCC3)nc2C(=O)NCC1] | ¹HNMR (400 MHz, CD₃OD) δ: 8.78 (d, J = 6.4 Hz, 1H), 8.63 (s, 1H), 8.55 (s, 1H), 8.51 (d, J = 6.4 Hz, 1H), 8.31 (s, 1H), 4.52-4.47 (m, 1H), 4.09-4.06 (m, 2H), 3.63-3.56 (m, 4H), 3.48-3.45 (m, 2H), 3.35-3.31 (m, 2H), 3.20-3.16 (m, 2H), 2.95 (s, 3H), 2.18-2.09 (m, 6H); ESI-MS (M + H)⁺: 539.2; HPLC: 214 nm: 99.86%, 254 nm: 99.85%. |
|---|---|---|
| 187 | 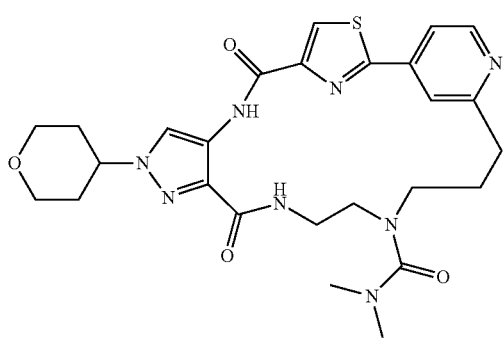 [SMILES: CN(C)C(=O)N1CCCc2cc(ccn2)-c2nc(cs2)C(=O)Nc2cn(C3CCOCC3)nc2C(=O)NCC1] | ¹HNMR (400 MHz, CDCl₃) δ: 11.61 (s, 1H), 8.68 (d, J = 5.6 Hz, 1H), 8.41 (s, 1H), 8.24 (s, 1H), 7.81-7.79 (m, 2H), 4.40-4.31 (m, 2H), 4.15-4.12 (m, 2H), 3.60-3.53 (m, 5H), 3.45-3.24 (m, 6H), 3.20 (s, 3H), 2.94 (t, J = 7.6 Hz, 2H), 2.19-2.07 (m, 6H); ESI-MS (M + H)⁺: 553.1; HPLC: 214 nm: 97.29%, 254 nm: 97.53%. |
| 188 | 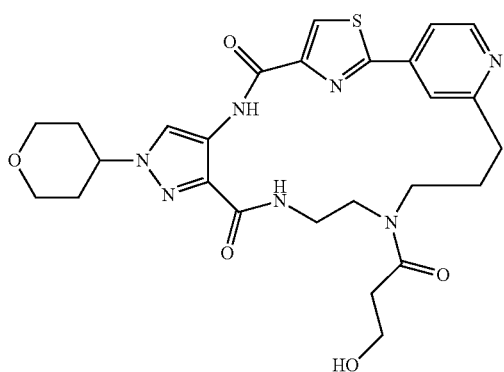 [SMILES: O=C1Nc2cn(C3CCOCC3)nc2C(=O)NCCN(C(=O)CCO)CCCc2cc(ccn2)-c2nc1cs2] | ¹HNMR (400 MHz, CDCl₃) δ: 12.69 (s, 1H), 8.73-8.71 (m, 1H), 8.62-8.60 (m, 1H), 8.17-8.14 (m, 2H), 7.43-7.39 (m, 1H), 7.16-7.07 (m, 1H), 4.39-4.31 (m, 1H), 4.15-4.12 (m, 2H), 3.95-3.90 (m, 2H), 3.80-3.50 (m, 8H), 3.06-2.98 (m, 2H), 2.65-2.45 (m, 4H), 2.19-2.04 (m, 4H); ESI-MS (M + H)⁺: 554.2; HPLC: 214 nm: 99.70%, 254 nm: 100.00%. |
| 189 | 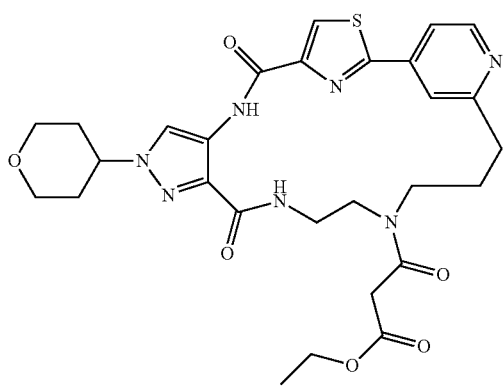 [SMILES: CCOC(=O)CC(=O)N1CCCc2cc(ccn2)-c2nc(cs2)C(=O)Nc2cn(C3CCOCC3)nc2C(=O)NCC1] | ESI-MS (M + H)⁺: 596.2. |

| | | |
|---|---|---|
| 190 | 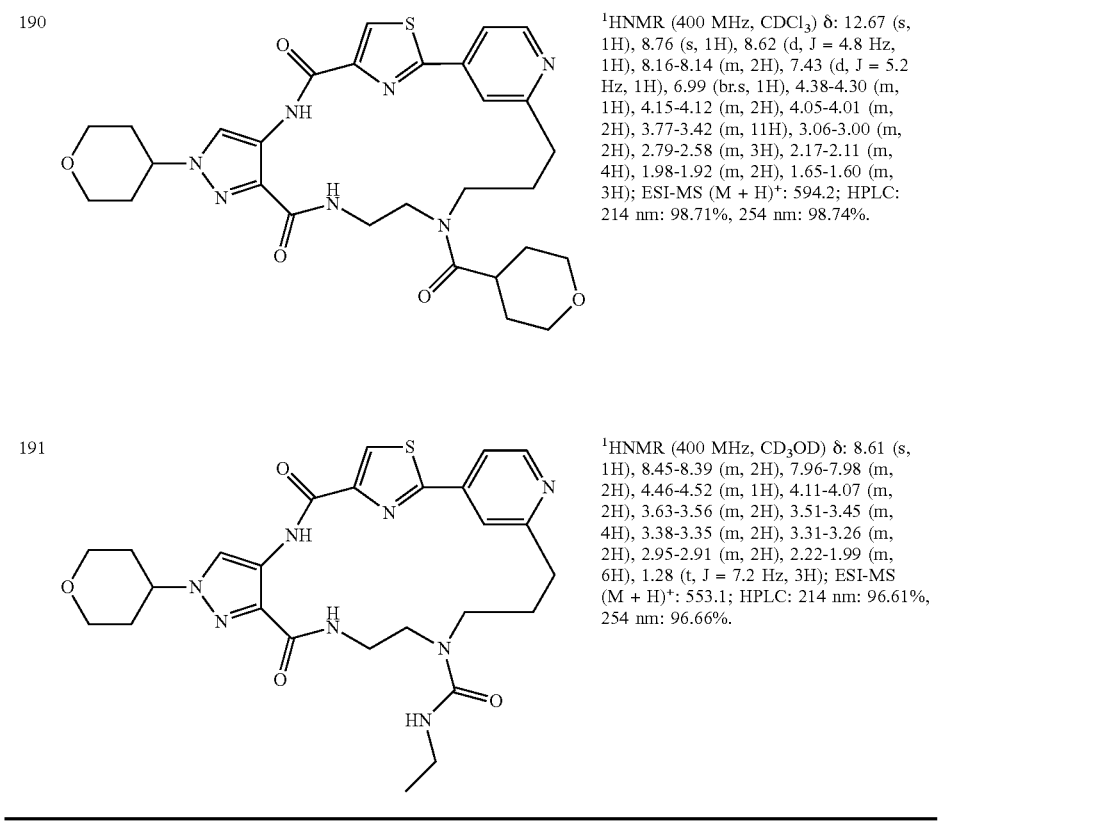 | ¹HNMR (400 MHz, CDCl₃) δ: 12.67 (s, 1H), 8.76 (s, 1H), 8.62 (d, J = 4.8 Hz, 1H), 8.16-8.14 (m, 2H), 7.43 (d, J = 5.2 Hz, 1H), 6.99 (br.s, 1H), 4.38-4.30 (m, 1H), 4.15-4.12 (m, 2H), 4.05-4.01 (m, 2H), 3.77-3.42 (m, 11H), 3.06-3.00 (m, 2H), 2.79-2.58 (m, 3H), 2.17-2.11 (m, 4H), 1.98-1.92 (m, 2H), 1.65-1.60 (m, 3H); ESI-MS (M + H)⁺: 594.2; HPLC: 214 nm: 98.71%, 254 nm: 98.74%. |
| 191 | | ¹HNMR (400 MHz, CD₃OD) δ: 8.61 (s, 1H), 8.45-8.39 (m, 2H), 7.96-7.98 (m, 2H), 4.46-4.52 (m, 1H), 4.11-4.07 (m, 2H), 3.63-3.56 (m, 2H), 3.51-3.45 (m, 4H), 3.38-3.35 (m, 2H), 3.31-3.26 (m, 2H), 2.95-2.91 (m, 2H), 2.22-1.99 (m, 6H), 1.28 (t, J = 7.2 Hz, 3H); ESI-MS (M + H)⁺: 553.1; HPLC: 214 nm: 96.61%, 254 nm: 96.66%. |
Scheme 192
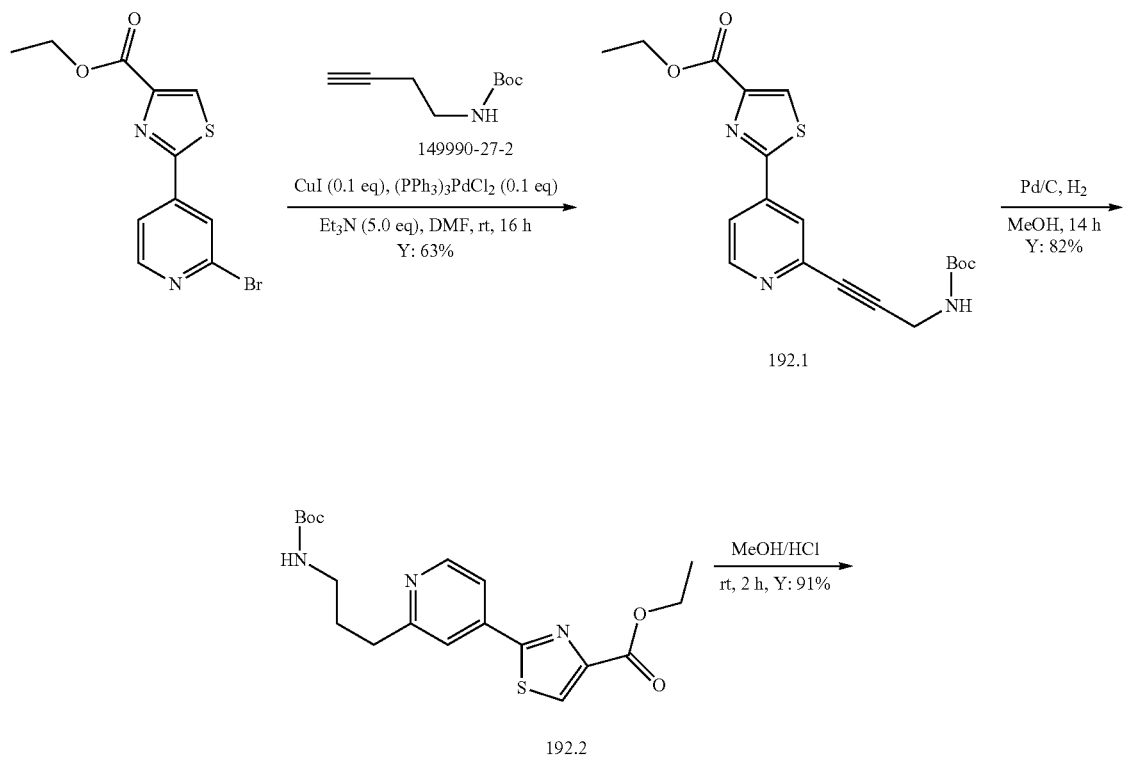

-continued
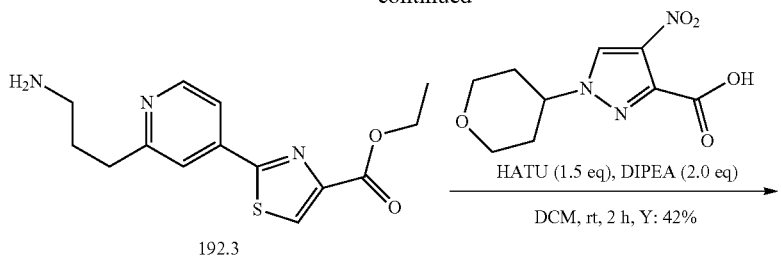
192.3
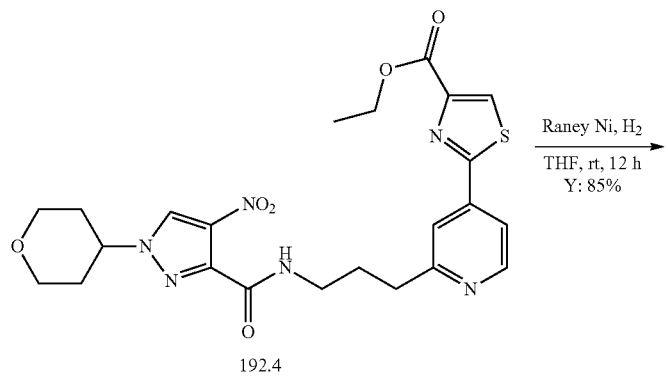
192.4
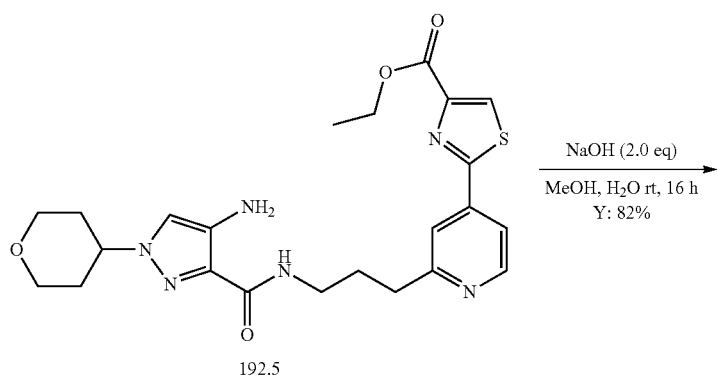
192.5
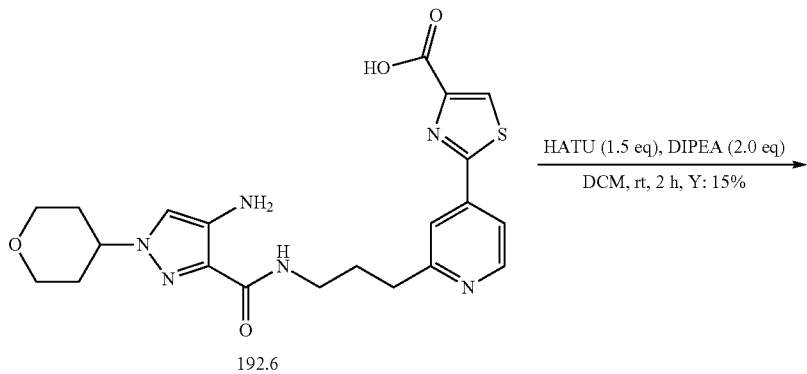
192.6
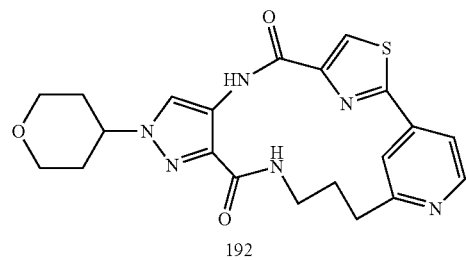
192

Synthesis of 192.1

To a solution of ethyl 2-(2-bromopyridin-4-yl)thiazole-4-carboxylate (2.0 g, 6.4 mmol, 1.0 eq) and tert-butyl but-3-ynylcarbamate (1.1 g, 6.4 mmol, 1.0 eq) in Et$_3$N/DMF (1:1, 20 mL), CuI (122 mg, 0.64 mmol, 0.1 eq) and (PPh$_3$)$_2$PdCl$_2$ (449 mg, 0.64 mmol, 0.1 eq) were added. The mixture was stirred at room temperature for 12 h under nitrogen atmosphere, concentrated under reduced pressure, diluted with ethyl acetate (200 mL), filtered by Celite. The filtrate was washed with H$_2$O (100 mL×3), brine (100 mL×2). The organic layer was dried over anhydrous Na$_2$SO$_4$ and concentrated under reduced pressure. The residue was purified by silica gel column (PE/EA=4/1) to give 192.1 (1.56 g, yield: 63%) as a yellow solid; ESI-MS (M+H)$^+$: 388.2.

Synthesis of 192.2

To a solution of 192.1 (1.5 g, 3.9 mmol, 1.0 eq) in MeOH (150 mL), Pd/C (150 mg, 10% wt) was added. The mixture was stirred at room temperature for 4 h under H$_2$ atmosphere (50 atm) and then filtered by Celite. The filtrate was concentrated under reduced pressure. The residue was purified by silica gel column (PE/EA=5/1) to give 192.2 (1.4 g, yield: 92%) as a yellow oil; ESI-MS (M+H)$^+$: 392.1.

Synthesis of 192.3

To a solution of 192.2 (1.5 g, 3.8 mmol, 1.0 eq) in MeOH (30 mL), HCl/MeOH (5.6 mL, 16.8 mmol, 4.4 eq, 3 M) was added. The mixture was stirred at room temperature for 2 h and then evaporated in vacuo to give 192.3 (1.35 g, yield: 91%) as a yellow oil; ESI-MS (M+H)$^+$: 292.2.

Synthesis of 192.4

To a solution of 192.3 (1.0 eq) and 4-nitro-1-(tetrahydro-2H-pyran-4-yl)-1H-pyrazole-3-carboxylic acid (1.0 eq) in CH$_2$Cl$_2$, DIPEA (2.0 eq) and HATU (1.5 eq) were added. The mixture was stirred at room temperature for 2 h and then washed with H$_2$O (50 mL×3). The organic layer was dried over anhydrous sodium sulfate and concentrated under reduced pressure. The residue was purified by pre-TLC (MeOH/DCM=1/10) to give afford 192.4 as a white solid 760 mg, yield: 43%; ESI-MS (M+H)$^+$: 515.1.

Synthesis of 192.5

To a solution of 192.4 (145 mg, 0.28 mmol, 1.0 eq) in THF (100 mL), raney Ni (29 mg, 20% wt) was added. The mixture was stirred at room temperature under hydrogen atmosphere for 16 h and then filtered by Celite. The filtrate was concentrated under reduced pressure to give 195.5 (16 mg, yield: 85%) as a yellow oil; ESI-MS (M+H)$^+$: 485.2.

Synthesis of 192.6

To a solution of 192.5 (115 mg, 0.24 mmol, 1.0 eq) in MeOH (20 mL) and H$_2$O (4 mL), NaOH (19 mg, 0.48 mmol, 2.0 eq) was added. The mixture was stirred at 60° C. for 2 h. After cooling down, the solution was adjusted to pH=4 with HCl (1 M) and concentrated under reduced pressure. The residue was purified by prep-HPLC (MeCN in H$_2$O—0.05% NH$_3$H$_2$O from 5%-95%) to give 192.6 (90 mg, yield: 82%) as a white solid; ESI-MS (M+H)$^+$: 457.1.

Synthesis of 192

To a solution of 192.6 (1.0 eq) in CH$_2$Cl$_2$, DIPEA (2.0 eq) and HATU (1.5 eq) were added. The mixture was stirred at room temperature for 2 h and then washed with H$_2$O (30 mL×3). The organic layer was dried over anhydrous sodium sulfate and concentrated under reduced pressure. The residue was purified by prep-HPLC (CH$_3$CN in H$_2$O—0.05% NH$_4$HCO$_3$ from 5% to 95%) to afford 192 as a white solid 13 mg, yield: 15%; $^1$HNMR (400 MHz, CD$_3$OD) δ: 8.54 (d, J=5.2 Hz, 1H), 8.46 (s, 1H), 8.13 (s, 1H), 7.72 (s, 1H), 7.39-7.36 (m, 1H), 4.31-4.23 (m, 1H), 4.08-4.05 (m, 2H), 3.72-3.68 (m, 2H), 3.55-3.47 (m, 2H), 3.12-3.09 (m, 2H), 2.31-2.27 (m, 2H), 2.04-1.98 (m, 4H); ESI-MS (M+H)$^+$: 439.2; HPLC: 214 nm: 99.75%, 254 nm: 99.75%.

Scheme 195

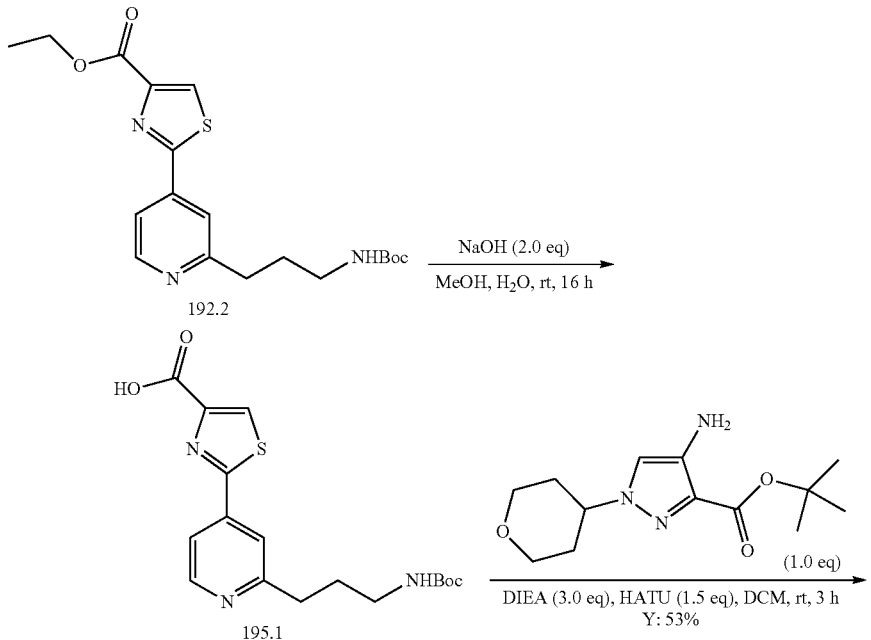

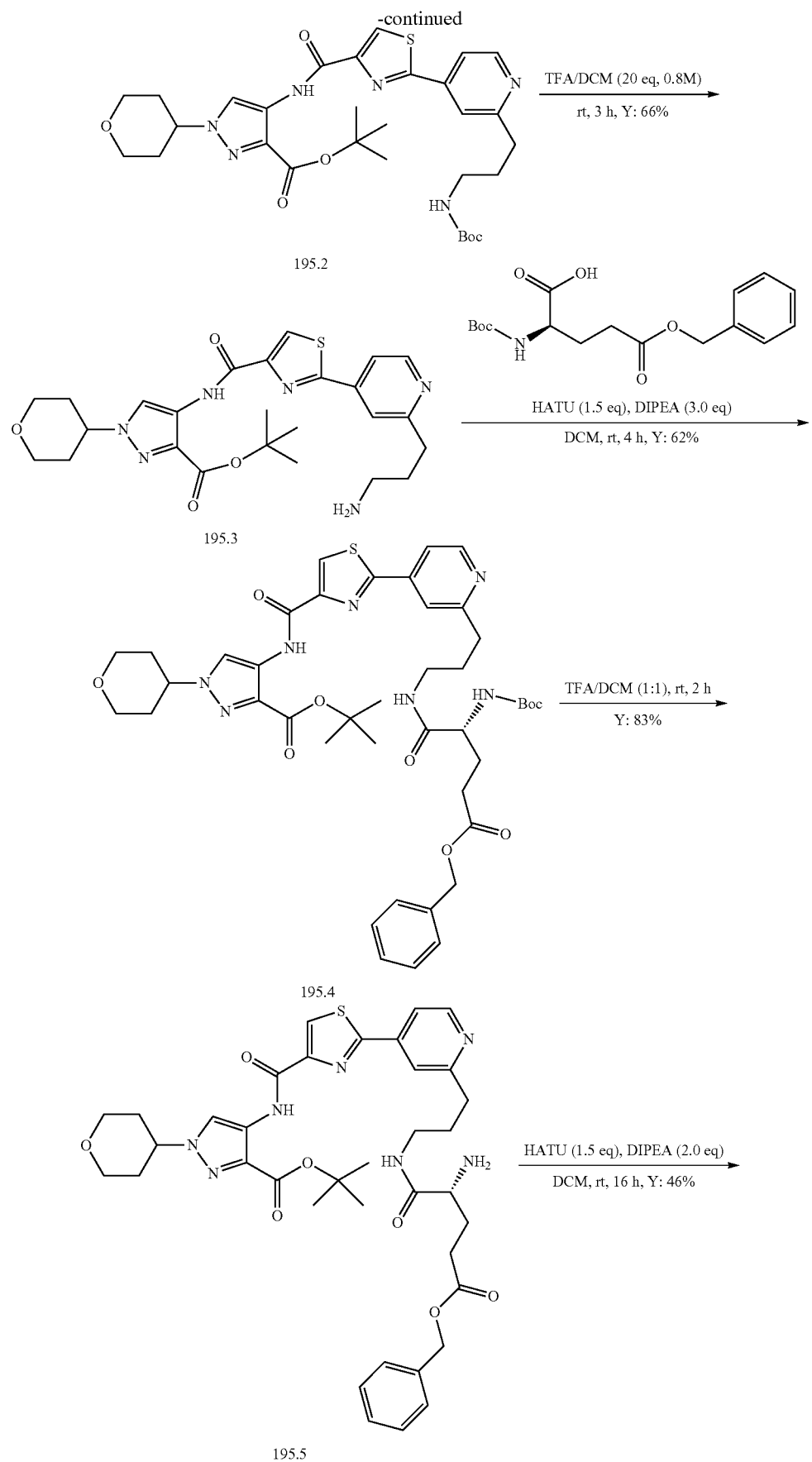

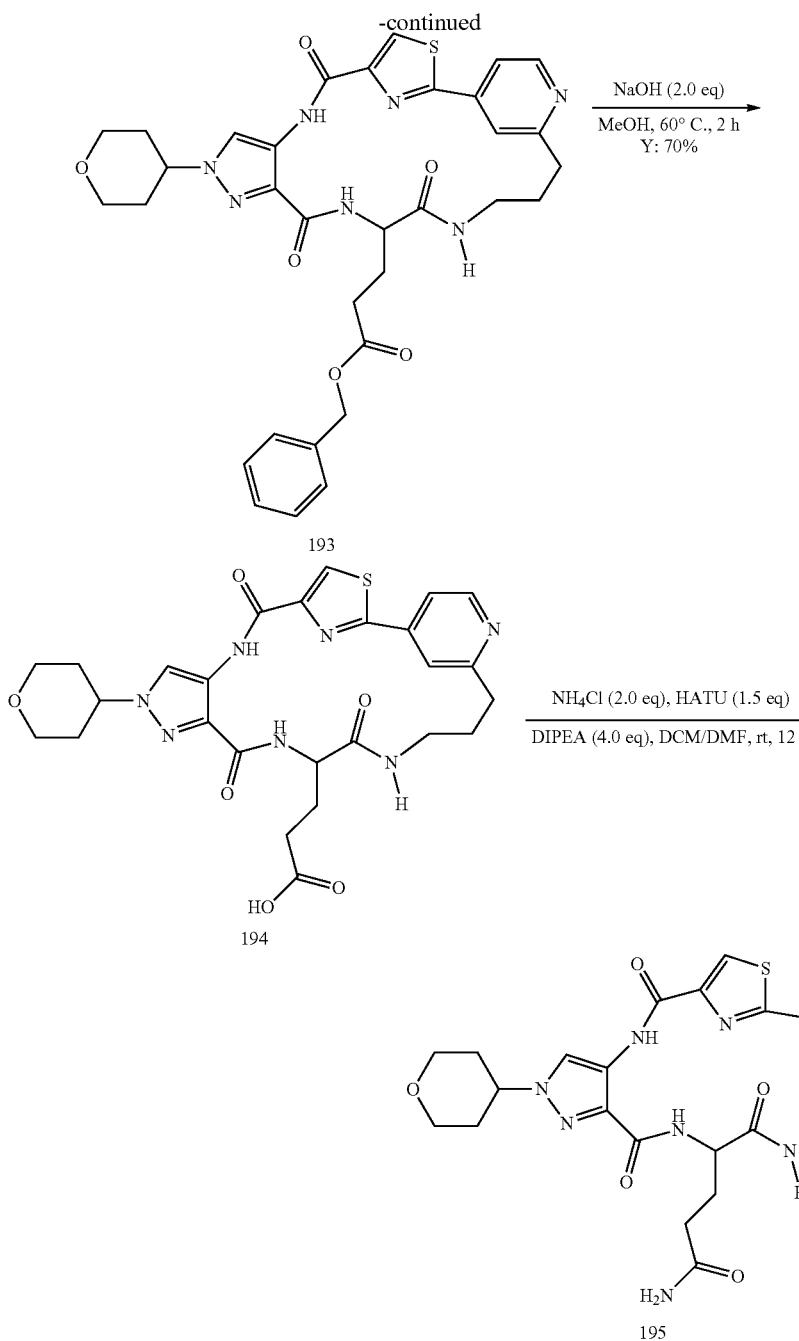

Synthesis of 195.2

The hydrolysis of 192.2 to produce 195.1 utilized a similar procedure as 192.6. The amide coupling of 195.1 to tert-butyl 4-amino-1-(tetrahydro-2H-pyran-4-yl)-1H-pyrazole-3-carboxylate utilized a similar procedure as 192.4. The residue was purified by pre-TLC (MeOH/DCM=1/20) to afford a white solid 450 mg, yield: 53%; $^1$HNMR (400 MHz, CDCl$_3$) δ: 10.78 (s, 1H), 8.68 (d, J=5.2 Hz, 1H), 8.42 (s, 1H), 8.29 (s, 1H), 7.79 (s, 1H), 7.71 (d, J=4.8 Hz, 1H), 4.79 (br. S, 1H), 4.51-4.44 (m, 1H), 4.15-4.10 (m, 2H), 3.57-3.49 (m, 2H), 3.21 (d, J=6.0 Hz, 2H), 2.97 (t, J=7.6 Hz, 2H), 2.16-2.08 (m, 4H), 2.04-1.98 (m, 2H), 1.71 (s, 9H), 1.44 (s, 9H); ESI-MS (M+H)$^+$: 613.1.

Synthesis of 195.3

To a solution of 195.2 (450 mg, 0.74 mmol, 1.0 eq) in DCM (17 mL), TFA (1 mL) was added. The mixture was stirred at room temperature for 3 h. The reaction was quenched with aqueous saturated NaHCO$_3$ solution (10 mL). The resulted solution was extracted with DCM (20 mL×3). The combined organic layers were washed with brine (20 mL×2), dried over anhydrous sodium sulfate and concentrated under reduced pressure to give 195.3 (250 mg, yield: 66%) as a yellow oil; ESI-MS (M+H)$^+$: 513.1.

Synthesis of 195.4

The amide coupling was similar to 192.4 utilizing a 195.3 and (R)-5-(benzyloxy)-2-((tert-butoxycarbonyl)amino)-5- oxopentanoic acid. The residue was purified by pre-TLC (MeOH/DCM=1/10) to afford 195.4 as a white solid (402 mg, yield: 62%); ESI-MS (M+H)+: 832.2.

Synthesis of 195.5

The deprotection of the BOC and tBu was similar to the procedure for 195.3 to afford 195.5 as a yellow oil (270 mg, yield: 83%); ESI-MS (M+H)+: 776.2.

Synthesis of 193

Compound 195.5 was cyclized utilizing the procedure for 192. The residue was purified by prep-HPLC (CH$_3$CN in H$_2$O—0.05% NH$_4$HCO$_3$ from 5% to 95%) to afford 193 as a white solid 120 mg, yield: 46%; $^1$HNMR (400 MHz, CDCl$_3$) δ: 11.98 (s, 1H), 8.60 (d, J=5.2 Hz, 1H), 8.46 (s, 1H), 8.18 (s, 1H), 8.14 (s, 1H), 7.38-7.33 (m, 6H), 7.12 (d, J=5.2 Hz, 1H), 6.93 (t, J=6.0 Hz, 1H), 5.22-5.19 (m, 2H), 4.36-4.25 (m, 2H), 4.13-4.10 (m, 2H), 3.66-3.58 (m, 1H), 3.57-3.50 (m, 2H), 3.09-3.00 (m, 2H), 2.92-2.86 (m, 1H), 2.72-2.55 (m, 2H), 2.35-2.12 (m, 2H), 2.17-2.08 (m, 5H), 2.01-1.90 (m, 1H); ESI-MS (M+H)+: 613.1; HPLC: 214 nm: 100.00%, 254 nm: 100.00%.

Synthesis of 194

To a solution of 193 (100 mg, 0.15 mmol, 1.0 eq) in MeOH (20 mL) and H$_2$O (4 mL), NaOH (12 mg, 0.3 mmol, 2.0 eq) was added. The mixture was stirred at 60° C. for 2 h. After cooling down, the solution was adjusted to pH=4 with HCl (1 M) and concentrated under reduced pressure. The residue was purified by prep-HPLC (MeCN in H$_2$O—0.05% NH$_3$H$_2$O from 5%-95%) to give 194 (60 mg, yield: 70%) as a white solid. $^1$HNMR (400 MHz, DMSO-d$_6$) δ: 12.13 (s, 1H), 8.64-8.62 (m, 1H), 8.59 (d, J=4.4 Hz, 1H), 8.56 (s, 1H), 8.44-8.41 (m, 1H), 8.35 (s, 1H), 8.31 (s, 1H), 7.69 (d, J=4.4 Hz, 1H), 4.59-4.51 (m, 1H), 4.18-4.14 (m, 1H), 4.02-3.98 (m, 2H), 3.85-3.45 (m, 3H), 3.16-3.08 (m, 1H), 2.74-2.67 (m, 2H), 2.47-2.32 (m, 2H), 2.14-1.89 (m, 7H), 1.75-1.67 (m, 1H); ESI-MS (M+H)+: 568.3.

Synthesis of 195

To a solution of 194 (25 mg, 0.044 mmol, 1.0 eq) in CH$_2$Cl$_2$ (30 mL), DIPEA (110 mg, 0.88 mmol, 20.0 eq), HATU (25 mg, 0.066 mmol, 1.5 eq) and NH$_4$Cl (24 mg, 0.44 mmol, 10.0 eq) were added. The mixture was stirred at room temperature for 2 h and then washed with H$_2$O (20 mL×2). The organic layer was dried over anhydrous sodium sulfate and concentrated under reduced pressure. The residue was purified by prep-HPLC (MeCN in H$_2$O—0.05% NH$_3$H$_2$O from 5%-95%) to give 195 (10 mg, yield: 40%) as a white solid. $^1$HNMR (400 MHz, CD$_3$OD) δ: 8.58 (s, 1H), 8.54 (d, J=5.2 Hz, 1H), 8.26 (s, 1H), 8.23 (s, 1H), 7.51 (d, J=5.2 Hz, 1H), 4.48-4.40 (m, 1H), 4.30 (t, J=5.2 Hz, 1H), 4.17-4.13 (m, 2H), 3.93-3.74 (m, 1H), 3.64-3.58 (m, 2H), 3.25-3.17 (m, 1H), 2.94-2.80 (m, 2H), 2.53-2.42 (m, 2H), 2.24-1.99 (m, 8H); ESI-MS (M+H)+: 567.3; HPLC: 214 nm: 100.00%, 254 nm: 100.00%.

The following compounds were synthesized similar to scheme 195 utilizing the appropriate amino acid.

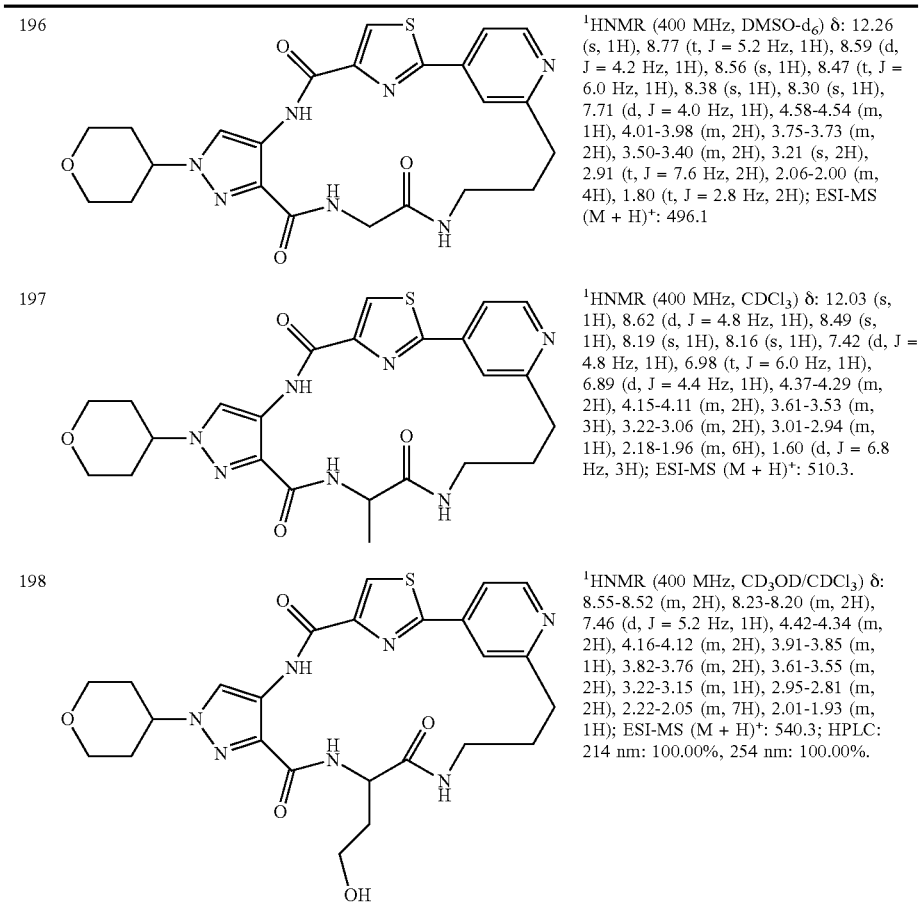

| | | |
|---|---|---|
| 196 | | $^1$HNMR (400 MHz, DMSO-d$_6$) δ: 12.26 (s, 1H), 8.77 (t, J = 5.2 Hz, 1H), 8.59 (d, J = 4.2 Hz, 1H), 8.56 (s, 1H), 8.47 (t, J = 6.0 Hz, 1H), 8.38 (s, 1H), 8.30 (s, 1H), 7.71 (d, J = 4.0 Hz, 1H), 4.58-4.54 (m, 1H), 4.01-3.98 (m, 2H), 3.75-3.73 (m, 2H), 3.50-3.40 (m, 2H), 3.21 (s, 2H), 2.91 (t, J = 7.6 Hz, 2H), 2.06-2.00 (m, 4H), 1.80 (t, J = 2.8 Hz, 2H); ESI-MS (M + H)+: 496.1 |
| 197 | | $^1$HNMR (400 MHz, CDCl$_3$) δ: 12.03 (s, 1H), 8.62 (d, J = 4.8 Hz, 1H), 8.49 (s, 1H), 8.19 (s, 1H), 8.16 (s, 1H), 7.42 (d, J = 4.8 Hz, 1H), 6.98 (t, J = 6.0 Hz, 1H), 6.89 (d, J = 4.4 Hz, 1H), 4.37-4.29 (m, 2H), 4.15-4.11 (m, 2H), 3.61-3.53 (m, 3H), 3.22-3.06 (m, 2H), 3.01-2.94 (m, 1H), 2.18-1.96 (m, 6H), 1.60 (d, J = 6.8 Hz, 3H); ESI-MS (M + H)+: 510.3. |
| 198 | | $^1$HNMR (400 MHz, CD$_3$OD/CDCl$_3$) δ: 8.55-8.52 (m, 2H), 8.23-8.20 (m, 2H), 7.46 (d, J = 5.2 Hz, 1H), 4.42-4.34 (m, 2H), 4.16-4.12 (m, 2H), 3.91-3.85 (m, 1H), 3.82-3.76 (m, 2H), 3.61-3.55 (m, 2H), 3.22-3.15 (m, 1H), 2.95-2.81 (m, 2H), 2.22-2.05 (m, 7H), 2.01-1.93 (m, 1H); ESI-MS (M + H)+: 540.3; HPLC: 214 nm: 100.00%, 254 nm: 100.00%. |

| | | |
|---|---|---|
| 199 | 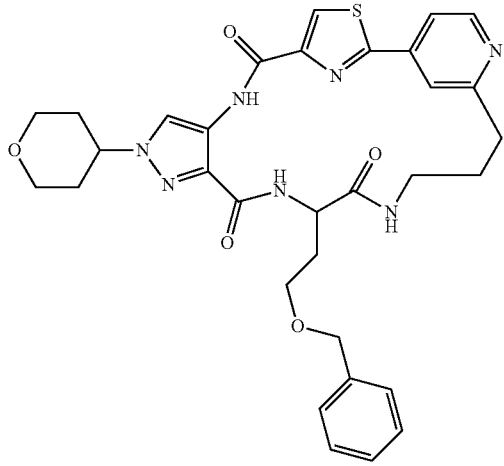 [SMILES: O=C1Nc2cn(C3CCOCC3)nc2C(=O)NC(CCOCc2ccccc2)C(=O)NCCCc2cc(ccn2)-c2nc1cs2] | ¹HNMR (400 MHz, DMSO-d₆) δ: 12.14 (s, 1H), 8.59 (d, J = 5.2 Hz, 1H), 8.57 (s, 1H), 8.46 (t, J = 4.4 Hz, 1H), 8.38 (d, J = 4.4 Hz, 1H), 8.36 (s, 1H), 8.31 (s, 1H), 7.70 (d, J = 5.2 Hz, 1H), 7.39-7.26 (m, 5H), 4.59-4.44 (m, 3H), 4.33-4.29 (m, 1H), 3.99-3.96 (m, 2H), 3.71-3.55 (m, 3H), 3.48-3.41 (m, 2H), 3.17-3.10 (m, 1H), 2.73-2.66 (m, 3H), 2.14-1.89 (m, 7H); ESI-MS (M + H)⁺: 630.3; HPLC: 214 nm: 100.00%, 254 nm: 100.00%. |
| 200 | 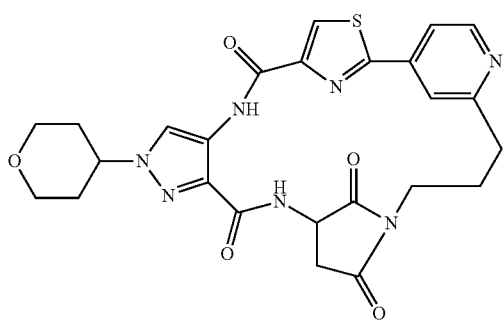 [SMILES: O=C1Nc2cn(C3CCOCC3)nc2C(=O)NC2CC(=O)N(CCCc3cc(ccn3)-c3nc1cs3)C2=O] | ¹HNMR (400 MHz, CDCl₃) δ: 11.71 (s, 1H), 8.59 (d, J = 5.2 Hz, 1H), 8.55 (s, 1H), 8.27 (s, 1H), 8.15 (s, 1H), 7.50 (d, J = 7.2 Hz, 1H), 7.38 (d, J = 7.2 Hz, 1H), 4.36-4.25 (m, 2H), 4.15-4.11 (m, 2H), 3.90-3.85 (m, 1H), 3.79-3.72 (m, 1H), 3.58-3.54 (m, 2H), 3.15-3.12 (m, 2H), 3.07-2.93 (m, 2H), 2.40-2.37 (m, 1H), 2.17-2.11 (m, 5H); ESI-MS (M + H)⁺: 536.3; HPLC: 214 nm: 100.00%, 254 nm: 100.00%. |
| 201 | 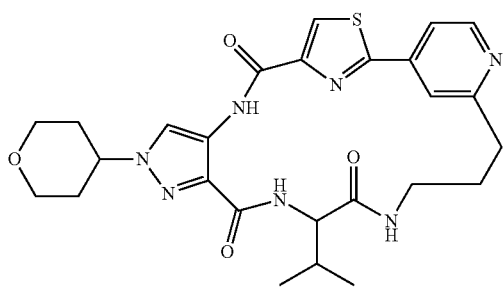 | ¹HNMR (400 MHz, DMSO-d₆) δ: 12.02 (s, 1H), 8.61-8.57 (m, 2H), 8.41-8.32 (m, 3H), 7.97 (d, J = 4.4 Hz, 1H), 7.71 (d, J = 5.2 Hz, 1H), 4.61-4.53 (m, 1H), 4.01-3.98 (m, 2H), 3.92-3.88 (m, 1H), 3.58-3.56 (m, 1H), 3.50-3.45 (m, 2H), 3.21-3.14 (m, 1H), 2.76-2.68 (m, 2H), 2.19-1.93 (m, 6H), 1.70-1.67 (m, 1H), 1.07 (d, J = 6.8 Hz, 3H), 0.99 (d, J = 6.8 Hz, 3H); ESI-MS (M + H)⁺: 613.1; HPLC: 214 nm: 100.00%, 254 nm: 100.00%. |
Scheme 202
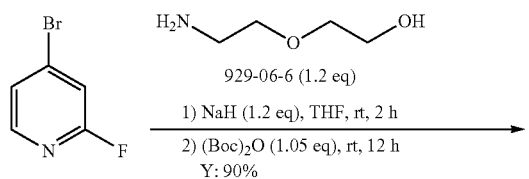

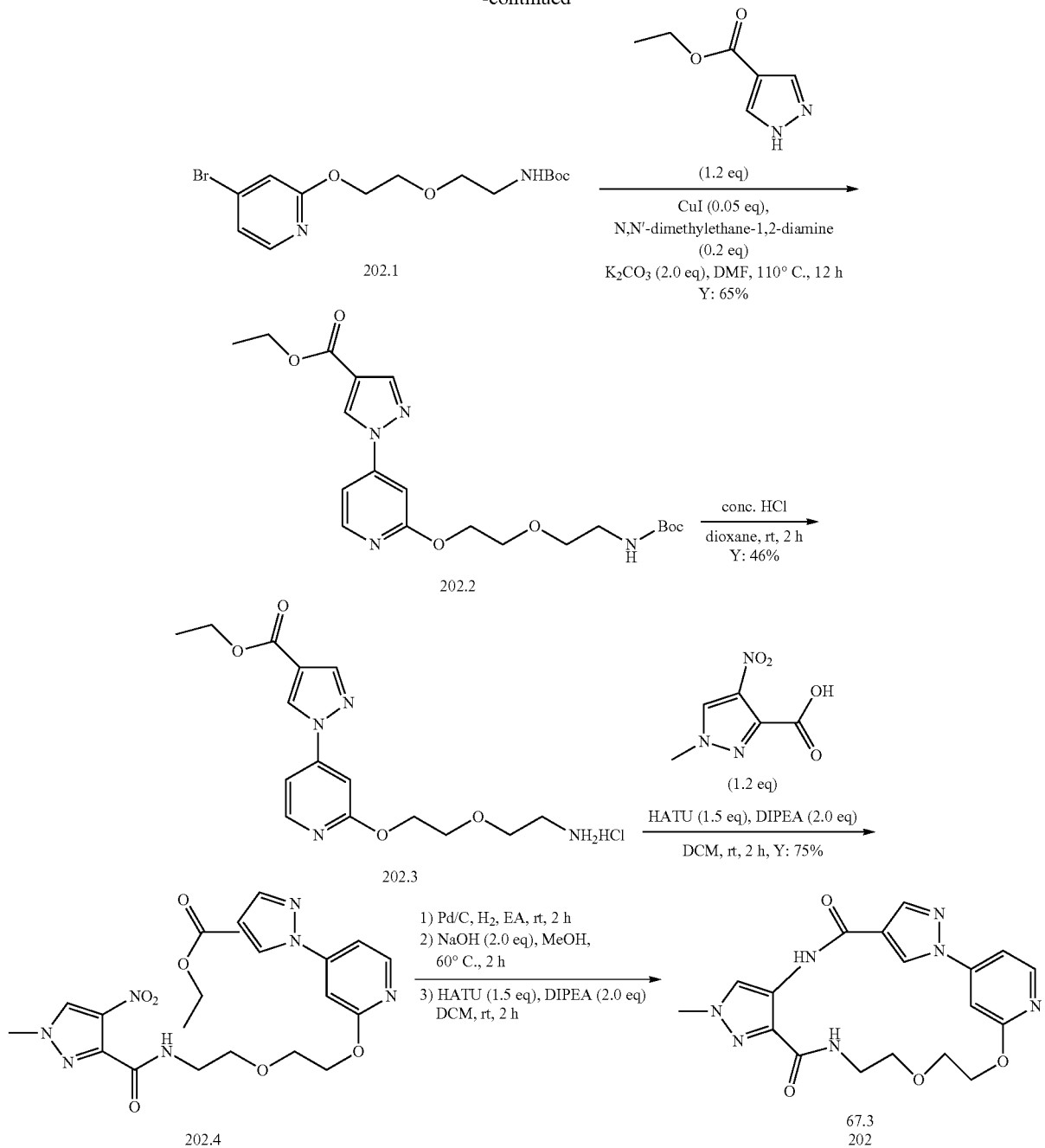

Synthesis of 202.1

To a solution of 2-(2-Aminoethoxy)ethanol (37.8 g, 0.36 mol, 1.2 eq) in THF (200 mL) was added NaH (14.4 g, 60% in mineral oil, 0.36 mol, 1.2 eq) at 0° C. portionwise. After 20 min, a solution of 4-Bromo-2-fluoropyridine (52.5 g, 0.3 mol, 1.0 eq) in THF (100 mL) was added. The mixture was stirred at rt for 2 h. Then Boc$_2$O (67.3 g, 0.31 mol, 1.05 eq) was added. The mixture was stirred at rt for 12 h and diluted with water (300 mL). The mixture was extracted with EtOAc (200 m×3), and the combined organics were dried and concentrated. The residue was purified by column chromatography on silica gel to give 202.1 as colorless oil (97 g, Y: 90%). ESI-MS (M+H)$^+$: 361.2. $^1$H NMR (400 MHz, CDCl$_3$) δ: 7.97 (d, J=5.6 Hz, 1H), 7.05-7.01 (m, 2H), 4.46 (t, J=4.8 Hz, 2H), 3.80 (t, J=4.8 Hz, 2H), 3.67 (t, J=4.8 Hz, 2H), 3.33 (t, J=4.8 Hz, 2H), 1.45 (s, 9H).

Synthesis of 202.2

A mixture of 202.1 (5.0 g, 14 mmol, 1.0 eq), Ethyl 4-pyrazolecarboxylate (2.4 g, 17 mmol, 1.2 eq), K$_2$CO$_3$ (3.0 g, 28 mmol, 2.0 eq), CuI (133 mg, 0.7 mmol, 0.05 eq) and N,N'-dimethylethane-1,2-diamine (205 mg, 2.8 mmol. 0.2 eq) in DMF (15 mL) was stirred at 110° C. for 12 h under N$_2$ atmosphere. The mixture was diluted with H$_2$O (50 mL) and extracted with EtOAc (50 mL×3). The combined organics were dried and concentrated. The residue was purified by column chromatography on silica gel (petroleum ether/EtOAc=4:1) to give 202.2 as yellow solid (3.8 g, Y: 65%). ESI-MS (M+H)+: 421.1.

Synthesis of 202.3

To a solution of 202.2 (3.8 g, 9.0 mmol, 1.0 eq) in dioxane (30 mL) was added conc. HCl (5 mL). The mixture was stirred for 12 h at rt and concentrated. The residue was recrystallized with DCM and EtOH to give 202.3 as yellow solid (1.3 g, Y: 46%). ESI-MS (M+H)+: 321.2. 1H NMR (400 MHz, CD$_3$OD) δ: 9.24 (s, 1H), 8.39 (d, J=6.8 Hz, 1H), 8.24 (s, 1H), 7.96-7.93 (m, 2H), 4.75-4.74 (m, 2H), 4.38 (q, J=7.6 Hz, 2H), 4.02 (t, J=4.0 Hz, 2H), 3.86 (t, J=4.8 Hz, 2H), 3.17 (t, J=4.8 Hz, 2H), 1.41 (t, J=7.2 Hz, 3H).

Synthesis of 202.4

To a solution of 202.3 (500 mg, 1.4 mmol, 1.0 eq) and 1-methyl-4-nitro-1H-pyrazole-3-carboxylic acid (291 mg, 1.7 mmol, 1.2 eq) in CH$_2$Cl$_2$ (80 mL), DIPEA (362 mg, 2.8 mmol, 2.0 eq) and HATU (798 mg, 2.1 mmol, 1.5 eq) were added. The reaction mixture was stirred at room temperature for 2 h and washed with H$_2$O (30 mL×3). The organic layer was dried over anhydrous sodium sulfate and concentrated under reduced pressure. The residue was purified by pre-TLC (MeOH/DCM=1/20) to give 202.4 (490 mg, yield: 75%) as a yellow oil; ESI-MS (M+H)+: 474.2.

Synthesis of 202

To a solution of 202.4 (490 mg, 1.04 mmol, 1.0 eq) in ethyl acetate (30 mL) was added Pd/C (50 mg, 10% wt). The mixture was stirred at room temperature under hydrogen for 2 h and filtered by Celite. The filtrate was concentrated under reduced pressure. The residue was dissolved in MeOH (50 mL) and H$_2$O (1 mL), and then NaOH (83 mg, 2.08 mmol, 2.0 eq) was added. The resulted solution was stirred at 60° C. for 2 h, adjusted to pH=4 with HCl (1 M) and evaporated under reduced pressure. The resulted residue was dissolved in CH$_2$Cl$_2$ (150 mL), then DIPEA (335 mg, 2.60 mmol, 2.5 eq) and HATU (593 mg, 1.56 mmol, 1.5 eq) were added. The resulted mixture was stirred at room temperature for 2 h and washed with water (50 mL×3). The organic layer was dried over anhydrous sodium sulfate and concentrated under reduced pressure. The residue was purified by recrystallization in MeOH (5 mL) to give 202 (23.7 mg, yield: 4.1% (three steps)) as a white solid. $^1$H NMR (400 MHz, CDCl$_3$) δ: 10.12 (s, 1H), 9.00 (s, 1H), 8.38-8.36 (m, 1H), 8.17 (s, 1H), 7.76 (s, 1H), 7.57-7.56 (m, 1H), 7.01-6.96 (m, 2H), 4.49-4.46 (m, 2H), 3.96-3.88 (m, 5H), 3.80-3.77 (m, 2H), 3.69-3.65 (m, 2H); ESI-MS (M+H)+: 398.2; HPLC: 214 nm: 98.59%, 254 nm: 96.84%.

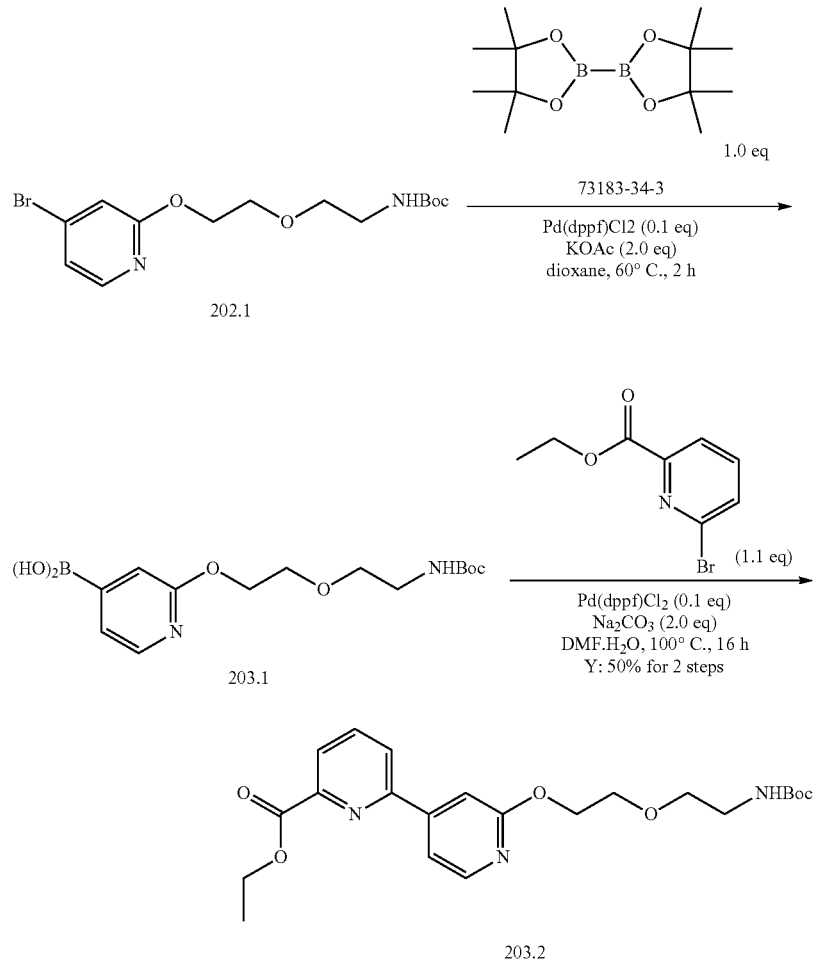

Synthesis of 203.1

A mixture of 202.1 (3.60 g, 10 mmol, 1.0 eq), Bis(pinacolato)diboron (2.54 g, 10 mmol, 1.0 eq), KOAc (1.96 g, 20 mmol, 2.0 eq) and Pd(dppf)Cl$_2$ (816 mg, 1 mmol, 0.1 eq) in dioxane (100 mL) was stirred at 60° C. for 2 h under N$_2$ atmosphere. After cooling to rt, the mixture was filtered and the filtrate was concentrated to give a dark brown oil. Compound 203.1 was used to the next step without further purification. ESI-MS (M+H)$^+$: 327.1

Synthesis of 203.2

A mixture of 203.1 (10 mmol, 1.0 eq), 6-BROMOPYRIDINE-2-CARBOXYLIC ACID ETHYL ESTER (2.53 g, 11 mmol, 1.1 eq), Na$_2$CO$_3$ (2.12 g, 20 mmol, 2.0 eq) and Pd(dppf)Cl$_2$ (816 mg, 1 mmol. 0.1 eq) in DMF/H$_2$O (10 mL, 3/1, v/v) was stirred at 100° C. for 16 h under N$_2$ atmosphere. The mixture was diluted with H$_2$O (50 mL) and extracted with EtOAc (50 mL×3). The combined organics were dried and concentrated. The residue was purified by column chromatography on silica gel (petroleum ether/EtOAc=4:1) to give 203.2 as white solid (2.1 g, Y: 50% for 2 steps). ESI-MS (M+H)$^+$: 432.1.

Synthesis 203

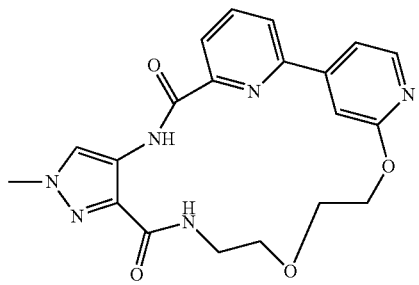

203

A similar procedure as seen in 202 utilizing 203.2 afforded 203 as white solid 208 mg, yield: 48.6%; $^1$H NMR (400 MHz, CDCl$_3$) □ □: 12.86 (s, 1H), 8.57 (s, 1H), 8.31-8.30 (d, J=5.6 Hz, 1H), 8.19-8.18 (m, 2H), 8.05-7.96 (m, 2H), 7.40-7.39 (m, 1H), 6.86 (s, 1H), 4.61-4.59 (t, J=5.2 Hz, 2H), 4.13-4.09 (t, J=7.2 Hz, 2H), 3.40-3.97 (t, J=5.6 Hz, 2H), 3.94 (s, 3H), 3.67-3.62 (t, J=6.8 Hz, 2H); ESI-MS (M+1)$^+$: 408.1; HPLC: 214 nm: 96.33%, 254 nm: 99.63%.

Compound 204 to 207 where made using a similar procedure as seen in 203.

| | | |
|---|---|---|
| 204 | 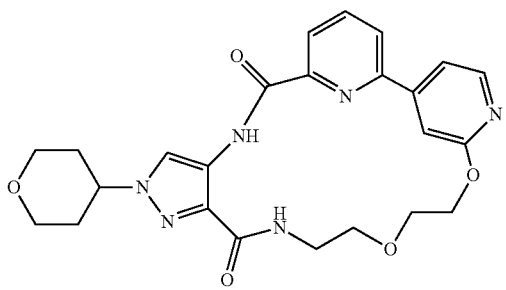 | $^1$H NMR (400 MHz, CDCl$_3$) □ □: 12.86 (s, 1H), 8.54 (s, 1H), 8.29 (d, J = 5.6 Hz, 1H), 8.26 (s, 1H), 8.17 (d, J = 7.6 Hz, 1H), 8.04-7.96 (m, 2H), 7.37 (d, J = 4.0 Hz, 1H), 6.90 (t, J = 6.8 Hz, 1H), 4.58 (t, J = 5.2 Hz, 2H), 4.37-4.29 (m, 1H), 4.15-4.10 (m, 4H), 3.98 (t, J = 5.2 Hz, 2H), 3.69-3.64 (m, 2H), 3.59-3.52 (m, 2H), 2.20-2.12 (m, 4H); ESI-MS (M + 1)$^+$: 479.2; HPLC: 214 nm: 96.98%, 254 nm: 97.82%. |
| 205 | 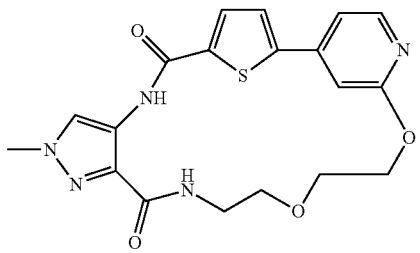 [SMILES: Cn1cc2c(n1)C(=O)NCCOCCOc1cc(ccn1)-c1ccc(s1)C(=O)N2] | $^1$H NMR (400 MHz, DCl in D$_2$O, 35%) δ: 7.82 (s, 1H), 7.33-7.32 (m, 1H), 6.90 (s, 1H), 6.80 (s, 1H), 6.67 (s, 1H), 6.62 (s, 1H), 3.89-3.87 (m, 2H), 3.23 (s, 3H), 3.06-3.04 (m, 2H), 2.89-2.84 (m, 2H), 2.70-2.68 (m, 2H); ESI-MS (M + H)$^+$: 414.1; HPLC: 214 nm: 97.23%, 254 nm: 100%. |
| 206 | 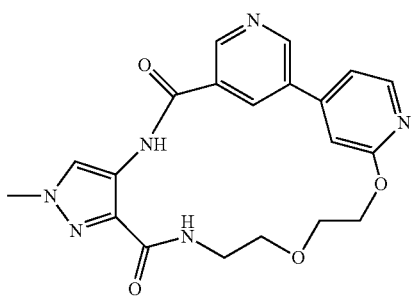 [SMILES: Cn1cc2c(n1)C(=O)NCCOCCOc1cc(ccn1)-c1cncc(c1)C(=O)N2] | $^1$H NMR (400 MHz, CDCl$_3$) □ □: 11.46 (s, 1H), 9.29 (s, 1H), 9.14 (s, 1H), 8.76 (s, 1H), 8.38 (s, 1H), 8.02 (s, 1H), 7.35-7.30 (m, 2H), 6.95 (s, 1H), 4.56-4.53 (m, 2H), 4.04-4.01 (m, 2H), 3.95 (s, 3H), 3.89-3.86 (m, 2H), 3.67-3.64 (m, 2H); ESI-MS (M + 1)$^+$: 408.1; HPLC: 214 nm: 96.78%, 254 nm: 94.35%. |

| | | |
|---|---|---|
| 207 | 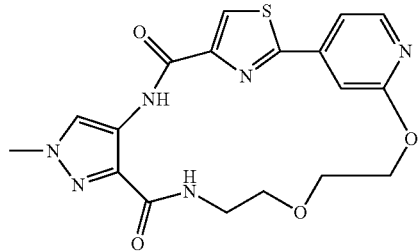 | ¹H NMR (400 MHz, CDCl₃) δ: 8.36 (s, 1H), 8.24-8.22 (m, 1H), 8.11 (s, 1H), 7.92 (s, 1H), 7.31 (s, 1H), 7.08-7.07 (m, 1H), 4.49-4.45 (m, 2H), 4.06-4.02 (m, 2H), 3.94 (s, 3H), 3.84-3.81 (m, 2H), 3.65-3.62 (m, 2H); ESI-MS (M + H)⁺: 414.1; HPLC: 214 nm: 96.56%, 254 nm: 97.08% |
| 208 | 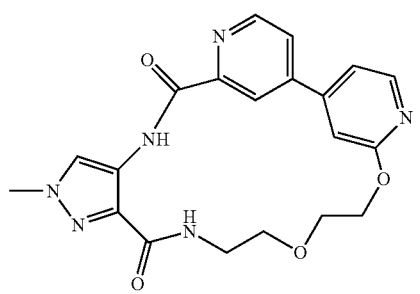 [SMILES: Cn1cc2c(n1)C(=O)NCCOCCOc1cc(ccn1)-c1ccnc(c1)C(=O)N2] | ¹H NMR (400 MHz, CDCl₃) δ: 11.08 (s, 1H), 8.38 (d, J = 5.2 Hz, 1H), 8.07 (s, 1H), 7.97 (d, J = 6.4 Hz, 1H), 7.92 (s, 1H), 7.45 (d, J = 5.2 Hz, 1H), 7.17 (d, J = 6.0 Hz, 1H), 6.95 (d, J = 4.8 Hz, 1H), 6.94 (d, J = 4.0 Hz, 1H), 4.43 (t, J = 4.0 Hz, 2H), 3.93-3.88 (m, 4H), 3.80 (s, 3H), 3.57 (t, J = 6.4 Hz, 2H); ESI-MS (M + 1)⁺: 409.1; HPLC: 214 nm: 100%, 254 nm: 100%. |
| 209 | 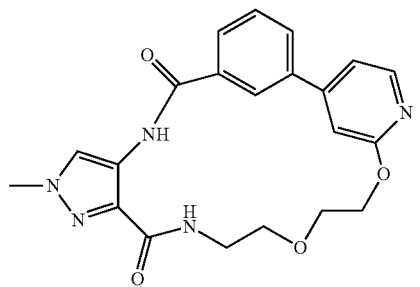 [SMILES: Cn1cc2c(n1)C(=O)NCCOCCOc1cc(ccn1)-c1cccc(c1)C(=O)N2] | ¹H NMR (400 MHz, CDCl₃) δ: 11.39 (s, 1H), 8.49 (s, 1H), 8.31 (d, J = 5.2 Hz, 1H), 8.11 (d, J = 8.0 Hz, 1H), 8.04 (s, 1H), 7.90 (d, J = 7.6 Hz, 1H), 7.65 (t, J = 7.6 Hz, 1H), 7.39 (s, 1H), 7.29 (d, J = 7.6 Hz, 1H), 6.91 (s, 1H), 4.58 (t, J = 6.4 Hz, 2H), 4.03 (t, J = 7.2 Hz, 2H), 3.94 (s, 3H), 3.91 (t, J = 6.4 Hz, 2H), 3.66 (t, J = 6.0 Hz, 2H); ESI-MS (M + 1)⁺: 408.1; HPLC: 214 nm: 100%, 254 nm: 100%. |
| 210 | 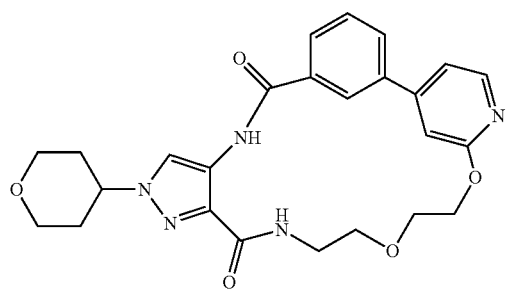 | ¹H NMR (400 MHz, CDCl₃) δ: 11.42 (s, 1H), 8.49 (s, 1H), 8.31 (d, J = 5.6 Hz, 1H), 8.12 (s, 1H), 8.09 (d, J = 8.0 Hz, 1H), 7.90 (d, J = 7.6 Hz, 1H), 7.63 (t, J = 7.6 Hz, 1H), 7.38 (s, 1H), 7.28-7.26 (m, 1H), 6.97 (t, J = 6.0 Hz 1H), 4.55 (t, J = 6.8 Hz, 2H), 4.35-4.29 (m, 1H), 4.14-4.11 (m, 2H), 4.02 (t, J = 6.4 Hz, 2H), 3.91 (t, J = 6.8 Hz, 2H), 3.68-3.63 (m, 2H), 3.58-3.52 (m, 2H), 2.20-2.08 (m, 4H); ESI-MS (M + 1)⁺: 478.2; HPLC: 214 nm: 97.79%, 254 nm: 97.59%. |
| 211 | 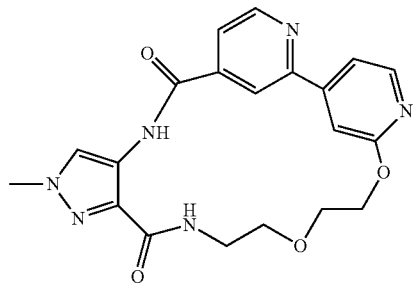 | ¹H NMR (400 MHz, CDCl₃) δ: 11.65 (s, 1H), 8.92 (s, 1H), 8.55 (s, 1H), 8.41 (s, 1H), 8.03 (s, 1H), 7.91-7.84 (m, 2H), 7.50 (s, 1H), 6.97 (s, 1H), 4.54-4.49 (m, 2H), 4.08-4.06 (m, 2H), 3.95 (s, 3H), 3.88-3.85 (m, 2H), 3.66-3.63 (m, 2H); ESI-MS (M + 1)⁺: 408.1; HPLC: 214 nm: 97.98%, 254 nm: 97.31%. |

212

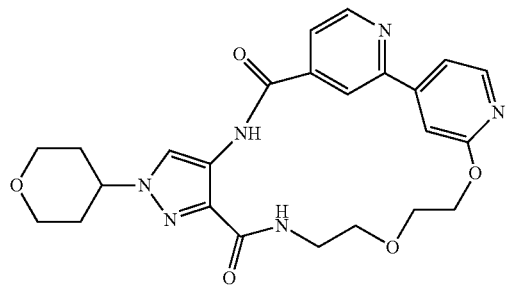

Scheme 213

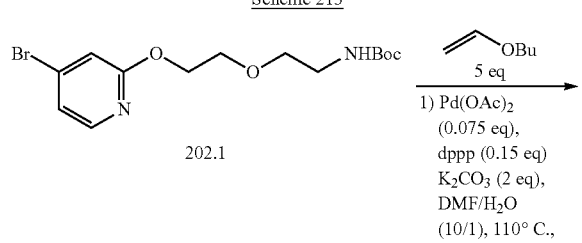

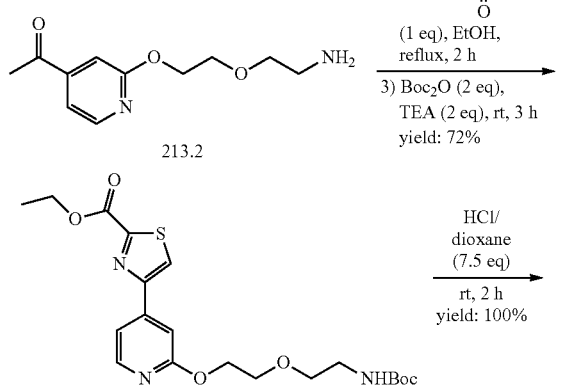

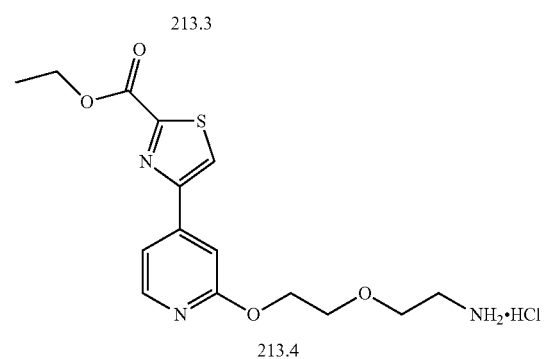

Synthesis of 213.1

To a solution of 202.1 (5.4 g, 15 mmol, 1.0 eq) and 1-(vinyloxy)butane (7.5 g, 75 mmol, 5 eq) in DMF (50 mL) and H$_2$O (5 mL), Pd(OAc)$_2$ (235 mg, 1.05 mmol, 0.07 eq), dppp (884 mg, 2.1 mmol, 0.14 eq) and K$_2$CO$_3$ (3.1 g, 22.5 mmol, 1.5 eq) were added under nitrogen. The mixture was stirred at 110° C. for 16 h under nitrogen. After cooling down to room temperature, the reaction solution was filtered by Celite. The filtrate was diluted with ethyl acetate (300 mL), washed with H$_2$O (50 mL×3) and brine (50 mL×2), dried over anhydrous Na$_2$SO$_4$ and concentrated under reduced pressure. The residue was purified by column chromatography on silica gel (PE/EA=30/1 to 5/1) to give 213.1 as a colorless oil (2.2 g, Y: 38%); ESI-MS (M+H)$^+$: 381.2.

Synthesis of 213.2

To a solution of 213.1 (2.1 g, 5.5 mmol, 1.0 eq) in THF (20 mL) was added HCl (3 mL, 6.0 mmol, 1.1 eq, 2 M). The mixture was stirred at room temperature for 3 h. The reaction was quenched with aqueous NaHCO$_3$ solution (6 mL). The resulted solution was diluted with ethyl acetate (200 mL) and washed with aqueous NaHCO$_3$ solution (30 mL), brine (30 mL). The organic layer was dried over anhydrous Na$_2$SO$_4$ and concentrated under reduced pressure. The residue was purified by column chromatography on silica gel (PE/EA=20/1 to 5/1) to give 213.2 as a colorless oil (1.2 g, Y: 67%). $^1$H NMR (400 MHz, CDCl$_3$) δ: 8.28 (d, J=5.2 Hz, 1H), 7.32 (d, J=5.2 Hz, 1H), 7.24 (s, 1H), 4.51 (t, J=4.8 Hz, 2H), 3.83 (t, J=4.8 Hz, 2H), 3.60 (t, J=5.2 Hz, 2H), 3.36-3.33 (m, 2H), 2.58 (s, 3H), 1.44 (s, 9H); ESI-MS (M+H)$^+$: 325.2.

Synthesis of 213.3

A solution of 213.2 (1.44 g, 4.4 mmol, 1.0 eq), Bu$_4$NBr$_3$ (2.37 g, 4.9 mmol, 1.1 eq) in THF (20 mL) was stirred at room temperature for 14 h. The reaction mixture was concentrated under reduced pressure. The residue was dissolved in EtOH (20 mL) and Ethyl 2-amino-2-thioxoacetate (585 mg, 4.4 mmol, 1 eq) was added. The resulting mixture was refluxed for 2 h. After cooled down to room temperature, Boc$_2$O (1.92 g, 8.8 mmol, 2 eq) and TEA (889 mg, 8.8 mmol, 2 eq) were added. The resulting mixture was stirred at room temperature for another 3 h and then concentrated under reduced pressure. The residue was purified by column chromatography on silica gel (PE/EA=10/1 to 3/1) to give 213.3 as a light yellow solid (1.4 g, Y: 72%); ESI-MS (M+H)$^+$: 438.2.

Synthesis of 213.4

A mixture of 213.3 (1.4 g, 3.2 mmol, 1.0 eq) and HCl/dioxane (6 mL, 24 mmol, 7.5 eq, 4 M) was stirred at room temperature for 2 h. The precipitate was collected by filtration and washed with ether (10 mL) to give 213.4 (1.2 g, Y: 100%) as a white solid. $^1$H NMR (400 MHz, CD$_3$OD) δ: 9.02 (s, 1H), 8.43 (d, J=6.4 Hz, 1H), 8.24 (s, 1H), 8.08 (dd, J=1.2 Hz, 6.4 Hz, 1H), 4.83-4.81 (m, 2H), 4.54 (q, J=7.6 Hz, 2H), 4.07-4.04 (m, 2H), 3.85 (t, J=5.2 Hz, 2H), 3.20 (t, J=5.2 Hz, 2H), 1.47 (t, J=7.6 Hz, 3H); ESI-MS (M+H)$^+$: 338.1.

Synthesis of 213

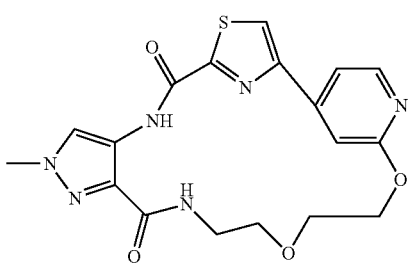 [SMILES: Cn1cc2c(n1)C(=O)NCCOCCOc1cc(ccn1)-c1csc(n1)C(=O)N2]

The synthesis of compound 213 was similar to 202 utilizing 213.4 and 1-methyl-4-nitro-1H-pyrazole-3-carboxylic acid to afford 213 as a white solid 13.8 mg; $^1$H NMR (400 MHz, CDCl$_3$) δ: 12.63 (s, 1H), 8.30 (d, J=5.6 Hz, 1H), 8.16 (s, 1H), 8.01 (s, 1H), 7.91 (s, 1H), 7.25 (s, 1H), 6.90 (d, J=6.0 Hz, 1H), 4.58-4.54 (m, 2H), 4.17-4.13 (m, 2H), 3.94 (s, 3H), 3.86-3.83 (m, 2H), 3.65-3.61 (m, 2H); ESI-MS (M+H)$^+$: 414.1; HPLC: 214 nm: 95.22%, 254 nm: 96.87%.

Synthesis of 214

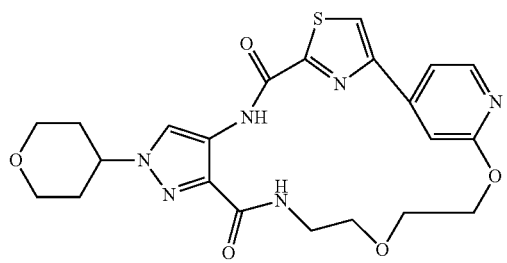 [SMILES: O=C1Nc2cn(C3CCOCC3)nc2C(=O)NCCOCCOc2cc(ccn2)-c2csc1n2]

The synthesis of compound 214 was similar to 202 utilizing 213.4 and 4-nitro-1-(tetrahydro-2H-pyran-4-yl)-1H-pyrazole-3-carboxylic acid to afford 214 as a yellow solid 26 mg, yield: 7.7%; $^1$H NMR (400 MHz, CDCl$_3$) δ: 12.64 (s, 1H), 8.30 (d, J=5.2 Hz, 1H), 8.16 (s, 1H), 8.09 (s, 1H), 7.91 (s, 1H), 7.25 (s, 1H), 6.91 (t, J=6.0 Hz, 1H), 4.57-4.53 (m, 2H), 4.36-4.30 (m, 1H), 4.18-4.12 (m, 4H), 3.87-3.84 (m, 2H), 3.67-3.63 (m, 2H), 3.59-3.52 (m, 2H), 2.16-2.08 (m, 4H); ESI-MS (M+H)$^+$: 485.2; HPLC: 214 nm: 94.30%, 254 nm: 94.39%.

Scheme 215

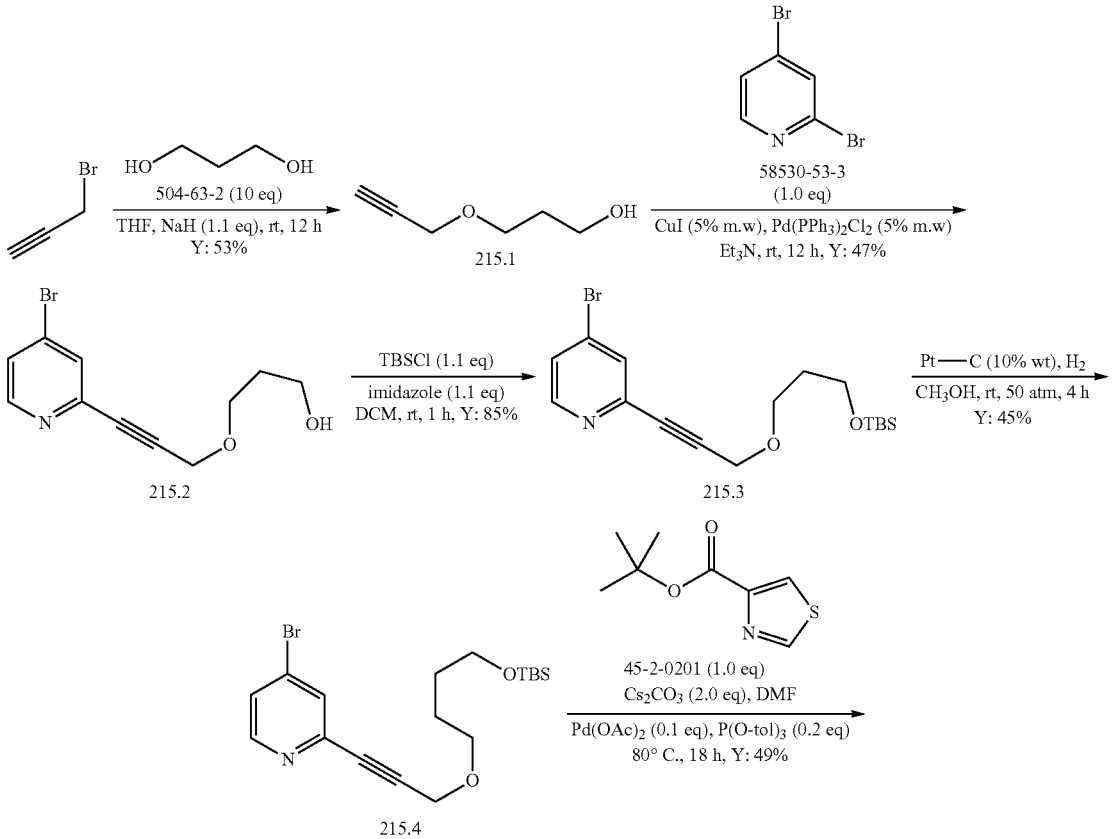

-continued
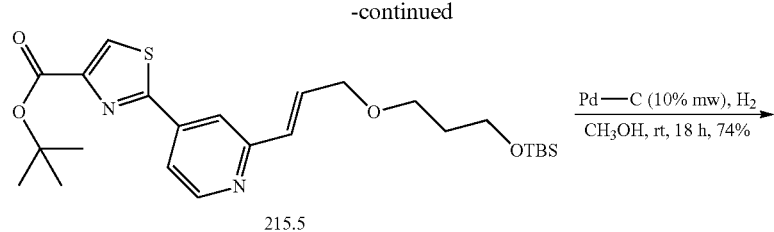
215.5
Pd—C (10% mw), H₂
―――――――――――――→
CH₃OH, rt, 18 h, 74%
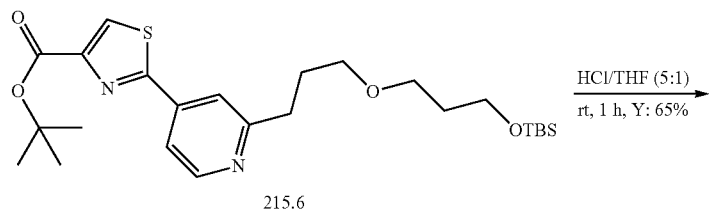
215.6
HCl/THF (5:1)
―――――――――→
rt, 1 h, Y: 65%
215.7
MsCl (1.5 eq), TEA (2.0 eq)
――――――――――――――→
rt, 1 h, Y: 100%
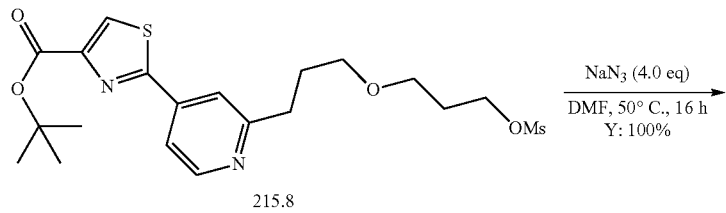
215.8
NaN₃ (4.0 eq)
―――――――――→
DMF, 50° C., 16 h
Y: 100%
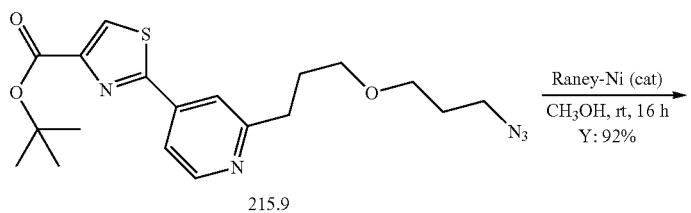
215.9
Raney-Ni (cat)
―――――――――→
CH₃OH, rt, 16 h
Y: 92%
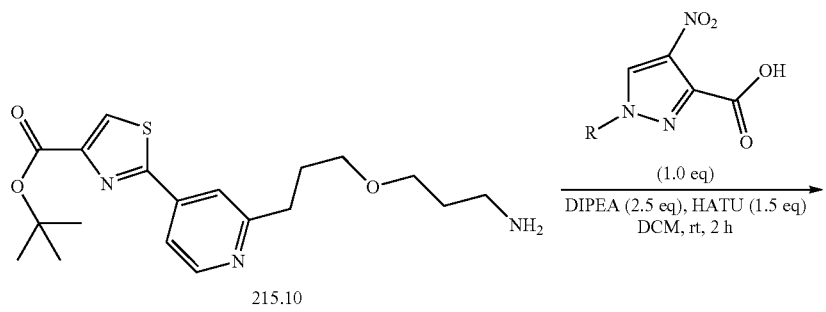
215.10
(1.0 eq)
―――――――――――――――→
DIPEA (2.5 eq), HATU (1.5 eq)
DCM, rt, 2 h

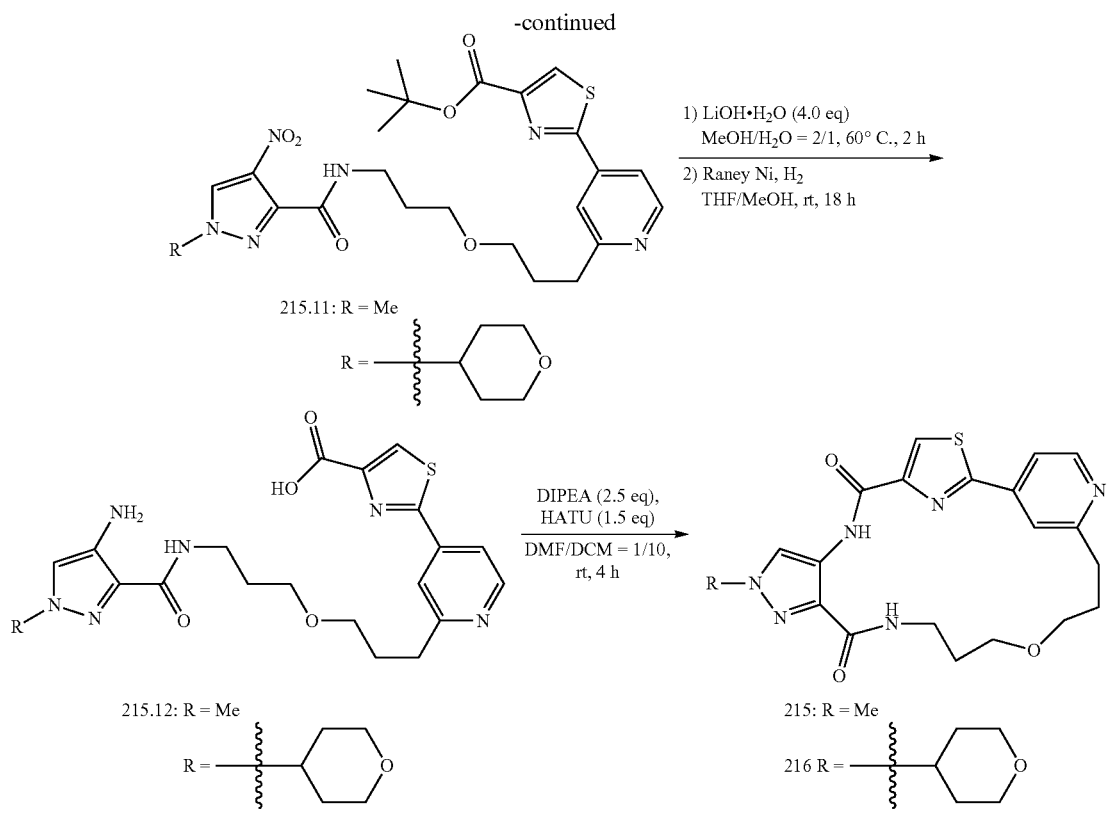

Synthesis of 215.1

To a solution of propane-1,3-diol (30.4 g, 400 mmol, 4.0 eq) in THF (150 mL), NaH (8.0 g, 200 mmol, 2.0 eq) was added at 0° C. The mixture was stirred at 0° C. for 30 min and then 3-bromoprop-1-yne (11.8 g, 100 mmol, 1.0 eq) was added. The mixture was stirred at room temperature for 12 h. The reaction was quenched with $H_2O$ (10 mL) and the solvent was removed in vacuo. The residue was diluted with ethyl acetate (250 mL) and washed with $H_2O$ (100 mL×3), brine (100 mL×3). The organic layer was dried over anhydrous $Na_2SO_4$ and concentrated under reduced pressure. The residue was purified by silica gel column (PE/EA=1/1) to give 215.1 (6.0 g, yield: 53%) as a yellow oil. $^1$H NMR (400 MHz, CDCl$_3$) δ: 4.16 (d, J=2.4 Hz, 2H), 3.80-3.70 (m, 4H), 2.44 (t, J=2.4 Hz, 1H), 1.90-1.84 (m, 2H); ESI-MS (M+H)$^+$: 115.1.

Synthesis of 215.2

To a mixture of 2,4-dibromopyridine (8.0 g, 33.9 mmol, 1.0 eq) and 215.1 (3.9 g, 33.9 mmol, 1.0 eq) in Et$_3$N (80 mL), CuI (400 mg, 5% wt) and Pd(PPh$_3$)$_2$Cl$_2$ (400 mg, 5% wt) were added. The mixture was stirred at room temperature for 16 h under N$_2$ atmosphere, concentrated under reduced pressure and diluted with ethyl acetate (200 mL). The precipitate was filtered off by Celite and the filtrate was washed with $H_2O$ (100 mL×2), brine (100 mL). The organic layer was dried over anhydrous Na$_2$SO$_4$ and concentrated under reduced pressure. The residue was purified by silica gel column (PE/EA=1/1) to give 215.2 (4.3 g, yield: 47%) as a yellow oil. $^1$H NMR (400 MHz, CDCl$_3$) δ: 8.38 (d, J=5.6 Hz, 1H), 7.65-7.62 (m, 1H), 7.47-7.43 (m, 1H), 4.40 (s, 2H), 3.81-3.76 (m, 4H), 2.45 (br. s, 1H), 1.91-1.86 (m, 2H); ESI-MS (M+H)$^+$: 270.1.

Synthesis of 215.3

To a solution of 215.2 (8.6 g, 32.0 mmol, 1.0 eq) and imidazole (2.3 g, 35.2 mmol, 1.1 eq) in DCM (100 mL), TBSCl (5.3 g, 35.2 mmol, 1.1 eq) was added. The mixture was stirred at room temperature for 1 h. The precipitate was filtered off and the filtrate was washed with $H_2O$ (100 mL×2). The organic layer was dried over anhydrous Na$_2$SO$_4$ and concentrated under reduced pressure to give 215.3 (10.4 g, yield: 85%) as a yellow oil; ESI-MS (M+H)$^+$: 384.1.

Synthesis of 215.4

To a solution of 215.3 (8.0 g, 20.9 mmol, 1.0 eq) in MeOH (150 mL), Pt—C (800 mg, 10% wt) was added. The mixture was stirred at room temperature for 4 h under H$_2$ atmosphere (50 atm). The catalyst was filtered off by Celite and the filtrate was concentrated under reduced pressure. The residue was purified by silica gel column (PE/EA=10/1) to give 215.4 (3.6 g, yield: 45% (mixture)) as a yellow oil; ESI-MS (M+H)$^+$: 386.1, 388.1.

Synthesis of 215.5

To a solution of 215.4 (3.6 g, 9.4 mmol, 1.0 eq) and tert-butyl thiazole-4-carboxylate (1.7 g, 9.4 mmol, 1.0 eq) in DMF (80 mL), Pd(OAc)$_2$ (203 mg, 0.9 mmol, 0.1 eq), P(o-tol)$_3$ (578 mg, 1.9 mmol, 0.2 eq) and Cs$_2$CO$_3$ (6.5 g, 19.8 mmol, 2.0 eq) were added. The mixture was stirred at 80° C. for 18 h under N$_2$ atmosphere, diluted with ethyl acetate (200 mL) and filtered by Celite. The filtrate was washed with H₂O (100 mL×3) and brine (100 mL). The organic layer was dried over anhydrous Na$_2$SO$_4$ and concentrated under reduced pressure. The residue was purified by silica gel column (PE/EA=5/1) to give 215.5 (2.2 g, yield: 49% (mixture)) as yellow oil; ESI-MS (M+H)$^+$: 491.2, 493.2.

Synthesis of 215.6

To a solution of 215.5 (2.8 g, 5.7 mmol, 1.0 eq) in MeOH (80 mL), Pd/C (280 mg, 10% wt) was added. The mixture was stirred at room temperature for 18 h under H$_2$ atmosphere. The catalyst was filtered off by Celite and the filtrate was concentrated under reduced pressure to give 215.6 (2.0 g, yield: 74%) as a yellow oil; ESI-MS (M+H)$^+$: 493.2.

Synthesis of 215.7

To a solution of 215.6 (2.0 g, 4.1 mmol, 1.0 eq) in THF (20 mL), HCl/MeOH (4 mL, 12.0 mmol, 3.0 eq, 3 M) was added. The mixture was stirred at room temperature for 1 h. The solvent was removed in vacuo. The residue was purified by silica gel column (PE/EA=1/1) to give 215.7 (1.4 g, yield: 65%) as yellow oil; ESI-MS (M+H)$^+$: 379.1.

Synthesis of 215.8

To a solution of 215.7 (1.4 g, 3.7 mmol, 1.0 eq) and Et$_3$N (747 mg, 7.4 mmol, 2.0 eq) in DCM (60 mL), MsCl (633 mg, 5.6 mmol, 1.5 eq) was added at 0° C. The mixture was stirred at room temperature for 1 h and then washed with saturated NaHCO$_3$ solution (50 mL×2), brine (50 mL). The organic layer was dried over anhydrous sodium sulfate and concentrated under reduced pressure to give 215.8 (1.7 g, yield: 100%) as a yellow oil; ESI-MS (M+H)$^+$: 457.2.

Synthesis of 215.9

To a solution of 215.8 (1.7 g, 3.7 mmol, 1.0 eq) in DMF (25 mL), NaN$_3$ (962 mg, 14.8 mmol, 4.0 eq) was added. The mixture was stirred at 50° C. for 16 h, diluted with ethyl acetate (100 mL) and washed with H$_2$O (100 mL×3), brine (100 mL). The organic layer was dried over anhydrous sodium sulfate and concentrated under reduced pressure to give 215.9 (1.5 g, yield: 100%) as a yellow oil; ESI-MS (M+H)$^+$: 404.2.

Synthesis of 215.10

To a solution of 215.9 (1.5 g, 3.7 mmol, 1.0 eq) in THF (150 mL), raney Ni (150 mg, 10% wt) was added. The mixture was stirred at room temperature for 16 h under H$_2$ atmosphere. The catalyst was filtered off by Celite and the filtrate was concentrated under reduced pressure to give 215.10 (1.3 g, yield: 92%) as a yellow oil; ESI-MS (M+H)$^+$: 378.2.

Synthesis of 215.11

To a solution of 215.10 (450 mg, 1.2 mmol, 1.0 eq) and 1-methyl-4-nitro-1H-pyrazole-3-carboxylic acid (205 mg, 1.2 mmol, 1.0 eq) in CH$_2$Cl$_2$ (30 mL), DIPEA (387 mg, 3.0 mmol, 2.5 eq) and HATU (680 mg, 1.8 mmol, 1.5 eq) were added. The mixture was stirred at room temperature for 2 h and then washed with H$_2$O (20 mL×2). The organic layer was dried over anhydrous sodium sulfate and concentrated under reduced pressure. The residue was purified by pre-TLC (MeOH/DCM=1/20) to give 215.11 (400 mg, yield: 63%) as a yellow oil; ESI-MS (M+H)$^+$: 531.0.

Synthesis of 215.12

To a solution of 215.11 (350 mg, 0.66 mmol, 1.0 eq) in MeOH (20 mL) and H$_2$O (10 mL), LiOH.H$_2$O (111 mg, 2.64 mmol, 4.0 eq) was added. The mixture was stirred at 60° C. for 2 h. After cooling down, the mixture was adjusted to pH=4 with HCl (1 M). The solvent was removed in vacuo. The residue was dissolved in mixed solvents of THF (40 mL) and MeOH (20 mL) and then raney Ni (105 mg, 30% wt) was added. The mixture was stirred at room temperature for 18 h under H$_2$ atmosphere. The catalyst was filtered off by Celite and the filtrate was concentrated under reduced pressure. The residue was purified by prep-HPLC (CH$_3$CN in H$_2$O—0.05% NH$_4$HCO$_3$ from 5% to 95%) to give 215.12 (200 mg, yield: 60% (two steps)) as a yellow oil; ESI-MS (M+H)$^+$: 445.2.

Synthesis of 215

To a solution of 215.12 (150 mg, 0.34 mmol, 1.0 eq) in CH$_2$Cl$_2$ (150 mL) and DMF (15 mL), DIPEA (108 mg, 0.84 mmol, 2.5 eq) and HATU (193 mg, 0.51 mmol, 1.5 eq) were added. The mixture was stirred at room temperature for 4 h and then washed with H$_2$O (50 mL×3). The organic layer was dried over anhydrous sodium sulfate and concentrated under reduced pressure. The residue was purified by recrystallization in MeOH (2 mL) to give 215 (17 mg, yield: 12%) as a white solid. $^1$H NMR (400 MHz, CDCl$_3$) δ: 12.40 (s, 1H), 8.64 (d, J=4.8 Hz, 1H), 8.56 (s, 1H), 8.16 (s, 1H), 8.14 (s, 1H), 7.44-7.43 (m, 1H), 6.92 (t, J=6.4 Hz, 1H), 3.94 (s, 3H), 3.72-3.67 (m, 2H), 3.65-3.59 (m, 4H), 3.11 (t, J=6.4 Hz, 2H), 2.27-2.20 (m, 2H), 1.88-1.83 (m, 2H); ESI-MS (M+H)$^+$: 426.8; HPLC: 214 nm: 97.23%, 254 nm: 98.72%.

Synthesis of 216

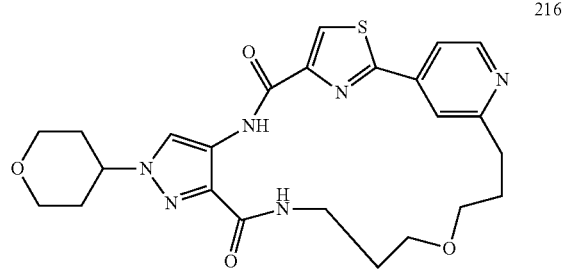 [SMILES: O=C1Nc2cn(C3CCOCC3)nc2C(=O)NCCCOCCCc2cc(ccn2)-c2nc1cs2]

The synthesis of compound 216 was similar to 216 utilizing 215.10 and 4-nitro-1-(tetrahydro-2H-pyran-4-yl)-1H-pyrazole-3-carboxylic acid to afford 216 as a white solid 25 mg, yield: 14%; $^1$H NMR (400 MHz, CDCl$_3$) δ: 12.41 (s, 1H), 8.64 (d, J=4.4 Hz, 1H), 8.54 (s, 1H), 8.21 (s, 1H), 8.16 (s, 1H), 7.43-7.41 (m, 1H), 6.95 (t, J=6.8 Hz, 1H), 4.37-4.29 (m, 1H), 4.14-4.12 (m, 2H), 3.73-3.68 (m, 2H), 3.65-3.52 (m, 6H), 3.10 (t, J=6.8 Hz, 2H), 2.27-2.20 (m, 2H), 2.17-2.11 (m, 4H), 1.88-1.86 (m, 2H); ESI-MS (M+H)$^+$: 496.8; HPLC: 214 nm: 96.18%, 254 nm: 96.92%.

263

Scheme 217

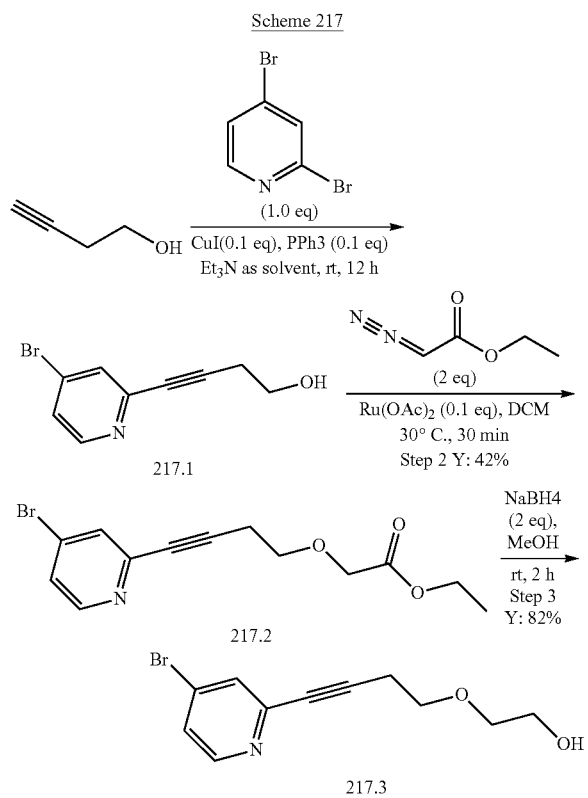

Synthesis of 217.1

The synthesis of compound 217.1 was similar to 215.2 utilizing but-3-yn-1-ol to afford 217.1 as a dark red oil 29.0 g, yield: 82%; ESI-MS (M+H)$^+$: 225.1, 227.1.

Synthesis of 217.2

To a solution of 217.1 (8.0 g, 35.5 mmol, 1.0 eq) and Rh(CH$_3$CO$_2$)$_2$ (160 mg, 0.48 mmol, 0.01 eq) in DCM (50 mL), Ethyl azidoacetate (8.1 g, 71.0 mmol, 2.0 eq) was added slowly at room temperature. The mixture was stirred at room temperature for 16 h and concentrated under reduced pressure. The residue was purified by silica gel column (PE/EA=10/1) to give 217.2 (4.5 g, yield: 42%) as a colorless oil; ESI-MS (M+H)$^+$: 312.1, 314.1.

Synthesis of 217.3

To a solution of 217.2 (4.5 g, 14.4 mmol, 1.0 eq) in methanol (100 mL), NaBH$_4$ (1.6 g, 43.3 mmol, 3.0 eq) was added. The mixture was stirred at room temperature for 16 h and concentrated under reduced pressure. The residue was

264 dissolved in ethyl acetate (100 mL) and washed with H$_2$O (80 mL×2). The organic layer was dried over anhydrous sodium sulfate and concentrated under reduced pressure to give 217.3 (3.2 g, yield: 82%) as a colorless oil. $^1$H NMR (400 MHz, CDCl$_3$) δ: 8.27 (d, J=5.2 Hz, 1H), 7.48 (s, 1H), 7.29 (d, J=5.2 Hz, 1H), 3.70 (t, J=5.2 Hz, 2H), 3.64 (t, J=6.8 Hz, 2H), 3.51 (t, J=5.6 Hz, 2H), 2.65 (t, J=6.8 Hz, 2H); ESI-MS (M+H)$^+$: 270.2, 272.1.

Synthesis of 217

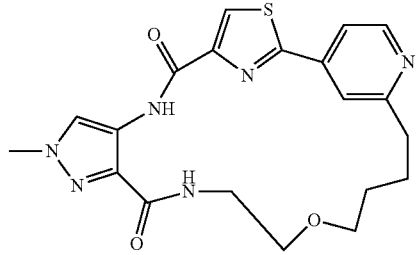

The synthesis of compound 217 was similar to 215 utilizing 217.3 to afford 217 a white solid 16 mg, yield: 19%; $^1$H NMR (400 MHz, CDCl$_3$) δ: 12.02 (s, 1H), 8.62 (d, J=4.8 Hz, 1H), 8.46 (s, 1H), 8.18 (s, 1H), 8.16 (s, 1H), 7.44-7.43 (m, 1H), 6.92 (t, J=6.4 Hz, 1H), 3.92 (s, 3H), 3.72-3.67 (m, 2H), 3.65-3.59 (m, 4H), 3.03 (t, J=6.4 Hz, 2H), 2.15-2.11 (m, 2H), 1.86-1.80 (m, 2H); ESI-MS (M+H)$^+$: 426.8; HPLC: 214 nm: 96.48%, 254 nm: 96.12%.

Synthesis of 218

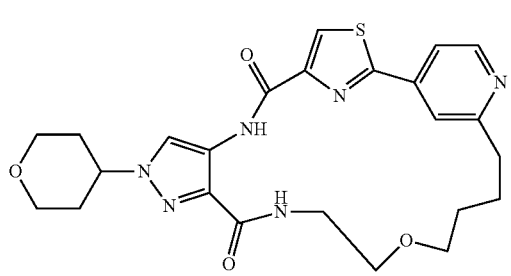

The synthesis of compound 218 was similar to 216 utilizing 217.3 to afford 218 a white solid 6 mg, yield: 3%; $^1$H NMR (400 MHz, CDCl$_3$) δ: 12.03 (s, 1H), 8.64 (m, 1H), 8.45 (s, 1H), 8.24 (s, 1H), 8.17 (s, 1H), 7.43-7.41 (m, 1H), 6.97 (t, J=6.8 Hz, 1H), 4.31-4.30 (m, 1H), 4.14-4.11 (m, 2H), 3.79-3.68 (m, 2H), 3.68-3.64 (m, 2H), 3.64-3.57 (m, 2H), 3.57-3.50 (m, 2H), 3.01 (t, J=6.8 Hz, 2H), 2.27-2.11 (m, 6H), 1.88-1.86 (m, 2H); ESI-MS (M+H)$^+$: 496.8; HPLC: 214 nm: 99.36%, 254 nm: 98.71%.

Scheme 219

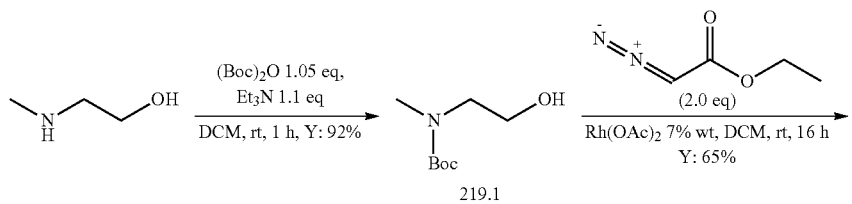

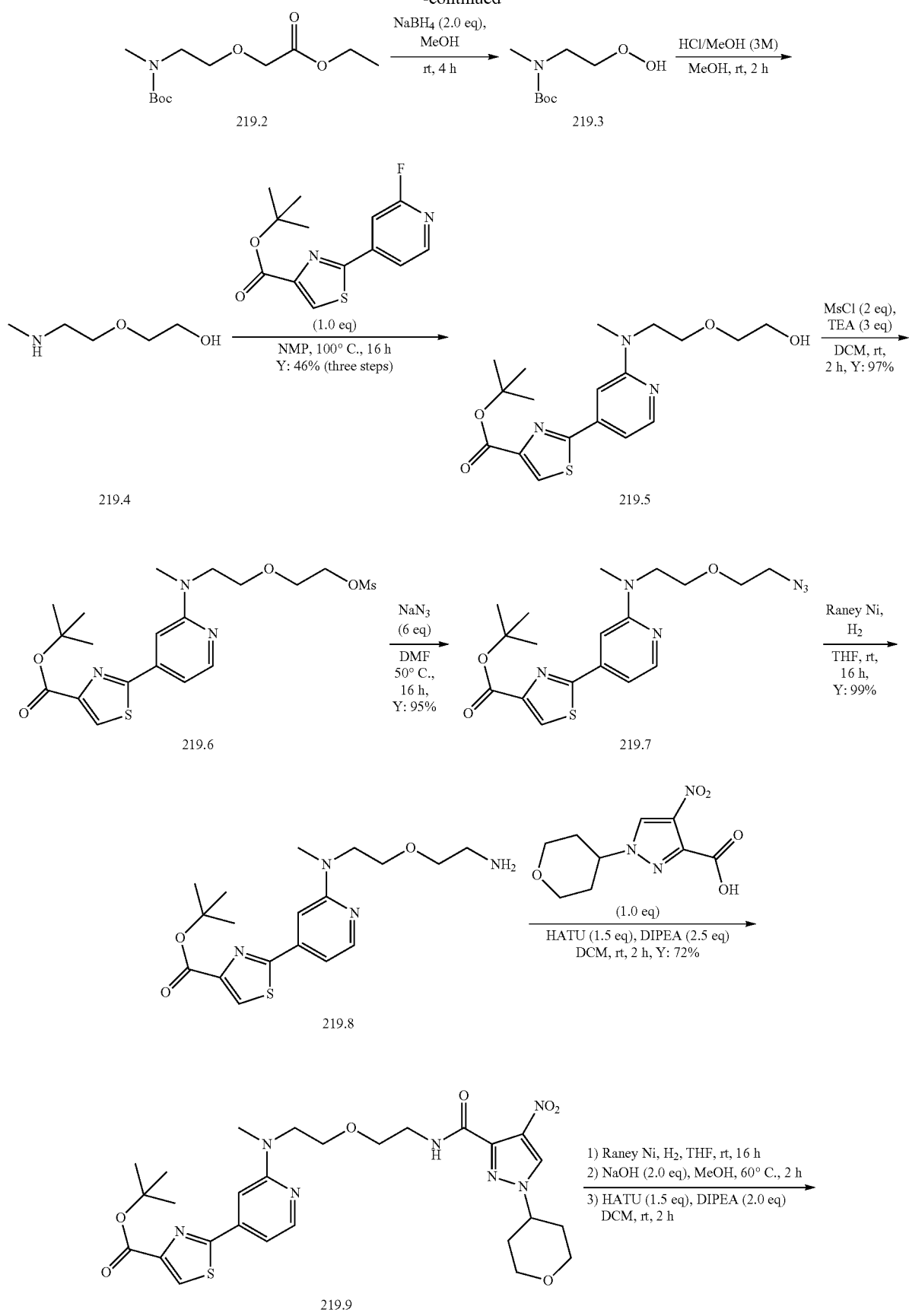

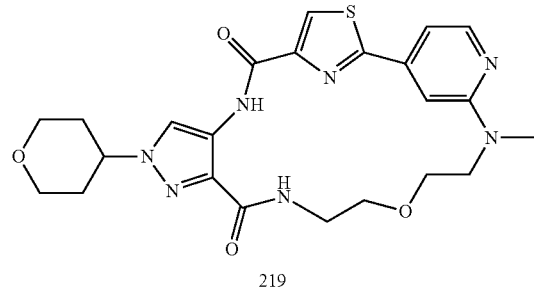 [SMILES: CN1CCOCCNC(=O)c2nn(C3CCOCC3)cc2NC(=O)c2csc(n2)-c2ccnc1c2]

Synthesis of 219.1

To a solution of 2-(methylamino)ethanol (750 mg, 10 mmol, 1.0 eq) and Et₃N (1.1 g, 11 mmol, 1.1 eq) in DCM (100 mL), Boc₂O (2.3 g, 10.5 mmol, 1.05 eq) was added. The mixture was stirred at room temperature for 2 h and then washed with H₂O (80 mL×3). The organic layer was dried over anhydrous sodium sulfate and concentrated under reduced pressure to give 219.1 (1.6 g, yield: 92%) as a yellow oil; ESI-MS (M+H)⁺: 176.2.

Synthesis of 219.2

To a solution of 219.1 (1.6 g, 9.2 mmol, 1.0 eq) and Ru(OAc)₂ (113 mg, 0.5 mmol, 7% wt) in DCM (100 mL), ethyl azidoacetate (2.1 g, 18.4 mmol, 2.0 eq) was added dropwise. The mixture was stirred at room temperature for 16 h and then concentrated under reduced pressure. The residue was purified by silica gel column (PE/EA=4/1) to give 219.2 (1.6 g, yield: 65%) as a light yellow oil. ¹H NMR (400 MHz, CDCl₃) δ: 4.23 (q, J=6.8 Hz, 2H), 4.08 (s, 2H), 3.68-3.64 (m, 2H), 3.46-3.42 (m, 2H), 2.94 (s, 3H), 1.46 (s, 9H), 1.29 (t, J=7.2 Hz, 3H); ESI-MS (M+H)⁺: 262.2.

Synthesis of 219.3

To a solution of 219.2 (1.6 g, 6.0 mmol, 1.0 eq) in MeOH (100 mL), NaBH₄ (450 mg, 12.0 mmol, 2.0 eq) was added. The reaction mixture was stirred at room temperature for 4 h and then concentrated under reduced pressure. The residue was diluted with ethyl acetate (150 mL) and washed with H₂O (50 mL×3). The organic layer was dried over anhydrous sodium sulfate and concentrated under reduced pressure to give 219.3 (1.24 g, yield: 95%) as a light yellow oil; ESI-MS (M+H)⁺: 220.2.

Synthesis of 219.4

A solution of 219.3 (1.24 g, 5.6 mmol, 1.0 eq) in HCl/MeOH (20 mL, 3 M) was stirred at room temperature for 2 h and then concentrated under reduced pressure to give 219.4 (600 mg, yield: 90%) as a white solid; ESI-MS (M+H)⁺: 120.1.

Synthesis of 219.5

To a solution of 219.4 (600 mg, 5.0 mmol, 1.0 eq) in NMP (20 mL), tert-butyl 2-(2-fluoropyridin-4-yl)thiazole-4-carboxylate (1.4 g, 5.0 mmol, 1.0 eq) was added. The mixture was stirred at 100° C. for 16 h. After cooled down, the solution was diluted with ethyl acetate (100 mL) and washed with water (50 ml×5). The organic layer was dried over anhydrous sodium sulfate and concentrated under reduced pressure. The residue was purified by silica gel (PE/EA=1/1) to give 219.5 (880 mg, yield: 46%) as a yellow oil; ESI-MS (M+H)⁺: 380.2.

Synthesis of 219.6

To a solution of 219.5 (880 mg, 2.3 mmol, 1.0 eq) and TEA (1.0 ml, 6.9 mmol, 3.0 eq) in DCM (100 mL), MsCl (524 mg, 4.6 mmol, 2.0 eq) was added. The mixture was stirred at room temperature for 2 h and then washed with water (50 mL×3). The organic layer was dried over anhydrous sodium sulfate and concentrated under reduced pressure to give 219.6 (950 mg, yield: 97%) as a red oil; ESI-MS (M+H)⁺: 458.2.

Synthesis of 219.7

To a solution of 219.6 (950 mg, 2.1 mmol, 1.0 eq) in DMF (100 mL), NaN₃ (811 mg, 12.6 mmol, 6.0 eq) was added. The mixture was stirred at 50° C. for 16 h. After cooled down, the solution was diluted with ethyl acetate (150 mL) and washed with water (100 ml×5). The organic layer was dried over anhydrous sodium sulfate and concentrated under reduced pressure to give 219.7 (800 mg, yield: 95%) as a yellow oil; ESI-MS (M+H)⁺: 405.2.

Synthesis of 219.8

To a solution of 219.7 (800 mg, 2.0 mmol, 1.0 eq) in THF (100 mL), raney Ni (80 mg, 10% wt) was added. The mixture was stirred at room temperature under hydrogen for 16 h and then filtered by Celite. The filtrate was concentrated under reduced pressure to give 219.8 (740 mg, yield: 99%) as a yellow oil; ESI-MS (M+H)⁺: 379.2.

Synthesis of 219.9

To a solution of 219.8 (600 mg, 1.6 mmol, 1.0 eq) and 4-nitro-1-(tetrahydro-2H-pyran-4-yl)-1H-pyrazole-3-carboxylic acid (574 mg, 2.4 mmol, 1.5 eq) in DCM (100 mL), DIPEA (1.0 ml, 4.8 mmol, 3.0 eq) and HATU (1.22 g, 3.2 mmol, 2.0 eq) were added. The mixture was stirred at room temperature for 2 h and then washed with water (50 mL×3). The organic layer was dried over anhydrous sodium sulfate and concentrated under reduced pressure. The residue was purified by silica gel column (MeOH/DCM=1/20) to give 219.9 (760 mg, yield: 80%) as a light yellow oil; ESI-MS (M+H)⁺: 602.2.

Synthesis of 219

To a solution of 219.9 (760 mg, 1.26 mmol, 1.0 eq) in THF (100 mL) was added Raney Ni (150 mg, 20% wt). The mixture was stirred at room temperature under hydrogen for 16 h and filtered by Celite. The filtration was concentrated under reduced pressure. The residue was dissolved in MeOH (50 mL) and H₂O (10 mL), and then NaOH (120 mg, 2.52 mmol, 2.0 eq) was added. The resulted solution was stirred at 60° C. for 2 h, adjusted to pH=4 with HCl (2 M) and evaporated under reduced pressure. The resulted residue was dissolved in CH₂Cl₂ (150 mL), then DIPEA (407 mg, 3.2 mmol, 2.5 eq) and HATU (719 mg, 1.89 mmol, 1.5 eq) were added. The resulted mixture was stirred at room temperature for 1 h and washed with water (100 mL×3). The organic layer was dried over anhydrous sodium sulfate and concentrated under reduced pressure. The residue was purified by recrystallization in MeOH (10 mL) to give 219 (330 mg, yield: 42.7% (three steps)) as a yellow solid. ¹H NMR (400 MHz, CDCl₃) δ: 12.56 (s, 1H), 8.24 (d, J=5.2 Hz, 1H), 8.13 (s, 1H), 8.09 (s, 1H), 7.87 (s, 1H), 6.99 (t, J=6.0 Hz, 1H), 6.82 (d, J=5.2 Hz, 1H), 4.32-4.29 (m, 1H), 4.14-4.11 (m, 2H), 4.04-4.00 (m, 2H), 3.82-3.81 (m, 2H), 3.69-3.54 (m, 4H), 3.54-3.51 (m, 2H), 3.22 (s, 3H), 2.15-2.10 (m, 4H); ESI-MS (M+H)⁺: 498.2; HPLC: 214 nm: 96.29%, 254 nm: 99.41%.

Synthesis of 220

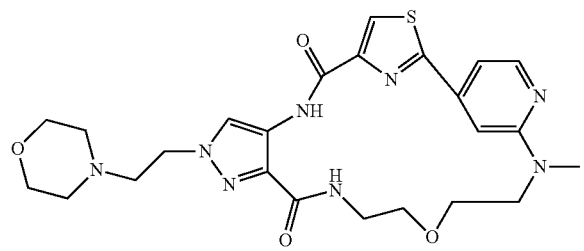

220

The synthesis of compound 220 was similar to 219 utilizing 1-(2-morpholinoethyl)-4-nitro-1H-pyrazole-3-carboxylic acid to afford to afford 220 (206 mg) as a yellow solid, yield: 32%; ¹H NMR (400 MHz, CDCl₃) δ: 12.55 (s, 1H), 8.24 (d, J=5.2 Hz, 1H), 8.15 (s, 1H), 8.09 (s, 1H), 7.88 (s, 1H), 6.88-6.83 (m, 2H), 4.24 (t, J=6.4 Hz, 2H), 4.03 (t, J=6.8 Hz, 2H), 3.83 (t, J=4.8 Hz, 2H), 3.72-3.62 (m, 8H), 3.23 (s, 3H), 2.83 4.24 (t, J=6.8 Hz, 2H), 2.50-2.48 (m, 4H); ESI-MS (M+H)⁺: 527.2; HPLC: 214 nm: 91.05%, 254 nm: 95.79%.

Synthesis of 221

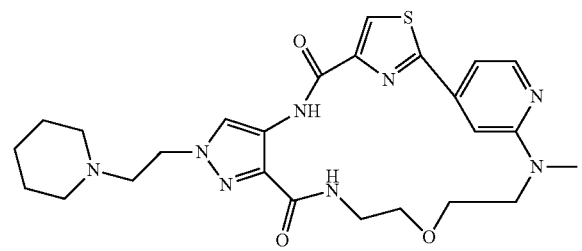

221

The synthesis of compound 221 was similar to 219 utilizing 4-nitro-1-(2-(piperidin-1-yl)ethyl)-1H-pyrazole-3-carboxylic acid to afford to afford 221 (115 mg) as a yellow solid, yield: 14%; ¹H NMR (400 MHz, CDCl₃) δ: 12.55 (s, 1H), 8.23 (d, J=5.2 Hz, 1H), 8.14 (s, 1H), 8.08 (s, 1H), 7.89 (s, 1H), 6.90 (t, J=6.0 Hz, 1H), 6.85-6.83 (m, 1H), 4.23 (t, J=6.8 Hz, 2H), 4.05-4.00 (m, 2H), 3.82 (t, J=5.2 Hz, 2H), 3.71-3.61 (m, 4H), 3.22 (s, 3H), 2.78 (t, J=6.8 Hz, 2H), 2.46-2.42 (m, 4H), 1.62-1.57 (m, 4H), 1.46-1.44 (m, 2H); ESI-MS (M+H)⁺: 525.2; HPLC: 214 nm: 97.79%, 254 nm: 99.63%.

Synthesis of 222

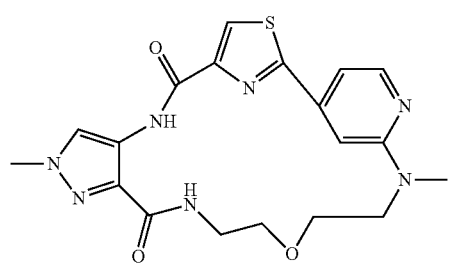

222

The synthesis of compound 220 was similar to 219 utilizing 1-methyl-4-nitro-1H-pyrazole-3-carboxylic acid to afford to afford 222 (147 mg) as a yellow solid, yield: 24% (three steps); ¹H NMR (400 MHz, CDCl₃) δ: 9.51 (s, 1H), 8.24 (d, J=5.2 Hz, 1H), 8.15 (s, 1H), 8.14 (s, 1H), 7.81 (s, 1H), 6.85-6.84 (m, 1H), 6.61-6.59 (m, 1H), 4.12 (s, 3H), 3.81-3.76 (m, 4H), 3.69-3.65 (m, 4H), 3.21 (s, 3H); ESI-MS (M+H)⁺: 428.1; HPLC: 214 nm: 96.29%, 254 nm: 99.38%.

Scheme 223

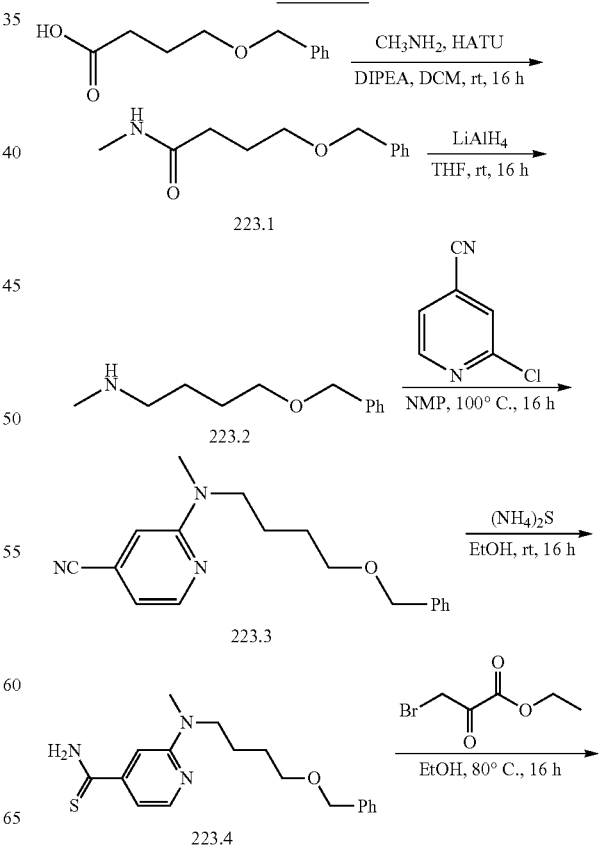

-continued

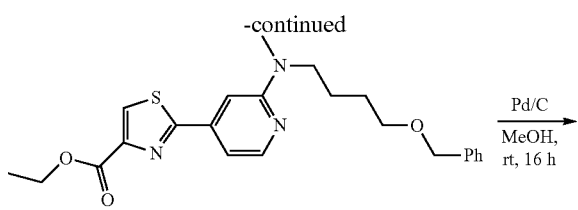

223.5

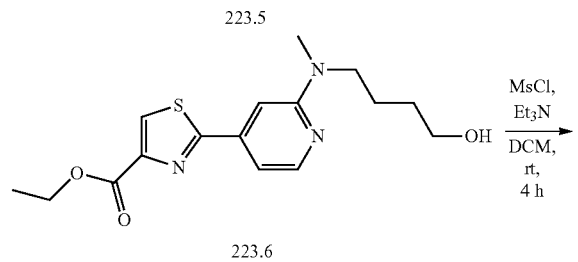

223.6

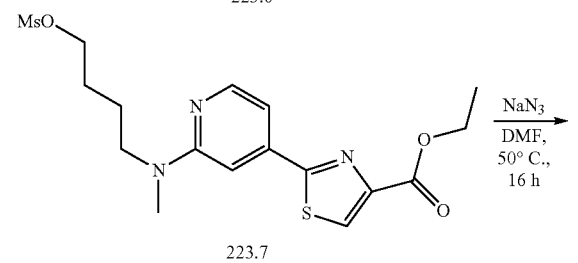

223.7

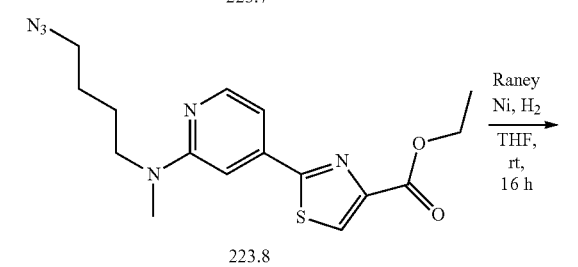

223.8

223.9

Synthesis of 223.1

To a solution of 4-(benzyloxy)butanoic acid (4.5 g, 23.2 mmol, 1.0 eq) in CH$_2$Cl$_2$ (100 mL), DIPEA (8.9 g, 69.6 mmol, 3.0 eq), HATU (13.2 g, 34.8 mmol, 1.5 eq) and CH$_3$NH$_2$ (1.4 g, 46.4 mmol, 2.0 eq) were added. The reaction mixture was stirred at room temperature for 16 h and then washed with H$_2$O (50 mL×2). The organic layer was dried over anhydrous sodium sulfate and concentrated under reduced pressure. The residue was purified by silica gel column (EA/PE=1/2) to give 223.1 (3.6 g, yield: 75%) as a yellow oil.

Synthesis of 223.2

To a solution of 223.1 (3.60 g, 17.4 mmol, 1.0 eq) in THF (100 mL), LiAlH$_4$ (1.98 g, 52.2 mmol, 3.0 eq) was added. The mixture was stirred at room temperature for 16 h under N$_2$ atmosphere. The reaction was quenched with Na$_2$SO$_4$·10H$_2$O and then filtered by Celite. The filtrate was concentrated under reduced pressure, diluted with DCM (300 mL) and washed with H$_2$O (100 mL×2). The organic layer was dried over anhydrous Na$_2$SO$_4$ and concentrated under reduced pressure. The residue was purified by silica gel column (PE/EA=3/1) to give 223.2 (3.1 g, yield: 93%) as a yellow oil.

Synthesis of 223.3

To a solution of 223.2 (3.1 g, 16.1 mmol, 1.0 eq) in NMP (30 mL), 2-Chloro-4-pyridinecarbonitrile (2.6 g, 19.3 mmol, 1.2 eq) was added. The mixture was stirred at 100° C. for 16 h, diluted with ethyl acetate (200 mL) and washed with H$_2$O (80 mL), brine (80 mL×3). The organic layer was dried over sodium sulfate and concentrated under reduced pressure. The residue was purified by silica gel column (EA/PE=1/10) to give 223.3 (3.2 g, yield: 68%) as a yellow solid; ESI-MS (M+H)$^+$: 296.1.

Synthesis of 223.4

To a mixture of 223.3 (3.2 g, 10.8 mmol, 1.0 eq) in EtOH (200 mL), (NH$_3$)$_2$S (9 mL, 21.7 mmol, 2.0 eq, 20% in H$_2$O) was added. The reaction mixture was stirred at room temperature for 16 h. The solvent was removed in vacuo to give 223.4 (3.6 g, crude) as a yellow solid which was directly used in the next step without further purification; ESI-MS (M+H)$^+$: 330.1.

Synthesis of 223.5

To a mixture of 223.4 (3.5 g, 10.6 mol, 1.0 eq) in EtOH (200 mL) was added ethyl 3-bromo-2-oxopropanoate (2.5 g, 12.8 mol, 1.2 eq) at room temperature. The reaction mixture was stirred at 80° C. for 16 h. The solution was cooled down to 0° C. The precipitate was collected by filtration and washed with H$_2$O (20 mL×3) to give 223.5 (2.2 g, yield: 49% (two steps)) as a yellow solid; ESI-MS (M+H)$^+$: 426.1.

Synthesis of 223.6

To a solution of 223.5 (2.2 g, 5.17 mmol, 1.0 eq) in MeOH (100 mL), Pd/C (440 mg, 20% wt) was added. The mixture was stirred at room temperature for 16 h under H$_2$ atmosphere and then filtered by Celite. The filtrate was concentrated under reduced pressure to give 223.6 (1.5 g, yield: 88%) as a yellow oil; ESI-MS (M+H)$^+$: 336.1.

Synthesis of 223.7

To a solution of 223.6 (1.5 g, 4.5 mmol, 1.0 eq) and Et$_3$N (588 mg, 5.8 mmol, 1.3 eq) in DCM (100 mL), MsCl (616 mg, 5.4 mmol, 1.2 eq) was added at 0° C. The mixture was stirred at room temperature for 16 h and then washed with brine (30 mL×3). The organic layer was dried over anhydrous sodium sulfate and concentrated under reduced pressure to give 223.7 (1.7 g, yield: 94%) as a yellow solid; ESI-MS (M+H)$^+$: 414.1.

Synthesis of 223.8

To a solution of 223.7 (1.7 g, 4.1 mmol, 1.0 eq) in DMF (15 mL), NaN$_3$ (1.3 g, 20.6 mmol, 5.0 eq) was added. The mixture was stirred at 50° C. for 16 h, diluted with ethyl acetate (100 mL) and washed with H$_2$O (50 mL), brine (50 mL×3). The organic layer was dried over anhydrous sodium sulfate and concentrated under reduced pressure to give 223.8 (1.5 g, crude) as a yellow oil; ESI-MS (M+H)$^+$: 361.2.

Synthesis of 223.9

To a solution of 223.8 (1.5 g, 4.17 mmol, 1.0 eq) in THF (100 mL), Raney Ni (300 mg, 20% wt) was added. The mixture was stirred at room temperature for 16 h under H₂ atmosphere and then filtered by Celite. The filtrate was concentrated under reduced pressure to give 223.9 (953 mg, yield: 69% (two steps)) as a yellow solid; ESI-MS (M+H)⁺: 335.1.

Synthesis of 223

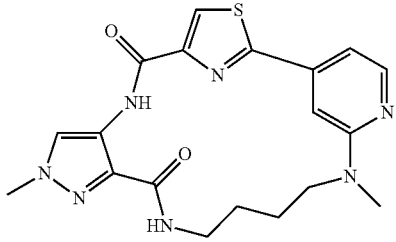

The synthesis of compound 223 was similar to 222 utilizing 223.9 to afford to afford 223 (76 mg) as a yellow solid, yield: 13%; ¹H NMR (400 MHz, CDCl₃) δ: 9.69 (s, 1H), 8.26 (d, J=5.2 Hz, 1H), 8.22 (s, 1H), 8.07 (s, 1H), 7.43 (s, 1H), 6.74 (d, J=4.8 Hz, 1H), 6.66-6.64 (m, 1H), 4.02 (s, 3H), 3.57-3.50 (m, 4H), 3.25 (s, 3H), 2.02-1.88 (m, 4H), ESI-MS (M+H)⁺: 412.2; HPLC: 214 nm: 100%, 254 nm: 100%.

Synthesis of 224

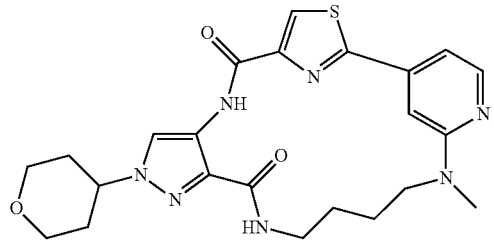

The synthesis of compound 224 was similar to 219 utilizing 223.9 to afford to afford 224 (120 mg) as a yellow solid, yield: 17%; ¹H NMR (400 MHz, CDCl₃) δ: 12.91 (s, 1H), 8.21 (d, J=5.6 Hz, 1H), 8.08 (s, 1H), 8.05 (s, 1H), 8.01 (s, 1H), 6.93 (t, J=6.0 Hz, 1H), 6.78 (dd, J₁=5.2 Hz, J₂=1.2 Hz, 1H), 4.37-4.28 (m, 1H), 4.15-4.11 (m, 2H), 3.76-3.72 (m, 2H), 3.58-3.43 (m, 4H), 3.21 (s, 3H), 2.19-2.00 (m, 6H), 1.81-1.78 (m, 2H); ESI-MS (M+H)⁺: 482.1.

Scheme 225

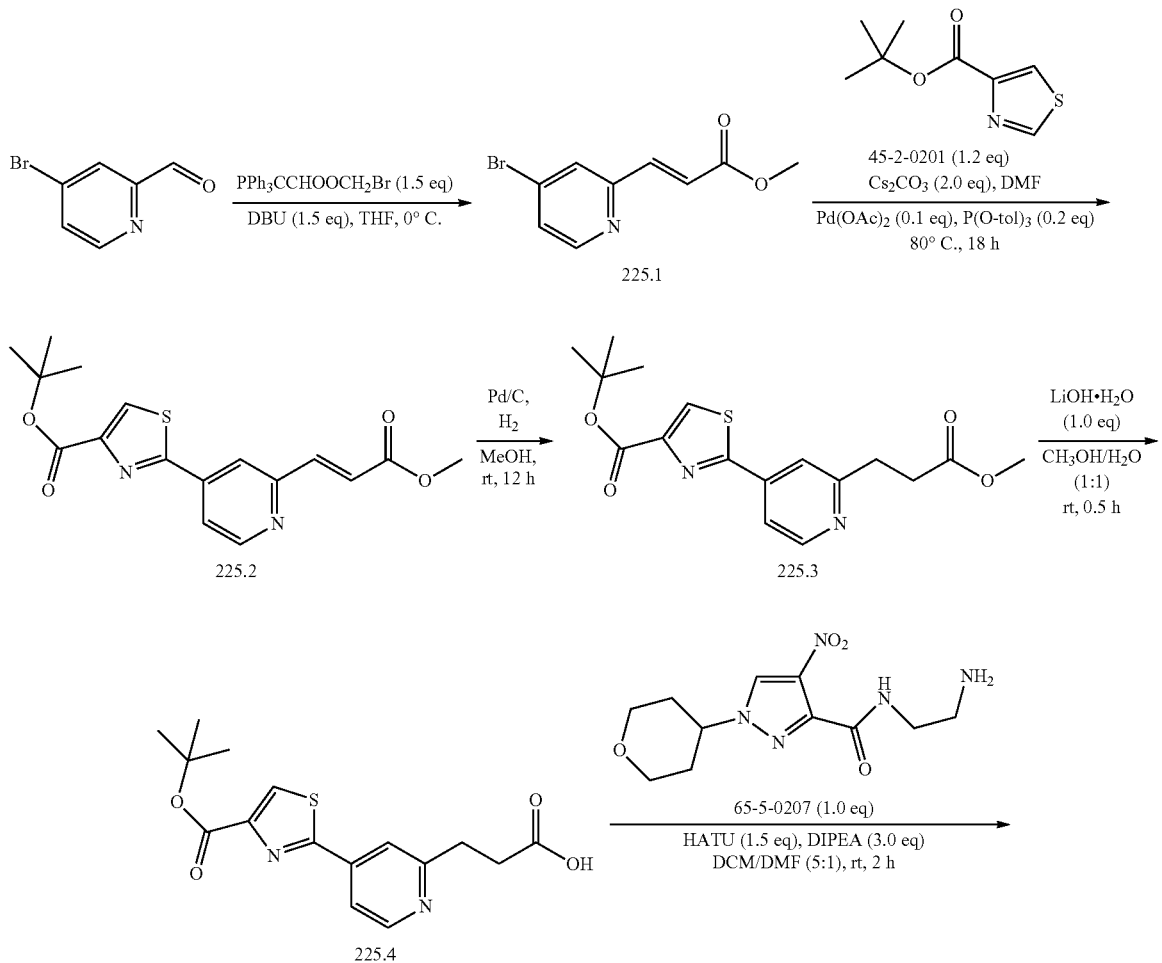

-continued

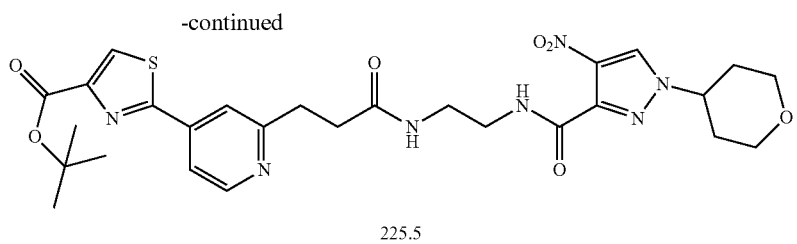

225.5

Synthesis of 225.1

To a mixture of PPh₃CCHOOCH₂Br (4.5 g, 10.9 mmol, 1.0 eq) in THF (50 mL) was added DBU (2.5 g, 16.3 mmol, 1.5 eq) at 0° C. under nitrogen atmosphere. After stirring for 30 min, 4-bromopicolinaldehyde (2.0 g, 10.9 mmol, 1.0 eq) was added. The reaction mixture was stirred for 1 h at room temperature and concentrated under reduced pressure. The residue was diluted with ethyl acetate (200 mL), washed with water (200 mL×3). The organic layer was dried over anhydrous Na$_2$SO$_4$ and concentrated under reduced pressure to give 225.1 (2.5 g, yield: 90%) as a yellow solid. $^1$H NMR (400 MHz, CDCl$_3$) δ: 8.52 (d, J=4.8 Hz, 1H), 8.07 (s, 1H), 7.70 (d, J=4.8 Hz, 1H), 7.60 (d, J=15.6 Hz, 1H), 6.87 (t, J=15.6 Hz, 1H), 3.77 (s, 3H); ESI-MS (M+H)$^+$: 270.2, 272.1.

Synthesis of 225.2

The synthesis of compound 225.2 was similar to 215.5 utilizing 225.1 to afford to afford 225.2 as a yellow oil (1.2 g), yield: 38%; $^1$H NMR (400 MHz, CDCl$_3$) δ: 8.59-8.58 (m, 1H), 8.20 (s, 1H), 7.97-7.96 (m, 1H), 7.89-7.88 (m, 1H), 7.60 (d, J=15.6 Hz, 1H), 6.87 (t, J=15.2 Hz, 1H), 3.77 (s, 3H), 1.64 (s, 9H); ESI-MS (M+H)$^+$: 347.1.

Synthesis of 225.3

To a solution of 225.2 (1.2 g, 3.5 mmol, 1.0 eq) in CH$_3$OH (15 mL), Pd/C (120 mg, 10% wt) was added. The mixture was stirred at room temperature for 16 h under H$_2$ atmosphere and then filtered by Celite. The filtrate was concentrated under reduced pressure to give 225.3 (2.1 g, yield: 92%) as a yellow oil; ESI-MS (M+H)$^+$: 349.1.

Synthesis of 225.4

To a solution of 225.3 (1.1 g, 3.2 mmol, 1.0 eq) in MeOH/H$_2$O (5/1, 15 mL), LiOH (199 mg, 4.8 mmol, 1.5 eq) was added. The mixture was stirred for 30 min at room temperature, adjusted to pH=3-4 with HCl (1 M) and then concentrated under reduced pressure. The resulted residue was diluted with ethyl acetate (100 mL), washed with water (100 mL×3). The organic layer were dried over anhydrous Na$_2$SO$_4$ and concentrated under reduced pressure to give 225.4 (0.6 g, yield: 55%) as a yellow solid. $^1$H NMR (400 MHz, CDCl$_3$) δ: 8.64-8.62 (m, 1H), 8.22 (s, 1H), 7.99-7.98 (m, 1H), 7.89-7.88 (m, 1H), 3.94 (t, J=4.2 Hz, 2H), 3.29 (t, J=4.2 Hz, 2H), 1.64 (s, 9H); ESI-MS (M+H)$^+$: 335.0.

Synthesis of 225

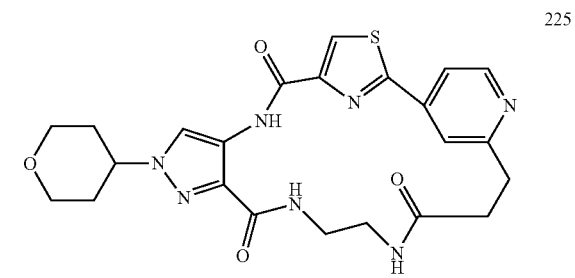 [SMILES: O=C1CCc2cc(ccn2)-c2nc(cs2)C(=O)Nc2cn(C3CCOCC3)nc2C(=O)NCCN1]

225

The synthesis of compound 225 was similar to 219 utilizing 225.5 and 169.2 to afford to afford 225 as a white solid 15 mg, yield: 11%; $^1$H NMR (400 MHz, CDCl$_3$) δ: 12.02 (s, 1H), 8.69-8.59 (m, 2H), 8.31-8.15 (m, 3H), 7.43-7.41 (m, 1H), 7.27-7.25 (m, 1H), 4.37-4.31 (m, 1H), 4.15-4.13 (m, 2H), 3.61-3.53 (m, 6H), 3.38-3.34 (m, 2H), 2.75-2.71 (m, 2H), 2.17-2.13 (m, 4H); ESI-MS (M+H)$^+$: 497.2; HPLC: 214 nm: 99.48%, 254 nm: 100.00%.

Alternate Synthesis for Compound 203

Compound 203 was synthesized by the method described above. Compound 203 can also be synthesized by the following method.

General Synthesis Schemes and Synthesis of Compound GG

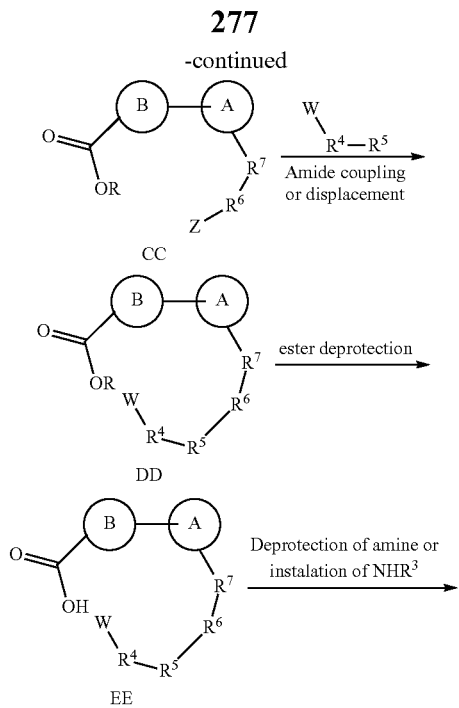

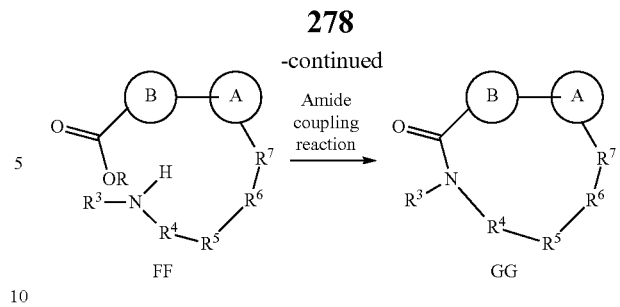

Compound BB can synthesized by attaching to an $ZR^6R^7$ and to a commercially aromatic ring by either displacement reaction or pd coupling reactions (ex Suzuki, Ullmann Buchwald, Stille). The synthesis of biaryl CC can be synthesized by standard carbon-carbon coupling reaction (ex Suzuki, Stille, copper coupling reactions) between coupling partners commercially available AA and BB. By amide coupling or displacement reactions $WR^4R^5$ can be added to CC to afford DD. The ester is deprotected to afford EE. The Amine of FF is either unmasked or the amine may be installed by a displacement reaction. The macrocyle GG is can formed by a standard amide coupling reaction to afford GG.

Synthesis of Compound CC.1

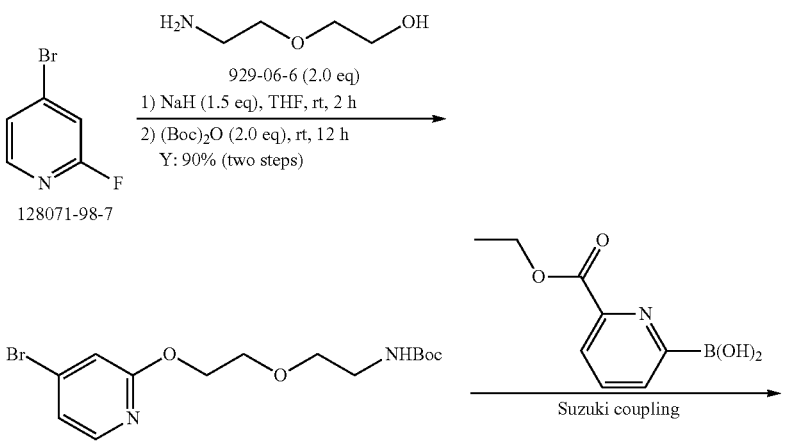

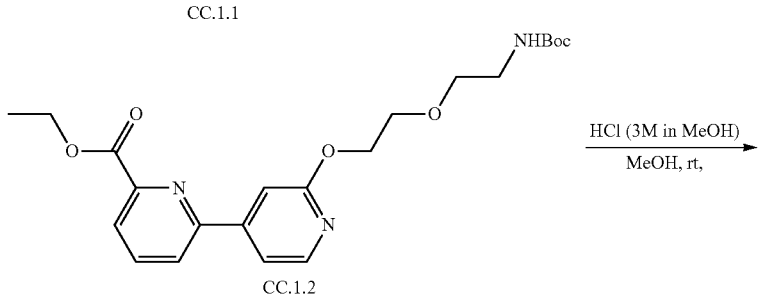

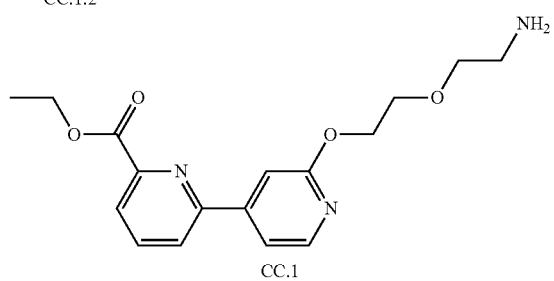

Compound CC.1.1 can be synthesized by displacement followed by protection of the amine with BOC. The Biaryl CC.1.2 is formed by a Suzuki between CC.1.1 and the boronic acid. The amine is deprotected to form CC.1.

Synthesis of Compound CC.2

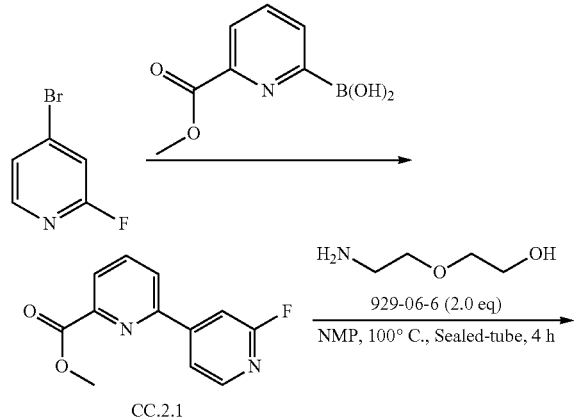

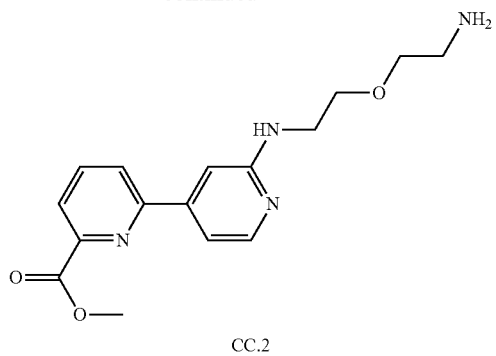

The biaryl CC.2.1 can be formed by a Pd coupling reaction between a boronic acid and bromide. The linker is installed by a displacement between an amine and CC.2.1 to afford CC.2.2. The amine is installed by forming the forming linker with a leaving group CC.2.3, and then displacing with azide followed by reduction to for the primary amine CC.2.

Synthesis of Compound CC.3

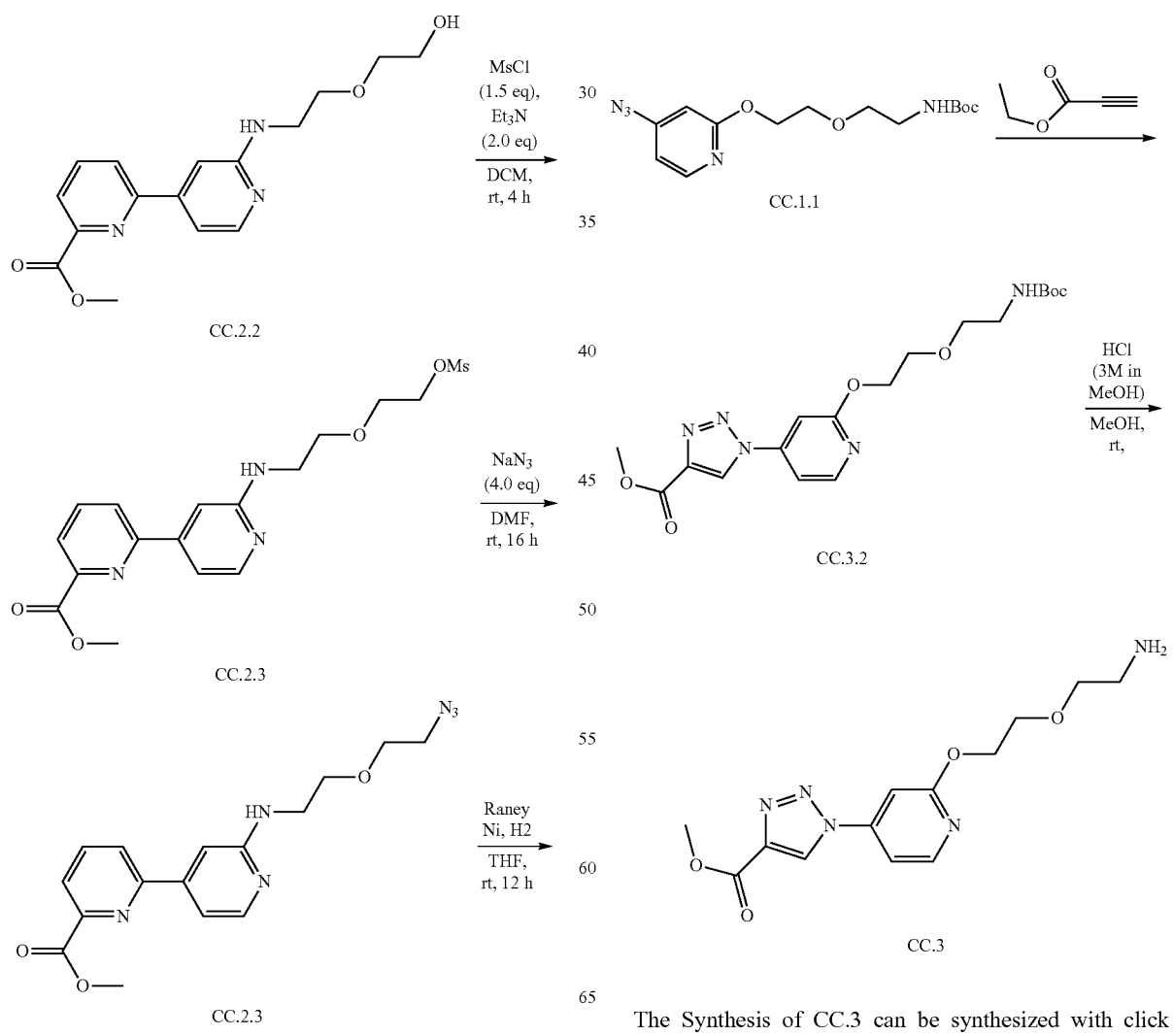

The Synthesis of CC.3 can be synthesized with click chemistry between an alkyne and azide to afford CC.3

Synthesis of Compound CC.4
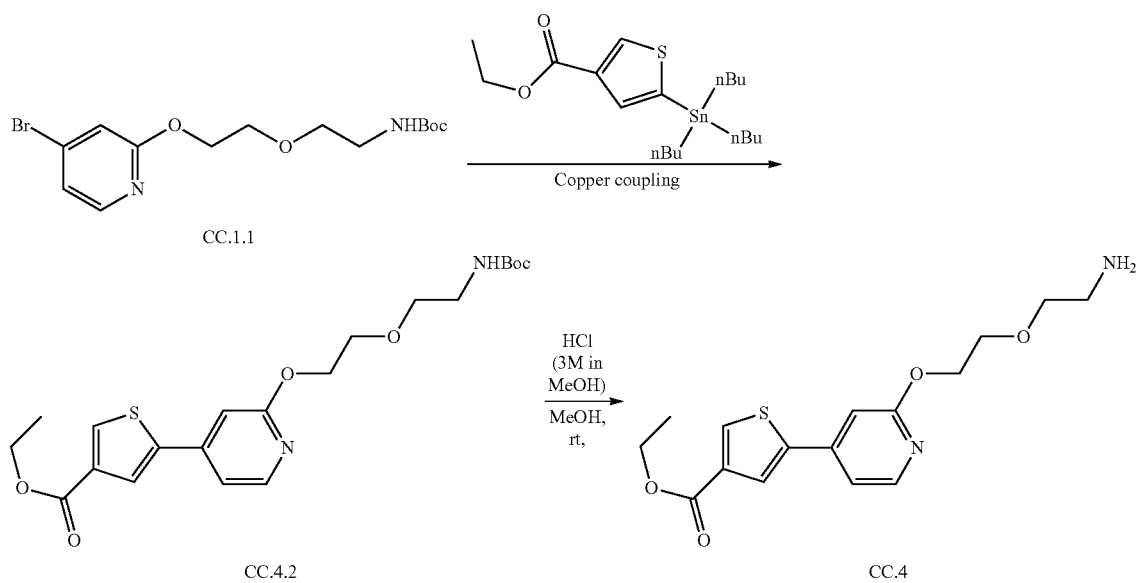
A stille coupling between and appropriate tin reagent and a bromide can afford CC.4.
Synthesis of CC.5
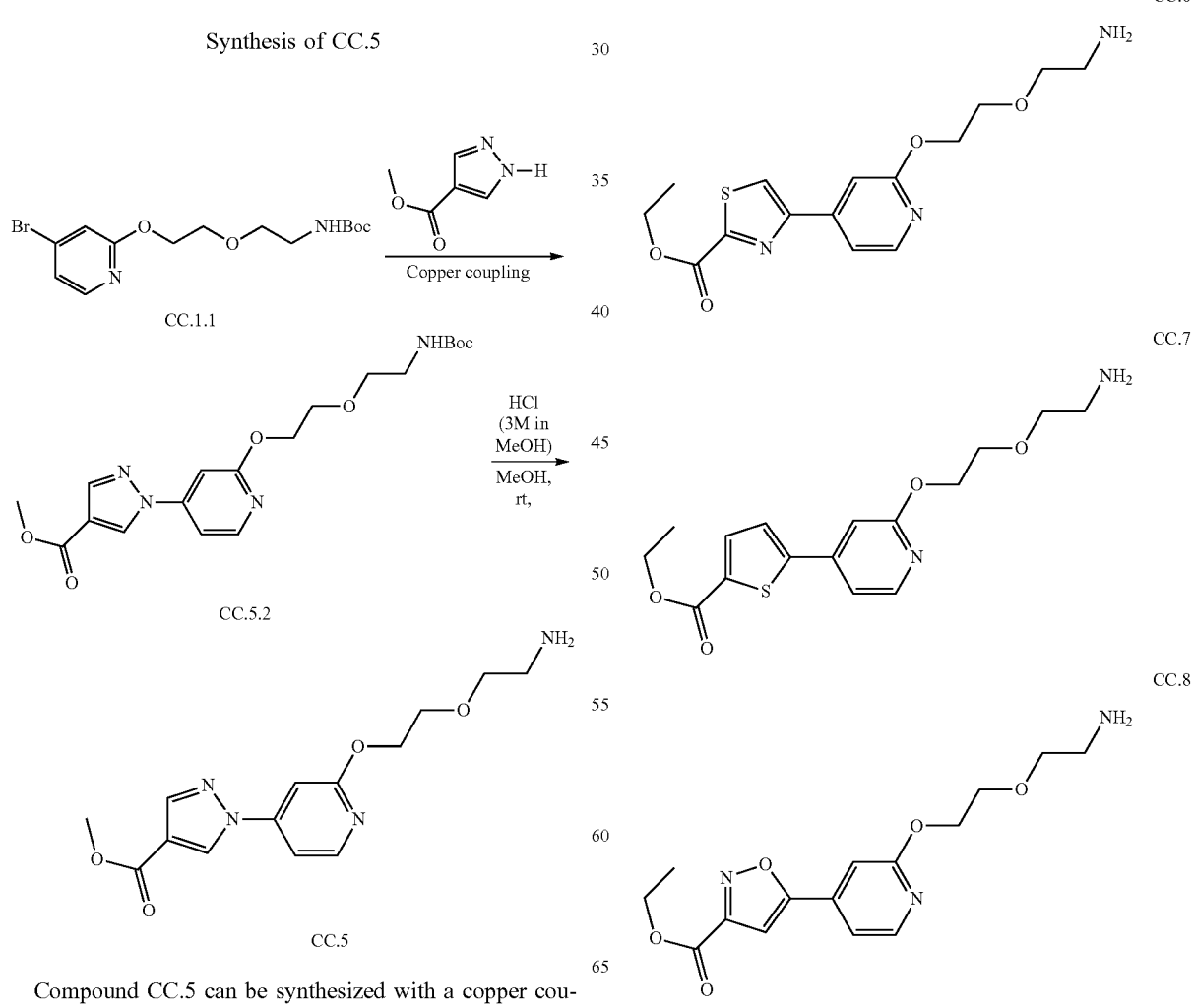
Compound CC.5 can be synthesized with a copper coupling between the bromide CC.1.1 and pyrazole ester.

Compounds CC.6, CC.7, and CC.8 can be synthesized similar to compound CC.4 by utilizing the appropriate tin coupling partner with CC.1.1
Compound CC.1 is coupled to the pyrrazole acid to afford 1.1. The ester is hydrolyzed to form followed by reduction of the nitro to deprotect the amine. The macrocycle is
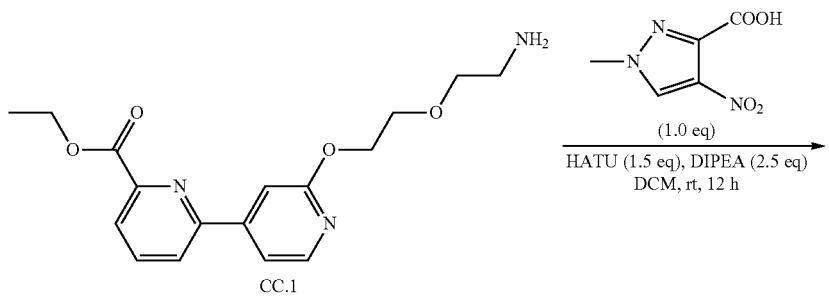
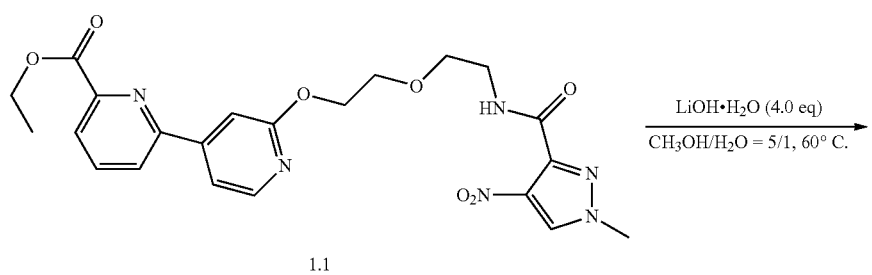
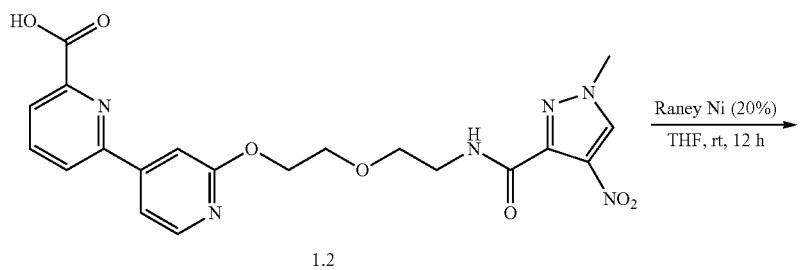
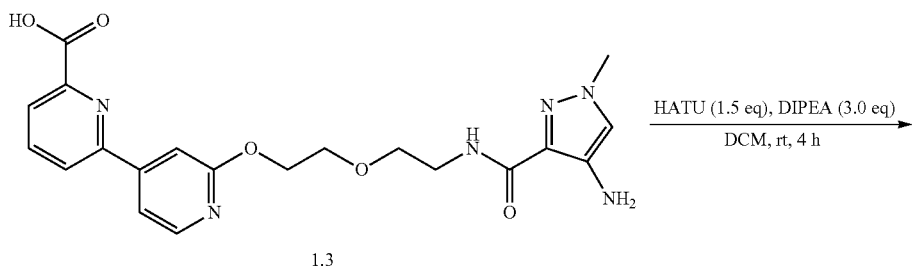
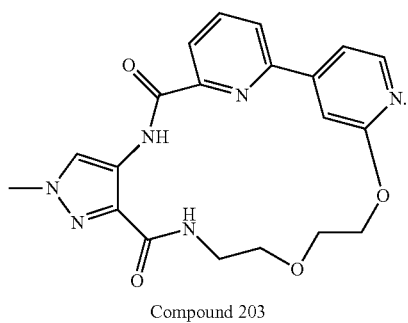
Compound 203 formed by a amide coupling reaction to afford Compound 203.

Example 226

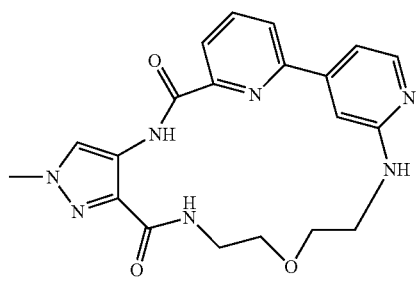

226

The Synthesis of Compound 226 is similar to the synthesis of Compound 203 except that Compound CC.2 is utilized.

Example 227

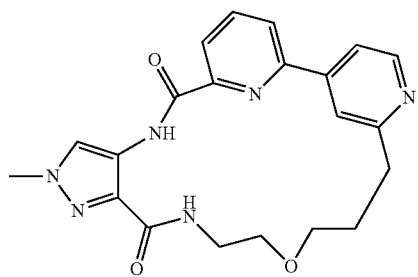

227

The Synthesis of Compound 227 is similar to the synthesis of Compound 203 except that Compound CC.3 is utilized.

Examples 228 to 233

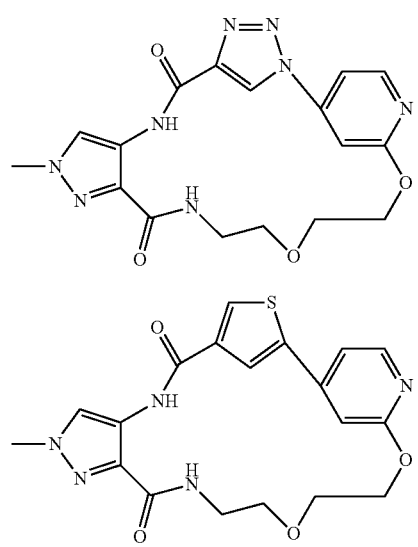

228

229

230

231

232

233

The Examples 228 to 233 can be synthesized utilized similar chemistry as Example 141 utilizing the appropriate amine—Ester CC.3 to CC.8.

Examples 209, 206, 211, 208, and 234 to 241

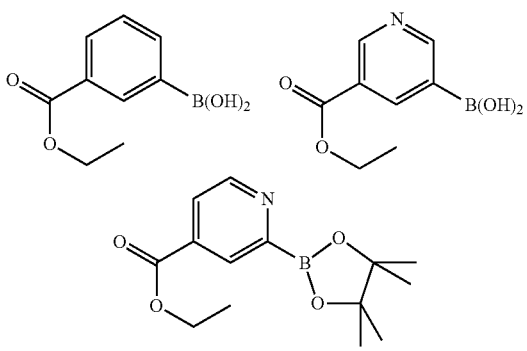

287
-continued
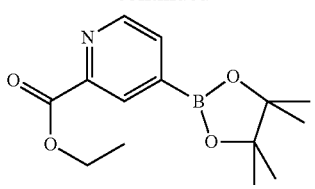
Example 209, 206, 211, 208 and 234 to 241 can be synthesized using a similar method as alternative synthesis for 203 utilizing the appropriate commercially available boron containing coupling partner.
209
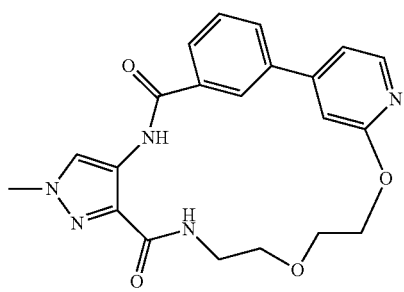
206
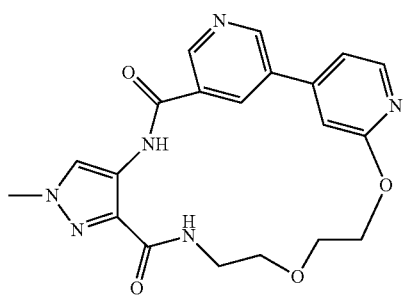
211
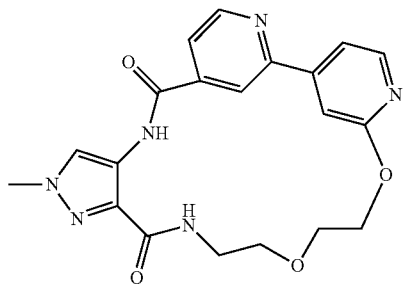
208
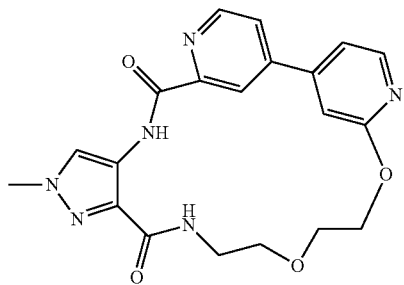
288
-continued
234
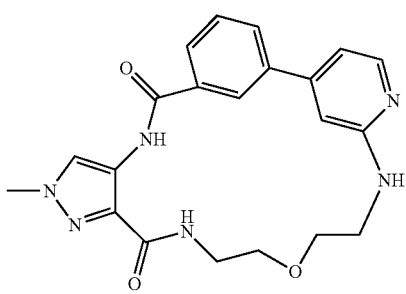
235
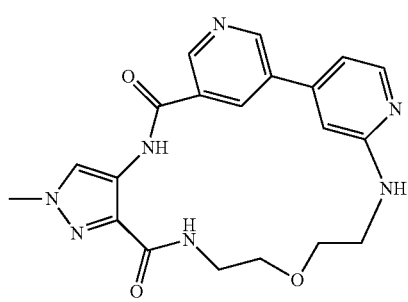
236
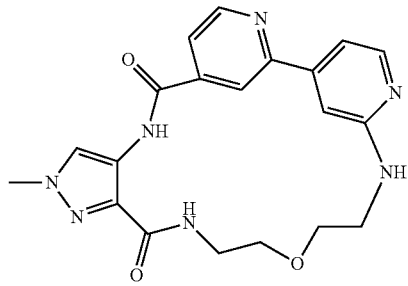
237
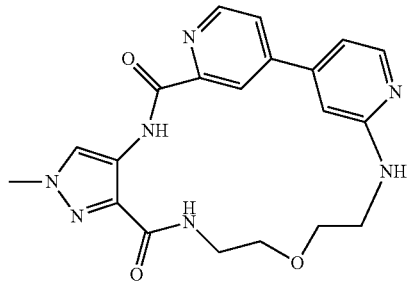
238
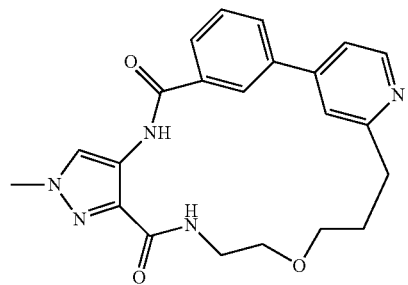

-continued

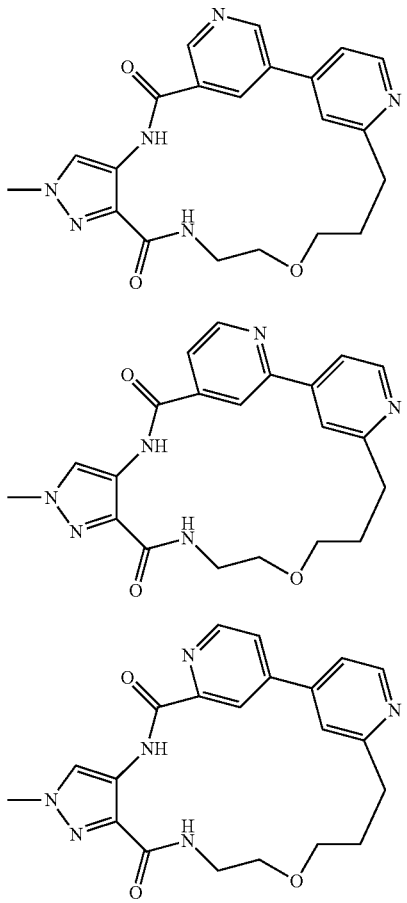

239

240

241

ASSAY EXAMPLES

Biochemical Assay

The biochemical assay is in a AlphaScreen format. The kinase reaction is based on the IRAK-4 phosphorylation of a biotin labeled peptide. The phosphopeptide is incubated with anti-phosphothreonine antibody as well as streptavidin- and protein A-coated beads. Binding of the protein-A coated beads to the antibody and the streptavidin beads to the peptide, leads to an energy transfer from one bead to the other, ultimately producing a luminescent/fluorescent signal.

Generally, the kinase reaction is carried out at 1 nM IRAK4, 1.6 µM peptide, 10 µM ATP in reaction buffer 50 mM Hepes, 60 mM NaCl, 5 mM MgCl2, 0.25 mM MnCl2, 2 mM DTT, 0.01% BSA, 0.01% Tween-20) for 3.5 h at RT.

Cell-Based Assay:

The cell-based assays is based on IL-6 ELISA quantification. Briefly, A549 cells are cultured in DMEM with 10% FBS medium. When cells reach 80% confluence they are trypsin treated and seeded in 96-well plate at 2.5×10^4 cells/well. Then, 20 ul of compound serial dilutions (starting at 10 uM, 10 points) are added to the cell plate; incubate for 1 hour at 37 C and stimulated with 2 ng/ml human IL-1 beta 37 C overnight. The next day 100 ul of cell supernatant per well are analyzed on a Human IL-6 Quantikine ELISA kit from R&D Systems.

The compounds described herein were tested for in the above biochemical and cell-based assays. The results are provided below, wherein the compound number corresponds to the numbers set forth in the examples above, "+" represents an I050 of less than 10 uM, "++" represents an I050 of less than or equal to 1 uM, and a "+++" represents an I050 of less than or equal to 0.1 uM, "†" represents an EC50 of greater than 10 uM, "††" represents an EC50 of less than 10 uM, and "†††" represents an EC50 of less than 1 uM.

| Example Number | Structure | Biochemical IRAK4 IC50 (uM) | Celluar Data EC50 (uM) |
|---|---|---|---|
| 1 | 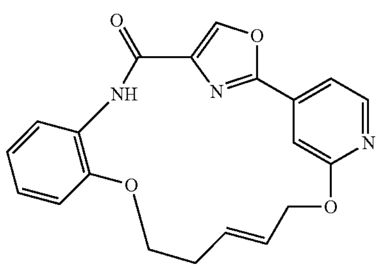 [SMILES: O=C1Nc2ccccc2OCC/C=C/COc2cc(ccn2)-c2nc1co2] | +++ | |
| 2 | 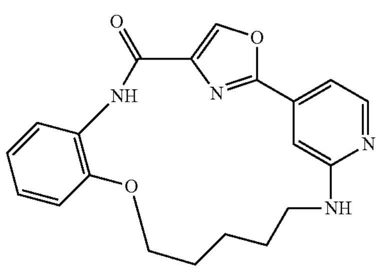 [SMILES: O=C1Nc2ccccc2OCCCCCNc2cc(ccn2)-c2nc1co2] | +++ | ††† |

-continued

| Example Number | Structure | Biochemical IRAK4 IC50 (uM) | Celluar Data EC50 (uM) |
|---|---|---|---|
| 3 | 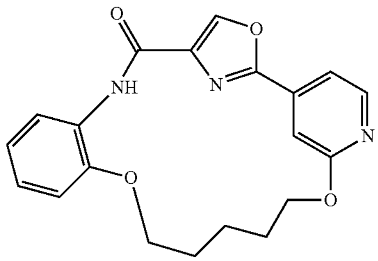 [SMILES: O=C1Nc2ccccc2OCCCCCOc2cc(ccn2)-c2nc1co2] | ++ | |
| 4 | 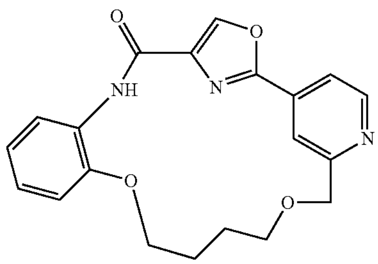 [SMILES: O=C1Nc2ccccc2OCCCCCCc2cc(ccn2)-c2nc1co2] | +++ | † |
| 5 | 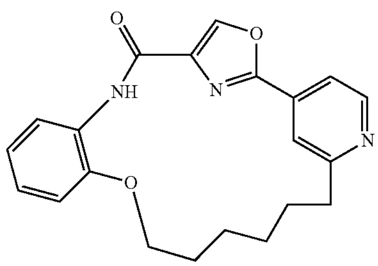 | +++ | |
| 6 | 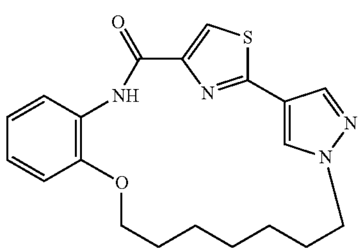 | ++ | |
| 7 | 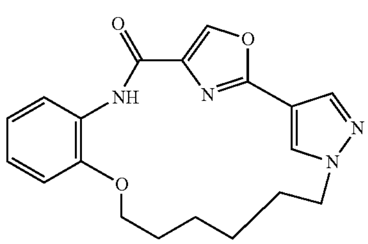 [SMILES: O=C1Nc2ccccc2OCCCCCCn2cc(cn2)-c2nc1co2] | +++ | †† |
| 8 | 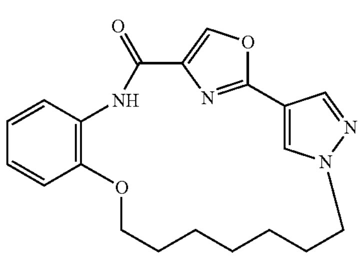 [SMILES: O=C1Nc2ccccc2OCCCCCCCn2cc(cn2)-c2nc1co2] | +++ | |

| Example Number | Structure | Biochemical IRAK4 IC50 (uM) | Celluar Data EC50 (uM) |
|---|---|---|---|
| 9 | 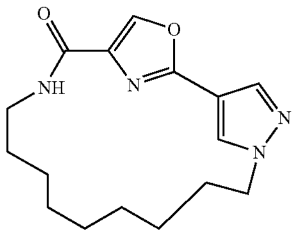 [SMILES: O=C1NCCCCCCCCCn2cc(cn2)-c2nc1co2] | ++ | |
| 10 | 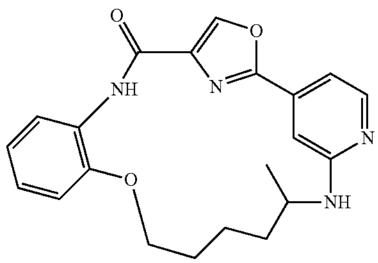 [SMILES: CC1CCCCOc2ccccc2NC(=O)c2coc(n2)-c2ccnc(c2)N1] | +++ | |
| 11 | 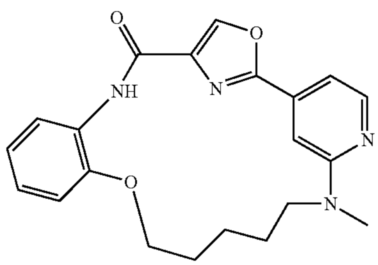 [SMILES: CN1CCCCCOc2ccccc2NC(=O)c2coc(n2)-c2ccnc1c2] | ++ | |
| 12 | 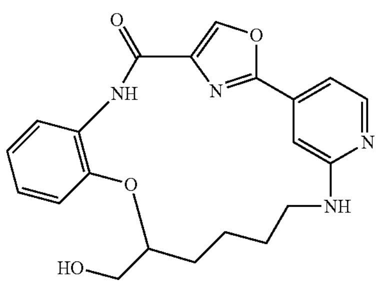 [SMILES: O=C1Nc2ccccc2OC(CO)CCCCNc2cc(ccn2)-c2nc1co2] | +++ | ††† |
| 13 | 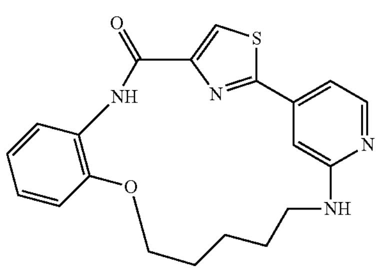 | +++ | |
| 14 | 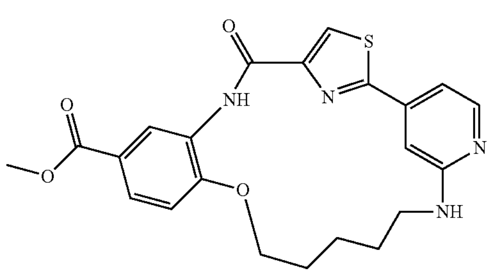 [SMILES: COC(=O)c1ccc2c(c1)NC(=O)c1csc(n1)-c1ccnc(c1)NCCCCCO2] | >10 | |

-continued
| Example Number | Structure | Biochemical IRAK4 IC50 (uM) | Celluar Data EC50 (uM) |
|---|---|---|---|
| 15 | 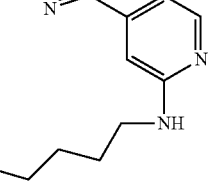 | + | |
| 16 | 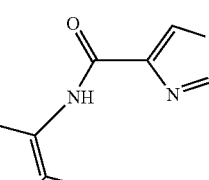 | +++ | † |
| 17 | 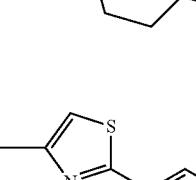 | +++ | |
| 18 | 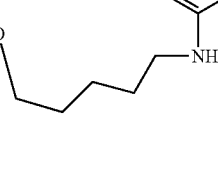 | +++ | |
| 19 | 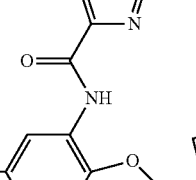 | +++ | |

-continued
| Example Number | Structure | Biochemical IRAK4 IC50 (uM) | Celluar Data EC50 (uM) |
|---|---|---|---|
| 20 | 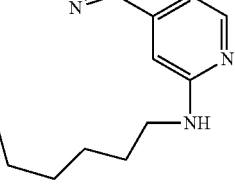 | | +++ |
| 21 | 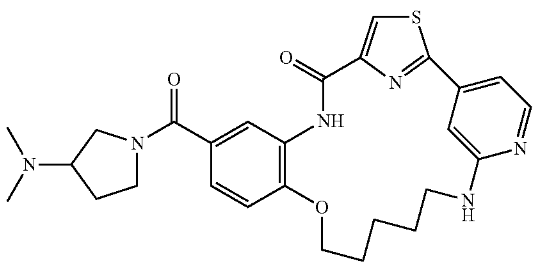 [SMILES: CN(C)C1CCN(C(=O)c2ccc3c(c2)NC(=O)c2csc(n2)-c2ccnc(c2)NCCCCCO3)C1] | | +++ |
| 22 | 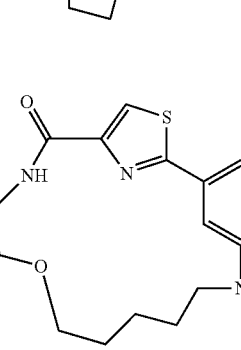 | | +++ |
| 23 | 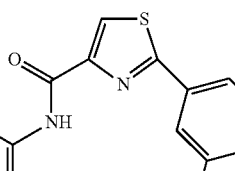 | | +++ |
| 24 | 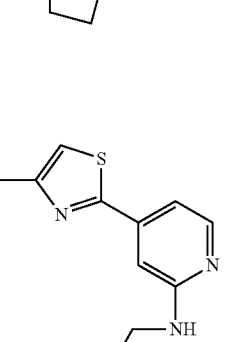 | | +++ |

-continued

| Example Number | Structure | Biochemical IRAK4 IC50 (uM) | Celluar Data EC50 (uM) |
|---|---|---|---|
| 25 | 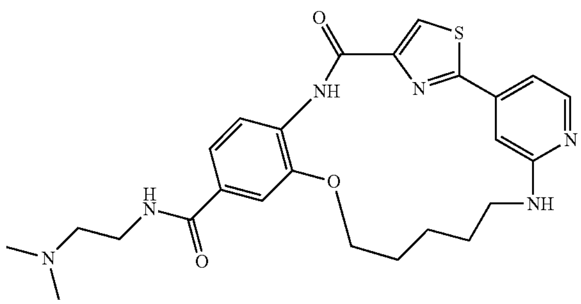 [SMILES: CN(C)CCNC(=O)c1ccc2c(c1)OCCCCCNc1cc(ccn1)-c1nc(cs1)C(=O)N2] | +++ | |
| 26 | 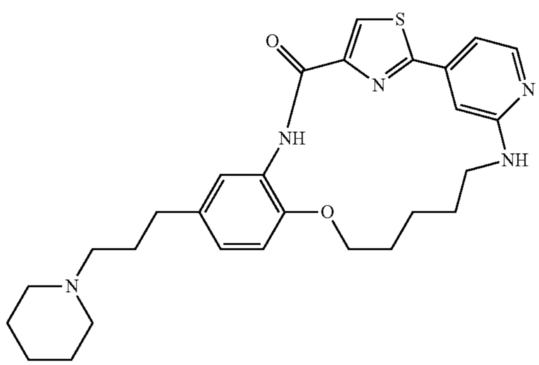 [SMILES: O=C1Nc2cc(CCCN3CCCCC3)ccc2OCCCCCNc2cc(ccn2)-c2nc1cs2] | +++ | |
| 27 | 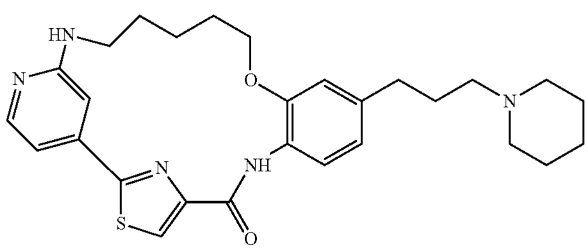 [SMILES: O=C1Nc2ccc(CCCN3CCCCC3)cc2OCCCCCNc2cc(ccn2)-c2nc1cs2] | +++ | |
| 28 | 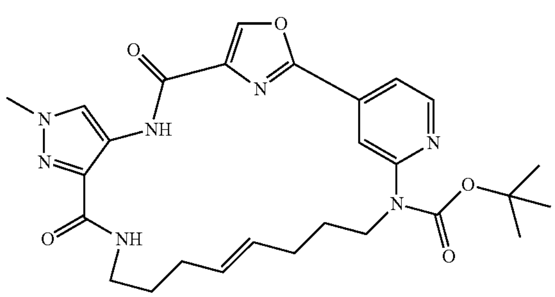 [SMILES: Cn1cc2c(n1)C(=O)NCCC/C=C/CCCN(C(=O)OC(C)(C)C)c1cc(ccn1)-c1nc(co1)C(=O)N2] | ++ | |
| 29 | 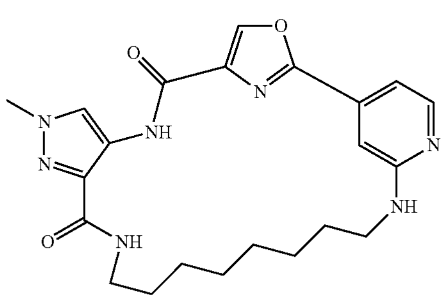 [SMILES: Cn1cc2c(n1)C(=O)NCCCCCCCCNc1cc(ccn1)-c1nc(co1)C(=O)N2] | +++ | ††† |

-continued

| Example Number | Structure | Biochemical IRAK4 IC50 (uM) | Celluar Data EC50 (uM) |
|---|---|---|---|
| 31 | 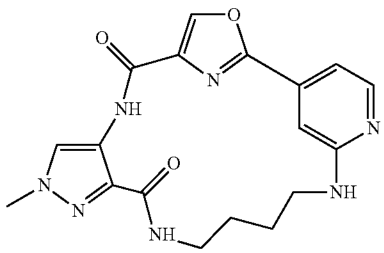 [SMILES: Cn1cc2c(n1)C(=O)NCCCCNc1cc(ccn1)-c1nc(co1)C(=O)N2] | +++ | |
| 32 | 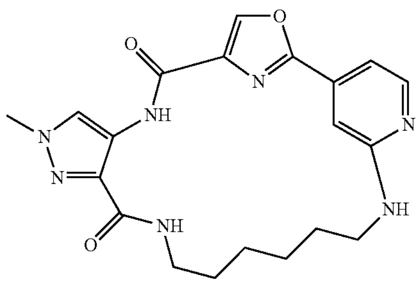 [SMILES: Cn1cc2c(n1)C(=O)NCCCCCCNc1cc(ccn1)-c1nc(co1)C(=O)N2] | +++ | ††† |
| 33 | 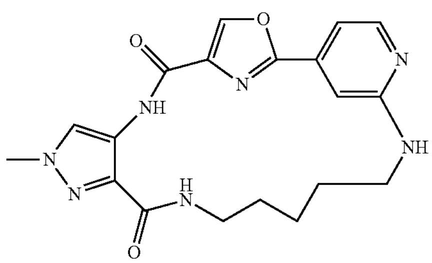 [SMILES: Cn1cc2c(n1)C(=O)NCCCCCNc1cc(ccn1)-c1nc(co1)C(=O)N2] | +++ | |
| 34 | 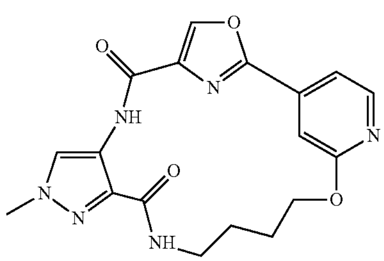 [SMILES: Cn1cc2c(n1)C(=O)NCCCCOc1cc(ccn1)-c1nc(co1)C(=O)N2] | +++ | ††† |
| 35 | 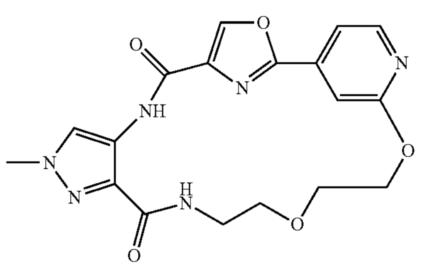 | +++ | |
| 36 | 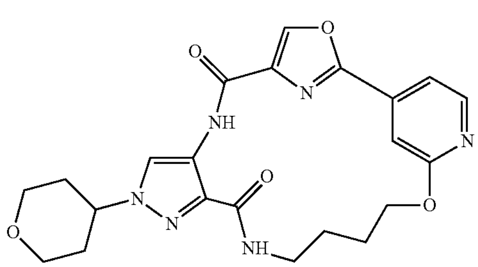 [SMILES: O=C1Nc2cn(C3CCOCC3)nc2C(=O)NCCCCOc2cc(ccn2)-c2nc1co2] | +++ | |

-continued

| Example Number | Structure | Biochemical IRAK4 IC50 (uM) | Celluar Data EC50 (uM) |
|---|---|---|---|
| 37 | 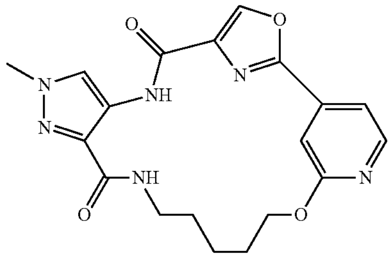 [SMILES: Cn1cc2c(n1)C(=O)NCCCCCOc1cc(ccn1)-c1nc(co1)C(=O)N2] | +++ | |
| 38 | 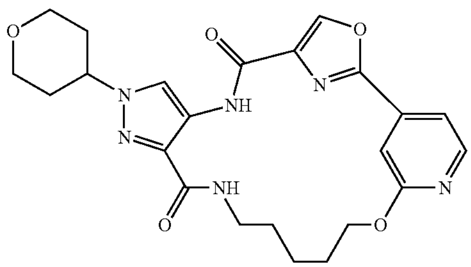 [SMILES: O=C1Nc2cn(C3CCOCC3)nc2C(=O)NCCCCCOc2cc(ccn2)-c2nc1co2] | +++ | |
| 39 | 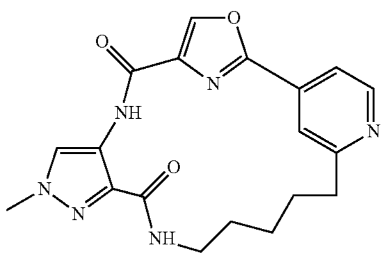 [SMILES: Cn1cc2c(n1)C(=O)NCCCCCc1cc(ccn1)-c1nc(co1)C(=O)N2] | +++ | |
| 40 | 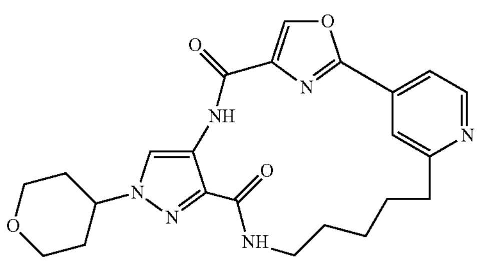 [SMILES: O=C1Nc2cn(C3CCOCC3)nc2C(=O)NCCCCCc2cc(ccn2)-c2nc1co2] | +++ | †† |
| 41 | 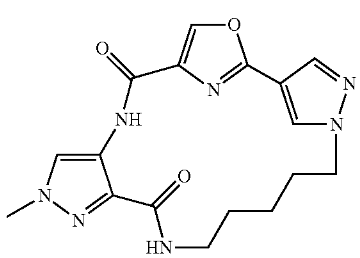 [SMILES: Cn1cc2c(n1)C(=O)NCCCCCn1cc(cn1)-c1nc(co1)C(=O)N2] | ++ | |
| 42 | 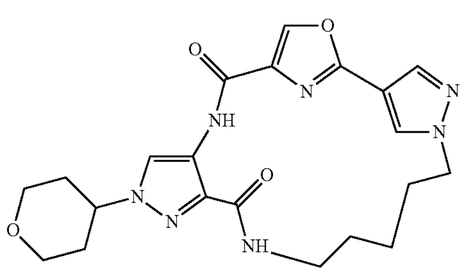 [SMILES: O=C1Nc2cn(C3CCOCC3)nc2C(=O)NCCCCCn2cc(cn2)-c2nc1co2] | ++ | |

-continued

| Example Number | Structure | Biochemical IRAK4 IC50 (uM) | Celluar Data EC50 (uM) |
|---|---|---|---|
| 43 | 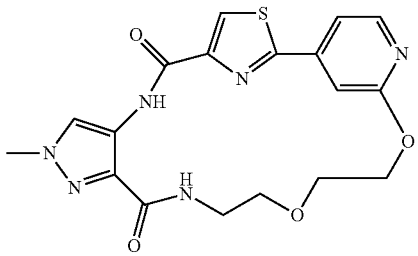 [SMILES: Cn1cc2c(n1)C(=O)NCCOCCOc1cc(ccn1)-c1nc(cs1)C(=O)N2] | +++ | †† |
| 44 | 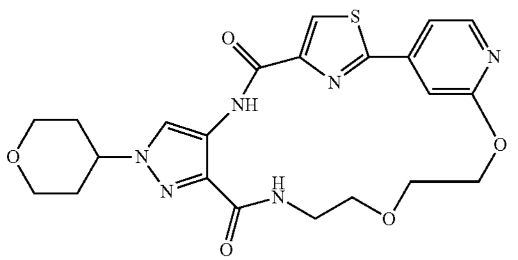 [SMILES: O=C1Nc2cn(C3CCOCC3)nc2C(=O)NCCOCCOc2cc(ccn2)-c2nc1cs2] | +++ | †† |
| 45 | 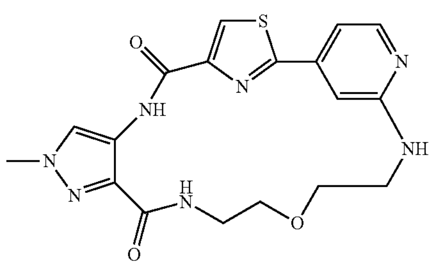 | +++ | ††† |
| 46 | 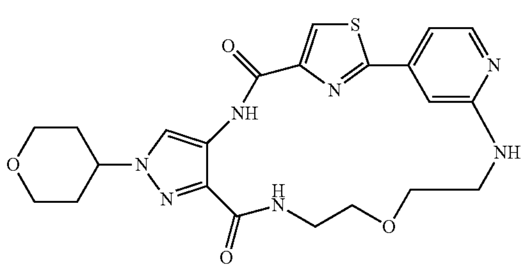 [SMILES: O=C1Nc2cn(C3CCOCC3)nc2C(=O)NCCOCCNc2cc(ccn2)-c2nc1cs2] | +++ | ††† |
| 47 | 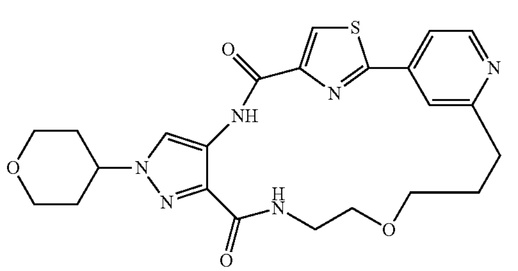 [SMILES: O=C1Nc2cn(C3CCOCC3)nc2C(=O)NCCOCCCc2cc(ccn2)-c2nc1cs2] | +++ | ††† |
| 48 | 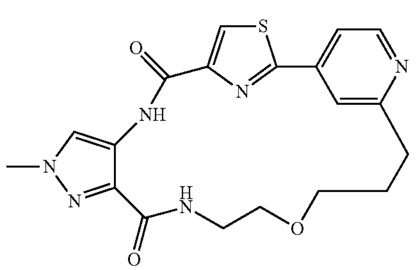 [SMILES: Cn1cc2c(n1)C(=O)NCCOCCCc1cc(ccn1)-c1nc(cs1)C(=O)N2] | +++ | †† |

| Example Number | Structure | Biochemical IRAK4 IC50 (uM) | Cellular Data EC50 (uM) |
|---|---|---|---|
| 49 | 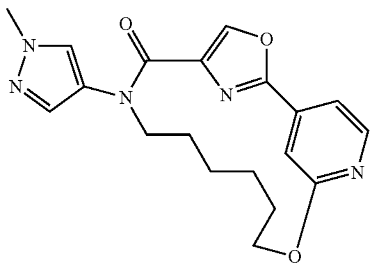 [SMILES: Cn1cc(N2CCCCCCOc3cc(ccn3)-c3nc(co3)C2=O)cn1] | | |
| 50 | 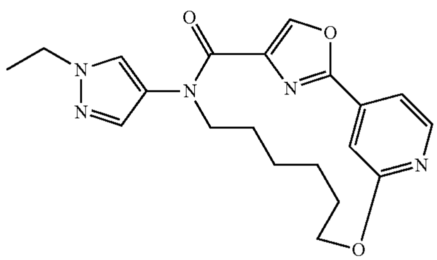 [SMILES: CCn1cc(N2CCCCCCOc3cc(ccn3)-c3nc(co3)C2=O)cn1] | >10 | |
| 51 | 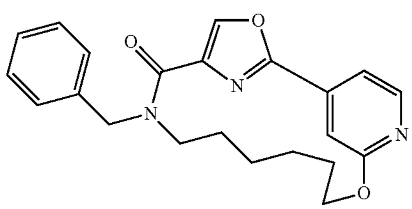 [SMILES: O=C1c2coc(n2)-c2ccnc(c2)OCCCCCCN1Cc1ccccc1] | + | |
| 52 | 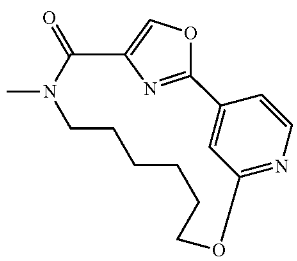 [SMILES: CN1CCCCCCOc2cc(ccn2)-c2nc(co2)C1=O] | >10 | |
| 53 | 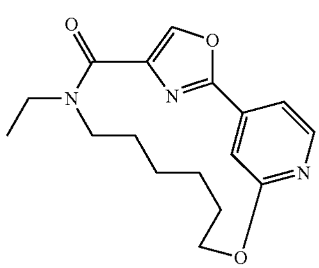 [SMILES: CCN1CCCCCCOc2cc(ccn2)-c2nc(co2)C1=O] | +++ | |
| 54 | 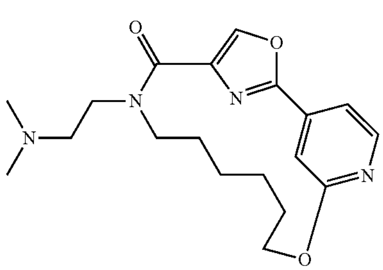 [SMILES: CN(C)CCN1CCCCCCOc2cc(ccn2)-c2nc(co2)C1=O] | ++ | |

-continued
| Example Number | Structure | Biochemical IRAK4 IC50 (uM) | Celluar Data EC50 (uM) |
|---|---|---|---|
| 55 | 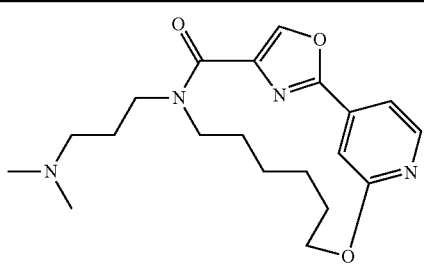 | >10 | |
| 56 | 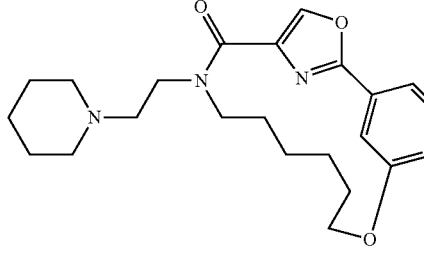 | >10 | |
| 57 | 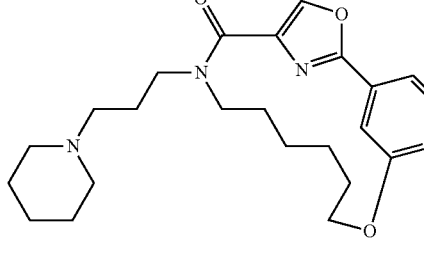 | >10 | |
| 58 | 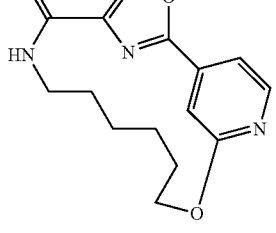 | ++ | |
| 59 | 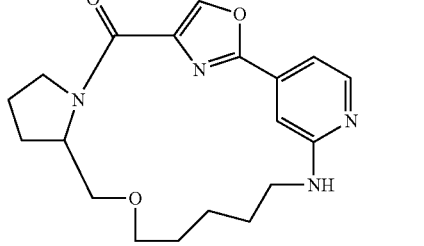 | +++ | |
| 61 | 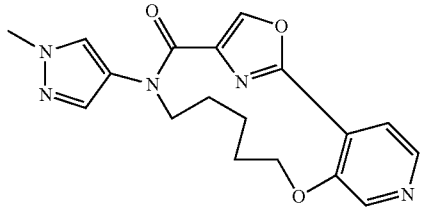 [SMILES: Cn1cc(N2CCCCCOc3cnccc3-c3nc(co3)C2=O)cn1] | ++ | |

-continued

| Example Number | Structure | Biochemical IRAK4 IC50 (uM) | Celluar Data EC50 (uM) |
|---|---|---|---|
| 62 | 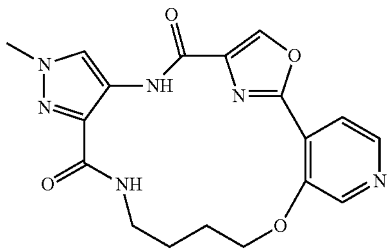 [SMILES: Cn1cc2c(n1)C(=O)NCCCCOc1cnccc1-c1nc(co1)C(=O)N2] | | ++ |
| 63 | 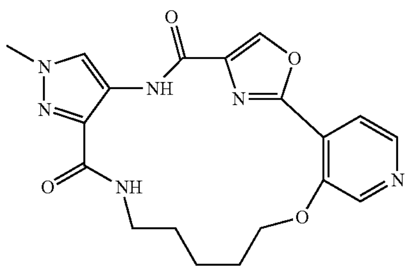 [SMILES: Cn1cc2c(n1)C(=O)NCCCCCOc1cnccc1-c1nc(co1)C(=O)N2] | | +++ |
| 64 | 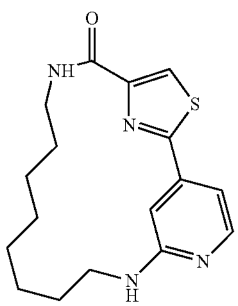 [SMILES: O=C1NCCCCCCCCNc2cc(ccn2)-c2nc1cs2] | | ++ |
| 65 | 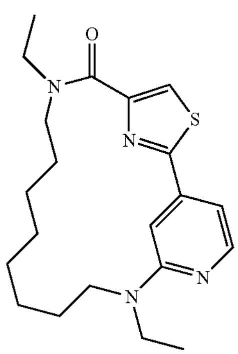 [SMILES: CCN1CCCCCCCCN(CC)c2cc(ccn2)-c2nc(cs2)C1=O] | | + |
| 66 | 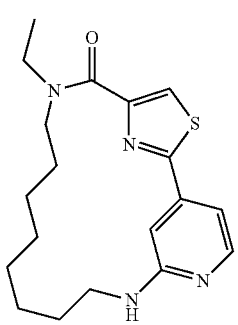 [SMILES: CCN1CCCCCCCCNc2cc(ccn2)-c2nc(cs2)C1=O] | | ++ |

| Example Number | Structure | Biochemical IRAK4 IC50 (uM) | Celluar Data EC50 (uM) |
|---|---|---|---|
| 67 | 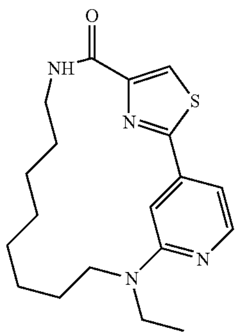 [SMILES: CCN1CCCCCCCCNC(=O)c2csc(n2)-c2ccnc1c2] | | ++ |
| 68 | 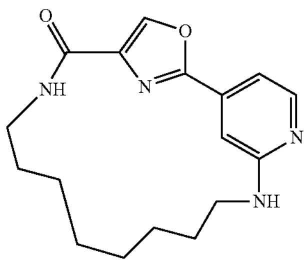 [SMILES: O=C1NCCCCCCCCNc2cc(ccn2)-c2nc1co2] | | +++ |
| 69 | 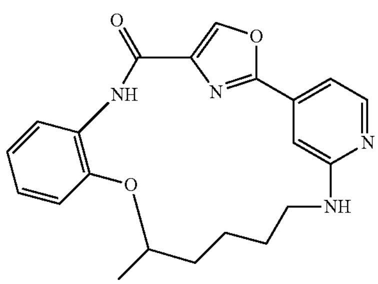 [SMILES: CC1CCCCNc2cc(ccn2)-c2nc(co2)C(=O)Nc2ccccc2O1] | | +++ |
| 70 | 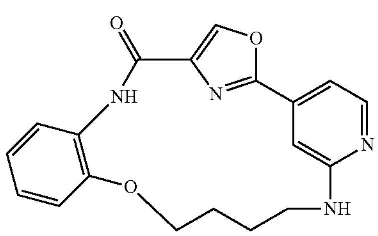 [SMILES: O=C1Nc2ccccc2OCCCCNc2cc(ccn2)-c2nc1co2] | | >10 |
| 71 | 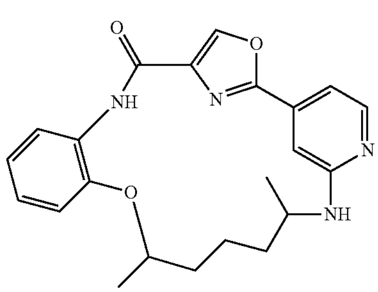 [SMILES: CC1CCCC(C)Oc2ccccc2NC(=O)c2coc(n2)-c2ccnc(c2)N1] | | +++ |

-continued

| Example Number | Structure | Biochemical IRAK4 IC50 (uM) | Celluar Data EC50 (uM) |
|---|---|---|---|
| 72 | 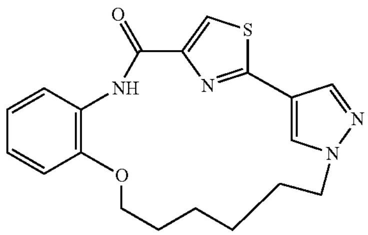 [SMILES: O=C1Nc2ccccc2OCCCCCCn2cc(cn2)-c2nc1cs2] | +++ | |
| 73 | 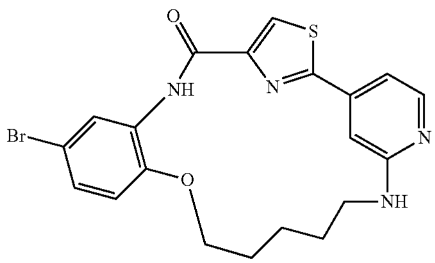 [SMILES: O=C1Nc2cc(Br)ccc2OCCCCCNc2cc(ccn2)-c2nc1cs2] | +++ | |
| 74 | 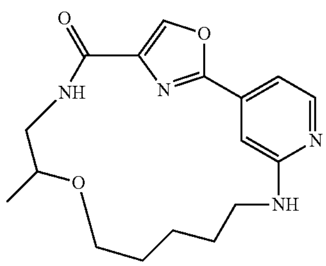 [SMILES: CC1CNC(=O)c2coc(n2)-c2ccnc(c2)NCCCCCO1] | + | |
| 75 | 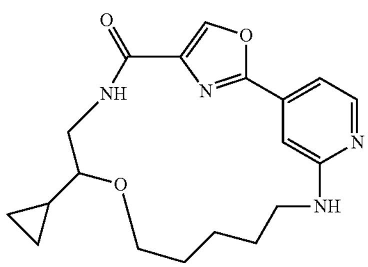 [SMILES: O=C1NCC(C2CC2)OCCCCCNc2cc(ccn2)-c2nc1co2] | ++ | |
| 76 | 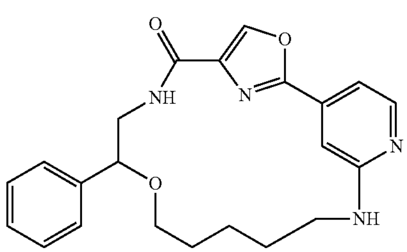 [SMILES: O=C1NCC(c2ccccc2)OCCCCCNc2cc(ccn2)-c2nc1co2] | +++ | |
| 77 | 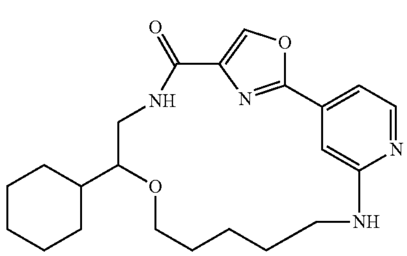 [SMILES: O=C1NCC(C2CCCCC2)OCCCCCNc2cc(ccn2)-c2nc1co2] | >10 | |

| Example Number | Structure | Biochemical IRAK4 IC50 (uM) | Celluar Data EC50 (uM) |
|---|---|---|---|
| 78 | 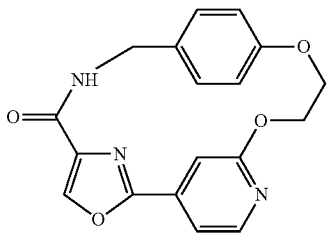 [SMILES: O=C1NCc2ccc(cc2)OCCOc2cc(ccn2)-c2nc1co2] | + | |
| 79 | 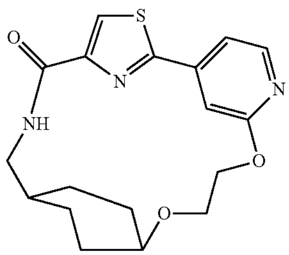 [SMILES: O=C1NCC2CCC(CC2)OCCOc2cc(ccn2)-c2nc1cs2] | | |
| 80 | 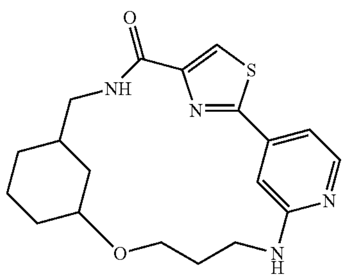 [SMILES: O=C1NCC2CCCC(C2)OCCCNc2cc(ccn2)-c2nc1cs2] | + | |
| 81 | 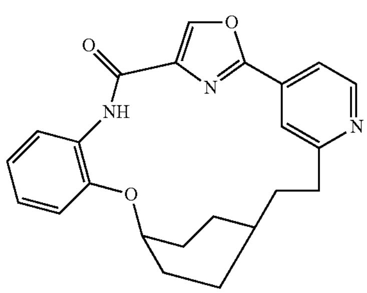 [SMILES: O=C1Nc2ccccc2OC2CCC(CCc3cc(ccn3)-c3nc1co3)CC2] | +++ | |
| 82 | 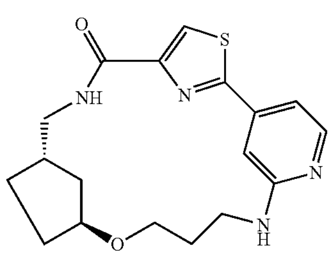 [SMILES: O=C1NC[C@H]2CC[C@@H](C2)OCCCNc2cc(ccn2)-c2nc1cs2] | ++ | †† |
| 83 | 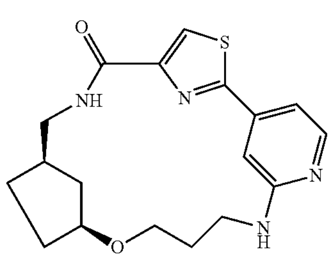 [SMILES: O=C1NC[C@@H]2CC[C@@H](C2)OCCCNc2cc(ccn2)-c2nc1cs2] | +++ | †† |

-continued

| Example Number | Structure | Biochemical IRAK4 IC50 (uM) | Celluar Data EC50 (uM) |
| --- | --- | --- | --- |
| 84 | 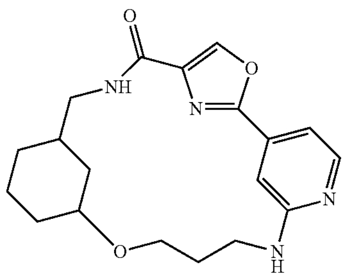 | | |
| 85 | 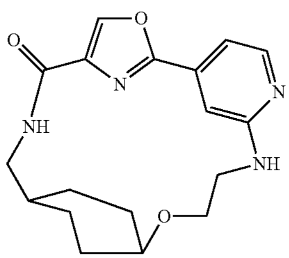 | | ++ |
| 86 | 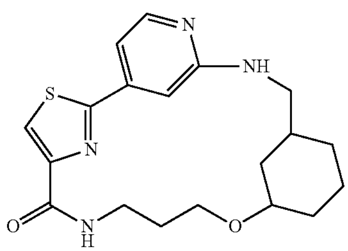 [SMILES: O=C1NCCCOC2CCCC(CNc3cc(ccn3)-c3nc1cs3)C2] | | >10 |
| 87 | 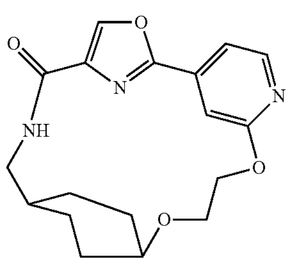 [SMILES: O=C1NCC2CCC(CC2)OCCOc2cc(ccn2)-c2nc1co2] | | |
| 88 | 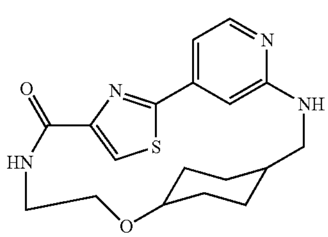 [SMILES: O=C1NCCOC2CCC(CC2)CNc2cc(ccn2)-c2nc1cs2] | | + |
| 89 | 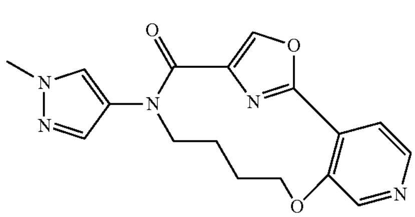 [SMILES: Cn1cc(N2CCCCOc3cnccc3-c3nc(co3)C2=O)cn1] | | >10 |

-continued

| Example Number | Structure | Biochemical IRAK4 IC50 (uM) | Celluar Data EC50 (uM) |
|---|---|---|---|
| 90 | 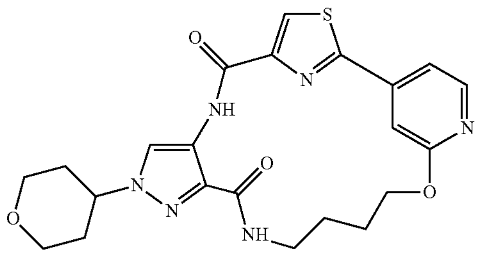 [SMILES: O=C1Nc2cn(C3CCOCC3)nc2C(=O)NCCCCOc2cc(ccn2)-c2nc1cs2] | +++ | †† |
| 91 | 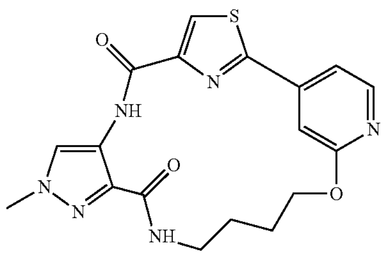 | +++ | ††† |
| 92 | 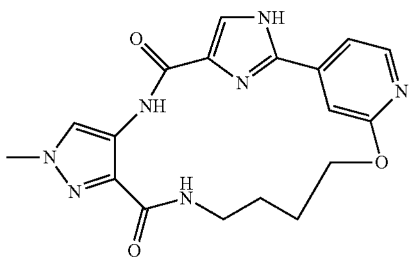 [SMILES: Cn1cc2c(n1)C(=O)NCCCCOc1cc(ccn1)-c1nc(c[nH]1)C(=O)N2] | + | |
| 93 | 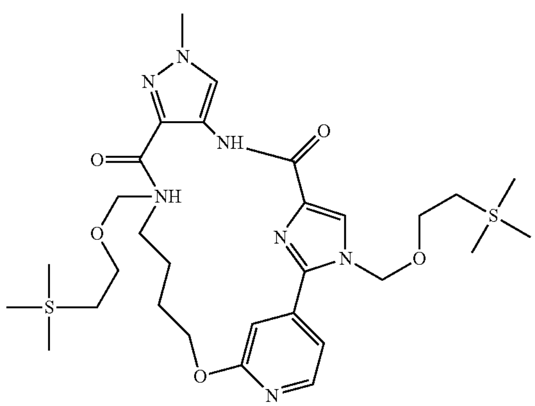 | + | |
| 94 | 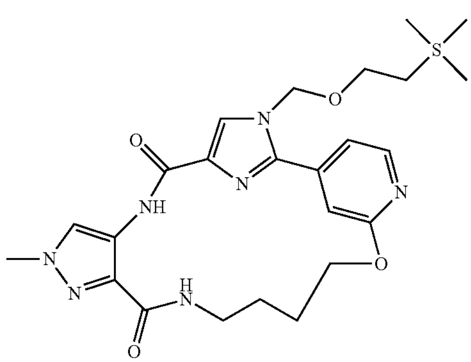 | >10 | |

-continued

| Example Number | Structure | Biochemical IRAK4 IC50 (uM) | Celluar Data EC50 (uM) |
|---|---|---|---|
| 95 | 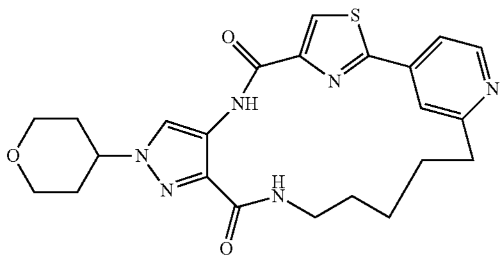 [SMILES: O=C1Nc2cn(C3CCOCC3)nc2C(=O)NCCCCCc2cc(ccn2)-c2nc1cs2] | +++ | ††† |
| 96 | 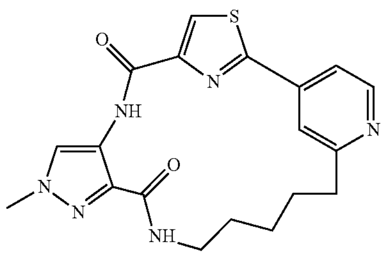 | +++ | †† |
| 97 | 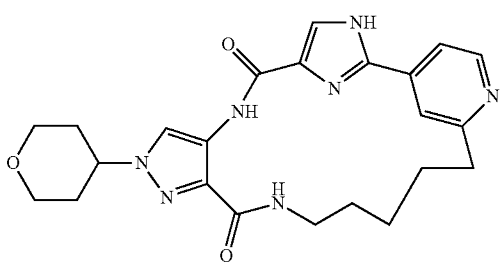 [SMILES: O=C1Nc2cn(C3CCOCC3)nc2C(=O)NCCCCCc2cc(ccn2)-c2nc1c[nH]2] | + | |
| 98 | 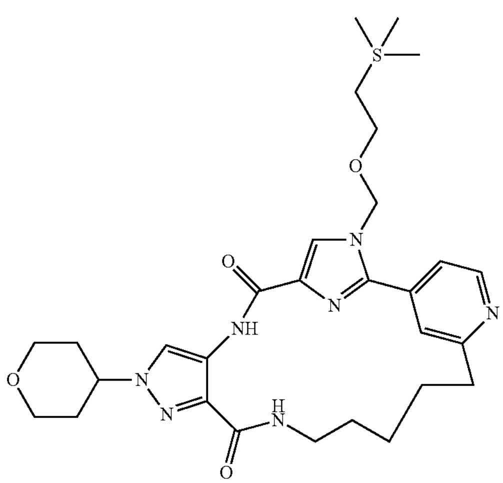 [SMILES: CS(C)(C)CCOCn1cc2nc1-c1ccnc(c1)CCCCCNC(=O)c1nn(C3CCOCC3)cc1NC2=O] | + | |

| Example Number | Structure | Biochemical IRAK4 IC50 (uM) | Cellular Data EC50 (uM) |
|---|---|---|---|
| 99 | 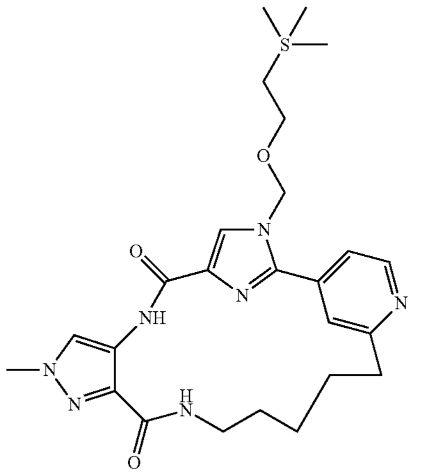 [SMILES: Cn1cc2c(n1)C(=O)NCCCCCc1cc(ccn1)-c1nc(cn1COCCS(C)(C)C)C(=O)N2] | + | |
| 100 | 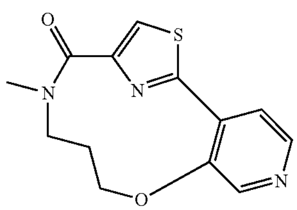 [SMILES: CN1CCCOc2cnccc2-c2nc(cs2)C1=O] | >10 | |
| 101 | 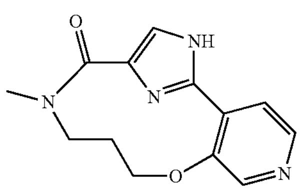 [SMILES: CN1CCCOc2cnccc2-c2nc(c[nH]2)C1=O] | >10 | |
| 102 | 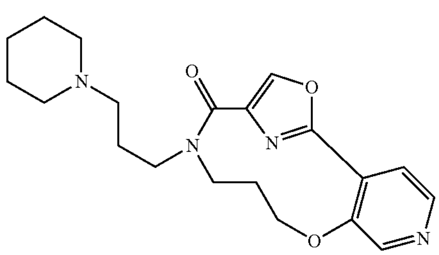 [SMILES: O=C1c2coc(n2)-c2ccncc2OCCCN1CCCN1CCCCC1] | >10 | |
| 103 | 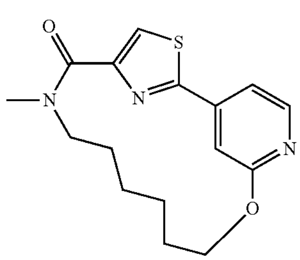 [SMILES: CN1CCCCCCOc2cc(ccn2)-c2nc(cs2)C1=O] | + | |

-continued
| Example Number | Structure | Biochemical IRAK4 IC50 (uM) | Celluar Data EC50 (uM) |
|---|---|---|---|
| 104 | 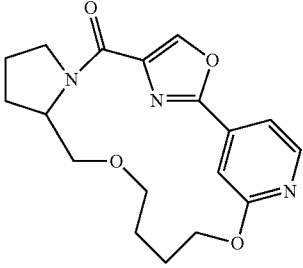 | + | |
| 105 | 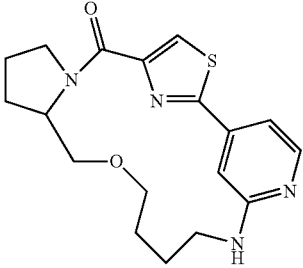 | ++ | |
| 106 | 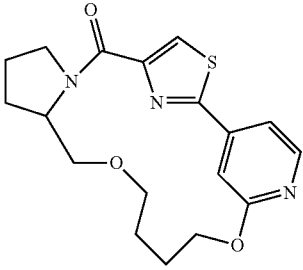 [SMILES: O=C1c2csc(n2)-c2ccnc(c2)OCCCCOCC2CCCN12] | + | |
| 107 | 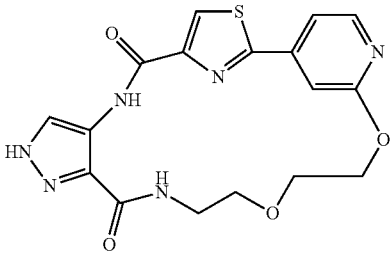 [SMILES: O=C1Nc2c[nH]nc2C(=O)NCCOCCOc2cc(ccn2)-c2nc1cs2] | +++ | † |
| 108 | 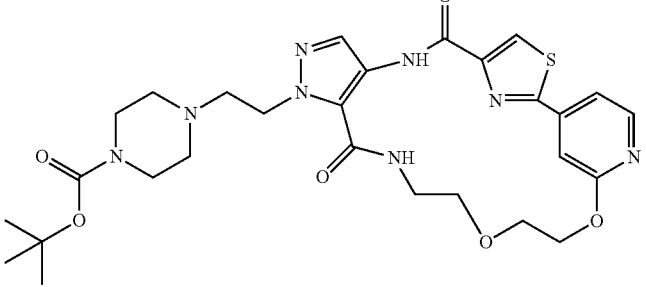 | ++ | † |

-continued
| Example Number | Structure | Biochemical IRAK4 IC50 (uM) | Celluar Data EC50 (uM) |
|---|---|---|---|
| 109 | 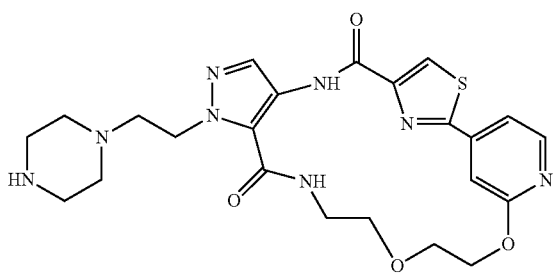 [SMILES: O=C1Nc2cnn(CCN3CCNCC3)c2C(=O)NCCOCCOc2cc(ccn2)-c2nc1cs2] | + | † |
| 110 | 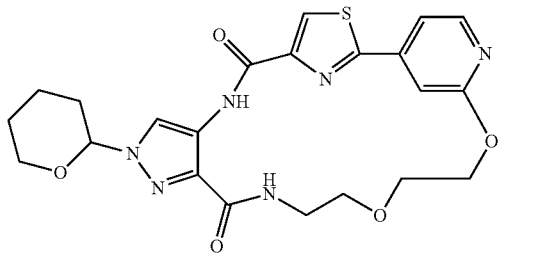 [SMILES: O=C1Nc2cn(C3CCCCO3)nc2C(=O)NCCOCCOc2cc(ccn2)-c2nc1cs2] | +++ | †† |
| 111 | 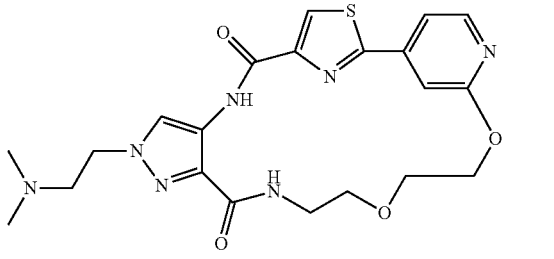 [SMILES: CN(C)CCn1cc2c(n1)C(=O)NCCOCCOc1cc(ccn1)-c1nc(cs1)C(=O)N2] | ++ | † |
| 112 | 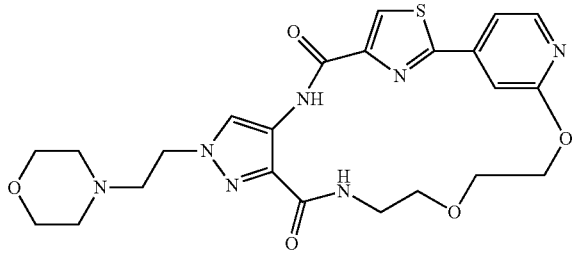 [SMILES: O=C1Nc2cn(CCN3CCOCC3)nc2C(=O)NCCOCCOc2cc(ccn2)-c2nc1cs2] | +++ | †† |
| 113 | 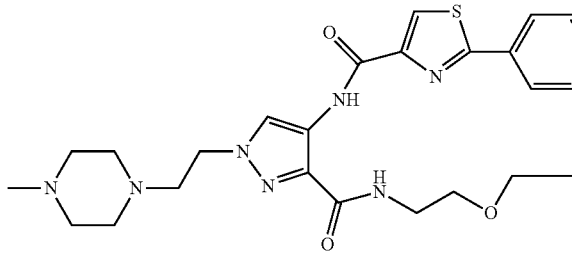 | +++ | †† |

-continued

| Example Number | Structure | Biochemical IRAK4 IC50 (uM) | Celluar Data EC50 (uM) |
|---|---|---|---|
| 114 | 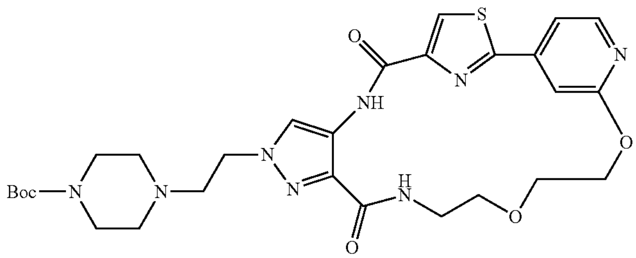 [SMILES: CC(C)(C)OC(=O)N1CCN(CCn2cc3c(n2)C(=O)NCCOCCOc2cc(ccn2)-c2nc(cs2)C(=O)N3)CC1] | +++ | † |
| 115 | 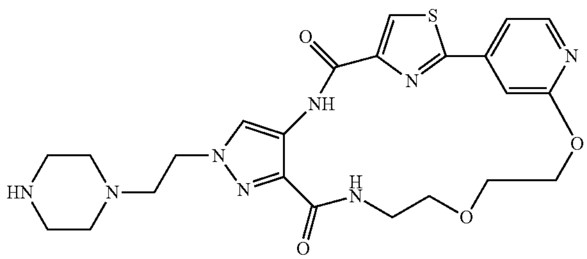 [SMILES: O=C1Nc2cn(CCN3CCNCC3)nc2C(=O)NCCOCCOc2cc(ccn2)-c2nc1cs2] | +++ | †† |
| 116 | 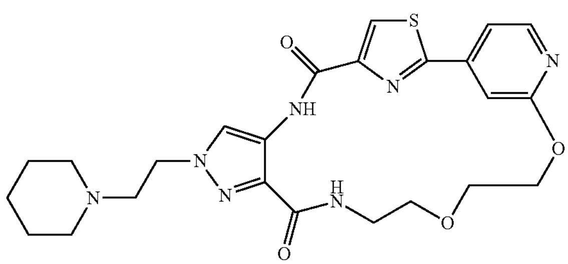 [SMILES: O=C1Nc2cn(CCN3CCCCC3)nc2C(=O)NCCOCCOc2cc(ccn2)-c2nc1cs2] | +++ | † |
| 117 | 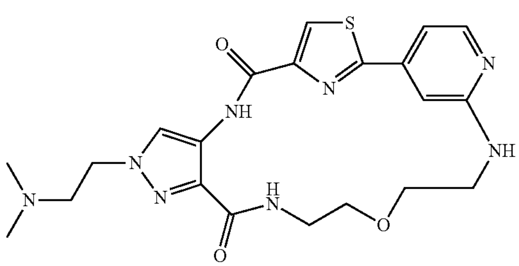 [SMILES: CN(C)CCn1cc2c(n1)C(=O)NCCOCCNc1cc(ccn1)-c1nc(cs1)C(=O)N2] | +++ | †† |
| 118 | 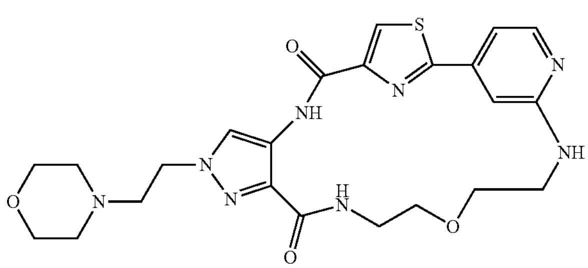 [SMILES: O=C1Nc2cn(CCN3CCOCC3)nc2C(=O)NCCOCCNc2cc(ccn2)-c2nc1cs2] | +++ | ††† |
| 119 | 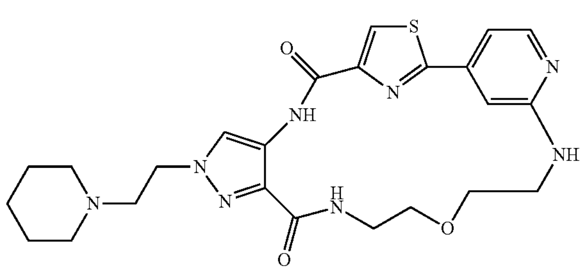 [SMILES: O=C1Nc2cn(CCN3CCCCC3)nc2C(=O)NCCOCCNc2cc(ccn2)-c2nc1cs2] | +++ | ††† |

| Example Number | Structure | Biochemical IRAK4 IC50 (uM) | Celluar Data EC50 (uM) |
|---|---|---|---|
| 120 | 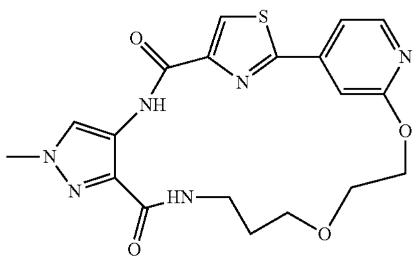 [SMILES: Cn1cc2c(n1)C(=O)NCCCOCCOc1cc(ccn1)-c1nc(cs1)C(=O)N2] | +++ | ††† |
| 121 | 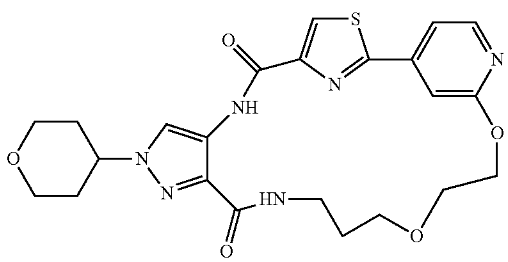 | +++ | †† |
| 122 | 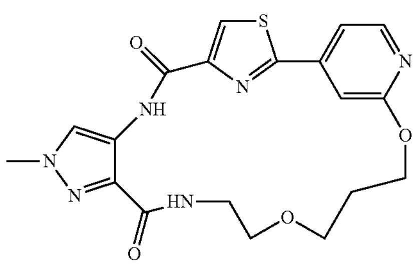 [SMILES: Cn1cc2c(n1)C(=O)NCCOCCCOc1cc(ccn1)-c1nc(cs1)C(=O)N2] | +++ | ††† |
| 123 | 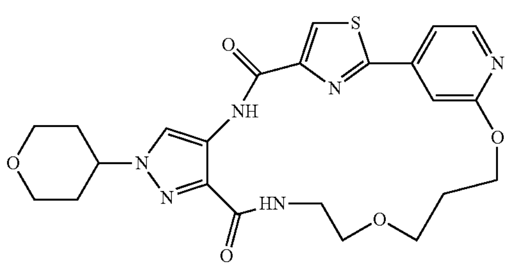 [SMILES: O=C1Nc2cn(C3CCOCC3)nc2C(=O)NCCOCCCOc2cc(ccn2)-c2nc1cs2] | +++ | ††† |
| 124 | 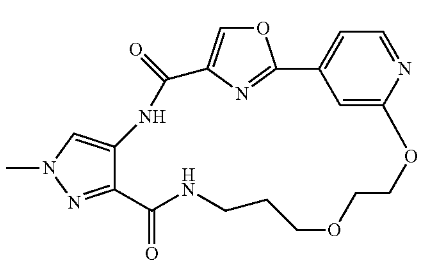 [SMILES: Cn1cc2c(n1)C(=O)NCCCOCCOc1cc(ccn1)-c1nc(co1)C(=O)N2] | +++ | ††† |

| Example Number | Structure | Biochemical IRAK4 IC50 (uM) | Celluar Data EC50 (uM) |
|---|---|---|---|
| 125 | 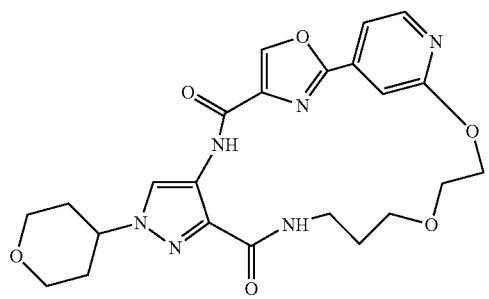 [SMILES: O=C1Nc2cn(C3CCOCC3)nc2C(=O)NCCCOCCOc2cc(ccn2)-c2nc1co2] | +++ | ††† |
| 126 | 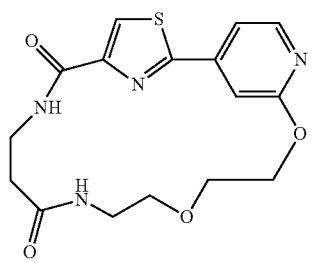 [SMILES: O=C1CCNC(=O)c2csc(n2)-c2ccnc(c2)OCCOCCN1] | ++ | † |
| 127 | 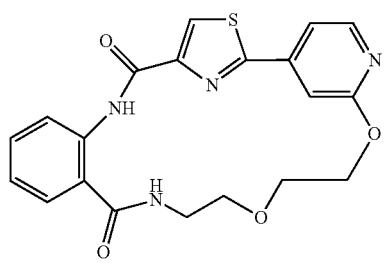 [SMILES: O=C1Nc2ccccc2C(=O)NCCOCCOc2cc(ccn2)-c2nc1cs2] | +++ | ††† |
| 128 | 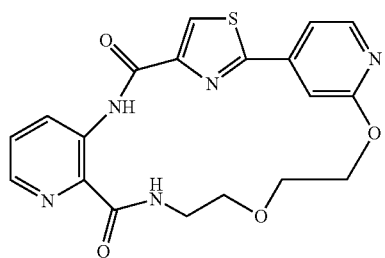 | +++ | † |
| 129 | 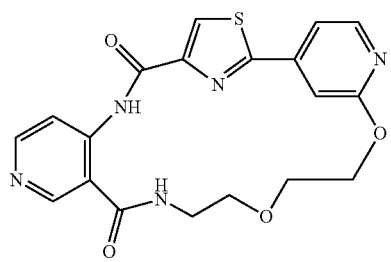 [SMILES: O=C1Nc2ccncc2C(=O)NCCOCCOc2cc(ccn2)-c2nc1cs2] | +++ | ††† |

-continued

| Example Number | Structure | Biochemical IRAK4 IC50 (uM) | Cellular Data EC50 (uM) |
|---|---|---|---|
| 130 | 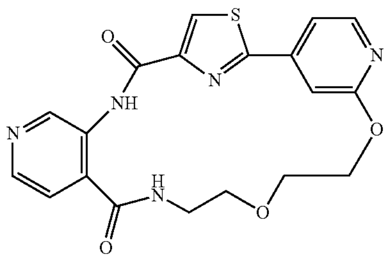 [SMILES: O=C1Nc2cnccc2C(=O)NCCOCCOc2cc(ccn2)-c2nc1cs2] | +++ | ††† |
| 131 | 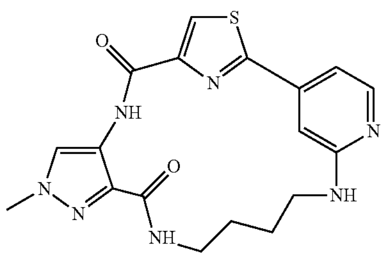 | +++ | ††† |
| 132 | 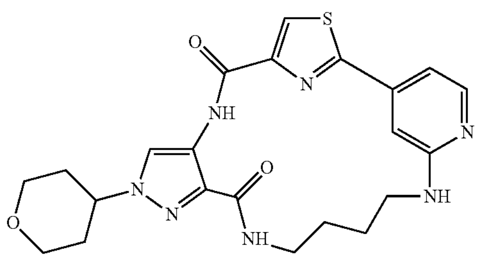 [SMILES: O=C1Nc2cn(C3CCOCC3)nc2C(=O)NCCCCNc2cc(ccn2)-c2nc1cs2] | +++ | ††† |
| 133 | 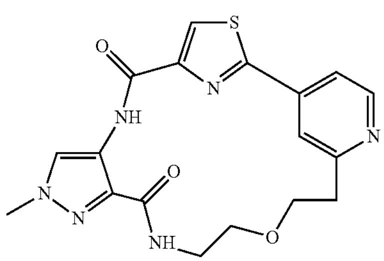 | ++ | †† |
| 134 | 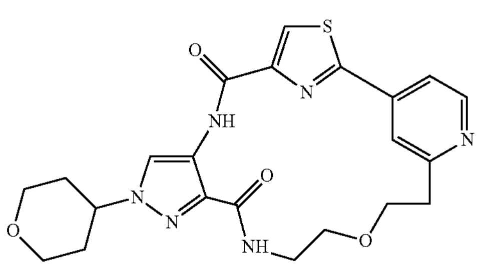 [SMILES: O=C1Nc2cn(C3CCOCC3)nc2C(=O)NCCOCCc2cc(ccn2)-c2nc1cs2] | +++ | † |
| 135 | 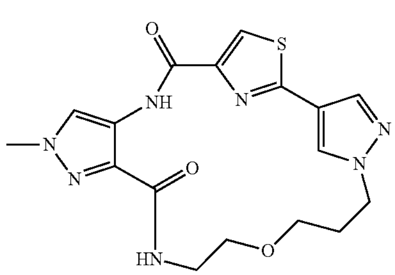 [SMILES: Cn1cc2c(n1)C(=O)NCCOCCCn1cc(cn1)-c1nc(cs1)C(=O)N2] | +++ | ††† |

-continued

| Example Number | Structure | Biochemical IRAK4 IC50 (uM) | Celluar Data EC50 (uM) |
|---|---|---|---|
| 136 | 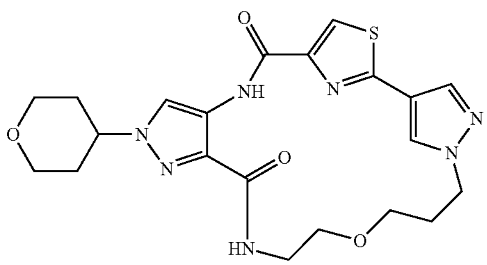 [SMILES: O=C1Nc2cn(C3CCOCC3)nc2C(=O)NCCOCCCn2cc(cn2)-c2nc1cs2] | +++ | ††† |
| 137 | 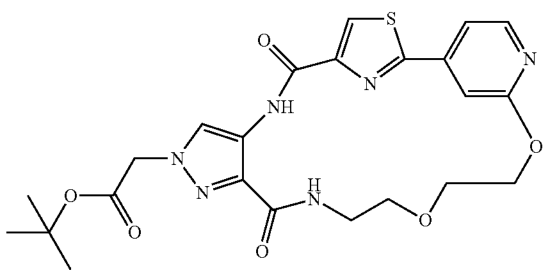 [SMILES: CC(C)(C)OC(=O)Cn1cc2c(n1)C(=O)NCCOCCOc1cc(ccn1)-c1nc(cs1)C(=O)N2] | +++ | † |
| 138 | 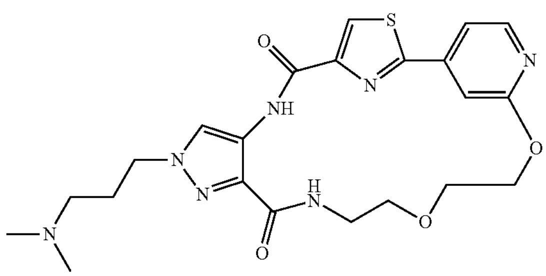 [SMILES: CN(C)CCCn1cc2c(n1)C(=O)NCCOCCOc1cc(ccn1)-c1nc(cs1)C(=O)N2] | +++ | † |
| 139 | 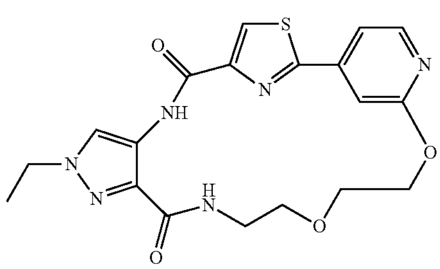 [SMILES: CCn1cc2c(n1)C(=O)NCCOCCOc1cc(ccn1)-c1nc(cs1)C(=O)N2] | +++ | † |
| 140 | 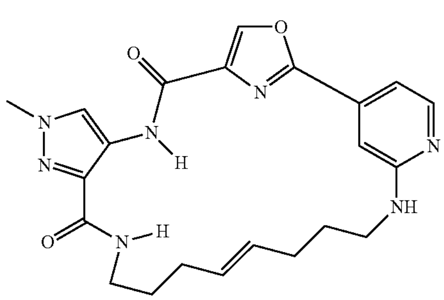 [SMILES: Cn1cc2c(n1)C(=O)NCCC/C=C/CCCNc1cc(ccn1)-c1nc(co1)C(=O)N2] | +++ | ††† |

-continued

| Example Number | Structure | Biochemical IRAK4 IC50 (uM) | Celluar Data EC50 (uM) |
|---|---|---|---|
| 141 | 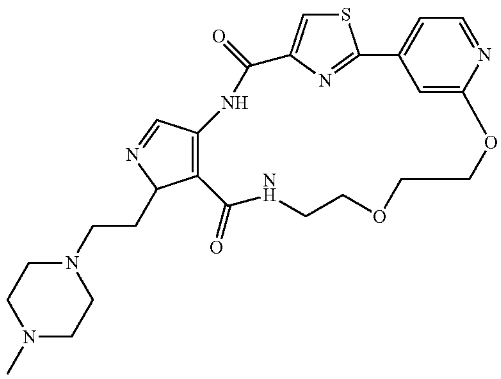 [SMILES: CN1CCN(CCC2N=CC3=C2C(=O)NCCOCCOc2cc(ccn2)-c2nc(cs2)C(=O)N3)CC1] | + | |
| 142 | 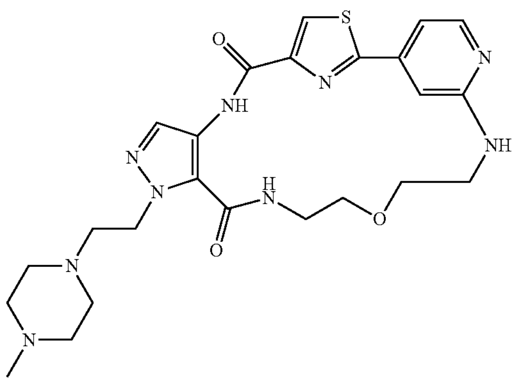 [SMILES: CN1CCN(CCn2ncc3c2C(=O)NCCOCCNc2cc(ccn2)-c2nc(cs2)C(=O)N3)CC1] | ++ | † |
| 143 | 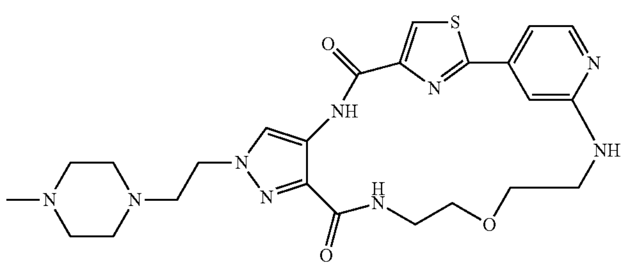 [SMILES: CN1CCN(CCn2cc3c(n2)C(=O)NCCOCCNc2cc(ccn2)-c2nc(cs2)C(=O)N3)CC1] | +++ | †† |
| 144 | 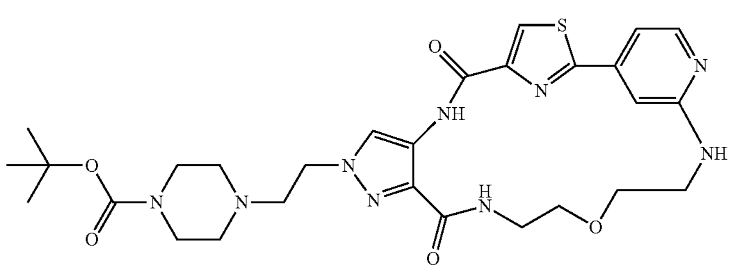 [SMILES: CC(C)(C)OC(=O)N1CCN(CCn2cc3c(n2)C(=O)NCCOCCNc2cc(ccn2)-c2nc(cs2)C(=O)N3)CC1] | +++ | †† |
| 145 | 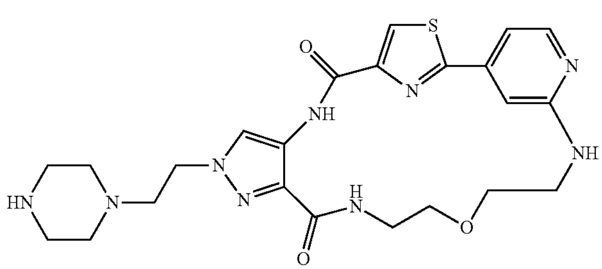 [SMILES: O=C1Nc2cn(CCN3CCNCC3)nc2C(=O)NCCOCCNc2cc(ccn2)-c2nc1cs2] | +++ | †† |

-continued

| Example Number | Structure | Biochemical IRAK4 IC50 (uM) | Celluar Data EC50 (uM) |
|---|---|---|---|
| 146 | 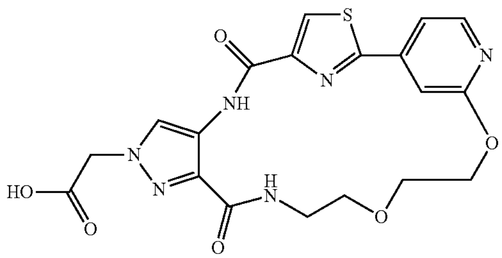 [SMILES: O=C(O)Cn1cc2c(n1)C(=O)NCCOCCOc1cc(ccn1)-c1nc(cs1)C(=O)N2] | + | † |
| 147 | 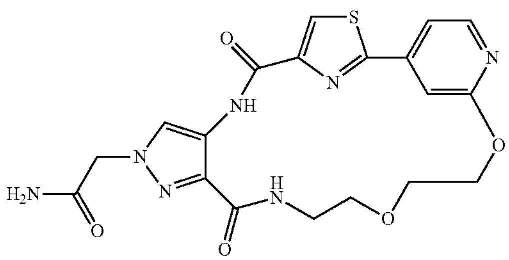 [SMILES: NC(=O)Cn1cc2c(n1)C(=O)NCCOCCOc1cc(ccn1)-c1nc(cs1)C(=O)N2] | ++ | † |
| 148 | 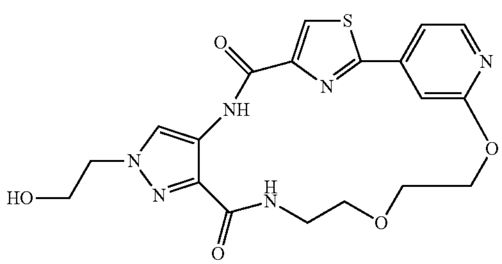 [SMILES: O=C1Nc2cn(CCO)nc2C(=O)NCCOCCOc2cc(ccn2)-c2nc1cs2] | ++ | † |
| 149 | 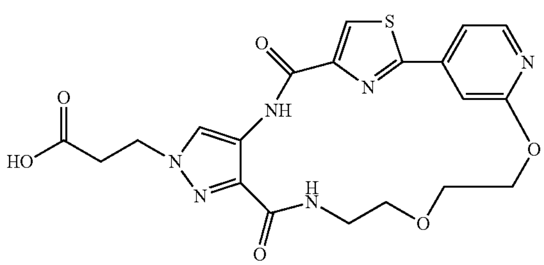 [SMILES: O=C(O)CCn1cc2c(n1)C(=O)NCCOCCOc1cc(ccn1)-c1nc(cs1)C(=O)N2] | ++ | † |
| 150 | 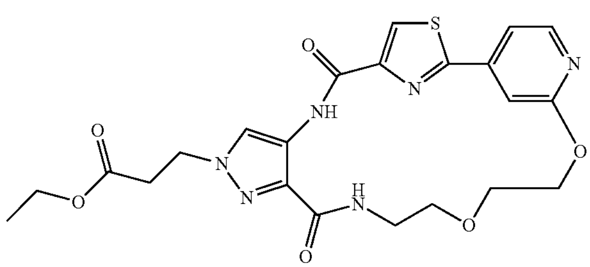 [SMILES: CCOC(=O)CCn1cc2c(n1)C(=O)NCCOCCOc1cc(ccn1)-c1nc(cs1)C(=O)N2] | +++ | † |
| 151 | 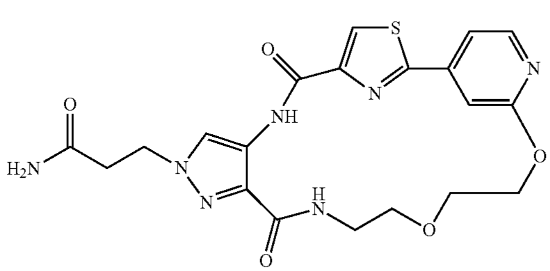 [SMILES: NC(=O)CCn1cc2c(n1)C(=O)NCCOCCOc1cc(ccn1)-c1nc(cs1)C(=O)N2] | ++ | † |

-continued
| Example Number | Structure | Biochemical IRAK4 IC50 (uM) | Celluar Data EC50 (uM) |
|---|---|---|---|
| 152 | 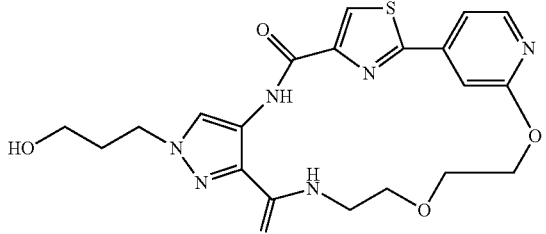 | +++ | † |
| 153 | 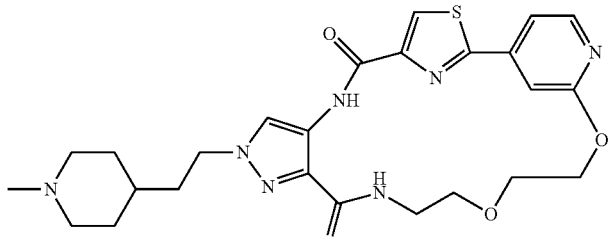 | +++ | † |
| 154 | 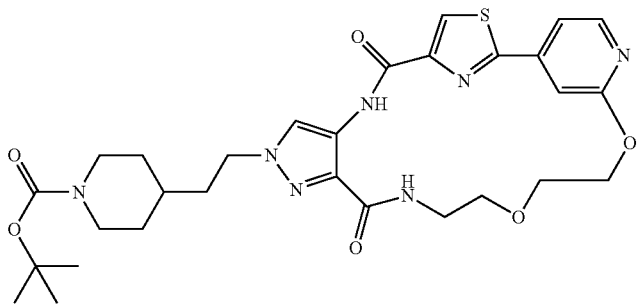 [SMILES: CC(C)(C)OC(=O)N1CCC(CCn2cc3c(n2)C(=O)NCCOCCOc2cc(ccn2)-c2nc(cs2)C(=O)N3)CC1] | +++ | † |
| 155 | 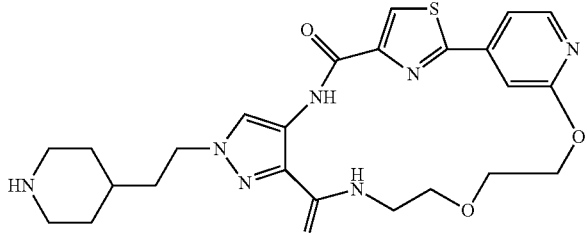 | +++ | † |
| 156 | 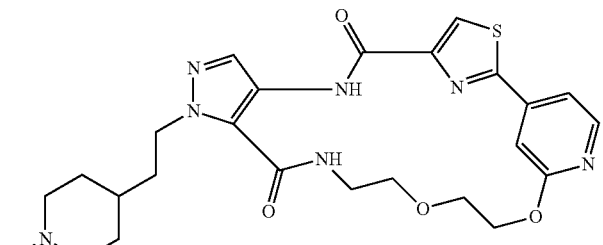 | + | |

| Example Number | Structure | Biochemical IRAK4 IC50 (uM) | Celluar Data EC50 (uM) |
|---|---|---|---|
| 157 | 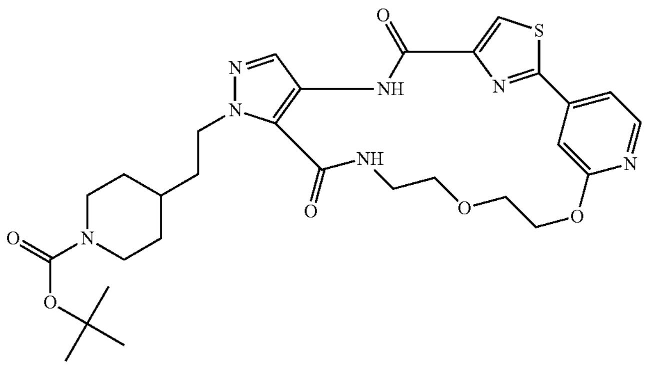 [SMILES: CC(C)(C)OC(=O)N1CCC(CCn2ncc3c2C(=O)NCCOCCOc2cc(ccn2)-c2nc(cs2)C(=O)N3)CC1] | + | |
| 158 | 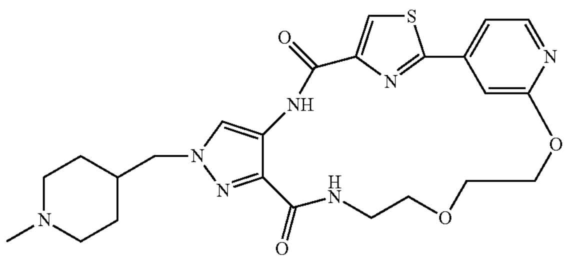 [SMILES: CN1CCC(Cn2cc3c(n2)C(=O)NCCOCCOc2cc(ccn2)-c2nc(cs2)C(=O)N3)CC1] | ++ | † |
| 159 | 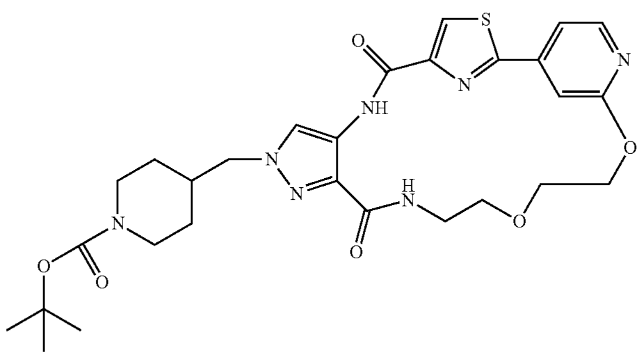 [SMILES: CC(C)(C)OC(=O)N1CCC(Cn2cc3c(n2)C(=O)NCCOCCOc2cc(ccn2)-c2nc(cs2)C(=O)N3)CC1] | +++ | †† |
| 160 | 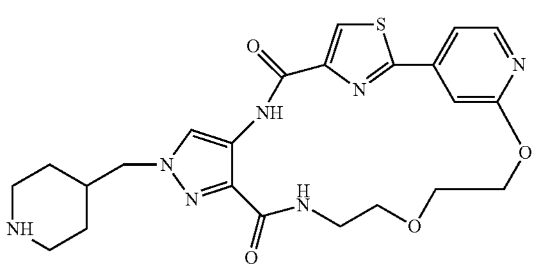 [SMILES: O=C1Nc2cn(CC3CCNCC3)nc2C(=O)NCCOCCOc2cc(ccn2)-c2nc1cs2] | ++ | † |
| 161 | 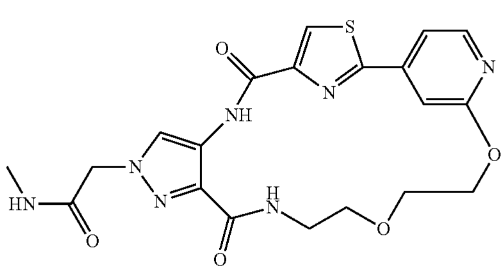 [SMILES: CNC(=O)Cn1cc2c(n1)C(=O)NCCOCCOc1cc(ccn1)-c1nc(cs1)C(=O)N2] | +++ | † |

-continued

| Example Number | Structure | Biochemical IRAK4 IC50 (uM) | Celluar Data EC50 (uM) |
|---|---|---|---|
| 162 | 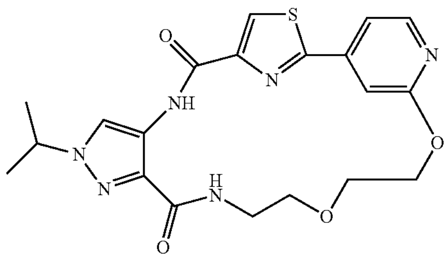 [SMILES: CC(C)n1cc2c(n1)C(=O)NCCOCCOc1cc(ccn1)-c1nc(cs1)C(=O)N2] | +++ | † |
| 163 | 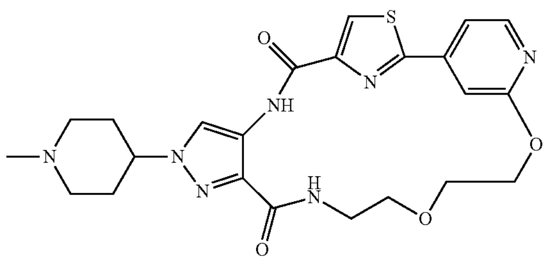 [SMILES: CN1CCC(n2cc3c(n2)C(=O)NCCOCCOc2cc(ccn2)-c2nc(cs2)C(=O)N3)CC1] | +++ | † |
| 164 | 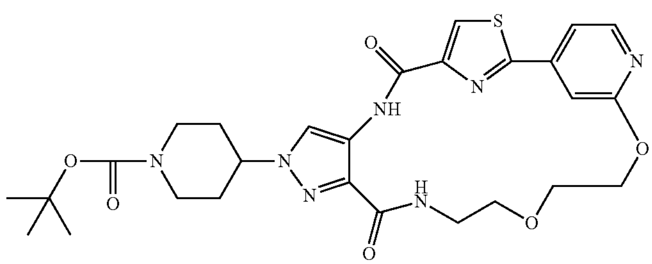 [SMILES: CC(C)(C)OC(=O)N1CCC(n2cc3c(n2)C(=O)NCCOCCOc2cc(ccn2)-c2nc(cs2)C(=O)N3)CC1] | +++ | †† |
| 165 | 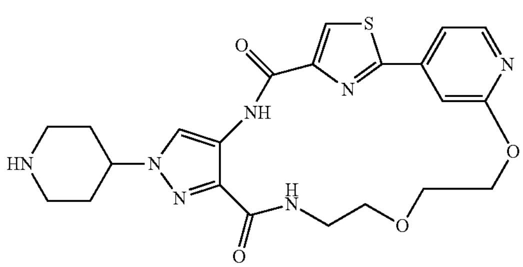 [SMILES: O=C1Nc2cn(C3CCNCC3)nc2C(=O)NCCOCCOc2cc(ccn2)-c2nc1cs2] | +++ | |
| 166 | 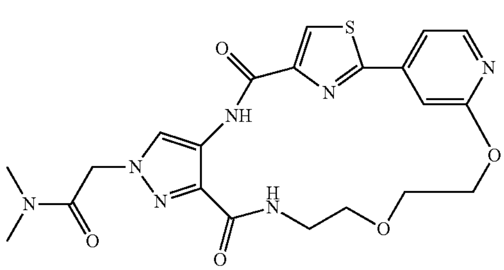 [SMILES: CN(C)C(=O)Cn1cc2c(n1)C(=O)NCCOCCOc1cc(ccn1)-c1nc(cs1)C(=O)N2] | ++ | † |

-continued

| Example Number | Structure | Biochemical IRAK4 IC50 (uM) | Celluar Data EC50 (uM) |
|---|---|---|---|
| 167 | 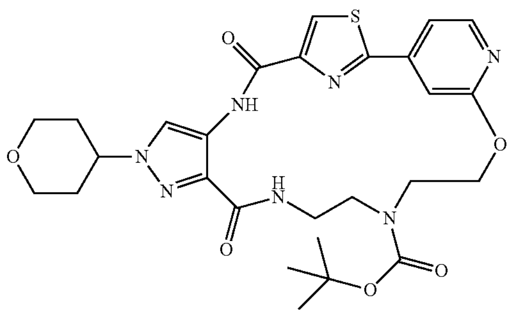 [SMILES: CC(C)(C)OC(=O)N1CCNC(=O)c2nn(C3CCOCC3)cc2NC(=O)c2csc(n2)-c2ccnc(c2)OCC1] | ++ | |
| 168 | 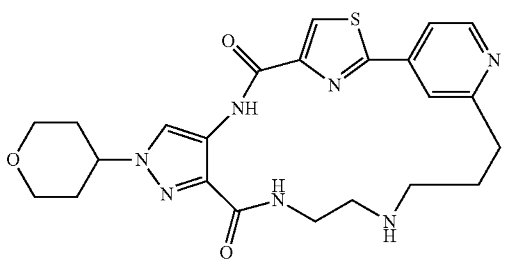 [SMILES: O=C1Nc2cn(C3CCOCC3)nc2C(=O)NCCNCCCc2cc(ccn2)-c2nc1cs2] | +++ | |
| 169 | 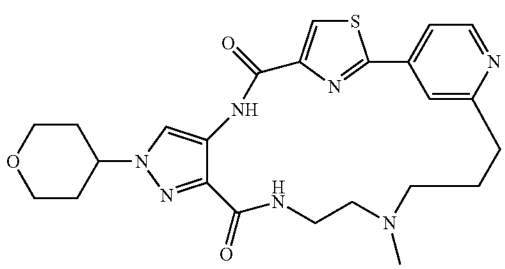 [SMILES: CN1CCCc2cc(ccn2)-c2nc(cs2)C(=O)Nc2cn(C3CCOCC3)nc2C(=O)NCC1] | +++ | † |
| 170 | 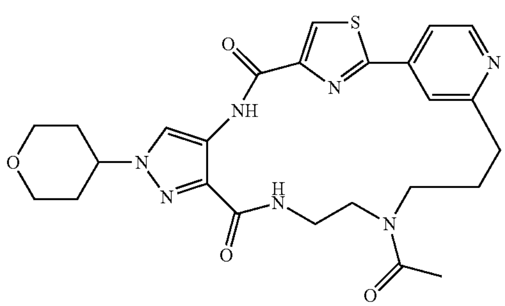 [SMILES: CC(=O)N1CCCc2cc(ccn2)-c2nc(cs2)C(=O)Nc2cn(C3CCOCC3)nc2C(=O)NCC1] | +++ | ††† |
| 171 | 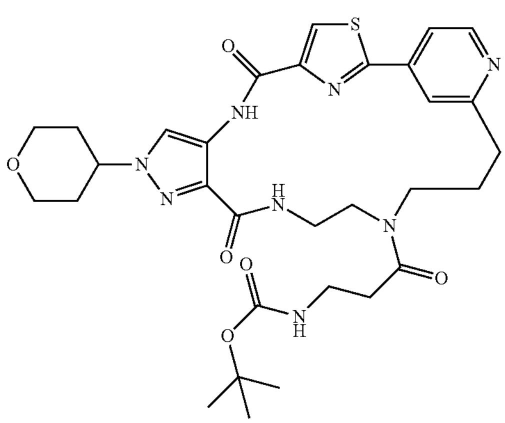 [SMILES: CC(C)(C)OC(=O)NCCC(=O)N1CCCc2cc(ccn2)-c2nc(cs2)C(=O)Nc2cn(C3CCOCC3)nc2C(=O)NCC1] | +++ | |

US 9,617,282 B2

353                                                                                                       354
-continued

| Example Number | Structure | Biochemical IRAK4 IC50 (uM) | Celluar Data EC50 (uM) |
|---|---|---|---|
| 171 | | | +++ |
| 171 | | | ++ |
| 174 | 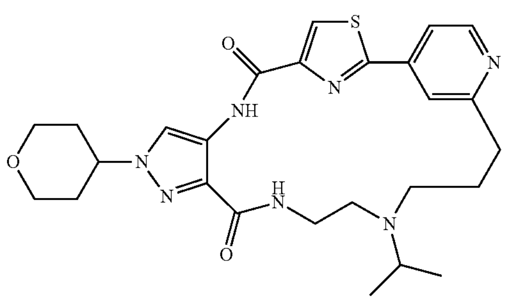 [SMILES: CC(C)N1CCCc2cc(ccn2)-c2nc(cs2)C(=O)Nc2cn(C3CCOCC3)nc2C(=O)NCC1] | | +++ |
| 175 | 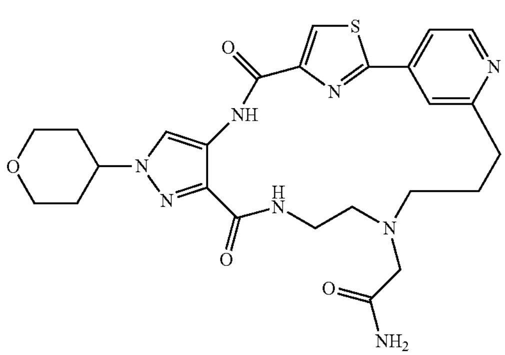 [SMILES: NC(=O)CN1CCCc2cc(ccn2)-c2nc(cs2)C(=O)Nc2cn(C3CCOCC3)nc2C(=O)NCC1] | | ++ |

-continued

| Example Number | Structure | Biochemical IRAK4 IC50 (uM) | Celluar Data EC50 (uM) |
|---|---|---|---|
| 176 | 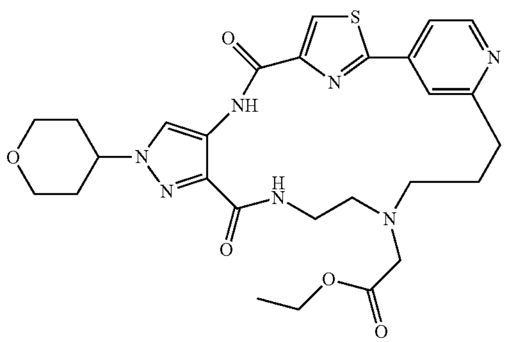 [SMILES: CCOC(=O)CN1CCCc2cc(ccn2)-c2nc(cs2)C(=O)Nc2cn(C3CCOCC3)nc2C(=O)NCC1] | | >10 |
| 177 | 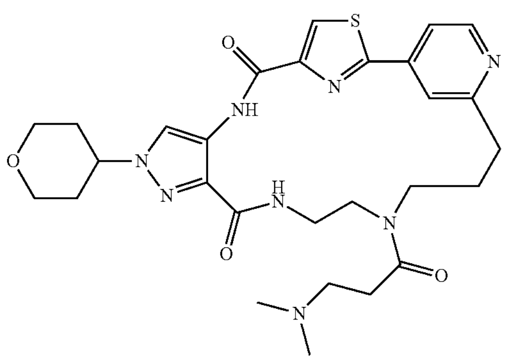 [SMILES: CN(C)CCC(=O)N1CCCc2cc(ccn2)-c2nc(cs2)C(=O)Nc2cn(C3CCOCC3)nc2C(=O)NCC1] | | +++ |
| 178 | 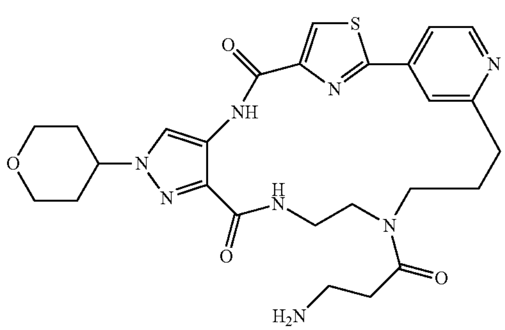 [SMILES: NCCC(=O)N1CCCc2cc(ccn2)-c2nc(cs2)C(=O)Nc2cn(C3CCOCC3)nc2C(=O)NCC1] | | +++ |
| 179 | 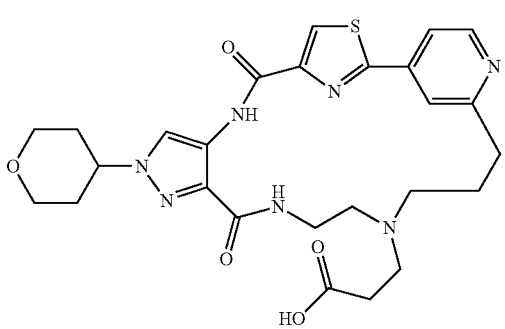 [SMILES: O=C(O)CCN1CCCc2cc(ccn2)-c2nc(cs2)C(=O)Nc2cn(C3CCOCC3)nc2C(=O)NCC1] | | +++ |

-continued

| Example Number | Structure | Biochemical IRAK4 IC50 (uM) | Celluar Data EC50 (uM) |
|---|---|---|---|
| 180 | 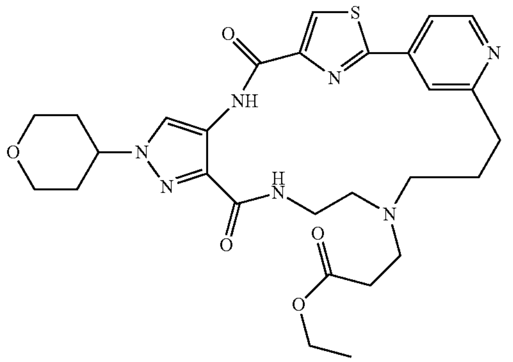 [SMILES: CCOC(=O)CCN1CCCc2cc(ccn2)-c2nc(cs2)C(=O)Nc2cn(C3CCOCC3)nc2C(=O)NCC1] | | +++ |
| 181 | 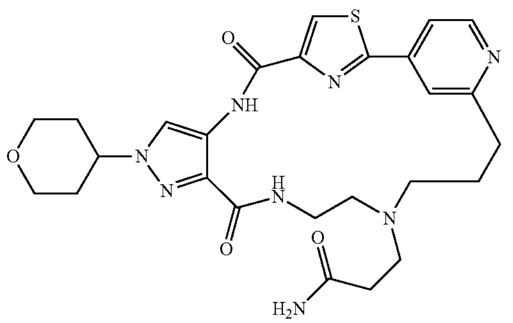 [SMILES: NC(=O)CCN1CCCc2cc(ccn2)-c2nc(cs2)C(=O)Nc2cn(C3CCOCC3)nc2C(=O)NCC1] | | +++ |
| 182 | 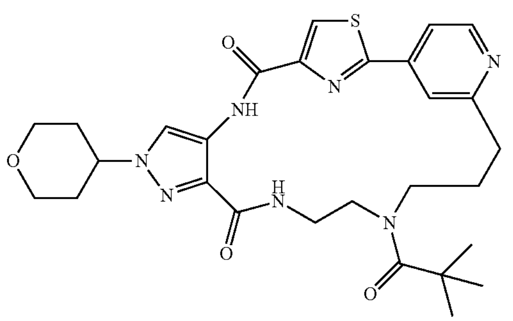 [SMILES: CC(C)(C)C(=O)N1CCCc2cc(ccn2)-c2nc(cs2)C(=O)Nc2cn(C3CCOCC3)nc2C(=O)NCC1] | | ++ |
| 183 | 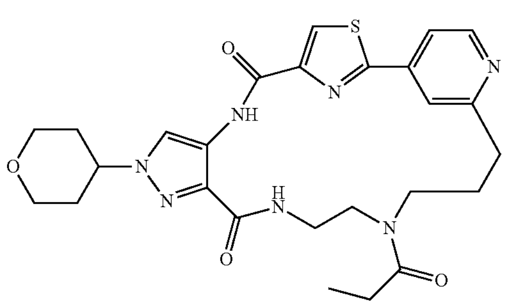 [SMILES: CCC(=O)N1CCCc2cc(ccn2)-c2nc(cs2)C(=O)Nc2cn(C3CCOCC3)nc2C(=O)NCC1] | | +++ |

-continued
| Example Number | Structure | Biochemical IRAK4 IC50 (uM) | Celluar Data EC50 (uM) |
|---|---|---|---|
| 184 | 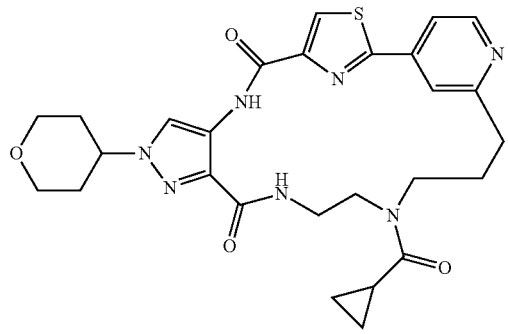 [SMILES: O=C1Nc2cn(C3CCOCC3)nc2C(=O)NCCN(C(=O)C2CC2)CCCc2cc(ccn2)-c2nc1cs2] | +++ | |
| 185 | 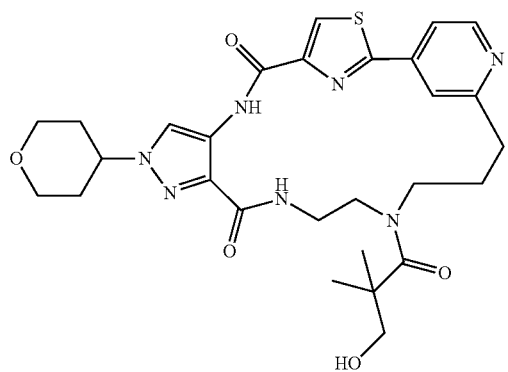 [SMILES: CC(C)(CO)C(=O)N1CCCc2cc(ccn2)-c2nc(cs2)C(=O)Nc2cn(C3CCOCC3)nc2C(=O)NCC1] | +++ | |
| 186 | 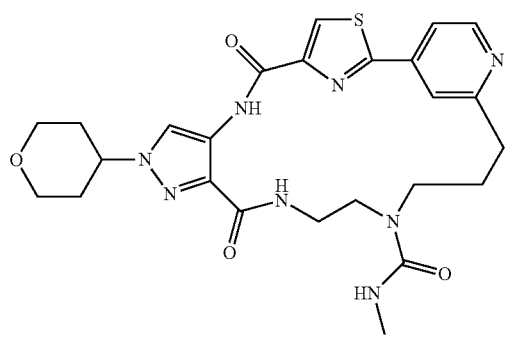 [SMILES: CNC(=O)N1CCCc2cc(ccn2)-c2nc(cs2)C(=O)Nc2cn(C3CCOCC3)nc2C(=O)NCC1] | +++ | |
| 187 | 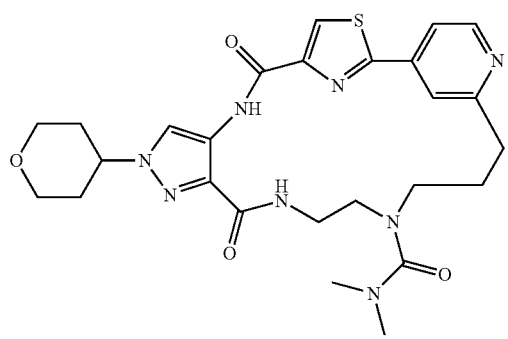 [SMILES: CN(C)C(=O)N1CCCc2cc(ccn2)-c2nc(cs2)C(=O)Nc2cn(C3CCOCC3)nc2C(=O)NCC1] | ++ | |

-continued

| Example Number | Structure | Biochemical IRAK4 IC50 (uM) | Celluar Data EC50 (uM) |
|---|---|---|---|
| 188 | 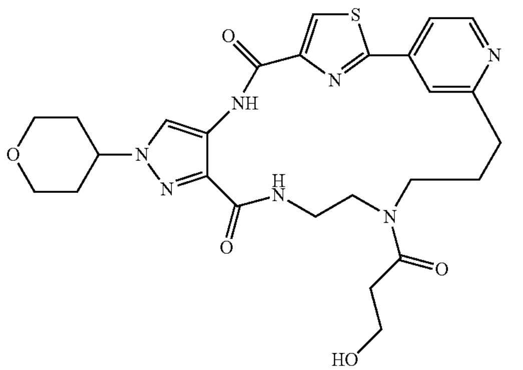 [SMILES: O=C1Nc2cn(C3CCOCC3)nc2C(=O)NCCN(C(=O)CCO)CCCc2cc(ccn2)-c2nc1cs2] | +++ | |
| 189 | 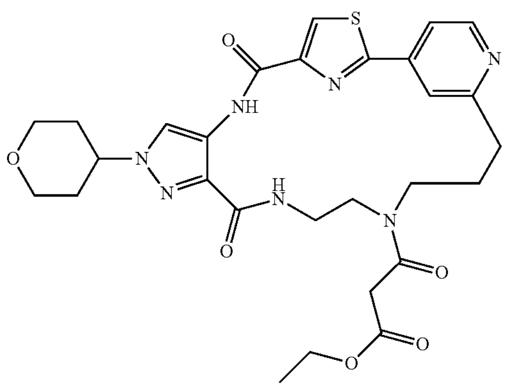 [SMILES: CCOC(=O)CC(=O)N1CCCc2cc(ccn2)-c2nc(cs2)C(=O)Nc2cn(C3CCOCC3)nc2C(=O)NCC1] | +++ | |
| 190 | 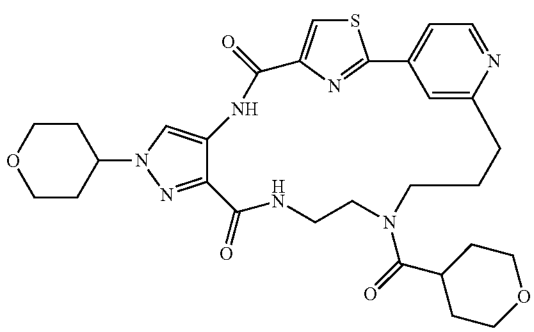 [SMILES: O=C1Nc2cn(C3CCOCC3)nc2C(=O)NCCN(C(=O)C2CCOCC2)CCCc2cc(ccn2)-c2nc1cs2] | +++ | |
| 191 | 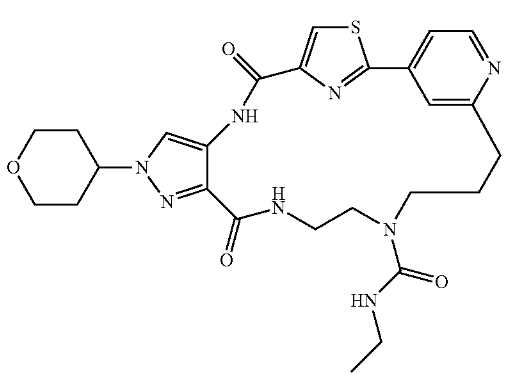 [SMILES: CCNC(=O)N1CCCc2cc(ccn2)-c2nc(cs2)C(=O)Nc2cn(C3CCOCC3)nc2C(=O)NCC1] | +++ | |

| Example Number | Structure | Biochemical IRAK4 IC50 (uM) | Celluar Data EC50 (uM) |
|---|---|---|---|
| 192 | 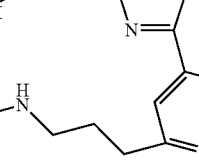 | | + |
| 193 | 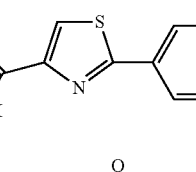 | | ++ |
| 194 | 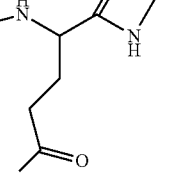 | | + |
| 195 | 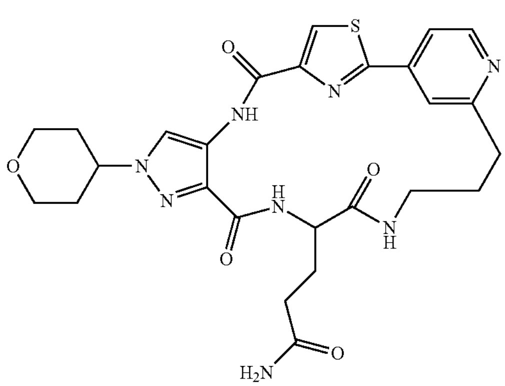 [SMILES: NC(=O)CCC1NC(=O)c2nn(C3CCOCC3)cc2NC(=O)c2csc(n2)-c2ccnc(c2)CCCNC1=O] | | ++ |

-continued

| Example Number | Structure | Biochemical IRAK4 IC50 (uM) | Celluar Data EC50 (uM) |
|---|---|---|---|
| 196 | 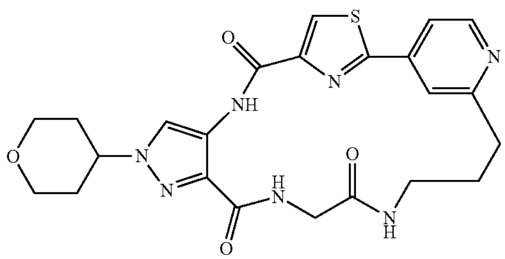 [SMILES: O=C1CNC(=O)c2nn(C3CCOCC3)cc2NC(=O)c2csc(n2)-c2ccnc(c2)CCCN1] | | +++ |
| 197 | 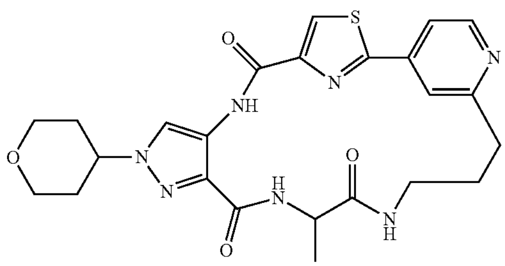 [SMILES: CC1NC(=O)c2nn(C3CCOCC3)cc2NC(=O)c2csc(n2)-c2ccnc(c2)CCCNC1=O] | | ++ |
| 198 | 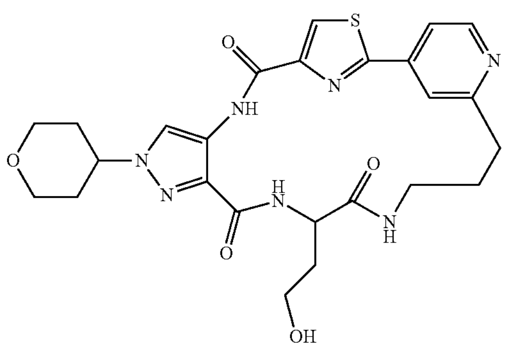 [SMILES: O=C1Nc2cn(C3CCOCC3)nc2C(=O)NC(CCO)C(=O)NCCCc2cc(ccn2)-c2nc1cs2] | | + |
| 199 | 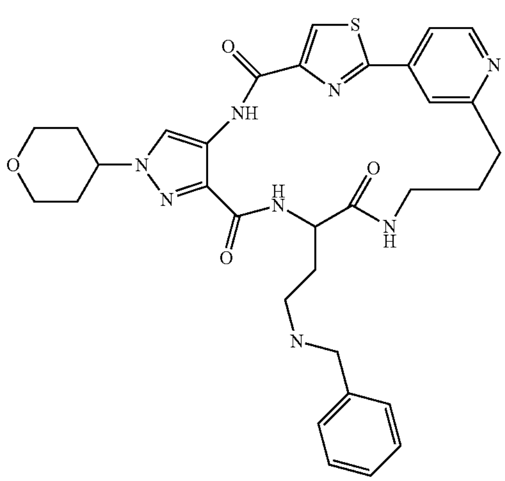 [SMILES: O=C1Nc2cn(C3CCOCC3)nc2C(=O)NC(CCNCc2ccccc2)C(=O)NCCCc2cc(ccn2)-c2nc1cs2] | | >10 |

| Example Number | Structure | Biochemical IRAK4 IC50 (uM) | Cellular Data EC50 (uM) |
|---|---|---|---|
| 200 | 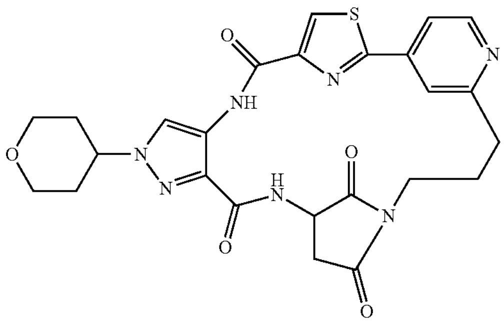 [SMILES: O=C1Nc2cn(C3CCOCC3)nc2C(=O)NC2CC(=O)N(CCCc3cc(ccn3)-c3nc1cs3)C2=O] | +++ | †† |
| 201 | 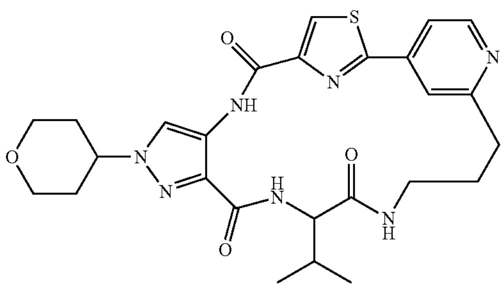 [SMILES: CC(C)C1NC(=O)c2nn(C3CCOCC3)cc2NC(=O)c2csc(n2)-c2ccnc(c2)CCCNC1=O] | + | |
| 202 | 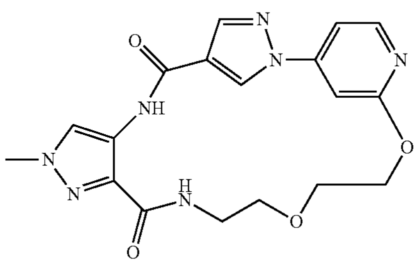 [SMILES: Cn1cc2c(n1)C(=O)NCCOCCOc1cc(ccn1)-n1cc(cn1)C(=O)N2] | + | |
| 203 | 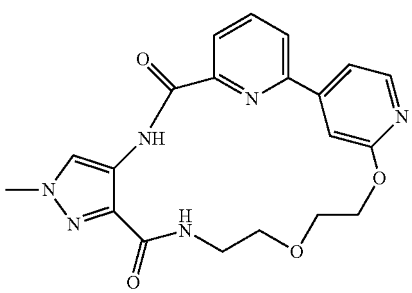 [SMILES: Cn1cc2c(n1)C(=O)NCCOCCOc1cc(ccn1)-c1cccc(n1)C(=O)N2] | +++ | |
| 204 | 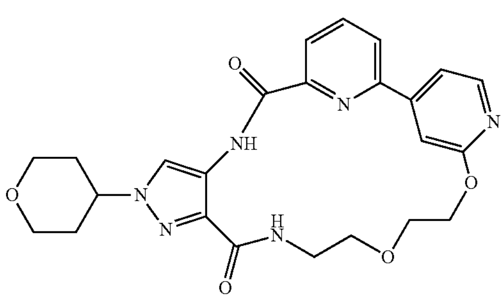 | ++ | |

| Example Number | Structure | Biochemical IRAK4 IC50 (uM) | Celluar Data EC50 (uM) |
| --- | --- | --- | --- |
| 205 | 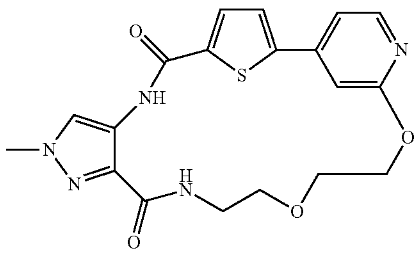 [SMILES: Cn1cc2c(n1)C(=O)NCCOCCOc1cc(ccn1)-c1ccc(s1)C(=O)N2] | >10 | |
| 206 | 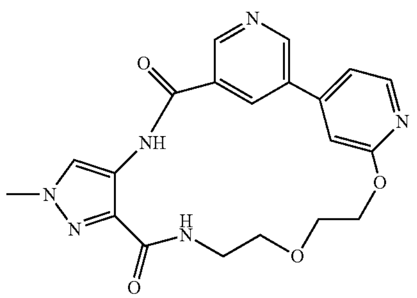 [SMILES: Cn1cc2c(n1)C(=O)NCCOCCOc1cc(ccn1)-c1cncc(c1)C(=O)N2] | | + |
| 207 | 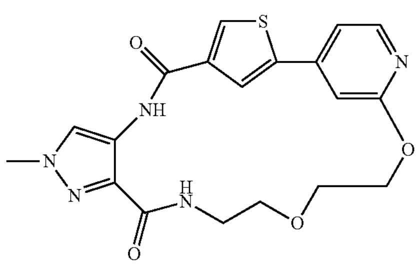 [SMILES: Cn1cc2c(n1)C(=O)NCCOCCOc1cc(ccn1)-c1cc(cs1)C(=O)N2] | | +++ |
| 208 | 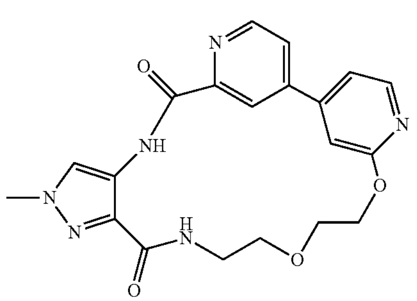 [SMILES: Cn1cc2c(n1)C(=O)NCCOCCOc1cc(ccn1)-c1ccnc(c1)C(=O)N2] | | |
| 209 | 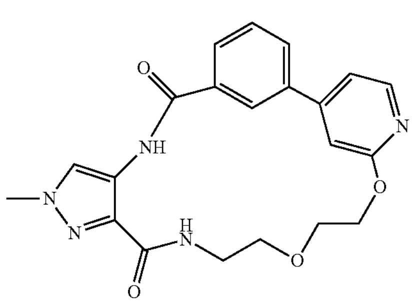 [SMILES: Cn1cc2c(n1)C(=O)NCCOCCOc1cc(ccn1)-c1cccc(c1)C(=O)N2] | | ++ |

-continued

| Example Number | Structure | Biochemical IRAK4 IC50 (uM) | Celluar Data EC50 (uM) |
|---|---|---|---|
| 210 | 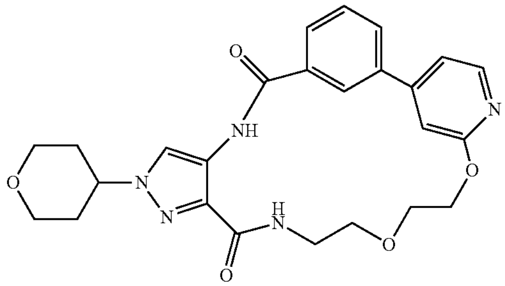 [SMILES: O=C1Nc2cn(C3CCOCC3)nc2C(=O)NCCOCCOc2cc(ccn2)-c2cccc1c2] | | +++ |
| 211 | 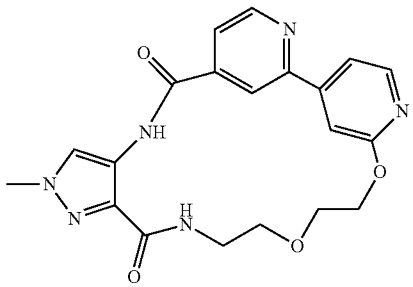 [SMILES: Cn1cc2c(n1)C(=O)NCCOCCOc1cc(ccn1)-c1cc(ccn1)C(=O)N2] | | ++ |
| 212 | 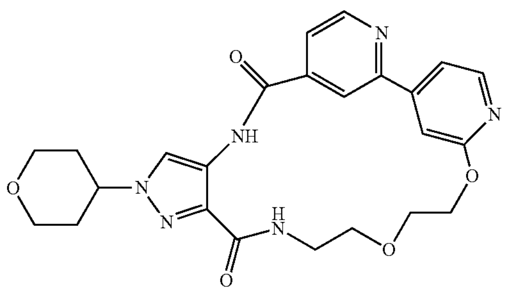 | | ++ |
| 213 | 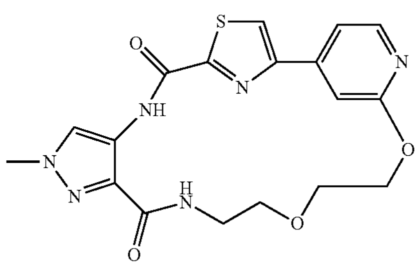 [SMILES: Cn1cc2c(n1)C(=O)NCCOCCOc1cc(ccn1)-c1csc(n1)C(=O)N2] | | + |
| 214 | 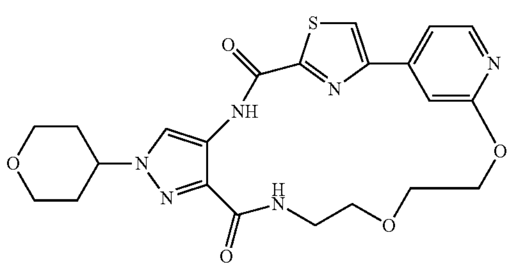 [SMILES: O=C1Nc2cn(C3CCOCC3)nc2C(=O)NCCOCCOc2cc(ccn2)-c2csc1n2] | | ++ |

-continued

| Example Number | Structure | Biochemical IRAK4 IC50 (uM) | Celluar Data EC50 (uM) |
|---|---|---|---|
| 215 | 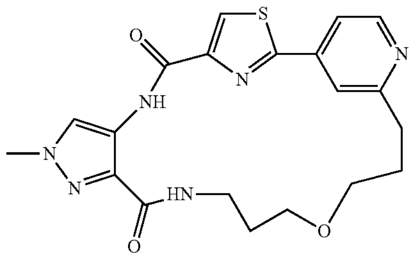 [SMILES: Cn1cc2c(n1)C(=O)NCCCOCCCc1cc(ccn1)-c1nc(cs1)C(=O)N2] | +++ | |
| 216 | 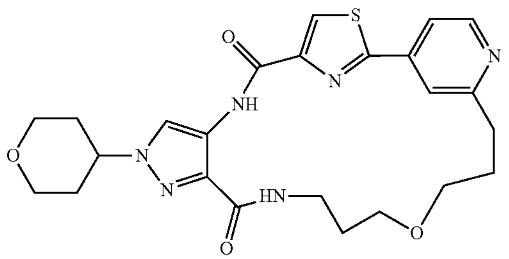 [SMILES: O=C1Nc2cn(C3CCOCC3)nc2C(=O)NCCCOCCCc2cc(ccn2)-c2nc1cs2] | +++ | |
| 217 | 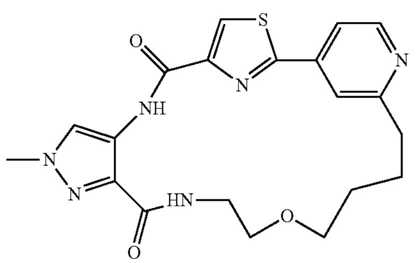 | +++ | †† |
| 218 | 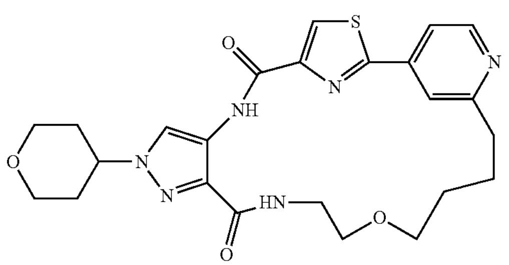 [SMILES: O=C1Nc2cn(C3CCOCC3)nc2C(=O)NCCOCCCCc2cc(ccn2)-c2nc1cs2] | +++ | †† |
| 219 | 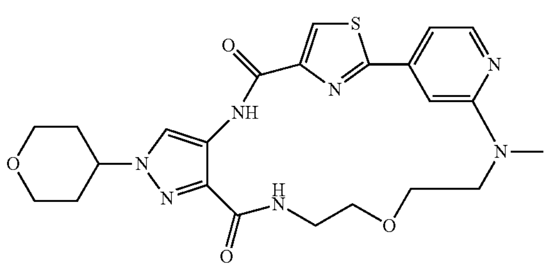 [SMILES: CN1CCOCCNC(=O)c2nn(C3CCOCC3)cc2NC(=O)c2csc(n2)-c2ccnc1c2] | +++ | |
| 220 | 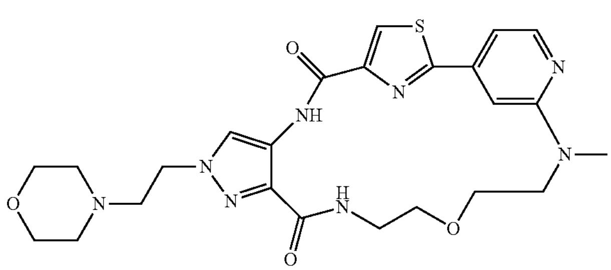 [SMILES: CN1CCOCCNC(=O)c2nn(CCN3CCOCC3)cc2NC(=O)c2csc(n2)-c2ccnc1c2] | +++ | |

| Example Number | Structure | Biochemical IRAK4 IC50 (uM) | Cellular Data EC50 (uM) |
|---|---|---|---|
| 221 | 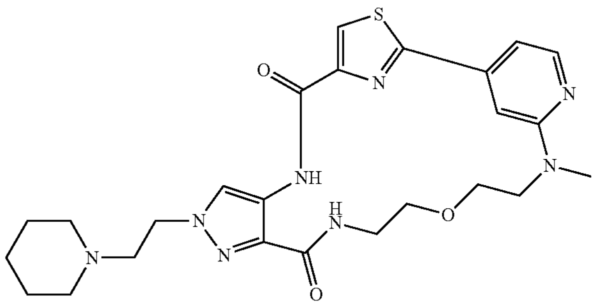 [SMILES: CN1CCOCCNC(=O)c2nn(CCN3CCCCC3)cc2NC(=O)c2csc(n2)-c2ccnc1c2] | | +++ |
| 222 | 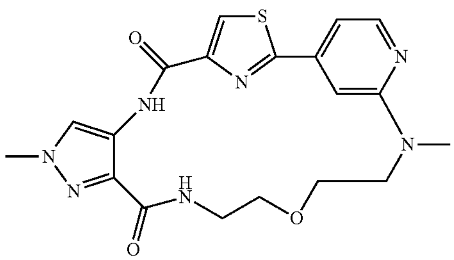 | | +++ |
| 223 | 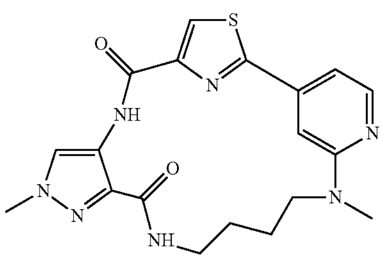 | | +++ |
| 224 | 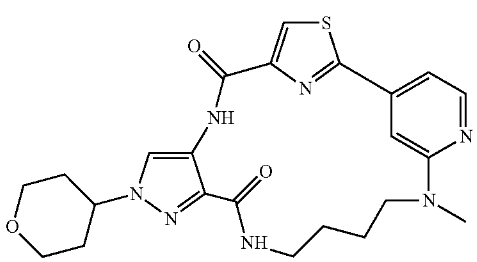 [SMILES: CN1CCCCNC(=O)c2nn(C3CCOCC3)cc2NC(=O)c2csc(n2)-c2ccnc1c2] | | +++ |
| 225 | 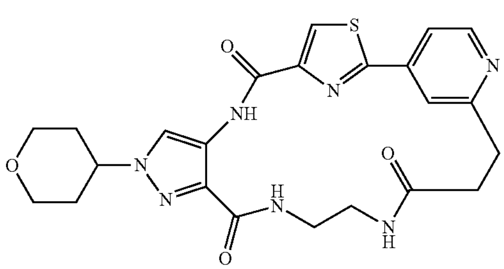 [SMILES: O=C1CCc2cc(ccn2)-c2nc(cs2)C(=O)Nc2cn(C3CCOCC3)nc2C(=O)NCCN1] | | +++ |

+

Other embodiments are within the scope of the following claims.

What is claimed is:

1. A compound of Formula III, or a pharmaceutically acceptable salt thereof,

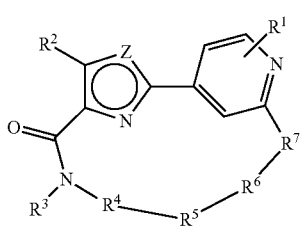

Formula III wherein
Z is S,
$R^1$ is hydrogen or lower alkyl,
$R^2$ is chosen from hydrogen and lower alkyl,
$R^3$ is chosen from hydrogen, lower alkyl optionally substituted with alkoxy, amino, N-(alkyl)amino, N,N-(dialkyl)amino, or phenyl, heterocycloalkyl, and heteroaryl,
wherein phenyl, heterocycloalkyl, and heteroaryl are optionally substituted with one or two groups independently chosen from lower alkyl and wherein alkoxy is optionally substituted with tri(alkyl)silyl, wherein heteroaryl is a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic, and heterocycloalkyl is a completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states;
$R^4$ is chosen from heteroarylene and arylene, each of which is optionally substituted, or $R^4$ and $R^3$ taken together with the nitrogen to which they are bound, form an optionally substituted 3- to 7-membered heterocycloalkyl ring, or $R^4$ is an alkylene chain having 1-3 carbon atoms that is optionally substituted with one or two groups independently chosen from lower alkyl and cycloalkyl, each of which groups is optionally substituted with hydroxyl or alkoxy, or $R^4$ is absent, wherein heteroarylene is a divalent 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic, and arylene is divalent monocyclic, bicyclic or tricyclic aromatic hydrocarbon groups having from 6 to 14 carbon atoms in the ring portion, and the 3- to 7-membered heterocycloalkyl ring is a completely saturated monocyclic, bicyclic or tricyclic heterocyclyl comprising at least one of which is a heteroatom, wherein the heteroatoms are independently selected from O, S and N, and wherein N and S can be optionally oxidized to various oxidation states;
$R^5$ is chosen from C(O)NR$^{51}$, NR$^{52}$, and O, or $R^5$ is absent, provided that if $R^4$ is absent, then $R^5$ is absent,
$R^6$ is an alkylene or alkenylene chain having one or two double bonds,
wherein the alkylene or alkenylene chain has 2 to 10 carbon atoms,
wherein the alkylene or alkenylene chain is optionally substituted with one or two groups independently chosen from lower alkyl and cycloalkyl, each of which groups is optionally substituted with hydroxyl or alkoxy, and
further wherein one or two of the carbon atoms in the alkylene chain is optionally replaced by an O, S, SO, SO$_2$, or NR$^{61}$, and
wherein two of the carbon atoms in the alkylene chain, are optionally connected by a two or three carbon atom alkylene chain to form a 5- to 7-membered ring,
$R^7$ is chosen from NR$^{71}$ and O, or $R^7$ is absent,
$R^{51}$ is chosen from hydrogen and lower alkyl,
$R^{52}$ is chosen from hydrogen, lower alkyl, and C(O)OR$^{81}$,
$R^{61}$ is chosen from hydrogen, lower alkyl, and C(O)OR$^{81}$,
$R^{71}$ is chosen from hydrogen, lower alkyl, and —C(O)OR$^{81}$, and
$R^{81}$ is lower alkyl.

2. The compound of claim 1, or a pharmaceutically acceptable salt thereof,
wherein, $R^4$ is heteroarylene optionally substituted with one or more $R^{41}$ wherein for each occurrence, $R^{41}$ is independently chosen from
heterocycloalkyl,
lower alkyl optionally substituted with —C(O)OR$^9$, —C(O)NR$^{10}$R$^{11}$, hydroxy, amino, N-(alkyl)amino, N,N-(dialkyl)amino, cycloalkyl, or heterocycloalkyl,
—C(O)OR$^9$,
hydroxyl, and
—C(O)NR$^{10}$R$^{11}$,
wherein $R^9$ is chosen from hydrogen and lower alkyl,
wherein $R^{10}$ and $R^{11}$ are independently hydrogen and lower alkyl, or $R^{10}$ and $R^{11}$, together with the nitrogen to which they are bound form a heterocycloalkyl, and
wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

3. The compound of claim 2, or a pharmaceutically acceptable salt thereof, wherein the compound of Formula III is chosen from compounds of Formula VI

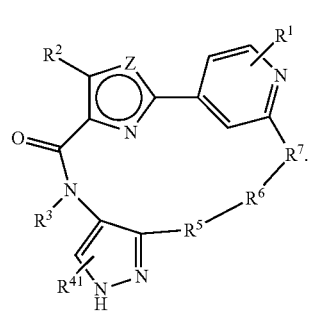

Formula VI

4. The compound of claim 2, or a pharmaceutically acceptable salt thereof, wherein the compound of Formula III is chosen from compounds of Formula VIII

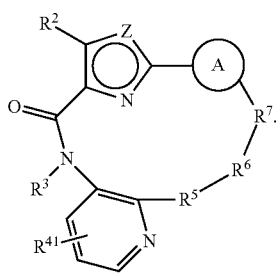

Formula VIII

5. The compound of claim 1, or a pharmaceutically acceptable salt thereof, wherein $R^4$ is arylene optionally substituted with one or more $R^{42}$ wherein for each occurrence, $R^{42}$ is independently chosen from
heterocycloalkyl,
lower alkyl optionally substituted with —C(O)OR$^9$, amino, N-(alkyl)amino, N,N-(dialkyl)amino, cycloalkyl, or heterocycloalkyl,
—C(O)OR$^9$,
hydroxyl, and
—C(O)NR$^{10}$R$^{11}$,
wherein R$^9$ is chosen from hydrogen and lower alkyl,
wherein R$^{10}$ and R$^{11}$ are independently hydrogen and lower alkyl, or R$^9$ and R$^{10}$, together with the nitrogen to which they are bound form a heterocycloalkyl, and
wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

6. The compound of claim 1, or a pharmaceutically acceptable salt thereof, wherein $R^3$ and $R^4$ taken together with the nitrogen to which they are bound, form a 3- to 7-membered heterocycloalkyl ring optionally substituted with one or more R$^{44}$ wherein for each occurrence, R$^{44}$ is independently chosen from
heterocycloalkyl,
lower alkyl optionally substituted with —C(O)OR$^9$, amino, N-(alkyl)amino, N,N-(dialkyl)amino, cycloalkyl, or heterocycloalkyl,
—C(O)OR$^9$,
hydroxyl, and
—C(O)NR$^{10}$R$^{11}$,
wherein R$^9$ is chosen from hydrogen and lower alkyl,
wherein R$^{10}$ and R$^{11}$ are independently hydrogen and lower alkyl, or R$^{10}$ and R$^{11}$, together with the nitrogen to which they are bound form a heterocycloalkyl, and
wherein each lower alkyl, cycloalkyl and heterocycloalkyl is optionally substituted with one, two, or three groups independently chosen from —C(O)OR$^9$, lower alkyl, lower alkoxy, hydroxyl, halogen, amino, N-(alkyl)amino, N,N-(dialkyl)amino, and heterocycloalkyl.

7. The compound of claim 1, or a pharmaceutically acceptable salt thereof, wherein $R^3$ is chosen from hydrogen, lower alkyl optionally substituted with amino, N-(alkyl)amino) or N,N-(dialkyl)amino, benzyl, piperidin-1-yl, and 1H-pyrazol-4-yl, wherein each of benzyl, piperidin-1-yl, and 1H-pyrazol-4-yl is optionally substituted with one or two groups independently chosen from lower alkyl.

8. The compound of claim 1, or a pharmaceutically acceptable salt thereof, wherein $R^5$ is —C(O)NR$^{51}$—, O or absent.

9. The compound of claim 1, or a pharmaceutically acceptable salt thereof, wherein $R^7$ is NR$^{71}$ or O.

10. The compound of claim 1, or a pharmaceutically acceptable salt thereof, wherein $R^7$ is absent.

11. The compound of claim 1, or a pharmaceutically acceptable salt thereof, wherein $R^6$ is an alkylene or alkenylene chain having one or two double bonds, wherein the alkylene or alkenylene chain has 4 to 8 carbon atoms and wherein the alkylene or alkenylene chain is optionally substituted with one or two groups independently chosen from lower alkyl and cycloalkyl, each of which groups is optionally substituted with hydroxyl or alkoxy, and further wherein one or two of the carbon atoms in the alkylene chain is optionally replaced by an O, S, SO, SO$_2$, or NR$^{61}$, and further wherein two of the carbon atoms in the alkylene chain, are optionally connected by a two or three carbon atom alkylene chain to form a 5- to 7-membered ring.

12. The compound of claim 1, or a pharmaceutically acceptable salt thereof, wherein the compound is selected from one of the following compounds:

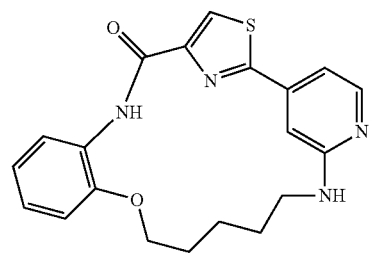

13

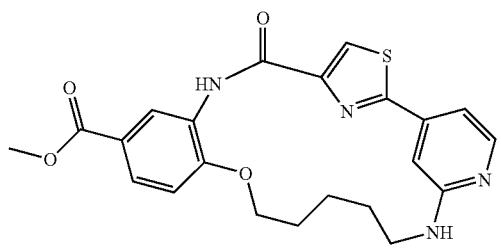

14

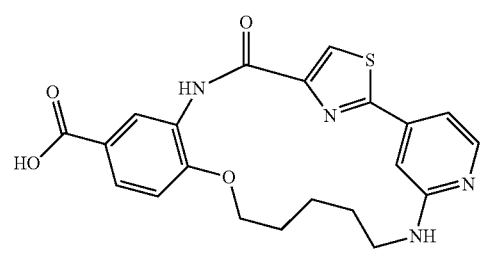

15

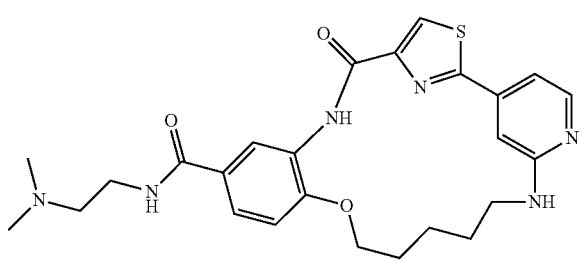

16

-continued
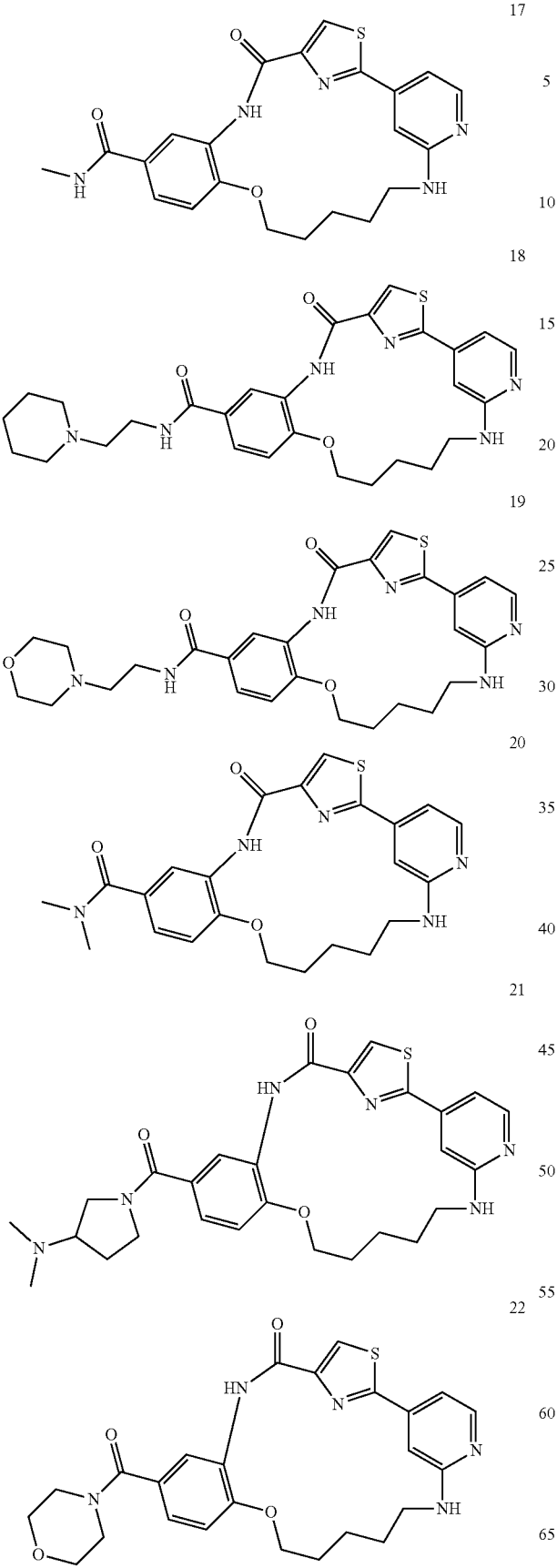
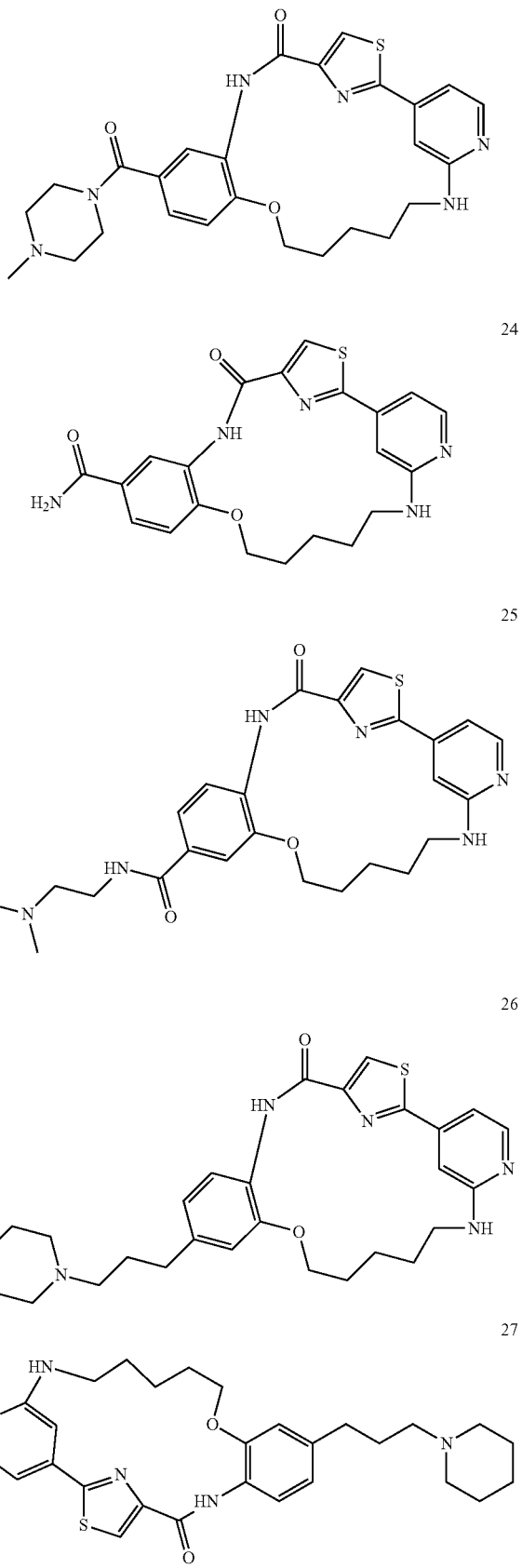

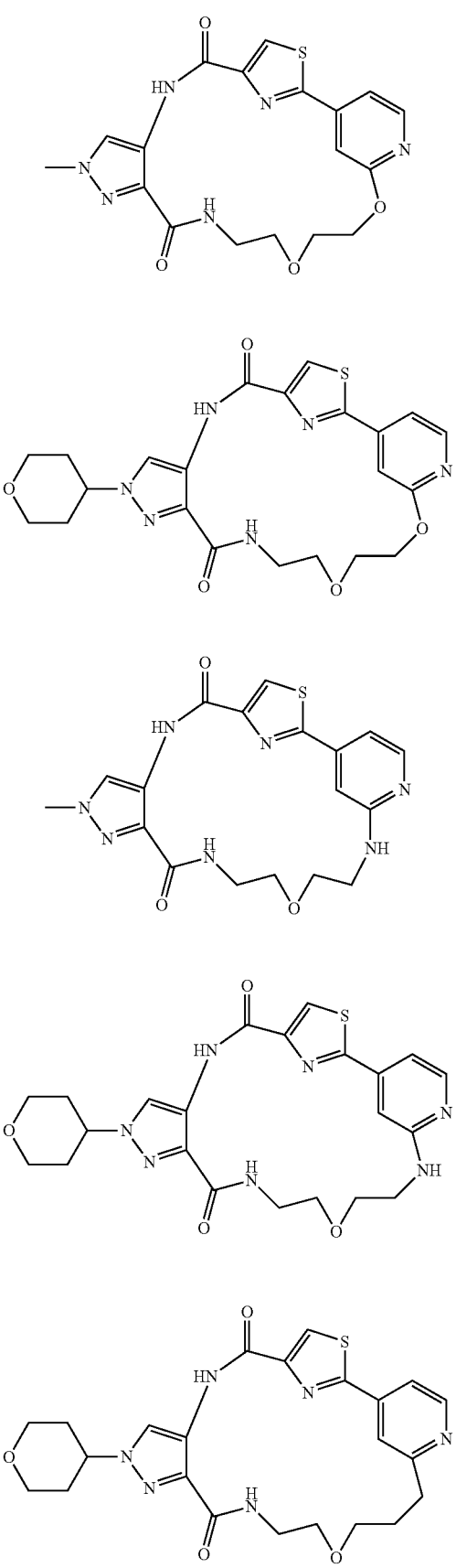

| 385 -continued | 386 -continued |
|---|---|
| 73 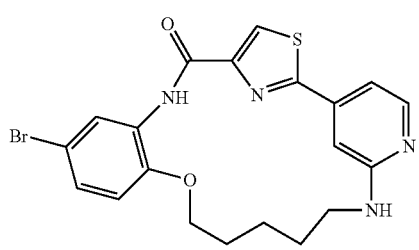 | 88 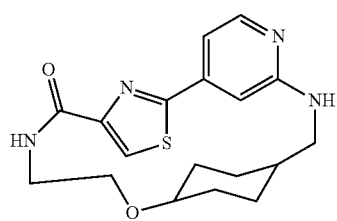 |
| 79 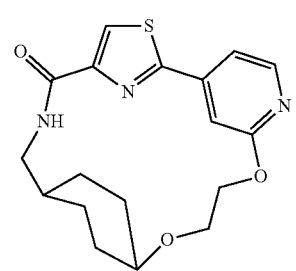 | 90 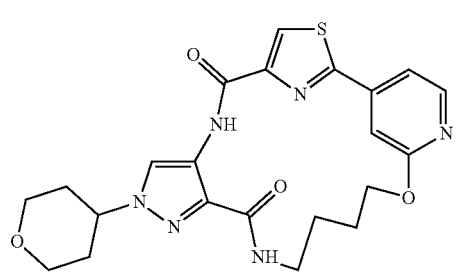 |
| 80 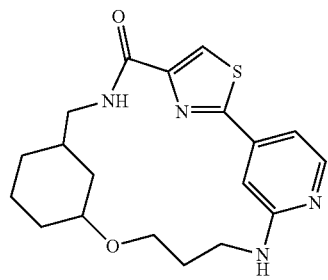 | 91 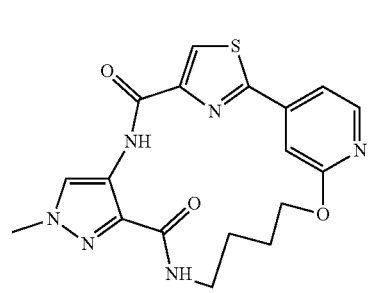 |
| 82 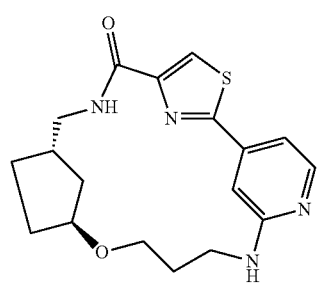 | 95 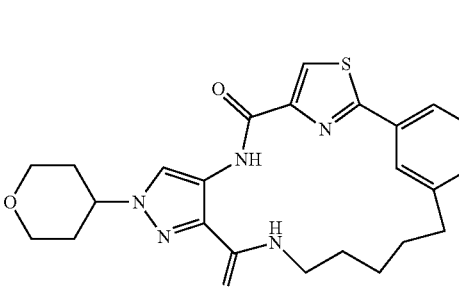 |
| 83 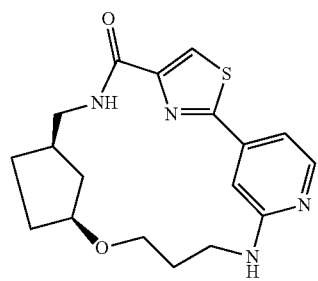 | 96 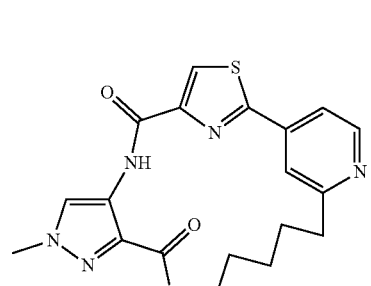 |
| 86 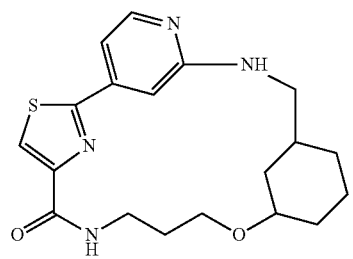 | 100 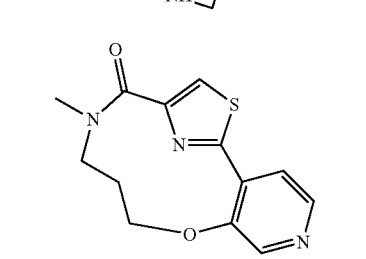 |

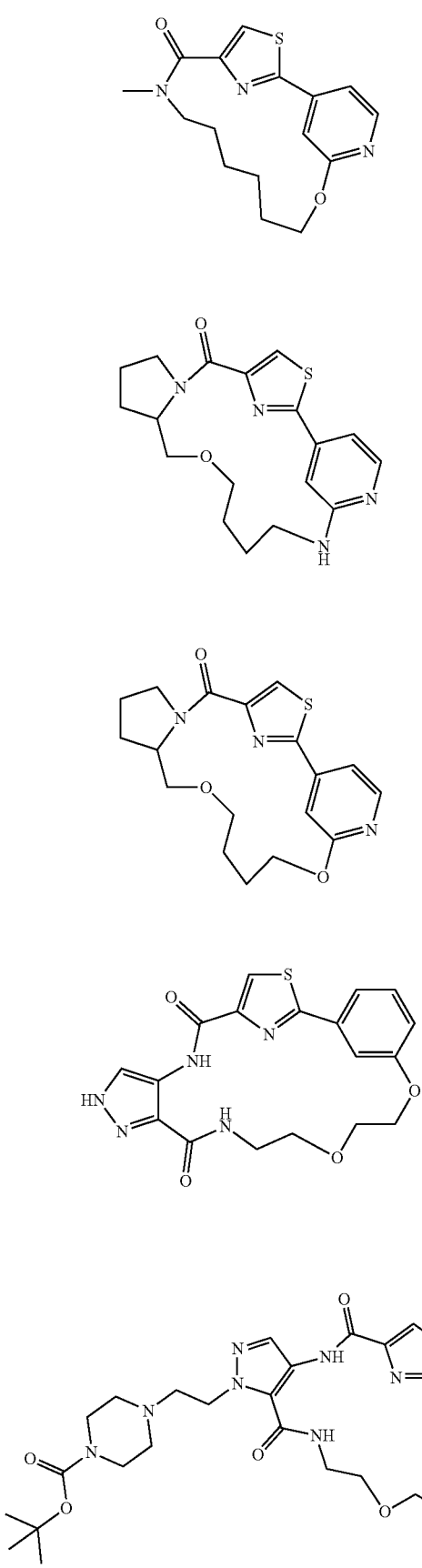
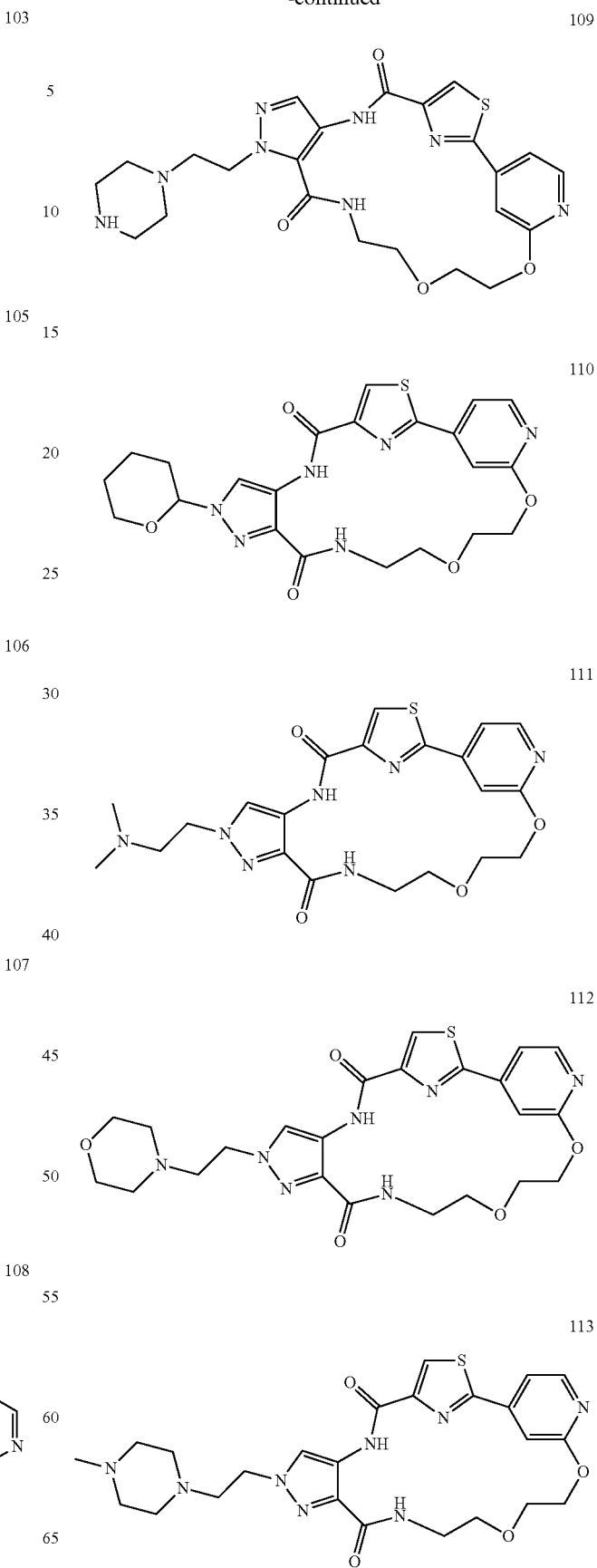

114
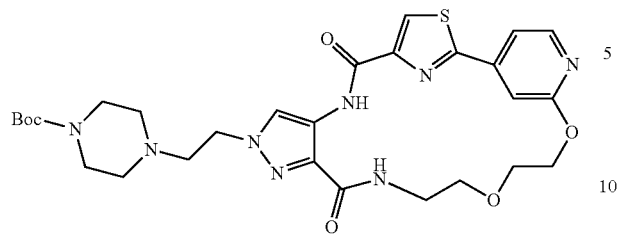
115
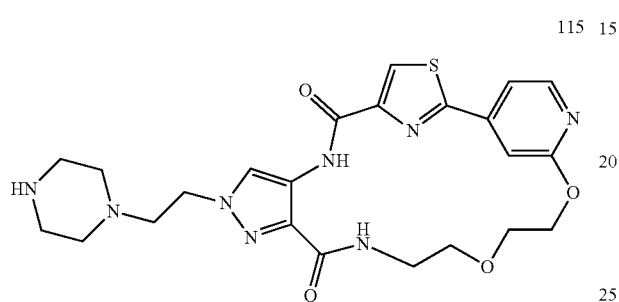
116
119
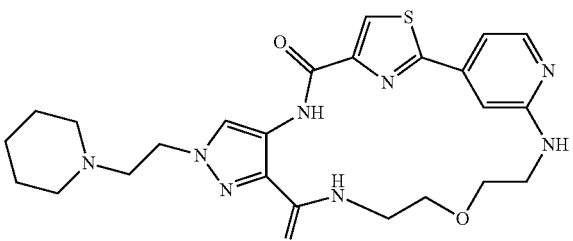
120
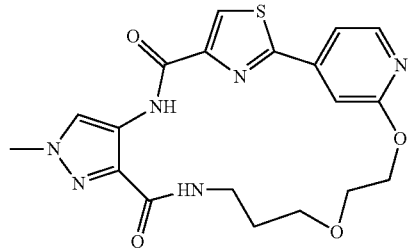
121
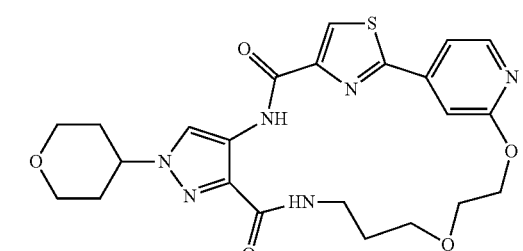
122
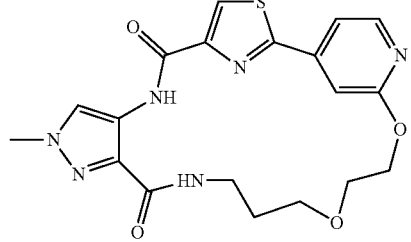
124
117
118
125 (shown as 125 visually is 117/118 on left)
126
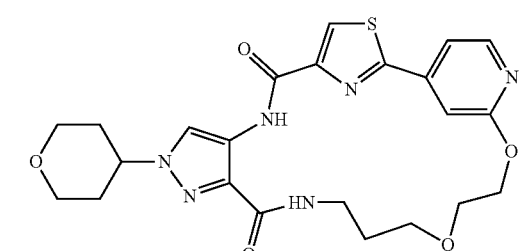
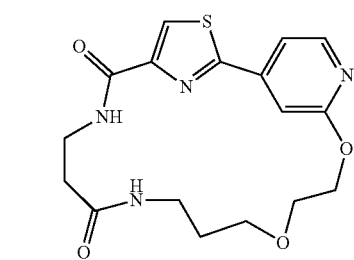

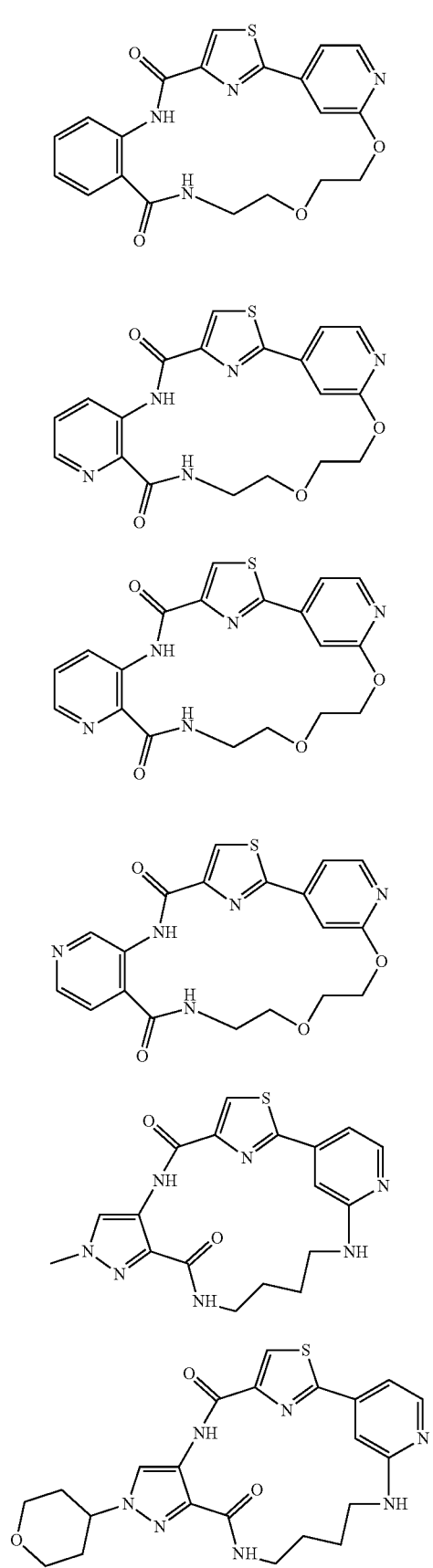
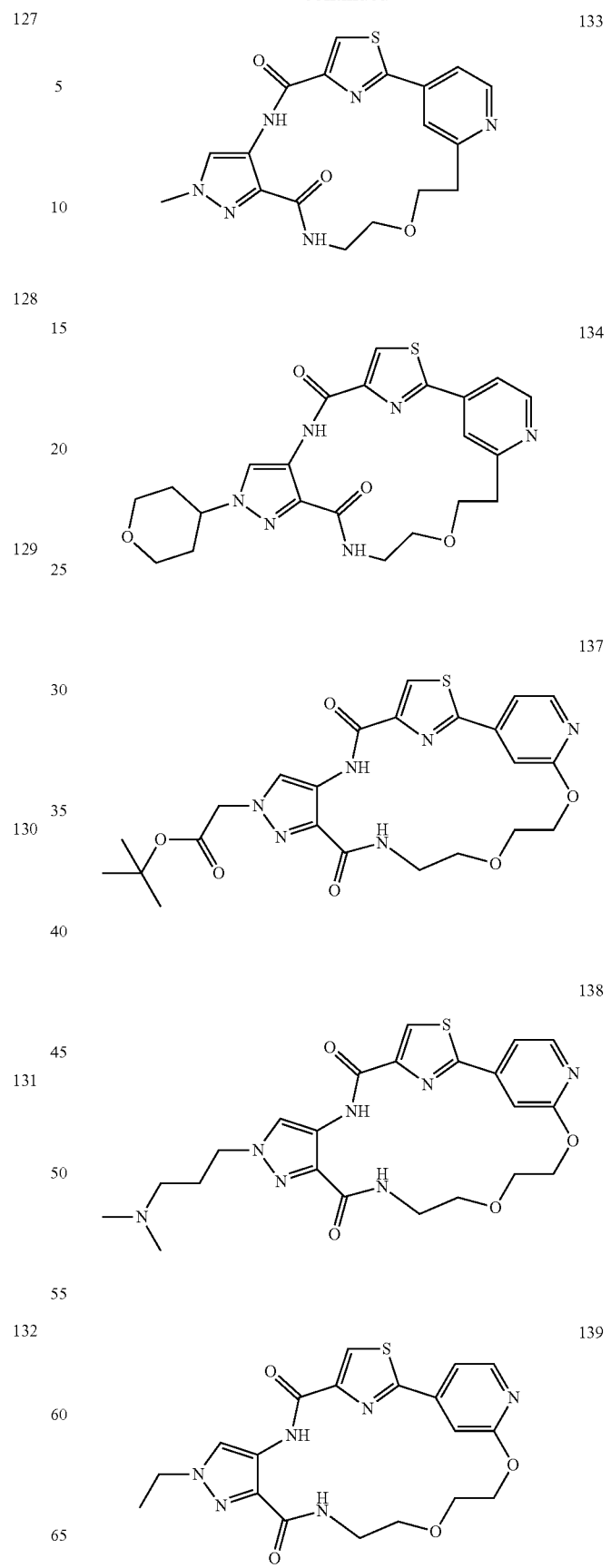

141
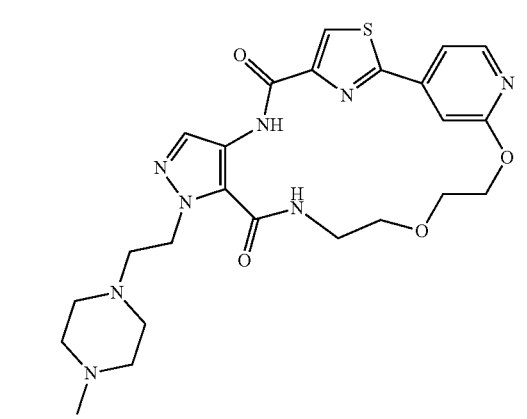
142
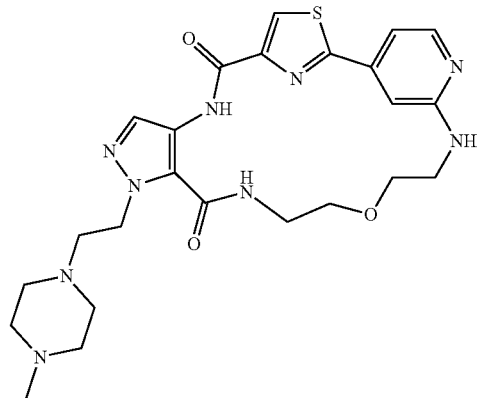
143
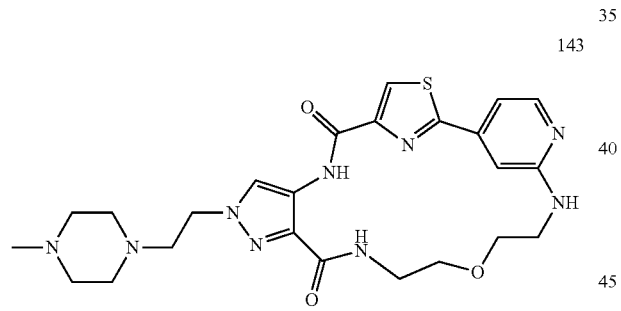
144
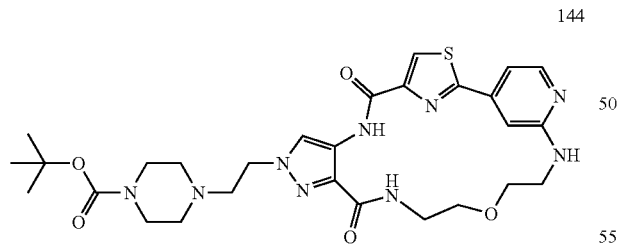
145
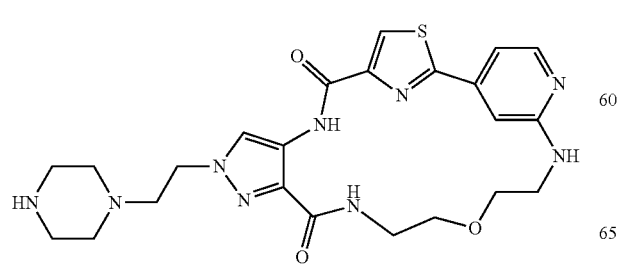
146
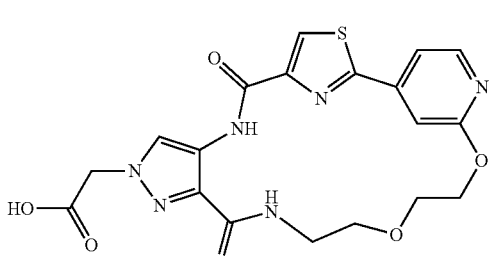
147
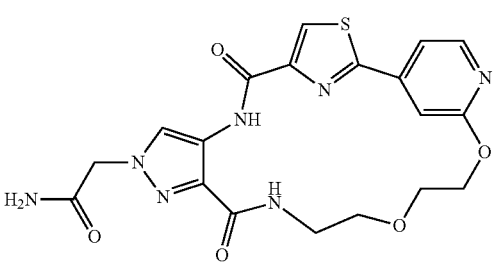
148
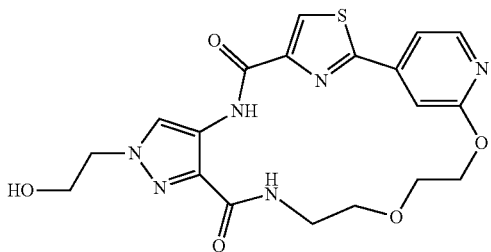
149
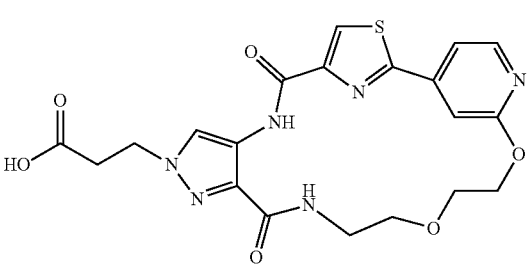
150
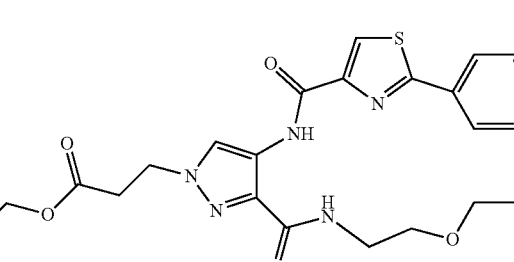
151
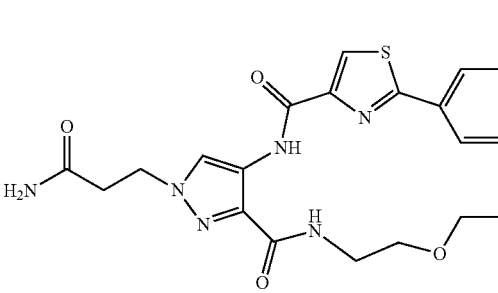

395
-continued
152
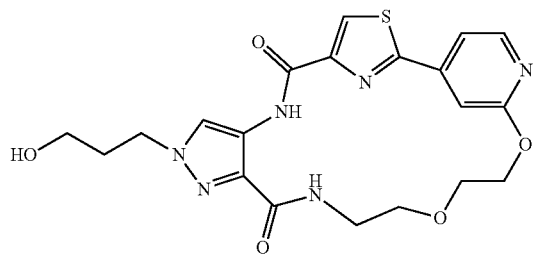
153
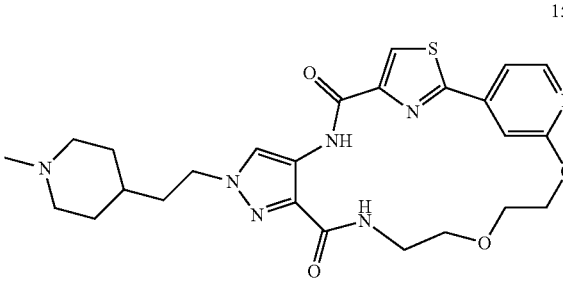
154
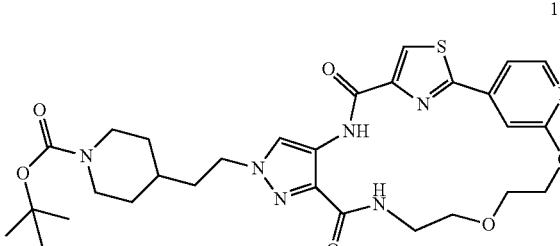
155
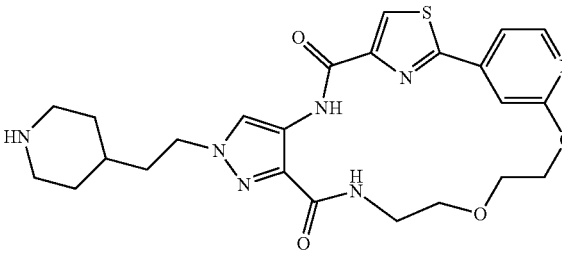
156
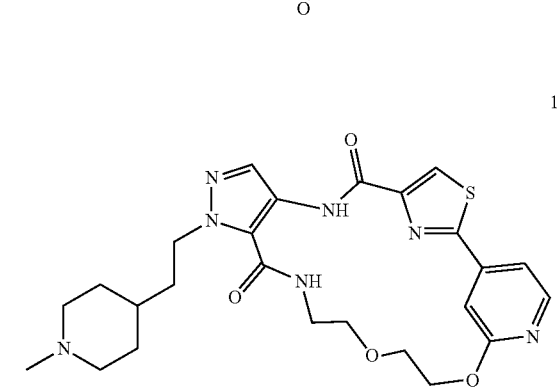
396
-continued
157
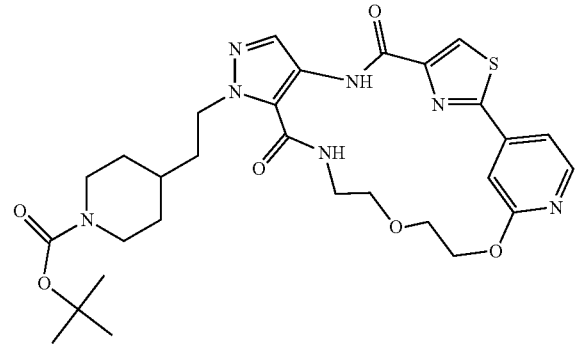
158
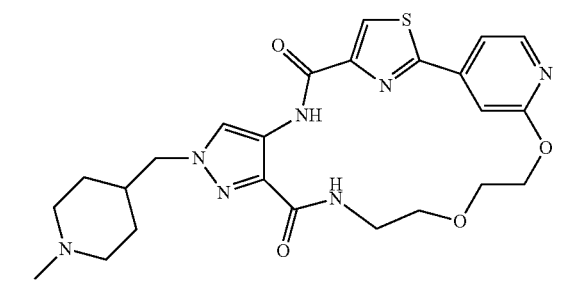
159
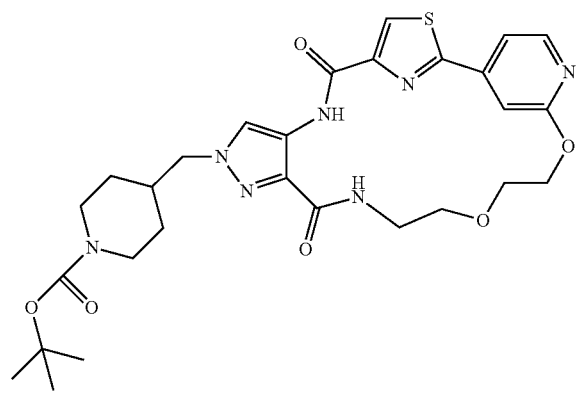
160
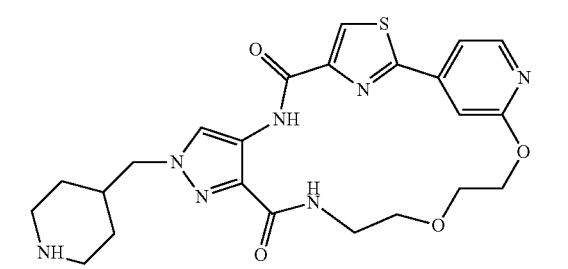
161
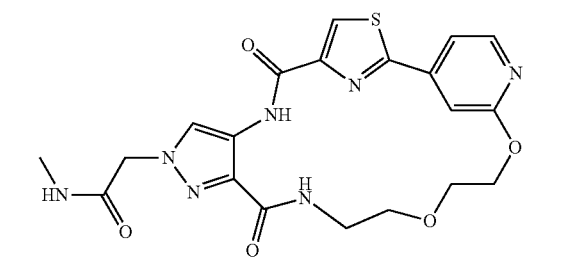

397
-continued
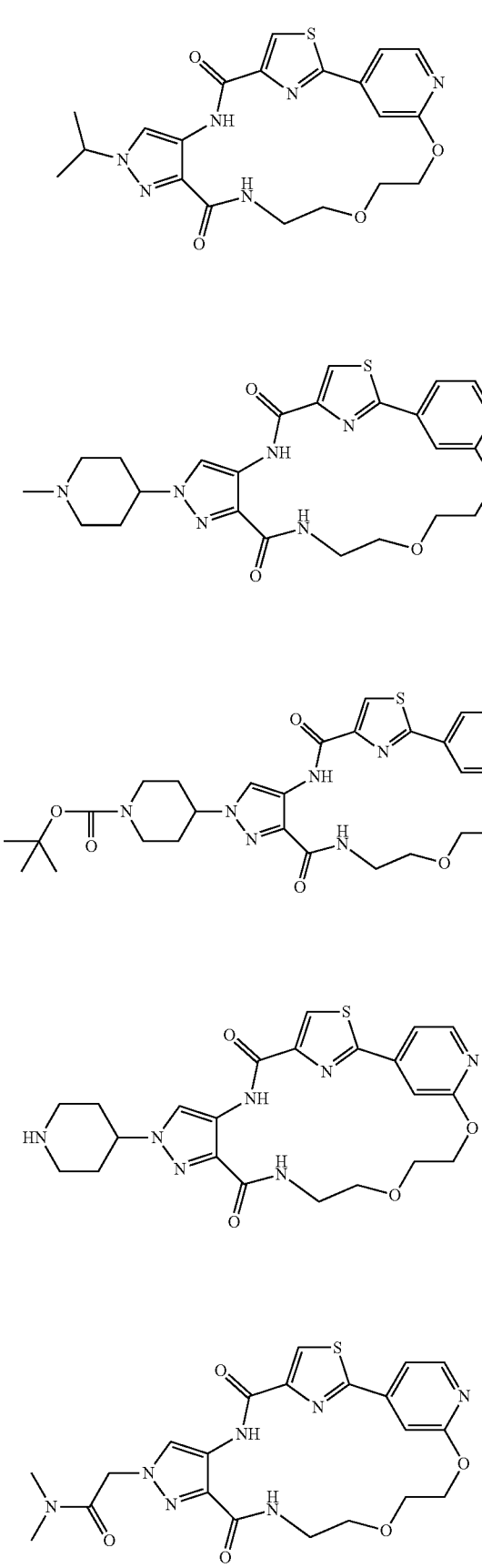
398
-continued
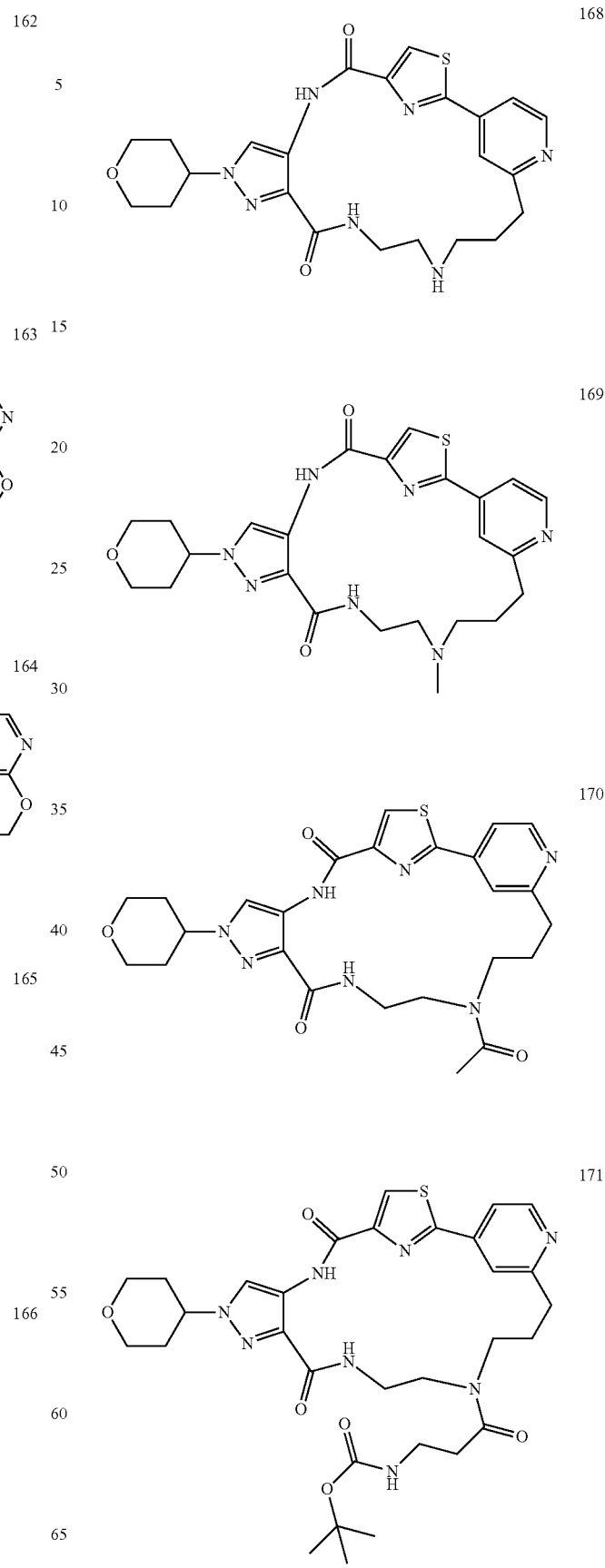

399
-continued
172
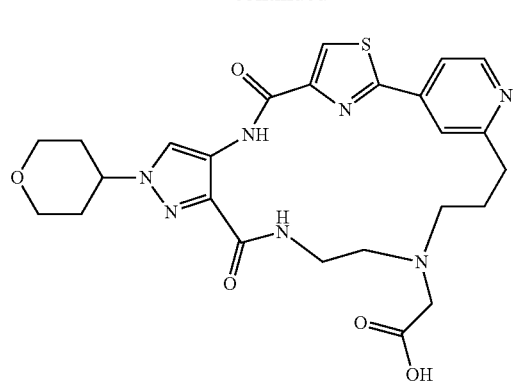
173
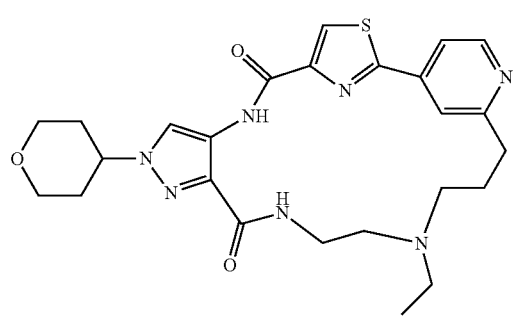
174
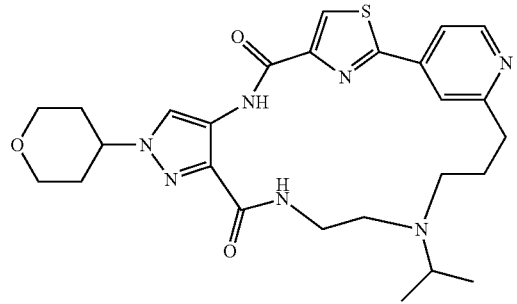
175
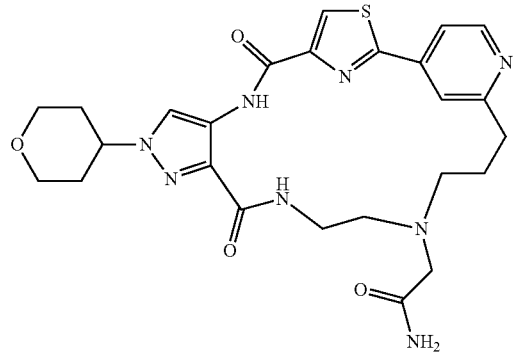
400
-continued
176
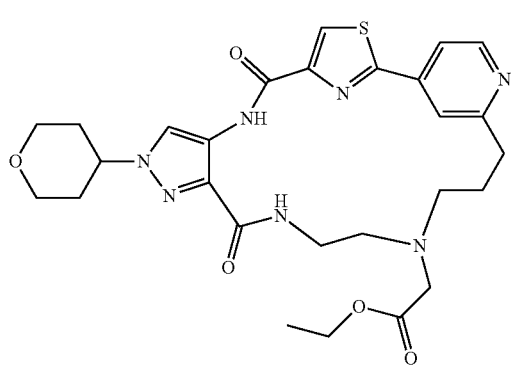
177
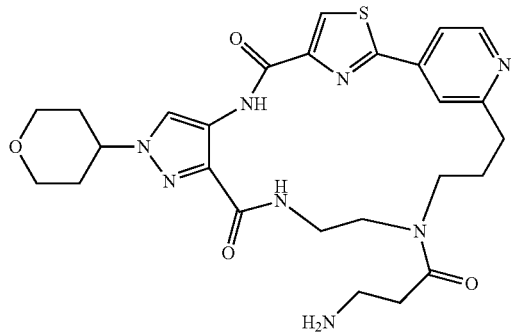
178
179

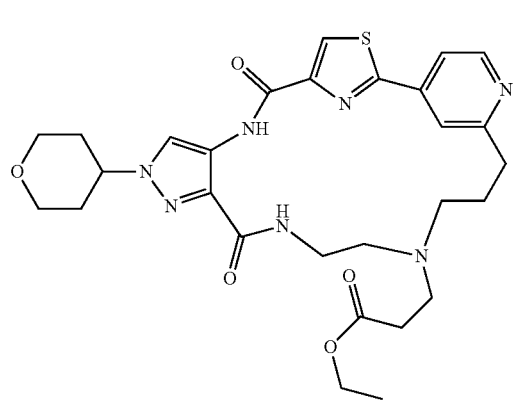
180
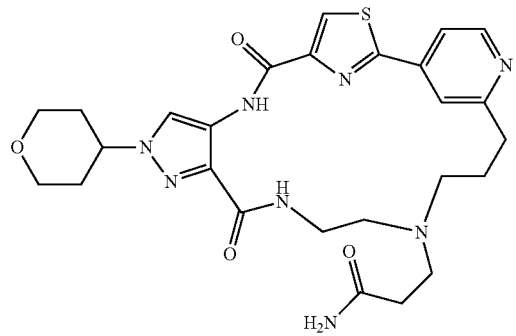
181
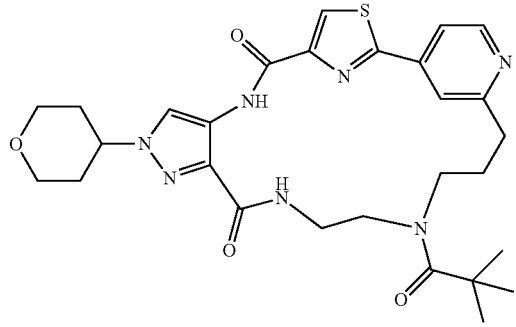
182
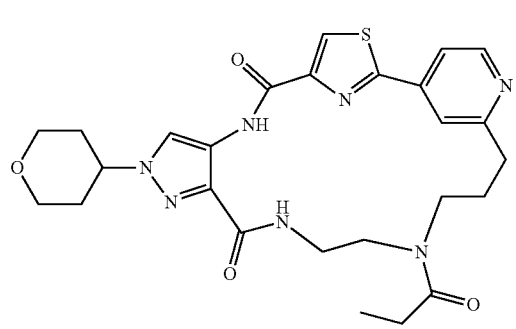
183
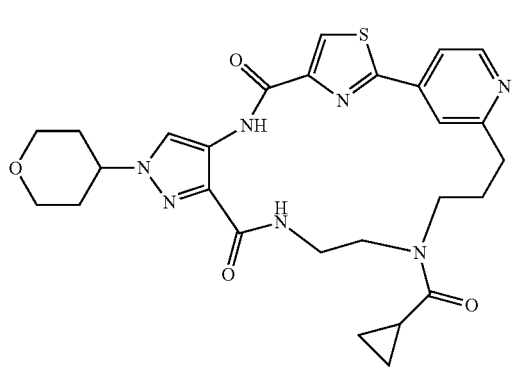
184
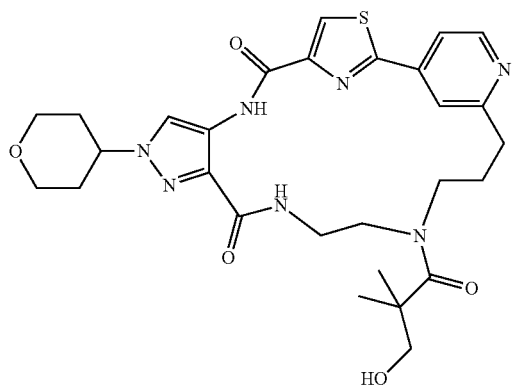
185
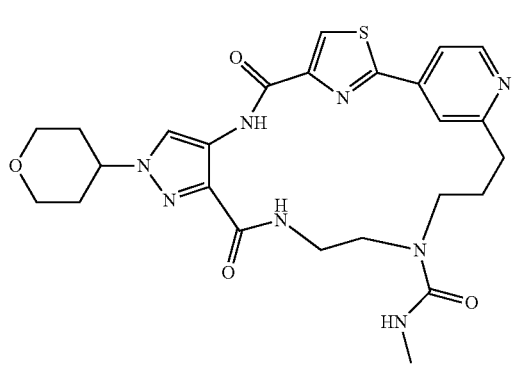
186
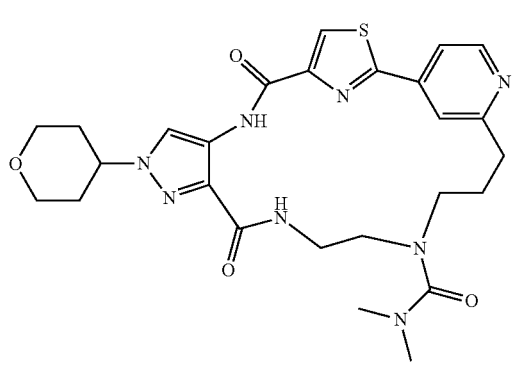
187

| 403 -continued | 404 -continued |
|---|---|
| 188 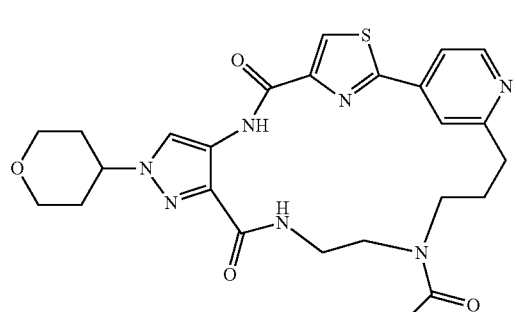 | 192 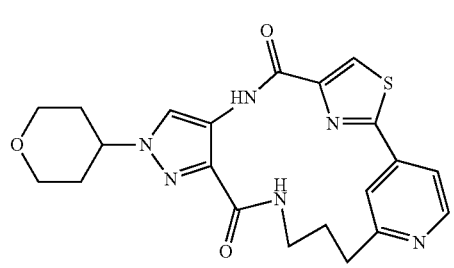 |
| 189 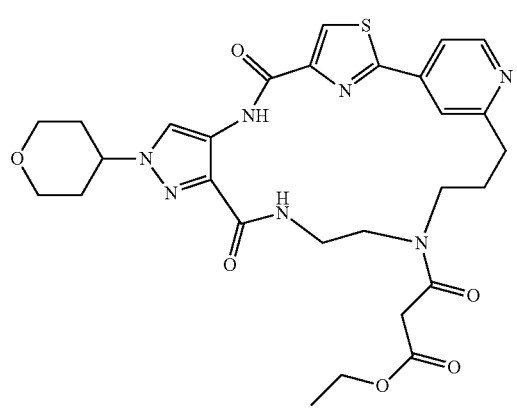 | 193 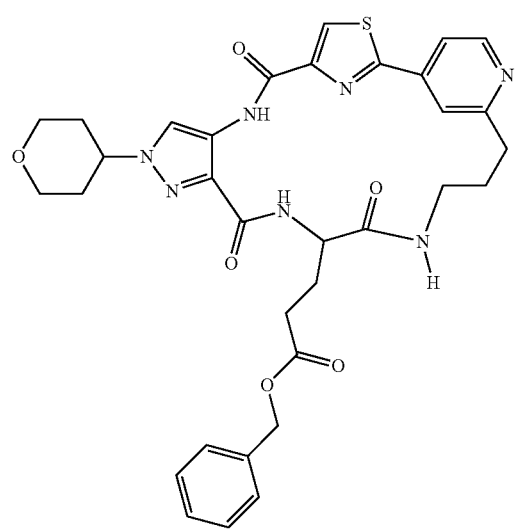 |
| 190 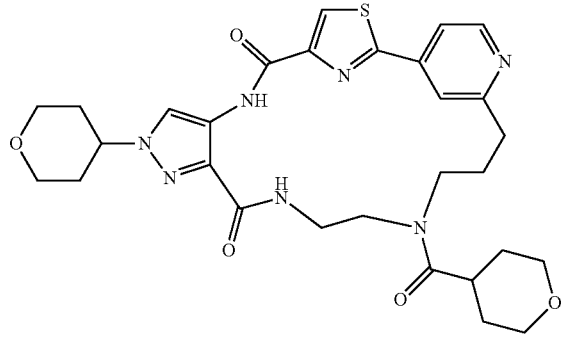 | 194 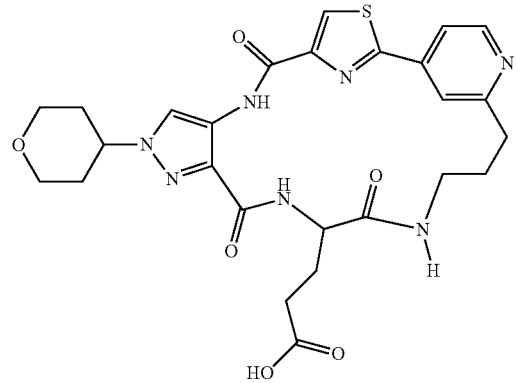 |
| 191 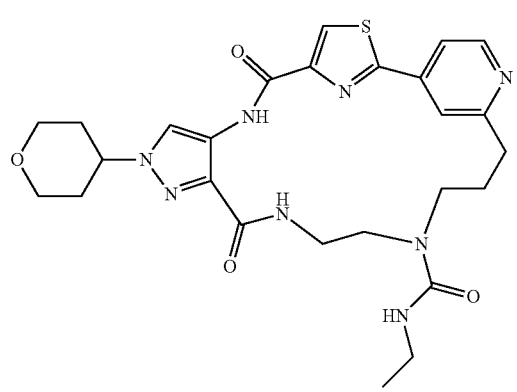 | 195 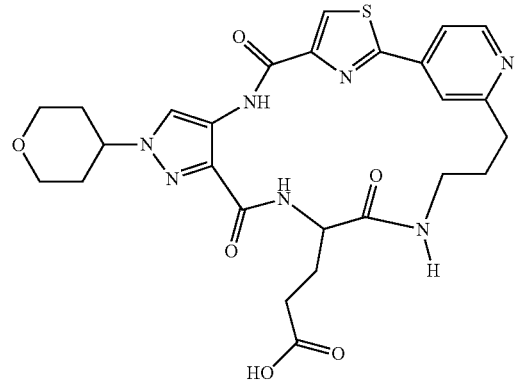 |

196
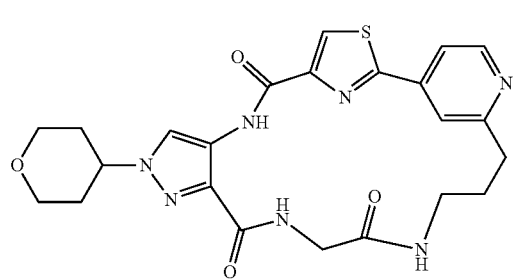
197
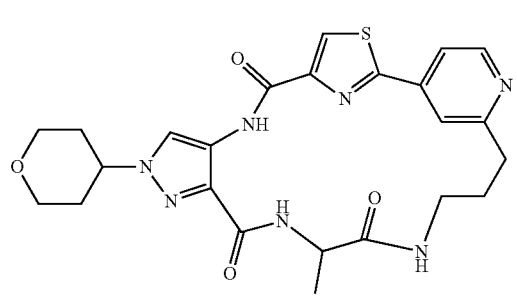
198
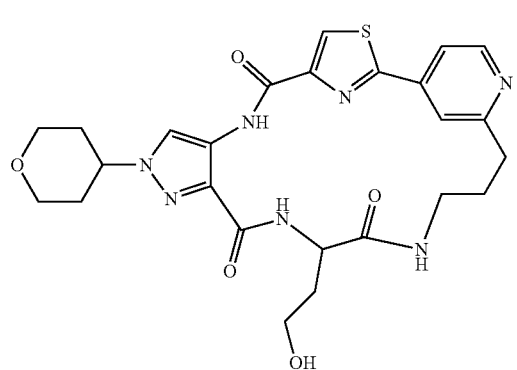
199
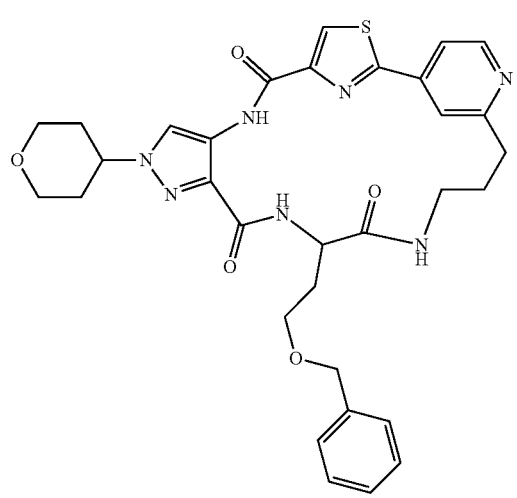
200
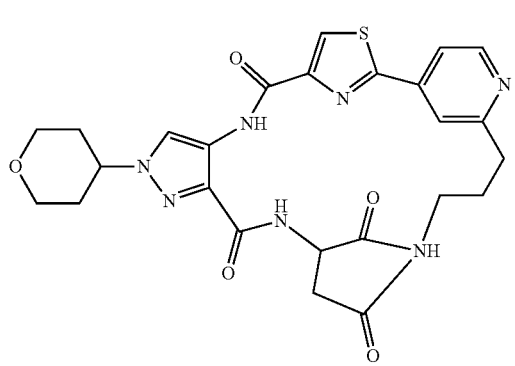
201
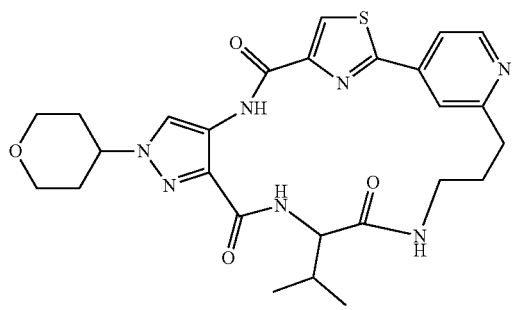
213
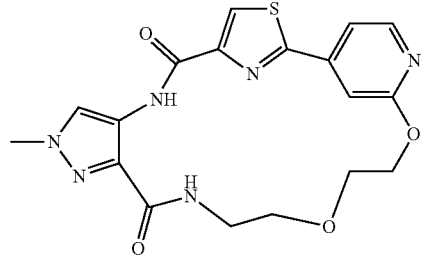
214
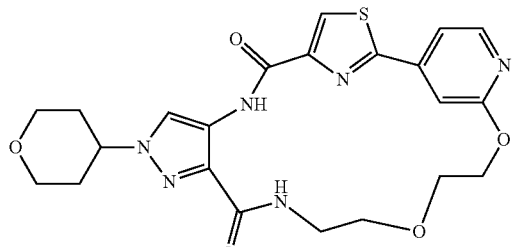
215
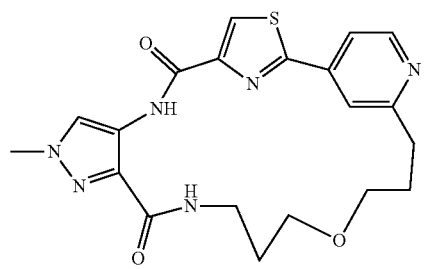

216
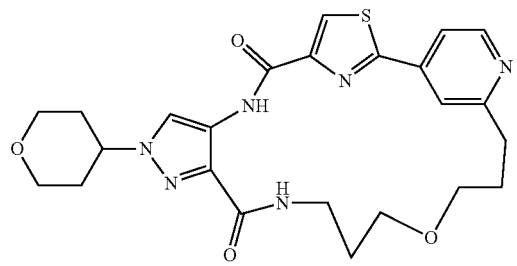
217
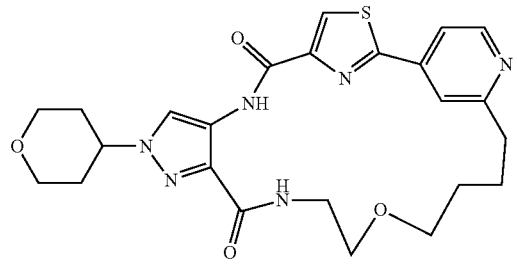
218
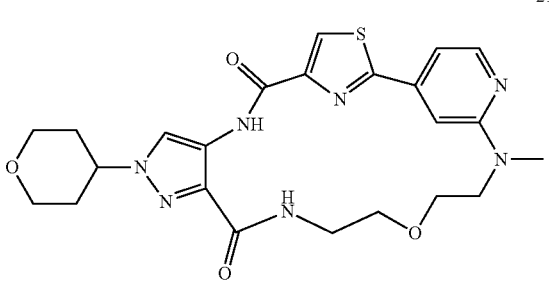
219
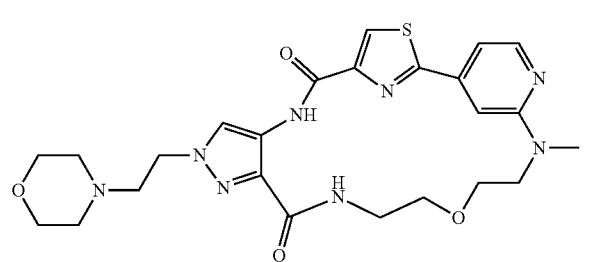
220
221
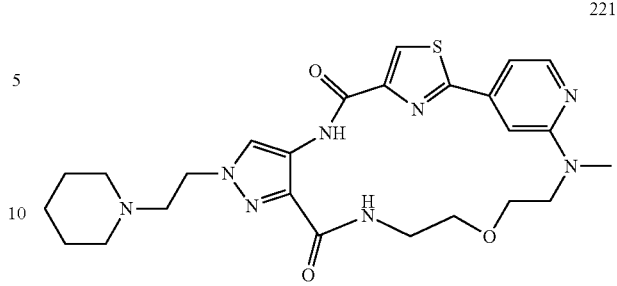
222
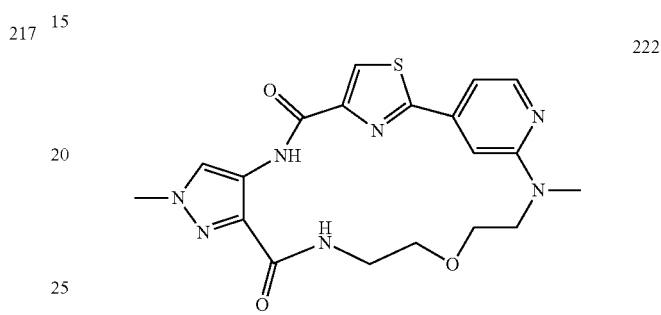
223
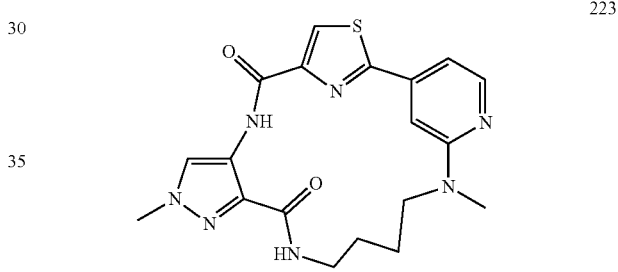
224
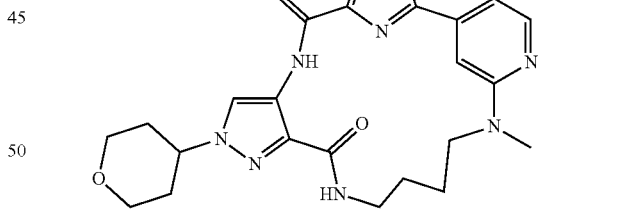
225
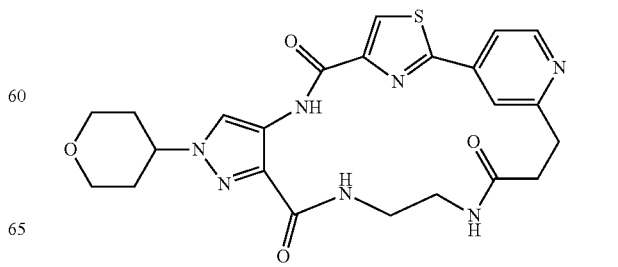

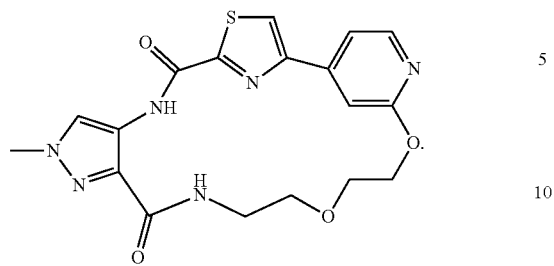
231
13. A pharmaceutical composition comprising at least one compound of claim 1, or a pharmaceutically acceptable salt thereof, and at least one pharmaceutically acceptable excipient.
* * * * *